(12) United States Patent
Salemme et al.

(10) Patent No.: US 9,102,526 B2
(45) Date of Patent: Aug. 11, 2015

(54) NODE POLYPEPTIDES FOR NANOSTRUCTURE ASSEMBLY

(75) Inventors: F. Raymond Salemme, Yardley, PA (US); Patricia C. Weber, Yardley, PA (US); Mark A. Rould, South Burlington, VT (US)

(73) Assignee: IMIPLEX LLC, Yardley, PA (US)

( * ) Notice: Subject to any disclaimer, the term of this patent is extended or adjusted under 35 U.S.C. 154(b) by 1240 days.

(21) Appl. No.: 12/892,911

(22) Filed: Sep. 28, 2010

(65) Prior Publication Data

US 2011/0085939 A1 Apr. 14, 2011

Related U.S. Application Data

(63) Continuation-in-part of application No. PCT/US2009/053628, filed on Aug. 13, 2009, which is a continuation-in-part of application No. 12/589,529, filed on Apr. 27, 2009, now abandoned.

(60) Provisional application No. 61/136,097, filed on Aug. 12, 2008, provisional application No. 61/246,699, filed on Sep. 29, 2009.

(51) Int. Cl.
*B82Y 30/00* (2011.01)

(52) U.S. Cl.
CPC ..................................... *B82Y 30/00* (2013.01)

(58) Field of Classification Search
None
See application file for complete search history.

(56) References Cited

U.S. PATENT DOCUMENTS

| | | | |
|---|---|---|---|
| 4,839,293 A | 6/1989 | Cantor et al. |
| 4,933,275 A | 6/1990 | Wands et al. |
| 5,258,627 A | 11/1993 | Turin |
| 5,672,691 A | 9/1997 | Kopetzki et al. |
| 5,891,993 A | 4/1999 | Dawson et al. |
| 5,948,668 A | 9/1999 | Hartman et al. |
| 5,948,688 A | 9/1999 | Weber et al. |
| 6,022,951 A | 2/2000 | Sano et al. |
| 6,156,493 A | 12/2000 | Stayton |
| 6,165,750 A | 12/2000 | Stayton |
| 6,211,388 B1 | 4/2001 | Tsuji et al. |
| 6,218,506 B1 | 4/2001 | Krafft et al. |
| 6,232,085 B1 | 5/2001 | Pantoliano et al. |
| 6,268,158 B1 | 7/2001 | Pantoliano et al. |
| 6,291,192 B1 | 9/2001 | Pantoliano et al. |
| 6,485,984 B1 | 11/2002 | Kim |
| 6,490,532 B1 | 12/2002 | Hogue et al. |
| 6,492,492 B1 | 12/2002 | Stayton |
| 6,653,127 B1 | 11/2003 | Malcolm et al. |
| 6,743,771 B2 | 6/2004 | Douglas et al. |
| 6,756,039 B1 | 6/2004 | Yeates et al. |
| 6,849,458 B2 | 2/2005 | Pantoliano et al. |
| 6,859,736 B2 | 2/2005 | Blankenbecler et al. |
| 7,039,621 B2 | 5/2006 | Agrafiotis et al. |
| 7,045,537 B1 | 5/2006 | Woolfson et al. |
| 7,122,321 B2 | 10/2006 | Pantoliano et al. |
| 7,138,255 B2 | 11/2006 | Vodyanoy et al. |
| 7,139,739 B2 | 11/2006 | Agrafiotis et al. |
| 7,144,991 B2 | 12/2006 | Goshorn et al. |
| 7,188,055 B2 | 3/2007 | Agrafiotis et al. |
| 7,217,557 B1 | 5/2007 | Noel et al. |
| 7,803,575 B2 | 9/2010 | Borchert et al. |
| 2001/0047074 A1 | 11/2001 | Kissel et al. |
| 2002/0037908 A1 | 3/2002 | Douglas et al. |
| 2003/0027194 A1 | 2/2003 | Kurz et al. |
| 2003/0077803 A1 | 4/2003 | Walker et al. |
| 2003/0171257 A1 | 9/2003 | Stirbl et al. |
| 2003/0198967 A1 | 10/2003 | Matson et al. |
| 2004/0014186 A1 | 1/2004 | Kumar |
| 2004/0152872 A1 | 8/2004 | Wohlfahrt et al. |
| 2005/0027103 A1 | 2/2005 | Tang et al. |
| 2005/0048078 A1 | 3/2005 | Sakasegawa et al. |
| 2005/0053525 A1 | 3/2005 | Segal et al. |
| 2005/0130258 A1 | 6/2005 | Trent et al. |
| 2005/0192757 A1 | 9/2005 | Umeyama et al. |
| 2005/0221343 A1 | 10/2005 | Waldo et al. |
| 2006/0003381 A1 | 1/2006 | Gilmore et al. |
| 2006/0009620 A1 | 1/2006 | Woolfson et al. |
| 2006/0030053 A1 | 2/2006 | Seymour et al. |
| 2006/0089808 A1 | 4/2006 | Agrafiotis et al. |

(Continued)

FOREIGN PATENT DOCUMENTS

WO WO-2006/058226 A2 6/2006
WO WO-2008/112980 A2 9/2008

(Continued)

OTHER PUBLICATIONS

Adams et al., "Structure of the Pleckstrin Homology Domain from Phospholipase C Delta in Complex with Inositol Trisphosphate" Protein Data Bank, Code: 1MAIL, Last Modified on Feb. 24, 2009 (www.rcsb.org/pdb/explore/explore.do?structureId=1mai).

Benach et al., "The 2.35 A structure of the TenA homolog from *Pyrococcus furiosus* supports an enzymatic function in thiamine metabolism" (2005) *Acta Crystallogr.,Sect.D* 61: 589-598 (pdb code:lrtw).

Blum et al., "An engineered virus as a scaffold for three-dimensional self-assembly on the nanoscale" *Small* (2005)1:702.

Blum et al., "Cowpea mosaic virus as a scaffold for 3-D patterning of gold nanoparticles" *Nano Lett* (2004)4:867.

Case et al., "The Amber biomolecular simulation programs" (2005) *J. Computat. Chem.* 26, 1668-1688 (://amber.scripps.edu/).

(Continued)

*Primary Examiner* — Anand Desai
(74) *Attorney, Agent, or Firm* — Venable LLP; Lars H. Genieser; Michael A. Gollin

(57) ABSTRACT

Engineered proteins are used in the assembly of two-dimensional and three-dimensional nanostructure assemblies, based on systematic design and production of protein node structures that can be interconnected, for example, with streptavidin or streptavidin-incorporating struts to produce structures with defined dimensions and geometry. Nanostructure assemblies having utility as functional devices or as resists for the patterning of substrates have architectures including polygons, polyhedra, two-dimensional lattices, and three-dimensional lattices.

64 Claims, 48 Drawing Sheets

(56) References Cited

U.S. PATENT DOCUMENTS

| | | |
|---|---|---|
| 2006/0134072 A1 | 6/2006 | Pedrozo et al. |
| 2007/0087356 A1 | 4/2007 | Chatterjee et al. |
| 2007/0178572 A1 | 8/2007 | Gamblin et al. |
| 2007/0256250 A1 | 11/2007 | Knight |
| 2008/0003662 A1 | 1/2008 | Trachtenberg |
| 2008/0248972 A1 | 10/2008 | Nishizawa et al. |
| 2010/0256342 A1 | 10/2010 | Salemme et al. |
| 2011/0085939 A1 | 4/2011 | Salemme et al. |
| 2012/0059156 A1 | 3/2012 | Salemme et al. |
| 2014/0178962 A1 | 6/2014 | Salemme et al. |

FOREIGN PATENT DOCUMENTS

| | | |
|---|---|---|
| WO | WO-2009/055068 A1 | 4/2009 |
| WO | WO-2010/019725 A2 | 2/2010 |

OTHER PUBLICATIONS

Castro et al., "Homogeneous biocatalysis in organic solvents and water-organic mixtures" *Crit Rev Biotechnol* (2003)23:195-231.
Chatterji et al., "A virus-based nanoblock with tunable electrostatic properties" *Nano Lett* (2005)5:597.
Chatterji et al., "New addresses on an addressable virus nanoblock; uniquely reactive Lys residues on cowpea mosaic virus" *Chem Biol* (2004)11:855.
Cherny et al., "Analysis of Various Sequence-Specific Triplexes by Electron and Atomic Force Microscopies" *Biophysical J* (1998)74:1015-1023.
Cosgrove et al., "The structural basis of sirtuin substrate affinity" (2006) *Biochemistry* 45: 7511-7521 (pdb code: 2h2i).
Deng Y, Wang Y, Holtz B, Li J, Traaseth N, Veglia G, Stottrup BJ, Elde R, Pei, Guo A, Zhu X-Y "Fluidic and Air-Stable Supported Lipid Bilayer and Cell-Mimicking Microarrays" *J Am Chem Soc* (2008) Apr. 12, 2008 web publication.
Eigler et al., "Positioning single atoms with a scanning tunnelling microscope" *Nature* (1990)344:524-526.
Esposito et al., "Structural study of a single-point mutant of Sulfolobus solfataricus alcohol dehydrogenase with enhanced activity" (2003) *Febs Lett*. 539: 14-18 (pdb code: 1into).
Falkner et al., "Virus crystals as nanocomposite scaffolds" *J Am Chem Soc* (2005)127:5274.
Fitzpatrick et al., "Enzyme Crystal Structure in a Neat Organic Solvent" *Proc Nat Acad Sci USA* (1993)90:8653.
Gonzalez et al., "Interaction of Biotin with Streptavidin" *J Biol Chem* (1997)272:112288-11294.
Green NM "A Spectrophotometric Assay for Avidin and Biotin Based on Binding of Dyes by Avidin" *Biochem J* (1965)294:23c-24c.
Green NM "Avidin and Streptavidin" *Meth Enzymol* (1990)243:51-67.
Green NM "Avidin" *Adv Prot Chem* (1975)29:85-133.
Gupta MN, Roy I "Enzymes in organic media: Forms, functions and applications" *Eur J Biochem* (2004)271:2575-2583.
Hartmann et al., "Imaging and manipulation properties of nanoparticles in scanning tunneling microscopy" *Nanotechnology* (1996)7:376-380.
Hatzor-de Picciotto et al., "Arrays of Cu2+-Complexed Organic Clusters Grown on Gold Nano Dots" (2007) Journal of Experimental Nanoscience, 2: 3-11.
Hla et al., "STM Control of Chemical Reactions: Single-Molecule Synthesis" *Annu Rev Phys Chem* (2003)54:307-309.
Hofmann et al., "Iminobiotin affinity columns and their application to retrieval of streptavidin" *Proc Natl Acad Sci USA* (1980)77:4666-4668.
Humphrey et al., "VMD: visual molecular dynamics" J Mol Graph. Feb. 1996;14(1):33-8-27-8. Retrieved From: http://www.ks.uiuc.edu/Research/vmd/.
International Preliminary Report on Patentability issued in International Application No. PCT/US2009/053628 dated Nov. 1, 2011.
International Preliminary Report on Patentability issued in International Application No. PCT/US2008/012174 dated Apr. 27, 2010.
International Preliminary Report on Patentability issued in International Application No. PCT/US2010/034248 dated Nov. 15, 2011.
International Search Report issued in International Application No. PCT/US2008/012174 dated Feb. 2, 2009.
International Search Report issued in International Application No. PCT/US2009/053628 dated Jul. 14, 2010.
International Search Report issued in International Application No. PCT/US2010/034248 dated Aug. 19, 2010.
International Technology Roadmap for Semiconductors (://www.itrs.net/reports.html>), pp. 1-3, accessed Sep. 25, 2012.
Izard et al., "Principles of quasi-equivalence and Euclidean geometry govern the assembly of cubic and dodecahedral cores of pyruvate dehydrogenase complexes" (1999) *Proc. Natl. Acad. Sci. USA* 96: 1240-1245 (pdb code: 1b5s).
Jones A "O: A Macromolecule Modeling Environment," Crystallographic and Modeling Methods in Molecular Design, 1990, pp. 189-199.
Jones, et al., "Using known substructures in protein model building and crystallography," The EMBO Journal, vol. 5, No. 4, 1986 pp. 819-822.
Judy JW, "Microelectromechanical systems (MEMS): fabrication, design and applications" (2001) *Smart Mater. Struct*. 10 1115-1134.
Kim et al., "Crystal structure of a small heat-shock protein" (1998) *Nature* 394: 595-599 (pdb code: 1shs).
Kisker et al., "A left-hand beta-helix revealed by the crystal structure of a carbonic anhydrase from the archaeon *Methanosarcina thermophila*" (1996) EMBO J. v15 pp. 2323-2330 (pdb code: 1thj).
Kitago et al., "Structure of 5'-deoxy-5'-methylthioadenosine phosphorylase homologue from *Sulfolobus tokodaii*" Protein Data Bank, Code: 1V4N, Last Modified on Feb. 24, 2009 (www.rcsb.org/pdb/explore/explore.do?structureId=1v4n)*Sulfolobus tokodaii* Protein Data Bank, Code: 1V4N, Last Modified on Feb. 24, 2009.
Lawrence et al., "Shape complementarity at protein/protein interfaces" *J Mol Biol* (1993)234:946-950.
Lee et al., "Protein Nanoarrays Generated by Dip-Pen Nanolithography" *Science* (2002)295:1702-1705.
Lee et al., "The interpretation of protein structures: Estimation of static accessibility" (1971) *J. Mol. Biol*. 55, 379-400.
Levene et al., "Zero-Mode Waveguides for Single-Molecule Analysis at High Concentrations" (2003) Science 299: 682-686.
Liu et al., "Nanofabrication of Self-Assembled Monolayers Using Scanning Probe Lithography" *Nanotechnology* (1996)7:376-380.
Liu et al., "Positioning protein molecules on surfaces: A nanoengineering approach to supramolecular chemistry" *Proc Nat Acad Sci* (2002)99:5165-5170.
Loo et al., "Effect of reducing disulfide-cotaining proteins on electrospray ionization spectra" *Anal Chem* (1990)62:693-698.
Massant et al., "Refined structure of *Pyrococcus furiosus* ornithine carbamoyltransferase at 1.87 A" (2003) *Acta Crystallogr*., Sect.D 59: 2140-2149 (pdb code: 1pvv).
Medalsy et al., "SP1 Protein-Based Nanostructures and Arrays" (2008) *Nano Lett*., 8 (2), 473-477.
Merrifield et al., "An instrument for automated synthesis of peptides" *Anal Chem* (1966)38:1905-1914.
Merrifield et al., "Automated Peptide Synthesis" *Nature* (1965)207:522-523.
Ni et al., "Structure of the arginine repressor from *Bacillus stearothermophilus*." (1999) *Nat.Struct.Biol*. 6: 427-432 (pdb code: 1b4b).
Nordlund, HR, et. al. Construction of a Dual Chain Pseudotetrameric Chicken Avidin by Combining Two Circularly Permuted Avidins J. Biol. Chem. 279:36715-36719 (2004).
Padilla et al., "Nanohedra: Using symmetry to design self-assembling protein cages, layers, crystals, and filaments" *Proc Nat Acad Sci USA* (2001)98:2217-2221.
Pantoliano et al., "High Density Miniaturized Thermal Shift Assay as a General Strategy for Drug Discovery" *J Biomol Screening* (2001)6:429-440.
Phillips et al., "The Biological Frontiers of Physics" Physics Today (May 2006) p. 38-43.
Protein Data Bank. /www.rcsb.org/pdb/>, pp. 1-2, accessed Sep. 25, 2012.

(56) References Cited

OTHER PUBLICATIONS

Ringler et al., "Self-Assembly of Proteins into Designed Networks" *Science* (2003)302:106-109.
Rogers et al., "Recent progress in Soft Lithography" (2005) *Materials Today* 8:50-56.
Rothemund PWK "Folding DNA to create nanoscale shapes and patterns" *Nature* (2006)440:297-302.
Rupley et al., "Protein hydration and function" *Adv Protein Chem* (1991)41:37-172.
Saridakis et al., "Insights into ligand binding and catalysis of a central step in NAD+ synthesis: structures of *Methanobacterium thermoautotrophicum* NMN adenylyltransferase complexes." (2001) J.Biol.Chem. 276: 7225-7232 (pdb code: 1hyb).
Saveanu et al., "Structural and nucleotide-binding properties of YajQ and YnaF, two *Escherichia coli* proteins of unknown function" *Prot Sci* (2002)11:2551-2560.
Schulten K "VMD" <://www.ks.uiuc.edu/Research/vmd/>, pp. 1-2, accessed Sep. 25, 2012.
Schwarzenbacher et al. "Crystal structure of a phosphoribosylaminoimidazole mutase PurE (TM0446) from *Thermotoga maritima* at 1.77 A resolution" (2004) Proteins 55: 474-478 (pdb code: 1o4v).
Schwarzenbacher et al., "Crystals Structure of Uronate Isomerase (TM0064) From *Thermotoga maritima* at 2.85 A Resolution" Proteins: Struct, Funct & Bioinform (2003)53:142-145.
Seeman NC "From Genes to Machines: DNA Nanomechanical Devices" Trends in Biochemical Sciences (2005a)30:119-235.
Seeman NC "Structural DNA Nanotechnology: An Overview" Methods in Molecular Biology 303: Bionanotechnology Protocols, Editors, Sandra J. Rosenthal and David W. Wright, Humana Press, Totowa, NJ (2005b) pp. 143-166.
Shih et al., "1.7-kilobase single-stranded DNA that folds into a nanoscale octahedron" Nature (2004)427:618-621.
Siegele "Universal Stress Proteins in *Escherichia coli*" J Bacteriol (2005) 187:6253-6254.
Skerra et al., "Use of the Strep-tag and Streptavidin for Detection and Purification of Recombinant Proteins" *Meth. Enzymology* (2000)326:271-204.
Sleytr et al., "S Layers as Basic Building Block for a Molecular Construction Kit" (2008) FEBS J. 274:323-334.
Sligar et al., "Protein engineering for molecular electronics" Curr Opin Biotechnol (1992)3:388-393.
Smith et al., Surface Plasmon Resonance Imaging as a Tool to Monitor Biomolecular Interactions in an Array Based Format. Appl. Spectroscopy, 2003, 57, 320A-332A.
Soukka et al., "Utilization of Kinetically Enhanced Monovalent Binding Affinity by Immunoassays Based on Multivalent Nanoparticle-Antibody Bioconjugates" Anal Chem (2001) 73:2254-2260.
Sousa et al., "Structure of the universal stress protein of *Haemophilus influenzae*" Structure (2001)9:1135-1141.
Teplyakov et al., "Crystal structure of inorganic pyrophosphatase from *Thermus thermophilus*" (1994) Protein Sci. 3: 1098-1107 (pdb code: 2prd).
Wada et al., "Crystal Structure of IPP isomerase at P43212" Protein Data Bank, Code: 1VCG, Last Modified on Jul. 13, 2011 (www.rcsb.org/pdb/explore/explore.do?structureId=1vcg).
Weber et al., "Crystallographic and Thermodynamic Comparison of Natural and Synthetic Ligands Bound to Streptavidin" *J Amer Chem Soc* (1992)114:3197-3200.
Weber et al., "Structural Origins of High Affinity Biotin Binding to Streptavidin" *Science* (1989)243:85-88.
Weber et al., "Structure-Based Design of Synthetic Azobenzene Ligands for Streptavidin" *J Amer Chem Soc* (1994)116:2717-2724.
Weber S (1999) <//jcrystal.com/steffenweber/gallery/Fullerenes/Fullerenes.html>, pp. 1-4, accessed Sep. 25, 2012.
Whitesides et al., "Beyond molecules: Self-assembly of mesoscopic and macroscopic components" Proc Nat Acad Sci USA (2002)99:4769-4774.

Whitesides et al., "Molecular Self Assembly and Nanochemistry: A chemical strategy for the synthesis for the synthesis of nanostructures" (1991) Science 254, 1312-1319.
Xia et al., "Soft Lithography" (1998) Annu. Rev. Mater. Sci. 28, 153-184.
Zaks et al., "Enzymatic catalysis in nonaqueous solvents" J Biol Chem (1988)263:3194-3201.
Zarembinski et al., "Structure-based assignment of the biochemical function of a hypothetical protein: A test case of structural genomics" Proc Natl Acad Sci USA (1998)95:15189-15193.
Zhu et al., "Crystal Structure of Tt0030 from *Thermus thermophilus*" Protein Data Bank, Code: 2IEL, Last Modified on Feb. 24, 2007 (www.rcsb.org/pdb/explore/explore.do?structureId=2iel).
Restriction Requirement issued in U.S. Appl. No. 12/589,529 dated Jul. 26, 2011.
Restriction Requirement issued in U.S. Appl. No. 12/766,658 dated Jul. 31, 2012.
Dotan et al., "Self-Assembly of a Tetrahedral Lectin into Predesigned Diamondlike Protein Crystals," Angewwandte Chemie International Edition, vol. 38, Iss. 16, pp. 2363-2366 (1999) and online abstract at /www3.interscience.wiley.com/cgi-bin/abstract/63001579/ABSTRACT accessed Jul. 29, 2005.
Livnah et al., "Three-dimensional structures of avidin and the avidin-biotin complex," Proc. Natl. Acad. Sci. USA, vol. 90, pp. 5076-5080 (1993).
Restriction Requirement issued in U.S. Appl. No. 13/319,989 dated May 17, 2013.
Restriction Requirement issued in U.S. Appl. No. 13/319,989 dated Nov. 21, 2013.
Ringler et al., "Self-Assembly of Proteins into Designed Networks", Science, 302 (2003) 106-109: Supporting Online Material, 8 pages.
Halford, "Catalyst Goes Viral", Chemical & Engineering News, (Jun. 14, 2010) 13.
Adams et al., "Structure and properties of the atypical iron superoxide dismutase from *Methanobacterium thermoautotrophicum*", Protein Data Bank Entry 1MA1, accessed from the Internet on Aug. 9, 2014, www.rcsb.org/pdb/explore/explore.do?structureId=1ma1.
Alber et al., "Kinetic and Spectroscopic Characterization of the Gamma-Carbonic Anhydrase from the Methanoarchaeon Methanosarcina thermophile" Biochemistry (1999)38:13119-13128.
Allert et al., "Computational design of receptors for an organophosphate surrogate of the nerve agent soman" Proc Natl Acad Sci USA (2004)101:7907-7912.
Asada et al., "Crystal structure of inosine-5'-monophosphate dehydrogenase from *Pyrococcus horikoshii* OT3", Protein Data Bank Entry 2CU0, accessed from the Internet on Aug. 10, 2014, www.rcsb.org/pdb/explore/explore.do?structureId=2cu0.
Ashwell et al., Uronic Acid Metabolism in Bacteria I. Purification and Properties of Uronic Acid Isomerase in *Escherichia coli* J Biol Chem (1960)235:1559-1565.
Barat et al., "Metabolic biotinylation of recombinant antibody by biotin ligase retained in the endoplasmic reticulum" Biomol Eng (2007)24:283-291.
Biteau et al., "ATP-dependent reduction of cysteine-sulfinic acid by *S. cerevisiae* sulphlredoxin" Nature (2003)425:980-984.
Carvalho-Alves et al., "Stoichiometric Photolabeling of Two Distinct Low and High Affinity nucleotide Sites in Sarcoplasmic Reticulum ATPase" J Biol Chem (1985) 260:4282-4287.
Chapman-Smith et al., "Molecular Biology of biotin attachment to proteins" J Nutr (1999)129:477S-484S.
Collins et al., "Crystals structure of a heptameric Sm-like protein complex from archea: Implications for the structure and evolution of snRNPs" J Mol Biol (2001) 309:915-923.
Cornell et al., "A Second Generation Force Field for the Simulation of Proteins, Nucleic Acids, and Organic Molecules" J Am Chem Soc (1995) 117:5179-5197.
Das et al., "Macromolecular Modeling with Rosetta" Annu Rev Biochem (2008) 77:363-382.
Ebihara et al., "Structure-based functional identification of a novel heme-binding protein from *Thermus thermophilus* HBB" J Struct Funct Genom (2005) 6:21-32.

(56) References Cited

OTHER PUBLICATIONS

Ermolova et al., "Site-Directed Alkylation of Cysteine Replacements in the Lactose Permease of *Escherichia coli*: Helices I, II, VI, and XI" Biochemistry (2006) 45:4182-4189.

Faust et al., "Synthesis of a Protein-reactive ATP analog and Its Application for the Affinity Labeling of Rabbit-Muscle Actin" Eur J Biochem (1974) 43:273-279.

Finzel et al., "Molecular Modeling with Substructure Libraries Derived from Known Protein Structures" In Crystallographic and Modeling Methods in Molecular Design (S Ealick & C Bugg eds.) Springer Verlag, New York (1990) pp. 175-189.

Ge et al., "Enzyme-Based CO2 Capture for Advanced Life Support" Life Support & Biosphere Science (2002) 8:181-189.

Green NM "A Spectrophotometric Assay for Avidin and Biotin Based on Binding of Dyes by Avidin" Biochem. J (1965) 94:23c-24c.

Guex N "Swiss-PdbViewer: A new fast and easy to use PDB viewer for the Macintosh" Experientia (1996) 52:A26.

Guex et al., "Protein Modelling for All" Trends Biochem Sci (1999) 24:364-367.

Hernandez et al., "Dynamic Protein Complexes: Insights from Mass Spectrometry" J Biol Chem (2001) 276:46685-46688.

Holmberg et al., "The biotin-streptavidin interaction can be reversibly broken using water at elevated temperatures" Electrophoresis (2005) 26:501-10.

Horlick et al., "Permuteins of interleukin 1β: A simplified approach for the construction of permuted proteins having new termini" Prot Eng (1992) 5:427-431.

Horovitz et al., "An accurate method for determination of receptor-ligand and enzyme-inhibitor dissociation constants from displacement curves" Proc Natl Acad Sci USA (1987) 84:6654-6658.

Jacobson et al., "ATP binding to a protease-resistant core of actin" Proc Nat Acad Sci (1976) 73:2742-2746.

Jaenicke R "Stability and folding of ultrastable proteins: eye lens crystallins and enzymes from thermophiles" FASEB J (1996) 10:84-92.

Jeyakanthan et al., "Observation of a calcium-binding site in the gamma-class carbonic anhydrase from *Pyrococcus horikoshii*" Acta Cryst D (2008)64:1012-1019 (pdb code: 1v3w).

Kay et al., "High Throughput Biotinylation of Proteins" Meth Mol Biol (2009)498:185-198.

Khalifah RG "Carbon dioxide hydration activity of carbonic anhydrase. I. Stop-flow kinetic studies on the native human isoenzymes B and C" J Biol Chem (1971) 246:2561-2573.

Kirk et al., "Optimising the recovery of recombinant thermostable proteins expressed in mesophilic hosts" J Biotechnol (1995) 42:177-84.

Krishnaswamy et al., "Free energies of protein-protein association determined by electrospray ionization mass spectrometry correlate accurately with values obtained by solution methods" Protein Sci (2006) 15:1465-1475.

Kumar et al., "Factors enhancing protein thermostability" Prot Eng (2000) 13:179-191.

Kurzban et al., "The Quaternary Structure of Streptavidin in Urea" J Biol Chem (1991) 266:14470-14477.

Lepock et al., "Contribution of Conformational Stability and Reversibility of Unfolding to the Increased Thermostability of Human and Bovine Superoxide Dismutase Mutated at Free Cysteines" J Biol Chem (1990) 265:21612-21618.

Maren TH, "A simplified micromethod for the determination of carbonic anhydrase and its inhibitors" J Pharmacol Exp Ther (1960) 130:26-29.

Matulis et al., "Thermodynamic Stability of Carbonic Anhydrase: Measurements of Binding Affinity and Stoichiometry Using ThermoFluor" Biochemistry (2005) 44:5258-66.

Merrifield RB "Solid Phase peptide Synthesis. I. The Synthesis of a Tetrapeptide" J Am Chem Soc (1963) 85:2149-2154.

Mohan et al., "Continuum model calculations of solvation energies: Accurate evaluation of electrostatic contributions" J Phys Chem (1992) 96:6428-36.

Mohan et al., "Docking: Successes and Challenges" Curr Pharmaceutical Design (2005) 11:323-333.

Neves-Peterse et al., "Photonic activation of disulfide bridges achieves oriented protein immobilization on biosensor surfaces" Prot Sci (2006) 15:343-351.

Pantazatos et al., "Rapid refinement of crystallographic protein construct definition employing enhanced hydrogen/deuterium exchange MS" Proc Natl Acad Sci USA (2004) 101:751-756.

Potier et al., "Using nondenaturing mass spectrometry to detect fortuitous ligands in orphan nuclear receptors" Protein Sci (2003) 12:725-733.

Repo et al., "Binding properties of HABA-type azo derivatives to avidin and avidin-related protein 4" Chem Biol (2006) 13:1029-1039.

Riddles et al., "Reassessment of Ellman's Reagent" Meth Enzymol (1983) 91:49-60.

Salemme FR "Cooperative motion and hydrogen exchange stability in protein β-sheets", Nature (1982) 299:754-756.

Sano et al., "Cooperative Biotin Binding by Streptavidin Electrophoretic Behavior and Subunit Association of Streptavidin in the Presence of 6M Urea" J Biol Chem (1990) 265:3369-3373.

Sano et al., "Expression of a cloned streptavidin gene in *Escherichia coli*" Proc Natl Acad Sci USA (1990) 87:142-146.

Sano et al., "Recombinant Core Streptavidins a Minimum-sized Core Streptavidin has Enhanced Structural Stability and Higher Accessibility to Biotinylated Macromolecules" J Biol Chem (1995) 270:28204-28209.

Sasaki et al., "Two-dimensional arrangement of a functional protein by cysteine-gold interaction: enzyme activity and characterization of a protein monolayer on a gold substrate" Biophysical Journal (1997) 72:1842-1848.

Shimkus et al., "A chemically cleavable biotinylated nucleotide: Usefulness in the recovery of protein-DNA complexes from avidin affinity columns" Proc Natl Acad Sci USA (1985) 82:2593-2597.

Sorensen et al., "Production of recombinant thermostable proteins expressed in *Escherichia coli*: completion of protein synthesis is the bottleneck" J Chromatogr B Analyt Technol Biomed Life Sci (2003) 786:207-214.

Spraggon et al., "On the use of DXMS to produce more crystallizable proteins: Structures of the T. maritima proteins TM0160 and TM1171" Prot Sci (2004) 13:3187-3199.

Spura et al., "Biotinylation of Substituted Cysteines in the Nicotinic Acetylcholine Receptor Reveals Distinct Binding Modes for a-Bungarotoxin and Erabutoxin" J Biol Chem (2000) 275:22452-22460.

Suter "Isolation and Characterization of Highly Purified Streptavidin Obtained in a Two-Step Purification Procedure from *Streptomyces avidinii* Grown in a Synthetic Medium" J Immunol Meth (1988) 113:83-91.

Taremi et al., "Construction and Expression of a Novel Fully Activated Recombinant Single-chain Hepatitis C Virus Protease" Prot Sci (1998) 7:2143-2149.

Thompson LD, Weber PC "Expression of Streptavidin from a Synthetic Gene" Gene (1993)136:243-6.

Waner et al., "Thermal and Sodium Dodecylsulfate Induced Transitions of Streptavidin" Biophys J (2004) 87:2701-2713.

Wasserman et al., "A Molecular Dynamics Investigation of the Elastomeric Restoring Force in Elastin" Biopolymers (1990) 29:1613-1631.

Wendoloski et al., "Molecular Dynamics Simulation of a Phospholipid Micelle" Science (1989) 243:636-638.

Wendoloski et al., "PROBIT: A Statistical Approach to Modeling Proteins from Partial Coordinate Data Using Substructure Libraries" J Mol Graphics (1992)10:124-126.

Woo et al., Reversing the inactivation of peroxlredoxins caused by cysteine sulfinic acid formation Science (2003) 300:653-658.

Wu et al., "Engineering Soluble Monomeric Streptavidin with Reversible Biotin Binding Capability" J Biol Chem (2005) 280:23225-23231.

Wu et al., "Binding of ATP to brain glutamate decarboxylase as studied by affinity chromatography" J Neurochem (1984) 42:1607-1612.

(56) References Cited

OTHER PUBLICATIONS

Yamashita et al., "Type 2 isopentenyl diphosphate isomerase from a thermoacidophilic archaeon Sulfolobus Shibatae" Eur J Biochem (2004) 271:1087-1093.

Yu et al., "Crystal structures of catalytic complexes of the Fe(II)-oxoglutarate-dependent DNA repair enzyme AlkB give insight into promiscuous substrate recognition and oxidation chemistry" Nature (2006) 439:879-884.

Zhang et al., "Determination of amide hydrogen exchange by mass spectrometry: a new tool for protein structure elucidation" Prot Sci (1993) 2:522-531.

Zimmerman et al., "Characterization of CamH from *Methanosarcina thermophila*, founding member of a subclass of the gamma class of carbonic anhydrases" J Bacteriol (2010) 192:1353-1360.

Zofall et al., "Two novel dATP analogs for DNA photoaffinity labeling" Nuc Acids Res (2000) 28:4382-4390.

Cloutier et al., "Streptabody, a highly avidity molecule made by tetramerization of in vivo biotinylated, a phage display-selected scFv fragments on streptavidin," Molecular Immunology 37: 1067-1077 (2000).

Drexler (ed.) et al., "Productive Nanosystems: A Technology Roadmap 2007", Battelle Memorial Institute and Foresight Nanotech Institute, 2007.

Filing Receipt in U.S. Appl. No. 13/398,820 dated Mar. 1, 2012.
Notice of Allowance issued in U.S. Appl. No. 12/766,658 dated Dec. 19, 2014.
Notice of Allowance issued in U.S. Appl. No. 12/766,658 dated Jul. 31, 2014.
Notice of Allowance issued in U.S. Appl. No. 12/766,658 dated Mar. 14, 2014.
Notice of Allowance issued in U.S. Appl. No. 12/766,658 dated Nov. 6, 2014.
Office Action issued in U.S. Appl. No. 12/766,658 dated Jan. 4, 2013.
Office Action issued in U.S. Appl. No. 12/766,658 dated Sep. 19, 2013.
Office Action issued in U.S. Appl. No. 13/319,989 dated Jun. 2, 2014.
Peel et al., "Short Communications : Inactivation by Substrate plus Oxygen of the Pyruvate Dehydrogenase of a Strictly Anaerobic Bacterium", Biochem. J. (1965) 94:21c-22c.
Restriction Requirement in U.S. Appl. No. 13/797,283 dated May 15, 2014.
Restriction Requirement in U.S. Appl. No. 13/797,283 dated Oct. 16, 2014.
Schaffer et al., "The structure of secondary cell wall polymers: how Gram-positive bacteria stick their cell walls together," Microbiology (2005), 151, 643-651.
Sletyr et al., "S-layers as a basic building block in a molecular construction kit," 2007, FEBS Journal, vol. 274, pp. 323-334.
Office Action issued in U.S. Appl. No. 13/319,989 dated Feb. 5, 2015.
U.S. Appl. No. 13/398,820: Restriction Requirement mailed Apr. 10, 2015.

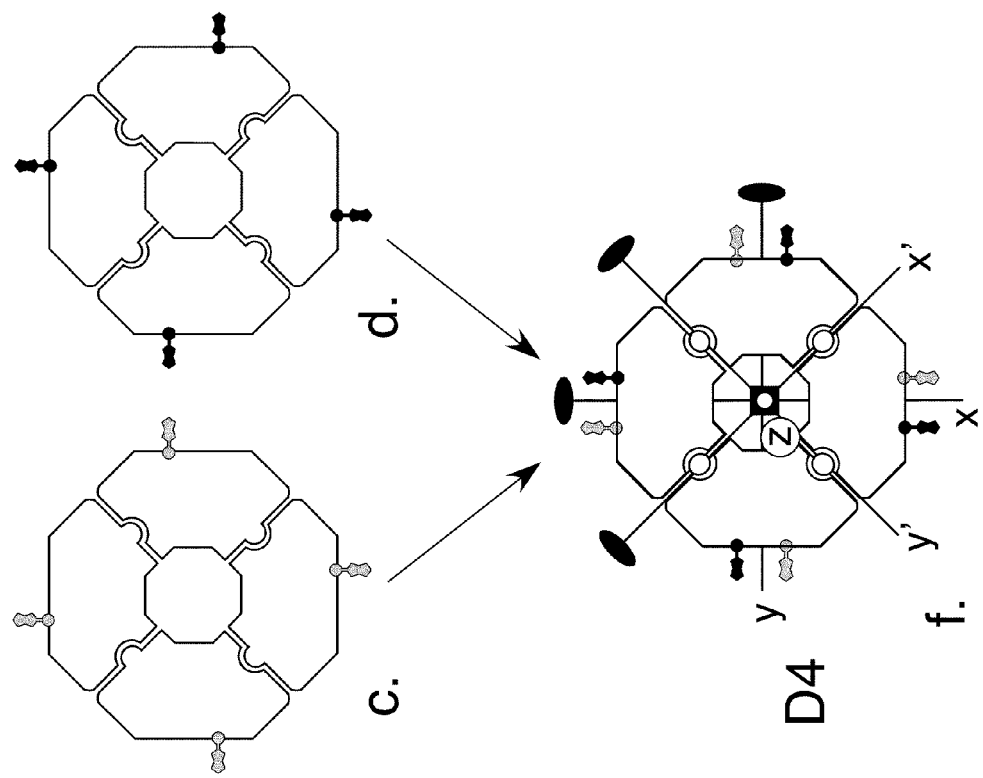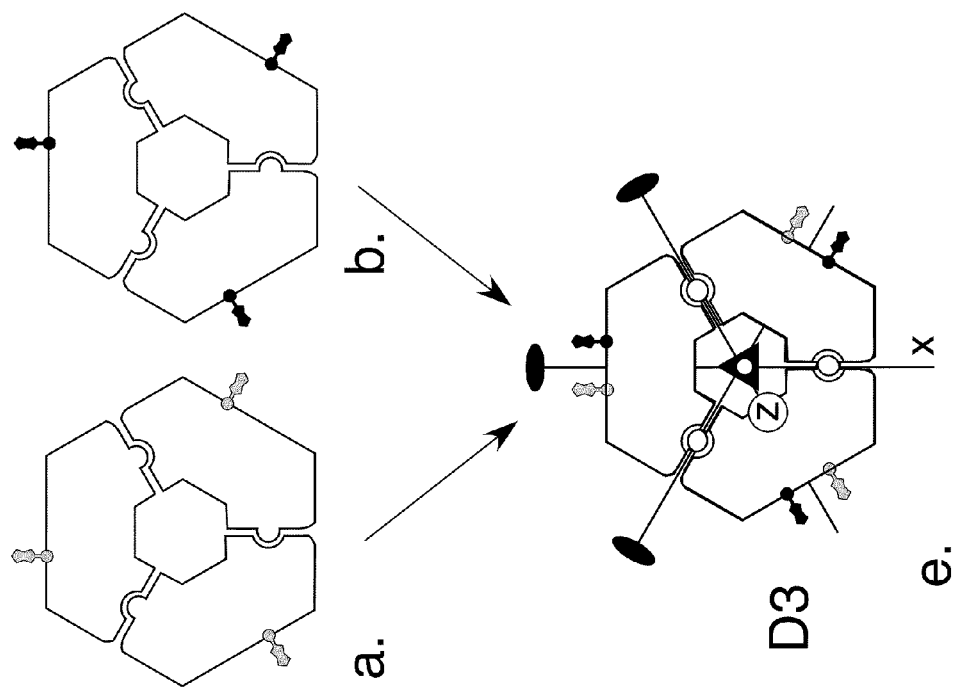
Fig. 15

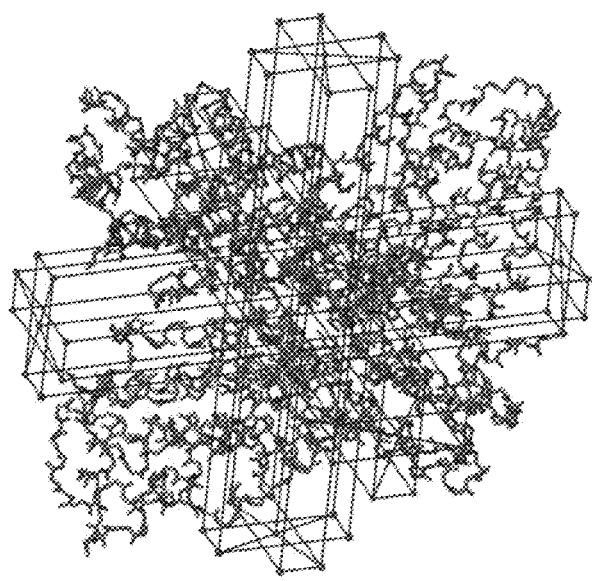
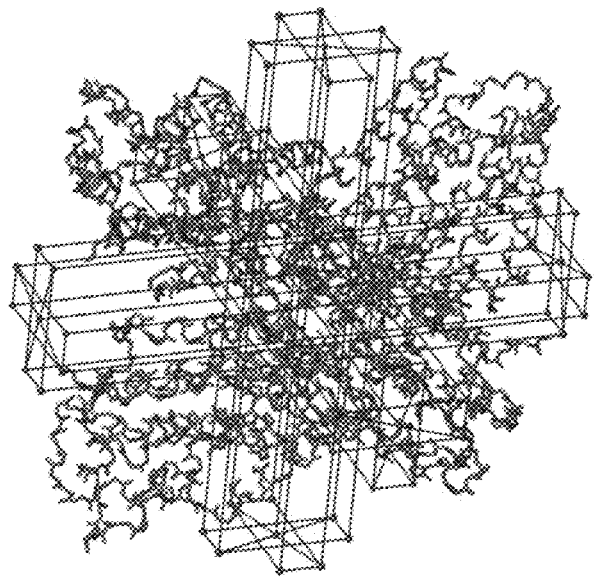
pdb code:1rtw
D2
Fig 23.

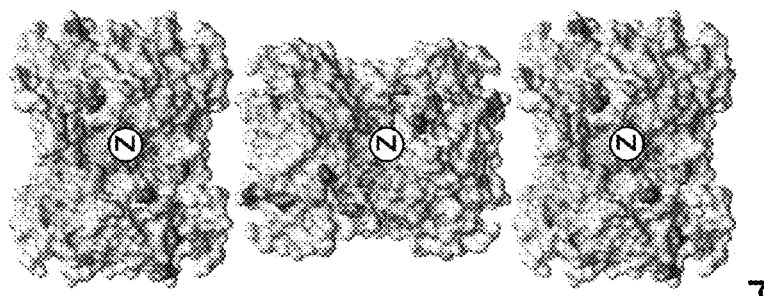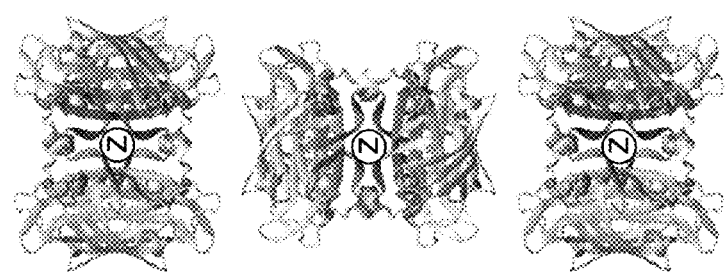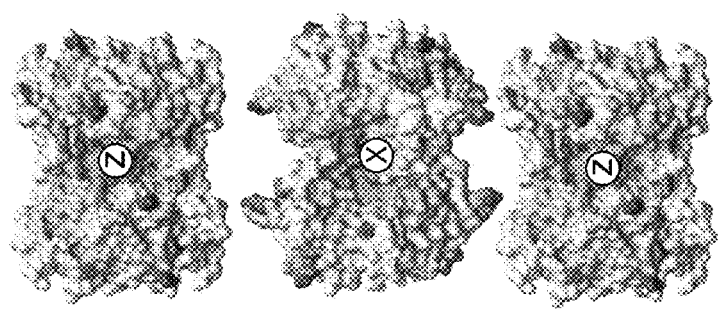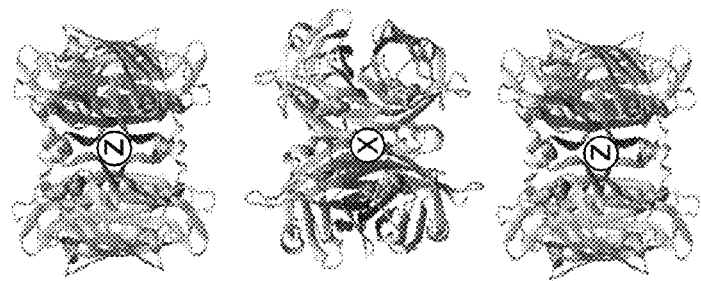
Fig 28.

Electrophoretic analyses of (4-Fold NODE):SAV complexes.

SEQUENCE LISTING

<160> NUMBER OF SEQ ID NOS: 251

<210> SEQ ID NO 1
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

```
Met Gln Glu Ile Thr Val Asp Glu Phe Ser Asn Ile Arg Glu Asn Pro
1               5                   10                  15

Val Thr Pro Trp Asn Pro Glu Pro Ser Ala Pro Val Ile Asp Pro Thr
            20                  25                  30

Ala Tyr Ile Asp Pro Glu Ala Ser Val Ile Gly Glu Val Thr Ile Gly
        35                  40                  45

Ala Asn Val Met Val Ser Pro Met Ala Ser Ile Arg Ser Asp Glu Gly
    50                  55                  60

Met Pro Ile Phe Val Gly Asp Arg Ser Asn Val Gln Asp Gly Val Val
65                  70                  75                  80

Leu His Ala Leu Glu Thr Ile Asn Glu Glu Gly Glu Pro Ile Glu Asp
                85                  90                  95

Asn Ile Val Glu Val Asp Gly Lys Glu Tyr Ala Val Tyr Ile Gly Asn
                100                 105                 110

Asn Val Ser Leu Ala His Gln Ser Gln Val His Gly Pro Ala Ala Val
            115                 120                 125

Gly Asp Asp Thr Phe Ile Gly Met Gln Ala Phe Val Phe Lys Ser Lys
        130                 135                 140

Val Gly Asn Asn Cys Val Leu Glu Pro Arg Ser Ala Ala Ile Gly Val
145                 150                 155                 160

Thr Ile Pro Asp Gly Arg Tyr Ile Pro Ala Gly Met Val Val Thr Ser
                165                 170                 175
```

```
Gln Ala Glu Ala Asp Lys Leu Pro Glu Val Thr Asp Tyr Ala Tyr
            180                 185                 190

Ser His Thr Asn Glu Ala Val Val Tyr Val Asn Val His Leu Ala Glu
            195                 200                 205

Gly Tyr Lys Glu Thr Ser
        210

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Gln Glu Ile Thr Val Asp Glu Phe Ser Asn Ile Arg Glu Asn Pro
1               5                   10                  15

Val Thr Pro Trp Asn Pro Glu Pro Ser Ala Pro Val Ile Asp Pro Thr
            20                  25                  30

Ala Tyr Ile Asp Pro Glu Ala Ser Val Ile Gly Glu Val Thr Ile Gly
        35                  40                  45

Ala Asn Val Met Val Ser Pro Met Ala Ser Ile Arg Ser Asp Glu Gly
    50                  55                  60

Met Pro Ile Phe Val Gly Asp Arg Ser Asn Val Gln Asp Gly Val Val
65                  70                  75                  80

Leu His Ala Leu Glu Thr Ile Asn Glu Glu Gly Glu Pro Ile Glu Asp
                85                  90                  95

Asn Ile Val Glu Val Asp Gly Lys Glu Tyr Ala Val Tyr Ile Gly Asn
            100                 105                 110

Asn Val Ser Leu Ala His Gln Ser Gln Val His Gly Pro Ala Ala Val
        115                 120                 125

Gly Asp Asp Thr Phe Ile Gly Met Gln Ala Phe Val Phe Lys Ser Lys
    130                 135                 140

Val Gly Asn Asn Cys Val Leu Glu Pro Arg Ser Ala Ala Ile Gly Val
145                 150                 155                 160

Thr Ile Pro Asp Gly Arg Tyr Ile Pro Ala Gly Met Val Val Thr Ser
                165                 170                 175

Gln Ala Glu Ala Asp Lys Leu Pro Glu Val Thr Asp Tyr Ala Tyr
            180                 185                 190

Ser His Thr Asn Glu Ala Val Val Tyr Val Asn Val His Leu Ala Glu
            195                 200                 205

Gly Tyr Lys Glu Thr Ser
        210

<210> SEQ ID NO 3
<211> LENGTH: 207
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Glu Phe Ser Asn Ile Arg Glu Asn Pro Val Thr Pro Trp Asn Pro
1               5                   10                  15

Glu Pro Ser Ala Pro Val Ile Asp Pro Thr Ala Tyr Ile Asp Pro Glu
            20                  25                  30
```

```
Ala Ser Val Ile Gly Glu Val Thr Ile Gly Ala Asn Val Met Val Ser
        35                  40                  45
Pro Met Ala Ser Ile Arg Ser Asp Glu Gly Met Pro Ile Phe Val Gly
 50                  55                  60
Asp Arg Ser Asn Val Gln Asp Gly Val Val Leu His Ala Leu Glu Thr
 65                  70                  75                  80
Ile Asn Glu Glu Gly Glu Pro Ile Glu Asp Asn Ile Val Glu Val Asp
                85                  90                  95
Gly Lys Glu Tyr Ala Val Tyr Ile Gly Asn Asn Val Ser Leu Ala His
            100                 105                 110
Gln Ser Gln Val His Gly Pro Ala Val Gly Asp Asp Thr Phe Ile
            115                 120                 125
Gly Met Gln Ala Phe Val Phe Lys Ser Lys Val Gly Asn Asn Cys Val
        130                 135                 140
Leu Glu Pro Arg Ser Ala Ala Ile Gly Val Thr Ile Pro Asp Gly Arg
145                 150                 155                 160
Tyr Ile Pro Ala Gly Met Val Val Thr Ser Gln Ala Glu Ala Asp Lys
                165                 170                 175
Leu Pro Val Thr Asp Asp Tyr Ala Tyr Ser His Thr Asn Glu Ala
            180                 185                 190
Val Val Tyr Val Asn Val His Leu Ala Glu Gly Tyr Lys Gln Thr
        195                 200                 205

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Gly Ser Gly Gly Gly
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Ser Gly Gly Gly Gly
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Gln Glu Ile Thr Val
1               5

<210> SEQ ID NO 7
<211> LENGTH: 463
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7
```

| | | | | | | | | | | | | | | |
|---|---|---|---|---|---|---|---|---|---|---|---|---|---|---|
| Met | Gly | Ser | Asp | Lys | Ile | His | His | His | His | His | Met | Phe | Leu | Gly |
| 1 | | | | 5 | | | | | 10 | | | | | 15 |
| Glu | Asp | Tyr | Leu | Leu | Thr | Asn | Arg | Ala | Ala | Val | Arg | Leu | Phe | Asn | Glu |
| | | | 20 | | | | | 25 | | | | | 30 | | |
| Val | Lys | Asp | Leu | Pro | Ile | Val | Asp | Pro | His | Asn | His | Leu | Asp | Ala | Lys |
| | | | 35 | | | | | 40 | | | | | 45 | | |
| Asp | Ile | Val | Glu | Asn | Lys | Pro | Trp | Asn | Asp | Ile | Trp | Glu | Val | Glu | Gly |
| | 50 | | | | | 55 | | | | | 60 | | | | |
| Ala | Thr | Asp | His | Tyr | Val | Trp | Glu | Leu | Met | Arg | Arg | Cys | Gly | Val | Ser |
| 65 | | | | | 70 | | | | | 75 | | | | | 80 |
| Glu | Glu | Tyr | Ile | Thr | Gly | Ser | Arg | Ser | Asn | Lys | Glu | Lys | Trp | Leu | Ala |
| | | | | 85 | | | | | 90 | | | | | 95 | |
| Leu | Ala | Lys | Val | Phe | Pro | Arg | Phe | Val | Gly | Asn | Pro | Thr | Tyr | Glu | Trp |
| | | | 100 | | | | | 105 | | | | | 110 | | |
| Ile | His | Leu | Asp | Leu | Trp | Arg | Phe | Asn | Ile | Lys | Lys | Val | Ile | Ser |
| | | 115 | | | | | 120 | | | | | 125 | | |
| Glu | Glu | Thr | Ala | Glu | Ile | Trp | Glu | Glu | Thr | Lys | Lys | Lys | Leu | Pro |
| | | 130 | | | | | 135 | | | | | 140 | | |
| Glu | Met | Thr | Pro | Gln | Lys | Leu | Leu | Arg | Asp | Met | Lys | Val | Glu | Ile | Leu |
| 145 | | | | | 150 | | | | | 155 | | | | | 160 |
| Cys | Thr | Thr | Asp | Asp | Pro | Val | Ser | Thr | Leu | Glu | His | His | Arg | Lys | Ala |
| | | | 165 | | | | | 170 | | | | | 175 | | |
| Lys | Glu | Ala | Val | Glu | Gly | Val | Thr | Ile | Leu | Pro | Thr | Trp | Arg | Pro | Asp |
| | | | 180 | | | | | 185 | | | | | 190 | | |
| Arg | Ala | Met | Asn | Val | Asp | Lys | Glu | Gly | Trp | Arg | Glu | Tyr | Val | Glu | Lys |
| | | | 195 | | | | | 200 | | | | | 205 | | |
| Met | Gly | Glu | Arg | Tyr | Gly | Glu | Asp | Thr | Ser | Thr | Leu | Asp | Gly | Phe | Leu |
| | | 210 | | | | | 215 | | | | | 220 | | | |
| Asn | Ala | Leu | Trp | Lys | Ser | His | Glu | His | Phe | Lys | Glu | His | Gly | Cys | Val |
| 225 | | | | | 230 | | | | | 235 | | | | | 240 |
| Ala | Ser | Asp | His | Ala | Leu | Leu | Glu | Pro | Ser | Val | Tyr | Tyr | Val | Asp | Glu |
| | | | 245 | | | | | 250 | | | | | 255 | | |
| Asn | Arg | Ala | Arg | Ala | Val | His | Gly | Lys | Ala | Phe | Ser | Gly | Glu | Lys | Leu |
| | | | 260 | | | | | 265 | | | | | 270 | | |
| Thr | Gln | Asp | Glu | Ile | Asn | Asp | Tyr | Lys | Ala | Phe | Met | Met | Val | Gln | Phe |
| | | 275 | | | | | 280 | | | | | 285 | | | |
| Gly | Lys | Met | Asn | Gln | Glu | Thr | Asn | Trp | Val | Thr | Gln | Leu | His | Ile | Gly |
| | | 290 | | | | | 295 | | | | | 300 | | | |
| Ala | Leu | Arg | Asp | Tyr | Arg | Asp | Ser | Leu | Phe | Lys | Thr | Leu | Gly | Pro | Asp |
| 305 | | | | | 310 | | | | | 315 | | | | | 320 |
| Ser | Gly | Gly | Asp | Ile | Ser | Thr | Asn | Phe | Leu | Arg | Ile | Ala | Glu | Gly | Leu |
| | | | 325 | | | | | 330 | | | | | 335 | | |
| Arg | Tyr | Phe | Leu | Asn | Glu | Phe | Asp | Gly | Lys | Leu | Lys | Ile | Val | Leu | Tyr |
| | | | 340 | | | | | 345 | | | | | 350 | | |
| Val | Leu | Asp | Pro | Thr | His | Leu | Pro | Thr | Ile | Ser | Thr | Ile | Ala | Arg | Ala |
| | | 355 | | | | | 360 | | | | | 365 | | | |
| Phe | Pro | Asn | Val | Tyr | Val | Gly | Ala | Pro | Trp | Trp | Phe | Asn | Asp | Ser | Pro |
| | | 370 | | | | | 375 | | | | | 380 | | | |

```
Phe Gly Met Glu Met His Leu Lys Tyr Leu Ala Ser Val Asp Leu Leu
385                 390                 395                 400

Tyr Asn Leu Ala Gly Met Val Thr Asp Ser Arg Lys Leu Leu Ser Phe
                405                 410                 415

Gly Ser Arg Thr Glu Met Phe Arg Arg Val Leu Ser Asn Val Val Gly
            420                 425                 430

Glu Met Val Glu Lys Gly Gln Ile Pro Ile Lys Glu Ala Arg Glu Leu
        435                 440                 445

Val Lys His Val Ser Tyr Asp Gly Pro Lys Ala Leu Phe Phe Gly
    450                 455                 460

<210> SEQ ID NO 8
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Met Ile Glu Pro Lys Glu Lys Ala Ser Ile Gly Ile Ile Gly Gly
1               5                   10                  15

Ser Gly Leu Tyr Asp Pro Gln Ile Leu Thr Asn Val Lys Glu Ile Lys
            20                  25                  30

Val Tyr Thr Pro Tyr Gly Pro Ser Asp Asn Ile Ile Leu Gly Glu
        35                  40                  45

Leu Glu Gly Arg Lys Val Ala Phe Leu Pro Arg His Gly Arg Gly His
50                  55                  60

Arg Ile Pro Pro His Lys Ile Asn Tyr Arg Ala Asn Ile Trp Ala Leu
65                  70                  75                  80

Lys Ser Leu Gly Val Lys Trp Val Ile Ala Val Ser Ala Val Gly Ser
                85                  90                  95

Leu Arg Leu Asp Tyr Lys Pro Gly Asp Phe Val Val Pro Asn Gln Phe
            100                 105                 110

Ile Asp Met Thr Lys Gly Arg Thr Tyr Thr Phe Phe Asp Gly Pro Thr
        115                 120                 125

Val Ala His Val Ser Met Ala Asp Pro Phe Cys Glu His Leu Arg Ser
130                 135                 140

Ile Ile Leu Asp Ser Ala Lys Asp Leu Gly Ile Thr Thr His Asp Lys
145                 150                 155                 160

Gly Thr Tyr Ile Cys Ile Glu Gly Pro Arg Phe Ser Thr Arg Ala Glu
                165                 170                 175

Ser Ile Val Trp Lys Glu Val Phe Lys Ala Asp Ile Ile Gly Met Thr
            180                 185                 190

Leu Val Pro Glu Val Asn Leu Ala Cys Glu Ala Glu Met Cys Tyr Ser
        195                 200                 205

Val Ile Gly Met Val Thr Asp Tyr Asp Val Phe Ala Asp Ile Pro Val
    210                 215                 220

Thr Ala Glu Glu Val Thr Lys Val Met Ala Glu Asn Thr Ala Lys Val
225                 230                 235                 240

Lys Lys Leu Leu Tyr Glu Val Ile Arg Arg Leu Pro Glu Lys Pro Asp
                245                 250                 255

Glu Arg Lys Cys Ser Cys Cys Gln Ala Leu Lys Thr Ala Leu Val Leu
            260                 265                 270

Glu His His His His His His His His
```

```
                275                 280

<210> SEQ ID NO 9
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Asn Ile Arg Glu Arg Lys Arg Lys His Leu Glu Ala Cys Leu Glu
1               5                   10                  15

Gly Glu Val Ala Tyr Gln Lys Thr Thr Thr Gly Leu Glu Gly Phe Arg
            20                  25                  30

Leu Arg Tyr Gln Ala Leu Ala Gly Leu Ala Leu Ser Glu Val Asp Leu
        35                  40                  45

Thr Thr Pro Phe Leu Gly Lys Thr Leu Lys Ala Pro Phe Leu Ile Gly
    50                  55                  60

Ala Met Thr Gly Gly Glu Asn Gly Glu Arg Ile Asn Leu Ala Leu
65                  70                  75                  80

Ala Glu Ala Ala Glu Ala Leu Gly Val Gly Met Met Leu Gly Ser Gly
                85                  90                  95

Arg Ile Leu Leu Glu Arg Pro Glu Ala Leu Arg Ser Phe Arg Val Arg
            100                 105                 110

Lys Val Ala Pro Lys Ala Leu Leu Ile Ala Asn Leu Gly Leu Ala Gln
        115                 120                 125

Leu Arg Arg Tyr Gly Arg Asp Asp Leu Leu Arg Leu Val Glu Met Leu
    130                 135                 140

Glu Ala Asp Ala Leu Ala Phe His Val Asn Pro Leu Gln Glu Ala Val
145                 150                 155                 160

Gln Arg Gly Asp Thr Asp Phe Arg Gly Leu Val Glu Arg Leu Ala Glu
                165                 170                 175

Leu Leu Pro Leu Pro Phe Pro Val Met Val Lys Glu Val Gly His Gly
            180                 185                 190

Leu Ser Arg Glu Ala Ala Leu Ala Leu Arg Asp Leu Pro Leu Ala Ala
        195                 200                 205

Val Asp Val Ala Gly Ala Gly Gly Thr Ser Trp Ala Arg Val Glu Glu
    210                 215                 220

Trp Val Arg Phe Gly Glu Val Arg His Pro Glu Leu Cys Glu Ile Gly
225                 230                 235                 240

Ile Pro Thr Ala Arg Ala Ile Leu Glu Val Arg Glu Val Leu Pro His
                245                 250                 255

Leu Pro Leu Val Ala Ser Gly Gly Val Tyr Thr Gly Thr Asp Gly Ala
            260                 265                 270

Lys Ala Leu Ala Leu Gly Ala Asp Leu Leu Ala Val Ala Arg Pro Leu
        275                 280                 285

Leu Arg Pro Ala Leu Glu Gly Ala Glu Arg Val Ala Ala Trp Ile Gly
    290                 295                 300

Asp Tyr Leu Glu Glu Leu Arg Thr Ala Leu Phe Ala Ile Gly Ala Arg
305                 310                 315                 320

Asn Pro Lys Glu Ala Arg Gly Arg Val Glu Arg Val
                325                 330

<210> SEQ ID NO 10
<211> LENGTH: 249
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Glu Arg His Val Pro Glu Pro Thr His Thr Leu Glu Gly Trp His
1               5                   10                  15

Val Leu His Asp Phe Arg Leu Leu Asp Phe Ala Arg Trp Phe Ser Ala
            20                  25                  30

Pro Leu Glu Ala Arg Glu Asp Ala Trp Glu Glu Leu Lys Gly Leu Val
        35                  40                  45

Arg Glu Trp Arg Glu Leu Glu Glu Ala Gly Gln Gly Ser Tyr Gly Ile
    50                  55                  60

Tyr Gln Val Val Gly His Lys Ala Asp Leu Leu Phe Leu Asn Leu Arg
65                  70                  75                  80

Pro Gly Leu Asp Pro Leu Leu Glu Ala Glu Ala Arg Leu Ser Arg Ser
                85                  90                  95

Ala Phe Ala Arg Tyr Leu Gly Arg Ser Tyr Ser Phe Tyr Ser Val Val
            100                 105                 110

Glu Leu Gly Ser Gln Glu Lys Pro Leu Asp Pro Glu Ser Pro Tyr Val
        115                 120                 125

Lys Pro Arg Leu Thr Pro Arg Val Pro Lys Ser Gly Tyr Val Cys Phe
130                 135                 140

Tyr Pro Met Asn Lys Arg Arg Gln Gly Gln Asp Asn Trp Tyr Met Leu
145                 150                 155                 160

Pro Ala Lys Glu Arg Ala Ser Leu Met Lys Ala His Gly Glu Thr Gly
                165                 170                 175

Arg Lys Tyr Gln Gly Glu Val Met Gln Val Ile Ser Gly Ala Gln Gly
            180                 185                 190

Leu Asp Asp Trp Glu Trp Gly Val Asp Leu Phe Ser Glu Asp Pro Val
        195                 200                 205

Gln Phe Lys Lys Ile Val Tyr Glu Met Arg Phe Asp Glu Val Ser Ala
    210                 215                 220

Arg Tyr Gly Glu Phe Gly Pro Phe Val Gly Lys Tyr Leu Asp Glu
225                 230                 235                 240

Glu Ala Leu Arg Ala Phe Leu Gly Leu
                245

<210> SEQ ID NO 11
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ser Ile Asp Ala Ala Lys
    130                 135                 140

Lys Ala Gly Val Asn Asn Gly Asn Pro Leu Asp Ala Val Gln Gln
145                 150                 155

<210> SEQ ID NO 12
<211> LENGTH: 205
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Asn Asp Leu Glu Lys Lys Phe Tyr Glu Leu Pro Glu Leu Pro Tyr
1               5                   10                  15

Pro Tyr Asp Ala Leu Glu Pro His Ile Ser Arg Glu Gln Leu Thr Ile
            20                  25                  30

His His Gln Lys His His Gln Ala Tyr Val Asp Gly Ala Asn Ala Leu
        35                  40                  45

Leu Arg Lys Leu Asp Glu Ala Arg Glu Ser Asp Thr Asp Val Asp Ile
50                  55                  60

Lys Ala Ala Leu Lys Glu Leu Ser Phe His Val Gly Gly Tyr Val Leu
65                  70                  75                  80

His Leu Phe Phe Trp Gly Asn Met Gly Pro Ala Asp Glu Cys Gly Gly
                85                  90                  95

Glu Pro Ser Gly Lys Leu Ala Glu Tyr Ile Glu Lys Asp Phe Gly Ser
            100                 105                 110

Phe Glu Arg Phe Arg Lys Glu Phe Ser Gln Ala Ala Ile Ser Ala Glu
        115                 120                 125

Gly Ser Gly Trp Ala Val Leu Thr Tyr Cys Gln Arg Thr Asp Arg Leu
    130                 135                 140

Phe Ile Met Gln Val Glu Lys His Asn Val Asn Val Ile Pro His Phe
145                 150                 155                 160

Arg Ile Leu Leu Val Leu Asp Val Trp Glu His Ala Tyr Tyr Ile Asp
                165                 170                 175

Tyr Arg Asn Val Arg Pro Asp Tyr Val Glu Ala Phe Trp Asn Ile Val
            180                 185                 190

Asn Trp Lys Glu Val Glu Lys Arg Phe Glu Asp Ile Leu
        195                 200                 205

<210> SEQ ID NO 13
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Met Arg Ala Val Arg Leu Val Glu Ile Gly Lys Pro Leu Ser Leu Gln
1               5                   10                  15

Glu Ile Gly Val Pro Lys Pro Lys Gly Pro Gln Val Leu Ile Lys Val
            20                  25                  30

Glu Ala Ala Gly Val Cys His Ser Asp Val His Met Arg Gln Gly Arg
        35                  40                  45

Phe Gly Asn Leu Arg Ile Val Glu Asp Leu Gly Val Lys Leu Pro Val
    50                  55                  60

Thr Leu Gly His Glu Ile Ala Gly Lys Ile Glu Val Gly Asp Glu
65                  70                  75                  80

Val Val Gly Tyr Ser Lys Gly Asp Leu Val Ala Val Asn Pro Trp Gln
                85                  90                  95

Gly Glu Gly Asn Cys Tyr Tyr Cys Arg Ile Gly Glu Glu His Leu Cys
            100                 105                 110

Asp Ser Pro Arg Trp Leu Gly Ile Asn Phe Asp Gly Ala Tyr Ala Glu
        115                 120                 125

Tyr Val Ile Val Pro His Tyr Lys Tyr Met Tyr Lys Leu Arg Arg Leu
    130                 135                 140

Asn Ala Val Glu Ala Ala Pro Leu Thr Cys Ser Gly Ile Thr Thr Tyr
145                 150                 155                 160

Arg Ala Val Arg Lys Ala Ser Leu Asp Pro Thr Lys Thr Leu Leu Val
                165                 170                 175

Val Gly Ala Gly Gly Gly Leu Gly Thr Met Ala Val Gln Ile Ala Lys
            180                 185                 190

Ala Val Ser Gly Ala Thr Ile Ile Gly Val Asp Val Arg Glu Glu Ala
        195                 200                 205

Val Glu Ala Ala Lys Arg Ala Gly Ala Asp Tyr Val Ile Asn Ala Ser
    210                 215                 220

Met Gln Asp Pro Leu Ala Glu Ile Arg Arg Ile Thr Glu Ser Lys Gly
225                 230                 235                 240

Val Asp Ala Val Ile Asp Leu Asn Tyr Ser Glu Lys Thr Leu Ser Val
                245                 250                 255

Tyr Pro Lys Ala Leu Ala Lys Gln Gly Lys Tyr Val Met Val Gly Leu
            260                 265                 270

Phe Gly Ala Asp Leu His Tyr His Ala Pro Leu Ile Thr Leu Ser Glu
        275                 280                 285

Ile Gln Phe Val Gly Ser Leu Val Gly Asn Gln Ser Asp Phe Leu Gly
    290                 295                 300

Ile Met Arg Leu Ala Glu Ala Gly Lys Val Lys Pro Met Ile Thr Lys
305                 310                 315                 320

Thr Met Lys Leu Glu Glu Ala Asn Glu Ala Ile Asp Asn Leu Glu Asn
                325                 330                 335

Phe Lys Ala Ile Gly Arg Gln Val Leu Ile Pro
            340                 345

<210> SEQ ID NO 14
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Phe Ser Glu Glu Leu Ile Lys Glu Asn Glu Asn Ile Trp Arg Arg
1               5                   10                  15
```

```
Phe Leu Pro His Lys Phe Leu Ile Glu Met Ala Glu Asn Thr Ile Lys
             20                  25                  30

Lys Glu Asn Phe Glu Lys Trp Leu Val Asn Asp Tyr Tyr Phe Val Lys
         35                  40                  45

Asn Ala Leu Arg Phe Met Ala Leu Leu Met Ala Lys Ala Pro Asp Asp
 50                  55                  60

Leu Leu Pro Phe Phe Ala Glu Ser Ile Tyr Tyr Ile Ser Lys Glu Leu
 65                  70                  75                  80

Glu Met Phe Glu Lys Lys Ala Gln Glu Leu Gly Ile Ser Leu Asn Gly
                 85                  90                  95

Glu Ile Asp Trp Arg Ala Lys Ser Tyr Val Asn Tyr Leu Leu Ser Val
            100                 105                 110

Ala Ser Leu Gly Ser Phe Leu Glu Gly Phe Thr Ala Leu Tyr Cys Glu
            115                 120                 125

Glu Lys Ala Tyr Tyr Glu Ala Trp Lys Trp Val Arg Glu Asn Leu Lys
130                 135                 140

Glu Arg Ser Pro Tyr Gln Glu Phe Ile Asn His Trp Ser Ser Gln Glu
145                 150                 155                 160

Phe Gly Glu Tyr Val Lys Arg Ile Glu Lys Ile Leu Asn Ser Leu Ala
                165                 170                 175

Glu Lys His Gly Glu Phe Glu Lys Glu Arg Ala Arg Glu Val Phe Lys
            180                 185                 190

Glu Val Ser Lys Phe Glu Leu Ile Phe Trp Asp Ile Ala Tyr Gly Gly
            195                 200                 205

Glu Gly Asn Val Leu Glu His His His His His
        210                 215                 220

<210> SEQ ID NO 15
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ala Leu Val Asp Val Phe Ile Lys Leu Asp Gly Thr Gly Asn Leu Leu
1               5                   10                  15

Val Leu Arg Thr Leu Pro Gly Asn Ala His Ala Ile Gly Val Leu Leu
             20                  25                  30

Asp Asn Leu Asp Trp Asp Glu Ile Val Gly Thr Ile Cys Gly Asp Asp
         35                  40                  45

Thr Cys Leu Ile Ile Cys Arg Thr Pro Lys Asp Ala Lys Lys Val Ser
 50                  55                  60

Asn Gln Leu Leu Ser Met Leu
 65                  70

<210> SEQ ID NO 16
<211> LENGTH: 181
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Met Thr Met Arg Gly Leu Leu Val Gly Arg Met Gln Pro Phe His
1               5                   10                  15
```

```
Arg Gly Ala Leu Gln Val Ile Lys Ser Ile Leu Glu Glu Val Asp Glu
         20                  25                  30

Leu Ile Ile Cys Ile Gly Ser Ala Gln Leu Ser His Ser Ile Arg Asp
             35                  40                  45

Pro Phe Thr Ala Gly Glu Arg Val Met Met Leu Thr Lys Ala Leu Ser
         50                  55                  60

Glu Asn Gly Ile Pro Ala Ser Arg Tyr Tyr Ile Ile Pro Val Gln Asp
65                  70                  75                  80

Ile Glu Cys Asn Ala Leu Trp Val Gly His Ile Lys Met Leu Thr Pro
                 85                  90                  95

Pro Phe Asp Arg Val Tyr Ser Gly Asn Pro Leu Val Gln Arg Leu Phe
            100                 105                 110

Ser Glu Asp Gly Tyr Glu Val Thr Ala Pro Pro Leu Phe Tyr Arg Asp
        115                 120                 125

Arg Tyr Ser Gly Thr Glu Val Arg Arg Met Leu Asp Asp Gly Asp
130                 135                 140

Trp Arg Ser Leu Leu Pro Glu Ser Val Val Glu Val Ile Asp Glu Ile
145                 150                 155                 160

Asn Gly Val Glu Arg Ile Lys His Leu Ala Lys Lys Glu Val Ser Glu
                165                 170                 175

Leu Gly Gly Ile Ser
            180

<210> SEQ ID NO 17
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Asn Leu Lys Ser Leu Pro Val Gly Asp Lys Ala Pro Glu Val Val
1               5                   10                  15

His Met Val Ile Glu Val Pro Arg Gly Ser Gly Asn Lys Tyr Glu Tyr
             20                  25                  30

Asp Pro Asp Leu Gly Ala Ile Lys Leu Asp Arg Val Leu Pro Gly Ala
         35                  40                  45

Gln Phe Tyr Pro Gly Asp Tyr Gly Phe Ile Pro Ser Thr Leu Ala Glu
     50                  55                  60

Asp Gly Asp Pro Leu Asp Gly Leu Val Leu Ser Thr Tyr Pro Leu Leu
65                  70                  75                  80

Pro Gly Val Val Glu Val Arg Val Val Gly Leu Leu Met Glu
                 85                  90                  95

Asp Glu Lys Gly Gly Asp Ala Lys Val Ile Gly Val Val Ala Glu Asp
                100                 105                 110

Gln Arg Leu Asp His Ile Gln Asp Ile Gly Asp Val Pro Glu Gly Val
            115                 120                 125

Lys Gln Glu Ile Gln His Phe Phe Glu Thr Tyr Lys Ala Leu Glu Ala
130                 135                 140

Lys Lys Gly Lys Trp Val Lys Val Thr Gly Trp Arg Asp Arg Lys Ala
145                 150                 155                 160

Ala Leu Glu Glu Val Arg Ala Cys Ile Ala Arg Tyr Lys Gly
                165                 170
```

<210> SEQ ID NO 18
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Gly Ser Asp Lys Ile His His His His His Val Pro Arg Val
1               5                   10                  15

Gly Ile Ile Met Gly Ser Asp Ser Asp Leu Pro Val Met Lys Gln Ala
            20                  25                  30

Ala Glu Ile Leu Glu Glu Phe Gly Ile Asp Tyr Glu Thr Ile Val
        35                  40                  45

Ser Ala His Arg Thr Pro Asp Arg Met Phe Glu Tyr Ala Lys Asn Ala
    50                  55                  60

Glu Glu Arg Gly Ile Glu Val Ile Ile Ala Gly Ala Gly Ala Ala
65                  70                  75                  80

His Leu Pro Gly Met Val Ala Ser Ile Thr His Leu Pro Val Ile Gly
                85                  90                  95

Val Pro Val Lys Thr Ser Thr Leu Asn Gly Leu Asp Ser Leu Phe Ser
            100                 105                 110

Ile Val Gln Met Pro Gly Gly Val Pro Val Ala Thr Val Ala Ile Asn
        115                 120                 125

Asn Ala Lys Asn Ala Gly Ile Leu Ala Ala Ser Ile Leu Gly Ile Lys
    130                 135                 140

Tyr Pro Glu Ile Ala Arg Lys Val Lys Glu Tyr Lys Glu Arg Met Lys
145                 150                 155                 160

Arg Glu Val Leu Glu Lys Ala Gln Arg Leu Glu Gln Ile Gly Tyr Lys
                165                 170                 175

Glu Tyr Leu Asn Gln Lys Glu
            180

<210> SEQ ID NO 19
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Lys Met Lys Glu Phe Leu Asp Leu Leu Asn Glu Ser Arg Leu Thr
1               5                   10                  15

Val Thr Leu Thr Gly Ala Gly Ile Ser Thr Pro Ser Gly Ile Pro Asp
            20                  25                  30

Phe Arg Gly Pro Asn Gly Ile Tyr Lys Lys Tyr Ser Gln Asn Val Phe
        35                  40                  45

Asp Ile Asp Phe Phe Tyr Ser His Pro Glu Glu Phe Tyr Arg Phe Ala
    50                  55                  60

Lys Glu Gly Ile Phe Pro Met Leu Gln Ala Lys Pro Asn Leu Ala His
65                  70                  75                  80

Val Leu Leu Ala Lys Leu Glu Glu Lys Gly Leu Ile Glu Ala Val Ile
                85                  90                  95

Thr Gln Asn Ile Asp Arg Leu His Gln Arg Ala Gly Ser Lys Lys Val
            100                 105                 110

Ile Glu Leu His Gly Asn Val Glu Glu Tyr Tyr Cys Val Arg Cys Glu

```
                    115                 120                 125
Lys Lys Tyr Thr Val Glu Asp Val Ile Lys Lys Leu Glu Ser Ser Asp
        130                 135                 140

Val Pro Leu Cys Asp Asp Cys Asn Ser Leu Ile Arg Pro Asn Ile Val
145                 150                 155                 160

Phe Phe Gly Glu Asn Leu Pro Gln Asp Ala Leu Arg Glu Ala Ile Gly
                165                 170                 175

Leu Ser Ser Arg Ala Ser Leu Met Ile Val Leu Gly Ser Ser Leu Val
            180                 185                 190

Val Tyr Pro Ala Ala Glu Leu Pro Leu Ile Thr Val Arg Ser Gly Gly
        195                 200                 205

Lys Leu Val Ile Val Asn Leu Gly Glu Thr Pro Phe Asp Asp Ile Ala
210                 215                 220

Thr Leu Lys Tyr Asn Met Asp Val Val Glu Phe Ala Arg Arg Val Met
225                 230                 235                 240

Glu Glu Gly Gly Ile Ser
                245

<210> SEQ ID NO 20
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Ala Arg Tyr Leu Val Val Ala His Arg Thr Ala Lys Ser Pro Glu
1               5                   10                  15

Leu Ala Ala Lys Leu Lys Glu Leu Leu Ala Gln Asp Pro Glu Ala Arg
            20                  25                  30

Phe Val Leu Leu Val Pro Ala Val Pro Pro Gly Trp Val Tyr Glu
        35                  40                  45

Glu Asn Glu Val Arg Arg Ala Glu Glu Ala Ala Ala Ala Lys
    50                  55                  60

Arg Ala Leu Glu Ala Gln Gly Ile Pro Val Glu Glu Ala Lys Ala Gly
65                  70                  75                  80

Asp Ile Ser Pro Leu Leu Ala Ile Glu Glu Leu Leu Ala His Pro
                85                  90                  95

Gly Ala Tyr Gln Gly Ile Val Leu Ser Thr Leu Pro Pro Gly Leu Ser
                100                 105                 110

Arg Trp Leu Arg Leu Asp Val His Thr Gln Ala Glu Arg Phe Gly Leu
            115                 120                 125

Pro Val Ile His Val Ile Ala Gln Ala Ala
        130                 135

<210> SEQ ID NO 21
<211> LENGTH: 315
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Val Val Ser Leu Ala Gly Arg Asp Leu Leu Cys Leu Gln Asp Tyr
1               5                   10                  15

Thr Ala Glu Glu Ile Trp Thr Ile Leu Glu Thr Ala Lys Met Phe Lys
```

```
            20                  25                  30
Ile Trp Gln Lys Ile Gly Lys Pro His Arg Leu Leu Glu Gly Lys Thr
        35                  40                  45
Leu Ala Met Ile Phe Gln Lys Pro Ser Thr Arg Thr Arg Val Ser Phe
    50                  55                  60
Glu Val Ala Met Ala His Leu Gly Gly His Ala Leu Tyr Leu Asn Ala
65                  70                  75                  80
Gln Asp Leu Gln Leu Arg Arg Gly Glu Thr Ile Ala Asp Thr Ala Arg
                85                  90                  95
Val Leu Ser Arg Tyr Val Asp Ala Ile Met Ala Arg Val Tyr Asp His
            100                 105                 110
Lys Asp Val Glu Asp Leu Ala Lys Tyr Ala Thr Val Pro Val Ile Asn
        115                 120                 125
Gly Leu Ser Asp Phe Ser His Pro Cys Gln Ala Leu Ala Asp Tyr Met
    130                 135                 140
Thr Ile Trp Glu Lys Lys Gly Thr Ile Lys Gly Val Lys Val Val Tyr
145                 150                 155                 160
Val Gly Asp Gly Asn Asn Val Ala His Ser Leu Met Ile Ala Gly Thr
                165                 170                 175
Lys Leu Gly Ala Asp Val Val Ala Thr Pro Glu Gly Tyr Glu Pro
            180                 185                 190
Asp Glu Lys Val Ile Lys Trp Ala Glu Gln Asn Ala Ala Glu Ser Gly
        195                 200                 205
Gly Ser Phe Glu Leu Leu His Asp Pro Val Lys Ala Val Lys Asp Ala
    210                 215                 220
Asp Val Ile Tyr Thr Asp Val Trp Ala Ser Met Gly Gln Glu Ala Glu
225                 230                 235                 240
Ala Glu Glu Arg Arg Lys Ile Phe Arg Pro Phe Gln Val Asn Lys Asp
                245                 250                 255
Leu Val Lys His Ala Lys Pro Asp Tyr Met Phe Met His Cys Leu Pro
            260                 265                 270
Ala His Arg Gly Glu Glu Val Thr Asp Asp Val Ile Asp Ser Pro Asn
        275                 280                 285
Ser Val Val Trp Asp Gln Ala Glu Asn Arg Leu His Ala Gln Lys Ala
    290                 295                 300
Val Leu Ala Leu Val Met Gly Gly Ile Lys Phe
305                 310                 315

<210> SEQ ID NO 22
<211> LENGTH: 716
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gaaggagata tacatatgca agagattacc gttgacgaat ttagcaatat ccgtgaaaac      60
ccggttaccc cgtggaaccc ggaaccgagc gccccggtt attgacccga ccgcctatat     120
tgacccggaa gcaagcgtga ttggtgaagt tacgattggc gcaaatgtta tggttagccc     180
gatggcgagc attcgcagcg atgaaggtat gccgattttt gtgggttgtc gtagcaatgt     240
tcaagatggt gttgtcctgc acgcactgga aacgattaat gaagaaggtg aaccgattga     300
agataatatt gttgaagttg atggcaaaga atacgcagtt tatattggta ataatgttag     360
```

```
cctggcccat cagagccaag tccacggtcc ggccgcaggc gatgatacgt ttattggcat    420
gcaagcgttc gttttaaaa gcaaagtggg taataatgca gttctggaac cgcgtagcgc    480
agcgattggt gtcacgatcc cggatggtcg ctatatcccg gccggtatgg tcgttaccag    540
ccaagcagaa gcagacaaac tgccggaagt caccgatgat tacgcctata gccataccaa    600
tgaagccgtt gtttgtgtga atgttcatct ggcggaaggt tacaaagaaa cgattgaagg    660
ccgtcatcac caccacccac cactaagacc cagctttctt gtacaaagtg gtcccc       716
```

<210> SEQ ID NO 23
<211> LENGTH: 2029
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
ggggacaagt ttgtacaaaa aagcaggcac cgaaggagat atacatatgg atgaatttag     60
caatatccgc gaaaatccgg tgaccccgtg gaatccggaa ccgagcgccc ccggttattg    120
atccgacggc atacatcgac ccggaagcca gcgtgattgg tgaagttacc atcggcgcca    180
atgttatggt cagcccgatg gcgagcatcc gcagcgatga aggcatgccg atctttgtgg    240
gctgtcgtag caatgtgcag gatggcgttg ttctgcacgc gctggaaacc attaatgaag    300
aaggcgaacc gattgaagac aatattgttg aagtggacgg taaggaatat gcagtgtaca    360
tcggtaacaa cgtcagcctg gcccatcaga gccaagtcca tggtccggcc gccgtgggcg    420
atgataccat tggcatgcaa gcgttcgtgt ttaaaagcaa agttggcaat aatgcagttc    480
tggaaccgcg cagcgcggcg atcggcgtga ccattccgga tggtcgttac atccggccg    540 gcatggtggt caccagccaa gcggaggccg ataaactgcc ggaagtcacc gatgactatg    600
cctatagcca caccaatgag gccgtcgtgt gcgtgaacgt tcatctggcc gaaggttata    660
aagaaacggg tggtagcggc ggcggcgatg aatttagcaa tatccgcgaa aatccggtga    720
ccccgtggaa tccggagccg agcgcaccgg ttarrgatcc gaccgcatat attgatccgg    780
aggccagcgt tatcggcgaa gttacgatcg cgaatgttat ggtgagcccg atggcgagca    840
ttcgcagcga tgagggtatg ccgattttg tgggctgccg tagcaatgtg caagatggtg    900
tggtcctgca cgcactggag acgattaacg aggaaggtga accgatcgag gacaacattg    960
tcgaagtgga cggtaaggag tatgcggtgt atatcggcaa caacgttagc ctggcccacc   1020
agagccaggt gcacggcccg gcagcagtgg gcgatgacac gtttattggc atgcaggcgt   1080
tcgttttcaa aagcaaagtt ggcaataacg cagttctgga accgcgtagc gcagcgattg   1140
gcgttaccat cccggatggc cgttatatcc cggccggtat ggtcgttacg caggcggaag   1200
cagataaact gccggaagtt accgatgact atgcctatag ccataccaat gaggcagttg   1260
tttgtgtcaa tgtccatctg gcggaaggct acaaagaaac gggtggtagc ggtggcggtg   1320
atgaattcag caacatccgt gaaaacccgg tgaccccgtg gaacccggaa ccgagcgcgc   1380
cggtcattga tccgaccgca tatatcgatc cggaggcaag cgtcattggc gaagttacga   1440
ttggcgccaa cgtgatggtc agcccgatgg ccagcatccg cagcgatgaa ggcatgccga   1500
tttttgttgg ttgccgtagc aacgttcagg atggcgtggt cctgcacgca ctggaaacca   1560
ttaacgaaga agagccgatt gaagataaca tcgttgaggt cgacggtaaa gaatatgccg   1620
tgtatatcgg caacaacgtt agcctggccc atcaaagcca agttcatggt ccggccgcgg   1680
```

```
ttggtgatga cacgttcatt ggcatgcagg cgtttgtgtt taagagcaaa gtgggtaata   1740
atgccgttct ggagccgcgc agcgccgcaa tcggcgtcac catcccggac ggtcgctaca   1800
ttccggcagg catggtcgtg accagccaag ccgaagcgga caaactgccg gaagtcaccg   1860
atgattagca tacagccaca ccaacgaggc ggtcgtgtgt gttaatgtgc atctggcgga   1920
aggttataaa gaaacgattg aaggccgtca tcaccaccat cattgaaccc agctttcttg   1980
tacaaagtgg tgatgatccg gctgctaaca aagcccgaaa ggaagctga              2029
```

<210> SEQ ID NO 24
<211> LENGTH: 2068
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
cgatgcgtcc ggcgtagagg atcgagatct cgatcccgcg aaattaatac gactcactat    60
agggagacca caacggtttc cctctagatc acaagtttgt acaaaaaagc aggcaccgaa   120
ggagatatac atatggatga atttagcaat attcgcgaaa acccggttac cccgtggaac   180
ccggaaccga gcgcgccggt tatcgacccg acggcctaca ttgatccgga ggcaagcgtg   240
attggtgaag tgacgattgg tgcaaatgtc atggtgagcc cgatggcgag cattcgtagc   300
gatgaaggta tgccgatttt cgttggttgt cgtagcaatg ttcaagatgg tgttgttctg   360
cacgccctgg aaaccattaa tgaagaaggt gagccgattg aagacaacat cgttgaagtt   420
gatggtaaag aatacgcggt ttatatcggc aacaacgtca gcctggcaca tcagagccaa   480
gttcatggtc cggcagcagt gggcgatgat acgattggta tgcaagcatt cgttttttaaa   540 agcaaagttg gtaataatgc agttctggaa ccgcgcagcg cagcaattgg tgttaccatt   600
ccggatggtc gttatatccc ggccggtatg gtggtgacga gccaggcgga agcagataaa   660
ctgccggaag tgacggatga ttatgcctat agccatacca atgaagcagt cgtgtgtgtt   720
aacgtgcacc tggccgaagg ttacaaagaa acgggcggtg gtagcggtgg cggcgatgaa   780
tttagcaata ccgtgaaaac ccggttaccc gtggaatccg gaaccgagcg caccggttat   840
tgatccgacg gcatatatcg acccggaggc aagcgtgatt ggcgaagtta cgggcgcaaa   900
tgtgatggtt agcccgatgg ccagcattcg tagcgatgaa ggcatgccga ttttgtggc   960 tgccgcagca atgttcaaga tggtgttgtc ctgcacgcac tggagaccat caatgaagaa   1020
ggtgaaccga ttgaagataa catcgtcgaa gttgacggca agaatatgc ggtgtatatt   1080 ggcaataatg tcagcctggc acatcaaagc caagttcacg gtccggcagc agtgggcgat   1140 gatacccttta ttggcatgca agcgtttgtt ttcaaaagca agtcggcaa taatgcagtt   1200 ctggaaccgc gcgcagcgca gcgattggcg tcacgatccc ggatggtcgt tatattccgg   1260
ccggcatggt ggtgagccag gcagaagcag ataaactgcc ggaagtgacc gatgactatg   1320
cctatagcca tacgaacgaa gccgttgttt gcgtgaacgt gcacctggca gaaggctaca   1380
aagaaaccgg tggtggcagc ggcggcggtg atgaattcag caatattcgc gaaaatccgg   1440
tcaccccgtg gaatccggaa ccgagcgccc cggtcattga cccgacggca tatattgatc   1500
cggaagcaag cgttattggt gaagttacga ttggtgcaaa cgtgatggtg agcccgatgg   1560
cgagcattcg cagcgatgag ggcatgccga ttttgtggg cgatcgcagc aatgttcaag   1620
atggtgttgt cctgcacgcc ctggaaacca tcaatgaagg cgaaccgatt gaagacaata   1680
```

```
ttgtggaagt cgatggtaaa gaatacgcag tctatattgg taataatgtt agcctggcac    1740
atcagagcca agtccacggt ccggccgcag tgggtgatga cagtttattg gtatgcaagc    1800
atttgtgttt aaaagcaaag tcggtaacaa tgcagttctg gaaccgcgca gcgcagcaat    1860
cggcgttacg atcccggatg ccgttatat cccggcgggt atggtggtta cgagccaagc     1920
agaagcggat aaactgccgg aagttacgga tgattatgcc tatagccata cgaacgaagc    1980
ggttgtctac gttaacgtgc atctggcgga gggttacaaa gaaacgattg agggtcatca    2040
tcaccatcat cattgaaacc cagctttc                                       2068
```

<210> SEQ ID NO 25
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Met Gln Glu Ile Thr Val Asp Glu Phe Ser Asn Ile Arg Glu Asn Pro
1               5                   10                  15

Val Thr Pro Trp Asn Pro Glu Pro Ser Ala Pro Val Ile Asp Pro Thr
            20                  25                  30

Ala Tyr Ile Asp Pro Glu Ala Ser Val Ile Gly Glu Val Thr Ile Gly
        35                  40                  45

Ala Asn Val Met Val Ser Pro Met Ala Ser Ile Arg Ser Asp Glu Gly
    50                  55                  60

Met Pro Ile Phe Val Gly Cys Arg Ser Asn Val Gln Asp Gly Val Val
65                  70                  75                  80

Leu His Ala Leu Glu Thr Ile Asn Glu Glu Gly Glu Pro Ile Glu Asp
                85                  90                  95

Asn Ile Val Glu Val Asp Gly Lys Glu Tyr Ala Val Tyr Ile Gly Asn
            100                 105                 110

Asn Val Ser Leu Ala His Gln Ser Gln Val His Gly Pro Ala Ala Val
        115                 120                 125

Gly Asp Asp Thr Phe Ile Gly Met Gln Ala Phe Val Phe Lys Ser Lys
    130                 135                 140

Val Gly Asn Asn Ala Val Leu Glu Pro Arg Ser Ala Ala Ile Gly Val
145                 150                 155                 160

Thr Ile Pro Asp Gly Arg Tyr Ile Pro Ala Gly Met Val Val Thr Ser
                165                 170                 175

Gln Ala Glu Ala Asp Lys Leu Pro Glu Val Thr Asp Asp Tyr Ala Tyr
            180                 185                 190

Ser His Thr Asn Glu Ala Val Val Cys Val Asn Val His Leu Ala Glu
        195                 200                 205

Gly Tyr Lys Glu Thr Ile Glu Gly Arg His His His His His
    210                 215                 220
```

<210> SEQ ID NO 26
<211> LENGTH: 644
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Asp Glu Phe Ser Asn Ile Arg Glu Asn Pro Val Thr Pro Trp Asn

-continued

```
1               5                   10                  15
Pro Glu Pro Ser Ala Pro Val Ile Asp Pro Thr Ala Tyr Ile Asp Pro
                20                  25                  30

Glu Ala Ser Val Ile Gly Glu Val Thr Ile Gly Ala Asn Val Met Val
                35                  40                  45

Ser Pro Met Ala Ser Ile Arg Ser Asp Glu Gly Met Pro Ile Phe Val
    50                  55                  60

Gly Cys Arg Ser Asn Val Gln Asp Gly Val Val Leu His Ala Leu Glu
65                  70                  75                  80

Thr Ile Asn Glu Glu Gly Glu Pro Ile Glu Asp Asn Ile Val Glu Val
                85                  90                  95

Asp Gly Lys Glu Tyr Ala Val Tyr Ile Gly Asn Asn Val Ser Leu Ala
                100                 105                 110

His Gln Ser Gln Val His Gly Pro Ala Ala Val Gly Asp Asp Phe Thr
                115                 120                 125

Ile Gly Met Gln Ala Phe Val Phe Lys Ser Lys Val Gly Asn Asn Ala
                130                 135                 140

Val Leu Glu Pro Arg Ser Ala Ala Ile Gly Val Thr Ile Pro Asp Gly
145                 150                 155                 160

Arg Tyr Ile Pro Ala Gly Met Val Val Thr Ser Gln Ala Glu Ala Asp
                165                 170                 175

Lys Leu Pro Glu Val Thr Asp Asp Tyr Ala Tyr Ser His Thr Asn Glu
                180                 185                 190

Ala Val Val Cys Val Asn Val His Leu Ala Glu Gly Tyr Lys Glu Thr
                195                 200                 205

Gly Gly Ser Gly Gly Gly Asp Glu Phe Ser Asn Ile Arg Glu Asn Pro
                210                 215                 220

Val Thr Pro Trp Asn Pro Glu Pro Ser Ala Pro Val Ile Asp Pro Thr
225                 230                 235                 240

Ala Tyr Ile Asp Pro Glu Ala Ser Val Ile Gly Glu Val Thr Ile Gly
                245                 250                 255

Ala Asn Val Met Val Ser Pro Met Ala Ser Ile Arg Ser Asp Glu Gly
                260                 265                 270

Met Pro Ile Phe Val Gly Cys Arg Ser Asn Val Gln Asp Gly Val Val
                275                 280                 285

Leu His Ala Leu Glu Thr Ile Asn Glu Glu Gly Glu Pro Ile Glu Asp
                290                 295                 300

Asn Ile Val Glu Val Asp Gly Lys Glu Tyr Ala Val Tyr Ile Gly Asn
305                 310                 315                 320

Asn Val Ser Leu Ala His Gln Ser Gln Val His Gly Pro Ala Ala Val
                325                 330                 335

Gly Asp Asp Thr Phe Ile Gly Met Gln Ala Phe Val Phe Lys Ser Lys
                340                 345                 350

Val Gly Asn Asn Ala Val Leu Glu Pro Arg Ser Ala Ala Ile Gly Val
                355                 360                 365

Thr Ile Pro Asp Gly Arg Tyr Ile Pro Ala Gly Met Val Val Thr Ser
                370                 375                 380

Gln Ala Glu Ala Asp Lys Leu Pro Glu Val Thr Asp Asp Tyr Ala Tyr
385                 390                 395                 400

Ser His Thr Asn Glu Ala Val Val Cys Val Asn Val His Leu Ala Glu
                405                 410                 415

Gly Tyr Lys Glu Thr Gly Gly Ser Gly Gly Gly Asp Glu Phe Ser Asn
                420                 425                 430
```

```
Ile Arg Glu Asn Pro Val Thr Pro Trp Asn Pro Gly Pro Ser Ala Pro
        435                 440                 445

Val Ile Asp Pro Thr Ala Tyr Ile Asp Pro Glu Ala Ser Val Ile Gly
    450                 455                 460

Glu Val Thr Ile Gly Ala Asn Val Met Val Ser Pro Met Ala Ser Ile
465                 470                 475                 480

Arg Ser Asp Glu Gly Met Pro Ile Phe Val Gly Cys Arg Ser Asn Val
                485                 490                 495

Gln Asp Gly Val Val Leu His Ala Leu Glu Thr Ile Asn Glu Glu Gly
            500                 505                 510

Glu Pro Ile Glu Asp Asn Ile Val Glu Val Asp Gly Lys Glu Tyr Ala
        515                 520                 525

Val Tyr Ile Gly Asn Asn Val Ser Leu Ala His Gln Ser Gln Val His
    530                 535                 540

Gly Pro Ala Ala Val Gly Asp Asp Thr Phe Ile Gly Met Gln Ala Phe
545                 550                 555                 560

Val Phe Lys Ser Lys Val Gly Asn Asn Ala Val Leu Glu Pro Arg Ser
                565                 570                 575

Ala Ala Ile Gly Val Thr Ile Pro Asp Gly Arg Tyr Ile Pro Ala Gly
            580                 585                 590

Met Val Val Thr Ser Gln Ala Glu Ala Asp Lys Leu Pro Glu Val Thr
        595                 600                 605

Asp Asp Tyr Ala Tyr Ser His Thr Asn Glu Ala Val Val Cys Val Asn
    610                 615                 620

Val His Leu Ala Glu Gly Tyr Lys Glu Thr Ile Glu Gly Arg His His
625                 630                 635                 640

His His His His

<210> SEQ ID NO 27
<211> LENGTH: 644
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Asp Glu Phe Ser Asn Ile Arg Glu Asn Pro Val Thr Pro Trp Asn
1               5                   10                  15

Pro Glu Pro Ser Ala Pro Val Ile Asp Pro Thr Ala Tyr Ile Asp Pro
            20                  25                  30

Glu Ala Ser Val Ile Gly Glu Val Thr Ile Gly Ala Asn Val Met Val
        35                  40                  45

Ser Pro Met Ala Ser Ile Arg Ser Asp Glu Gly Met Pro Ile Phe Val
    50                  55                  60

Gly Cys Arg Ser Asn Val Gln Asp Gly Val Val Leu His Ala Leu Glu
65                  70                  75                  80

Thr Ile Asn Glu Glu Gly Glu Pro Ile Glu Asp Asn Ile Val Glu Val
                85                  90                  95

Asp Gly Lys Glu Tyr Ala Val Tyr Ile Gly Asn Asn Val Ser Leu Ala
            100                 105                 110

His Gln Ser Gln Val His Gly Pro Ala Ala Val Gly Asp Asp Thr Phe
        115                 120                 125

Ile Gly Met Gln Ala Phe Val Phe Lys Ser Lys Val Gly Asn Asn Ala
    130                 135                 140
```

```
Val Leu Glu Pro Arg Ser Ala Ala Ile Gly Val Thr Ile Pro Asp Gly
145                 150                 155                 160

Arg Tyr Ile Pro Ala Gly Met Val Val Thr Ser Gln Ala Glu Ala Asp
            165                 170                 175

Lys Leu Pro Glu Val Thr Asp Asp Tyr Ala Tyr Ser His Thr Asn Glu
            180                 185                 190

Ala Val Val Cys Val Asn Val His Leu Ala Glu Gly Tyr Lys Glu Thr
            195                 200                 205

Gly Gly Ser Gly Gly Gly Asp Glu Phe Ser Asn Ile Arg Glu Asn Pro
            210                 215                 220

Val Thr Pro Trp Asn Pro Glu Pro Ser Ala Pro Val Ile Asp Pro Thr
225                 230                 235                 240

Ala Tyr Ile Asp Pro Glu Ala Ser Val Ile Gly Glu Val Thr Ile Gly
            245                 250                 255

Ala Asn Val Met Val Ser Pro Met Ala Ser Ile Arg Ser Asp Glu Gly
            260                 265                 270

Met Pro Ile Phe Val Gly Cys Arg Ser Asn Val Gln Asp Gly Val Val
            275                 280                 285

Leu His Ala Leu Glu Thr Ile Asn Glu Glu Glu Pro Ile Glu Asp
            290                 295                 300

Asn Ile Val Glu Val Asp Gly Lys Glu Tyr Ala Val Tyr Ile Gly Asn
305                 310                 315                 320

Asn Val Ser Leu Ala His Gln Ser Gln Val His Gly Pro Ala Ala Val
            325                 330                 335

Gly Asp Asp Thr Phe Ile Gly Met Gln Ala Phe Val Phe Lys Ser Lys
            340                 345                 350

Val Gly Asn Asn Ala Val Leu Glu Pro Arg Ser Ala Ala Ile Gly Val
            355                 360                 365

Thr Ile Pro Asp Gly Arg Tyr Ile Pro Ala Gly Met Val Val Thr Ser
370                 375                 380

Gln Ala Glu Ala Asp Lys Leu Pro Glu Val Thr Asp Asp Tyr Ala Tyr
385                 390                 395                 400

Ser His Thr Asn Glu Ala Val Val Cys Val Asn Val His Leu Ala Glu
            405                 410                 415

Gly Tyr Lys Glu Thr Gly Gly Ser Gly Gly Gly Asp Glu Phe Ser Asn
            420                 425                 430

Ile Arg Glu Asn Pro Val Thr Pro Trp Asn Pro Glu Pro Ser Ala Pro
            435                 440                 445

Val Ile Asp Pro Thr Ala Tyr Ile Asp Pro Glu Ala Ser Val Ile Gly
            450                 455                 460

Glu Val Thr Ile Gly Ala Asn Val Met Val Ser Pro Met Ala Ser Ile
465                 470                 475                 480

Arg Ser Asp Glu Gly Met Pro Ile Phe Val Gly Asp Arg Ser Asn Val
            485                 490                 495

Gln Asp Gly Val Val Leu His Ala Leu Glu Thr Ile Asn Glu Glu Gly
            500                 505                 510

Glu Pro Ile Glu Asp Asn Ile Val Glu Val Asp Gly Lys Glu Tyr Ala
            515                 520                 525

Val Tyr Ile Gly Asn Asn Val Ser Leu Ala His Gln Ser Gln Val His
            530                 535                 540

Gly Pro Ala Ala Val Gly Asp Asp Thr Phe Ile Gly Met Gln Ala Phe
545                 550                 555                 560
```

Val Phe Lys Ser Lys Val Gly Asn Asn Ala Val Leu Glu Pro Arg Ser
              565                 570                 575

Ala Ala Ile Gly Val Thr Ile Pro Asp Gly Arg Tyr Ile Pro Ala Gly
          580                 585                 590

Met Val Val Thr Ser Gln Ala Glu Ala Asp Lys Leu Pro Glu Val Thr
         595                 600                 605

Asp Asp Tyr Ala Tyr Ser His Thr Asn Glu Ala Val Val Tyr Val Asn
     610                 615                 620

Val His Leu Ala Glu Gly Tyr Lys Glu Thr Ile Glu Gly Arg His His
625                 630                 635                 640

His His His His

<210> SEQ ID NO 28
<211> LENGTH: 1071
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
atgagctatt atcaccatca tcatcatcat gactatgata tcccgaccac cgaaaatctg      60
tatttccaag gtatgaacat ccgtgaacgc aaacgtaaac atctggaagc ggccctggaa     120
ggtgaagttg catatcaaaa aacgaccacc ggtctggaag gtttccgtct cgctatcaa     180 gccctggccg gtctggcact gtgtgaagtc gatctgtgta cccgttttct gggtaaaacg     240
ctgaaagccc gttcctgat tggtgcaatg acgggtggtc aagaaaacgg tgaacgtatc     300
aatctggcac tggccgaagc cgccgaagcc ctgggtgtgg gtatgatgct gggtagcggc     360
cgtattctgc tggagcgtcc ggaagccctg cgtagctttc gtgtccgtaa agttgcaccg     420
aaagcactgc tgattgcgaa tctgggtctg gcacaactgc gtcgttatgg tcgcgatgat     480
ctgctgcgcc tggtcgaaat gctggaagcc gatgccctgg cctttcatgt taatccgctg     540
caagaagcag tccaacgtgg tgataccgat ttccgtggtc tggttgaacg tctggccgaa     600
ctgctgccgc tgccgttccc ggttatggtc aaagaagttg ccacggtct gagccgtgaa     660 gcagccctgg cactgcgtga tctgccgctg ccgcagttg atgttgcagg tgcgggtggt     720
acgagctggg cacgtgttga agaatgggtt cgttttggtg aagtccgcca cccggaactg     780
agcgaaattg gcattccgac ggcccgcgcg attctggaag ttcgtgaagt tctgccgcat     840 ctgccgctg ttgcaagcgg cggtgtttat accggcaccg atggcgcaaa agcactggca     900
ctgggcgccg atctgctggc ggttgcgcgt ccgctgctgc gcccggccct ggaaggtgca     960
gaacgtgttg cggcgtggat tggtgattac ctggaagaac tgcgtaccgc actgtttgcg    1020
attggtgcac gtaatccgaa agaagcccgc ggtcgtgtcg aacgcgtcta a             1071

<210> SEQ ID NO 29
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Ser Tyr Tyr His His His His His His Asp Tyr Asp Ile Pro Thr
1               5                   10                  15

Thr Glu Asn Leu Tyr Phe Gln Gly Met Asn Ile Arg Glu Arg Lys Arg

```
                20                  25                  30
Lys His Leu Glu Ala Ala Leu Glu Gly Glu Val Ala Tyr Gln Lys Thr
             35                  40                  45

Thr Thr Gly Leu Glu Gly Phe Arg Leu Arg Tyr Gln Ala Leu Ala Gly
 50                  55                  60

Leu Ala Leu Cys Glu Val Asp Leu Cys Thr Pro Phe Leu Gly Lys Thr
 65                  70                  75                  80

Leu Lys Ala Pro Phe Leu Ile Gly Ala Met Thr Gly Gly Glu Glu Asn
                 85                  90                  95

Gly Glu Arg Ile Asn Leu Ala Leu Ala Glu Ala Glu Ala Leu Gly
             100                 105                 110

Val Gly Met Met Leu Gly Ser Gly Arg Ile Leu Leu Glu Arg Pro Glu
             115                 120                 125

Ala Leu Arg Ser Phe Arg Val Arg Lys Val Ala Pro Lys Ala Leu Leu
             130                 135                 140

Ile Ala Asn Leu Gly Leu Ala Gln Leu Arg Arg Tyr Gly Arg Asp Asp
145                 150                 155                 160

Leu Leu Arg Leu Val Glu Met Leu Glu Ala Asp Ala Leu Ala Phe His
                 165                 170                 175

Val Asn Pro Leu Gln Glu Ala Val Gln Arg Gly Asp Thr Asp Phe Arg
             180                 185                 190

Gly Leu Val Glu Arg Leu Ala Glu Leu Pro Leu Pro Phe Pro Val
             195                 200                 205

Met Val Lys Glu Val Gly His Gly Leu Ser Arg Glu Ala Ala Leu Ala
             210                 215                 220

Leu Arg Asp Leu Pro Leu Ala Ala Val Asp Val Ala Gly Ala Gly Gly
225                 230                 235                 240

Thr Ser Trp Ala Arg Val Glu Glu Trp Val Arg Phe Gly Glu Val Arg
                 245                 250                 255

His Pro Glu Leu Ser Glu Ile Gly Ile Pro Thr Ala Arg Ala Ile Leu
             260                 265                 270

Glu Val Arg Glu Val Leu Pro His Leu Pro Leu Val Ala Ser Gly Gly
             275                 280                 285

Val Tyr Thr Gly Thr Asp Gly Ala Lys Ala Leu Ala Leu Gly Ala Asp
             290                 295                 300

Leu Leu Ala Val Ala Arg Pro Leu Leu Arg Pro Ala Leu Glu Gly Ala
305                 310                 315                 320

Glu Arg Val Ala Ala Trp Ile Gly Asp Tyr Leu Glu Glu Leu Arg Thr
                 325                 330                 335

Ala Leu Phe Ala Ile Gly Ala Arg Asn Pro Lys Glu Ala Arg Gly Arg
             340                 345                 350

Val Glu Arg Val
         355

<210> SEQ ID NO 30
<211> LENGTH: 372
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Lys Phe Leu Lys Asn Val Leu Glu Glu Gly Ser Lys Leu Glu Glu
1               5                   10                  15
```

```
Phe Asn Glu Leu Glu Leu Ser Pro Glu Asp Lys Glu Leu Glu Tyr
                 20                  25                  30

Leu Gln Gln Thr Lys Ala Lys Ile Thr Val Val Gly Cys Gly Gly Ala
         35                  40                  45

Gly Asn Asn Thr Ile Thr Arg Leu Lys Met Glu Gly Ile Glu Gly Ala
 50                  55                  60

Lys Thr Val Ala Ile Asn Thr Asp Ala Gln Gln Leu Ile Arg Thr Lys
 65                  70                  75                  80

Ala Asp Lys Lys Ile Leu Ile Gly Lys Lys Leu Thr Arg Gly Leu Gly
                 85                  90                  95

Ala Gly Gly Asn Pro Lys Ile Gly Glu Glu Ala Ala Lys Glu Ser Ala
            100                 105                 110

Glu Glu Ile Lys Ala Ala Ile Gln Asp Ser Asp Met Val Phe Ile Thr
        115                 120                 125

Cys Gly Leu Gly Gly Gly Thr Gly Thr Gly Ser Ala Pro Val Val Ala
130                 135                 140

Glu Ile Ser Lys Lys Ile Gly Ala Leu Thr Val Ala Val Val Thr Leu
145                 150                 155                 160

Pro Phe Val Met Glu Gly Lys Val Arg Met Lys Asn Ala Met Glu Gly
                165                 170                 175

Leu Glu Arg Leu Lys Gln His Thr Asp Thr Leu Val Val Ile Pro Asn
            180                 185                 190

Glu Lys Leu Phe Glu Ile Val Pro Asn Met Pro Leu Lys Leu Ala Phe
        195                 200                 205

Lys Val Ala Asp Glu Val Leu Ile Asn Ala Val Lys Gly Leu Val Glu
210                 215                 220

Leu Ile Thr Lys Asp Gly Leu Ile Asn Val Asp Phe Ala Asp Val Lys
225                 230                 235                 240

Ala Val Met Asn Asn Gly Gly Leu Ala Met Ile Gly Ile Gly Glu Ser
                245                 250                 255

Asp Ser Glu Lys Arg Ala Lys Glu Ala Val Ser Met Ala Leu Asn Ser
            260                 265                 270

Pro Leu Leu Asp Val Asp Ile Asp Gly Ala Thr Gly Ala Leu Ile His
        275                 280                 285

Val Met Gly Pro Glu Asp Leu Thr Leu Glu Glu Ala Arg Glu Val Val
290                 295                 300

Ala Thr Val Ser Ser Arg Leu Asp Pro Asn Ala Thr Ile Ile Trp Gly
305                 310                 315                 320

Ala Thr Ile Asp Glu Asn Leu Glu Asn Thr Val Arg Val Leu Leu Val
                325                 330                 335

Ile Thr Gly Val Gln Ser Arg Ile Glu Phe Thr Asp Thr Gly Leu Lys
            340                 345                 350

Arg Lys Lys Leu Glu Leu Thr Gly Ile Pro Lys Ile Gly Ser His His
        355                 360                 365

His His His His
    370

<210> SEQ ID NO 31
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31
```

Met Pro Phe Glu Ile Val Phe Glu Gly Ala Lys Glu Phe Ala Gln Leu
1               5                   10                  15

Ile Asp Thr Ala Ser Lys Leu Ile Asp Glu Ala Ala Phe Lys Val Thr
            20                  25                  30

Glu Asp Gly Ile Ser Met Arg Ala Met Asp Pro Ser Arg Val Val Leu
        35                  40                  45

Ile Asp Leu Asn Leu Pro Ser Ser Ile Phe Ser Lys Tyr Glu Val Val
    50                  55                  60

Glu Pro Glu Thr Ile Gly Val Asn Leu Asp His Leu Lys Lys Ile Leu
65                  70                  75                  80

Lys Arg Gly Lys Ala Lys Asp Thr Leu Ile Leu Lys Lys Gly Glu Glu
                85                  90                  95

Asn Phe Leu Glu Ile Thr Ile Gln Gly Thr Ala Thr Arg Thr Phe Arg
            100                 105                 110

Val Pro Leu Ile Asp Val Glu Glu Met Glu Val Asp Leu Pro Glu Leu
        115                 120                 125

Pro Phe Thr Ala Lys Val Val Val Leu Gly Glu Val Leu Lys Asp Ala
    130                 135                 140

Val Lys Asp Ala Ser Leu Val Ser Asp Ser Ile Lys Phe Ile Ala Arg
145                 150                 155                 160

Glu Asn Glu Phe Ile Met Lys Ala Glu Gly Glu Thr Gln Glu Val
                165                 170                 175

Ile Lys Leu Thr Leu Glu Asp Glu Gly Leu Leu Asp Ile Glu Val Gln
            180                 185                 190

Glu Glu Thr Lys Ser Ala Tyr Gly Val Ser Tyr Leu Ser Asp Met Val
                195                 200                 205

Lys Gly Leu Gly Lys Ala Asp Glu Val Thr Ile Lys Phe Gly Asn Glu
            210                 215                 220

Met Pro Met Gln Met Glu Tyr Tyr Ile Arg Asp Glu Gly Arg Leu Thr
225                 230                 235                 240

Phe Leu Leu Ala Pro Arg Val Glu Glu
                245

<210> SEQ ID NO 32
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Pro Phe Glu Ile Val Phe Glu Gly Ala Lys Glu Phe Ala Gln Leu
1               5                   10                  15

Ile Asp Thr Ala Ser Lys Leu Ile Asp Glu Ala Ala Phe Lys Val Thr
            20                  25                  30

Glu Asp Gly Ile Ser Met Arg Ala Met Asp Pro Ser Arg Val Val Leu
        35                  40                  45

Ile Asp Leu Asn Leu Pro Ser Ser Ile Phe Ser Lys Tyr Glu Val Val
    50                  55                  60

Glu Pro Glu Thr Ile Gly Val Asn Leu Asp His Leu Lys Lys Ile Leu
65                  70                  75                  80

Lys Arg Gly Lys Ala Lys Asp Thr Leu Ile Leu Lys Lys Gly Glu Glu
                85                  90                  95

Asn Phe Leu Glu Ile Thr Ile Gln Gly Thr Ala Thr Arg Thr Phe Arg

```
              100                 105                 110
Val Pro Leu Ile Asp Val Glu Met Glu Val Asp Leu Pro Glu Leu
            115                 120                 125
Pro Phe Thr Ala Lys Val Val Leu Gly Glu Val Leu Lys Asp Ala
            130                 135                 140
Val Lys Asp Ala Ser Leu Val Ser Asp Ser Ile Lys Phe Ile Ala Arg
145                 150                 155                 160
Glu Asn Glu Phe Ile Met Lys Ala Glu Gly Thr Gln Glu Val Glu
                165                 170                 175
Ile Lys Leu Thr Leu Glu Asp Glu Gly Leu Leu Asp Ile Glu Val Gln
                180                 185                 190
Glu Glu Thr Lys Ser Ala Tyr Gly Val Ser Tyr Leu Ser Asp Met Val
                195                 200                 205
Lys Gly Leu Gly Lys Ala Asp Val Thr Ile Lys Phe Gly Asn Glu
                210                 215                 220
Met Pro Met Gln Met Glu Tyr Tyr Ile Arg Asp Glu Gly Arg Leu Thr
225                 230                 235                 240
Phe Leu Leu Ala Pro Arg Val Glu Glu
                245

<210> SEQ ID NO 33
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Ile Ile Val Tyr Thr Thr Phe Pro Asp Trp Glu Ser Ala Glu Lys
1               5                   10                  15
Val Val Lys Thr Leu Leu Lys Glu Arg Met Ile Ala Cys Ala Asn Leu
                20                  25                  30
Arg Glu His Arg Ala Phe Tyr Trp Trp Glu Gly Lys Ile Glu Glu Asp
            35                  40                  45
Lys Glu Val Gly Ala Ile Leu Lys Thr Arg Glu Asp Leu Trp Glu Glu
        50                  55                  60
Leu Lys Glu Arg Ile Lys Glu Leu His Pro Tyr Asp Val Pro Ala Ile
65                  70                  75                  80
Ile Arg Ile Asp Val Asp Asp Val Asn Glu Asp Tyr Leu Lys Trp Leu
                85                  90                  95
Ile Glu Glu Thr Lys Lys
            100

<210> SEQ ID NO 34
<211> LENGTH: 192
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Lys Asn Lys Val Val Val Thr Gly Val Pro Gly Val Gly Ser
1               5                   10                  15
Thr Thr Ser Ser Gln Leu Ala Met Asp Asn Leu Arg Lys Glu Gly Val
                20                  25                  30
Asn Tyr Lys Met Val Ser Phe Gly Ser Val Met Phe Glu Val Ala Lys
```

```
            35                  40                  45

Glu Glu Asn Leu Val Ser Asp Arg Asp Gln Met Arg Lys Met Asp Pro
 50                  55                  60

Glu Thr Gln Lys Arg Ile Gln Lys Met Ala Gly Arg Lys Ile Ala Glu
65                  70                  75                  80

Met Ala Lys Glu Ser Pro Val Ala Val Asp Thr His Ser Thr Val Ser
                85                  90                  95

Thr Pro Lys Gly Tyr Leu Pro Gly Leu Pro Ser Trp Val Leu Asn Glu
            100                 105                 110

Leu Asn Pro Asp Leu Ile Ile Val Val Glu Thr Thr Gly Asp Glu Ile
        115                 120                 125

Leu Met Arg Arg Met Ser Asp Glu Thr Arg Val Arg Asp Leu Asp Thr
    130                 135                 140

Ala Ser Thr Ile Glu Gln His Gln Phe Met Asn Arg Cys Ala Ala Met
145                 150                 155                 160

Ser Tyr Gly Val Leu Thr Gly Ala Thr Val Lys Ile Val Gln Asn Arg
                165                 170                 175

Asn Gly Leu Leu Asp Gln Ala Val Glu Glu Leu Thr Asn Val Leu Arg
            180                 185                 190

<210> SEQ ID NO 35
<211> LENGTH: 192
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Lys Asn Lys Leu Val Val Val Thr Gly Val Pro Gly Val Gly Gly
1               5                   10                  15

Thr Thr Ile Thr Gln Lys Ala Met Glu Lys Leu Ser Glu Glu Gly Ile
            20                  25                  30

Asn Tyr Lys Met Val Asn Phe Gly Thr Val Met Phe Glu Val Ala Gln
        35                  40                  45

Glu Glu Asn Leu Val Glu Asp Arg Asp Gln Met Arg Lys Leu Asp Pro
 50                  55                  60

Asp Thr Gln Lys Arg Ile Gln Lys Leu Ala Gly Arg Lys Ile Ala Glu
65                  70                  75                  80

Met Val Lys Glu Ser Pro Val Val Asp Thr His Ser Thr Ile Lys
                85                  90                  95

Thr Pro Lys Gly Tyr Leu Pro Gly Leu Pro Val Trp Val Leu Asn Glu
            100                 105                 110

Leu Asn Pro Asp Ile Ile Val Val Glu Thr Ser Gly Asp Glu Ile
        115                 120                 125

Leu Ile Arg Arg Leu Asn Asp Glu Thr Arg Asn Arg Asp Leu Glu Thr
    130                 135                 140

Thr Ala Gly Ile Glu Glu His Gln Ile Met Asn Arg Ala Ala Ala Met
145                 150                 155                 160

Thr Tyr Gly Val Leu Thr Gly Ala Thr Val Lys Ile Ile Gln Asn Lys
                165                 170                 175

Asn Asn Leu Leu Asp Tyr Ala Val Glu Glu Leu Ile Ser Val Leu Arg
            180                 185                 190

<210> SEQ ID NO 36
<211> LENGTH: 645
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

| | | | | | | | | | | | | | | | |
|---|---|---|---|---|---|---|---|---|---|---|---|---|---|---|---|
| Met | Leu | Gly | Val | Cys | Tyr | Tyr | Pro | Glu | His | Trp | Pro | Lys | Glu | Arg | Trp |
| 1 | | | | 5 | | | | | 10 | | | | | 15 | |
| Lys | Glu | Asp | Ala | Arg | Arg | Met | Arg | Glu | Ala | Gly | Leu | Ser | His | Val | Arg |
| | | | 20 | | | | | 25 | | | | | 30 | | |
| Ile | Gly | Glu | Phe | Ala | Trp | Ala | Leu | Leu | Glu | Pro | Glu | Pro | Gly | Arg | Leu |
| | | | | 35 | | | | | 40 | | | | | 45 | |
| Glu | Trp | Gly | Trp | Leu | Asp | Glu | Ala | Ile | Ala | Thr | Leu | Ala | Ala | Glu | Gly |
| | 50 | | | | | 55 | | | | | 60 | | | | |
| Leu | Lys | Val | Val | Leu | Gly | Thr | Pro | Thr | Ala | Thr | Pro | Pro | Lys | Trp | Leu |
| 65 | | | | | 70 | | | | | 75 | | | | | 80 |
| Val | Asp | Arg | Tyr | Pro | Glu | Ile | Leu | Pro | Val | Asp | Arg | Glu | Gly | Arg | Arg |
| | | | | 85 | | | | | 90 | | | | | 95 | |
| Arg | Arg | Phe | Gly | Gly | Arg | Arg | His | Tyr | Cys | Phe | Ser | Ser | Pro | Val | Tyr |
| | | | | 100 | | | | | 105 | | | | | 110 | |
| Arg | Glu | Glu | Ala | Arg | Arg | Ile | Val | Thr | Leu | Leu | Ala | Glu | Arg | Tyr | Gly |
| | | | | 115 | | | | | 120 | | | | | 125 | |
| Gly | Leu | Glu | Ala | Val | Ala | Gly | Phe | Gln | Thr | Asp | Asn | Glu | Tyr | Gly | Cys |
| | 130 | | | | | 135 | | | | | 140 | | | | |
| His | Asp | Thr | Val | Arg | Cys | Tyr | Cys | Pro | Arg | Cys | Gln | Glu | Ala | Phe | Arg |
| 145 | | | | | 150 | | | | | 155 | | | | | 160 |
| Gly | Trp | Leu | Glu | Ala | Arg | Tyr | Gly | Thr | Ile | Glu | Ala | Leu | Asn | Glu | Ala |
| | | | | 165 | | | | | 170 | | | | | 175 | |
| Trp | Gly | Thr | Ala | Phe | Trp | Ser | Gln | Arg | Tyr | Arg | Ser | Phe | Ala | Glu | Val |
| | | | | 180 | | | | | 185 | | | | | 190 | |
| Glu | Leu | Pro | His | Leu | Thr | Val | Ala | Glu | Pro | Asn | Pro | Ser | His | Leu | Leu |
| | | | | 195 | | | | | 200 | | | | | 205 | |
| Asp | Tyr | Tyr | Arg | Phe | Ala | Ser | Asp | Gln | Val | Arg | Ala | Phe | Asn | Arg | Leu |
| | 210 | | | | | 215 | | | | | 220 | | | | |
| Gln | Val | Glu | Ile | Leu | Arg | Ala | His | Ala | Pro | Gly | Lys | Phe | Val | Thr | His |
| 225 | | | | | 230 | | | | | 235 | | | | | 240 |
| Asn | Phe | Met | Gly | Phe | Phe | Thr | Asp | Leu | Asp | Ala | Phe | Ala | Leu | Ala | Gln |
| | | | | 245 | | | | | 250 | | | | | 255 | |
| Asp | Leu | Asp | Phe | Ala | Ser | Trp | Asp | Ser | Tyr | Pro | Leu | Gly | Phe | Thr | Asp |
| | | | | 260 | | | | | 265 | | | | | 270 | |
| Leu | Met | Pro | Leu | Pro | Pro | Glu | Glu | Lys | Leu | Arg | Tyr | Ala | Arg | Thr | Gly |
| | | | | 275 | | | | | 280 | | | | | 285 | |
| His | Pro | Asp | Val | Ala | Ala | Phe | His | His | Asp | Leu | Tyr | Arg | Gly | Val | Gly |
| | 290 | | | | | 295 | | | | | 300 | | | | |
| Arg | Gly | Arg | Phe | Trp | Val | Met | Glu | Gln | Gln | Pro | Gly | Pro | Val | Asn | Trp |
| 305 | | | | | 310 | | | | | 315 | | | | | 320 |
| Ala | Pro | His | Asn | Pro | Ser | Pro | Ala | Pro | Gly | Met | Val | Arg | Leu | Trp | Thr |
| | | | | 325 | | | | | 330 | | | | | 335 | |
| Trp | Glu | Ala | Leu | Ala | His | Gly | Ala | Glu | Val | Val | Ser | Tyr | Phe | Arg | Trp |
| | | | | 340 | | | | | 345 | | | | | 350 | |
| Arg | Gln | Ala | Pro | Phe | Ala | Gln | Glu | Gln | Met | His | Ala | Gly | Leu | His | Arg |
| | | | | 355 | | | | | 360 | | | | | 365 | |
| Pro | Asp | Ser | Ala | Pro | Asp | Gln | Gly | Phe | Phe | Glu | Ala | Lys | Arg | Val | Ala |
| | 370 | | | | | 375 | | | | | 380 | | | | |

```
Glu Glu Leu Ala Ala Leu Ala Leu Pro Pro Val Ala Gln Ala Pro Val
385                 390                 395                 400

Ala Leu Val Phe Asp Tyr Glu Ala Ala Trp Ile Tyr Glu Val Gln Pro
            405                 410                 415

Gln Gly Ala Glu Trp Ser Tyr Leu Gly Leu Val Tyr Leu Phe Tyr Ser
        420                 425                 430

Ala Leu Arg Arg Leu Gly Leu Asp Val Asp Val Val Pro Pro Gly Ala
    435                 440                 445

Ser Leu Arg Gly Tyr Ala Phe Ala Val Val Pro Ser Leu Pro Ile Val
450                 455                 460

Arg Glu Glu Ala Leu Ala Phe Arg Glu Ala Glu Gly Pro Val Leu
465                 470                 475                 480

Phe Gly Pro Arg Ser Gly Ser Lys Thr Glu Thr Phe Gln Ile Pro Lys
            485                 490                 495

Glu Leu Pro Pro Gly Pro Leu Gln Ala Leu Leu Pro Leu Lys Val Val
        500                 505                 510

Arg Val Glu Ser Leu Pro Pro Gly Leu Leu Glu Val Ala Glu Gly Ala
    515                 520                 525

Leu Gly Arg Phe Pro Leu Gly Leu Trp Arg Glu Trp Val Glu Ala Pro
530                 535                 540

Leu Lys Pro Leu Leu Thr Phe Gln Asp Gly Lys Gly Ala Leu Tyr Arg
545                 550                 555                 560

Glu Gly Arg Tyr Leu Tyr Leu Ala Ala Trp Pro Ser Pro Glu Leu Ala
            565                 570                 575

Gly Arg Leu Leu Ser Ala Leu Ala Glu Ala Gly Leu Lys Val Leu
        580                 585                 590

Ser Leu Pro Glu Gly Leu Arg Leu Arg Arg Gly Thr Trp Val Phe
    595                 600                 605

Ala Phe Asn Tyr Gly Pro Glu Ala Val Glu Ala Pro Ala Ser Glu Gly
610                 615                 620

Ala Arg Phe Leu Leu Gly Ser Arg Arg Val Gly Pro Tyr Asp Leu Ala
625                 630                 635                 640

Val Trp Glu Glu Ala
            645

<210> SEQ ID NO 37
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Val Asp Tyr Arg Val Val Phe His Ile Asp Glu Asp Asp Glu Ser
1               5                   10                  15

Arg Val Leu Leu Leu Ile Ser Asn Val Arg Asn Leu Met Ala Asp Leu
            20                  25                  30

Glu Ser Val Arg Ile Glu Val Val Ala Tyr Ser Met Gly Val Asn Val
        35                  40                  45

Leu Arg Arg Asp Ser Glu Tyr Ser Gly Asp Val Ser Glu Leu Thr Gly
    50                  55                  60

Gln Gly Val Arg Phe Cys Ala Cys Ser Asn Thr Leu Arg Ala Ser Gly
65                  70                  75                  80

Met Asp Gly Asp Asp Leu Leu Glu Gly Val Asp Val Val Ser Ser Gly
```

```
                        85                  90                  95
Val Gly His Ile Val Arg Arg Gln Thr Glu Gly Trp Ala Tyr Ile Arg
                100                 105                 110

Pro

<210> SEQ ID NO 38
<211> LENGTH: 308
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Asp Trp Lys Gly Arg Asp Val Ile Ser Ile Arg Asp Phe Ser Lys
1               5                   10                  15

Glu Asp Ile Glu Thr Val Leu Ala Thr Ala Glu Arg Leu Glu Arg Glu
            20                  25                  30

Leu Lys Glu Lys Gly Gln Leu Gly Tyr Ala Lys Gly Lys Ile Leu Ala
        35                  40                  45

Thr Leu Phe Phe Glu Pro Ser Thr Arg Thr Arg Leu Ser Phe Glu Ser
    50                  55                  60

Ala Met His Arg Leu Gly Gly Ala Val Ile Gly Phe Ala Glu Ala Ser
65                  70                  75                  80

Thr Ser Ser Val Lys Lys Gly Glu Ser Leu Arg Asp Thr Ile Lys Thr
                85                  90                  95

Val Glu Gln Tyr Cys Asp Val Ile Val Ile Arg His Pro Lys Glu Gly
            100                 105                 110

Ala Ala Arg Leu Ala Ala Glu Val Ala Glu Val Pro Val Ile Asn Ala
        115                 120                 125

Gly Asp Gly Ser Asn Gln His Pro Thr Gln Thr Leu Leu Asp Leu Tyr
    130                 135                 140

Thr Ile Lys Lys Glu Phe Gly Arg Ile Asp Gly Leu Lys Ile Gly Leu
145                 150                 155                 160

Leu Gly Asp Leu Lys Tyr Gly Arg Thr Val His Ser Leu Ala Glu Ala
                165                 170                 175

Leu Thr Phe Tyr Asp Val Glu Leu Tyr Leu Ile Ser Pro Glu Leu Leu
            180                 185                 190

Arg Met Pro Arg His Ile Val Glu Glu Leu Arg Glu Lys Gly Met Lys
        195                 200                 205

Val Val Glu Thr Thr Thr Leu Glu Asp Val Ile Gly Lys Leu Asp Val
    210                 215                 220

Leu Tyr Val Thr Arg Ile Gln Lys Glu Arg Phe Pro Asp Glu Gln Glu
225                 230                 235                 240

Tyr Leu Lys Val Lys Gly Ser Tyr Gln Val Asn Leu Lys Val Leu Glu
                245                 250                 255

Lys Ala Lys Asp Glu Leu Arg Ile Met His Pro Leu Pro Arg Val Asp
            260                 265                 270

Glu Ile His Pro Glu Val Asp Asn Thr Lys His Ala Ile Tyr Phe Arg
        275                 280                 285

Gln Val Phe Asn Gly Val Pro Val Arg Met Ala Leu Leu Ala Leu Val
    290                 295                 300

Leu Gly Val Ile
305
```

```
<210> SEQ ID NO 39
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Asn Ala Glu Ile Asn Pro Leu His Ala Tyr Phe Lys Leu Pro Asn
1               5                   10                  15

Thr Val Ser Leu Val Ala Gly Ser Ser Glu Gly Thr Pro Leu Asn
            20                  25                  30

Ala Phe Asp Gly Ala Leu Leu Asn Ala Gly Ile Gly Asn Val Asn Leu
        35                  40                  45

Ile Arg Ile Ser Ala Ile Met Pro Pro Glu Ala Glu Ile Val Pro Leu
    50                  55                  60

Pro Lys Leu Pro Met Gly Ala Leu Val Pro Thr Ala Tyr Gly Tyr Ile
65                  70                  75                  80

Ile Ser Asp Val Pro Gly Glu Thr Ile Ser Ala Ala Ile Ser Val Ala
                85                  90                  95

Ile Pro Lys Asp Lys Ser Leu Cys Gly Leu Ile Met Glu Tyr Glu Gly
            100                 105                 110

Lys Cys Ser Lys Lys Glu Ala Glu Lys Thr Val Arg Glu Met Ala Lys
        115                 120                 125

Ile Gly Phe Glu Met Arg Gly Trp Glu Leu Asp Arg Ile Glu Ser Ile
    130                 135                 140

Ala Val Glu His Thr Val Glu Lys Leu Gly Cys Ala Phe Ala Ala Ala
145                 150                 155                 160

Ala Leu Trp Tyr Lys
                165

<210> SEQ ID NO 40
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid

<400> SEQUENCE: 40

Xaa Ile Met Pro Pro Glu Ala Glu Ile Val Pro Leu Pro Lys Leu Pro
1               5                   10                  15

Met Gly Ala Leu Val Pro Thr Ala Tyr Gly Tyr Ile Ile Ser Asp Val
            20                  25                  30

Pro Gly Glu Thr Ile Ser Ala Ala Ile Ser Val Ala Ile Pro Lys Asp
        35                  40                  45

Lys Ser Leu Cys Gly Leu Ile Met Glu Tyr Glu Gly Lys Cys Ser Lys
    50                  55                  60

Lys Glu Ala Glu Lys Thr Val Arg Glu Met Ala Lys Ile Gly Phe Glu
65                  70                  75                  80

Met Arg Gly Trp Glu Leu Asp Arg Ile Glu Ser Ile Ala Val Glu His
                85                  90                  95

Thr Val Glu Lys Leu Gly Cys Ala Phe Ala Ala Ala Leu Trp Tyr
            100                 105                 110
```

Lys

<210> SEQ ID NO 41
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Asn Ala Glu Ile Asn Pro Leu His Ala Tyr Phe Lys Leu Pro Asn
1               5                   10                  15

Thr Val Ser Leu Val Ala Gly Ser Ser Glu Gly Glu Thr Pro Leu Asn
            20                  25                  30

Ala Phe Asp Gly Ala Leu Leu Asn Ala Gly Ile Gly Asn Val Asn Leu
        35                  40                  45

Ile Arg Ile Ser
    50

<210> SEQ ID NO 42
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Gly Ser Asp Lys Ile His His His His His Met Ile Leu Val
1               5                   10                  15

Tyr Ser Thr Phe Pro Asn Glu Glu Lys Ala Leu Glu Ile Gly Arg Lys
            20                  25                  30

Leu Leu Glu Lys Arg Leu Ile Ala Cys Phe Asn Ala Phe Glu Ile Arg
        35                  40                  45

Ser Gly Tyr Trp Trp Lys Gly Glu Ile Val Gln Asp Lys Glu Trp Ala
    50                  55                  60

Ala Ile Phe Lys Thr Thr Glu Glu Lys Glu Lys Glu Leu Tyr Glu Glu
65                  70                  75                  80

Leu Arg Lys Leu His Pro Tyr Glu Thr Pro Ala Ile Phe Thr Leu Lys
                85                  90                  95

Val Glu Asn Val Leu Thr Glu Tyr Met Asn Trp Leu Arg Glu Ser Val
            100                 105                 110

Leu

<210> SEQ ID NO 43
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Glu Ile Thr Val Asp Glu Phe Ser Asn Ile Arg Glu Asn Pro Val
1               5                   10                  15

Thr Pro Trp Asn Pro Glu Pro Ser Ala Pro Val Ile Asp Pro Thr Ala
            20                  25                  30

Tyr Ile Asp Pro Gln Ala Ser Val Ile Gly Glu Val Thr Ile Gly Ala
        35                  40                  45

```
Asn Val Met Val Ser Pro Met Ala Ser Ile Arg Ser Asp Glu Gly Met
 50                  55                  60

Pro Ile Phe Val Gly Asp Arg Ser Asn Val Gln Asp Gly Val Val Leu
 65                  70                  75                  80

His Ala Leu Glu Thr Ile Asn Glu Glu Gly Glu Pro Ile Glu Asp Asn
                 85                  90                  95

Ile Val Glu Val Asp Gly Lys Glu Tyr Ala Val Tyr Ile Gly Asn Asn
            100                 105                 110

Val Ser Leu Ala His Gln Ser Gln Val His Gly Pro Ala Ala Val Gly
        115                 120                 125

Asp Asp Thr Phe Ile Gly Met Gln Ala Phe Val Phe Lys Ser Lys Val
130                 135                 140

Gly Asn Asn Cys Val Leu Glu Pro Arg Ser Ala Ala Ile Gly Val Thr
145                 150                 155                 160

Ile Pro Asp Gly Arg Tyr Ile Pro Ala Gly Met Val Val Thr Ser Gln
                165                 170                 175

Ala Glu Ala Asp Lys Leu Pro Glu Val Thr Asp Asp Tyr Ala Tyr Ser
            180                 185                 190

His Thr Asn Glu Ala Val Val Tyr Val Asn Val His Leu Ala Glu Gly
        195                 200                 205

Tyr Lys Glu Thr Ser
210

<210> SEQ ID NO 44
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Val Arg Gly Ile Arg Gly Ala Ile Thr Val Glu Glu Asp Thr Pro
  1               5                  10                  15

Glu Ala Ile His Gln Ala Thr Arg Glu Leu Leu Leu Lys Met Leu Glu
             20                  25                  30

Ala Asn Gly Ile Gln Ser Tyr Glu Glu Leu Ala Ala Val Ile Phe Thr
         35                  40                  45

Val Thr Glu Asp Leu Thr Ser Ala Phe Pro Ala Glu Ala Ala Arg Gln
 50                  55                  60

Ile Gly Met His Arg Val Pro Leu Leu Ser Ala Arg Glu Val Pro Val
 65                  70                  75                  80

Pro Gly Ser Leu Pro Arg Val Ile Arg Val Leu Ala Leu Trp Asn Thr
                 85                  90                  95

Asp Thr Pro Gln Asp Arg Val Arg His Val Tyr Leu Arg Glu Ala Val
            100                 105                 110

Arg Leu Arg Pro Asp Leu Glu Ser Ala Gln
        115                 120

<210> SEQ ID NO 45
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45
```

```
Met Ile Ile Val Tyr Thr Thr Phe Pro Asp Trp Glu Ser Ala Glu Lys
1               5                   10                  15

Val Val Lys Thr Leu Leu Lys Glu Arg Leu Ile Ala Cys Ala Asn Leu
            20                  25                  30

Arg Glu His Arg Ala Phe Tyr Trp Trp Glu Gly Lys Ile Glu Glu Asp
        35                  40                  45

Lys Glu Val Gly Ala Ile Leu Lys Thr Arg Glu Asp Leu Trp Glu Glu
    50                  55                  60

Leu Lys Glu Arg Ile Lys Glu Leu His Pro Tyr Asp Val Pro Ala Ile
65                  70                  75                  80

Ile Arg Ile Asp Val Asp Val Asn Glu Asp Tyr Leu Lys Trp Leu
                85                  90                  95

Ile Glu Glu Thr Lys Lys
                100
```

<210> SEQ ID NO 46
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Met Arg Arg Gly Ser Gly Asn Pro Glu Arg Pro Ser Leu Ser Arg Asp
1               5                   10                  15

Gly Leu Arg Val Pro Pro Cys Pro Gly Lys Arg Gly Pro Gly His
            20                  25                  30

Phe Ser Gly Tyr His Gly Gly Met Glu Gly Ile Arg Arg Ala Ala Gln
        35                  40                  45

Arg Ala Ala Glu Glu Phe Leu Gln Ala Phe Pro Met Ala Pro Gly Ser
    50                  55                  60

Leu Phe Val Leu Gly Ser Thr Ser Glu Val Leu Gly Glu Arg Val
65                  70                  75                  80

Gly Thr Arg Pro Ser Leu Glu Ala Ala His Ala Val Leu Glu Gly Leu
                85                  90                  95

Leu Pro Pro Leu Leu Glu Arg Gly Val His Val Ala Val Gln Ala Cys
                100                 105                 110

Glu His Leu Asn Arg Ala Leu Val Val Glu Arg Glu Thr Ala Arg Ala
            115                 120                 125

Phe Gly Lys Glu Glu Val Ala Val Phe Pro His Pro Lys Ala Gly Gly
    130                 135                 140

Ala Lys Ala Thr Ala Ala Phe Leu Arg Phe Arg Asp Pro Val Met Val
145                 150                 155                 160

Glu Ser Leu Lys Ala Gln Ala His Gly Gly Met Asp Ile Gly Gly Val
                165                 170                 175

Leu Ile Gly Met His Leu Arg Pro Val Ala Val Pro Leu Arg Leu Ser
                180                 185                 190

Val Arg Lys Ile Gly Glu Ala Val Leu Leu Ala Ala Lys Thr Arg Pro
            195                 200                 205

Lys Leu Val Gly Gly Ala Arg Ala Val Tyr Thr Arg Glu Glu Met Leu
    210                 215                 220

Lys Lys Leu Glu Glu Phe Leu Pro Lys Pro Pro
225                 230                 235
```

<210> SEQ ID NO 47

```
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Gly Ser Asp Lys Ile His His His His His Met Glu Tyr Lys
1               5                   10                  15

Lys Phe Val Glu Ala Arg Arg Glu Leu Asn Glu Lys Val Leu Ser Arg
                20                  25                  30

Gly Thr Leu Asn Thr Lys Arg Phe Phe Asn Leu Asp Ser Ala Val Tyr
            35                  40                  45

Arg Pro Gly Lys Leu Asp Val Lys Thr Lys Glu Leu Met Gly Leu Val
        50                  55                  60

Ala Ser Thr Val Leu Arg Cys Asp Asp Cys Ile Arg Tyr His Leu Val
65                  70                  75                  80

Arg Cys Val Gln Glu Gly Ala Ser Asp Glu Ile Phe Glu Ala Leu
                85                  90                  95

Asp Ile Ala Leu Val Val Gly Gly Ser Ile Val Ile Pro His Leu Arg
                100                 105                 110

Arg Ala Val Gly Phe Leu Glu Glu Leu Arg Glu Met Glu Lys Asn Gly
            115                 120                 125

Glu Thr Ile Ser Leu
        130

<210> SEQ ID NO 48
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Thr Asp Met Ser Ile Lys Phe Glu Leu Ile Asp Val Pro Ile Pro
1               5                   10                  15

Gln Gly Thr Asn Val Ile Ile Gly Gln Ala His Phe Ile Lys Thr Val
                20                  25                  30

Glu Asp Leu Tyr Glu Ala Leu Val Thr Ser Val Pro Gly Val Lys Phe
            35                  40                  45

Gly Ile Ala Phe Cys Glu Ala Ser Gly Lys Arg Leu Val Arg His Glu
        50                  55                  60

Ala Asn Asp Glu Glu Leu Arg Asn Leu Ala Ile Asp Leu Cys Lys Lys
65                  70                  75                  80

Ile Ala Ala Gly His Val Phe Val Ile Tyr Ile Arg Asn Ala Trp Pro
                85                  90                  95

Ile Asn Val Leu Asn Ala Ile Lys Asn Val Pro Glu Val Arg Ile
                100                 105                 110

Phe Ala Ala Thr Ala Asn Pro Leu Lys Val Ile Val Ala Glu Val Glu
            115                 120                 125

Pro Glu Arg Arg Gly Val Gly Val Val Asp Gly His Ser Pro Leu
        130                 135                 140

Gly Val Glu Thr Glu Lys Asp Arg Glu Glu Arg Lys Lys Phe Leu Arg
145                 150                 155                 160

Glu Val Val Lys Tyr Lys Leu
                165
```

<210> SEQ ID NO 49
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Tyr Glu Leu Tyr Thr Leu Leu Ala Glu Tyr Asp Thr Ile Tyr
1               5                   10                  15

Arg Arg Arg Ile Glu Arg Val Lys Ala Glu Ile Asp Phe Val Glu Glu
            20                  25                  30

Ile Phe Lys Glu Asp Ala Lys Arg Glu Val Arg Val Leu Asp Leu
        35                  40                  45

Ala Cys Gly Thr Gly Ile Pro Thr Leu Glu Leu Ala Glu Arg Gly Tyr
    50                  55                  60

Glu Val Val Gly Leu Asp Leu His Glu Glu Met Leu Arg Val Ala Arg
65                  70                  75                  80

Arg Lys Ala Lys Glu Arg Asn Leu Lys Ile Glu Phe Leu Gln Gly Asp
                85                  90                  95

Val Leu Glu Ile Ala Phe Lys Asn Glu Phe Asp Ala Val Thr Met Phe
            100                 105                 110

Phe Ser Thr Ile Met Tyr Phe Asp Glu Asp Leu Arg Lys Leu Phe
        115                 120                 125

Ser Lys Val Ala Glu Ala Leu Lys Pro Gly Gly Val Phe Ile Thr Asp
130                 135                 140

Phe Pro Cys Trp Phe Tyr Gly Gly Arg Asp Gly Pro Val Val Trp Asn
145                 150                 155                 160

Glu Gln Lys Gly Glu Glu Lys Leu Val Ile Met Asp Trp Arg Glu Val
                165                 170                 175

Glu Pro Ala Val Gln Lys Leu Arg Phe Lys Arg Leu Val Gln Ile Leu
            180                 185                 190

Arg Pro Asn Gly Glu Val Lys Ala Phe Leu Val Asp Asp Glu Leu Asn
        195                 200                 205

Ile Tyr Thr Pro Arg Glu Val Arg Leu Leu Ala Glu Lys Tyr Phe Glu
    210                 215                 220

Lys Val Lys Ile Tyr Gly Asn Leu Lys Arg Glu Leu Ser Pro Asn Asp
225                 230                 235                 240

Met Arg Tyr Trp Ile Val Gly Ile Ala Lys Ser Phe
                245                 250

<210> SEQ ID NO 50
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gly Ser His Met Glu Thr Val Phe Thr Glu Lys Ala Pro Lys Pro Val
1               5                   10                  15

Gly Pro Tyr Ser Gln Ala Ile Lys Val Gly Asn Thr Leu Tyr Val Ser
            20                  25                  30

Gly Gln Ile Pro Ile Asp Pro Arg Thr Asn Glu Ile Val Lys Gly Asp
        35                  40                  45

-continued

```
Ile Lys Val Gln Thr Arg Gln Val Leu Asp Asn Ile Lys Glu Ile Val
 50                  55                  60

Lys Ala Ala Gly Phe Ser Leu Ser Asp Val Ala Met Ala Phe Val Phe
 65                  70                  75                  80

Leu Lys Asp Met Asn Met Phe Asn Asp Phe Asn Ser Val Tyr Ala Glu
                 85                  90                  95

Tyr Phe Lys Asp Lys Pro Pro Ala Arg Val Thr Val Glu Val Ser Arg
            100                 105                 110

Leu Pro Lys Asp Ala Leu Ile Glu Ile Ala Val Ile Cys Ser Lys Gly
        115                 120                 125
```

<210> SEQ ID NO 51
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Met Gly Ser Asp Lys Ile His His His His His Met Lys Arg Phe
 1               5                  10                  15

Val Glu Thr Asp Lys Ala Pro Lys Ala Ile Gly Pro Tyr Ser Gln Ala
                 20                  25                  30

Val Val Val Gly Asn Met Met Phe Val Ser Gly Gln Ile Pro Ile Asp
             35                  40                  45

Pro Glu Thr Gly Glu Leu Val Gln Gly Thr Ile Glu Glu Lys Thr Glu
 50                  55                  60

Arg Val Leu Glu Asn Leu Lys Ala Ile Leu Glu Ala Gly Gly Phe Ser
 65                  70                  75                  80

Leu Lys Asp Val Val Lys Val Thr Val Phe Thr Thr Ser Met Asp Tyr
                 85                  90                  95

Phe Gln Arg Val Asn Glu Val Tyr Ser Arg Tyr Phe Gly Asp His Arg
            100                 105                 110

Pro Ala Arg Ser Phe Val Ala Val Ala Gln Leu Pro Arg Asn Val Glu
        115                 120                 125

Ile Glu Ile Glu Ala Ile Ala Val Lys Glu Gly Glu
    130                 135                 140
```

<210> SEQ ID NO 52
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Gly Ser Ser His His His His His Ser Ser Gly Leu Val Pro Arg
 1               5                  10                  15

Gly Ser His Met Asp Leu Val Pro Leu Lys Leu Val Thr Ile Val Ala
                 20                  25                  30

Glu Ser Leu Leu Glu Lys Arg Leu Val Glu Val Lys Arg Leu Gly
             35                  40                  45

Ala Lys Gly Tyr Thr Ile Thr Pro Ala Arg Gly Glu Gly Ser Arg Gly
     50                  55                  60

Ile Arg Ser Val Asp Trp Glu Gly Gln Asn Ile Arg Leu Glu Thr Ile
 65                  70                  75                  80
```

-continued

Val Ser Glu Glu Val Ala Leu Arg Ile Leu Gln Arg Leu Gln Glu Glu
                85                  90                  95

Tyr Phe Pro His Tyr Ala Val Ile Ala Tyr Val Glu Asn Val Trp Val
            100                 105                 110

Val Arg Gly Glu Lys Tyr Val
        115

<210> SEQ ID NO 53
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Val Glu Val Glu His Trp Asn Thr Leu Arg Leu Arg Ile Tyr Ile
1               5                   10                  15

Gly Glu Asn Asp Lys Trp Glu Gly Arg Pro Leu Tyr Lys Val Ile Val
            20                  25                  30

Glu Lys Leu Arg Glu Met Gly Ile Ala Gly Ala Thr Val Tyr Arg Gly
        35                  40                  45

Ile Tyr Gly Phe Gly Lys Lys Ser Arg Val His Ser Ser Asp Val Ile
    50                  55                  60

Arg Leu Ser Thr Asp Leu Pro Ile Ile Val Glu Val Val Asp Arg Gly
65                  70                  75                  80

His Asn Ile Glu Lys Val Val Asn Val Ile Lys Pro Met Ile Lys Asp
                85                  90                  95

Gly Met Ile Thr Val Glu Pro Thr Ile Val Leu Trp Val Gly Thr Gln
            100                 105                 110

Glu Glu Ile Lys Lys Phe Glu Glu Asp Ala Ile Ala Glu Arg Gln
        115                 120                 125

<210> SEQ ID NO 54
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Arg Asn Gly Arg Ala Gly Pro Ser Asp Ser Ala Phe Ser Phe Thr Lys
1               5                   10                  15

Ser Arg Ala Arg Val Leu Thr Glu Ala Pro Lys Val Thr Phe Lys Asp
            20                  25                  30

Val Ala Gly Ala Glu Glu Ala Lys Glu Glu Leu Lys Glu Ile Val Glu
        35                  40                  45

Phe Leu Lys Asn Pro Ser Arg Phe His Glu Met Gly Ala Arg Ile Pro
    50                  55                  60

Lys Gly Val Leu Leu Val Gly Pro Pro Gly Val Gly Lys Thr His Leu
65                  70                  75                  80

Ala Arg Ala Val Ala Gly Glu Ala Arg Val Pro Phe Ile Thr Ala Ser
                85                  90                  95

Gly Ser Asp Phe Val Glu Met Phe Val Gly Val Gly Ala Ala Arg Val
            100                 105                 110

Arg Asp Leu Phe Glu Thr Ala Lys Arg His Ala Pro Cys Ile Val Phe
        115                 120                 125

Ile Asp Glu Ile Asp Ala Val Gly Arg Lys Arg Gly Ser Val Gly
        130                 135                 140

Gly Gly Asn Asp Glu Arg Glu Gln Thr Leu Asn Gln Leu Leu Val Glu
145                 150                 155                 160

Met Asp Gly Phe Glu Lys Asp Thr Ala Ile Val Val Met Ala Ala Thr
                165                 170                 175

Asn Arg Pro Asp Ile Leu Asp Pro Ala Leu Leu Arg Pro Gly Arg Phe
                180                 185                 190

Asp Arg Gln Ile Ala Ile Asp Ala Pro Asp Val Lys Gly Arg Glu Gln
                195                 200                 205

Ile Leu Arg Ile His Ala Arg Gly Lys Pro Leu Ala Glu Asp Val Asp
210                 215                 220

Leu Ala Leu Leu Ala Lys Arg Thr Pro Gly Phe Val Gly Ala Asp Leu
225                 230                 235                 240

Glu Asn Leu Leu Asn Glu Ala Ala Leu Leu Ala Ala Arg Glu Gly Arg
                245                 250                 255

Arg Lys Ile Thr Met Lys Asp Leu Glu Glu Ala Ala Asp Arg Val Met
                260                 265                 270

Met Leu Pro Ala Lys Lys Ser Leu Val Leu Ser Pro Arg Asp Arg Arg
                275                 280                 285

Ile Thr Ala Tyr His Glu Ala Gly His Ala Leu Ala Ala His Phe Leu
                290                 295                 300

Glu His Ala Asp Gly Val His Lys Val Thr Ile Val Pro Arg Gly Arg
305                 310                 315                 320

Ala Leu Gly Phe Met Met Pro Arg Arg Glu Asp Met Leu His Trp Ser
                325                 330                 335

Arg Lys Arg Leu Leu Asp Gln Ile Ala Val Ala Leu Ala Gly Arg Ala
                340                 345                 350

Ala Glu Glu Ile Val Phe Asp Asp Val Thr Thr Gly Ala Glu Asn Asp
                355                 360                 365

Phe Arg Gln Ala Thr Glu Leu Ala Arg Arg Met Ile Thr Glu Trp Gly
                370                 375                 380

Met His Pro Glu Phe Gly Pro Val Ala Tyr Ala Val Arg Glu Asp Thr
385                 390                 395                 400

Tyr Leu Gly Gly Tyr Asp Val Arg Gln Tyr Ser Glu Glu Thr Ala Lys
                405                 410                 415

Arg Ile Asp Glu Ala Val Arg Arg Leu Ile Glu Gln Tyr Gln Arg
                420                 425                 430

Val Lys Ala Leu Leu Leu Glu Lys Arg Glu Val Leu Glu Arg Val Ala
                435                 440                 445

Glu Thr Leu Leu Glu Arg Glu Thr Leu Thr Ala Glu Glu Phe Gln Arg
                450                 455                 460

Val Val Glu Gly Leu Pro Leu Glu Ala Pro Glu Glu Ala Arg Glu Glu
465                 470                 475                 480

Arg Glu Pro Pro Arg Val Val Pro Lys Val Lys Pro Gly Gly Ala Leu
                485                 490                 495

Gly Gly Ala

<210> SEQ ID NO 55
<211> LENGTH: 143
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

```
Met Val Thr Gly Met Phe Ser Leu Gly Arg Thr Tyr Leu Phe Arg Val
1               5                   10                  15

Pro Glu Gly Glu Glu Leu Leu Thr Tyr Ile Lys Asn Phe Cys Lys Lys
            20                  25                  30

Glu Gly Ile Glu Thr Ala Ile Ile Asn Gly Ile Gly Thr Leu Lys Asn
        35                  40                  45

Pro Lys Ile Gly Tyr Phe Leu Glu Glu Lys Leu Glu Tyr Lys Val Ile
    50                  55                  60

Pro Leu Lys Gly Ser Tyr Glu Leu Ile Ser Leu Ile Gly Asn Val Ser
65                  70                  75                  80

Leu Lys Asp Gly Glu Pro Phe Val His Ala His Val Ser Leu Gly Asn
                85                  90                  95

Glu Glu Gly Ile Val Phe Gly Gly His Leu Val Glu Gly Glu Val Phe
            100                 105                 110

Val Ala Glu Ile Phe Leu Gln Glu Leu Lys Gly Glu Lys Ile Glu Arg
        115                 120                 125

Lys Pro Thr Lys Tyr Gly Leu Ala Leu Trp Glu Glu Leu Lys Leu
    130                 135                 140
```

<210> SEQ ID NO 56
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

```
Met Phe Lys Ile Val Tyr Pro Asn Ala Lys Asp Phe Phe Ser Phe Ile
1               5                   10                  15

Asn Ser Ile Thr Asn Val Thr Asp Ser Ile Ile Leu Asn Phe Thr Glu
            20                  25                  30

Asp Gly Ile Phe Ser Arg His Leu Thr Glu Asp Lys Val Leu Met Ala
        35                  40                  45

Ile Met Arg Ile Pro Lys Asp Val Leu Ser Glu Tyr Ser Ile Asp Ser
    50                  55                  60

Pro Thr Ser Val Lys Leu Asp Val Ser Ser Val Lys Lys Ile Leu Ser
65                  70                  75                  80

Lys Ala Ser Ser Lys Lys Ala Thr Ile Glu Leu Thr Glu Thr Asp Ser
                85                  90                  95

Gly Leu Lys Ile Ile Ile Arg Asp Glu Lys Ser Gly Ala Lys Ser Thr
            100                 105                 110

Ile Tyr Ile Lys Ala Glu Lys Gly Gln Val Glu Gln Leu Thr Glu Pro
        115                 120                 125

Lys Val Asn Leu Ala Val Asn Phe Thr Thr Asp Glu Ser Val Leu Asn
    130                 135                 140

Val Ile Ala Ala Asp Val Thr Leu Val Gly Glu Glu Met Arg Ile Ser
145                 150                 155                 160

Thr Glu Glu Asp Lys Ile Lys Ile Glu Ala Gly Glu Gly Lys Arg
                165                 170                 175

Tyr Val Ala Phe Leu Met Lys Asp Lys Pro Leu Lys Glu Leu Ser Ile
            180                 185                 190

Asp Thr Ser Ala Ser Ser Ser Tyr Ser Ala Glu Met Phe Lys Asp Ala
```

```
                195                 200                 205
Val Lys Gly Leu Arg Gly Phe Ser Ala Pro Thr Met Val Ser Phe Gly
    210                 215                 220

Glu Asn Leu Pro Met Lys Ile Asp Val Glu Ala Val Ser Gly Gly His
225                 230                 235                 240

Met Ile Phe Trp Ile Ala Pro Arg Leu Leu Glu His His His His
                245                 250                 255

His

<210> SEQ ID NO 57
<211> LENGTH: 422
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Gly Leu Tyr Arg Lys Tyr Ile Glu Tyr Pro Val Leu Ile Lys Ile
1               5                   10                  15

Leu Ile Gly Leu Ile Leu Gly Ala Ile Val Gly Leu Ile Leu Gly His
                20                  25                  30

Tyr Gly Tyr Ala His Ala Val His Thr Tyr Val Lys Pro Phe Gly Asp
            35                  40                  45

Leu Phe Val Arg Leu Leu Lys Met Leu Val Met Pro Ile Val Phe Ala
        50                  55                  60

Ser Leu Val Val Gly Ala Ala Ser Ile Ser Pro Ala Arg Leu Gly Arg
65                  70                  75                  80

Val Gly Val Lys Ile Val Val Tyr Tyr Leu Leu Thr Ser Ala Phe Ala
                85                  90                  95

Val Thr Leu Gly Ile Ile Met Ala Arg Leu Phe Asn Pro Gly Ala Gly
            100                 105                 110

Ile His Leu Ala Val Gly Gly Gln Gln Phe Gln Pro His Gln Ala Pro
        115                 120                 125

Pro Leu Val His Ile Leu Leu Asp Ile Val Pro Thr Asn Pro Phe Gly
130                 135                 140

Ala Leu Ala Asn Gly Gln Val Leu Pro Thr Ile Phe Phe Ala Ile Ile
145                 150                 155                 160

Leu Gly Ile Ala Ile Thr Tyr Leu Met Asn Ser Glu Asn Glu Lys Val
                165                 170                 175

Arg Lys Ser Ala Glu Thr Leu Leu Asp Ala Ile Asn Gly Leu Ala Glu
            180                 185                 190

Ala Met Tyr Lys Ile Val Asn Gly Val Met Gln Tyr Ala Pro Ile Gly
        195                 200                 205

Val Phe Ala Leu Ile Ala Tyr Val Met Ala Glu Gln Gly Val His Val
210                 215                 220

Val Gly Glu Leu Ala Lys Val Thr Ala Ala Val Tyr Val Gly Leu Thr
225                 230                 235                 240

Leu Gln Ile Leu Leu Val Tyr Phe Val Leu Leu Lys Ile Tyr Gly Ile
                245                 250                 255

Asp Pro Ile Ser Phe Ile Lys His Ala Lys Asp Ala Met Leu Thr Ala
            260                 265                 270

Phe Val Thr Arg Ser Ser Ser Gly Thr Leu Pro Val Thr Met Arg Val
        275                 280                 285

Ala Lys Glu Met Gly Ile Ser Glu Gly Ile Tyr Ser Phe Thr Leu Pro
```

```
                290                 295                 300
Leu Gly Ala Thr Ile Asn Met Asp Gly Thr Ala Leu Tyr Gln Gly Val
305                 310                 315                 320

Cys Thr Phe Phe Ile Ala Asn Ala Leu Gly Ser His Leu Thr Val Gly
                325                 330                 335

Gln Gln Leu Thr Ile Val Leu Thr Ala Val Leu Ala Ser Ile Gly Thr
            340                 345                 350

Ala Gly Val Pro Gly Ala Gly Ala Ile Met Leu Ala Met Val Leu His
        355                 360                 365

Ser Val Gly Leu Pro Leu Thr Asp Pro Asn Val Ala Ala Ala Tyr Ala
        370                 375                 380

Met Ile Leu Gly Ile Asp Ala Ile Leu Asp Met Gly Arg Thr Met Val
385                 390                 395                 400

Asn Val Thr Gly Asp Leu Thr Gly Thr Ala Ile Val Ala Lys Thr Glu
                405                 410                 415

Gly Thr Leu Val Pro Arg
            420

<210> SEQ ID NO 58
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Lys Trp Val Met Ser Thr Lys Tyr Val Glu Ala Gly Glu Leu Lys Glu
1               5                   10                  15

Gly Ser Tyr Val Val Ile Asp Gly Glu Pro Cys Arg Val Val Glu Ile
            20                  25                  30

Glu Lys Ser Lys Thr Gly Lys His Gly Ser Ala Lys Ala Arg Ile Val
        35                  40                  45

Ala Val Gly Val Phe Asp Gly Gly Lys Arg Thr Leu Ser Leu Pro Val
    50                  55                  60

Asp Ala Gln Val Glu Val Pro Ile Ile Glu Lys Phe Thr Ala Gln Ile
65                  70                  75                  80

Leu Ser Val Ser Gly Asp Val Ile Gln Leu Met Asp Met Arg Asp Tyr
                85                  90                  95

Lys Thr Ile Glu Val Pro Met Lys Tyr Val Glu Glu Ala Lys Gly
            100                 105                 110

Arg Leu Ala Pro Gly Ala Glu Val Glu Val Trp Gln Ile Leu Asp Arg
        115                 120                 125

Tyr Lys Ile Ile Arg Val Lys Gly
    130                 135

<210> SEQ ID NO 59
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Gly Ser Ser His His His His His His Ser Ser Gly Arg Glu Asn
1               5                   10                  15

Leu Tyr Phe Gln Gly His Met Asn Gly Ala Arg Lys Trp Phe Phe Pro
```

```
                20                  25                  30
Asp Gly Tyr Ile Pro Asn Gly Lys Arg Gly Tyr Leu Val Ser His Glu
            35                  40                  45

Ser Leu Cys Ile Met Asn Thr Gly Asp Glu Thr Ala Lys Ile Arg Ile
        50                  55                  60

Thr Phe Leu Phe Glu Asp Ser Lys Pro Val Val His Glu Val Glu Ile
65                  70                  75                  80

Ser Pro Met Lys Ser Leu His Leu Arg Leu Asp Lys Leu Gly Ile Pro
                85                  90                  95

Lys Cys Lys Pro Tyr Ser Ile Met Ala Glu Ser Asn Val Pro Val Val
            100                 105                 110

Met Gln Leu Ser Arg Leu Asp Val Gly Lys Asn His Tyr Thr Leu Met
        115                 120                 125

Thr Thr Ile Gly Tyr Trp Glu Glu Gly Ser
130                 135

<210> SEQ ID NO 60
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Gly Ser Asp Lys Ile His His His His His Met Lys Glu Ala
1               5                   10                  15

Leu Thr Phe Asp Asp Val Leu Leu Val Pro Gln Tyr Ser Glu Val Leu
                20                  25                  30

Pro Lys Asp Val Lys Ile Asp Thr Arg Leu Thr Arg Gln Ile Arg Ile
            35                  40                  45

Asn Ile Pro Leu Val Ser Ala Ala Met Asp Thr Val Thr Glu Ala Ala
        50                  55                  60

Leu Ala Lys Ala Leu Ala Arg Glu Gly Gly Ile Gly Ile Ile His Lys
65                  70                  75                  80

Asn Leu Thr Pro Asp Glu Gln Ala Arg Gln Val Ser Ile Val Lys Lys
                85                  90                  95

Thr Glu Asn Gly Ile Ile Tyr Asp Pro Ile Thr Val Thr Pro Asp Met
            100                 105                 110

Thr Val Lys Glu Ala Ile Asp Leu Met Ala Glu Tyr Lys Ile Gly Gly
        115                 120                 125

Leu Pro Val Val Asp Glu Glu Gly Arg Leu Val Gly Leu Leu Thr Asn
130                 135                 140

Arg Asp Val Arg Phe Glu Lys Asn Leu Ser Lys Lys Ile Lys Asp Leu
145                 150                 155                 160

Met Thr Pro Arg Glu Lys Leu Ile Val Ala Pro Pro Asp Ile Ser Leu
                165                 170                 175

Glu Lys Ala Lys Glu Ile Leu His Gln His Arg Ile Glu Lys Leu Pro
            180                 185                 190

Leu Val Ser Lys Asp Asn Lys Leu Val Gly Leu Ile Thr Ile Lys Asp
        195                 200                 205

Ile Met Ser Val Ile Glu His Pro Asn Ala Ala Arg Asp Glu Lys Gly
210                 215                 220

Arg Leu Leu Val Gly Ala Ala Val Gly Thr Ser Pro Glu Thr Met Glu
225                 230                 235                 240
```

```
Arg Val Glu Lys Leu Val Lys Ala Gly Val Asp Ile Val Ile Asp
                245                 250                 255

Thr Ala His Gly His Ser Arg Val Ile Glu Thr Leu Glu Met Ile
            260                 265                 270

Lys Ala Asp Tyr Pro Asp Leu Pro Val Ala Gly Asn Val Ala Thr
        275                 280                 285

Pro Glu Gly Thr Glu Ala Leu Ile Lys Ala Gly Ala Asp Ala Val Lys
    290                 295                 300

Val Gly Val Gly Pro Gly Ser Ile Cys Thr Thr Arg Val Val Ala Gly
305                 310                 315                 320

Val Gly Val Pro Gln Leu Thr Ala Val Met Glu Cys Ser Glu Val Ala
                325                 330                 335

Arg Lys Tyr Asp Val Pro Ile Ile Ala Asp Gly Gly Ile Arg Tyr Ser
            340                 345                 350

Gly Asp Ile Val Lys Ala Leu Ala Ala Gly Ala Glu Ser Val Met Val
        355                 360                 365

Gly Ser Ile Phe Ala Gly Thr Glu Glu Ala Pro Gly Glu Thr Ile Leu
    370                 375                 380

Tyr Gln Gly Arg Lys Tyr Lys Ala Tyr Arg Gly Met Gly Ser Leu Gly
385                 390                 395                 400

Ala Met Arg Ser Gly Ser Ala Asp Arg Tyr Gly Gln Glu Gly Glu Asn
                405                 410                 415

Lys Phe Val Pro Glu Gly Ile Glu Gly Met Val Pro Tyr Lys Gly Thr
            420                 425                 430

Val Lys Asp Val Val His Gln Leu Val Gly Leu Arg Ser Gly Met
        435                 440                 445

Gly Tyr Ile Gly Ala Arg Thr Ile Lys Glu Leu Gln Glu Lys Ala Val
    450                 455                 460

Phe Val Lys Ile Thr Pro Ala Gly Val Lys Glu Ser His Pro His Asp
465                 470                 475                 480

Ile Ile Ile Thr Lys Glu Ser Pro Asn Tyr Trp Val Gln Ala
                485                 490

<210> SEQ ID NO 61
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Gly Lys Phe Val Glu Lys Leu Glu Lys Ala Ile Lys Gly Tyr Thr
1               5                   10                  15

Phe Asp Asp Val Leu Leu Ile Pro Gln Ala Thr Glu Val Glu Pro Lys
                20                  25                  30

Asp Val Asp Val Ser Thr Arg Ile Thr Pro Asn Val Lys Leu Asn Ile
            35                  40                  45

Pro Ile Leu Ser Ala Ala Met Asp Thr Val Thr Glu Trp Glu Met Ala
        50                  55                  60

Val Ala Met Ala Arg Glu Gly Gly Leu Gly Val Ile His Arg Asn Met
65                  70                  75                  80

Gly Ile Glu Glu Gln Val Glu Gln Val Lys Arg Val Lys Arg Ala Glu
                85                  90                  95

Arg Leu Ile Val Glu Asp Val Ile Thr Ile Ala Pro Asp Glu Thr Val
            100                 105                 110
```

Asp Phe Ala Leu Phe Leu Met Glu Lys His Gly Ile Asp Gly Leu Pro
            115                 120                 125

Val Val Glu Asp Glu Lys Val Val Gly Ile Ile Thr Lys Lys Asp Ile
        130                 135                 140

Ala Ala Arg Glu Gly Lys Leu Val Lys Glu Leu Met Thr Lys Glu Val
145                 150                 155                 160

Ile Thr Val Pro Glu Ser Ile Glu Val Glu Ala Leu Lys Ile Met
                165                 170                 175

Ile Glu Asn Arg Ile Asp Arg Leu Pro Val Val Asp Glu Arg Gly Lys
            180                 185                 190

Leu Val Gly Leu Ile Thr Met Ser Asp Leu Val Ala Arg Lys Lys Tyr
        195                 200                 205

Lys Asn Ala Val Arg Asp Glu Asn Gly Glu Leu Leu Val Ala Ala Ala
210                 215                 220

Val Ser Pro Phe Asp Ile Lys Arg Ala Ile Glu Leu Asp Lys Ala Gly
225                 230                 235                 240

Val Asp Val Ile Val Val Asp Thr Ala His Ala His Asn Leu Lys Ala
                245                 250                 255

Ile Lys Ser Met Lys Glu Met Arg Gln Lys Val Asp Ala Asp Phe Ile
            260                 265                 270

Val Gly Asn Ile Ala Asn Pro Lys Ala Val Asp Asp Leu Thr Phe Ala
        275                 280                 285

Asp Ala Val Lys Val Gly Ile Gly Pro Gly Ser Ile Cys Thr Thr Arg
290                 295                 300

Ile Val Ala Gly Val Gly Val Pro Gln Ile Thr Ala Val Ala Met Val
305                 310                 315                 320

Ala Asp Arg Ala Gln Glu Tyr Gly Leu Tyr Val Ile Ala Asp Gly Gly
                325                 330                 335

Ile Arg Tyr Ser Gly Asp Ile Val Lys Ala Ile Ala Ala Gly Ala Asp
            340                 345                 350

Ala Val Met Leu Gly Asn Leu Leu Ala Gly Thr Lys Glu Ala Pro Gly
        355                 360                 365

Lys Glu Val Ile Ile Asn Gly Arg Lys Tyr Lys Gln Tyr Arg Gly Met
370                 375                 380

Gly Ser Leu Gly Ala Met Met Lys Gly Gly Ala Glu Arg Tyr Tyr Gln
385                 390                 395                 400

Gly Gly Tyr Met Lys Thr Arg Lys Phe Val Pro Glu Gly Val Glu Gly
                405                 410                 415

Val Val Pro Tyr Arg Gly Thr Val Ser Glu Val Leu Tyr Gln Leu Val
            420                 425                 430

Gly Gly Leu Lys Ala Gly Met Gly Tyr Val Gly Ala Arg Asn Ile Arg
        435                 440                 445

Glu Leu Lys Glu Lys Gly Glu Phe Val Ile Ile Thr His Ala Gly Ile
450                 455                 460

Lys Glu Ser His Pro His Asp Ile Ile Ile Thr Asn Glu Ala Pro Asn
465                 470                 475                 480

Tyr Pro Leu Glu Lys Phe
                485

<210> SEQ ID NO 62
<211> LENGTH: 200
<212> TYPE: PRT
<213> ORGANISM: Artificial Sequence
<220> FEATURE:

-continued

<223> OTHER INFORMATION: Description of Artificial Sequence: Synthetic
     polypeptide

<400> SEQUENCE: 62

```
Met Arg Ala Arg Leu Tyr Ala Ala Phe Arg Gln Val Gly Glu Asp Leu
1               5                   10                  15

Phe Ala Gln Gly Leu Ile Ser Ala Thr Ala Gly Asn Phe Ser Val Arg
            20                  25                  30

Thr Lys Gly Gly Phe Leu Ile Thr Lys Ser Gly Val Gln Lys Ala Arg
        35                  40                  45

Leu Thr Pro Glu Asp Leu Leu Glu Val Pro Leu Glu Gly Pro Ile Pro
    50                  55                  60

Glu Gly Ala Ser Val Glu Ser Val Val His Arg Glu Val Tyr Arg Arg
65                  70                  75                  80

Thr Gly Ala Arg Ala Leu Val His Ala His Pro Arg Val Ala Val Ala
                85                  90                  95

Leu Ser Phe His Leu Ser Arg Leu Arg Pro Leu Asp Leu Glu Gly Gln
            100                 105                 110

His Tyr Leu Lys Glu Val Pro Val Leu Ala Pro Lys Thr Val Ser Ala
        115                 120                 125

Thr Glu Glu Ala Ala Leu Ser Val Ala Glu Ala Leu Arg Glu His Arg
    130                 135                 140

Ala Cys Leu Leu Arg Gly His Gly Ala Phe Ala Val Gly Leu Lys Glu
145                 150                 155                 160

Ala Pro Glu Glu Ala Leu Leu Glu Ala Tyr Gly Leu Met Thr Thr Leu
                165                 170                 175

Glu Glu Ser Ala Gln Ile Leu Leu Tyr His Arg Leu Trp Gln Gly Ala
            180                 185                 190

Gly Pro Ala Leu Gly Gly Gly Glu
        195                 200
```

<210> SEQ ID NO 63
<211> LENGTH: 200
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 63

```
Met Arg Ala Arg Leu Tyr Ala Ala Phe Arg Gln Val Gly Glu Asp Leu
1               5                   10                  15

Phe Ala Gln Gly Leu Ile Ser Ala Thr Ala Gly Asn Phe Ser Val Arg
            20                  25                  30

Thr Lys Gly Gly Phe Leu Ile Thr Lys Ser Gly Val Gln Lys Ala Arg
        35                  40                  45

Leu Thr Pro Glu Asp Leu Leu Glu Val Pro Leu Glu Gly Pro Ile Pro
    50                  55                  60

Glu Gly Ala Ser Val Glu Ser Val Val His Arg Glu Val Tyr Arg Arg
65                  70                  75                  80

Thr Gly Ala Arg Ala Leu Val His Ala His Pro Arg Val Ala Val Ala
                85                  90                  95

Leu Ser Phe His Leu Ser Arg Leu Arg Pro Leu Asp Leu Glu Gly Gln
            100                 105                 110

His Tyr Leu Lys Glu Val Pro Val Leu Ala Pro Lys Thr Val Ser Ala
        115                 120                 125
```

```
Thr Glu Glu Ala Ala Leu Ser Val Ala Glu Ala Leu Arg Glu His Arg
    130                 135                 140

Ala Cys Leu Leu Arg Gly His Gly Ala Phe Ala Val Gly Leu Lys Glu
145                 150                 155                 160

Ala Pro Glu Glu Ala Leu Leu Glu Ala Tyr Gly Leu Met Thr Thr Leu
                165                 170                 175

Glu Glu Ser Ala Gln Ile Leu Leu Tyr His Arg Leu Trp Gln Gly Ala
            180                 185                 190

Gly Pro Ala Leu Gly Gly Gly Glu
        195                 200

<210> SEQ ID NO 64
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Ser Glu Ala Ala Gln Thr Leu Asp Gly Trp Tyr Cys Leu His Asp
1               5                   10                  15

Phe Arg Thr Ile Asp Trp Ser Ala Trp Lys Thr Leu Pro Asn Glu Glu
                20                  25                  30

Arg Glu Ala Ala Ile Ser Glu Phe Leu Ala Leu Val Asp Gln Trp Glu
            35                  40                  45

Thr Thr Glu Ser Glu Lys Gln Gly Ser His Ala Val Tyr Thr Ile Val
        50                  55                  60

Gly Gln Lys Ala Asp Ile Leu Phe Met Ile Leu Arg Pro Thr Leu Asp
65                  70                  75                  80

Glu Leu His Glu Ile Glu Thr Ala Leu Asn Lys Thr Lys Leu Ala Asp
                85                  90                  95

Tyr Leu Leu Pro Ala Tyr Ser Tyr Val Ser Val Val Glu Leu Ser Asn
            100                 105                 110

Tyr Leu Ala Ser Gly Ser Glu Asp Pro Tyr Gln Ile Pro Glu Val Arg
        115                 120                 125

Arg Arg Leu Tyr Pro Ile Leu Pro Lys Thr Asn Tyr Ile Cys Phe Tyr
130                 135                 140

Pro Met Asp Lys Arg Arg Gln Gly Asn Asp Asn Trp Tyr Met Leu Ser
145                 150                 155                 160

Met Glu Gln Arg Arg Glu Leu Met Arg Ala His Gly
                165                 170

<210> SEQ ID NO 65
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Ala Asn Leu Thr Glu Lys Phe Leu Arg Ile Phe Ala Arg Arg Gly
1               5                   10                  15

Lys Ser Ile Ile Leu Ala Tyr Asp His Gly Ile Glu His Gly Pro Ala
                20                  25                  30

Asp Phe Met Asp Asn Pro Asp Ser Ala Asp Pro Glu Tyr Ile Leu Arg
            35                  40                  45
```

```
Leu Ala Arg Asp Ala Gly Phe Asp Gly Val Val Phe Gln Arg Gly Ile
 50                  55                  60

Ala Glu Lys Tyr Tyr Asp Gly Ser Val Pro Leu Ile Leu Lys Leu Asn
 65                  70                  75                  80

Gly Lys Thr Thr Leu Tyr Asn Gly Pro Val Ser Val Ala Asn Cys
                 85                  90                  95

Ser Val Glu Glu Ala Val Ser Leu Gly Ala Ser Ala Val Gly Tyr Thr
            100                 105                 110

Ile Tyr Pro Gly Ser Gly Phe Glu Trp Lys Met Phe Glu Glu Leu Ala
            115                 120                 125

Arg Ile Lys Arg Asp Ala Val Lys Phe Asp Leu Pro Leu Val Val Glu
130                 135                 140

Ser Phe Pro Arg Gly Gly Lys Val Val Asn Glu Thr Ala Pro Glu Ile
145                 150                 155                 160

Val Ala Tyr Ala Ala Arg Ile Ala Leu Glu Leu Gly Ala Asp Ala Met
                165                 170                 175

Lys Ile Lys Tyr Thr Gly Asp Pro Lys Thr Phe Ser Trp Ala Val Lys
            180                 185                 190

Val Ala Gly Lys Val Pro Val Leu Met Ser Gly Gly Pro Lys Thr Lys
            195                 200                 205

Thr Glu Glu Asp Phe Leu Lys Gln Val Glu Gly Val Leu Glu Ala Gly
        210                 215                 220

Ala Leu Gly Ile Ala Val Gly Arg Asn Val Trp Gln Arg Arg Asp Ala
225                 230                 235                 240

Leu Lys Phe Ala Arg Ala Leu Ala Glu Leu Val Tyr Gly Gly Lys Lys
                245                 250                 255

Leu Ala Glu Pro Leu Asn Val
            260

<210> SEQ ID NO 66
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Thr Lys Lys Val Gly Ile Val Asp Thr Thr Phe Ala Arg Val Asp
 1               5                  10                  15

Met Ala Ser Ile Ala Ile Lys Lys Leu Lys Glu Leu Ser Pro Asn Ile
             20                  25                  30

Lys Ile Ile Arg Lys Thr Val Pro Gly Ile Lys Asp Leu Pro Val Ala
            35                  40                  45

Cys Lys Lys Leu Leu Glu Glu Glu Gly Cys Asp Ile Val Met Ala Leu
 50                  55                  60

Gly Met Pro Gly Lys Ala Glu Lys Asp Lys Val Cys Ala His Glu Ala
 65                  70                  75                  80

Ser Leu Gly Leu Met Leu Ala Gln Leu Met Thr Asn Lys His Ile Ile
                 85                  90                  95

Glu Val Phe Val His Glu Asp Glu Ala Lys Asp Lys Glu Leu Asp
            100                 105                 110

Trp Leu Ala Lys Arg Arg Ala Glu Glu His Ala Glu Asn Val Tyr Tyr
            115                 120                 125

Leu Leu Phe Lys Pro Glu Tyr Leu Thr Arg Met Ala Gly Lys Gly Leu
            130                 135                 140
```

```
Arg Gln Gly Phe Glu Asp Ala Gly Pro Ala Arg Glu
145                 150                 155
```

<210> SEQ ID NO 67
<211> LENGTH: 269
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

```
Gly Ser His Met Glu Glu Lys Arg Leu Ser Ala Lys Lys Gly Leu Pro
1               5                   10                  15

Pro Gly Thr Leu Val Tyr Thr Gly Lys Tyr Arg Glu Asp Phe Glu Ile
                20                  25                  30

Glu Val Met Asn Tyr Ser Ile Glu Glu Phe Arg Glu Phe Lys Thr Thr
            35                  40                  45

Asp Val Glu Ser Val Leu Pro Phe Arg Asp Ser Ser Thr Pro Thr Trp
        50                  55                  60

Ile Asn Ile Thr Gly Ile His Arg Thr Asp Val Val Gln Arg Val Gly
65                  70                  75                  80

Glu Phe Phe Gly Thr His Pro Leu Val Leu Glu Asp Ile Leu Asn Val
                85                  90                  95

His Gln Arg Pro Lys Val Glu Phe Phe Glu Asn Tyr Val Phe Ile Val
            100                 105                 110

Leu Lys Met Phe Thr Tyr Asp Lys Asn Leu His Glu Leu Glu Ser Glu
        115                 120                 125

Gln Val Ser Leu Ile Leu Thr Lys Asn Cys Val Leu Met Phe Gln Glu
    130                 135                 140

Lys Ile Gly Asp Val Phe Asp Pro Val Arg Glu Arg Ile Arg Tyr Asn
145                 150                 155                 160

Arg Gly Ile Ile Arg Lys Lys Arg Ala Asp Tyr Leu Leu Tyr Ser Leu
                165                 170                 175

Ile Asp Ala Leu Val Asp Asp Tyr Phe Val Leu Leu Glu Lys Ile Asp
            180                 185                 190

Asp Glu Ile Asp Val Leu Glu Glu Val Leu Glu Arg Pro Glu Lys
        195                 200                 205

Glu Thr Val Gln Arg Thr His Gln Leu Lys Arg Asn Leu Val Glu Leu
    210                 215                 220

Arg Lys Thr Ile Trp Pro Leu Arg Glu Val Leu Ser Ser Leu Tyr Arg
225                 230                 235                 240

Asp Val Pro Pro Leu Ile Glu Lys Glu Thr Val Pro Tyr Phe Arg Asp
                245                 250                 255

Val Tyr Asp His Thr Ile Gln Ile Ala Asp Thr Val Glu
            260                 265
```

<210> SEQ ID NO 68
<211> LENGTH: 354
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Gly Ser His Met Glu Glu Lys Arg Leu Ser Ala Lys Lys Gly Leu Pro
1               5                   10                  15
```

Pro Gly Thr Leu Val Tyr Thr Gly Lys Tyr Arg Glu Asp Phe Glu Ile
            20                  25                  30

Glu Val Met Asn Tyr Ser Ile Glu Glu Phe Arg Glu Phe Lys Thr Thr
        35                  40                  45

Asp Val Glu Ser Val Leu Pro Phe Arg Asp Ser Ser Thr Pro Thr Trp
    50                  55                  60

Ile Asn Ile Thr Gly Ile His Arg Thr Asp Val Val Gln Arg Val Gly
65                  70                  75                  80

Glu Phe Phe Gly Ile His Pro Leu Val Leu Glu Asp Ile Leu Asn Val
                85                  90                  95

His Gln Arg Pro Lys Val Glu Phe Phe Glu Asn Tyr Val Phe Ile Val
            100                 105                 110

Leu Lys Met Phe Thr Tyr Asp Lys Asn Leu His Glu Leu Glu Ser Glu
        115                 120                 125

Gln Val Ser Leu Ile Leu Thr Lys Asn Cys Val Leu Met Phe Gln Glu
    130                 135                 140

Lys Ile Gly Asp Val Phe Asp Pro Val Arg Glu Arg Ile Arg Tyr Asn
145                 150                 155                 160

Arg Gly Ile Ile Arg Lys Lys Arg Ala Asp Tyr Leu Leu Tyr Ser Leu
                165                 170                 175

Ile Asp Ala Leu Val Asp Asp Tyr Phe Val Leu Leu Glu Lys Ile Asp
            180                 185                 190

Asp Glu Ile Asp Val Leu Glu Glu Glu Val Leu Glu Arg Pro Glu Lys
        195                 200                 205

Glu Thr Val Gln Arg Thr His Gln Leu Lys Arg Asn Leu Val Glu Leu
    210                 215                 220

Arg Lys Thr Ile Trp Pro Leu Arg Glu Val Leu Ser Ser Leu Tyr Arg
225                 230                 235                 240

Asp Val Pro Pro Leu Ile Glu Lys Glu Thr Val Pro Tyr Phe Arg Asp
                245                 250                 255

Val Tyr Asp His Thr Ile Gln Ile Ala Asp Thr Val Glu Thr Phe Arg
            260                 265                 270

Asp Ile Val Ser Gly Leu Leu Asp Val Tyr Leu Ser Ser Val Ser Asn
        275                 280                 285

Lys Thr Asn Glu Val Met Lys Val Leu Thr Ile Ile Ala Thr Ile Phe
    290                 295                 300

Met Pro Leu Thr Phe Ile Ala Gly Ile Tyr Gly Met Asn Phe Glu Tyr
305                 310                 315                 320

Met Pro Glu Leu Arg Trp Lys Trp Gly Tyr Pro Val Val Leu Ala Val
                325                 330                 335

Met Gly Val Ile Ala Val Ile Met Val Val Tyr Phe Lys Lys Lys Lys
            340                 345                 350

Trp Leu

<210> SEQ ID NO 69
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gly Ser His Met Arg Ile Pro Ala Thr Ile Lys Lys Lys Met Ala Leu
1               5                   10                  15

```
Pro Pro Ala Thr Pro Val Phe Thr Gly Glu Lys Lys Val Glu Glu Thr
            20                  25                  30

Lys Ile Thr Ala Ala Ile Tyr Asp Glu Lys Ser Val Glu Phe Lys Glu
            35                  40                  45

Leu Glu Val Gly Glu Leu Glu Ser Val Val Arg Ser Ala Leu Ala Leu
 50                  55                  60

Asn Lys Lys Leu Trp Ile Asp Val Gly Val His Asp Glu Ser Leu
 65                  70                  75                  80

Ile Ala Lys Ile Cys Glu Phe Leu Gly Ile His Pro Leu Ala Ala Glu
                85                  90                  95

Asp Ile Leu Asn Thr Ala Gln Arg Val Lys Ile Glu Asp Tyr Asp Asp
            100                 105                 110

His Leu Phe Leu Val Leu Lys Ile Leu Leu Tyr Asn Glu Thr Leu Glu
            115                 120                 125

Ile Asp Gln Leu Ser Leu Val Leu Lys Lys Asn Leu Val Ala Thr Phe
130                 135                 140

Glu Glu Arg Glu Tyr Trp Ile Leu Asp Ser Ile Arg Ser Arg Leu Lys
145                 150                 155                 160

Ser Gly Gly Arg Met Arg Lys Leu Ala Gly Asp Tyr Leu Ala Tyr Thr
                165                 170                 175

Ile Leu Asp Ala Val Val Asp Ser Tyr Phe Glu Ala Leu Leu Lys Ile
            180                 185                 190

Ser Asp Glu Ile Glu Val Leu Glu Asp Glu Val Val Ser Gly Asp Ser
            195                 200                 205

Thr Leu Ile Gly Lys Ile His Ser Leu Lys Arg Glu Ile Leu Ala Phe
210                 215                 220

Arg Asn Ala Val Trp Pro Leu Arg Asp Val Leu Ser Phe Phe Thr Arg
225                 230                 235                 240

Val Glu His Glu Leu Ile Gly Glu Val Lys Val Tyr Tyr Arg Asp
                245                 250                 255

Val Tyr Asp His Ala Val Arg Leu Met Glu
            260                 265

<210> SEQ ID NO 70
<211> LENGTH: 354
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gly Ser His Met Glu Glu Lys Arg Leu Ser Ala Lys Lys Gly Leu Pro
1               5                   10                  15

Pro Gly Thr Leu Val Tyr Thr Gly Lys Tyr Arg Glu Asp Phe Glu Ile
            20                  25                  30

Glu Val Met Asn Tyr Ser Ile Gly Glu Phe Arg Glu Phe Lys Thr Thr
            35                  40                  45

Asp Val Glu Ser Val Leu Pro Phe Arg Asp Ser Ser Thr Pro Thr Trp
 50                  55                  60

Ile Asn Ile Thr Gly Ile His Arg Thr Asp Val Val Gln Arg Val Gly
 65                  70                  75                  80

Glu Phe Phe Gly Ile His Pro Leu Val Leu Glu Asp Ile Leu Asn Val
                85                  90                  95

His Gln Arg Pro Lys Val Glu Phe Phe Glu Asn Tyr Val Phe Ile Val
```

100                 105                 110
Leu Lys Met Phe Thr Tyr Asp Lys Asn Leu His Glu Leu Glu Ser Glu
            115                 120                 125

Gln Val Ser Leu Ile Leu Thr Lys Asn Cys Val Leu Met Phe Gln Glu
        130                 135                 140

Lys Ile Gly Asp Val Phe Asp Pro Val Arg Glu Arg Ile Arg Tyr Asn
145                 150                 155                 160

Arg Gly Ile Ile Arg Lys Lys Arg Ala Asp Tyr Leu Leu Tyr Ser Leu
                165                 170                 175

Ile Asp Ala Leu Val Asp Asp Tyr Phe Val Leu Leu Glu Lys Ile Asp
                180                 185                 190

Asp Glu Ile Asp Val Leu Glu Glu Val Leu Glu Arg Pro Glu Lys
            195                 200                 205

Glu Thr Val Gln Arg Thr His Gln Leu Lys Arg Asn Leu Val Glu Leu
        210                 215                 220

Arg Lys Thr Ile Trp Pro Leu Arg Glu Val Leu Ser Ser Leu Tyr Arg
225                 230                 235                 240

Asp Val Pro Pro Leu Ile Glu Lys Glu Thr Val Pro Tyr Phe Arg Asp
                245                 250                 255

Val Tyr Asp His Thr Ile Gln Ile Ala Asp Thr Val Glu Thr Phe Arg
                260                 265                 270

Asp Ile Val Ser Gly Leu Leu Asp Val Tyr Leu Ser Ser Val Ser Asn
            275                 280                 285

Lys Thr Asn Glu Val Met Lys Val Leu Thr Ile Ile Ala Thr Ile Phe
        290                 295                 300

Met Pro Leu Thr Phe Ile Ala Gly Ile Tyr Gly Met Asn Phe Glu Tyr
305                 310                 315                 320

Met Pro Glu Leu Arg Trp Lys Trp Gly Tyr Pro Val Val Leu Ala Val
                325                 330                 335

Met Gly Val Ile Ala Val Ile Met Val Val Tyr Phe Lys Lys Lys Lys
            340                 345                 350

Trp Leu

<210> SEQ ID NO 71
<211> LENGTH: 363
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Met Gly Ser Asp Lys Ile His His His His His Met Glu Glu Lys
1               5                   10                  15

Arg Leu Ser Ala Lys Lys Gly Leu Pro Pro Gly Thr Leu Val Tyr Thr
            20                  25                  30

Gly Lys Tyr Arg Glu Asp Phe Glu Ile Glu Val Met Asn Tyr Ser Ile
        35                  40                  45

Glu Glu Phe Arg Glu Phe Lys Thr Thr Asp Val Glu Ser Val Leu Pro
    50                  55                  60

Phe Arg Asp Ser Ser Thr Pro Thr Trp Ile Asn Ile Thr Gly Ile His
65                  70                  75                  80

Arg Thr Asp Val Val Gln Arg Val Gly Glu Phe Phe Gly Ile His Pro
                85                  90                  95

Leu Val Leu Glu Asp Ile Leu Asn Val His Gln Arg Pro Lys Val Glu

```
            100                 105                 110
Phe Phe Glu Asn Tyr Val Phe Ile Val Leu Lys Met Phe Thr Tyr Asp
        115                 120                 125

Lys Asn Leu His Glu Leu Gly Ser Glu Gln Val Ser Leu Ile Leu Thr
130                 135                 140

Lys Asn Cys Val Leu Met Phe Gln Glu Lys Ile Gly Asp Val Phe Asp
145                 150                 155                 160

Pro Val Arg Glu Arg Ile Arg Tyr Asn Arg Gly Ile Ile Arg Lys Lys
                165                 170                 175

Arg Ala Asp Tyr Leu Leu Tyr Ser Leu Ile Asp Ala Leu Val Asp Asp
                180                 185                 190

Tyr Phe Val Leu Leu Glu Lys Ile Asp Asp Glu Ile Asp Val Leu Glu
        195                 200                 205

Glu Glu Val Leu Glu Arg Pro Glu Lys Glu Thr Val Gln Arg Thr His
        210                 215                 220

Gln Leu Lys Arg Asn Leu Val Glu Leu Arg Lys Thr Ile Trp Pro Leu
225                 230                 235                 240

Arg Glu Val Leu Ser Ser Leu Tyr Arg Asp Val Pro Pro Leu Ile Glu
                245                 250                 255

Lys Glu Thr Val Pro Tyr Phe Arg Asp Val Tyr Asp His Thr Ile Gln
                260                 265                 270

Ile Ala Asp Thr Val Glu Thr Phe Arg Asp Ile Val Ser Gly Leu Leu
                275                 280                 285

Asp Val Tyr Leu Ser Ser Val Ser Asn Lys Thr Asn Glu Val Met Lys
        290                 295                 300

Val Leu Thr Ile Ile Ala Thr Ile Phe Met Pro Leu Thr Phe Ile Ala
305                 310                 315                 320

Gly Ile Tyr Gly Met Asn Phe Glu Tyr Met Pro Glu Leu Arg Trp Lys
                325                 330                 335

Trp Gly Tyr Pro Val Val Leu Ala Val Met Gly Val Ile Ala Val Ile
                340                 345                 350

Met Val Val Tyr Phe Lys Lys Lys Trp Leu
        355                 360

<210> SEQ ID NO 72
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met Ala Ser Asp Ile Ser Lys Cys Phe Ala Thr Leu Gly Ala Thr Leu
1               5                   10                  15

Gln Asp Ser Ile Gly Lys Gln Val Leu Val Lys Leu Arg Asp Ser His
                20                  25                  30

Glu Ile Arg Gly Ile Leu Arg Ser Phe Asp Gln His Val Asn Leu Leu
            35                  40                  45

Leu Glu Asp Ala Glu Glu Ile Ile Asp Gly Asn Val Tyr Lys Arg Gly
        50                  55                  60

Thr Met Val Val Arg Gly Glu Asn Val Leu Phe Ile Ser Pro Val Pro
65                  70                  75                  80

Gly
```

```
<210> SEQ ID NO 73
<211> LENGTH: 77
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gly Ala Met Val Leu Pro Asn Gln Met Val Lys Ser Met Val Gly Lys
1               5                   10                  15

Ile Ile Arg Val Glu Met Lys Gly Glu Glu Asn Gln Leu Val Gly Lys
                20                  25                  30

Leu Glu Gly Val Asp Asp Tyr Met Asn Leu Tyr Leu Thr Asn Ala Met
            35                  40                  45

Glu Cys Lys Gly Glu Glu Lys Val Arg Ser Leu Gly Glu Ile Val Leu
    50                  55                  60

Arg Gly Asn Asn Val Val Leu Ile Gln Pro Gln Glu Glu
65                  70                  75

<210> SEQ ID NO 74
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Met Ser Ile Ala Val Gly Met Ile Glu Thr Arg Gly Phe Pro Ala Val
1               5                   10                  15

Val Glu Ala Ala Asp Ser Met Val Lys Ala Ala Arg Val Thr Leu Val
                20                  25                  30

Gly Tyr Glu Lys Ile Gly Ser Gly Arg Val Thr Val Ile Val Arg Gly
            35                  40                  45

Asp Val Ser Gly Val Gln Ala Ser Val Ser Ala Gly Ile Glu Ala Ala
    50                  55                  60

Asn Arg Val Asn Gly Gly Glu Val Leu Ser Thr His Ile Ile Ala Arg
65                  70                  75                  80

Pro His Glu Asn Leu Glu Tyr Val Leu Pro Ile Arg Tyr Thr Glu Glu
                85                  90                  95

Val Glu Gln Phe Arg Thr Tyr Gly Val Pro Arg Gly Leu Glu His His
                100                 105                 110

His His His His
        115

<210> SEQ ID NO 75
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Met Ser Ala Gln Ser Ala Val Gly Ser Ile Glu Thr Ile Gly Phe Pro
1               5                   10                  15

Gly Ile Leu Ala Ala Ala Asp Ala Met Val Lys Ala Gly Arg Ile Thr
                20                  25                  30

Ile Val Gly Tyr Ile Arg Ala Gly Ser Ala Arg Phe Thr Leu Asn Ile
            35                  40                  45
```

```
Arg Gly Asp Val Gln Glu Val Lys Thr Ala Met Ala Ala Gly Ile Asp
         50                  55                  60

Ala Ile Asn Arg Thr Glu Gly Ala Asp Val Lys Thr Trp Val Ile Ile
 65                  70                  75                  80

Pro Arg Pro His Glu Asn Val Val Ala Val Leu Pro Ile Asp Phe Ser
                 85                  90                  95

Pro Glu Val Glu Pro Phe Arg Glu Ala Ala Glu Gly Leu Asn Arg Arg
            100                 105                 110

Gly Val Pro Arg Gly Leu Glu His His His His His
            115                 120                 125

<210> SEQ ID NO 76
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Phe Gln Gly Pro Leu Gly Ser His Met Thr Ile Ser Pro Lys Glu Lys
 1               5                  10                  15

Glu Lys Ile Ala Ile His Glu Ala Gly His Ala Leu Met Gly Leu Val
             20                  25                  30

Ser Asp Asp Asp Lys Val His Lys Ile Ser Ile Pro Arg Gly
         35                  40                  45

Met Ala Leu Gly Val Thr Gln Gln Leu Pro Ile Glu Asp Lys His Ile
 50                  55                  60

Tyr Asp Lys Lys Asp Leu Tyr Asn Lys Ile Leu Val Leu Leu Gly Gly
 65                  70                  75                  80

Arg Ala Ala Glu Glu Val Phe Phe Gly Lys Asp Gly Ile Thr Thr Gly
                 85                  90                  95

Ala Glu Asn Asp Leu Gln Arg Ala Thr Asp Leu Ala Tyr Arg Met Val
            100                 105                 110

Ser Met Trp Gly Met Ser Asp Lys Val Gly Pro Ile Ala Ile Arg Arg
            115                 120                 125

Val Ala Asn Pro Phe Leu Gly Gly Met Thr Thr Ala Val Asp Thr Ser
130                 135                 140

Pro Asp Leu Leu Arg Glu Ile Asp Glu Glu Val Lys Arg Ile Ile Thr
145                 150                 155                 160

Glu Gln Tyr Glu Lys Ala Lys Ala Ile Val Glu Glu Tyr Lys Glu Pro
                165                 170                 175

Leu Lys Ala Val Val Lys Lys Leu Leu Glu Lys Glu Thr Ile Thr Cys
            180                 185                 190

Glu Glu Phe Val Glu Val Phe Lys Leu Tyr Gly Ile Glu Leu Lys Asp
            195                 200                 205

Lys Cys Lys Lys Glu Glu Leu Phe Asp Lys Asp Arg Lys Ser Glu Glu
        210                 215                 220

Asn Lys Glu Leu Lys Ser Glu Glu Val Lys Glu Glu Val Val
225                 230                 235

<210> SEQ ID NO 77
<211> LENGTH: 247
<212> TYPE: PRT
<213> ORGANISM: Artificial Sequence
<220> FEATURE:
<223> OTHER INFORMATION: Description of Artificial Sequence: Synthetic
```

```
polypeptide

<400> SEQUENCE: 77

Met Thr Arg Arg Val Lys Thr Gly Ile Pro Gly Val Asp Glu Ile Leu
1               5                   10                  15

His Gly Gly Ile Pro Glu Arg Asn Val Val Leu Leu Ser Gly Gly Pro
            20                  25                  30

Gly Thr Gly Lys Thr Ile Phe Ser Gln Gln Phe Leu Trp Asn Gly Leu
        35                  40                  45

Lys Met Gly Glu Pro Gly Ile Tyr Val Ala Leu Glu Glu His Pro Val
50                  55                  60

Gln Val Arg Gln Asn Met Ala Gln Phe Gly Trp Asp Val Lys Pro Tyr
65                  70                  75                  80

Glu Glu Lys Gly Met Phe Ala Met Val Asp Ala Phe Thr Ala Gly Ile
                85                  90                  95

Gly Lys Ser Lys Glu Tyr Glu Lys Tyr Ile Val His Asp Leu Thr Asp
            100                 105                 110

Ile Arg Glu Phe Ile Glu Val Leu Arg Gln Ala Ile Arg Asp Ile Asn
        115                 120                 125

Ala Lys Arg Val Val Asp Ser Val Thr Thr Leu Tyr Ile Asn Lys
130                 135                 140

Pro Ala Met Ala Arg Ser Ile Ile Leu Gln Leu Lys Arg Val Leu Ala
145                 150                 155                 160

Gly Thr Gly Cys Thr Ser Ile Phe Val Ser Gln Val Ser Val Gly Glu
                165                 170                 175

Arg Gly Phe Gly Gly Pro Gly Val Glu His Gly Val Asp Gly Ile Ile
            180                 185                 190

Arg Leu Asp Leu Asp Glu Ile Asp Gly Glu Leu Lys Arg Ser Leu Ile
        195                 200                 205

Val Trp Lys Met Arg Gly Thr Ser His Ser Met Arg Arg His Pro Phe
210                 215                 220

Asp Ile Thr Asp Lys Gly Ile Ile Val Tyr Pro Asp Lys Val Leu Lys
225                 230                 235                 240

Arg Gly Lys Val Leu Glu Leu
                245

<210> SEQ ID NO 78
<211> LENGTH: 207
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Met Gln Met Asn Ser Glu Lys Phe Phe Lys Leu Phe Arg Val Gly Glu
1               5                   10                  15

Thr Val Leu Val Glu Tyr Ser Gly Thr Ser Arg Ala Glu Leu Leu Leu
            20                  25                  30

Tyr Tyr Ile Val Asn Asn Ser Lys Leu Pro Ile Val Val Asp Asp Ile
        35                  40                  45

Leu Asp Thr Tyr Tyr Glu Phe Tyr Thr Arg Leu Lys Val Ala Gly Phe
    50                  55                  60

Asp Val Ala Pro Leu Glu Asn Val Gln Val Ile Lys Met Gly Gly Thr
65                  70                  75                  80

Lys Asp Ile Gly Arg Val Ile Gly Arg Leu Asn Ile Ser Lys Tyr Val
```

```
                    85                  90                  95
Ile Ser Glu Gln Glu Tyr Met Glu Ile Val Ser Gln Leu Lys Asp Tyr
            100                 105                 110

Pro Val Ile Asn Pro Val Leu Gly Leu His Lys Leu Ile Leu Leu Gly
        115                 120                 125

Asn Thr Phe Glu Asn Ile Asn Val Val Lys Met Val Ser Asn Tyr Val
    130                 135                 140

Gly Arg Glu Glu Arg Ile Ala Phe Tyr Phe Val Asn Arg Asn Val Ile
145                 150                 155                 160

Glu Lys His Ser Ser Pro Ile Leu Asp Leu Leu Glu Glu Val Val Thr
                165                 170                 175

Ser Ile Leu Glu Ile Thr Asp Ser Gly Ile Ile Lys Lys Ser Ile
            180                 185                 190

Lys Asp Glu Ile Ala Gly Lys Ile Val Ser Pro Leu Leu Asn Phe
        195                 200                 205

<210> SEQ ID NO 79
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Ala Asp Val Thr Gly Ile Ala Leu Gly Met Ile Glu Thr Arg Gly
1               5                   10                  15

Leu Val Pro Ala Ile Glu Ala Ala Asp Ala Met Thr Lys Ala Ala Glu
            20                  25                  30

Val Arg Leu Val Gly Arg Gln Phe Val Gly Gly Gly Tyr Val Thr Val
        35                  40                  45

Leu Val Arg Gly Glu Thr Gly Ala Val Asn Ala Ala Val Arg Ala Gly
    50                  55                  60

Ala Asp Ala Cys Glu Arg Val Gly Asp Gly Leu Val Ala Ala His Ile
65                  70                  75                  80

Ile Ala Arg Val His Ser Glu Val Glu Asn Ile Leu Pro Lys Ala Pro
                85                  90                  95

Gln Ala

<210> SEQ ID NO 80
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Ala Glu Arg Pro Leu Asp Val Ile His Arg Ser Leu Asp Lys Asp
1               5                   10                  15

Val Leu Val Ile Leu Lys Lys Gly Phe Glu Phe Arg Gly Arg Leu Ile
            20                  25                  30

Gly Tyr Asp Ile His Leu Asn Val Val Leu Ala Asp Ala Glu Met Ile
        35                  40                  45

Gln Asp Gly Glu Val Val Lys Arg Tyr Gly Lys Ile Val Ile Arg Gly
    50                  55                  60

Asp Asn Val Leu Ala Ile Ser Pro Thr Glu Glu
65                  70                  75
```

<210> SEQ ID NO 81
<211> LENGTH: 77
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Pro Pro Arg Pro Leu Asp Val Leu Asn Arg Ser Leu Lys Ser Pro
1               5                   10                  15

Val Ile Val Arg Leu Lys Gly Gly Arg Glu Phe Arg Gly Thr Leu Asp
            20                  25                  30

Gly Tyr Asp Ile His Met Asn Leu Val Leu Leu Asp Ala Glu Glu Ile
        35                  40                  45

Gln Asn Gly Glu Val Val Arg Lys Val Gly Ser Val Val Ile Arg Gly
    50                  55                  60

Asp Thr Val Val Phe Val Ser Pro Ala Pro Gly Gly Glu
65                  70                  75

<210> SEQ ID NO 82
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gly Ser Val Ile Asp Val Ser Ser Gln Arg Val Asn Val Gln Arg Pro
1               5                   10                  15

Leu Asp Ala Leu Gly Asn Ser Leu Asn Ser Pro Val Ile Ile Lys Leu
            20                  25                  30

Lys Gly Asp Arg Glu Phe Arg Gly Val Leu Lys Ser Phe Asp Leu His
        35                  40                  45

Met Asn Leu Val Leu Asn Asp Ala Glu Glu Leu Glu Asp Gly Glu Val
    50                  55                  60

Thr Arg Arg Leu Gly Thr Val Leu Ile Arg Gly Asp Asn Ile Val Tyr
65                  70                  75                  80

Ile Ser Pro

<210> SEQ ID NO 83
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Ile Asp Val Ser Ser Gln Arg Val Asn Val Gln Arg Pro Leu Asp
1               5                   10                  15

Ala Leu Gly Asn Ser Leu Asn Ser Pro Val Ile Ile Lys Leu Lys Gly
            20                  25                  30

Asp Arg Glu Phe Arg Gly Val Leu Lys Ser Phe Asp Leu His Met Asn
        35                  40                  45

Leu Val Leu Asn Asp Ala Glu Glu Leu Glu Asp Gly Glu Val Thr Arg
    50                  55                  60

Arg Leu Gly Thr Val Leu Ile Arg Gly Asp Asn Ile Val Tyr Ile Ser

Arg Gly Lys Leu Ala Ala
                85

<210> SEQ ID NO 84
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Met Ile Asp Val Ser Ser Gln Arg Val Asn Val Gln Arg Pro Leu Asp
1               5                   10                  15

Ala Leu Gly Asn Ser Leu Asn Ser Pro Val Ile Ile Lys Leu Lys Gly
            20                  25                  30

Asp Arg Glu Phe Arg Gly Val Leu Lys Ser Phe Asp Leu His Met Asn
        35                  40                  45

Leu Val Leu Asn Asp Ala Glu Glu Leu Glu Asp Gly Glu Val Thr Arg
    50                  55                  60

Arg Leu Gly Thr Val Leu Ile Arg Gly Asp Asn Ile Val Tyr Ile Ser
65                  70                  75                  80

Arg Gly Lys Leu Ala
                85

<210> SEQ ID NO 85
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Phe Val Ala Glu Leu Asn Asn Leu Leu Gly Arg Glu Val Gln Val Val
1               5                   10                  15

Leu Ser Asn Gly Glu Val Tyr Lys Gly Val Leu His Ala Val Asp Asn
            20                  25                  30

Gln Leu Asn Ile Val Leu Ala Asn Ala Ser Asn Lys Ala Gly Glu Lys
        35                  40                  45

Phe Asn Arg Val Phe Ile Met Tyr Arg Tyr Ile Val His Ile Asp Ser
    50                  55                  60

Thr Glu Arg Arg Ile Asp Met Arg Glu Phe Ala Lys Gln Ala Glu Lys
65                  70                  75                  80

Ile Phe Pro Gly Met Val Lys Tyr Ile Glu Glu Thr Asn Val Val Leu
                85                  90                  95

Ile Gly Asp Lys Val Arg Val Ser Glu Ile Gly Val Glu Gly Val Gly
            100                 105                 110

Pro Val Ala Glu Arg Ala Lys Arg Leu Phe Glu Glu Phe Leu Lys Arg
        115                 120                 125

Tyr Ser
    130

<210> SEQ ID NO 86
<211> LENGTH: 83
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 86

Gly Ser Val Ile Asp Val Ser Ser Gln Arg Val Asn Val Gln Arg Pro
1               5                   10                  15

Leu Asp Ala Leu Gly Asn Ser Leu Asn Ser Pro Val Ile Ile Lys Leu
            20                  25                  30

Lys Gly Asp Arg Glu Phe Arg Gly Val Leu Lys Ser Phe Asp Leu His
        35                  40                  45

Met Asn Leu Val Leu Asn Asp Ala Glu Glu Leu Glu Asp Gly Glu Val
    50                  55                  60

Thr Arg Arg Leu Gly Thr Val Leu Ile Arg Gly Asp Asn Ile Val Tyr
65                  70                  75                  80

Ile Ser Pro

<210> SEQ ID NO 87
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Ala Glu Phe Phe Pro Glu Ile Pro Lys Val Gln Phe Glu Gly Lys Glu
1               5                   10                  15

Ser Thr Asn Pro Leu Ala Phe Lys Phe Tyr Asp Pro Glu Glu Ile Ile
            20                  25                  30

Asp Gly Lys Pro Leu Lys Asp His Leu Lys Phe Ser Val Ala Phe Trp
        35                  40                  45

His Thr Phe Val Asn Glu Gly Arg Asp Pro Phe Gly Asp Pro Thr Ala
    50                  55                  60

Asp Arg Pro Trp Asn Arg Tyr Thr Asp Pro Met Asp Lys Ala Phe Ala
65                  70                  75                  80

Arg Val Asp Ala Leu Phe Glu Phe Cys Glu Lys Leu Asn Ile Glu Tyr
                85                  90                  95

Phe Cys Phe His Asp Arg Asp Ile Ala Pro Glu Gly Lys Thr Leu Arg
            100                 105                 110

Glu Thr Asn Lys Ile Leu Asp Lys Val Val Glu Arg Ile Lys Glu Arg
        115                 120                 125

Met Lys Asp Ser Asn Val Lys Leu Leu Trp Gly Thr Ala Asn Leu Phe
    130                 135                 140

Ser His Pro Arg Tyr Met His Gly Ala Ala Thr Thr Cys Ser Ala Asp
145                 150                 155                 160

Val Phe Ala Tyr Ala Ala Ala Gln Val Lys Lys Ala Leu Glu Ile Thr
                165                 170                 175

Lys Glu Leu Gly Gly Glu Gly Tyr Val Phe Trp Gly Gly Arg Glu Gly
            180                 185                 190

Tyr Glu Thr Leu Leu Asn Thr Asp Leu Gly Phe Glu Leu Glu Asn Leu
        195                 200                 205

Ala Arg Phe Leu Arg Met Ala Val Asp Tyr Ala Lys Arg Ile Gly Phe
    210                 215                 220

Thr Gly Gln Phe Leu Ile Glu Pro Lys Pro Lys Glu Pro Thr Lys His
225                 230                 235                 240

Gln Tyr Asp Phe Asp Val Ala Thr Ala Tyr Ala Phe Leu Lys Ser His
                245                 250                 255

Gly Leu Asp Glu Tyr Phe Lys Phe Asn Ile Glu Ala Asn His Ala Thr
            260                 265                 270

Leu Ala Gly His Thr Phe Gln His Glu Leu Arg Met Ala Arg Ile Leu
        275                 280                 285

Gly Lys Leu Gly Ser Ile Asp Ala Asn Gln Gly Asp Leu Leu Leu Gly
    290                 295                 300

Trp Asp Thr Asp Gln Phe Pro Thr Asn Val Tyr Asp Thr Thr Leu Ala
305                 310                 315                 320

Met Tyr Glu Val Ile Lys Ala Gly Phe Thr Lys Gly Gly Leu Asn
                325                 330                 335

Phe Asp Ala Lys Val Arg Arg Ala Ser Tyr Lys Val Glu Asp Leu Phe
                340                 345                 350

Ile Gly His Ile Ala Gly Met Asp Thr Phe Ala Leu Gly Phe Lys Val
            355                 360                 365

Ala Tyr Lys Leu Val Lys Asp Gly Val Leu Asp Lys Phe Ile Glu Glu
    370                 375                 380

Lys Tyr Arg Ser Phe Arg Glu Gly Ile Gly Arg Asp Ile Val Glu Gly
385                 390                 395                 400

Lys Val Asp Phe Glu Lys Leu Glu Glu Tyr Ile Ile Asp Lys Glu Thr
                405                 410                 415

Ile Glu Leu Pro Ser Gly Lys Gln Glu Tyr Leu Glu Ser Leu Ile Asn
                420                 425                 430

Ser Tyr Ile Val Lys Thr Ile Leu Glu Leu Arg
            435                 440

<210> SEQ ID NO 88
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Tyr Glu Pro Lys Pro Glu His Arg Phe Thr Phe Gly Leu Trp Thr
1               5                   10                  15

Val Gly Asn Val Gly Arg Asp Pro Phe Gly Asp Ala Val Arg Glu Arg
            20                  25                  30

Leu Asp Pro Val Tyr Val His Lys Leu Ala Glu Leu Gly Ala Tyr
        35                  40                  45

Gly Val Asn Leu His Asp Glu Asp Leu Ile Pro Arg Gly Thr Pro Pro
50                  55                  60

Gln Glu Arg Asp Gln Ile Val Arg Arg Phe Lys Lys Ala Leu Asp Glu
65                  70                  75                  80

Thr Gly Leu Lys Val Pro Met Val Thr Ala Asn Leu Phe Ser Asp Pro
                85                  90                  95

Ala Phe Lys Asp Gly Ala Phe Thr Ser Pro Asp Pro Trp Val Arg Ala
            100                 105                 110

Tyr Ala Leu Arg Lys Ser Leu Glu Thr Met Asp Leu Gly Ala Glu Leu
        115                 120                 125

Gly Ala Glu Ile Tyr Val Val Trp Pro Gly Arg Glu Gly Ala Glu Val
    130                 135                 140

Glu Ala Thr Gly Lys Ala Arg Lys Val Trp Asp Trp Val Arg Glu Ala
145                 150                 155                 160

Leu Asn Phe Met Ala Ala Tyr Ala Glu Asp Gln Gly Tyr Gly Tyr Arg

```
                165                 170                 175
Phe Ala Leu Glu Pro Lys Pro Asn Glu Pro Arg Gly Asp Ile Tyr Phe
                180                 185                 190

Ala Thr Val Gly Ser Met Leu Ala Phe Ile His Thr Leu Asp Arg Pro
                195                 200                 205

Glu Arg Phe Gly Leu Asn Pro Glu Phe Ala His Glu Thr Met Ala Gly
            210                 215                 220

Leu Asn Phe Val His Ala Val Ala Gln Ala Leu Asp Ala Gly Lys Leu
225                 230                 235                 240

Phe His Ile Asp Leu Asn Asp Gln Arg Met Ser Arg Phe Asp Gln Asp
                245                 250                 255

Leu Arg Phe Gly Ser Glu Asn Leu Lys Ala Ala Phe Phe Leu Val Asp
            260                 265                 270

Leu Leu Glu Ser Ser Gly Tyr Gln Gly Pro Arg His Phe Asp Ala His
            275                 280                 285

Ala Leu Arg Thr Glu Asp Glu Glu Gly Val Trp Ala Phe Ala Arg Gly
        290                 295                 300

Cys Met Arg Thr Tyr Leu Ile Leu Lys Glu Arg Ala Glu Ala Phe Arg
305                 310                 315                 320

Glu Asp Pro Glu Val Lys Glu Leu Leu Ala Ala Tyr Tyr Gln Glu Asp
                325                 330                 335

Pro Ala Ala Leu Ala Leu Leu Gly Pro Tyr Ser Arg Glu Lys Ala Glu
            340                 345                 350

Ala Leu Lys Arg Ala Glu Leu Pro Leu Glu Ala Lys Arg Arg Arg Gly
            355                 360                 365

Tyr Ala Leu Glu Arg Leu Asp Gln Leu Ala Val Glu Tyr Leu Leu Gly
        370                 375                 380

Val Arg Gly
385

<210> SEQ ID NO 89
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Met Ile Ser Glu Thr Ile Arg Ser Gly Asp Trp Lys Gly Glu Lys His
1               5                   10                  15

Val Pro Val Ile Glu Tyr Glu Arg Gly Glu Leu Val Lys Val Lys
                20                  25                  30

Val Gln Val Gly Lys Glu Ile Pro His Pro Asn Thr Thr Glu His His
            35                  40                  45

Ile Arg Tyr Ile Glu Leu Tyr Phe Leu Pro Glu Gly Glu Asn Phe Val
50                  55                  60

Tyr Gln Val Gly Arg Val Glu Phe Thr Ala His Gly Glu Ser Val Asn
65                  70                  75                  80

Gly Pro Asn Thr Ser Asp Val Tyr Thr Glu Pro Ile Ala Tyr Phe Val
                85                  90                  95

Leu Lys Thr Lys Lys Gly Lys Leu Tyr Ala Leu Ser Tyr Cys Asn
                100                 105                 110

Ile His Gly Leu Trp Glu Asn Glu Val Thr Leu Glu
            115                 120
```

<210> SEQ ID NO 90
<211> LENGTH: 403
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

```
Met His Val Ser Pro Phe Asp Trp Arg Tyr Gly Ser Glu Glu Ile Arg
1               5                   10                  15

Arg Leu Phe Thr Asn Glu Ala Ile Ile Asn Ala Tyr Leu Glu Val Glu
            20                  25                  30

Arg Ala Leu Val Cys Ala Leu Glu Glu Leu Gly Val Ala Glu Arg Gly
        35                  40                  45

Cys Cys Glu Lys Val Asn Lys Ala Ser Val Ser Ala Asp Glu Val Tyr
    50                  55                  60

Arg Leu Glu Arg Glu Thr Gly His Asp Ile Leu Ser Leu Val Leu Leu
65                  70                  75                  80

Leu Glu Gln Lys Ser Gly Cys Arg Tyr Val His Tyr Gly Ala Thr Ser
                85                  90                  95

Asn Asp Ile Ile Asp Thr Ala Trp Ala Leu Leu Ile Arg Arg Ala Leu
            100                 105                 110

Ala Ala Val Lys Glu Lys Ala Arg Ala Val Gly Asp Gln Leu Ala Ser
        115                 120                 125

Met Ala Arg Lys Tyr Lys Thr Leu Glu Met Val Gly Arg Thr His Gly
    130                 135                 140

Gln Trp Ala Glu Pro Ile Thr Leu Gly Phe Lys Phe Ala Asn Tyr Tyr
145                 150                 155                 160

Tyr Glu Leu Tyr Ile Ala Cys Arg Gln Leu Ala Leu Ala Glu Glu Phe
                165                 170                 175

Ile Arg Ala Lys Ile Gly Gly Ala Val Gly Thr Met Ala Ser Trp Gly
            180                 185                 190

Glu Leu Gly Leu Glu Val Arg Arg Val Ala Glu Arg Leu Gly Leu
        195                 200                 205

Pro His His Val Ile Thr Thr Gln Val Ala Pro Arg Glu Ser Phe Ala
    210                 215                 220

Val Leu Ala Ser Ala Leu Ala Leu Met Ala Ala Val Phe Glu Arg Leu
225                 230                 235                 240

Ala Val Glu Ile Arg Glu Leu Ser Arg Pro Glu Ile Gly Glu Val Val
                245                 250                 255

Glu Gly Gly Gly Gly Ser Ser Ala Met Pro His Lys Ala Asn Pro Thr
            260                 265                 270

Ala Ser Glu Arg Ile Val Ser Leu Ala Arg Tyr Val Arg Ala Leu Thr
        275                 280                 285

His Val Ala Phe Glu Asn Val Ala Leu Trp His Glu Arg Asp Leu Thr
    290                 295                 300

Asn Ser Ala Asn Glu Arg Val Trp Ile Pro Glu Ala Leu Leu Ala Leu
305                 310                 315                 320

Asp Glu Ile Leu Thr Ser Ala Leu Arg Val Leu Lys Asn Val Tyr Ile
                325                 330                 335

Asp Glu Glu Arg Ile Thr Glu Asn Leu Gln Lys Ala Leu Pro Tyr Ile
            340                 345                 350

Leu Thr Glu Phe His Met Asn Arg Met Ile Lys Glu Gly Ala Ser Arg
        355                 360                 365
```

```
Ala Glu Ala Tyr Lys Lys Ala Lys Glu Val Lys Ala Leu Thr Phe Glu
            370                 375                 380

Tyr Gln Lys Trp Pro Val Glu Arg Leu Ile Glu Asp Ala Leu Ser Leu
385                 390                 395                 400

Lys Leu Cys

<210> SEQ ID NO 91
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Met Lys Phe Met Val Glu Val Arg Ile Arg Leu Lys Lys Gly Met Leu
1               5                   10                  15

Asn Pro Glu Ala Ala Thr Ile Glu Arg Ala Leu Ala Leu Leu Gly Tyr
            20                  25                  30

Glu Val Glu Asp Thr Asp Thr Thr Asp Val Ile Thr Phe Thr Met Asp
        35                  40                  45

Glu Asp Ser Leu Glu Ala Val Glu Arg Glu Val Glu Asp Met Cys Gln
    50                  55                  60

Arg Leu Leu Cys Asn Pro Val Ile His Asp Tyr Asp Val Ser Ile Asn
65                  70                  75                  80

Glu Met Ser Ser His
                85

<210> SEQ ID NO 92
<211> LENGTH: 313
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Met Lys Val Thr Ile Ile Gly Ala Ser Gly Arg Val Gly Ser Ala Thr
1               5                   10                  15

Ala Leu Leu Leu Ala Lys Glu Pro Phe Met Lys Asp Leu Val Leu Ile
            20                  25                  30

Gly Arg Glu His Ser Ile Asn Lys Leu Glu Gly Leu Arg Glu Asp Ile
        35                  40                  45

Tyr Asp Ala Leu Ala Gly Thr Arg Ser Asp Ala Asn Ile Tyr Val Glu
    50                  55                  60

Ser Asp Glu Asn Leu Arg Ile Ile Asp Glu Ser Asp Val Val Ile Ile
65                  70                  75                  80

Thr Ser Gly Val Pro Arg Lys Glu Gly Met Ser Arg Met Asp Leu Ala
            85                  90                  95

Lys Thr Asn Ala Lys Ile Val Gly Lys Tyr Ala Lys Lys Ile Ala Glu
            100                 105                 110

Ile Cys Asp Thr Lys Ile Phe Val Ile Thr Asn Pro Val Asp Val Met
            115                 120                 125

Thr Tyr Lys Ala Leu Val Asp Ser Lys Phe Glu Arg Asn Gln Val Phe
        130                 135                 140

Gly Leu Gly Thr His Leu Asp Ser Leu Arg Phe Lys Val Ala Ile Ala
145                 150                 155                 160
```

-continued

```
Lys Phe Phe Gly Val His Ile Asp Glu Val Arg Thr Arg Ile Ile Gly
            165                 170                 175
Glu His Gly Asp Ser Met Val Pro Leu Leu Ser Ala Thr Ser Ile Gly
        180                 185                 190
Gly Ile Pro Ile Gln Lys Phe Glu Arg Phe Lys Glu Leu Pro Ile Asp
    195                 200                 205
Glu Ile Ile Glu Asp Val Lys Thr Lys Gly Glu Gln Ile Ile Arg Leu
210                 215                 220
Lys Gly Gly Ser Glu Phe Gly Pro Ala Ala Ile Leu Asn Val Val
225                 230                 235                 240
Arg Cys Ile Val Asn Asn Glu Lys Arg Leu Leu Thr Leu Ser Ala Tyr
                245                 250                 255
Val Asp Gly Glu Phe Asp Gly Ile Arg Asp Val Cys Ile Gly Val Pro
            260                 265                 270
Val Lys Ile Gly Arg Asp Gly Ile Glu Glu Val Val Ser Ile Glu Leu
        275                 280                 285
Asp Lys Asp Glu Ile Ile Ala Phe Arg Lys Ser Ala Glu Ile Ile Lys
    290                 295                 300
Lys Tyr Cys Glu Glu Val Lys Asn Leu
305                 310
```

<210> SEQ ID NO 93
<211> LENGTH: 313
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

```
Met Lys Val Thr Ile Ile Gly Ala Ser Gly Arg Val Gly Ser Ala Thr
1               5                   10                  15
Ala Leu Leu Leu Ala Lys Glu Pro Phe Met Lys Asp Leu Val Leu Ile
            20                  25                  30
Gly Arg Glu His Ser Ile Asn Lys Leu Glu Gly Leu Arg Glu Asp Ile
        35                  40                  45
Tyr Asp Ala Leu Ala Gly Thr Arg Ser Asp Ala Asn Ile Tyr Val Glu
    50                  55                  60
Ser Asp Glu Asn Leu Arg Ile Asp Glu Ser Asp Val Val Ile Ile
65                  70                  75                  80
Thr Ser Gly Val Pro Arg Lys Glu Gly Met Ser Arg Met Asp Leu Ala
                85                  90                  95
Lys Thr Asn Ala Lys Ile Val Gly Lys Tyr Ala Lys Lys Ile Ala Glu
            100                 105                 110
Ile Cys Asp Thr Lys Ile Phe Val Ile Thr Asn Pro Val Asp Val Met
        115                 120                 125
Thr Tyr Lys Ala Leu Val Asp Ser Lys Phe Glu Arg Asn Gln Val Phe
    130                 135                 140
Gly Leu Gly Thr His Leu Asp Ser Leu Arg Phe Lys Val Ala Ile Ala
145                 150                 155                 160
Lys Phe Phe Gly Val His Ile Asp Glu Val Arg Thr Arg Ile Ile Gly
                165                 170                 175
Glu His Gly Asp Ser Met Val Pro Leu Leu Ser Ala Thr Ser Ile Gly
            180                 185                 190
Gly Ile Pro Ile Gln Lys Phe Glu Arg Phe Lys Glu Leu Pro Ile Asp
        195                 200                 205
```

Glu Ile Ile Glu Asp Val Lys Thr Lys Gly Glu Gln Ile Ile Arg Leu
    210                 215                 220

Lys Gly Gly Ser Glu Phe Gly Pro Ala Ala Ala Ile Leu Asn Val Val
225                 230                 235                 240

Arg Cys Ile Val Asn Asn Glu Lys Arg Leu Leu Thr Leu Ser Ala Tyr
                245                 250                 255

Val Asp Gly Glu Phe Asp Gly Ile Arg Asp Val Cys Ile Gly Val Pro
                260                 265                 270

Val Lys Ile Gly Arg Asp Gly Ile Glu Glu Val Val Ser Ile Glu Leu
            275                 280                 285

Asp Lys Asp Glu Ile Ile Ala Phe Arg Lys Ser Ala Glu Ile Ile Lys
    290                 295                 300

Lys Tyr Cys Glu Glu Val Lys Asn Leu
305                 310

<210> SEQ ID NO 94
<211> LENGTH: 313
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Met Lys Val Thr Ile Ile Gly Ala Ser Gly Arg Val Gly Ser Ala Thr
1               5                   10                  15

Ala Leu Leu Leu Ala Lys Glu Pro Phe Met Lys Asp Leu Val Leu Ile
            20                  25                  30

Gly Arg Glu His Ser Ile Asn Lys Leu Glu Gly Leu Arg Glu Asp Ile
        35                  40                  45

Tyr Asp Ala Leu Ala Gly Thr Arg Ser Asp Ala Asn Ile Tyr Val Glu
    50                  55                  60

Ser Asp Glu Asn Leu Arg Ile Ile Asp Glu Ser Asp Val Val Ile Ile
65                  70                  75                  80

Thr Ser Gly Val Pro Arg Lys Glu Gly Met Ser Arg Met Asp Leu Ala
                85                  90                  95

Lys Thr Asn Ala Lys Ile Val Gly Lys Tyr Ala Lys Lys Ile Ala Glu
            100                 105                 110

Ile Cys Asp Thr Lys Ile Phe Val Ile Thr Asn Pro Val Asp Val Met
        115                 120                 125

Thr Tyr Lys Ala Leu Val Asp Ser Lys Phe Glu Arg Asn Gln Val Phe
    130                 135                 140

Gly Leu Gly Thr His Leu Asp Ser Leu Arg Phe Lys Val Ala Ile Ala
145                 150                 155                 160

Lys Phe Phe Gly Val His Ile Asp Glu Val Arg Thr Arg Ile Ile Gly
                165                 170                 175

Glu His Gly Asp Ser Met Val Pro Leu Leu Ser Ala Thr Ser Ile Gly
            180                 185                 190

Gly Ile Pro Ile Gln Lys Phe Glu Arg Phe Lys Glu Leu Pro Ile Asp
        195                 200                 205

Glu Ile Ile Glu Asp Val Lys Thr Lys Gly Glu Gln Ile Ile Arg Leu
    210                 215                 220

Lys Gly Gly Ser Glu Phe Gly Pro Ala Ala Ala Ile Leu Asn Val Val
225                 230                 235                 240

Arg Cys Ile Val Asn Asn Glu Lys Arg Leu Leu Thr Leu Ser Ala Tyr

```
                245                 250                 255
Val Asp Gly Glu Phe Asp Gly Ile Arg Asp Val Cys Ile Gly Val Pro
            260                 265                 270

Val Lys Ile Gly Arg Asp Gly Ile Glu Glu Val Val Ser Ile Glu Leu
        275                 280                 285

Asp Lys Asp Glu Ile Ile Ala Phe Arg Lys Ser Ala Glu Ile Ile Lys
    290                 295                 300

Lys Tyr Cys Glu Glu Val Lys Asn Leu
305                 310

<210> SEQ ID NO 95
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Met Ile Arg Tyr Leu Arg Gly Leu Val Leu Lys Lys Glu Ala Gly Gly
1               5                   10                  15

Phe Val Leu Leu Ala Gly Gly Val Gly Phe Phe Leu Gln Ala Pro Thr
            20                  25                  30

Pro Phe Leu Gln Ala Leu Glu Glu Gly Lys Glu Val Gly Val His Thr
        35                  40                  45

His Leu Leu Leu Lys Glu Glu Gly Leu Ser Leu Tyr Gly Phe Pro Asp
    50                  55                  60

Glu Glu Asn Leu Ala Leu Phe Glu Leu Leu Leu Ser Val Ser Gly Val
65                  70                  75                  80

Gly Pro Lys Val Ala Leu Ala Leu Leu Ser Ala Leu Pro Pro Arg Leu
                85                  90                  95

Leu Ala Arg Ala Leu Leu Glu Gly Asp Ala Arg Leu Leu Thr Ser Ala
            100                 105                 110

Ser Gly Val Gly Arg Arg Leu Ala Glu Arg Ile Ala Leu Glu Leu Lys
        115                 120                 125

Gly Lys Val Pro Pro His Leu Leu Ala Gly Glu Lys Val Glu Ser Glu
    130                 135                 140

Ala Ala Glu Glu Ala Val Met Ala Leu Ala Ala Leu Gly Phe Lys Glu
145                 150                 155                 160

Ala Gln Ala Arg Ala Val Val Leu Asp Leu Leu Ala Gln Asn Pro Lys
                165                 170                 175

Ala Arg Ala Gln Asp Leu Ile Lys Glu Ala Leu Lys Arg Leu Arg Met
            180                 185                 190

Glu Asp Leu Ala Leu Arg Pro Lys Thr Leu Asp Glu Tyr Ile Gly Gln
        195                 200                 205

Glu Arg Leu Lys Gln Lys Leu Arg Val Tyr Leu Glu Ala Ala Lys Ala
    210                 215                 220

Arg Lys Glu Pro Leu Glu His Leu Leu Leu Phe Gly Pro Pro Gly Leu
225                 230                 235                 240

Gly Lys Thr Thr Leu Ala His Val Ile Ala His Glu Leu Gly Val Asn
                245                 250                 255

Leu Arg Val Thr Ser Gly Pro Ala Ile Glu Lys Pro Gly Asp Leu Ala
            260                 265                 270

Ala Ile Leu Ala Asn Ser Leu Glu Glu Gly Asp Ile Leu Phe Ile Asp
        275                 280                 285
```

```
Glu Ile His Arg Leu Ser Arg Gln Ala Glu Glu His Leu Tyr Pro Ala
    290                 295                 300

Met Glu Asp Phe Val Met Asp Ile Val Ile Gly Gln Gly Pro Ala Ala
305                 310                 315                 320

Arg Thr Ile Arg Leu Glu Leu Pro Arg Phe Thr Leu Ile Gly Ala Thr
                325                 330                 335

Thr Arg Pro Gly Leu Ile Thr Ala Pro Leu Leu Ser Arg Phe Gly Ile
            340                 345                 350

Val Glu His Leu Glu Tyr Tyr Thr Pro Glu Glu Leu Ala Gln Gly Val
        355                 360                 365

Met Arg Asp Ala Arg Leu Leu Gly Val Arg Ile Thr Glu Glu Ala Ala
370                 375                 380

Leu Glu Ile Gly Arg Arg Ser Arg Gly Thr Met Arg Val Ala Lys Arg
385                 390                 395                 400

Leu Phe Arg Arg Val Arg Asp Phe Ala Gln Val Ala Gly Glu Glu Val
                405                 410                 415

Ile Thr Arg Glu Arg Ala Leu Glu Ala Leu Ala Ala Leu Gly Leu Asp
            420                 425                 430

Glu Leu Gly Leu Glu Lys Arg Asp Arg Glu Ile Leu Glu Val Leu Ile
        435                 440                 445

Leu Arg Phe Gly Gly Gly Pro Val Gly Leu Ala Thr Leu Ala Thr Ala
450                 455                 460

Leu Ser Glu Asp Pro Gly Thr Leu Glu Glu Val His Glu Pro Tyr Leu
465                 470                 475                 480

Ile Arg Gln Gly Leu Leu Lys Arg Thr Pro Arg Gly Arg Val Ala Thr
                485                 490                 495

Glu Leu Ala Arg Arg His Leu
            500

<210> SEQ ID NO 96
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Met Arg Asp Pro Phe Met Glu Ala Leu Gly Leu Lys Val Leu His Leu
1               5                   10                  15

Ala Pro Gly Glu Ala Val Val Ala Gly Glu Val Arg Ala Asp His Leu
            20                  25                  30

Asn Leu His Gly Thr Ala His Gly Gly Phe Leu Tyr Ala Leu Ala Asp
        35                  40                  45

Ser Ala Phe Ala Leu Ala Ser Asn Thr Arg Gly Pro Ala Val Ala Leu
    50                  55                  60

Ser Cys Arg Met Asp Tyr Phe Arg Pro Leu Gly Ala Gly Ala Arg Val
65                  70                  75                  80

Glu Ala Arg Ala Val Glu Val Asn Leu Ser Arg Arg Thr Ala Thr Tyr
                85                  90                  95

Arg Val Glu Val Val Ser Glu Gly Lys Leu Val Ala Leu Phe Thr Gly
            100                 105                 110

Thr Val Phe Arg Leu Gly Gly Asp Gly Asp Asp Val Pro Ala Gly Thr
        115                 120                 125

Gly Asn Leu Ala Pro Arg Glu Ala
    130                 135
```

<210> SEQ ID NO 97
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

```
Met Asp Leu Ala Ala His Ile Asp His Thr Leu Leu Lys Pro Thr Ala
1               5                   10                  15

Thr Leu Glu Glu Val Ala Lys Ala Ala Glu Glu Ala Leu Glu Tyr Gly
            20                  25                  30

Phe Tyr Gly Leu Cys Ile Pro Pro Ser Tyr Val Ala Trp Val Arg Ala
        35                  40                  45

Arg Tyr Pro His Ala Pro Phe Arg Leu Val Thr Val Val Gly Phe Pro
    50                  55                  60

Leu Gly Tyr Gln Glu Lys Glu Val Lys Ala Leu Glu Ala Ala Leu Ala
65                  70                  75                  80

Cys Ala Arg Gly Ala Asp Glu Val Asp Met Val Leu His Leu Gly Arg
                85                  90                  95

Ala Lys Ala Gly Asp Leu Asp Tyr Leu Glu Ala Glu Val Arg Ala Val
            100                 105                 110

Arg Glu Ala Val Pro Gln Ala Val Leu Lys Val Ile Leu Glu Thr Gly
        115                 120                 125

Tyr Phe Ser Pro Glu Gly Ile Ala Arg Leu Ala Glu Ala Ala Ile Arg
    130                 135                 140

Gly Gly Ala Asp Phe Leu Lys Thr Ser Thr Gly Phe Gly Pro Arg Gly
145                 150                 155                 160

Ala Ser Leu Glu Asp Val Ala Leu Leu Val Arg Val Ala Gln Gly Arg
                165                 170                 175

Ala Gln Val Lys Ala Ala Gly Gly Ile Arg Asp Arg Glu Thr Ala Leu
            180                 185                 190

Arg Met Leu Lys Ala Gly Ala Ser Arg Leu Gly Thr Ser Ser Gly Val
        195                 200                 205

Ala Leu Val Ala Gly Glu Gly Gly Thr Leu Gly Tyr
    210                 215                 220
```

<210> SEQ ID NO 98
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

```
Gly Pro His Met Met Ile Asp Leu Arg Ser Asp Thr Val Thr Lys Pro
1               5                   10                  15

Thr Glu Glu Met Arg Lys Ala Met Ala Gln Ala Glu Val Gly Asp Asp
            20                  25                  30

Val Tyr Gly Glu Asp Pro Thr Ile Asn Glu Leu Glu Arg Leu Ala Ala
        35                  40                  45

Glu Thr Phe Gly Lys Glu Ala Ala Leu Phe Val Pro Ser Gly Thr Met
    50                  55                  60

Gly Asn Gln Val Ser Ile Met Ala His Thr Gln Arg Gly Asp Glu Val
65                  70                  75                  80
```

Ile Leu Glu Ala Asp Ser His Ile Phe Trp Tyr Glu Val Gly Ala Met
            85                  90                  95

Ala Val Leu Ser Gly Val Met Pro His Pro Val Pro Gly Lys Asn Gly
            100                 105                 110

Ala Met Asp Pro Asp Val Arg Lys Ala Ile Arg Pro Arg Asn Ile
            115                 120                 125

His Phe Pro Arg Thr Ser Leu Ile Ala Ile Glu Asn Thr His Asn Arg
            130                 135                 140

Ser Gly Gly Arg Val Val Pro Leu Glu Asn Ile Lys Glu Ile Cys Thr
145                 150                 155                 160

Ile Ala Lys Glu His Gly Ile Asn Val His Ile Asp Gly Ala Arg Ile
                165                 170                 175

Phe Asn Ala Ser Ile Ala Ser Gly Val Pro Val Lys Glu Tyr Ala Gly
            180                 185                 190

Tyr Ala Asp Ser Val Met Phe Cys Leu Ser Lys Gly Leu Cys Ala Pro
            195                 200                 205

Val Gly Ser Val Val Val Gly Asp Arg Asp Phe Ile Glu Arg Ala Arg
            210                 215                 220

Lys Ala Arg Lys Met Leu Gly Gly Met Arg Gln Ala Gly Val Leu
225                 230                 235                 240

Ala Ala Ala Gly Ile Ile Ala Leu Thr Lys Met Val Asp Arg Leu Lys
                245                 250                 255

Glu Asp His Glu Asn Ala Arg Phe Leu Ala Leu Lys Leu Lys Glu Ile
            260                 265                 270

Gly Tyr Ser Val Asn Pro Glu Asp Val Lys Thr Asn Met Val Ile Leu
            275                 280                 285

Arg Thr Asp Asn Leu Lys Val Asn Ala His Gly Phe Ile Glu Ala Leu
            290                 295                 300

Arg Asn Ser Gly Val Leu Ala Asn Ala Val Ser Asp Thr Glu Ile Arg
305                 310                 315                 320

Leu Val Thr His Lys Asp Val Ser Arg Asn Asp Ile Glu Glu Ala Leu
                325                 330                 335

Asn Ile Phe Glu Lys Leu Phe Arg Lys Phe Ser
            340                 345

<210> SEQ ID NO 99
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Met Arg Ala Val Arg Leu Val Glu Ile Gly Lys Pro Leu Ser Leu Gln
1               5                   10                  15

Glu Ile Gly Val Pro Lys Pro Lys Gly Pro Gln Val Leu Ile Lys Val
            20                  25                  30

Glu Ala Ala Gly Val Cys His Ser Asp Val His Met Arg Gln Gly Arg
        35                  40                  45

Phe Gly Asn Leu Arg Ile Val Glu Asp Leu Gly Val Lys Leu Pro Val
        50                  55                  60

Thr Leu Gly His Glu Ile Ala Gly Lys Ile Glu Glu Val Gly Asp Glu
65                  70                  75                  80

Val Val Gly Tyr Ser Lys Gly Asp Leu Val Ala Val Asn Pro Trp Gln

```
                    85                  90                  95
Gly Glu Gly Asn Cys Tyr Tyr Cys Arg Ile Gly Glu Glu His Leu Cys
            100                 105                 110

Asp Ser Pro Arg Trp Leu Gly Ile Asn Phe Asp Gly Ala Tyr Ala Glu
        115                 120                 125

Tyr Val Ile Val Pro His Tyr Lys Tyr Met Tyr Lys Leu Arg Arg Leu
    130                 135                 140

Asn Ala Val Glu Ala Ala Pro Leu Thr Cys Ser Gly Ile Thr Thr Tyr
145                 150                 155                 160

Arg Ala Val Arg Lys Ala Ser Leu Asp Pro Thr Lys Thr Leu Leu Val
                165                 170                 175

Val Gly Ala Gly Gly Leu Gly Thr Met Ala Val Gln Ile Ala Lys
            180                 185                 190

Ala Val Ser Gly Ala Thr Ile Ile Gly Val Asp Val Arg Glu Glu Ala
            195                 200                 205

Val Glu Ala Ala Lys Arg Ala Gly Ala Asp Tyr Val Ile Asn Ala Ser
210                 215                 220

Met Gln Asp Pro Leu Ala Glu Ile Arg Arg Ile Thr Glu Ser Lys Gly
225                 230                 235                 240

Val Asp Ala Val Ile Asp Leu Asn Asn Ser Glu Lys Thr Leu Ser Val
                245                 250                 255

Tyr Pro Lys Ala Leu Ala Lys Gln Gly Lys Tyr Val Met Val Gly Leu
            260                 265                 270

Phe Gly Ala Asp Leu His Tyr His Ala Pro Leu Ile Thr Leu Ser Glu
            275                 280                 285

Ile Gln Phe Val Gly Ser Leu Val Gly Asn Gln Ser Asp Phe Leu Gly
        290                 295                 300

Ile Met Arg Leu Ala Glu Ala Gly Lys Val Lys Pro Met Ile Thr Lys
305                 310                 315                 320

Thr Met Lys Leu Glu Glu Ala Asn Glu Ala Ile Asp Asn Leu Glu Asn
                325                 330                 335

Phe Lys Ala Ile Gly Arg Gln Val Leu Ile Pro
            340                 345

<210> SEQ ID NO 100
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Met Thr Thr Asn Leu Thr Asn Ser Asn Cys Val Glu Glu Tyr Lys Glu
1               5                   10                  15

Asn Gly Lys Thr Lys Ile Arg Ile Lys Pro Phe Asn Ala Leu Ile Glu
            20                  25                  30

Leu Tyr His His Gln Thr Pro Thr Gly Ser Ile Lys Glu Asn Leu Asp
        35                  40                  45

Lys Leu Glu Asn Tyr Val Lys Asp Val Val Lys Ala Lys Gly Leu Ala
    50                  55                  60

Ile Pro Thr Ser Gly Ala Phe Ser Asn Thr Arg Gly Thr Trp Phe Glu
65                  70                  75                  80

Val Met Ile Ala Ile Gln Ser Trp Asn Tyr Arg Val Lys Arg Glu Leu
                85                  90                  95
```

```
Asn Asp Tyr Leu Ile Ile Lys Met Pro Asn Val Lys Thr Phe Asp Phe
                100                 105                 110

Arg Lys Ile Phe Asp Asn Glu Thr Arg Glu Lys Leu His Gln Leu Glu
            115                 120                 125

Lys Ser Leu Leu Thr His Lys Gln Gln Val Arg Leu Ile Thr Ser Asn
130                 135                 140

Pro Asp Leu Leu Ile Ile Arg Gln Lys Asp Leu Ile Lys Ser Glu Tyr
145                 150                 155                 160

Asn Leu Pro Ile Asn Lys Leu Thr His Glu Asn Ile Asp Val Ala Leu
                165                 170                 175

Thr Leu Phe Lys Asp Ile Glu Gly Lys Cys Lys Trp Asp Ser Leu Val
            180                 185                 190

Ala Gly Val Gly Leu Lys Thr Ser Leu Arg Pro Asp Arg Arg Leu Gln
        195                 200                 205

Leu Val His Glu Gly Asn Ile Leu Lys Ser Leu Phe Ala His Leu Lys
210                 215                 220

Met Arg Tyr Trp Asn Pro Lys Ala Glu Phe Lys Tyr Tyr Gly Ala Ser
225                 230                 235                 240

Ser Glu Pro Val Ser Lys Ala Asp Asp Ala Leu Gln Thr Ala Ala
                245                 250                 255

Thr His Thr Ile Val Asn Val Asn Ser Thr Pro Glu Arg Ala Val Asp
            260                 265                 270

Asp Ile Phe Ser Leu Thr Ser Phe Glu Asp Ile Asp Lys Met Leu Asp
            275                 280                 285

Gln Ile Ile Lys Lys
        290

<210> SEQ ID NO 101
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Met Asn Val Glu Glu Met Lys Lys Ile Ala Ala Lys Glu Ala Leu Lys
1               5                   10                  15

Phe Ile Glu Asp Asp Met Val Ile Gly Leu Gly Thr Gly Ser Thr Thr
            20                  25                  30

Ala Tyr Phe Ile Lys Leu Leu Gly Glu Lys Leu Lys Arg Gly Glu Ile
        35                  40                  45

Ser Asp Ile Val Gly Val Pro Thr Ser Tyr Gln Ala Lys Leu Leu Ala
50                  55                  60

Ile Glu His Asp Ile Pro Ile Ala Ser Leu Asp Gln Val Asp Ala Ile
65                  70                  75                  80

Asp Val Ala Val Asp Gly Ala Asp Glu Val Asp Pro Asn Leu Asn Leu
                85                  90                  95

Ile Lys Gly Arg Gly Ala Ala Leu Thr Met Glu Lys Ile Ile Glu Tyr
            100                 105                 110

Arg Ala Gly Thr Phe Ile Val Leu Val Asp Glu Arg Lys Leu Val Asp
        115                 120                 125

Tyr Leu Cys Gln Lys Met Pro Val Pro Ile Glu Val Ile Pro Gln Ala
130                 135                 140

Trp Lys Ala Ile Ile Glu Glu Leu Ser Ile Phe Asn Ala Lys Ala Glu
145                 150                 155                 160
```

```
Leu Arg Met Gly Val Asn Lys Asp Gly Pro Val Ile Thr Asp Asn Gly
                165                 170                 175

Asn Phe Ile Ile Asp Ala Lys Phe Pro Arg Ile Asp Pro Leu Asp
            180                 185                 190

Met Glu Ile Glu Leu Asn Thr Ile Pro Gly Val Ile Glu Asn Gly Ile
            195                 200                 205

Phe Ala Asp Ile Ala Asp Ile Val Ile Val Gly Thr Arg Glu Gly Val
            210                 215                 220

Lys Lys Leu Glu Arg
225

<210> SEQ ID NO 102
<211> LENGTH: 295
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gly Ala His Met Lys Gly Ile Val Leu Ala Gly Gly Ser Gly Thr Arg
1               5                   10                  15

Leu Tyr Pro Ile Thr Arg Ala Val Ser Lys Gln Leu Leu Pro Ile Tyr
            20                  25                  30

Asp Lys Pro Met Ile Tyr Tyr Pro Leu Ser Val Leu Met Leu Ala Gly
            35                  40                  45

Ile Arg Asp Ile Leu Ile Ile Ser Thr Pro Arg Asp Leu Pro Leu Tyr
50                  55                  60

Arg Asp Leu Leu Gly Asp Gly Ser Gln Phe Gly Val Arg Phe Ser Tyr
65                  70                  75                  80

Arg Val Gln Glu Glu Pro Arg Gly Ile Ala Asp Ala Phe Ile Val Gly
            85                  90                  95

Lys Asp Phe Ile Gly Asp Ser Lys Val Ala Leu Val Leu Gly Asp Asn
            100                 105                 110

Val Phe Tyr Gly His Arg Phe Ser Glu Ile Leu Arg Arg Ala Ala Ser
            115                 120                 125

Leu Glu Asp Gly Ala Val Ile Phe Gly Tyr Tyr Val Arg Asp Pro Arg
            130                 135                 140

Pro Phe Gly Val Val Glu Phe Asp Ser Glu Gly Arg Val Ile Ser Ile
145                 150                 155                 160

Glu Glu Lys Pro Ser Arg Pro Lys Ser Asn Tyr Val Val Pro Gly Leu
            165                 170                 175

Tyr Phe Tyr Asp Asn Gln Val Val Glu Ile Ala Arg Arg Ile Glu Pro
            180                 185                 190

Ser Asp Arg Gly Glu Leu Glu Ile Thr Ser Val Asn Glu Glu Tyr Leu
            195                 200                 205

Arg Met Gly Lys Leu Arg Val Glu Leu Met Gly Arg Gly Met Ala Trp
            210                 215                 220

Leu Asp Thr Gly Thr His Asp Gly Leu Leu Glu Ala Ser Ser Phe Ile
225                 230                 235                 240

Glu Thr Ile Gln Lys Arg Gln Gly Phe Tyr Ile Ala Cys Leu Glu Glu
            245                 250                 255

Ile Ala Tyr Asn Asn Gly Trp Ile Thr Arg Glu Asp Val Leu Glu Met
            260                 265                 270

Ala Glu Lys Leu Glu Lys Thr Asp Tyr Gly Lys Tyr Leu Arg Asp Leu
```

```
                    275                 280                 285

Ala Glu Gly Asn Phe His Gly
    290                 295

<210> SEQ ID NO 103
<211> LENGTH: 181
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Val Met Thr Met Arg Gly Leu Leu Val Gly Arg Met Gln Pro Phe His
1               5                   10                  15

Arg Gly Ala Leu Gln Val Ile Lys Ser Ile Leu Glu Glu Val Asp Glu
            20                  25                  30

Leu Ile Ile Cys Ile Gly Ser Ala Gln Leu Ser His Ser Ile Arg Asp
        35                  40                  45

Pro Phe Thr Ala Gly Glu Arg Val Met Met Leu Thr Lys Ala Leu Ser
    50                  55                  60

Glu Asn Gly Ile Pro Ala Ser Arg Tyr Tyr Ile Ile Pro Val Gln Asp
65                  70                  75                  80

Ile Glu Cys Asn Ala Leu Trp Val Gly His Ile Lys Met Leu Thr Pro
                85                  90                  95

Pro Phe Asp Arg Val Tyr Ser Gly Asn Pro Leu Val Gln Arg Leu Phe
            100                 105                 110

Ser Glu Asp Gly Tyr Glu Val Thr Ala Pro Pro Leu Phe Tyr Arg Asp
        115                 120                 125

Arg Tyr Ser Gly Thr Glu Val Arg Arg Arg Met Leu Asp Asp Gly Asp
    130                 135                 140

Trp Arg Ser Leu Leu Pro Glu Ser Val Val Glu Val Ile Asp Glu Ile
145                 150                 155                 160

Asn Gly Val Glu Arg Ile Lys His Leu Ala Lys Lys Glu Val Ser Glu
                165                 170                 175

Leu Gly Gly Ile Ser
            180

<210> SEQ ID NO 104
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Met Arg Ala Val Arg Leu Val Glu Ile Gly Lys Pro Leu Ser Leu Gln
1               5                   10                  15

Glu Ile Gly Val Pro Lys Pro Lys Gly Pro Gln Val Leu Ile Lys Val
            20                  25                  30

Glu Ala Ala Gly Val Cys His Ser Asp Val His Met Arg Gln Gly Arg
        35                  40                  45

Phe Gly Asn Leu Arg Ile Val Glu Asp Leu Gly Val Lys Leu Pro Val
    50                  55                  60

Thr Leu Gly His Glu Ile Ala Gly Lys Ile Glu Glu Val Gly Asp Glu
65                  70                  75                  80

Val Val Gly Tyr Ser Lys Gly Asp Leu Val Ala Val Asn Pro Trp Gln
```

```
                    85                  90                  95
Gly Glu Gly Asn Cys Tyr Tyr Cys Arg Ile Gly Glu His Leu Cys
                100                 105                 110

Asp Ser Pro Arg Trp Leu Gly Ile Asn Phe Asp Gly Ala Tyr Ala Glu
                115                 120                 125

Tyr Val Ile Val Pro His Tyr Lys Tyr Met Tyr Lys Leu Arg Arg Leu
130                 135                 140

Asn Ala Val Glu Ala Ala Pro Leu Thr Cys Ser Gly Ile Thr Thr Tyr
145                 150                 155                 160

Arg Ala Val Arg Lys Ala Ser Leu Asp Pro Thr Lys Thr Leu Leu Val
                165                 170                 175

Val Gly Ala Gly Gly Leu Gly Thr Met Ala Val Gln Ile Ala Lys
                180                 185                 190

Ala Val Ser Gly Ala Thr Ile Ile Gly Val Asp Val Arg Glu Glu Ala
                195                 200                 205

Val Glu Ala Ala Lys Arg Ala Gly Ala Asp Tyr Val Ile Asn Ala Ser
210                 215                 220

Met Gln Asp Pro Leu Ala Glu Ile Arg Arg Ile Thr Glu Ser Lys Gly
225                 230                 235                 240

Val Asp Ala Val Ile Asp Leu Asn Tyr Ser Glu Lys Thr Leu Ser Val
                245                 250                 255

Tyr Pro Lys Ala Leu Ala Lys Gln Gly Lys Tyr Val Met Val Gly Leu
                260                 265                 270

Phe Gly Ala Asp Leu His Tyr His Ala Pro Leu Ile Thr Leu Ser Glu
                275                 280                 285

Ile Gln Phe Val Gly Ser Leu Val Gly Asn Gln Ser Asp Phe Leu Gly
                290                 295                 300

Ile Met Arg Leu Ala Glu Ala Gly Lys Val Lys Pro Met Ile Thr Lys
305                 310                 315                 320

Thr Met Lys Leu Glu Glu Ala Asn Glu Ala Ile Asp Asn Leu Glu Asn
                325                 330                 335

Phe Lys Ala Ile Gly Arg Gln Val Leu Ile Pro
                340                 345

<210> SEQ ID NO 105
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Met Gly Ser Asp Lys Ile His His His His His Met Lys Ile Asp
1               5                   10                  15

Ile Leu Asp Lys Gly Phe Val Glu Leu Val Asp Val Met Gly Asn Asp
                20                  25                  30

Leu Ser Ala Val Arg Ala Ala Val Ser Phe Asp Met Gly Leu Lys
                35                  40                  45

Asp Glu Glu Arg Asp Arg His Leu Ile Glu Tyr Leu Met Lys His Gly
50                  55                  60

His Glu Thr Pro Phe Glu His Ile Val Phe Thr Phe His Val Lys Ala
65                  70                  75                  80

Pro Ile Phe Val Ala Arg Gln Trp Phe Arg His Arg Ile Ala Ser Tyr
                85                  90                  95
```

```
Asn Glu Leu Ser Gly Arg Tyr Ser Lys Leu Ser Tyr Glu Phe Tyr Ile
                100                 105                 110

Pro Ser Pro Glu Arg Leu Glu Gly Tyr Lys Thr Thr Ile Pro Pro Glu
            115                 120                 125

Arg Val Thr Glu Lys Ile Ser Glu Ile Val Asp Lys Ala Tyr Arg Thr
        130                 135                 140

Tyr Leu Glu Leu Ile Glu Ser Gly Val Pro Arg Glu Val Ala Arg Ile
145                 150                 155                 160

Val Leu Pro Leu Asn Leu Tyr Thr Arg Phe Phe Trp Thr Val Asn Ala
                165                 170                 175

Arg Ser Leu Met Asn Phe Leu Asn Leu Arg Ala Asp Ser His Ala Gln
            180                 185                 190

Trp Glu Ile Gln Gln Tyr Ala Leu Ala Ile Ala Arg Ile Phe Lys Glu
        195                 200                 205

Lys Cys Pro Trp Thr Phe Glu Ala Phe Leu Lys Tyr Ala Tyr Lys Gly
            210                 215                 220

Asp Ile Leu Lys Glu Val Gln Val
225                 230

<210> SEQ ID NO 106
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Met Gly Ser Asp Lys Ile His His His His His Val Gly Lys Val
1               5                   10                  15

Ala Asp Thr Leu Lys Pro Gly Asp Arg Val Leu Leu Ser Phe Glu Asp
                20                  25                  30

Glu Ser Glu Phe Leu Val Asp Leu Glu Lys Asp Lys Lys Leu His Thr
            35                  40                  45

His Leu Gly Ile Ile Asp Leu Asn Glu Val Phe Glu Lys Gly Pro Gly
        50                  55                  60

Glu Ile Ile Arg Thr Ser Ala Gly Lys Lys Gly Tyr Ile Leu Ile Pro
65                  70                  75                  80

Ser Leu Ile Asp Glu Ile Met Asn Met Lys Arg Arg Thr Gln Ile Val
                85                  90                  95

Tyr Pro Lys Asp Ser Ser Phe Ile Ala Met Met Leu Asp Val Lys Glu
            100                 105                 110

Gly Asp Arg Ile Ile Asp Thr Gly Val Gly Ser Gly Ala Met Cys Ala
        115                 120                 125

Val Leu Ala Arg Ala Val Gly Ser Ser Gly Lys Val Phe Ala Tyr Glu
130                 135                 140

Lys Arg Glu Glu Phe Ala Lys Leu Ala Glu Ser Asn Leu Thr Lys Trp
145                 150                 155                 160

Gly Leu Ile Glu Arg Val Thr Ile Lys Val Arg Asp Ile Ser Glu Gly
                165                 170                 175

Phe Asp Glu Lys Asp Val Asp Ala Leu Phe Leu Asp Val Pro Asp Pro
            180                 185                 190

Trp Asn Tyr Ile Asp Lys Cys Trp Glu Ala Leu Lys Gly Gly Gly Arg
        195                 200                 205

Phe Ala Thr Val Cys Pro Thr Thr Asn Gln Val Gln Glu Thr Leu Lys
210                 215                 220
```

```
Lys Leu Gln Glu Leu Pro Phe Ile Arg Ile Glu Val Trp Glu Ser Leu
225                 230                 235                 240

Phe Arg Pro Tyr Lys Pro Val Pro Glu Arg Leu Arg Pro Val Asp Arg
                245                 250                 255

Met Val Ala His Thr Ala Tyr Met Ile Phe Ala Thr Lys Val Cys Arg
            260                 265                 270

Arg Glu Glu Thr Glu
            275
```

<210> SEQ ID NO 107
<211> LENGTH: 347
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 107

```
Met Arg Ala Val Arg Leu Val Glu Ile Gly Lys Pro Leu Ser Leu Gln
1               5                   10                  15

Glu Ile Gly Val Pro Lys Pro Lys Gly Pro Gln Val Leu Ile Lys Val
                20                  25                  30

Glu Ala Ala Gly Val Cys His Ser Asp Val His Met Arg Gln Gly Arg
            35                  40                  45

Phe Gly Asn Leu Arg Ile Val Glu Asp Leu Gly Val Lys Leu Pro Val
50                  55                  60

Thr Leu Gly His Glu Ile Ala Gly Lys Ile Glu Glu Val Gly Asp Glu
65                  70                  75                  80

Val Val Gly Tyr Ser Lys Gly Asp Leu Val Ala Val Asn Pro Trp Gln
                85                  90                  95

Gly Glu Gly Asn Cys Tyr Tyr Cys Arg Ile Gly Glu Glu His Leu Cys
            100                 105                 110

Asp Ser Pro Arg Trp Leu Gly Ile Asn Phe Asp Gly Ala Tyr Ala Glu
            115                 120                 125

Tyr Val Ile Val Pro His Tyr Lys Tyr Met Tyr Lys Leu Arg Arg Leu
130                 135                 140

Asn Ala Val Glu Ala Ala Pro Leu Thr Cys Ser Gly Ile Thr Thr Tyr
145                 150                 155                 160

Arg Ala Val Arg Lys Ala Ser Leu Asp Pro Thr Lys Thr Leu Leu Val
                165                 170                 175

Val Gly Ala Gly Gly Leu Gly Thr Met Ala Val Gln Ile Ala Lys
            180                 185                 190

Ala Val Ser Gly Ala Thr Ile Ile Gly Val Asp Val Arg Glu Glu Ala
            195                 200                 205

Val Glu Ala Ala Lys Arg Ala Gly Ala Asp Tyr Val Ile Asn Ala Ser
210                 215                 220

Met Gln Asp Pro Leu Ala Glu Ile Arg Arg Ile Thr Glu Ser Lys Gly
225                 230                 235                 240

Val Asp Ala Val Ile Asp Leu Asn Asn Ser Glu Lys Thr Leu Ser Val
                245                 250                 255

Tyr Pro Lys Ala Leu Ala Lys Gln Gly Lys Tyr Val Met Val Gly Leu
            260                 265                 270

Phe Gly Ala Asp Leu His Tyr His Ala Pro Leu Ile Thr Leu Ser Glu
            275                 280                 285

Ile Gln Phe Val Gly Ser Leu Val Gly Asn Gln Ser Asp Phe Leu Gly
```

```
            290                 295                 300
Ile Met Arg Leu Ala Glu Ala Gly Lys Val Lys Pro Met Ile Thr Lys
305                 310                 315                 320

Thr Met Lys Leu Glu Glu Ala Asn Glu Ala Ile Asp Asn Leu Glu Asn
                325                 330                 335

Phe Lys Ala Ile Gly Arg Gln Val Leu Ile Pro
                340                 345
```

<210> SEQ ID NO 108
<211> LENGTH: 101
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 108

```
Met Arg Arg Tyr Glu Val Asn Ile Val Leu Asn Pro Asn Leu Asp Gln
1               5                   10                  15

Ser Gln Leu Ala Leu Glu Lys Glu Ile Ile Gln Arg Ala Leu Glu Asn
                20                  25                  30

Tyr Gly Ala Arg Val Glu Lys Val Glu Glu Leu Gly Leu Arg Arg Leu
            35                  40                  45

Ala Tyr Pro Ile Ala Lys Asp Pro Gln Gly Tyr Phe Leu Trp Tyr Gln
        50                  55                  60

Val Glu Met Pro Glu Asp Arg Val Asn Asp Leu Ala Arg Glu Leu Arg
65                  70                  75                  80

Ile Arg Asp Asn Val Arg Arg Val Met Val Val Lys Ser Gln Glu Pro
                85                  90                  95

Phe Leu Ala Asn Ala
                100
```

<210> SEQ ID NO 109
<211> LENGTH: 284
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

```
Met Ile Val Val Ser Gly Ser Gln Ser Gln Asn Leu Ala Phe Lys Val
1               5                   10                  15

Ala Lys Leu Leu Asn Thr Lys Leu Thr Arg Val Glu Tyr Lys Arg Phe
                20                  25                  30

Pro Asp Asn Glu Ile Tyr Val Arg Ile Val Asp Glu Ile Asn Asp Asp
            35                  40                  45

Glu Ala Val Ile Ile Asn Thr Gln Lys Asn Gln Asn Asp Ala Ile Val
        50                  55                  60

Glu Thr Ile Leu Leu Cys Asp Ala Leu Arg Asp Glu Gly Val Lys Lys
65                  70                  75                  80

Ile Thr Leu Val Ala Pro Tyr Leu Ala Tyr Ala Arg Gln Asp Lys Lys
                85                  90                  95

Phe Asn Pro Gly Glu Ala Ile Ser Ile Arg Ala Leu Ala Lys Ile Tyr
                100                 105                 110

Ser Asn Ile Val Asp Lys Leu Ile Thr Ile Asn Pro His Glu Thr His
                115                 120                 125

Ile Lys Asp Phe Phe Thr Ile Pro Phe Ile Tyr Gly Asp Ala Val Pro
```

```
                130                 135                 140
Lys Leu Ala Glu Tyr Val Lys Asp Lys Leu Asn Asp Pro Ile Val Leu
145                 150                 155                 160

Ala Pro Asp Lys Gly Ala Leu Glu Phe Ala Lys Thr Ala Ser Lys Ile
                165                 170                 175

Leu Asn Ala Glu Tyr Asp Tyr Leu Glu Lys Thr Arg Leu Ser Pro Thr
            180                 185                 190

Glu Ile Gln Ile Ala Pro Lys Thr Leu Asp Ala Lys Asp Arg Asp Val
            195                 200                 205

Phe Ile Val Asp Asp Ile Ile Ser Thr Gly Gly Thr Met Ala Thr Ala
            210                 215                 220

Val Lys Leu Leu Lys Glu Gln Gly Ala Lys Lys Ile Ile Ala Ala Cys
225                 230                 235                 240

Val His Pro Val Leu Ile Gly Asp Ala Leu Asn Lys Leu Tyr Ser Ala
                245                 250                 255

Gly Val Glu Glu Val Val Gly Thr Asp Thr Tyr Leu Ser Glu Val Ser
            260                 265                 270

Lys Val Ser Val Ala Glu Val Ile Val Asp Leu Leu
            275                 280

<210> SEQ ID NO 110
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Met Arg Val Met Ile Thr Asp Lys Leu Arg Arg Asp Ser Glu Gln Ile
1               5                   10                  15

Trp Lys Lys Ile Phe Glu His Pro Phe Val Gln Leu Tyr Ser Gly
                20                  25                  30

Thr Leu Pro Leu Glu Lys Phe Lys Phe Tyr Val Leu Gln Asp Phe Asn
            35                  40                  45

Tyr Leu Val Gly Leu Thr Arg Ala Leu Ala Val Ile Ser Ser Lys Ala
    50                  55                  60

Glu Tyr Pro Leu Met Ala Glu Leu Ile Glu Leu Ala Arg Asp Glu Val
65                  70                  75                  80

Thr Val Glu Val Glu Asn Tyr Val Lys Leu Leu Lys Glu Leu Asp Leu
                85                  90                  95

Thr Leu Glu Asp Ala Ile Lys Thr Glu Pro Thr Leu Val Asn Ser Ala
            100                 105                 110

Tyr Met Asp Phe Met Leu Ala Thr Ala Tyr Lys Gly Asn Ile Ile Glu
            115                 120                 125

Gly Leu Thr Ala Leu Leu Pro Cys Phe Trp Ser Tyr Ala Glu Ile Ala
        130                 135                 140

Glu Tyr His Lys Asp Lys Leu Arg Asp Asn Pro Ile Lys Ile Tyr Arg
145                 150                 155                 160

Glu Trp Gly Lys Val Tyr Leu Ser Asn Glu Tyr Leu Asn Leu Val Gly
                165                 170                 175

Arg Leu Arg Lys Ile Ile Asp Ser Ser Gly His Ser Gly Tyr Asp Arg
            180                 185                 190

Leu Arg Arg Ile Phe Ile Thr Gly Ser Lys Phe Glu Leu Ala Phe Trp
        195                 200                 205
```

```
Glu Met Ala Trp Arg Gly Gly Asp Val Phe Leu Glu His His His His
    210                 215                 220

His His
225
```

```
<210> SEQ ID NO 111
<211> LENGTH: 314
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Met Asp Tyr Gly Met Tyr Phe Phe Glu His Val Thr Pro Tyr Glu Thr
1               5                   10                  15

Leu Val Arg Arg Met Glu Arg Val Ile Ala Ser Gly Lys Thr Pro Phe
            20                  25                  30

Gln Asp Tyr Phe Leu Phe Glu Ser Lys Gly Phe Gly Lys Val Leu Ile
        35                  40                  45

Leu Asp Lys Asp Val Gln Ser Thr Glu Arg Asp Glu Tyr Ile Tyr His
50                  55                  60

Glu Thr Leu Val His Pro Ala Met Leu Thr His Pro Glu Pro Lys Arg
65                  70                  75                  80

Val Leu Ile Val Gly Gly Gly Glu Gly Ala Thr Leu Arg Glu Val Leu
                85                  90                  95

Lys His Pro Thr Val Glu Lys Ala Val Met Val Asp Ile Asp Gly Glu
            100                 105                 110

Leu Val Glu Val Ala Lys Arg His Met Pro Glu Trp His Gln Gly Ala
        115                 120                 125

Phe Asp Asp Pro Arg Ala Val Leu Val Ile Asp Ala Arg Ala Tyr
        130                 135                 140

Leu Glu Arg Thr Glu Glu Arg Tyr Asp Val Val Ile Ile Asp Leu Thr
145                 150                 155                 160

Asp Pro Val Gly Glu Asp Asn Pro Ala Arg Leu Leu Tyr Thr Val Glu
                165                 170                 175

Phe Tyr Arg Leu Val Lys Ala His Leu Asn Pro Gly Gly Val Met Gly
            180                 185                 190

Met Gln Thr Gly Met Ile Leu Leu Thr His Arg Val His Pro Val
        195                 200                 205

Val His Arg Thr Val Arg Glu Ala Phe Arg Tyr Val Arg Ser Tyr Lys
    210                 215                 220

Asn His Ile Pro Gly Phe Phe Leu Asn Phe Gly Phe Leu Leu Ala Ser
225                 230                 235                 240

Asp Ala Phe Asp Pro Ala Ala Phe Ser Glu Gly Val Ile Glu Ala Arg
                245                 250                 255

Ile Arg Glu Arg Asn Leu Ala Leu Arg His Leu Thr Ala Pro Tyr Leu
            260                 265                 270

Glu Ala Met Phe Val Leu Pro Lys Asp Leu Leu Glu Ala Leu Glu Lys
        275                 280                 285

Glu Thr Met Val Ser Thr Asp Gln Asn Pro Phe Tyr Val Thr Pro Glu
    290                 295                 300

Gly Glu Ala Arg Gln Ala Pro Tyr Lys Gly
305                 310

<210> SEQ ID NO 112
```

<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Met Asp Phe Leu Asp Phe Glu Lys Val Phe Ser Phe Tyr Ser Lys Ala
1               5                   10                  15

Thr Lys Lys Gly Phe Ser Pro Phe Val Pro Ala Leu Glu Lys Ala
            20                  25                  30

Glu Glu Pro Ala Gly Asn Phe Phe Leu Asp Arg Lys Gly Asn Leu Phe
        35                  40                  45

Ser Ile Arg Glu Asp Phe Thr Lys Thr Val Leu Asn His Arg Lys Arg
50                  55                  60

Tyr Ser Pro Asp Ser Gln Ile Lys Val Trp Tyr Ala Asp Phe Val Tyr
65                  70                  75                  80

Arg Tyr Ser Gly Ser Asp Leu Val Ala Glu Tyr Gln Leu Gly Leu Glu
                85                  90                  95

Lys Val Pro Arg Asn Ser Leu Asp Asp Ser Leu Glu Val Leu Glu Ile
            100                 105                 110

Ile Val Glu Ser Ala Ser Glu Phe Phe Glu Gly Pro Val Ile Val Glu
        115                 120                 125

Ile Gly His Thr Gly Val Tyr Glu Asp Leu Leu Lys Glu Ile Pro Lys
130                 135                 140

Asp Leu His Glu Lys Val Leu Asn Leu Ile Asp Thr Lys Asn Leu Ala
145                 150                 155                 160

Glu Ile Glu Phe Leu Ser His Met Lys Lys Ile Asp Leu Ser Arg Val
                165                 170                 175

Glu Lys Ile Ile Glu Asp Ser Ile Tyr Arg Arg Ser Pro Glu His Leu
            180                 185                 190

Lys Thr Met Asp Leu Pro Leu Ser Val Arg Glu Asp Leu Leu Ser Ala
        195                 200                 205

Ser Ser Phe Leu Gln Glu Lys Phe Pro Thr Val Ser Val Glu Ile Asp
210                 215                 220

Leu Thr Leu Ala Arg Thr Ile Glu Glu Tyr Cys Gly Leu Ile Phe Thr
225                 230                 235                 240

Ile Tyr Asp Thr Ser Ser Ser Arg Leu Val Ala Ala Gly Gly Glu Tyr
                245                 250                 255

Thr Val Asn Gly Glu Lys Gly Val Gly Gly Ser Ile Phe Leu Glu Gly
            260                 265                 270

Lys Thr Cys
        275

<210> SEQ ID NO 113
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Met Leu Lys Leu Ala Ile Pro Lys Gly Arg Leu Glu Glu Lys Val Met
1               5                   10                  15

Thr Tyr Leu Lys Lys Thr Gly Val Ile Phe Glu Arg Glu Ser Ser Ile
            20                  25                  30

```
Leu Arg Glu Gly Lys Asp Ile Val Cys Phe Met Val Arg Pro Phe Asp
         35                  40                  45

Val Pro Thr Tyr Leu Val His Gly Val Ala Asp Ile Gly Phe Cys Gly
     50                  55                  60

Thr Asp Val Leu Leu Glu Lys Glu Thr Ser Leu Ile Gln Pro Phe Phe
 65                  70                  75                  80

Ile Pro Thr Asn Ile Ser Arg Met Val Leu Ala Gly Pro Lys Gly Arg
                 85                  90                  95

Gly Ile Pro Glu Gly Glu Lys Arg Ile Ala Thr Lys Phe Pro Asn Val
             100                 105                 110

Thr Gln Arg Tyr Cys Glu Ser Lys Gly Trp His Cys Arg Ile Ile Pro
         115                 120                 125

Leu Lys Gly Ser Val Glu Leu Ala Pro Ile Ala Gly Leu Ser Asp Leu
     130                 135                 140

Ile Val Asp Ile Thr Glu Thr Gly Arg Thr Leu Lys Glu Asn Asn Leu
145                 150                 155                 160

Glu Ile Leu Asp Glu Ile Phe Val Ile Arg Thr His Val Val Val Asn
                 165                 170                 175

Pro Val Ser Tyr Arg Thr Lys Arg Glu Lys Val Val Ser Phe Leu Glu
             180                 185                 190

Lys Leu Gln Glu Val Ile Glu His Asp Ser Asn Glu Gln Ser Arg Gly
         195                 200                 205

<210> SEQ ID NO 114
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Met Arg Ala Gly Leu Leu Glu Gly Val Ile Lys Glu Lys Gly Gly Val
 1               5                  10                  15

Pro Val Tyr Pro Ser Tyr Leu Ala Gly Glu Trp Gly Gly Ser Gly Gln
             20                  25                  30

Glu Ile Glu Val Lys Ser Pro Ile Asp Leu Ala Thr Ile Ala Lys Val
         35                  40                  45

Ile Ser Pro Ser Arg Glu Glu Val Glu Arg Thr Leu Asp Val Leu Phe
     50                  55                  60

Lys Arg Gly Arg Trp Ser Ala Arg Asp Met Pro Gly Thr Glu Arg Leu
 65                  70                  75                  80

Ala Val Leu Arg Lys Ala Ala Asp Ile Ile Glu Arg Asn Leu Asp Val
                 85                  90                  95

Phe Ala Glu Val Leu Val Met Asn Ala Gly Lys Pro Lys Ser Ala Ala
             100                 105                 110

Val Gly Glu Val Lys Ala Ala Val Asp Arg Leu Arg Leu Ala Glu Leu
         115                 120                 125

Asp Leu Lys Lys Ile Gly Gly Asp Tyr Ile Pro Gly Asp Trp Thr Tyr
     130                 135                 140

Asp Thr Leu Glu Thr Glu Gly Leu Val Arg Arg Glu Pro Leu Gly Val
145                 150                 155                 160

Val Ala Ala Ile Thr Pro Phe Asn Tyr Pro Leu Phe Asp Ala Val Asn
                 165                 170                 175

Lys Ile Thr Tyr Ser Phe Ile Tyr Gly Asn Ala Val Val Val Lys Pro
```

```
            180                 185                 190
Ser Ile Ser Asp Pro Leu Pro Ala Ala Met Ala Val Lys Ala Leu Leu
            195                 200                 205

Asp Ala Gly Phe Pro Asp Ala Ile Ala Leu Leu Asn Leu Pro Gly
    210                 215                 220

Lys Glu Ala Glu Lys Ile Val Ala Asp Arg Val Ala Val Ser
225                 230                 235                 240

Phe Thr Gly Ser Thr Glu Val Gly Glu Arg Val Val Lys Val Gly Gly
                245                 250                 255

Val Lys Gln Tyr Val Met Glu Leu Gly Gly Asp Pro Ala Ile Val
            260                 265                 270

Leu Glu Asp Ala Asp Leu Asp Leu Ala Ala Asp Lys Ile Ala Arg Gly
                275                 280                 285

Ile Tyr Ser Tyr Ala Gly Gln Arg Cys Asp Ala Ile Lys Leu Val Leu
            290                 295                 300

Ala Glu Arg Pro Val Tyr Gly Lys Leu Val Glu Val Ala Lys Arg
305                 310                 315                 320

Leu Ser Ser Leu Arg Val Gly Asp Pro Arg Asp Pro Thr Val Asp Val
                325                 330                 335

Gly Pro Leu Ile Ser Pro Ser Ala Val Asp Glu Met Met Ala Ala Ile
            340                 345                 350

Glu Asp Ala Val Glu Lys Gly Gly Arg Val Leu Ala Gly Gly Arg Arg
                355                 360                 365

Leu Gly Pro Thr Tyr Val Gln Pro Thr Phe Val Glu Ala Pro Ala Asp
            370                 375                 380

Arg Val Lys Asp Met Val Leu Tyr Lys Arg Glu Val Phe Ala Pro Val
385                 390                 395                 400

Ala Leu Ala Val Glu Val Lys Asp Leu Asp Gln Ala Ile Glu Leu Ala
                405                 410                 415

Asn Gly Arg Pro Tyr Gly Leu Asp Ala Ala Val Phe Gly Arg Asp Val
            420                 425                 430

Val Lys Ile Arg Arg Ala Val Arg Leu Leu Glu Val Gly Ala Ile Tyr
                435                 440                 445

Ile Asn Asp Met Pro Arg His Gly Ile Gly Tyr Tyr Pro Phe Gly Gly
            450                 455                 460

Arg Lys Lys Ser Gly Val Phe Arg Glu Gly Ile Gly Tyr Ala Val Glu
465                 470                 475                 480

Ala Val Thr Ala Tyr Lys Thr Ile Val Phe Asn Tyr Lys Gly Lys Gly
                485                 490                 495

Val Trp Lys Tyr Glu
            500

<210> SEQ ID NO 115
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Met Arg Val Asp Leu Asn Ser Asp Leu Gly Glu Ser Phe Gly Arg Tyr
1               5                   10                  15

Lys Leu Gly Leu Asp Glu Glu Val Met Lys Tyr Ile Thr Ser Ala Asn
                20                  25                  30
```

```
Val Ala Cys Gly Trp His Ala Gly Asp Pro Leu Val Met Arg Lys Thr
            35                  40                  45

Val Arg Leu Ala Lys Glu Asn Asp Val Gln Val Gly Ala His Pro Gly
 50                  55                  60

Tyr Pro Asp Leu Met Gly Phe Gly Arg Arg Tyr Met Lys Leu Thr Pro
 65                  70                  75                  80

Glu Glu Ala Arg Asn Tyr Ile Leu Tyr Gln Val Gly Ala Leu Tyr Ala
                 85                  90                  95

Phe Ala Lys Ala Glu Gly Leu Glu Leu Gln His Val Lys Pro His Gly
                100                 105                 110

Ala Leu Tyr Asn Ala Met Val Lys Glu Glu Asp Leu Ala Arg Ala Val
            115                 120                 125

Ile Glu Gly Ile Leu Asp Phe Asp Lys Asp Leu Ile Leu Val Thr Leu
130                 135                 140

Ser Asn Ser Arg Val Ala Asp Ile Ala Glu Glu Met Gly Leu Lys Val
145                 150                 155                 160

Ala His Glu Val Phe Ala Asp Arg Ala Tyr Asn Pro Asp Gly Thr Leu
                165                 170                 175

Val Pro Arg Gly Arg Pro Gly Ala Val Ile Glu Asp Lys Glu Glu Ile
            180                 185                 190

Ala Glu Arg Val Ile Ser Met Val Lys Asp Gly Gly Ile Arg Ala Ile
            195                 200                 205

Asn Gly Glu Trp Val Asp Leu Lys Val Asp Thr Ile Cys Val His Gly
            210                 215                 220

Asp Asn Pro Lys Ala Val Glu Ile Thr Ser Tyr Ile Arg Lys Val Leu
225                 230                 235                 240

Glu Glu Glu Gly Val Lys Ile Val Pro Met Lys Glu Phe Ile Arg
                245                 250                 255

<210> SEQ ID NO 116
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Met Ser Tyr Tyr His His His His His Asp Tyr Asp Ile Pro Thr
 1               5                  10                  15

Thr Glu Asn Leu Tyr Phe Gln Gly Ala Met Ala Val Glu Tyr Leu Val
                 20                  25                  30

Asp Ala Ser Ala Leu Tyr Ala Leu Ala Ala His Tyr Asp Lys Trp Ile
            35                  40                  45

Lys His Arg Glu Lys Leu Ala Ile Leu His Leu Thr Ile Tyr Glu Ala
 50                  55                  60

Gly Asn Ala Leu Trp Lys Glu Ala Arg Leu Gly Arg Val Asp Trp Ala
 65                  70                  75                  80

Ala Ala Ser Arg His Leu Lys Lys Val Met Ser Ser Phe Lys Val Leu
                 85                  90                  95

Glu Asp Pro Pro Leu Asp Glu Val Met Arg Val Ala Val Glu Arg Gly
                100                 105                 110

Leu Thr Phe Tyr Asp Ala Ser Tyr Ala Tyr Val Ala Glu Ser Ser Gly
            115                 120                 125

Leu Val Leu Val Thr Gln Asp Arg Glu Leu Leu Ala Lys Thr Lys Gly
130                 135                 140
```

```
Ala Ile Asp Val Glu Thr Leu Leu Val Arg Leu Ala Ala Gln
145                 150                 155
```

<210> SEQ ID NO 117
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

```
Met Ser Tyr Tyr His His His His His His Asp Tyr Asp Ile Pro Thr
1               5                   10                  15

Thr Glu Asn Leu Tyr Phe Gln Gly Ala Met Ala Val Glu Tyr Leu Val
                20                  25                  30

Asp Ala Ser Ala Leu Tyr Ala Leu Ala Ala His Tyr Asp Lys Trp Ile
            35                  40                  45

Lys His Arg Glu Lys Leu Ala Ile Leu His Leu Thr Ile Tyr Glu Ala
50                  55                  60

Gly Asn Ala Leu Trp Lys Glu Ala Arg Leu Gly Arg Val Asp Trp Ala
65                  70                  75                  80

Ala Ala Ser Arg His Leu Lys Lys Val Leu Ser Ser Phe Lys Val Leu
                85                  90                  95

Glu Asp Pro Pro Leu Asp Glu Val Leu Arg Val Ala Val Glu Arg Gly
            100                 105                 110

Leu Thr Phe Tyr Asp Ala Ser Tyr Ala Tyr Val Ala Glu Ser Ser Gly
        115                 120                 125

Leu Val Leu Val Thr Gln Asp Arg Glu Leu Leu Ala Lys Thr Lys Gly
    130                 135                 140

Ala Ile Asp Val Glu Thr Leu Leu Val Arg Leu Ala Ala Gln
145                 150                 155
```

<210> SEQ ID NO 118
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Met Lys Val Gly Ile Asn Gly Phe Gly Arg Ile Gly Arg Gln Val Phe
1               5                   10                  15

Arg Ile Leu His Glu Arg Gly Val Glu Val Ala Leu Ile Asn Asp Leu
                20                  25                  30

Thr Asp Asn Lys Thr Leu Ala His Leu Leu Lys Tyr Asp Ser Thr Tyr
            35                  40                  45

Gly Arg Phe Pro Gly Ala Val Gly Tyr Asp Glu Glu Asn Leu Tyr Val
        50                  55                  60

Asp Gly Lys Ala Ile Arg Ala Thr Ala Ile Lys Asp Pro Arg Glu Ile
65                  70                  75                  80

Pro Trp Lys Gln Ala Gly Val Gly Val Val Glu Ser Thr Gly Val
                85                  90                  95

Phe Thr Asp Gly Glu Lys Ala Arg Ala His Leu Glu Ala Gly Ala Lys
            100                 105                 110

Lys Val Ile Ile Thr Ala Pro Ala Lys Asn Glu Asp Ile Thr Val Val
        115                 120                 125
```

```
Leu Gly Val Asn His Glu Gln Tyr Asp Pro Ala Lys His His Ile Leu
            130                 135                 140

Ser Asn Ala Ser Cys Thr Thr Asn Ser Leu Ala Pro Val Met Lys Val
145                 150                 155                 160

Leu Glu Lys Ala Phe Gly Val Glu Lys Ala Leu Met Thr Thr Val His
                165                 170                 175

Ser Tyr Thr Asn Asp Gln Arg Leu Leu Asp Leu Pro His Lys Asp Leu
                180                 185                 190

Arg Arg Ala Arg Ala Ala Leu Asn Ile Ile Pro Thr Thr Thr Gly
                195                 200                 205

Ala Ala Lys Ala Thr Ala Leu Val Leu Pro Ser Leu Lys Gly Arg Phe
210                 215                 220

Asp Gly Met Ala Leu Arg Val Pro Thr Pro Thr Gly Ser Ile Ser Asp
225                 230                 235                 240

Ile Thr Ala Leu Leu Lys Arg Glu Val Thr Ala Glu Glu Val Asn Ala
                245                 250                 255

Ala Leu Lys Ala Ala Ala Glu Gly Pro Leu Lys Gly Ile Leu Ala Tyr
                260                 265                 270

Thr Glu Asp Glu Ile Val Leu Arg Asp Ile Val Met Asp Pro His Ser
                275                 280                 285

Ser Ile Val Asp Gly Lys Leu Thr Lys Ala Ile Gly Asn Leu Val Lys
                290                 295                 300

Val Phe Ala Trp Tyr Asp Asn Glu Trp Gly Tyr Ala Asn Arg Val Ala
305                 310                 315                 320

Asp Leu Val Glu Leu Val Leu Lys Lys Gly Val
                325                 330

<210> SEQ ID NO 119
<211> LENGTH: 550
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Met Asn Gly Ser Ala Asp Ala Gly Pro Arg Pro Arg Lys Tyr Val Phe
1               5                   10                  15

Ile Thr Gly Gly Val Val Ser Ser Leu Gly Lys Gly Ile Leu Thr Ser
                20                  25                  30

Ser Leu Gly Ala Leu Leu Arg Ala Arg Gly Tyr Arg Val Thr Ala Ile
            35                  40                  45

Lys Ile Asp Pro Tyr Val Asn Val Asp Ala Gly Thr Met Arg Pro Tyr
        50                  55                  60

Glu His Gly Glu Val Phe Val Thr Ala Asp Gly Ala Glu Thr Asp Leu
65                  70                  75                  80

Asp Ile Gly His Tyr Glu Arg Phe Leu Asp Met Asp Leu Ser Arg Gly
                85                  90                  95

Asn Asn Leu Thr Thr Gly Gln Val Tyr Leu Ser Val Ile Gln Lys Glu
            100                 105                 110

Arg Arg Gly Glu Tyr Leu Ser Gln Thr Val Gln Val Ile Pro His Ile
        115                 120                 125

Thr Asp Glu Ile Lys Glu Arg Ile Arg Lys Val Ala Glu Glu Gln Lys
    130                 135                 140

Ala Glu Ile Val Val Val Glu Val Gly Gly Thr Val Gly Asp Ile Glu
```

```
            145                 150                 155                 160
        Ser Leu Pro Phe Leu Glu Ala Ile Arg Gln Phe Arg Phe Asp Glu Gly
                        165                 170                 175

Glu Gly Asn Thr Leu Tyr Leu His Leu Thr Leu Val Pro Tyr Leu Glu
                        180                 185                 190

Thr Ser Glu Glu Phe Lys Thr Lys Pro Thr Gln His Ser Val Ala Thr
                        195                 200                 205

Leu Arg Gly Val Gly Ile Gln Pro Asp Ile Leu Val Leu Arg Ser Ala
                        210                 215                 220

Arg Pro Val Pro Glu Glu Val Arg Arg Lys Val Ala Leu Phe Thr Asn
        225                 230                 235                 240

Val Arg Pro Gly His Val Phe Ser Ser Pro Thr Val Glu His Leu Tyr
                        245                 250                 255

Glu Val Pro Leu Leu Leu Glu Glu Gln Gly Leu Gly Arg Ala Val Glu
                        260                 265                 270

Arg Ala Leu Gly Leu Glu Ala Val Ile Pro Asn Leu Ser Phe Trp Gln
                        275                 280                 285

Glu Ala Val Arg Val Leu Lys His Pro Glu Arg Thr Val Lys Ile Ala
                        290                 295                 300

Ile Ala Gly Lys Tyr Val Lys Met Pro Asp Ala Tyr Leu Ser Leu Leu
        305                 310                 315                 320

Glu Ala Leu Arg His Ala Gly Ile Lys Asn Arg Ala Arg Val Glu Val
                        325                 330                 335

Lys Trp Val Asp Ala Glu Ser Leu Glu Ala Ala Asp Leu Glu Glu Ala
                        340                 345                 350

Phe Arg Asp Val Ser Gly Ile Leu Val Pro Gly Gly Phe Gly Val Arg
                        355                 360                 365

Gly Ile Glu Gly Lys Val Arg Ala Ala Gln Tyr Ala Arg Glu Arg Lys
                        370                 375                 380

Ile Pro Tyr Leu Gly Ile Cys Leu Gly Leu Gln Ile Ala Val Ile Glu
        385                 390                 395                 400

Phe Ala Arg Asn Val Ala Gly Leu Lys Gly Ala Asn Ser Thr Glu Phe
                        405                 410                 415

Asp Pro His Thr Pro His Pro Val Ile Asp Leu Met Pro Glu Gln Leu
                        420                 425                 430

Glu Val Glu Gly Leu Gly Gly Thr Met Arg Leu Gly Asp Trp Pro Met
                        435                 440                 445

Arg Ile Lys Pro Gly Thr Leu Leu His Arg Leu Tyr Gly Lys Glu Glu
        450                 455                 460

Val Leu Glu Arg His Arg His Arg Tyr Glu Val Asn Pro Leu Tyr Val
        465                 470                 475                 480

Asp Gly Leu Glu Arg Ala Gly Leu Val Val Ser Ala Thr Thr Pro Gly
                        485                 490                 495

Met Arg Gly Arg Gly Ala Gly Leu Val Glu Ala Ile Glu Leu Lys Asp
                        500                 505                 510

His Pro Phe Phe Leu Gly Leu Gln Ser His Pro Glu Phe Lys Ser Arg
                        515                 520                 525

Pro Met Arg Pro Ser Pro Pro Phe Val Gly Phe Val Glu Ala Ala Leu
                        530                 535                 540

Ala Tyr Gln Glu Arg Ala
        545                 550

<210> SEQ ID NO 120
```

```
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Met Glu Tyr Arg Ile Glu Arg Asp Thr Met Gly Val Arg Val Pro
1               5                   10                  15

Ala Asp Lys Tyr Trp Gly Ala Gln Thr Gln Arg Ser Leu Glu Asn Phe
            20                  25                  30

Arg Ile Gly Thr Asp Arg Phe Arg Met Pro Leu Glu Ile Ile Arg Ala
        35                  40                  45

Tyr Gly Met Leu Lys Lys Ala Ala Arg Ala Asn Leu Glu Leu Gly
    50                  55                  60

Glu Leu Pro Glu Glu Ile Ala Lys Ala Ile Ile Gln Ala Ala Glu Glu
65                  70                  75                  80

Val Val Gln Gly Lys Trp Asp Asp His Phe Pro Leu Val Val Phe Gln
                85                  90                  95

Thr Gly Ser Gly Thr Gln Thr Asn Met Asn Val Asn Glu Val Ile Ala
            100                 105                 110

Asn Arg Ala Ser Glu Ile Leu Gly Lys Pro Leu Gly Ser Lys Tyr Ala
        115                 120                 125

His Pro Asn Asp His Val Asn Arg Gly Gln Ser Ser Asn Asp Thr Phe
    130                 135                 140

Pro Thr Ala Met Tyr Val Ala Val Ala Leu Ala Leu His Gln Arg Leu
145                 150                 155                 160

Tyr Pro Ala Val Glu Gly Leu Ile Arg Thr Phe Thr Ala Lys Ala Gln
                165                 170                 175

Ala Phe Asp Gln Ile Val Lys Val Gly Arg Thr His Leu Met Asp Ala
            180                 185                 190

Val Pro Ile Thr Leu Gly Gln Glu Ile Gly Ser Trp Ala Ala Gln Leu
        195                 200                 205

Lys Thr Thr Leu Ala Ala Val Lys Glu Met Glu Lys Gly Leu Tyr Asn
210                 215                 220

Leu Ala Ile Gly Gly Thr Ala Val Gly Thr Gly Leu Asn Ala His Pro
225                 230                 235                 240

Arg Phe Gly Glu Leu Val Ala Lys Tyr Leu Ala Glu Thr Gly Leu
                245                 250                 255

Pro Phe Arg Val Ala Glu Asn Arg Phe Ala Leu Ala His Asp
            260                 265                 270

Glu Leu Val Asn Val Met Gly Ala Ile Arg Thr Leu Ala Gly Ala Leu
        275                 280                 285

Met Lys Ile Gly Asn Asp Val Arg Trp Leu Ala Ser Gly Pro Tyr Ala
290                 295                 300

Gly Ile Gly Glu Ile Thr Ile Pro Ala Asn Glu Pro Gly Ser Ser Ile
305                 310                 315                 320

Met Pro Gly Lys Val Asn Pro Thr Gln Val Glu Ala Leu Thr Met Val
                325                 330                 335

Val Val Arg Val Tyr Gly Asn Asp His Thr Val Ala Phe Ala Gly Ser
            340                 345                 350

Gln Gly Asn Phe Gln Leu Asn Val Tyr Lys Pro Val Met Ala Tyr Ser
        355                 360                 365

Thr Leu Glu Ser Ile Asn Leu Leu Ala Asp Ala Val Ala Ser Phe Asp
```

```
                370                 375                 380
Ala His Leu Ala Gln Gly Ile Glu Pro Asn Leu Glu Arg Ile Glu Glu
385                 390                 395                 400

Tyr Leu Gln Lys Asn Pro Met Leu Ala Thr Ala Leu Asn Lys Ala Ile
                405                 410                 415

Gly Tyr Asp Lys Ala Ala Glu Ile Val Lys Lys Ala Leu Lys Glu Lys
                420                 425                 430

Lys Thr Leu Lys Gln Ala Ala Leu Glu Leu Gly Tyr Leu Thr Glu Glu
                435                 440                 445

Glu Phe Asp Arg Ile Val Val Pro Met Arg Leu Ala Lys Pro His Glu
                450                 455                 460

Gly Ala
465

<210> SEQ ID NO 121
<211> LENGTH: 394
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Met Gly Ser Asp Lys Ile His His His His His Met Val Lys Val
1               5                   10                  15

Leu Ile Leu Gly Gln Gly Tyr Val Ala Ser Thr Phe Val Ala Gly Leu
                20                  25                  30

Glu Lys Leu Arg Lys Gly Glu Ile Glu Pro Tyr Gly Val Pro Leu Ala
                35                  40                  45

Arg Glu Leu Pro Ile Gly Phe Glu Asp Ile Lys Ile Val Gly Ser Tyr
50                  55                  60

Asp Val Asp Arg Ala Lys Ile Gly Lys Lys Leu Ser Glu Val Val Lys
65                  70                  75                  80

Gln Tyr Trp Asn Asp Val Asp Ser Leu Thr Ser Asp Pro Glu Ile Arg
                85                  90                  95

Lys Gly Val His Leu Gly Ser Val Arg Asn Leu Pro Ile Glu Ala Glu
                100                 105                 110

Gly Leu Glu Asp Ser Met Thr Leu Lys Glu Ala Val Asp Thr Leu Val
                115                 120                 125

Lys Glu Trp Thr Glu Leu Asp Pro Asp Val Ile Val Asn Thr Cys Thr
130                 135                 140

Thr Glu Ala Phe Val Pro Phe Gly Asn Lys Glu Asp Leu Leu Lys Ala
145                 150                 155                 160

Ile Glu Asn Asn Asp Lys Glu Arg Leu Thr Ala Thr Gln Val Tyr Ala
                165                 170                 175

Tyr Ala Ala Leu Tyr Ala Asn Lys Arg Gly Gly Ala Ala Phe Val
                180                 185                 190

Asn Val Ile Pro Thr Phe Ile Ala Asn Asp Pro Ala Phe Val Glu Leu
                195                 200                 205

Ala Lys Glu Asn Asn Leu Val Val Phe Gly Asp Asp Gly Ala Thr Gly
                210                 215                 220

Ala Thr Pro Phe Thr Ala Asp Val Leu Ser His Leu Ala Gln Arg Asn
225                 230                 235                 240

Arg Tyr Val Lys Asp Val Ala Gln Phe Asn Ile Gly Gly Asn Met Asp
                245                 250                 255
```

```
Phe Leu Ala Leu Thr Asp Asp Gly Lys Asn Lys Ser Lys Glu Phe Thr
                260                 265                 270

Lys Ser Ser Ile Val Lys Asp Ile Leu Gly Tyr Asp Ala Pro His Tyr
            275                 280                 285

Ile Lys Pro Thr Gly Tyr Leu Glu Pro Leu Gly Asp Lys Lys Phe Ile
        290                 295                 300

Ala Ile His Ile Glu Tyr Val Ser Phe Asn Gly Ala Thr Asp Glu Leu
305                 310                 315                 320

Met Ile Asn Gly Arg Ile Asn Asp Ser Pro Ala Leu Gly Gly Leu Leu
                325                 330                 335

Val Asp Leu Val Arg Leu Gly Lys Ile Ala Leu Asp Arg Lys Glu Phe
            340                 345                 350

Gly Thr Val Tyr Pro Val Asn Ala Phe Tyr Met Lys Asn Pro Gly Pro
        355                 360                 365

Ala Glu Glu Lys Asn Ile Pro Arg Ile Ile Ala Tyr Glu Lys Met Arg
    370                 375                 380

Ile Trp Ala Gly Leu Lys Pro Lys Trp Leu
385                 390
```

<210> SEQ ID NO 122
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

```
Met Gly Ser Asp Lys Ile His His His His His Met Pro Lys Val
1               5                   10                  15

Thr Val Ser Ile Lys Val Val Pro Ala Val Glu Asp Gly Arg Leu His
            20                  25                  30

Glu Val Ile Asp Arg Ala Ile Glu Lys Ile Ser Ser Trp Gly Met Lys
        35                  40                  45

Tyr Glu Val Gly Pro Ser Asn Thr Thr Val Gly Glu Phe Glu Glu
    50                  55                  60

Ile Met Asp Arg Val Lys Glu Leu Ala Arg Tyr Leu Glu Gln Phe Ala
65                  70                  75                  80

Lys Arg Phe Val Leu Gln Leu Asp Ile Asp Tyr Lys Ala Gly Gly Ile
                85                  90                  95

Thr Ile Glu Glu Lys Val Ser Lys Tyr Arg
            100                 105
```

<210> SEQ ID NO 123
<211> LENGTH: 421
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

```
Met Gly Ser Asp Lys Ile His His His His His Met Lys Glu Lys
1               5                   10                  15

Val Val Leu Ala Tyr Ser Gly Gly Leu Asp Thr Ser Val Ile Leu Lys
            20                  25                  30

Trp Leu Cys Glu Lys Gly Phe Asp Val Ile Ala Tyr Val Ala Asn Val
        35                  40                  45
```

Gly Gln Lys Asp Asp Phe Val Ala Ile Lys Glu Lys Ala Leu Lys Thr
 50                  55                  60

Gly Ala Ser Lys Val Tyr Val Glu Asp Leu Arg Arg Glu Phe Val Thr
 65                  70                  75                  80

Asp Tyr Ile Phe Thr Ala Leu Leu Gly Asn Ala Met Tyr Glu Gly Arg
                 85                  90                  95

Tyr Leu Leu Gly Thr Ala Ile Ala Arg Pro Leu Ile Ala Lys Arg Gln
                100                 105                 110

Val Glu Ile Ala Glu Lys Gly Ala Gln Tyr Val Ala His Gly Ala
                115                 120                 125

Thr Gly Lys Gly Asn Asp Gln Val Arg Phe Glu Leu Thr Tyr Ala Ala
130                 135                 140

Leu Asn Pro Asn Leu Lys Val Ile Ser Pro Trp Lys Asp Pro Glu Phe
145                 150                 155                 160

Leu Ala Lys Phe Lys Gly Arg Thr Asp Leu Ile Asn Tyr Ala Met Glu
                165                 170                 175

Lys Gly Ile Pro Ile Lys Val Ser Lys Lys Arg Pro Tyr Ser Glu Asp
                180                 185                 190

Glu Asn Leu Met His Ile Ser His Glu Ala Gly Lys Leu Glu Asp Pro
                195                 200                 205

Ala His Ile Pro Asp Glu Asp Val Phe Thr Trp Thr Val Ser Pro Lys
210                 215                 220

Asp Ala Pro Asp Glu Glu Thr Leu Leu Glu Ile His Phe Glu Asn Gly
225                 230                 235                 240

Ile Pro Val Lys Val Asn Leu Lys Asp Gly Thr Glu Lys Thr Asp
                245                 250                 255

Pro Leu Glu Leu Phe Glu Tyr Leu Asn Glu Val Gly Ala Lys Asn Gly
                260                 265                 270

Val Gly Arg Leu Asp Met Val Glu Asn Arg Phe Ile Gly Ile Lys Ser
                275                 280                 285

Arg Gly Val Tyr Glu Thr Pro Gly Ala Thr Ile Leu Trp Ile Ala His
                290                 295                 300

Arg Asp Leu Glu Gly Ile Thr Met Asp Lys Glu Val Met His Leu Arg
305                 310                 315                 320

Asp Met Leu Ala Pro Lys Phe Ala Glu Leu Ile Tyr Asn Gly Phe Trp
                325                 330                 335

Phe Ser Pro Glu Met Glu Phe Leu Leu Ala Ala Phe Arg Lys Ala Gln
                340                 345                 350

Glu Asn Val Thr Gly Lys Val Thr Val Ser Ile Tyr Lys Gly Asn Val
                355                 360                 365

Met Pro Val Ala Arg Tyr Ser Pro Tyr Ser Leu Tyr Asn Pro Glu Leu
370                 375                 380

Ser Ser Met Asp Val Glu Gly Phe Asp Ala Thr Asp Ser Lys Gly
385                 390                 395                 400

Phe Ile Asn Ile His Ala Leu Arg Leu Lys Val His Gln Leu Val Lys
                405                 410                 415

Lys Gly Tyr Gln Arg
                420

<210> SEQ ID NO 124
<211> LENGTH: 325
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 124

Met Gly Ser Asp Lys Ile His His His His His His Met Ser Val Asn
1               5                   10                  15

Leu Lys Gly Arg Ser Leu Leu Thr Leu Leu Asp Phe Ser Pro Glu Glu
            20                  25                  30

Ile Arg Tyr Leu Leu Asp Ile Ser Lys Gln Val Lys Met Glu Asn Arg
        35                  40                  45

Ser Lys Leu Arg Thr Glu Arg Phe Lys Gly Met Thr Leu Ala Met Ile
    50                  55                  60

Phe Glu Lys Arg Ser Thr Arg Thr Arg Leu Ala Phe Glu Thr Ala Phe
65                  70                  75                  80

Ala Glu Glu Gly Gly His Pro Ile Phe Leu Ser Pro Asn Asp Ile His
                85                  90                  95

Leu Gly Ala Lys Glu Ser Leu Glu Asp Thr Ala Arg Val Leu Gly Arg
            100                 105                 110

Met Val Asp Ala Ile Met Phe Arg Gly Tyr Lys Gln Glu Thr Val Glu
        115                 120                 125

Lys Leu Ala Glu Tyr Ser Gly Val Pro Val Tyr Asn Gly Leu Thr Asp
    130                 135                 140

Glu Phe His Pro Thr Gln Ala Leu Ala Asp Leu Met Thr Ile Glu Glu
145                 150                 155                 160

Asn Phe Gly Arg Leu Lys Gly Val Lys Val Val Phe Met Gly Asp Thr
                165                 170                 175

Arg Asn Asn Val Ala Thr Ser Leu Met Ile Ala Cys Ala Lys Met Gly
            180                 185                 190

Met Asn Phe Val Ala Cys Gly Pro Glu Glu Leu Lys Pro Arg Ser Asp
        195                 200                 205

Val Phe Lys Arg Cys Gln Glu Ile Val Lys Glu Thr Asp Gly Ser Val
    210                 215                 220

Ser Phe Thr Ser Asn Leu Glu Glu Ala Leu Ala Gly Ala Asp Val Val
225                 230                 235                 240

Tyr Thr Asp Val Trp Ala Ser Met Gly Glu Glu Asp Lys Glu Lys Glu
                245                 250                 255

Arg Met Ala Leu Leu Lys Pro Tyr Gln Val Asn Glu Arg Val Met Glu
            260                 265                 270

Met Thr Gly Lys Ser Glu Thr Ile Phe Met His Cys Leu Pro Ala Val
        275                 280                 285

Lys Gly Gln Glu Val Thr Tyr Glu Val Ile Glu Gly Lys Gln Ser Arg
    290                 295                 300

Val Trp Asp Glu Ala Glu Asn Arg Lys His Thr Ile Lys Ala Val Met
305                 310                 315                 320

Ile Ala Thr Leu Leu
                325

<210> SEQ ID NO 125
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Met Gly Ser Asp Lys Ile His His His His His His Met Ile Val Val

```
            1               5                  10                 15
Leu Lys Pro Gly Ser Thr Glu Glu Asp Ile Arg Lys Val Val Lys Leu
            20                 25                 30

Ala Glu Ser Tyr Asn Leu Lys Cys His Ile Ser Lys Gly Gln Glu Arg
            35                 40                 45

Thr Val Ile Gly Ile Ile Gly Asp Asp Arg Tyr Val Ala Asp Lys
            50                 55                 60

Phe Glu Ser Leu Asp Cys Val Glu Ser Val Arg Val Leu Lys Pro
65                 70                 75                 80

Tyr Lys Leu Val Ser Arg Glu Phe His Pro Glu Asp Thr Val Ile Asp
                85                 90                 95

Leu Gly Asp Val Lys Ile Gly Asn Gly Tyr Phe Thr Ile Ile Ala Gly
                100                105                110

Pro Cys Ser Val Glu Gly Arg Glu Met Leu Met Glu Thr Ala His Phe
                115                120                125

Leu Ser Glu Leu Gly Val Lys Val Leu Arg Gly Gly Ala Tyr Lys Pro
                130                135                140

Arg Thr Ser Pro Tyr Ser Phe Gln Gly Leu Gly Glu Lys Gly Leu Glu
145                150                155                160

Tyr Leu Arg Glu Ala Ala Asp Lys Tyr Gly Met Tyr Val Val Thr Glu
                165                170                175

Ala Leu Gly Glu Asp Asp Leu Pro Lys Val Ala Glu Tyr Ala Asp Ile
                180                185                190

Ile Gln Ile Gly Ala Arg Asn Ala Gln Asn Phe Arg Leu Leu Ser Lys
                195                200                205

Ala Gly Ser Tyr Asn Lys Pro Val Leu Leu Lys Arg Gly Phe Met Asn
                210                215                220

Thr Ile Glu Glu Phe Leu Leu Ser Ala Glu Tyr Ile Ala Asn Ser Gly
225                230                235                240

Asn Thr Lys Ile Ile Leu Cys Glu Arg Gly Ile Arg Thr Phe Glu Lys
                245                250                255

Ala Thr Arg Asn Thr Leu Asp Ile Ser Ala Val Pro Ile Ile Arg Lys
                260                265                270

Glu Ser His Leu Pro Ile Leu Val Asp Pro Ser His Ser Gly Gly Arg
                275                280                285

Arg Asp Leu Val Ile Pro Leu Ser Arg Ala Ala Ile Ala Val Gly Ala
                290                295                300

His Gly Ile Ile Val Glu Val His Pro Glu Pro Glu Lys Ala Leu Ser
305                310                315                320

Asp Gly Lys Gln Ser Leu Asp Phe Glu Leu Phe Lys Glu Leu Val Gln
                325                330                335

Glu Met Lys Lys Leu Ala Asp Ala Leu Gly Val Lys Val Asn
                340                345                350

<210> SEQ ID NO 126
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Pro Glu Ile Ile Thr Pro Ile Thr Pro Phe Thr Lys Asp Asn Arg
1               5                  10                 15
```

```
Ile Asp Lys Glu Lys Leu Lys Ile His Ala Glu Asn Leu Ile Arg Lys
             20                  25                  30

Gly Ile Asp Lys Leu Phe Val Asn Gly Thr Thr Gly Leu Gly Pro Ser
         35                  40                  45

Leu Ser Pro Glu Glu Lys Leu Glu Asn Leu Lys Ala Val Tyr Asp Val
     50                  55                  60

Thr Asn Lys Ile Ile Phe Gln Val Gly Gly Leu Asn Leu Asp Asp Ala
 65                  70                  75                  80

Ile Arg Leu Ala Lys Leu Ser Lys Asp Phe Asp Ile Val Gly Ile Ala
                 85                  90                  95

Ser Tyr Ala Pro Tyr Tyr Pro Arg Met Ser Glu Lys His Leu Val
            100                 105                 110

Lys Tyr Phe Lys Thr Leu Cys Glu Val Ser Pro His Pro Val Tyr Leu
        115                 120                 125

Tyr Asn Tyr Pro Thr Ala Thr Gly Lys Asp Ile Asp Ala Lys Val Ala
    130                 135                 140

Lys Glu Ile Gly Cys Phe Thr Gly Val Lys Asp Thr Ile Glu Asn Ile
145                 150                 155                 160

Ile His Thr Leu Asp Tyr Lys Arg Leu Asn Pro Asn Met Leu Val Tyr
                165                 170                 175

Ser Gly Ser Asp Met Leu Ile Ala Thr Val Ala Ser Thr Gly Leu Asp
            180                 185                 190

Gly Asn Val Ala Ala Gly Ser Asn Tyr Leu Pro Glu Val Thr Val Thr
        195                 200                 205

Ile Lys Lys Leu Ala Met Glu Arg Lys Ile Asp Glu Ala Leu Lys Leu
    210                 215                 220

Gln Phe Leu His Asp Glu Val Ile Glu Ala Ser Arg Ile Phe Gly Ser
225                 230                 235                 240

Leu Ser Ser Asn Tyr Val Leu Thr Lys Tyr Phe Gln Gly Tyr Asp Leu
                245                 250                 255

Gly Tyr Pro Arg Pro Pro Ile Phe Pro Leu Asp Asp Glu Glu Glu Arg
            260                 265                 270

Gln Leu Ile Lys Lys Val Glu Gly Ile Arg Ala Lys Leu Val Glu Leu
        275                 280                 285

Lys Ile Leu Lys Glu
    290

<210> SEQ ID NO 127
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Thr Leu Gln Ile Gln Phe Lys Lys Tyr Glu Leu Pro Pro Leu Pro Tyr
 1                5                  10                  15

Lys Ile Asp Ala Leu Glu Pro Tyr Ile Ser Lys Asp Ile Ile Asp Val
             20                  25                  30

His Tyr Asn Gly His His Lys Gly Phe Val Asn Gly Ala Asn Ser Leu
         35                  40                  45

Leu Glu Arg Leu Glu Lys Val Val Lys Gly Asp Leu Gln Thr Gly Gln
     50                  55                  60

Tyr Asp Ile Gln Gly Ile Ile Arg Gly Leu Thr Phe Asn Ile Asn Gly
 65                  70                  75                  80
```

His Lys Leu His Ala Leu Tyr Trp Glu Asn Met Ala Pro Ser Gly Lys
                85                  90                  95
Gly Gly Gly Lys Pro Gly Gly Ala Leu Ala Asp Leu Ile Asn Lys Gln
            100                 105                 110
Tyr Gly Ser Phe Asp Arg Phe Lys Gln Val Phe Thr Glu Thr Ala Asn
        115                 120                 125
Ser Leu Pro Gly Thr Gly Trp Ala Val Leu Tyr Tyr Asp Thr Glu Ser
    130                 135                 140
Gly Asn Leu Gln Ile Met Thr Phe Glu Asn His Phe Gln Asn His Ile
145                 150                 155                 160
Ala Glu Ile Pro Ile Ile Leu Ile Leu Asp Glu Phe Glu His Ala Tyr
                165                 170                 175
Tyr Leu Gln Tyr Lys Asn Lys Arg Ala Asp Tyr Val Asn Ala Trp Trp
            180                 185                 190
Asn Val Val Asn Trp Asp Ala Ala Glu Lys Lys Leu Gln Lys Tyr Leu
        195                 200                 205
Thr Lys
    210

<210> SEQ ID NO 128
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Thr Leu Gln Ile Gln Phe Lys Lys Tyr Glu Leu Pro Pro Leu Pro Tyr
1               5                   10                  15
Lys Ile Asp Ala Leu Glu Pro Tyr Ile Ser Lys Asp Ile Ile Asp Val
            20                  25                  30
His Tyr Asn Gly His His Lys Gly Tyr Val Asn Gly Ala Asn Ser Leu
        35                  40                  45
Leu Glu Arg Leu Glu Lys Val Val Lys Gly Asp Leu Gln Thr Gly Gln
    50                  55                  60
Tyr Asp Ile Gln Gly Ile Ile Arg Gly Leu Thr Phe Asn Ile Asn Gly
65                  70                  75                  80
His Lys Leu His Ala Leu Tyr Trp Glu Asn Met Ala Pro Ser Gly Lys
                85                  90                  95
Gly Gly Gly Lys Pro Gly Gly Ala Leu Ala Asp Leu Ile Asn Lys Gln
            100                 105                 110
Tyr Gly Ser Phe Asp Arg Phe Lys Gln Val Phe Thr Glu Thr Ala Asn
        115                 120                 125
Ser Leu Pro Gly Thr Gly Trp Ala Val Leu Tyr Tyr Asp Thr Glu Ser
    130                 135                 140
Gly Asn Leu Gln Ile Met Thr Phe Glu Asn His Phe Gln Asn His Ile
145                 150                 155                 160
Ala Glu Ile Pro Ile Ile Leu Ile Leu Asp Glu Phe Glu His Ala Tyr
                165                 170                 175
Tyr Leu Gln Tyr Lys Asn Lys Arg Ala Asp Tyr Val Asn Ala Trp Trp
            180                 185                 190
Asn Val Val Asn Trp Asp Ala Ala Glu Lys Lys Leu Gln Lys Tyr Leu
        195                 200                 205
Thr Lys

-continued

210

<210> SEQ ID NO 129
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Met Arg Asp Pro Phe Met Glu Ala Leu Gly Leu Lys Val Leu His Leu
1               5                   10                  15

Ala Pro Gly Glu Ala Val Val Ala Gly Glu Val Arg Ala Asp His Leu
            20                  25                  30

Asn Leu His Gly Thr Ala His Gly Gly Phe Leu Tyr Ala Leu Ala Asp
        35                  40                  45

Ser Ala Phe Ala Leu Ala Ser Asn Thr Arg Gly Pro Ala Val Ala Leu
    50                  55                  60

Ser Cys Arg Met Asp Tyr Phe Arg Pro Leu Gly Ala Gly Ala Arg Val
65                  70                  75                  80

Glu Ala Arg Ala Val Glu Val Asn Leu Ser Arg Arg Thr Ala Thr Tyr
                85                  90                  95

Arg Val Glu Val Val Ser Glu Gly Lys Leu Val Ala Leu Phe Thr Gly
            100                 105                 110

Thr Val Phe Arg Leu Gly Gly Asp Gly Asp Asp Val Pro Ala Gly Thr
        115                 120                 125

Gly Asn Leu Ala Pro Arg Glu Ala
    130                 135

<210> SEQ ID NO 130
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Met Gly Leu Trp Phe Glu Glu Gly Ala Glu Glu Arg Gln Val Leu Gly
1               5                   10                  15

Pro Phe Arg Glu Phe Leu Lys Ala Glu Val Ala Pro Gly Ala Ala Glu
            20                  25                  30

Arg Asp Arg Thr Gly Ala Phe Pro Trp Asp Leu Val Arg Lys Leu Ala
        35                  40                  45

Glu Phe Gly Val Phe Gly Ala Leu Val Pro Glu Ala Tyr Gly Gly Ala
    50                  55                  60

Gly Leu Ser Thr Arg Leu Phe Ala Arg Met Val Glu Ala Ile Ala Tyr
65                  70                  75                  80

Tyr Asp Gly Ala Leu Ala Leu Thr Val Ala Ser His Asn Ser Leu Ala
                85                  90                  95

Thr Gly His Ile Leu Leu Ala Gly Ser Glu Ala Gln Lys Glu Ala Phe
            100                 105                 110

Leu Pro Lys Leu Ala Ser Gly Glu Ala Leu Gly Ala Trp Gly Leu Thr
        115                 120                 125

Glu Pro Gly Ser Gly Ser Asp Ala Ala Ala Leu Lys Thr Lys Ala Glu
    130                 135                 140

Lys Val Glu Gly Gly Trp Arg Leu Asn Gly Thr Lys Gln Phe Ile Thr

```
145                 150                 155                 160
Gln Gly Ser Val Ala Gly Val Tyr Val Met Ala Arg Thr Asp Pro
                165                 170                 175

Pro Pro Ser Pro Glu Arg Lys His Gln Gly Ile Ser Ala Phe Ala Phe
            180                 185                 190

Phe Arg Pro Glu Arg Gly Leu Lys Val Gly Arg Lys Glu Lys Leu
        195                 200                 205

Gly Leu Thr Ala Ser Asp Thr Ala Gln Leu Ile Leu Glu Asp Leu Phe
    210                 215                 220

Val Pro Glu Glu Ala Leu Leu Gly Glu Arg Gly Lys Gly Phe Tyr Asp
225                 230                 235                 240

Val Leu Arg Val Leu Asp Gly Gly Arg Ile Gly Ile Ala Ala Met Ala
                245                 250                 255

Val Gly Leu Gly Gln Ala Ala Leu Asp Tyr Ala Leu Ala Tyr Ala Lys
            260                 265                 270

Gly Arg Glu Ala Phe Gly Arg Pro Ile Ala Glu Phe Glu Gly Val Ser
        275                 280                 285

Phe Lys Leu Ala Glu Ala Ala Thr Glu Leu Glu Ala Ala Arg Leu Leu
    290                 295                 300

Tyr Leu Lys Ala Ala Glu Leu Lys Asp Ala Gly Arg Pro Phe Thr Leu
305                 310                 315                 320

Glu Ala Ala Gln Ala Lys Leu Phe Ala Ser Glu Ala Ala Val Lys Ala
                325                 330                 335

Cys Asp Glu Ala Ile Gln Ile Leu Gly Gly Tyr Gly Tyr Val Lys Asp
            340                 345                 350

Tyr Pro Val Glu Arg Tyr Trp Arg Asp Ala Arg Leu Thr Arg Ile Gly
        355                 360                 365

Glu Gly Thr Ser Glu Ile Leu Lys Leu Val Ile Ala Arg Arg Leu Leu
    370                 375                 380

Glu Ala Val
385

<210> SEQ ID NO 131
<211> LENGTH: 438
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Met Asp Tyr Thr Pro His Thr Glu Glu Ile Arg Glu Met Leu Arg
1               5                   10                  15

Arg Val Gly Ala Ala Ser Leu Glu Asp Leu Phe Ala His Leu Pro Lys
            20                  25                  30

Glu Ile Leu Ser Pro Pro Ile Asp Leu Pro Glu Pro Leu Pro Glu Trp
        35                  40                  45

Lys Val Leu Glu Glu Leu Arg Arg Leu Ala Ala Gln Asn Leu Pro Ala
    50                  55                  60

His Lys Ala Phe Leu Gly Gly Gly Val Arg Ser His Val Pro Pro
65                  70                  75                  80

Val Val Gln Ala Leu Ala Ala Arg Gly Glu Phe Leu Thr Ala Tyr Thr
                85                  90                  95

Pro Tyr Gln Pro Glu Val Ser Gln Gly Val Leu Gln Ala Thr Phe Glu
            100                 105                 110
```

```
Tyr Gln Thr Met Ile Ala Glu Leu Ala Gly Leu Glu Ile Ala Asn Ala
            115                 120                 125

Ser Met Tyr Asp Gly Ala Thr Ala Leu Ala Glu Gly Val Leu Leu Ala
        130                 135                 140

Leu Arg Glu Thr Gly Arg Met Gly Val Leu Val Ser Gln Gly Val His
145                 150                 155                 160

Pro Glu Tyr Arg Ala Val Leu Arg Ala Tyr Leu Glu Ala Val Gly Ala
                165                 170                 175

Lys Leu Leu Thr Leu Pro Leu Glu Gly Arg Thr Pro Leu Pro Glu
            180                 185                 190

Val Gly Glu Glu Val Gly Ala Val Val Gln Asn Pro Asn Phe Leu
        195                 200                 205

Gly Ala Leu Glu Asp Leu Gly Pro Phe Ala Glu Ala His Gly Ala
    210                 215                 220

Gly Ala Leu Phe Val Ala Val Ala Asp Pro Leu Ser Leu Gly Val Leu
225                 230                 235                 240

Lys Pro Pro Gly Ala Tyr Gly Ala Asp Ile Ala Val Gly Asp Gly Gln
                245                 250                 255

Ser Leu Gly Leu Pro Met Gly Phe Gly Gly Pro His Phe Gly Phe Leu
            260                 265                 270

Ala Thr Lys Lys Ala Phe Val Arg Gln Leu Pro Gly Arg Leu Val Ser
        275                 280                 285

Glu Thr Val Asp Val Glu Gly Arg Arg Gly Phe Ile Leu Thr Leu Gln
        290                 295                 300

Ala Arg Glu Gln Tyr Ile Arg Arg Ala Lys Ala Lys Ser Asn Ile Thr
305                 310                 315                 320

Thr Asn Ala Gln Leu Thr Ala Leu Met Gly Ala Met Tyr Leu Ala Ala
                325                 330                 335

Leu Gly Pro Glu Gly Leu Arg Glu Val Ala Leu Lys Ser Val Glu Met
            340                 345                 350

Ala His Lys Leu His Ala Leu Leu Glu Val Pro Gly Val Arg Pro
        355                 360                 365

Phe Thr Pro Lys Pro Phe Phe Asn Glu Phe Ala Leu Ala Leu Pro Lys
        370                 375                 380

Asp Pro Glu Ala Val Arg Arg Ala Leu Ala Glu Arg Gly Phe His Gly
385                 390                 395                 400

Ala Thr Pro Val Pro Arg Glu Tyr Gly Glu Asn Leu Ala Leu Phe Ala
                405                 410                 415

Ala Thr Glu Leu His Glu Glu Asp Leu Leu Ala Leu Arg Glu Ala
            420                 425                 430

Leu Lys Glu Val Leu Ala
        435

<210> SEQ ID NO 132
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Met Ser Phe Pro Leu Ile Phe Glu Arg Ser Arg Lys Gly Arg Arg Gly
1               5                   10                  15

Leu Lys Leu Val Lys Ala Val Pro Lys Ala Glu Asp Leu Ile Pro Lys
            20                  25                  30
```

```
Glu His Leu Arg Glu Val Pro Pro Arg Leu Pro Glu Val Asp Glu Leu
            35                  40                  45

Thr Leu Val Arg His Tyr Thr Gly Leu Ser Arg Arg Gln Val Gly Val
    50                  55                  60

Asp Thr Thr Phe Tyr Pro Leu Gly Ser Cys Thr Met Lys Tyr Asn Pro
65                  70                  75                  80

Lys Leu His Glu Glu Ala Ala Arg Leu Phe Ala Asp Leu His Pro Tyr
                85                  90                  95

Gln Asp Pro Arg Thr Ala Gln Gly Ala Leu Arg Leu Met Trp Glu Leu
            100                 105                 110

Gly Glu Tyr Leu Lys Ala Leu Thr Gly Met Asp Ala Ile Thr Leu Glu
            115                 120                 125

Pro Ala Ala Gly Ala His Gly Glu Leu Thr Gly Ile Leu Ile Ile Arg
    130                 135                 140

Ala Tyr His Glu Asp Arg Gly Glu Gly Arg Thr Arg Arg Val Val Leu
145                 150                 155                 160

Val Pro Asp Ser Ala His Gly Ser Asn Pro Ala Thr Ala Ser Met Ala
                165                 170                 175

Gly Tyr Gln Val Arg Glu Ile Pro Ser Gly Pro Glu Gly Glu Val Asp
            180                 185                 190

Leu Glu Ala Leu Lys Arg Glu Leu Gly Pro His Val Ala Ala Leu Met
            195                 200                 205

Leu Thr Asn Pro Asn Thr Leu Gly Leu Phe Glu Arg Arg Ile Leu Glu
    210                 215                 220

Ile Ser Arg Leu Cys Lys Glu Ala Gly Val Gln Leu Tyr Tyr Asp Gly
225                 230                 235                 240

Ala Asn Leu Asn Ala Ile Met Gly Trp Ala Arg Pro Gly Asp Met Gly
                245                 250                 255

Phe Asp Val Val His Leu Asn Leu His Lys Thr Phe Thr Val Pro His
            260                 265                 270

Gly Gly Gly Gly Pro Gly Ser Gly Pro Val Gly Val Lys Ala His Leu
    275                 280                 285

Ala Pro Tyr Leu Pro Val Pro Leu Val Glu Arg Gly Glu Glu Gly Phe
290                 295                 300

Tyr Leu Asp Phe Asp Arg Pro Lys Ser Ile Gly Arg Val Arg Ser Phe
305                 310                 315                 320

Tyr Gly Asn Phe Leu Ala Leu Val Arg Ala Trp Ala Tyr Ile Arg Thr
                325                 330                 335

Leu Gly Leu Glu Gly Leu Lys Lys Ala Ala Leu Ala Val Leu Asn
            340                 345                 350

Ala Arg Tyr Leu Lys Glu Leu Leu Lys Glu Lys Gly Tyr Arg Val Pro
            355                 360                 365

Tyr Asp Gly Pro Ser Met His Glu Phe Val Ala Gln Pro Pro Glu Gly
370                 375                 380

Phe Arg Ala Leu Asp Leu Ala Lys Gly Leu Leu Glu Leu Gly Phe His
385                 390                 395                 400

Pro Pro Thr Val Tyr Phe Pro Leu Ile Val Lys Glu Ala Leu Met Val
                405                 410                 415

Glu Pro Thr Glu Thr Glu Ala Lys Glu Thr Leu Glu Ala Phe Ala Glu
            420                 425                 430

Ala Met Gly Ala Leu Leu Lys Lys Pro Lys Glu Trp Leu Glu Asn Ala
            435                 440                 445
```

```
Pro Tyr Ser Thr Pro Val Arg Arg Leu Asp Glu Leu Arg Ala Asn Lys
            450                 455                 460

His Pro Lys Leu Thr Tyr Phe Asp Glu Gly
465                 470

<210> SEQ ID NO 133
<211> LENGTH: 333
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Ala Tyr Arg Ile Cys Leu Ile Glu Gly Asp Gly Ile Gly His Glu Val
1               5                   10                  15

Ile Pro Ala Ala Arg Arg Val Leu Glu Ala Thr Gly Leu Pro Leu Glu
            20                  25                  30

Phe Val Glu Ala Glu Ala Gly Trp Glu Thr Phe Glu Arg Arg Gly Thr
        35                  40                  45

Ser Val Pro Glu Glu Thr Val Glu Lys Ile Leu Ser Cys His Ala Thr
    50                  55                  60

Leu Phe Gly Ala Ala Thr Ser Pro Thr Arg Lys Val Pro Gly Phe Phe
65                  70                  75                  80

Gly Ala Ile Arg Tyr Leu Arg Arg Arg Leu Asp Leu Tyr Ala Asn Val
                85                  90                  95

Arg Pro Ala Lys Ser Arg Pro Val Pro Gly Ser Arg Pro Gly Val Asp
            100                 105                 110

Leu Val Ile Val Arg Glu Asn Thr Glu Gly Leu Tyr Val Glu Gln Glu
        115                 120                 125

Arg Arg Tyr Leu Asp Val Ala Ile Ala Asp Ala Val Ile Ser Lys Lys
    130                 135                 140

Ala Ser Glu Arg Ile Gly Arg Ala Ala Leu Arg Ile Ala Glu Gly Arg
145                 150                 155                 160

Pro Arg Lys Thr Leu His Ile Ala His Lys Ala Asn Val Leu Pro Leu
                165                 170                 175

Thr Gln Gly Leu Phe Leu Asp Thr Val Lys Glu Val Ala Lys Asp Phe
            180                 185                 190

Pro Leu Val Asn Val Gln Asp Ile Ile Val Asp Asn Cys Ala Met Gln
        195                 200                 205

Leu Val Met Arg Pro Glu Arg Phe Asp Val Ile Val Thr Thr Asn Leu
    210                 215                 220

Leu Gly Asp Ile Leu Ser Asp Leu Ala Ala Gly Leu Val Gly Gly Leu
225                 230                 235                 240

Gly Leu Ala Pro Ser Gly Asn Ile Gly Asp Thr Thr Ala Val Phe Glu
                245                 250                 255

Pro Val His Gly Ser Ala Pro Asp Ile Ala Gly Lys Gly Ile Ala Asn
            260                 265                 270

Pro Thr Ala Ala Ile Leu Ser Ala Ala Met Met Leu Asp Tyr Leu Gly
        275                 280                 285

Glu Lys Glu Ala Ala Lys Arg Val Glu Lys Ala Val Asp Leu Val Leu
    290                 295                 300

Glu Arg Gly Pro Arg Thr Pro Asp Leu Gly Gly Asp Ala Thr Thr Glu
305                 310                 315                 320

Ala Phe Thr Glu Ala Val Val Glu Ala Leu Lys Ser Leu
                325                 330
```

<210> SEQ ID NO 134
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Met Glu Arg Lys Ala Leu Val Thr Gly Gly Ser Arg Gly Ile Gly Arg
1               5                   10                  15

Ala Ile Ala Glu Ala Leu Val Ala Arg Gly Tyr Arg Val Ala Ile Ala
                20                  25                  30

Ser Arg Asn Pro Glu Glu Ala Ala Gln Ser Leu Gly Ala Val Pro Leu
            35                  40                  45

Pro Thr Asp Leu Glu Lys Asp Asp Pro Lys Gly Leu Val Lys Arg Ala
        50                  55                  60

Leu Glu Ala Leu Gly Gly Leu His Val Leu Val His Ala Ala Ala Val
65                  70                  75                  80

Asn Val Arg Lys Pro Ala Leu Glu Leu Ser Tyr Glu Glu Trp Arg Arg
                85                  90                  95

Val Leu Tyr Leu His Leu Asp Val Ala Phe Leu Leu Ala Gln Ala Ala
                100                 105                 110

Ala Pro His Met Ala Glu Ala Gly Trp Gly Arg Val Leu Phe Ile Gly
            115                 120                 125

Ser Val Thr Thr Phe Thr Ala Gly Gly Pro Val Pro Ile Pro Ala Tyr
130                 135                 140

Thr Thr Ala Lys Thr Ala Leu Leu Gly Leu Thr Arg Ala Leu Ala Lys
145                 150                 155                 160

Glu Trp Ala Arg Leu Gly Ile Arg Val Asn Leu Leu Cys Pro Gly Tyr
                165                 170                 175

Val Glu Thr Glu Phe Thr Leu Pro Leu Arg Gln Asn Pro Glu Leu Tyr
            180                 185                 190

Glu Pro Ile Thr Ala Arg Ile Pro Met Gly Arg Trp Ala Arg Pro Glu
        195                 200                 205

Glu Ile Ala Arg Val Ala Ala Val Leu Cys Gly Asp Glu Ala Glu Tyr
    210                 215                 220

Leu Thr Gly Gln Ala Val Ala Val Asp Gly Gly Phe Leu Ala Tyr
225                 230                 235

<210> SEQ ID NO 135
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Met Lys Val Leu Val Thr Gly Phe Glu Pro Phe Gly Gly Glu Lys Ile
1               5                   10                  15

Asn Pro Thr Glu Arg Ile Ala Lys Asp Leu Asp Gly Ile Lys Ile Gly
                20                  25                  30

Asp Ala Gln Val Phe Gly Arg Val Leu Pro Val Val Phe Gly Lys Ala
            35                  40                  45

Lys Glu Val Leu Glu Lys Thr Leu Glu Glu Ile Lys Pro Asp Ile Ala
        50                  55                  60

```
Ile His Val Gly Leu Ala Pro Gly Arg Ser Ala Ile Ser Ile Glu Arg
 65                  70                  75                  80

Ile Ala Val Asn Ala Ile Asp Ala Arg Ile Pro Asp Asn Glu Gly Lys
                 85                  90                  95

Lys Ile Glu Asp Glu Pro Ile Val Pro Gly Ala Pro Thr Ala Tyr Phe
            100                 105                 110

Ser Thr Leu Pro Ile Lys Lys Ile Met Lys Lys Leu His Glu Arg Gly
            115                 120                 125

Ile Pro Ala Tyr Ile Ser Asn Ser Ala Gly Leu Tyr Leu Ser Asn Tyr
        130                 135                 140

Val Met Tyr Leu Ser Leu His His Ser Ala Thr Lys Gly Tyr Pro Lys
145                 150                 155                 160

Met Ser Gly Phe Ile His Val Pro Tyr Ile Pro Glu Gln Ile Ile Asp
                165                 170                 175

Lys Ile Gly Lys Gly Gln Val Pro Pro Ser Met Ser Tyr Glu Met Ala
            180                 185                 190

Leu Glu Ala Val Lys Val Ala Ile Glu Val Ala Leu Glu Glu Leu Leu
        195                 200                 205

<210> SEQ ID NO 136
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Met Pro Leu Tyr Val Ile Asp Lys Pro Ile Thr Leu His Ile Leu Thr
1               5                   10                  15

Gln Leu Arg Asp Lys Tyr Thr Asp Gln Ile Asn Phe Arg Lys Asn Leu
            20                  25                  30

Val Arg Leu Gly Arg Ile Leu Gly Tyr Glu Ile Ser Asn Thr Leu Asp
        35                  40                  45

Tyr Glu Ile Val Glu Val Glu Thr Pro Leu Gly Val Lys Thr Lys Gly
    50                  55                  60

Val Asp Ile Thr Asp Leu Asn Asn Ile Val Ile Asn Ile Leu Arg
65                  70                  75                  80

Ala Ala Val Pro Leu Val Glu Gly Leu Leu Lys Ala Phe Pro Lys Ala
                85                  90                  95

Arg Gln Gly Val Ile Gly Ala Ser Arg Val Glu Val Asp Gly Lys Glu
            100                 105                 110

Val Pro Lys Asp Met Asp Val Tyr Ile Tyr Lys Lys Ile Pro Asp
            115                 120                 125

Ile Arg Ala Lys Val Asp Asn Val Ile Ala Asp Pro Met Ile Ala
        130                 135                 140

Thr Ala Ser Thr Met Leu Lys Val Leu Glu Val Val Lys Ala Asn
145                 150                 155                 160

Pro Lys Arg Ile Tyr Ile Val Ser Ile Ser Ser Glu Tyr Gly Val
                165                 170                 175

Asn Lys Ile Leu Ser Lys Tyr Pro Phe Ile Tyr Leu Phe Thr Val Ala
            180                 185                 190

Ile Asp Pro Glu Leu Asn Asn Lys Gly Tyr Ile Leu Pro Gly Leu Gly
        195                 200                 205

Asp Ala Gly Asp Arg Ala Phe Gly
```

-continued

<210> SEQ ID NO 137
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Met Leu Met Arg Pro Leu Asp Leu Thr Glu Lys Arg Gly Lys Lys Val
1               5                   10                  15

Thr Ile Tyr Phe Glu Gly Lys Glu Leu Glu Ala Tyr Glu Gly Glu Lys
            20                  25                  30

Leu Pro Val Ala Leu Leu Ala Asn Glu Ile Tyr Trp Leu Thr Thr Ser
        35                  40                  45

Asn Glu Gly Arg Lys Arg Gly Ala Phe Thr Phe Gly Pro Val Pro Met
    50                  55                  60

Thr Val Asn Gly Val Lys Gly Leu Glu Ala Arg Arg Ile Lys Val Lys
65                  70                  75                  80

Asp Gly Met Lys Ile Glu Arg Gln Gly Tyr Tyr Asp Phe His Glu Glu
                85                  90                  95

Pro Val Glu Pro Gly Glu Ile Glu Arg Val Val Asp Val Ala
            100                 105                 110

Ile Ile Gly Gly Gly Pro Ala Gly Ile Gly Ala Ala Leu Glu Leu Gln
            115                 120                 125

Gln Tyr Leu Thr Val Ala Leu Ile Glu Glu Arg Gly Trp Leu Gly Gly
    130                 135                 140

Asp Met Trp Leu Lys Gly Ile Lys Gln Glu Gly Phe Asn Lys Asp Ser
145                 150                 155                 160

Arg Lys Val Val Glu Glu Leu Val Gly Lys Leu Asn Glu Asn Thr Lys
                165                 170                 175

Ile Tyr Leu Glu Thr Ser Ala Leu Gly Val Phe Asp Lys Gly Glu Tyr
            180                 185                 190

Phe Leu Val Pro Val Val Arg Gly Asp Lys Leu Ile Glu Ile Leu Ala
        195                 200                 205

Lys Arg Val Val Leu Ala Thr Gly Ala Ile Asp Ser Thr Met Leu Phe
    210                 215                 220

Glu Asn Asn Asp Met Pro Gly Val Phe Arg Arg Asp Phe Ala Leu Glu
225                 230                 235                 240

Val Met Asn Val Trp Glu Val Ala Pro Gly Arg Lys Val Ala Val Thr
                245                 250                 255

Gly Ser Lys Ala Asp Glu Val Ile Gln Glu Leu Glu Arg Trp Gly Ile
            260                 265                 270

Asp Tyr Val His Ile Pro Asn Val Lys Arg Val Glu Gly Asn Glu Lys
        275                 280                 285

Val Glu Arg Val Ile Asp Met Asn Asn His Glu Tyr Lys Val Asp Ala
    290                 295                 300

Leu Ile Phe Ala Asp Gly Arg Arg Pro Asp Ile Asn Pro Ile Thr Gln
305                 310                 315                 320

Ala Gly Gly Lys Leu Arg Phe Arg Arg Gly Tyr Tyr Ser Pro Val Leu
                325                 330                 335

Asp Glu Tyr His Arg Ile Lys Asp Gly Ile Tyr Val Ala Gly Ser Ala
            340                 345                 350

```
Val Ser Ile Lys Pro His Tyr Ala Asn Tyr Leu Glu Gly Lys Leu Val
        355                 360                 365

Gly Ala Tyr Ile Leu Lys Glu Phe Gly Tyr Asp Ala Gln Pro Cys Ile
370                 375                 380

Tyr Glu Glu Lys Leu Arg Glu Tyr Glu Pro Glu Ser Leu Ser Ile Pro
385                 390                 395                 400

Arg Ile Pro Leu Asp Lys Phe Asn Leu Glu Asp Val Gln Ile Cys Gly
        405                 410                 415

Cys Asp Val Ser Leu Lys Lys Val Asp Glu Val Ile Arg Lys Gly Ile
        420                 425                 430

Thr Asp Leu Gln Ile Ile Lys Arg Leu Thr His Leu Ala Met Gly Phe
        435                 440                 445

Cys Gln Gly Arg Tyr Cys Leu Phe Asn Gly Ala Val Val Ser Gln
        450                 455                 460

Arg Thr Gly Lys Lys Leu Ser Glu Ile Asp Leu Pro Val Ala Arg Ser
465                 470                 475                 480

Pro Ile Lys Asn Val Lys Met Gly Ile Leu Ala Arg Arg
        485                 490

<210> SEQ ID NO 138
<211> LENGTH: 382
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Met Leu Pro Glu Lys Ser Glu Ile Val Val Ile Gly Gly Gly Ile Val
1               5                   10                  15

Gly Val Thr Ile Ala His Glu Leu Ala Lys Arg Gly Glu Glu Val Thr
            20                  25                  30

Val Ile Glu Lys Arg Phe Ile Gly Ser Gly Ser Thr Phe Arg Cys Gly
        35                  40                  45

Thr Gly Ile Arg Gln Gln Phe Asn Asp Glu Ala Asn Val Arg Val Met
    50                  55                  60

Lys Ser Val Glu Leu Trp Lys Lys Tyr Ser Glu Glu Tyr Gly Phe
65                  70                  75                  80

Ser Phe Lys Gln Thr Gly Tyr Leu Phe Leu Tyr Asp Asp Glu Glu
                85                  90                  95

Val Lys Thr Phe Lys Arg Asn Ile Glu Ile Gln Asn Lys Phe Gly Val
            100                 105                 110

Pro Thr Lys Leu Ile Thr Pro Glu Glu Ala Lys Glu Ile Val Pro Leu
        115                 120                 125

Leu Asp Ile Ser Glu Val Ile Ala Ala Ser Trp Asn Pro Thr Asp Gly
    130                 135                 140

Lys Ala Asp Pro Phe Glu Ala Thr Thr Ala Phe Ala Val Lys Ala Lys
145                 150                 155                 160

Glu Tyr Gly Ala Lys Leu Leu Glu Tyr Thr Glu Val Lys Gly Phe Leu
                165                 170                 175

Ile Glu Asn Asn Glu Ile Lys Gly Val Lys Thr Asn Lys Gly Ile Ile
            180                 185                 190

Lys Thr Gly Ile Val Val Asn Ala Thr Asn Ala Trp Ala Asn Leu Ile
        195                 200                 205

Asn Ala Met Ala Gly Ile Lys Thr Lys Ile Pro Ile Glu Pro Tyr Lys
    210                 215                 220
```

```
His Gln Ala Val Ile Thr Gln Pro Ile Lys Arg Gly Thr Ile Asn Pro
225                 230                 235                 240

Met Val Ile Ser Phe Lys Tyr Gly His Ala Tyr Leu Thr Gln Thr Phe
                245                 250                 255

His Gly Gly Ile Ile Gly Gly Ile Gly Tyr Glu Ile Gly Pro Thr Tyr
            260                 265                 270

Asp Leu Thr Pro Thr Tyr Glu Phe Leu Arg Glu Val Ser Tyr Tyr Phe
            275                 280                 285

Thr Lys Ile Ile Pro Ala Leu Lys Asn Leu Leu Ile Leu Arg Thr Trp
        290                 295                 300

Ala Gly Tyr Tyr Ala Lys Thr Pro Asp Ser Asn Pro Ala Ile Gly Arg
305                 310                 315                 320

Ile Glu Glu Leu Asn Asp Tyr Tyr Ile Ala Ala Gly Phe Ser Gly His
                325                 330                 335

Gly Phe Met Met Ala Pro Ala Val Gly Glu Met Val Ala Glu Leu Ile
            340                 345                 350

Thr Lys Gly Lys Thr Lys Leu Pro Val Glu Trp Tyr Asp Pro Tyr Arg
        355                 360                 365

Phe Glu Arg Gly Glu Leu Arg Thr Ala Ala Leu Gln Met Gly
    370                 375                 380

<210> SEQ ID NO 139
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Met Glu Ser Val Thr Arg Ile Lys Val Arg Tyr Ala Glu Thr Asp Gln
1               5                   10                  15

Met Gly Val Val His His Ser Val Tyr Ala Val Tyr Leu Glu Ala Ala
            20                  25                  30

Arg Val Asp Phe Leu Glu Arg Ala Gly Leu Pro Tyr His Arg Val Glu
        35                  40                  45

Ala Arg Gly Val Phe Phe Pro Val Val Glu Leu Gly Leu Thr Phe Arg
    50                  55                  60

Ala Pro Ala Arg Phe Gly Glu Val Val Glu Val Arg Thr Arg Leu Ala
65                  70                  75                  80

Glu Leu Ser Ser Arg Ala Leu Leu Phe Arg Tyr Arg Val Glu Arg Glu
                85                  90                  95

Gly Val Leu Leu Ala Glu Gly Phe Thr Arg His Leu Cys Gln Val Gly
            100                 105                 110

Glu Arg Ala Ala Arg Ile Pro Glu Asp Ile Tyr Arg Ala Leu Ser Val
        115                 120                 125

Leu His Leu Lys
    130

<210> SEQ ID NO 140
<211> LENGTH: 528
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140
```

-continued

```
Met Arg Gly Lys Ile Leu Ile Phe Leu His Ala His Leu Pro Tyr Val
1               5                   10                  15

His His Pro Glu Tyr Asp His Phe Leu Glu Glu Arg Trp Leu Phe Glu
            20                  25                  30

Ala Ile Thr Glu Thr Tyr Ile Pro Leu Leu Met Met Phe Asp Glu Ile
            35                  40                  45

Glu Asp Phe Arg Leu Thr Met Ser Ile Thr Pro Pro Leu Met Glu Met
50                  55                  60

Leu Ser Ser Arg Asp Leu Gln Glu Lys Tyr Glu Arg His Met Glu Lys
65                  70                  75                  80

Leu Ile Glu Leu Ala Asn Lys Glu Val Glu Arg Thr Lys Lys Glu His
                85                  90                  95

Pro Leu Lys His Lys Met Ala Lys Phe Tyr Arg Glu His Phe Glu Lys
                100                 105                 110

Ile Leu Asn Val Phe Arg Ser Tyr Asp Gly Asn Ile Leu Glu Gly Phe
            115                 120                 125

Lys Lys Tyr Gln Glu Thr Gly Lys Leu Glu Ile Val Thr Cys Asn Ala
            130                 135                 140

Thr His Ala Phe Leu Pro Leu Tyr Gln Met Tyr Pro Glu Val Val Asn
145                 150                 155                 160

Ala Gln Ile Thr Val Gly Val Lys Asn Tyr Glu Lys His Met Lys Lys
                165                 170                 175

His Pro Arg Gly Ile Trp Leu Ala Glu Cys Gly Tyr Tyr Gln Gly Leu
                180                 185                 190

Asp Leu Tyr Leu Ala Gln Asn Asn Val Glu Tyr Phe Phe Val Asp Ser
            195                 200                 205

His Ala Phe Trp Phe Ala Asp Glu Gln Pro Arg Tyr Gly Val Tyr Arg
210                 215                 220

Pro Ile Met Thr Pro Ser Gly Val Phe Ala Phe Ala Arg Asp Pro Glu
225                 230                 235                 240

Ser Ser Glu Gln Val Trp Ser Ala Ala Val Gly Tyr Pro Gly Asp Pro
                245                 250                 255

Arg Tyr Arg Glu Phe Tyr Arg Asp Ile Gly Phe Asp Arg Glu Met Glu
                260                 265                 270

Tyr Ile Lys Asp Tyr Ile Asp Pro Ser Gly Val Arg Ile Asn Thr Gly
            275                 280                 285

Ile Lys Tyr His Arg Ile Thr Ser Lys Ser Leu Asp Ala Ser Gln Lys
            290                 295                 300

Glu Tyr Tyr Asp Ile Asp Leu Ala Met Glu Ala Val Glu Glu His Ala
305                 310                 315                 320

Arg Asp Phe Leu His Lys Lys Glu Ser Gln Ala Arg Arg Leu Met Asp
                325                 330                 335

Ile Met Gly Val Glu Pro Val Ile Val Ala Pro Phe Asp Ala Glu Leu
            340                 345                 350

Phe Gly His Trp Trp Phe Glu Gly Val Phe Phe Leu Lys Arg Phe Phe
            355                 360                 365

Glu Leu Val Asn Glu Ser Lys Asp Leu Lys Leu Val Thr Ala Ser Glu
370                 375                 380

Val Ile Asp Thr Leu Glu Glu Val Gln Ile Ala Thr Pro Ala Asp Ser
385                 390                 395                 400

Ser Trp Gly Ala Gly Tyr Tyr Glu Thr Trp Leu Asn Gly Thr Asn
                405                 410                 415
```

```
Asp Trp Ile Tyr Arg His Leu His Glu Met Ile Glu Arg Met Ile Asp
                420                 425                 430

Leu Ser Lys Lys Tyr Tyr Asn Ser Ser Asp Pro Leu Val Glu Arg Val
            435                 440                 445

Leu Asn Gln Met Leu Arg Glu Leu Phe Leu Ala Gln Ser Ser Asp Trp
    450                 455                 460

Ala Phe Ile Met Thr Thr Arg Thr Ser Val Gln Tyr Ala Glu Asn Arg
465                 470                 475                 480

Thr Lys Leu His Ile Lys Arg Phe Leu Asn Leu Tyr Asp Gln Leu Val
                485                 490                 495

Ser Gly Arg Ile Asp Glu Glu Met Leu Arg Tyr Tyr Glu Trp Thr Asp
            500                 505                 510

Ala Ile Phe Pro Glu Ile Asn Phe Arg Val Met Ala Arg Asp Val Ile
        515                 520                 525

<210> SEQ ID NO 141
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Met Arg Ile Val Phe Asp Ile Gly Gly Ser Val Leu Val Pro Glu Asn
1               5                   10                  15

Pro Asp Ile Asp Phe Ile Lys Glu Ile Ala Tyr Gln Leu Thr Lys Val
                20                  25                  30

Ser Glu Asp His Glu Val Ala Val Val Gly Gly Gly Lys Leu Ala
            35                  40                  45

Arg Lys Tyr Ile Glu Val Ala Glu Lys Phe Asn Ser Ser Glu Thr Phe
    50                  55                  60

Lys Asp Phe Ile Gly Ile Gln Ile Thr Arg Ala Asn Ala Met Leu Leu
65                  70                  75                  80

Ile Ala Ala Leu Arg Glu Lys Ala Tyr Pro Val Val Val Glu Asp Phe
                85                  90                  95

Trp Glu Ala Trp Lys Ala Val Gln Leu Lys Lys Ile Pro Val Met Gly
                100                 105                 110

Gly Thr His Pro Gly His Thr Thr Asp Ala Val Ala Ala Leu Leu Ala
            115                 120                 125

Glu Phe Leu Lys Ala Asp Leu Leu Val Val Ile Thr Asn Val Asp Gly
    130                 135                 140

Val Tyr Thr Ala Asp Pro Lys Lys Asp Pro Thr Ala Lys Lys Ile Lys
145                 150                 155                 160

Lys Met Lys Pro Glu Glu Leu Leu Glu Ile Val Gly Lys Gly Ile Glu
                165                 170                 175

Lys Ala Gly Ser Ser Ser Val Ile Asp Pro Leu Ala Ala Lys Ile Ile
            180                 185                 190

Ala Arg Ser Gly Ile Lys Thr Ile Val Ile Gly Lys Glu Asp Ala Lys
    195                 200                 205

Asp Leu Phe Arg Val Ile Lys Gly Asp His Asn Gly Thr Thr Ile Glu
210                 215                 220

Pro
225

<210> SEQ ID NO 142
```

<211> LENGTH: 412
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 142

```
Met Glu Tyr Thr Thr Leu Ala Val Leu Ala Gly Leu Pro Glu Asp Pro
1               5                   10                  15

His Gly Ala Val Gly Leu Pro Ile Tyr Ala Val Ala Tyr Gly Phe
            20                  25                  30

Lys Thr Leu Glu Glu Gly Gln Glu Arg Phe Ala Thr Gly Gly Tyr
        35                  40                  45

Val Tyr Ala Arg Gln Lys Asp Pro Thr Ala Lys Ala Leu Glu Glu Arg
    50                  55                  60

Leu Lys Ala Leu Glu Gly Ala Leu Glu Ala Val Val Leu Ala Ser Gly
65                  70                  75                  80

Gln Ala Ala Thr Phe Ala Ala Leu Leu Ala Leu Leu Arg Pro Gly Asp
                85                  90                  95

Glu Val Val Ala Ala Lys Gly Leu Phe Gly Gln Thr Ile Gly Leu Phe
            100                 105                 110

Gly Gln Val Leu Ser Leu Met Gly Val Thr Val Arg Tyr Val Asp Pro
        115                 120                 125

Glu Pro Glu Ala Val Arg Glu Ala Leu Ser Ala Lys Thr Arg Ala Val
    130                 135                 140

Phe Val Glu Thr Val Ala Asn Pro Ala Leu Leu Val Pro Asp Leu Glu
145                 150                 155                 160

Ala Leu Ala Thr Leu Ala Glu Glu Ala Gly Val Ala Leu Val Val Asp
                165                 170                 175

Asn Thr Phe Gly Ala Ala Gly Ala Leu Cys Arg Pro Leu Ala Trp Gly
            180                 185                 190

Ala His Val Val Val Glu Ser Leu Thr Lys Trp Ala Ser Gly His Gly
        195                 200                 205

Ser Val Leu Gly Gly Ala Val Leu Ser Arg Glu Thr Glu Leu Trp Arg
    210                 215                 220

Asn Tyr Pro Gln Phe Leu Gln Pro Asp Leu Lys Gly Gln Ile Pro Trp
225                 230                 235                 240

Glu Ala Leu Arg Ala Arg Cys Phe Pro Glu Arg Val Arg Thr Leu Gly
                245                 250                 255

Leu Ser Leu Cys Gly Met Ala Leu Ser Pro Phe Asn Ala Tyr Leu Leu
            260                 265                 270

Phe Gln Gly Leu Glu Thr Val Ala Leu Arg Val Ala Arg Met Ser Glu
        275                 280                 285

Thr Ala Arg Phe Leu Ala Glu Arg Leu Gln Gly His Pro Lys Val Lys
    290                 295                 300

Ala Leu Arg Tyr Pro Gly Leu Pro Glu Asp Pro Ala His Arg Asn Ala
305                 310                 315                 320

Arg Lys Tyr Leu Ala Ser Gly Gly Pro Ile Leu Thr Leu Asp Leu Gly
                325                 330                 335

Asp Leu Glu Arg Ala Ser Arg Phe Leu Gly Ala Ile Arg Leu Leu Lys
            340                 345                 350

Ala Ala Asn Leu Gly Asp Ala Arg Thr Leu Leu Val His Pro Trp Thr
        355                 360                 365

Thr Thr His Ser Arg Leu Lys Glu Glu Ala Arg Leu Gln Ala Gly Val
```

```
                370                 375                 380
Thr Pro Gly Leu Val Arg Val Ser Val Gly Leu Glu Asp Pro Leu Asp
385                 390                 395                 400

Leu Leu Ala Leu Phe Glu Ala Leu Glu Ala Val
                405                 410

<210> SEQ ID NO 143
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Met Lys Ala Ile Ile Val Lys Pro Pro Asn Ala Gly Val Gln Val Lys
1               5                   10                  15

Asp Val Asp Glu Lys Lys Leu Asp Ser Tyr Gly Lys Ile Lys Ile Arg
                20                  25                  30

Thr Ile Tyr Asn Gly Ile Cys Gly Thr Asp Arg Glu Ile Val Asn Gly
            35                  40                  45

Lys Leu Thr Leu Ser Thr Leu Pro Lys Gly Lys Asp Phe Leu Val Leu
50                  55                  60

Gly His Glu Ala Ile Gly Val Val Glu Glu Ser Tyr His Gly Phe Ser
65                  70                  75                  80

Gln Gly Asp Leu Val Met Pro Val Asn Arg Arg Gly Cys Gly Ile Cys
                85                  90                  95

Arg Asn Cys Leu Val Gly Arg Pro Asp Phe Cys Glu Thr Gly Glu Phe
            100                 105                 110

Gly Glu Ala Gly Ile His Lys Met Asp Gly Phe Met Arg Glu Trp Trp
        115                 120                 125

Tyr Asp Asp Pro Lys Tyr Leu Val Lys Ile Pro Lys Ser Ile Glu Asp
130                 135                 140

Ile Gly Ile Leu Ala Gln Pro Leu Ala Asp Ile Glu Lys Ser Ile Glu
145                 150                 155                 160

Glu Ile Leu Glu Val Gln Lys Arg Val Pro Val Trp Thr Cys Asp Asp
                165                 170                 175

Gly Thr Leu Asn Cys Arg Lys Val Leu Val Val Gly Thr Gly Pro Ile
            180                 185                 190

Gly Val Leu Phe Thr Leu Leu Phe Arg Thr Tyr Gly Leu Glu Val Trp
        195                 200                 205

Met Ala Asn Arg Arg Glu Pro Thr Glu Val Glu Gln Thr Val Ile Glu
210                 215                 220

Glu Thr Lys Thr Asn Tyr Tyr Asn Ser Ser Asn Gly Tyr Asp Lys Leu
225                 230                 235                 240

Lys Asp Ser Val Gly Lys Phe Asp Val Ile Ile Asp Ala Thr Gly Ala
                245                 250                 255

Asp Val Asn Ile Leu Gly Asn Val Ile Pro Leu Leu Gly Arg Asn Gly
            260                 265                 270

Val Leu Gly Leu Phe Gly Phe Ser Thr Ser Gly Ser Val Pro Leu Asp
        275                 280                 285

Tyr Lys Thr Leu Gln Glu Ile Val His Thr Asn Lys Thr Ile Ile Gly
290                 295                 300

Leu Val Asn Gly Gln Lys Pro His Phe Gln Gln Ala Val Val His Leu
305                 310                 315                 320
```

```
Ala Ser Trp Lys Thr Leu Tyr Pro Lys Ala Lys Met Leu Ile Thr
            325                 330                 335

Lys Thr Val Ser Ile Asn Asp Glu Lys Glu Leu Leu Lys Val Leu Arg
        340                 345                 350

Glu Lys Glu His Gly Glu Ile Lys Ile Arg Ile Leu Trp Glu
        355                 360                 365

<210> SEQ ID NO 144
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Met Lys Ala Ile Ile Val Lys Pro Pro Asn Ala Gly Val Gln Val Lys
 1               5                  10                  15

Asp Val Asp Glu Lys Lys Leu Asp Ser Tyr Gly Lys Ile Lys Ile Arg
            20                  25                  30

Thr Ile Tyr Asn Gly Ile Cys Gly Ala Asp Arg Glu Ile Val Asn Gly
        35                  40                  45

Lys Leu Thr Leu Ser Thr Leu Pro Lys Gly Lys Asp Phe Leu Val Leu
    50                  55                  60

Gly His Glu Ala Ile Gly Val Val Glu Ser Tyr His Gly Phe Ser
65                  70                  75                  80

Gln Gly Asp Leu Val Met Pro Val Asn Arg Arg Gly Cys Gly Ile Cys
                85                  90                  95

Arg Asn Cys Leu Val Gly Arg Pro Asp Phe Cys Glu Thr Gly Glu Phe
            100                 105                 110

Gly Glu Ala Gly Ile His Lys Met Asp Gly Phe Met Arg Glu Trp Trp
        115                 120                 125

Tyr Asp Asp Pro Lys Tyr Leu Val Lys Ile Pro Lys Ser Ile Glu Asp
    130                 135                 140

Ile Gly Ile Leu Ala Gln Pro Leu Ala Asp Ile Glu Lys Ser Ile Glu
145                 150                 155                 160

Glu Ile Leu Glu Val Gln Lys Arg Val Pro Val Trp Thr Cys Asp Asp
                165                 170                 175

Gly Thr Leu Asn Cys Arg Lys Val Leu Val Gly Thr Gly Pro Ile
            180                 185                 190

Gly Val Leu Phe Thr Leu Leu Phe Arg Thr Tyr Gly Leu Glu Val Trp
        195                 200                 205

Met Ala Asn Arg Arg Glu Pro Thr Glu Val Gln Thr Val Ile Glu
    210                 215                 220

Glu Thr Lys Thr Asn Tyr Tyr Asn Ser Ser Asn Gly Tyr Asp Lys Leu
225                 230                 235                 240

Lys Asp Ser Val Gly Lys Phe Asp Val Ile Asp Ala Thr Gly Ala
                245                 250                 255

Asp Val Asn Ile Leu Gly Asn Val Ile Pro Leu Leu Gly Arg Asn Gly
            260                 265                 270

Val Leu Gly Leu Phe Gly Phe Ser Thr Ser Gly Ser Val Pro Leu Asp
        275                 280                 285

Tyr Lys Thr Leu Gln Glu Ile Val His Thr Lys Thr Ile Ile Gly
    290                 295                 300

Leu Val Asn Gly Gln Lys Pro His Phe Gln Gln Ala Val Val His Leu
305                 310                 315                 320
```

```
Ala Ser Trp Lys Thr Leu Tyr Pro Lys Ala Lys Met Leu Ile Thr
            325                 330                 335

Lys Thr Val Ser Ile Asn Asp Glu Lys Glu Leu Lys Val Leu Arg
            340                 345                 350

Glu Lys Glu His Gly Glu Ile Lys Ile Arg Ile Leu Trp Glu
            355                 360                 365

<210> SEQ ID NO 145
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Met Gly Leu Trp Phe Glu Glu Gly Ala Glu Arg Gln Val Leu Gly
1               5                   10                  15

Pro Phe Arg Glu Phe Leu Lys Ala Glu Val Ala Pro Gly Ala Glu
            20                  25                  30

Arg Asp Arg Thr Gly Ala Phe Pro Trp Asp Leu Val Arg Lys Leu Ala
            35                  40                  45

Glu Phe Gly Val Phe Gly Ala Leu Val Pro Glu Ala Tyr Gly Gly Ala
50                  55                  60

Gly Leu Ser Thr Arg Leu Phe Ala Arg Met Val Glu Ala Ile Ala Tyr
65                  70                  75                  80

Tyr Asp Gly Ala Leu Ala Leu Thr Val Ala Ser His Asn Ser Leu Ala
            85                  90                  95

Thr Gly His Ile Leu Leu Ala Gly Ser Glu Ala Gln Lys Glu Ala Phe
            100                 105                 110

Leu Pro Lys Leu Ala Ser Gly Glu Ala Leu Gly Ala Trp Gly Leu Thr
            115                 120                 125

Glu Pro Gly Ser Gly Ser Asp Ala Ala Ala Leu Lys Thr Lys Ala Glu
            130                 135                 140

Lys Val Glu Gly Gly Trp Arg Leu Asn Gly Thr Lys Gln Phe Ile Thr
145                 150                 155                 160

Gln Gly Ser Val Ala Gly Val Tyr Val Val Met Ala Arg Thr Asp Pro
            165                 170                 175

Pro Pro Ser Pro Glu Arg Lys His Gln Gly Ile Ser Ala Phe Ala Phe
            180                 185                 190

Phe Arg Pro Glu Arg Gly Leu Lys Val Gly Arg Lys Glu Glu Lys Leu
            195                 200                 205

Gly Leu Thr Ala Ser Asp Thr Ala Gln Leu Ile Leu Glu Asp Leu Phe
            210                 215                 220

Val Pro Glu Glu Ala Leu Leu Gly Glu Arg Gly Lys Gly Phe Tyr Asp
225                 230                 235                 240

Val Leu Arg Val Leu Asp Gly Gly Arg Ile Gly Ile Ala Ala Met Ala
            245                 250                 255

Val Gly Leu Gly Gln Ala Ala Leu Asp Tyr Ala Leu Ala Tyr Ala Lys
            260                 265                 270

Gly Arg Glu Ala Phe Gly Arg Pro Ile Ala Glu Phe Glu Gly Val Ser
            275                 280                 285

Phe Lys Leu Ala Glu Ala Ala Thr Glu Leu Glu Ala Ala Arg Leu Leu
            290                 295                 300

Tyr Leu Lys Ala Ala Glu Leu Lys Asp Ala Gly Arg Pro Phe Thr Leu
```

```
                305                 310                 315                 320
Glu Ala Ala Gln Ala Lys Leu Phe Ala Ser Glu Ala Ala Val Lys Ala
                    325                 330                 335
Cys Asp Glu Ala Ile Gln Ile Leu Gly Gly Tyr Gly Tyr Val Lys Asp
                    340                 345                 350
Tyr Pro Val Glu Arg Tyr Trp Arg Asp Ala Arg Leu Thr Arg Ile Gly
                    355                 360                 365
Glu Gly Thr Ser Glu Ile Leu Lys Leu Val Ile Ala Arg Arg Leu Leu
                    370                 375                 380
Glu Ala Val
385

<210> SEQ ID NO 146
<211> LENGTH: 334
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Met Lys Val Lys Val Gly Val Asn Gly Tyr Gly Thr Ile Gly Lys Arg
1               5                   10                  15
Val Ala Tyr Ala Val Thr Lys Gln Asp Asp Met Glu Leu Ile Gly Ile
                20                  25                  30
Thr Lys Thr Lys Pro Asp Phe Glu Ala Tyr Arg Ala Lys Glu Leu Gly
                35                  40                  45
Ile Pro Val Tyr Ala Ala Ser Glu Glu Phe Ile Pro Arg Phe Glu Lys
            50                  55                  60
Glu Gly Phe Glu Val Ala Gly Thr Leu Asn Asp Leu Leu Glu Lys Val
65                  70                  75                  80
Asp Ile Ile Val Asp Ala Thr Pro Gly Gly Ile Gly Ala Lys Asn Lys
                85                  90                  95
Pro Leu Tyr Glu Lys Ala Gly Val Lys Ala Ile Phe Gln Gly Gly Glu
                100                 105                 110
Lys Ala Asp Val Ala Glu Val Ser Phe Val Ala Gln Ala Asn Tyr Glu
                115                 120                 125
Ala Ala Leu Gly Lys Asn Tyr Val Arg Val Val Ser Cys Asn Thr Thr
            130                 135                 140
Gly Leu Val Arg Thr Leu Ser Ala Ile Arg Glu Tyr Ala Asp Tyr Val
145                 150                 155                 160
Tyr Ala Val Met Ile Arg Arg Ala Ala Asp Pro Asn Asp Thr Lys Arg
                165                 170                 175
Gly Pro Ile Asn Ala Ile Lys Pro Thr Val Glu Val Pro Ser His His
                180                 185                 190
Gly Pro Asp Val Gln Thr Val Ile Pro Ile Asn Ile Glu Thr Met Ala
                195                 200                 205
Phe Val Val Pro Thr Thr Leu Met His Val His Ser Val Met Val Glu
            210                 215                 220
Leu Lys Lys Pro Leu Thr Lys Asp Asp Val Ile Asp Ile Phe Glu Asn
225                 230                 235                 240
Thr Thr Arg Val Leu Leu Phe Glu Lys Glu Lys Gly Phe Asp Ser Thr
                245                 250                 255
Ala Gln Ile Ile Glu Phe Ala Arg Asp Leu His Arg Glu Trp Asn Asn
                260                 265                 270
```

```
Leu Tyr Glu Ile Ala Val Trp Lys Glu Ser Ile Asn Ile Lys Gly Asn
            275                 280                 285

Arg Leu Phe Tyr Ile Gln Ala Val His Gln Glu Ser Asp Val Ile Pro
        290                 295                 300

Glu Asn Ile Asp Ala Ile Arg Ala Met Phe Glu Leu Ala Asp Lys Trp
305                 310                 315                 320

Asp Ser Ile Lys Lys Thr Asn Lys Ser Leu Gly Ile Leu Lys
                325                 330

<210> SEQ ID NO 147
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Met Gly Leu Phe Ala Gly Lys Gly Val Leu Val Thr Gly Gly Ala Arg
1               5                   10                  15

Gly Ile Gly Arg Ala Ile Ala Gln Ala Phe Ala Arg Glu Gly Ala Leu
            20                  25                  30

Val Ala Leu Cys Asp Leu Arg Pro Glu Gly Lys Glu Val Ala Glu Ala
        35                  40                  45

Ile Gly Gly Ala Phe Phe Gln Val Asp Leu Glu Asp Glu Arg Glu Arg
    50                  55                  60

Val Arg Phe Val Glu Glu Ala Tyr Ala Leu Gly Arg Val Asp Val
65                  70                  75                  80

Leu Val Asn Asn Ala Ala Ile Ala Ala Pro Gly Ser Ala Leu Thr Val
                85                  90                  95

Arg Leu Pro Glu Trp Arg Arg Val Leu Glu Val Asn Leu Thr Ala Pro
            100                 105                 110

Met His Leu Ser Ala Leu Ala Ala Arg Glu Met Arg Lys Val Gly Gly
        115                 120                 125

Gly Ala Ile Val Asn Val Ala Ser Val Gln Gly Leu Phe Ala Glu Gln
    130                 135                 140

Glu Asn Ala Ala Tyr Asn Ala Ser Lys Gly Gly Leu Val Asn Leu Thr
145                 150                 155                 160

Arg Ser Leu Ala Leu Asp Leu Ala Pro Leu Arg Ile Arg Val Asn Ala
                165                 170                 175

Val Ala Pro Gly Ala Ile Ala Thr Glu Ala Val Leu Glu Ala Ile Ala
            180                 185                 190

Leu Ser Pro Asp Pro Glu Arg Thr Arg Arg Asp Trp Glu Asp Leu His
        195                 200                 205

Ala Leu Arg Arg Leu Gly Lys Pro Glu Glu Val Ala Glu Ala Val Leu
    210                 215                 220

Phe Leu Ala Ser Glu Lys Ala Ser Phe Ile Thr Gly Ala Ile Leu Pro
225                 230                 235                 240

Val Asp Gly Gly Met Thr Ala Ser Phe Met Met Ala Gly Arg Pro Val
                245                 250                 255

<210> SEQ ID NO 148
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 148

```
Met Ser Glu Lys Met Val Ala Ile Met Lys Thr Lys Pro Gly Tyr Gly
1               5                   10                  15

Ala Glu Leu Val Glu Val Asp Val Pro Lys Pro Gly Pro Gly Glu Val
            20                  25                  30

Leu Ile Lys Val Leu Ala Thr Ser Ile Cys Gly Thr Asp Leu His Ile
        35                  40                  45

Tyr Glu Trp Asn Glu Trp Ala Gln Ser Arg Ile Lys Pro Pro Gln Ile
    50                  55                  60

Met Gly His Glu Val Ala Gly Glu Val Val Glu Ile Gly Pro Gly Val
65                  70                  75                  80

Glu Gly Ile Glu Val Gly Asp Tyr Val Ser Val Glu Thr His Ile Val
                85                  90                  95

Cys Gly Lys Cys Tyr Ala Cys Arg Arg Gly Gln Tyr His Val Cys Gln
            100                 105                 110

Asn Thr Lys Ile Phe Gly Val Asp Thr Asp Gly Val Phe Ala Glu Tyr
        115                 120                 125

Ala Val Val Pro Ala Gln Asn Ile Trp Lys Asn Pro Lys Ser Ile Pro
130                 135                 140

Pro Glu Tyr Ala Thr Leu Gln Glu Pro Leu Gly Asn Ala Val Asp Thr
145                 150                 155                 160

Val Leu Ala Gly Pro Ile Ser Gly Lys Ser Val Leu Ile Thr Gly Ala
                165                 170                 175

Gly Pro Leu Gly Leu Leu Gly Ile Ala Val Ala Lys Ala Ser Gly Ala
            180                 185                 190

Tyr Pro Val Ile Val Ser Glu Pro Ser Asp Phe Arg Arg Glu Leu Ala
        195                 200                 205

Lys Lys Val Gly Ala Asp Tyr Val Ile Asn Pro Phe Glu Glu Asp Val
210                 215                 220

Val Lys Glu Val Met Asp Ile Thr Asp Gly Asn Gly Val Asp Val Phe
225                 230                 235                 240

Leu Glu Phe Ser Gly Ala Pro Lys Ala Leu Glu Gln Gly Leu Gln Ala
                245                 250                 255

Val Thr Pro Ala Gly Arg Val Ser Leu Leu Gly Leu Tyr Pro Gly Lys
            260                 265                 270

Val Thr Ile Asp Phe Asn Asn Leu Ile Ile Phe Lys Ala Leu Thr Ile
        275                 280                 285

Tyr Gly Ile Thr Gly Arg His Leu Trp Glu Thr Trp Tyr Thr Val Ser
    290                 295                 300

Arg Leu Leu Gln Ser Gly Lys Leu Asn Leu Asp Pro Ile Ile Thr His
305                 310                 315                 320

Lys Tyr Lys Gly Phe Asp Lys Tyr Glu Glu Ala Phe Glu Leu Met Arg
                325                 330                 335

Ala Gly Lys Thr Gly Lys Val Val Phe Met Leu Lys
            340                 345
```

<210> SEQ ID NO 149
<211> LENGTH: 387
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 149

```
Met Gly Leu Trp Phe Glu Gly Ala Glu Arg Gln Val Leu Gly
1               5                   10                  15

Pro Phe Arg Glu Phe Leu Lys Ala Glu Val Ala Pro Gly Ala Ala Glu
            20                  25                  30

Arg Asp Arg Thr Gly Ala Phe Pro Trp Asp Leu Val Arg Lys Leu Ala
            35                  40                  45

Glu Phe Gly Val Phe Gly Ala Leu Val Pro Glu Ala Tyr Gly Gly Ala
        50                  55                  60

Gly Leu Ser Thr Arg Leu Phe Ala Arg Met Val Glu Ala Ile Ala Tyr
65                  70                  75                  80

Tyr Asp Gly Ala Leu Ala Leu Thr Val Ala Ser His Asn Ser Leu Ala
                85                  90                  95

Thr Gly His Ile Leu Leu Ala Gly Ser Glu Ala Gln Lys Glu Ala Phe
            100                 105                 110

Leu Pro Lys Leu Ala Ser Gly Glu Ala Leu Gly Ala Trp Gly Leu Thr
        115                 120                 125

Glu Pro Gly Ser Gly Ser Asp Ala Ala Ala Leu Lys Thr Lys Ala Glu
    130                 135                 140

Lys Val Glu Gly Gly Trp Arg Leu Asn Gly Thr Lys Gln Phe Ile Thr
145                 150                 155                 160

Gln Gly Ser Val Ala Gly Val Tyr Val Val Met Ala Arg Thr Asp Pro
                165                 170                 175

Pro Pro Ser Pro Glu Arg Lys His Gln Gly Ile Ser Ala Phe Ala Phe
            180                 185                 190

Phe Arg Pro Glu Arg Gly Leu Lys Val Gly Arg Lys Glu Lys Leu
        195                 200                 205

Gly Leu Thr Ala Ser Asp Thr Ala Gln Leu Ile Leu Glu Asp Leu Phe
    210                 215                 220

Val Pro Glu Glu Ala Leu Leu Gly Glu Arg Gly Lys Gly Phe Tyr Asp
225                 230                 235                 240

Val Leu Arg Val Leu Asp Gly Gly Arg Ile Gly Ile Ala Ala Met Ala
                245                 250                 255

Val Gly Leu Gly Gln Ala Ala Leu Asp Tyr Ala Leu Ala Tyr Ala Lys
            260                 265                 270

Gly Arg Glu Ala Phe Gly Arg Pro Ile Ala Glu Phe Glu Gly Val Ser
        275                 280                 285

Phe Lys Leu Ala Glu Ala Ala Thr Glu Leu Glu Ala Ala Arg Leu Leu
    290                 295                 300

Tyr Leu Lys Ala Ala Glu Leu Lys Asp Ala Gly Arg Pro Phe Thr Leu
305                 310                 315                 320

Glu Ala Ala Gln Ala Lys Leu Phe Ala Ser Glu Ala Ala Val Lys Ala
                325                 330                 335

Cys Asp Glu Ala Ile Gln Ile Leu Gly Gly Tyr Gly Tyr Val Lys Asp
            340                 345                 350

Tyr Pro Val Glu Arg Tyr Trp Arg Asp Ala Arg Leu Thr Arg Ile Gly
        355                 360                 365

Glu Gly Thr Ser Glu Ile Leu Lys Leu Val Ile Ala Arg Arg Leu Leu
    370                 375                 380

Glu Ala Val
385

<210> SEQ ID NO 150
<211> LENGTH: 213
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Met Lys Val Leu Val Thr Gly Phe Glu Pro Phe Gly Gly Glu Lys Ile
1               5                   10                  15

Asn Pro Thr Glu Arg Ile Ala Lys Asp Leu Asp Gly Ile Lys Ile Gly
            20                  25                  30

Asp Ala Gln Val Phe Gly Arg Val Leu Pro Val Val Phe Gly Lys Ala
        35                  40                  45

Lys Glu Val Leu Glu Lys Thr Leu Glu Glu Ile Lys Pro Asp Ile Ala
    50                  55                  60

Ile His Val Gly Leu Ala Pro Gly Arg Ser Ala Ile Ser Ile Glu Arg
65                  70                  75                  80

Ile Ala Val Asn Ala Ile Asp Ala Arg Ile Pro Asp Asn Glu Gly Lys
                85                  90                  95

Lys Ile Glu Asp Glu Pro Ile Val Pro Gly Ala Pro Thr Ala Tyr Phe
            100                 105                 110

Ser Thr Leu Pro Ile Lys Lys Ile Met Lys Lys Leu His Glu Arg Gly
        115                 120                 125

Ile Pro Ala Tyr Ile Ser Asn Ser Ala Gly Leu Tyr Leu Cys Asn Tyr
    130                 135                 140

Val Met Tyr Leu Ser Leu His His Ser Ala Thr Lys Gly Tyr Pro Lys
145                 150                 155                 160

Met Ser Gly Phe Ile His Val Pro Tyr Ile Pro Glu Gln Ile Ile Asp
                165                 170                 175

Lys Ile Gly Lys Gly Gln Val Pro Pro Ser Met Cys Tyr Glu Met Glu
            180                 185                 190

Leu Glu Ala Val Lys Val Ala Ile Glu Val Ala Leu Thr Gln Asp Met
        195                 200                 205

Ile Asn Lys Ser Thr
    210

<210> SEQ ID NO 151
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Met Lys Val Asp Leu Asn Ala Asp Ala Gly Glu Ser Tyr Gly Ala Phe
1               5                   10                  15

Ala Tyr Gly His Asp Arg Glu Ile Phe Pro Leu Val Ser Ser Ala Asn
            20                  25                  30

Leu Ala Cys Gly Phe His Gly Ser Pro Gly Arg Ile Leu Glu Ala
        35                  40                  45

Val Arg Leu Ala Lys Ala His Gly Val Ala Val Gly Ala His Pro Gly
    50                  55                  60

Phe Pro Asp Leu Val Gly Phe Gly Arg Arg Glu Met Ala Leu Ser Pro
65                  70                  75                  80

Glu Glu Val Tyr Ala Asp Val Leu Tyr Gln Ile Gly Ala Leu Ser Ala
                85                  90                  95
```

```
Phe Leu Lys Ala Glu Gly Leu Pro Leu His His Val Lys Pro His Gly
                100                 105                 110

Ala Leu Tyr Leu Lys Ala Cys Arg Asp Arg Glu Thr Ala Arg Ala Ile
            115                 120                 125

Ala Leu Ala Val Lys Ala Phe Asp Pro Gly Leu Pro Leu Val Val Leu
        130                 135                 140

Pro Gly Thr Val Tyr Glu Glu Ala Arg Lys Ala Gly Leu Arg Val
145                 150                 155                 160

Val Leu Glu Ala Phe Pro Glu Arg Ala Tyr Leu Arg Ser Gly Gln Leu
                165                 170                 175

Ala Pro Arg Ser Met Pro Gly Ser Trp Ile Thr Asp Pro Glu Ala
            180                 185                 190

Ala Arg Arg Ala Leu Arg Met Val Leu Glu Gly Lys Val Glu Ala Leu
        195                 200                 205

Asp Gly Gly Glu Val Ala Val Arg Ala Asp Thr Leu Cys Ile His Gly
    210                 215                 220

Asp Asn Pro Asn Ala Pro Glu Val Ala Arg Ala Val Arg Glu Ala Leu
225                 230                 235                 240

Glu Gln Ala Gly Val Glu Val Arg Ala Phe
                245                 250

<210> SEQ ID NO 152
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Met Lys Ala Gln Glu Leu Gly Ile Lys Ile Gly Val Phe Lys Pro Gly
1               5                   10                  15

Lys Arg Asn Lys Ile Thr Asp Val Lys Gly Val Lys Val Gly His Val
            20                  25                  30

Thr Leu Ile Lys Gly Lys Gly Lys Leu Ile Pro Gly Lys Gly Pro Val
        35                  40                  45

Arg Thr Gly Val Thr Ala Ile Leu Pro His Glu Gly Asn Ile Tyr Lys
    50                  55                  60

Glu Lys Val Leu Ala Gly Ala Phe Val Met Asn Gly Tyr Ser Lys Pro
65                  70                  75                  80

Val Gly Leu Ile Gln Leu Trp Glu Leu Gly Thr Ile Glu Thr Pro Ile
                85                  90                  95

Ile Leu Thr Asn Thr Leu Ser Ile Gly Thr Ala Val Glu Gly Leu Leu
            100                 105                 110

Asp Tyr Ile Leu Glu Glu Asn Glu Asp Ile Gly Val Thr Thr Gly Ser
        115                 120                 125

Val Asn Pro Leu Val Leu Glu Cys Asn Asp Ser Tyr Leu Asn Asp Ile
    130                 135                 140

Arg Gly Arg His Val Lys Arg Glu His Val Val Glu Ala Ile Lys Arg
145                 150                 155                 160

Ala Asp Glu Asp Phe Glu Glu Gly Ala Val Gly Ala Gly Thr Gly Met
                165                 170                 175

Ser Ala Phe Glu Phe Lys Gly Gly Ile Gly Ser Ala Ser Arg Ile Val
            180                 185                 190

Glu Ile Glu Gly Lys Lys Tyr Thr Val Gly Ala Leu Val Leu Ser Asn
        195                 200                 205
```

```
Phe Gly Arg Arg Glu Asp Leu Thr Ile Ala Gly Val Pro Val Gly Leu
            210                 215                 220

Glu Leu Lys Asn Trp Pro Gly Arg Gly Gly Glu Gly Lys Gly Ser Ile
225                 230                 235                 240

Ile Met Ile Ile Ala Thr Asp Ala Pro Leu Thr Gly Arg Gln Leu Asn
                245                 250                 255

Arg Val Ala Lys Arg Ala Ile Val Gly Leu Ala Arg Thr Gly Gly Tyr
            260                 265                 270

Ala Tyr Asn Gly Ser Gly Asp Ile Ala Val Ala Phe Ser Thr Ala Asn
        275                 280                 285

Arg Ile Lys His Tyr Glu Lys Glu Val Ile Glu Ile Lys Ala Leu Pro
    290                 295                 300

Asp Ser Val Ile Ser Pro Leu Phe Lys Ala Thr Ala Glu Ala Val Glu
305                 310                 315                 320

Glu Ala Ile Ile Asn Ser Leu Leu Gly Ala Arg Thr Met Asp Gly Arg
                325                 330                 335

Asp Asn His Val Arg Tyr Ala Leu Pro Lys Glu Leu Leu Arg Ile
            340                 345                 350

Met Arg Arg Tyr Gly Arg Leu Glu Glu
        355                 360

<210> SEQ ID NO 153
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Met Arg Asp Pro Phe Met Glu Ala Leu Gly Leu Lys Val Leu His Leu
1               5                   10                  15

Ala Pro Gly Glu Ala Val Val Ala Gly Glu Val Arg Ala Asp His Leu
            20                  25                  30

Asp Leu His Gly Thr Ala His Gly Gly Phe Leu Tyr Ala Leu Ala Asp
        35                  40                  45

Ser Ala Phe Ala Leu Ala Ser Asn Thr Arg Gly Pro Ala Val Ala Leu
    50                  55                  60

Ser Cys Arg Met Asp Tyr Phe Arg Pro Leu Gly Ala Gly Ala Arg Val
65                  70                  75                  80

Glu Ala Arg Ala Val Glu Val Asn Leu Ser Arg Thr Ala Thr Tyr
            85                  90                  95

Arg Val Glu Val Val Ser Glu Gly Lys Leu Val Ala Leu Phe Thr Gly
            100                 105                 110

Thr Val Phe Arg Leu Gly Gly Asp Gly Asp Val Pro Ala Gly Thr
        115                 120                 125

Gly Asn Leu Ala Pro Arg Glu Ala
    130                 135

<210> SEQ ID NO 154
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154
```

```
Met Val Thr Ala Phe Ile Leu Met Val Thr Ala Ala Gly Lys Glu Arg
1               5                   10                  15

Glu Val Met Glu Lys Leu Leu Ala Met Pro Glu Val Lys Glu Ala Tyr
            20                  25                  30

Val Val Tyr Gly Glu Tyr Asp Leu Ile Val Lys Val Glu Thr Asp Thr
            35                  40                  45

Leu Lys Asp Leu Asp Gln Phe Ile Thr Glu Lys Ile Arg Lys Met Pro
        50                  55                  60

Glu Ile Gln Met Thr Ser Thr Met Ile Ala Ile
65                  70                  75

<210> SEQ ID NO 155
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Met Ala His Arg Thr Trp Gly Gly Arg Phe Gly Glu Gly Pro Asp Ala
1               5                   10                  15

Leu Ala Ala Arg Phe Asn Ala Ser Leu Ala Phe Asp Arg Ala Leu Trp
            20                  25                  30

Arg Glu Asp Leu Trp Gln Asn Arg Val His Ala Arg Met Leu His Ala
        35                  40                  45

Val Gly Leu Leu Ser Ala Glu Glu Leu Glu Ala Ile Leu Lys Gly Leu
    50                  55                  60

Asp Arg Ile Glu Glu Glu Ile Glu Ala Gly Thr Phe Pro Trp Arg Glu
65                  70                  75                  80

Glu Leu Glu Asp Val His Met Asn Leu Glu Ala Arg Leu Thr Glu Leu
                85                  90                  95

Val Gly Pro Pro Gly Gly Lys Leu His Thr Ala Arg Ser Arg Asn Asp
            100                 105                 110

Gln Val Ala Thr Asp Leu Arg Leu Tyr Leu Arg Gly Ala Ile Asp Glu
        115                 120                 125

Leu Leu Ala Leu Leu Ala Leu Arg Arg Val Leu Val Arg Glu Ala
    130                 135                 140

Glu Lys His Leu Asp Pro Leu Tyr Val Leu Pro Gly Tyr Thr His Leu
145                 150                 155                 160

Gln Arg Ala Gln Pro Val Leu Leu Ala His Trp Phe Leu Ala Tyr Tyr
                165                 170                 175

Glu Met Leu Lys Arg Asp Ala Gly Arg Leu Glu Asp Ala Lys Glu Arg
            180                 185                 190

Leu Asn Glu Ser Pro Leu Gly Ala Ala Ala Leu Ala Gly Thr Gly Phe
        195                 200                 205

Pro Ile Asp Arg His Phe Thr Ala Arg Glu Leu Gly Phe Lys Ala Pro
    210                 215                 220

Met Arg Asn Ser Leu Asp Ala Val Ala Ser Arg Asp Phe Ala Leu Glu
225                 230                 235                 240

Val Leu Ser Ala Leu Asn Ile Gly Met Leu His Leu Ser Arg Met Ala
                245                 250                 255

Glu Glu Leu Ile Leu Tyr Ser Thr Glu Glu Phe Gly Phe Val Glu Val
            260                 265                 270

Pro Asp Ala Phe Ala Thr Gly Ser Ser Ile Met Pro Gln Lys Lys Asn
```

```
                    275                 280                 285
Pro Asp Ile Leu Glu Leu Ile Arg Ala Lys Ala Gly Arg Val Leu Gly
290                 295                 300
Ala Phe Val Gly Leu Ser Ala Val Val Lys Gly Leu Pro Leu Ala Tyr
305                 310                 315                 320
Asn Lys Asp Leu Gln Glu Asp Lys Glu Pro Leu Leu Asp Ala Leu Ala
                325                 330                 335
Thr Tyr Arg Asp Ser Leu Arg Leu Leu Ala Ala Leu Leu Pro Gly Leu
                340                 345                 350
Lys Trp Arg Arg Glu Arg Met Trp Arg Ala Ala Glu Gly Gly Tyr Thr
                355                 360                 365
Leu Ala Thr Glu Leu Ala Asp Tyr Leu Ala Glu Lys Gly Leu Pro Phe
370                 375                 380
Arg Glu Ala His His Val Val Gly Arg Leu Val Arg Arg Leu Val Glu
385                 390                 395                 400
Glu Gly Arg Ala Leu Lys Asp Leu Thr Leu Glu Glu Leu Gln Ala His
                405                 410                 415
His Pro Leu Phe Ala Glu Asp Ala Leu Pro Leu Leu Arg Leu Glu Thr
                420                 425                 430
Ala Ile His Arg Arg Ser Tyr Gly Gly Thr Ala Pro Glu Ala Val
                435                 440                 445
Arg Glu Arg Leu Glu Glu Ala Lys Lys Glu Val Gly Leu Asp
450                 455                 460

<210> SEQ ID NO 156
<211> LENGTH: 385
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Met Leu Asp Phe Tyr Ala Leu Glu Asp Leu Leu Thr Pro Glu Glu Lys
1               5                   10                  15
Glu Val Gln Lys Ala Ala Arg Arg Phe Leu Glu Lys Glu Ala Leu Pro
                20                  25                  30
His Ile Arg Asp Trp Trp Glu Glu Gly Val Phe Pro Thr His Leu Ile
                35                  40                  45
Pro Arg Phe Ala Glu Leu Gly Phe Leu Gly Pro Thr Leu Pro Pro Glu
50                  55                  60
Tyr Gly Gly Ala Gly Val Ser Ser Ala Ala Tyr Gly Leu Ile Cys Tyr
65                  70                  75                  80
Glu Leu Glu Arg Val Asp Ser Gly Leu Arg Ser Phe Val Ser Val Gln
                85                  90                  95
Ser Ser Leu Val Met Tyr Pro Ile Tyr Ala Tyr Gly Ser Glu Glu Gln
                100                 105                 110
Lys Arg Glu Phe Leu Pro Lys Leu Ala Arg Gly Glu Met Val Gly Cys
                115                 120                 125
Phe Gly Leu Thr Glu Pro Asp Gly Gly Ser Asp Pro Tyr Gly Asn Met
130                 135                 140
Lys Thr Arg Ala Arg Arg Glu Gly Asp Thr Trp Val Leu Asn Gly Thr
145                 150                 155                 160
Lys Met Trp Ile Thr Asn Gly Asn Leu Ala His Leu Ala Val Ile Trp
                165                 170                 175
```

```
Ala Lys Asp Glu Gly Glu Val Leu Gly Phe Leu Val Pro Thr Asp
            180                 185                 190

Thr Pro Gly Phe Gln Ala Arg Glu Val Lys Arg Lys Met Ser Leu Arg
        195                 200                 205

Ala Ser Val Thr Ser Glu Leu Val Leu Glu Glu Val Arg Val Pro Glu
    210                 215                 220

Ser Leu Arg Leu Pro Lys Ala Leu Gly Leu Lys Ala Pro Leu Ser Cys
225                 230                 235                 240

Leu Thr Gln Ala Arg Phe Gly Ile Ala Trp Gly Ala Met Gly Ala Leu
                245                 250                 255

Glu Ala Val Tyr Glu Glu Ala Val Ala Phe Ala Lys Ser Arg Ser Thr
            260                 265                 270

Phe Gly Glu Pro Leu Ala Lys Lys Gln Leu Val Gln Ala Lys Leu Ala
        275                 280                 285

Glu Met Leu Ala Trp His Thr Glu Gly Leu Leu Ala Trp Arg Leu
    290                 295                 300

Ala Arg Leu Lys Asp Glu Gly Lys Leu Thr Pro Ala Gln Val Ser Leu
305                 310                 315                 320

Ala Lys Arg Gln Asn Val Trp Lys Ala Leu Gln Ala Ala Arg Met Ala
                325                 330                 335

Arg Asp Ile Leu Gly Gly Ser Gly Ile Thr Leu Glu Tyr His Ala Ile
            340                 345                 350

Arg His Met Leu Asn Leu Glu Thr Val Tyr Thr Tyr Glu Gly Thr His
        355                 360                 365

Asp Val His Thr Leu Val Leu Gly Arg Glu Ile Thr Gly Leu Asn Ala
    370                 375                 380

Phe
385

<210> SEQ ID NO 157
<211> LENGTH: 192
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Met Ile Leu Val Thr Gly Phe Glu Pro Phe Gly Ser Leu Glu His Asn
1               5                   10                  15

Pro Ser Gln Ala Leu Leu Asp Leu Leu Pro Ser Glu Val Asp Gly Lys
            20                  25                  30

Pro Leu Arg Lys Ala Val Leu Pro Val Asp Ala Glu Ala Leu Gly Glu
        35                  40                  45

Ala Leu Glu Asp Leu His Arg Glu Gly Pro Lys Ala Val Leu His Leu
    50                  55                  60

Gly Leu Ala Glu Asp Arg Pro Val Leu Thr Leu Glu Arg Leu Ala Val
65                  70                  75                  80

Asn Leu Leu Asp Phe Pro Arg Pro Asp Asn Arg Gly Arg Val Leu Glu
                85                  90                  95

Asp Leu Pro Ile Val Pro Gly Gly Pro Leu Ala Leu Pro Ala Arg Phe
            100                 105                 110

Pro Val Lys Pro Val Leu Ala Arg Trp Arg Glu Ala Gly Ile Pro Gly
        115                 120                 125

Arg Pro Ser Leu Ser Ala Gly Ser Tyr Leu Cys Asn Gln Ala Phe Tyr
    130                 135                 140
```

```
Leu Ser Leu Tyr Arg Leu Pro Glu Glu Val Pro Val Gly Phe Leu His
145                 150                 155                 160

Leu Pro Pro Asp Glu Thr Leu Ala Leu Lys Arg Pro Arg Pro Tyr Val
                165                 170                 175

Pro Leu Glu Val Gln Ala Arg Ala Val Arg Leu Ala Leu Glu His Leu
            180                 185                 190

<210> SEQ ID NO 158
<211> LENGTH: 419
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Met Leu Ser Arg Lys Ile Ile Glu Glu Ser Asp Ile Tyr Leu Ala Thr
1               5                   10                  15

Ser Thr Arg Asp Pro Glu Leu Phe Pro Leu Val Ile Asp His Gly Glu
            20                  25                  30

Gly Val Trp Ile Tyr Asp Val Asp Gly Asn Lys Tyr Leu Asp Phe Thr
        35                  40                  45

Ser Gly Ile Gly Val Asn Asn Leu Gly Trp Pro Ser His Pro Glu Val
    50                  55                  60

Ile Lys Ile Gly Ile Glu Gln Met Gln Lys Leu Ala His Ala Ala Ala
65                  70                  75                  80

Asn Asp Phe Tyr Asn Ile Pro Gln Leu Glu Leu Ala Lys Lys Leu Val
                85                  90                  95

Thr Tyr Ser Pro Gly Asn Phe Gln Lys Lys Val Phe Phe Ser Asn Ser
            100                 105                 110

Gly Thr Glu Ala Ile Glu Ala Ser Ile Lys Val Val Lys Asn Thr Gly
        115                 120                 125

Arg Lys Tyr Ile Ile Ala Phe Leu Gly Gly Phe His Gly Arg Thr Phe
    130                 135                 140

Gly Ser Ile Ser Leu Thr Ala Ser Lys Ala Val Gln Arg Ser Ile Val
145                 150                 155                 160

Gly Pro Phe Met Pro Gly Val Ile His Val Pro Tyr Pro Asn Pro Tyr
                165                 170                 175

Arg Asn Pro Trp His Ile Asn Gly Tyr Glu Asn Pro Ser Glu Leu Val
            180                 185                 190

Asn Arg Val Ile Glu Phe Ile Glu Asp Tyr Ile Phe Val Asn Leu Val
        195                 200                 205

Pro Pro Glu Glu Val Ala Gly Ile Phe Phe Glu Pro Ile Gln Gly Glu
    210                 215                 220

Gly Gly Tyr Val Ile Pro Pro Lys Asn Phe Phe Ala Glu Leu Gln Lys
225                 230                 235                 240

Leu Ala Lys Lys Tyr Gly Ile Leu Leu Val Asp Asp Glu Val Gln Met
                245                 250                 255

Gly Leu Gly Arg Thr Gly Lys Leu Phe Ala Ile Glu Asn Phe Asn Thr
            260                 265                 270

Val Pro Asp Val Ile Thr Leu Ala Lys Ala Leu Gly Gly Gly Ile Met
        275                 280                 285

Pro Ile Gly Ala Thr Ile Phe Arg Lys Asp Leu Asp Phe Lys Pro Gly
    290                 295                 300

Met His Ser Asn Thr Phe Gly Gly Asn Ala Leu Ala Cys Ala Ile Gly
```

```
                    305                 310                 315                 320
Ser Lys Val Ile Asp Ile Val Lys Asp Leu Leu Pro His Val Asn Glu
                325                 330                 335

Ile Gly Lys Ile Phe Ala Glu Glu Leu Gln Gly Leu Ala Asp Asp Val
            340                 345                 350

Arg Gly Ile Gly Leu Ala Trp Gly Leu Glu Tyr Asn Glu Lys Lys Val
        355                 360                 365

Arg Asp Arg Ile Ile Gly Glu Ser Phe Lys Arg Gly Leu Leu Leu Leu
    370                 375                 380

Pro Ala Gly Arg Ser Ala Ile Arg Val Ile Pro Pro Leu Val Ile Ser
385                 390                 395                 400

Glu Glu Glu Ala Lys Gln Gly Leu Asp Ile Leu Lys Lys Val Ile Lys
                405                 410                 415

Val Val Lys

<210> SEQ ID NO 159
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Met Ala Asp Lys Ile Lys Val Ser Leu Leu Gly Ser Thr Gly Met Val
1               5                   10                  15

Gly Gln Lys Met Val Lys Met Leu Ala Lys His Pro Tyr Leu Glu Leu
            20                  25                  30

Val Lys Val Ser Ala Ser Pro Ser Lys Ile Gly Lys Lys Tyr Lys Asp
        35                  40                  45

Ala Val Lys Trp Ile Glu Gln Gly Asp Ile Pro Glu Glu Val Gln Asp
    50                  55                  60

Leu Pro Ile Val Ser Thr Asn Tyr Glu Asp His Lys Asp Val Asp Val
65                  70                  75                  80

Val Leu Ser Ala Leu Pro Asn Glu Leu Ala Glu Ser Ile Glu Leu Glu
                85                  90                  95

Leu Val Lys Asn Gly Lys Ile Val Val Ser Asn Ala Ser Pro Phe Arg
            100                 105                 110

Met Asp Pro Asp Val Pro Leu Ile Asn Pro Glu Ile Asn Trp Glu His
        115                 120                 125

Leu Glu Leu Leu Lys Phe Gln Lys Glu Arg Lys Gly Trp Lys Gly Ile
    130                 135                 140

Leu Val Lys Asn Pro Asn Cys Thr Ala Ala Ile Met Ser Met Pro Ile
145                 150                 155                 160

Lys Pro Leu Ile Glu Ile Ala Thr Lys Ser Lys Ile Ile Ile Thr Thr
                165                 170                 175

Leu Gln Ala Val Ser Gly Ala Gly Tyr Asn Gly Ile Ser Phe Met Ala
            180                 185                 190

Ile Glu Gly Asn Ile Ile Pro Tyr Ile Lys Gly Glu Glu Asp Lys Ile
        195                 200                 205

Ala Lys Glu Leu Thr Lys Leu Asn Gly Lys Leu Glu Asn Asn Gln Ile
    210                 215                 220

Ile Pro Ala Asn Leu Asp Ser Thr Val Thr Ser Ile Arg Val Pro Thr
225                 230                 235                 240

Arg Val Gly His Met Gly Val Ile Asn Ile Val Thr Asn Glu Arg Ile
```

```
                        245                 250                 255
Asn Ile Glu Glu Ile Lys Lys Thr Leu Lys Asn Phe Lys Ser Leu Pro
                260                 265                 270

Gln Gln Lys Asn Leu Pro Thr Ala Pro Lys Gln Pro Ile Ile Val Arg
            275                 280                 285

Asp Glu Glu Asp Arg Pro Gln Pro Ile Ile Asp Val Asn Ala Glu Ser
        290                 295                 300

Gly Met Ala Val Thr Val Gly Arg Ile Arg His Glu Asn Asn Val Leu
305                 310                 315                 320

Arg Leu Val Val Leu Gly Asp Asn Leu Val Arg Gly Ala Ala Gly Ile
                325                 330                 335

Thr Ile Leu Thr Val Glu Val Met Lys Glu Leu Gly Tyr Ile
            340                 345                 350

<210> SEQ ID NO 160
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Met Thr Asp Met Ser Ile Lys Phe Glu Leu Ile Asp Val Pro Ile Pro
1               5                   10                  15

Gln Gly Thr Asn Val Ile Ile Gly Gln Ala His Phe Ile Lys Thr Val
            20                  25                  30

Glu Asp Leu Tyr Glu Ala Leu Val Thr Ser Val Pro Gly Val Lys Phe
        35                  40                  45

Gly Ile Ala Phe Cys Glu Ala Ser Gly Lys Arg Leu Val Arg His Glu
    50                  55                  60

Ala Asn Asp Glu Glu Leu Arg Asn Leu Ala Ile Asp Leu Cys Lys Lys
65                  70                  75                  80

Ile Ala Ala Gly His Val Phe Val Ile Tyr Ile Arg Asn Ala Trp Pro
                85                  90                  95

Ile Asn Val Leu Asn Ala Ile Lys Asn Val Pro Glu Val Val Arg Ile
            100                 105                 110

Phe Ala Ala Thr Ala Asn Pro Leu Lys Val Ile Val Ala Glu Val Glu
        115                 120                 125

Pro Glu Arg Arg Gly Val Val Gly Val Asp Gly His Ser Pro Leu
    130                 135                 140

Gly Val Glu Thr Glu Lys Asp Arg Glu Glu Arg Lys Lys Phe Leu Arg
145                 150                 155                 160

Glu Val Val Lys Tyr Lys Leu
                165

<210> SEQ ID NO 161
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Met Ala Leu His His His His His His Gly Val Thr Gly Glu Leu Arg
1               5                   10                  15

Arg Arg Ala Asp Gly Ile Trp Gln Arg Ile Leu Ala His Pro Phe Val
```

```
                20                  25                  30
Ala Glu Leu Tyr Ala Gly Thr Leu Pro Met Glu Lys Phe Lys Tyr Tyr
            35                  40                  45
Leu Leu Gln Asp Tyr Asn Tyr Leu Val Asn Phe Ala Lys Ala Leu Ser
        50                  55                  60
Leu Ala Ala Ser Arg Ala Pro Ser Val Asp Leu Met Lys Thr Ala Leu
65                  70                  75                  80
Glu Leu Ala Tyr Gly Thr Val Thr Gly Glu Met Ala Asn Tyr Glu Ala
                85                  90                  95
Leu Leu Lys Glu Val Gly Leu Ser Leu Arg Asp Ala Ala Glu Ala Glu
            100                 105                 110
Pro Asn Arg Val Asn Val Ser Tyr Met Ala Tyr Leu Lys Ser Thr Cys
        115                 120                 125
Ala Leu Glu Gly Phe Tyr Gln Cys Met Ala Ala Leu Leu Pro Cys Phe
    130                 135                 140
Trp Ser Tyr Ala Glu Ile Ala Glu Arg His Gly Gly Lys Leu Arg Glu
145                 150                 155                 160
Asn Pro Val His Val Tyr Lys Lys Trp Ala Ser Val Tyr Leu Ser Pro
                165                 170                 175
Glu Tyr Arg Gly Leu Val Glu Arg Leu Arg Ala Val Leu Asp Ser Ser
            180                 185                 190
Gly Leu Ser Ala Glu Glu Leu Trp Pro Tyr Phe Lys Gly Ala Ser Leu
        195                 200                 205
Tyr Glu Leu Glu Phe Trp Gln Ala Ala Tyr Glu Gly His
    210                 215                 220

<210> SEQ ID NO 162
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Met Val Lys Ser Lys Ala Ala Leu Leu Lys Lys Phe Ser Glu Pro Leu
1               5                   10                  15
Ser Ile Glu Asp Val Asn Ile Pro Glu Pro Gln Gly Glu Glu Val Leu
            20                  25                  30
Ile Arg Ile Gly Gly Ala Gly Val Cys Arg Thr Asp Leu Arg Val Trp
        35                  40                  45
Lys Gly Val Glu Ala Lys Gln Gly Phe Arg Leu Pro Ile Ile Leu Gly
    50                  55                  60
His Glu Asn Ala Gly Thr Ile Val Glu Val Gly Glu Leu Ala Lys Val
65                  70                  75                  80
Lys Lys Gly Asp Asn Val Val Val Tyr Ala Thr Trp Gly Asp Leu Thr
                85                  90                  95
Cys Arg Tyr Cys Arg Glu Gly Lys Phe Asn Ile Cys Lys Asn Gln Ile
            100                 105                 110
Ile Pro Gly Gln Thr Thr Asn Gly Gly Phe Ser Glu Tyr Met Leu Val
        115                 120                 125
Lys Ser Ser Arg Trp Leu Val Lys Leu Asn Ser Leu Ser Pro Val Glu
    130                 135                 140
Ala Ala Pro Leu Ala Asp Ala Gly Thr Thr Ser Met Gly Ala Ile Arg
145                 150                 155                 160
```

```
Gln Ala Leu Pro Phe Ile Ser Lys Phe Ala Glu Pro Val Val Ile Val
                165                 170                 175

Asn Gly Ile Gly Gly Leu Ala Val Tyr Thr Ile Gln Ile Leu Lys Ala
            180                 185                 190

Leu Met Lys Asn Ile Thr Ile Val Gly Ile Ser Arg Ser Lys Lys His
        195                 200                 205

Arg Asp Phe Ala Leu Glu Leu Gly Ala Asp Tyr Val Ser Glu Met Lys
    210                 215                 220

Asp Ala Glu Ser Leu Ile Asn Lys Leu Thr Asp Gly Leu Gly Ala Ser
225                 230                 235                 240

Ile Ala Ile Asp Leu Val Gly Thr Glu Thr Thr Tyr Asn Leu Gly
                245                 250                 255

Lys Leu Leu Ala Gln Glu Gly Ala Ile Ile Leu Val Gly Met Glu Gly
            260                 265                 270

Lys Arg Val Ser Leu Glu Ala Phe Asp Thr Ala Val Trp Asn Lys Lys
        275                 280                 285

Leu Leu Gly Ser Asn Tyr Gly Ser Leu Asn Asp Leu Glu Asp Val Val
    290                 295                 300

Arg Leu Ser Glu Ser Gly Lys Ile Lys Pro Tyr Ile Ile Lys Val Pro
305                 310                 315                 320

Leu Asp Asp Ile Asn Lys Ala Phe Thr Asn Leu Asp Glu Gly Arg Val
                325                 330                 335

Asp Gly Arg Gln Val Ile Thr Pro
            340

<210> SEQ ID NO 163
<211> LENGTH: 386
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Met Ser Leu Asp Ala Leu Glu Leu His Arg Phe Leu Lys Gly Lys Ile
1               5                   10                  15

Arg Thr Ala Leu Pro Val Glu Lys Val Asp Arg Glu Thr Leu Ser Leu
            20                  25                  30

Leu Tyr Thr Pro Gly Val Ala Asp Val Ala Arg Ala Cys Ala Glu Asp
        35                  40                  45

Pro Glu Lys Thr Tyr Val Tyr Thr Ser Arg Trp Asn Thr Val Ala Val
    50                  55                  60

Val Ser Asp Gly Ser Ala Val Leu Gly Leu Gly Asn Ile Gly Pro Tyr
65                  70                  75                  80

Gly Ala Leu Pro Val Met Glu Gly Lys Ala Phe Leu Phe Lys Ala Phe
                85                  90                  95

Ala Asp Ile Asp Ala Phe Pro Ile Cys Leu Ser Glu Ser Glu Glu
            100                 105                 110

Lys Ile Ile Ser Ile Val Lys Ser Leu Glu Pro Ser Phe Gly Gly Ile
        115                 120                 125

Asn Leu Glu Asp Ile Gly Ala Pro Lys Cys Phe Arg Ile Leu Gln Arg
    130                 135                 140

Leu Ser Glu Glu Met Asn Ile Pro Val Phe His Asp Asp Gln Gln Gly
145                 150                 155                 160

Thr Ala Val Val Val Ser Ala Ala Phe Leu Asn Ala Leu Lys Leu Thr
                165                 170                 175
```

Glu Lys Lys Ile Glu Glu Val Lys Val Val Asn Gly Ile Gly Ala
            180                 185                 190

Ala Gly Tyr Asn Ile Val Lys Phe Leu Leu Asp Leu Gly Val Lys Asn
            195                 200                 205

Val Val Ala Val Asp Arg Lys Gly Ile Leu Asn Glu Asn Asp Pro Glu
210                 215                 220

Thr Cys Leu Asn Glu Tyr His Leu Glu Ile Ala Arg Ile Thr Asn Pro
225                 230                 235                 240

Glu Arg Leu Ser Gly Asp Leu Glu Thr Ala Leu Gly Ala Asp Phe
            245                 250                 255

Phe Ile Gly Val Ser Arg Gly Asn Ile Leu Lys Pro Glu Trp Ile Lys
            260                 265                 270

Lys Met Ser Arg Lys Pro Val Ile Phe Ala Leu Ala Asn Pro Val Pro
            275                 280                 285

Glu Ile Asp Pro Glu Leu Ala Arg Glu Ala Gly Ala Phe Ile Val Ala
            290                 295                 300

Thr Gly Arg Ser Asp His Pro Asn Gln Val Asn Asn Leu Leu Ala Phe
305                 310                 315                 320

Pro Gly Ile Met Lys Gly Ala Val Glu Lys Arg Ser Lys Ile Thr Lys
            325                 330                 335

Asn Met Leu Leu Ser Ala Val Glu Ala Ile Ala Arg Ser Cys Glu Pro
            340                 345                 350

Glu Pro Glu Arg Ile Ile Pro Glu Ala Phe Asp Met Lys Val His Leu
            355                 360                 365

Asn Val Tyr Thr Ala Val Lys Gly Ser Ala Glu Gly His His His
            370                 375                 380

His His
385

<210> SEQ ID NO 164
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Thr Thr Val Met Lys Phe Gly Gly Thr Ser Val Gly Ser Gly Glu Arg
1               5                   10                  15

Ile Arg His Val Ala Lys Ile Val Thr Lys Arg Lys Glu Asp Asp
            20                  25                  30

Asp Val Val Val Val Ser Ala Met Ser Glu Val Thr Asn Ala Leu
            35                  40                  45

Val Glu Ile Ser Gln Gln Ala Leu Asp Val Arg Asp Ile Ala Lys Val
50                  55                  60

Gly Asp Phe Ile Lys Phe Ile Arg Glu Lys His Tyr Lys Ala Ile Glu
65                  70                  75                  80

Glu Ala Ile Lys Ser Glu Glu Ile Lys Glu Val Lys Lys Ile Ile
            85                  90                  95

Asp Ser Arg Ile Glu Glu Leu Glu Lys Val Leu Ile Gly Val Ala Tyr
            100                 105                 110

Leu Gly Glu Leu Thr Pro Lys Ser Arg Asp Tyr Ile Leu Ser Phe Gly
            115                 120                 125

Glu Arg Leu Ser Ser Pro Ile Leu Ser Gly Ala Ile Arg Asp Leu Gly

```
                130             135             140
Glu Lys Ser Ile Ala Leu Glu Gly Gly Glu Ala Gly Ile Ile Thr Asp
145                 150                 155                 160

Asn Asn Phe Gly Ser Ala Arg Val Lys Arg Leu Glu Val Lys Glu Arg
                165                 170                 175

Leu Leu Pro Leu Leu Lys Glu Gly Ile Ile Pro Val Val Thr Gly Phe
            180                 185                 190

Ile Gly Thr Thr Glu Glu Gly Tyr Ile Thr Thr Leu Gly Arg Gly Gly
        195                 200                 205

Ser Asp Tyr Ser Ala Ala Leu Ile Gly Tyr Gly Leu Asp Ala Asp Ile
    210                 215                 220

Ile Glu Ile Trp Thr Asp Val Ser Gly Val Tyr Thr Thr Asp Pro Arg
225                 230                 235                 240

Leu Val Pro Thr Ala Arg Arg Ile Pro Lys Leu Ser Tyr Ile Glu Ala
                245                 250                 255

Met Glu Leu Ala Tyr Phe Gly Ala Lys Val Leu His Pro Arg Thr Ile
            260                 265                 270

Glu Pro Ala Met Glu Lys Gly Ile Pro Ile Leu Val Lys Asn Thr Phe
        275                 280                 285

Glu Pro Glu Ser Glu Gly Thr Leu Ile Thr Asn Asp Met Glu Met Ser
    290                 295                 300

Asp Ser Ile Val Lys Ala Ile Ser Thr Ile Lys Asn Val Ala Leu Ile
305                 310                 315                 320

Asn Ile Phe Gly Ala Gly Met Val Gly Val Ser Gly Thr Ala Ala Arg
                325                 330                 335

Ile Phe Lys Ala Leu Gly Glu Glu Val Asn Val Ile Leu Ile Ser
            340                 345                 350

Gln Gly Ser Ser Glu Thr Asn Ile Ser Leu Val Val Ser Glu Glu Asp
        355                 360                 365

Val Asp Lys Ala Leu Lys Ala Leu Lys Arg Glu Phe Gly Asp Phe Gly
    370                 375                 380

Lys Lys Ser Phe Leu Asn Asn Asn Leu Ile Arg Asp Val Ser Val Asp
385                 390                 395                 400

Lys Asp Val Cys Val Ile Ser Val Val Gly Ala Gly Met Arg Gly Ala
                405                 410                 415

Lys Gly Ile Ala Gly Lys Ile Phe Thr Ala Val Ser Glu Ser Gly Ala
            420                 425                 430

Asn Ile Lys Met Ile Ala Gln Gly Ser Ser Glu Val Asn Ile Ser Phe
        435                 440                 445

Val Ile Asp Glu Lys Asp Leu Leu Asn Cys Val Arg Lys Leu His Glu
    450                 455                 460

Lys Phe Ile Glu Lys
465

<210> SEQ ID NO 165
<211> LENGTH: 313
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Met Gly Ser Ser His His His His His His Ser Ser Gly Leu Val Pro
1               5                   10                  15
```

```
Arg Gly Ser His Met Glu Ile Lys Lys Gly Thr Trp Ile Ile Lys Lys
            20                  25                  30

Gly Phe Ala Glu Met Phe Lys Gly Gly Val Ile Met Asp Val Thr Ser
        35                  40                  45

Ala Glu Gln Ala Lys Ile Ala Glu Glu Ala Gly Ala Val Ala Val Met
 50                  55                  60

Ala Leu Glu Arg Val Pro Ala Asp Ile Arg Lys Glu Gly Gly Val Ala
 65                  70                  75                  80

Arg Met Ala Ser Ile Ala Lys Ile Arg Glu Ile Met Glu Ala Val Ser
             85                  90                  95

Ile Pro Val Met Ala Lys Val Arg Ile Gly His Ile Ala Glu Ala Lys
                100                 105                 110

Ile Leu Glu Glu Leu Gly Val Asp Phe Ile Asp Glu Ser Glu Val Leu
            115                 120                 125

Thr Pro Ala Asp Asp Arg Phe His Ile Asn Lys His Glu Phe Lys Val
130                 135                 140

Pro Phe Val Cys Gly Ala Arg Asp Leu Gly Glu Ala Leu Arg Arg Ile
145                 150                 155                 160

Ala Glu Gly Ala Ala Met Ile Arg Thr Lys Gly Glu Ala Gly Thr Gly
                165                 170                 175

Asn Val Val Glu Ala Val Lys His Met Arg Arg Val Met Glu Gln Ile
            180                 185                 190

Lys Gln Val Thr Lys Met Glu Asp Glu Leu Val Ala Tyr Gly Lys
            195                 200                 205

Glu Ile Gly Ala Pro Val Glu Leu Leu Arg Glu Val Lys Arg Leu Gly
210                 215                 220

Arg Leu Pro Val Val Asn Phe Ala Ala Gly Gly Val Ala Thr Pro Ala
225                 230                 235                 240

Asp Ala Ala Leu Met Met Met Leu Gly Ala Asp Gly Val Phe Val Gly
                245                 250                 255

Ser Gly Ile Phe Lys Ser Lys Asp Pro Arg Lys Met Ala Lys Ala Met
            260                 265                 270

Val Leu Ala Val Thr Tyr Trp Asp Asn Pro Arg Ile Leu Leu Lys Ile
            275                 280                 285

Ser Glu Asp Ile Gly Glu Pro Met Arg Gly Leu Asp Val Glu Glu Leu
        290                 295                 300

Glu Val Arg Met Gln Glu Arg Gly Trp
305                 310

<210> SEQ ID NO 166
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Met Gly Ser Ser His His His His His His Ser Ser Gly Leu Val Pro
 1               5                  10                  15

Arg Gly Ser His Met Lys Ile Gly Val Leu Gly Val Gln Gly Asp Val
            20                  25                  30

Arg Glu His Val Glu Ala Leu His Lys Leu Gly Val Glu Thr Leu Ile
        35                  40                  45

Val Lys Leu Pro Glu Gln Leu Asp Met Val Asp Gly Leu Ile Leu Pro
 50                  55                  60
```

```
Gly Gly Glu Ser Thr Thr Met Ile Arg Ile Leu Lys Glu Met Asp Met
65                  70                  75                  80

Asp Glu Lys Leu Val Glu Arg Ile Asn Asn Gly Leu Pro Val Phe Ala
                85                  90                  95

Thr Cys Ala Gly Val Ile Leu Leu Ala Lys Arg Ile Lys Asn Tyr Ser
            100                 105                 110

Gln Glu Lys Leu Gly Val Leu Asp Ile Thr Val Glu Arg Asn Ala Tyr
        115                 120                 125

Gly Arg Gln Val Glu Ser Phe Glu Thr Phe Val Glu Ile Pro Ala Val
    130                 135                 140

Gly Lys Asp Pro Phe Arg Ala Ile Phe Ile Arg Ala Pro Arg Ile Val
145                 150                 155                 160

Glu Thr Gly Lys Asn Val Glu Ile Leu Ala Thr Tyr Asp Tyr Asp Pro
                165                 170                 175

Val Leu Val Lys Glu Gly Asn Ile Leu Ala Cys Thr Phe His Pro Glu
            180                 185                 190

Leu Thr Asp Asp Leu Arg Leu His Arg Tyr Phe Leu Glu Met Val Lys
        195                 200                 205

<210> SEQ ID NO 167
<211> LENGTH: 317
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Met Lys Asn Asn Gly Gly Ala Arg Val Val Ile Gly Ala Gly Phe
1               5                   10                  15

Val Gly Ala Ser Tyr Val Phe Ala Leu Met Asn Gln Gly Ile Ala Asp
            20                  25                  30

Glu Ile Val Leu Ile Asp Ala Asn Glu Ser Lys Ala Ile Gly Asp Ala
        35                  40                  45

Met Asp Phe Asn His Gly Lys Val Phe Ala Pro Lys Pro Val Asp Ile
    50                  55                  60

Trp His Gly Asp Tyr Asp Asp Cys Arg Asp Ala Asp Leu Val Val Ile
65                  70                  75                  80

Cys Ala Gly Ala Asn Gln Lys Pro Gly Glu Thr Arg Leu Asp Leu Val
            85                  90                  95

Asp Lys Asn Ile Ala Ile Phe Arg Ser Ile Val Glu Ser Val Met Ala
            100                 105                 110

Ser Gly Phe Gln Gly Leu Phe Leu Val Ala Thr Asn Pro Val Asp Ile
        115                 120                 125

Leu Thr Tyr Ala Thr Trp Lys Phe Ser Gly Leu Pro His Glu Arg Val
    130                 135                 140

Ile Gly Ser Gly Thr Ile Leu Asp Thr Ala Arg Phe Arg Phe Leu Leu
145                 150                 155                 160

Gly Glu Tyr Phe Ser Val Ala Pro Gln Asn Val His Ala Tyr Ile Ile
                165                 170                 175

Gly Glu His Gly Asp Thr Glu Leu Pro Val Trp Ser Gln Ala Tyr Ile
            180                 185                 190

Gly Val Met Pro Ile Arg Lys Leu Val Glu Ser Lys Gly Glu Glu Ala
        195                 200                 205

Gln Lys Asp Leu Glu Arg Ile Phe Val Asn Val Arg Asp Ala Ala Tyr
```

```
                    210                 215                 220
Gln Ile Ile Glu Lys Lys Gly Ala Thr Tyr Tyr Gly Ile Ala Met Gly
225                 230                 235                 240

Leu Ala Arg Val Thr Arg Ala Ile Leu His Asn Glu Asn Ala Ile Leu
                245                 250                 255

Thr Val Ser Ala Tyr Leu Asp Gly Leu Tyr Gly Glu Arg Asp Val Tyr
            260                 265                 270

Ile Gly Val Pro Ala Val Ile Asn Arg Asn Gly Ile Arg Glu Val Ile
        275                 280                 285

Glu Ile Glu Leu Asn Asp Asp Glu Lys Asn Arg Phe His His Ser Ala
    290                 295                 300

Ala Thr Leu Lys Ser Val Leu Ala Arg Ala Phe Thr Arg
305                 310                 315

<210> SEQ ID NO 168
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Met Asp Arg Leu Asp Phe Ser Ile Lys Leu Leu Arg Lys Val Gly His
1               5                   10                  15

Leu Leu Met Ile His Trp Gly Arg Val Asp Asn Val Glu Lys Lys Thr
                20                  25                  30

Gly Phe Lys Asp Ile Val Thr Glu Ile Asp Arg Glu Ala Gln Arg Met
            35                  40                  45

Ile Val Asp Glu Ile Arg Lys Phe Phe Pro Asp Glu Asn Ile Met Ala
        50                  55                  60

Glu Gly Ile Phe Glu Lys Gly Asp Arg Leu Trp Ile Ile Asp Pro
65                  70                  75                  80

Ile Asp Gly Thr Ile Asn Phe Val His Gly Leu Pro Asn Phe Ser Ile
                85                  90                  95

Ser Leu Ala Tyr Val Glu Asn Gly Glu Val Lys Leu Gly Val Val His
            100                 105                 110

Ala Pro Ala Leu Asn Glu Thr Leu Tyr Ala Glu Glu Gly Ser Gly Ala
        115                 120                 125

Phe Phe Asn Gly Glu Arg Ile Arg Val Ser Glu Asn Ala Ser Leu Glu
    130                 135                 140

Glu Cys Val Gly Ser Thr Gly Ser Tyr Val Asp Phe Thr Gly Lys Phe
145                 150                 155                 160

Ile Glu Arg Met Glu Lys Arg Thr Arg Arg Ile Arg Ile Leu Gly Ser
                165                 170                 175

Ala Ala Leu Asn Ala Ala Tyr Val Gly Ala Gly Arg Val Asp Phe Phe
            180                 185                 190

Val Thr Trp Arg Ile Asn Pro Trp Asp Ile Ala Ala Gly Leu Ile Ile
        195                 200                 205

Val Lys Glu Ala Gly Gly Met Val Thr Asp Phe Ser Gly Lys Glu Ala
    210                 215                 220

Asn Ala Phe Ser Lys Asn Phe Ile Phe Ser Asn Gly Leu Ile His Asp
225                 230                 235                 240

Glu Val Val Lys Val Val Asn Glu Val Val Glu Glu Ile Gly Gly Lys
                245                 250                 255
```

```
<210> SEQ ID NO 169
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Met Arg Lys Ala Leu Ile Thr Gly Ala Ser Arg Gly Ile Gly Arg Ala
1               5                   10                  15

Ile Ala Leu Arg Leu Ala Glu Asp Gly Phe Ala Leu Ala Ile His Tyr
                20                  25                  30

Gly Gln Asn Arg Glu Lys Ala Glu Glu Val Ala Glu Ala Arg Arg
        35                  40                  45

Arg Gly Ser Pro Leu Val Ala Val Leu Gly Ala Asn Leu Leu Glu Ala
    50                  55                  60

Glu Ala Ala Thr Ala Leu Val His Gln Ala Ala Glu Val Leu Gly Gly
65                  70                  75                  80

Leu Asp Thr Leu Val Asn Asn Ala Gly Ile Thr Arg Asp Thr Leu Leu
                85                  90                  95

Val Arg Met Lys Asp Glu Asp Trp Glu Ala Val Leu Glu Ala Asn Leu
                100                 105                 110

Ser Ala Val Phe Arg Thr Thr Arg Glu Ala Val Lys Leu Met Met Lys
            115                 120                 125

Ala Arg Phe Gly Arg Ile Val Asn Ile Thr Ser Val Val Gly Ile Leu
    130                 135                 140

Gly Asn Pro Gly Gln Ala Asn Tyr Val Ala Ser Lys Ala Gly Leu Ile
145                 150                 155                 160

Gly Phe Thr Arg Ala Val Ala Lys Glu Tyr Ala Gln Arg Gly Ile Thr
                165                 170                 175

Val Asn Ala Val Ala Pro Gly Phe Ile Glu Thr Glu Met Thr Glu Arg
            180                 185                 190

Leu Pro Gln Glu Val Lys Glu Ala Tyr Leu Lys Gln Ile Pro Ala Gly
        195                 200                 205

Arg Phe Gly Arg Pro Glu Glu Val Ala Glu Val Ala Phe Leu Val
    210                 215                 220

Ser Glu Lys Ala Gly Tyr Ile Thr Gly Gln Thr Leu Cys Val Asp Gly
225                 230                 235                 240

Gly Leu Thr Pro His
                245

<210> SEQ ID NO 170
<211> LENGTH: 481
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Met Ala Arg Thr Gly Ala Glu Tyr Ile Glu Ala Leu Lys Thr Arg Pro
1               5                   10                  15

Pro Asn Leu Trp Tyr Lys Gly Glu Lys Val Glu Asp Pro Thr Thr His
                20                  25                  30

Pro Val Phe Arg Gly Ile Val Arg Thr Met Ala Ala Leu Tyr Asp Leu
            35                  40                  45
```

-continued

```
Gln His Asp Pro Arg Tyr Arg Glu Val Leu Thr Tyr Glu Glu Glu Gly
 50                  55                  60
Lys Arg His Gly Met Ser Phe Leu Ile Pro Lys Thr Lys Glu Asp Leu
 65                  70                  75                  80
Lys Arg Arg Gly Gln Ala Tyr Lys Leu Trp Ala Asp Gln Asn Leu Gly
                 85                  90                  95
Met Met Gly Arg Ser Pro Asp Tyr Leu Asn Ala Val Val Met Ala Tyr
                100                 105                 110
Ala Ala Ser Ala Asp Tyr Phe Gly Glu Phe Ala Glu Asn Val Arg Asn
                115                 120                 125
Tyr Tyr Arg Tyr Leu Arg Asp Gln Asp Leu Ala Thr Thr His Ala Leu
130                 135                 140
Thr Asn Pro Gln Val Asn Arg Ala Arg Pro Ser Gly Gln Pro Asp
145                 150                 155                 160
Pro Tyr Ile Pro Val Gly Val Val Lys Gln Thr Glu Lys Gly Ile Val
                165                 170                 175
Val Arg Gly Ala Arg Met Thr Ala Thr Phe Pro Leu Ala Asp Glu Val
                180                 185                 190
Leu Ile Phe Pro Ser Ile Leu Leu Gln Ala Gly Ser Glu Lys Tyr Ala
                195                 200                 205
Leu Ala Phe Ala Leu Pro Thr Ser Thr Pro Gly Leu His Phe Val Cys
210                 215                 220
Arg Glu Ala Leu Val Gly Gly Asp Ser Pro Phe Asp His Pro Leu Ser
225                 230                 235                 240
Ser Arg Val Glu Glu Met Asp Cys Leu Val Ile Phe Asp Asp Val Leu
                245                 250                 255
Val Pro Trp Glu Arg Val Phe Ile Leu Gly Asn Val Glu Leu Cys Asn
                260                 265                 270
Asn Ala Tyr Gly Ala Thr Gly Ala Leu Asn His Met Ala His Gln Val
                275                 280                 285
Val Ala Leu Lys Thr Ala Lys Thr Glu Ala Phe Leu Gly Val Ala Ala
                290                 295                 300
Leu Met Ala Glu Gly Ile Gly Ala Asp Val Tyr Gly His Val Gln Glu
305                 310                 315                 320
Lys Ile Ala Glu Ile Ile Val Tyr Leu Glu Ala Met Arg Ala Phe Trp
                325                 330                 335
Thr Arg Ala Glu Glu Ala Lys Glu Asn Ala Tyr Gly Leu Leu Val
                340                 345                 350
Pro Asp Arg Gly Ala Leu Asp Gly Ala Arg Asn Leu Tyr Pro Arg Leu
                355                 360                 365
Tyr Pro Arg Ile Arg Glu Ile Leu Glu Gln Ile Gly Ala Ser Gly Leu
370                 375                 380
Ile Thr Leu Pro Ser Glu Lys Asp Phe Lys Gly Pro Leu Gly Pro Phe
385                 390                 395                 400
Leu Glu Lys Phe Leu Gln Gly Ala Ala Leu Glu Ala Lys Glu Arg Val
                405                 410                 415
Ala Leu Phe Arg Leu Ala Trp Asp Met Thr Leu Ser Gly Phe Gly Ala
                420                 425                 430
Arg Gln Glu Leu Tyr Glu Arg Phe Phe Gly Asp Pro Val Arg Met
                435                 440                 445
Tyr Gln Thr Leu Tyr Asn Val Tyr Asn Lys Glu Pro Tyr Lys Glu Arg
450                 455                 460
Ile His Ala Phe Leu Lys Glu Ser Leu Lys Val Phe Glu Glu Val Gln
```

```
465                 470                 475                 480

Ala

<210> SEQ ID NO 171
<211> LENGTH: 319
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Met Lys Arg Ile Gly Val Leu Thr Ser Gly Gly Asp Ser Pro Gly Met
1               5                   10                  15

Asn Ala Ala Ile Arg Ser Val Val Arg Lys Ala Ile Tyr His Gly Val
            20                  25                  30

Glu Val Tyr Gly Val Tyr His Gly Tyr Ala Gly Leu Ile Ala Gly Asn
        35                  40                  45

Ile Lys Lys Leu Glu Val Gly Asp Val Gly Asp Ile Ile His Arg Gly
    50                  55                  60

Gly Thr Ile Leu Tyr Thr Ala Arg Cys Pro Glu Phe Lys Thr Glu Glu
65                  70                  75                  80

Gly Gln Lys Lys Gly Ile Glu Gln Leu Lys Lys His Gly Ile Gln Gly
                85                  90                  95

Leu Val Val Ile Gly Gly Asp Gly Ser Tyr Gln Gly Ala Lys Lys Leu
            100                 105                 110

Thr Glu His Gly Phe Pro Cys Val Gly Val Pro Gly Thr Ile Asp Asn
        115                 120                 125

Asp Ile Pro Gly Thr Asp Phe Thr Ile Gly Phe Asp Thr Ala Leu Asn
    130                 135                 140

Thr Val Ile Asp Ala Ile Asp Lys Ile Arg Asp Thr Ala Thr Ser His
145                 150                 155                 160

Glu Arg Thr Tyr Val Ile Glu Val Met Gly Arg His Ala Gly Asp Ile
                165                 170                 175

Ala Leu Trp Ser Gly Leu Ala Gly Gly Ala Glu Thr Ile Leu Ile Pro
            180                 185                 190

Glu Ala Asp Tyr Asp Met Asn Asp Val Ile Ala Arg Leu Lys Arg Gly
        195                 200                 205

His Glu Arg Gly Lys Lys His Ser Ile Ile Ile Val Ala Glu Gly Val
    210                 215                 220

Gly Ser Gly Val Asp Phe Gly Arg Gln Ile Gln Glu Ala Thr Gly Phe
225                 230                 235                 240

Glu Thr Arg Val Thr Val Leu Gly His Val Gln Arg Gly Gly Ser Pro
                245                 250                 255

Thr Ala Phe Asp Arg Val Leu Ala Ser Arg Leu Gly Ala Arg Ala Val
            260                 265                 270

Glu Leu Leu Leu Glu Gly Lys Gly Gly Arg Cys Val Gly Ile Gln Asn
        275                 280                 285

Asn Gln Leu Val Asp His Asp Ile Ala Glu Ala Leu Ala Asn Lys His
    290                 295                 300

Thr Ile Asp Gln Arg Met Tyr Ala Leu Ser Lys Glu Leu Ser Ile
305                 310                 315

<210> SEQ ID NO 172
<211> LENGTH: 449
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 172

| | | | | | | | | | | | | | | |
|---|---|---|---|---|---|---|---|---|---|---|---|---|---|---|
| Ser | Lys | Tyr | Val | Asp | Arg | Val | Ile | Ala | Glu | Val | Glu | Lys | Lys | Tyr | Ala |
| 1 | | | | 5 | | | | | 10 | | | | | 15 | |
| Asp | Glu | Pro | Glu | Phe | Val | Gln | Thr | Val | Glu | Glu | Val | Leu | Ser | Ser | Leu |
| | | | 20 | | | | | 25 | | | | | 30 | | |
| Gly | Pro | Val | Val | Asp | Ala | His | Pro | Glu | Tyr | Glu | Glu | Val | Ala | Leu | Leu |
| | | | 35 | | | | | 40 | | | | | 45 | | |
| Glu | Arg | Met | Val | Ile | Pro | Glu | Arg | Val | Ile | Glu | Phe | Arg | Val | Pro | Trp |
| | 50 | | | | | 55 | | | | | 60 | | | | |
| Glu | Asp | Asp | Asn | Gly | Lys | Val | His | Val | Asn | Thr | Gly | Tyr | Arg | Val | Gln |
| 65 | | | | | 70 | | | | | 75 | | | | | 80 |
| Phe | Asn | Gly | Ala | Ile | Gly | Pro | Tyr | Leu | Gly | Gly | Leu | Arg | Phe | Ala | Pro |
| | | | | 85 | | | | | 90 | | | | | 95 | |
| Ser | Val | Asn | Leu | Ser | Ile | Met | Lys | Phe | Leu | Gly | Phe | Glu | Gln | Ala | Phe |
| | | | 100 | | | | | 105 | | | | | 110 | | |
| Lys | Asp | Ser | Leu | Thr | Thr | Leu | Pro | Met | Gly | Gly | Ala | Lys | Gly | Gly | Ser |
| | | | 115 | | | | | 120 | | | | | 125 | | |
| Asp | Phe | Asp | Pro | Asn | Gly | Lys | Ser | Asp | Arg | Glu | Val | Met | Arg | Phe | Cys |
| 130 | | | | | 135 | | | | | 140 | | | | | |
| Gln | Ala | Phe | Met | Thr | Glu | Leu | Tyr | Arg | His | Ile | Gly | Pro | Asp | Ile | Asp |
| 145 | | | | | 150 | | | | | 155 | | | | | 160 |
| Val | Pro | Ala | Gly | Asp | Leu | Gly | Val | Gly | Ala | Arg | Glu | Ile | Gly | Tyr | Met |
| | | | | 165 | | | | | 170 | | | | | 175 | |
| Tyr | Gly | Gln | Tyr | Arg | Lys | Ile | Val | Gly | Gly | Phe | Tyr | Asn | Gly | Val | Leu |
| | | | 180 | | | | | 185 | | | | | 190 | | |
| Thr | Gly | Lys | Ala | Arg | Ser | Phe | Gly | Gly | Ser | Leu | Val | Arg | Pro | Glu | Ala |
| | | | 195 | | | | | 200 | | | | | 205 | | |
| Thr | Gly | Tyr | Gly | Ser | Val | Tyr | Tyr | Val | Glu | Ala | Val | Met | Lys | His | Glu |
| | 210 | | | | | 215 | | | | | 220 | | | | |
| Asn | Asp | Thr | Leu | Val | Gly | Lys | Thr | Val | Ala | Leu | Ala | Gly | Phe | Gly | Asn |
| 225 | | | | | 230 | | | | | 235 | | | | | 240 |
| Val | Ala | Trp | Gly | Ala | Ala | Lys | Lys | Leu | Ala | Glu | Leu | Gly | Ala | Lys | Ala |
| | | | | 245 | | | | | 250 | | | | | 255 | |
| Val | Thr | Leu | Ser | Gly | Pro | Asp | Gly | Tyr | Ile | Tyr | Asp | Pro | Glu | Gly | Ile |
| | | | 260 | | | | | 265 | | | | | 270 | | |
| Thr | Thr | Glu | Glu | Lys | Ile | Asn | Tyr | Met | Leu | Glu | Met | Arg | Ala | Ser | Gly |
| | | | 275 | | | | | 280 | | | | | 285 | | |
| Arg | Asn | Lys | Val | Gln | Asp | Tyr | Ala | Asp | Lys | Phe | Gly | Val | Gln | Phe | Phe |
| | 290 | | | | | 295 | | | | | 300 | | | | |
| Pro | Gly | Glu | Lys | Pro | Trp | Gly | Gln | Lys | Val | Asp | Ile | Ile | Met | Pro | Cys |
| 305 | | | | | 310 | | | | | 315 | | | | | 320 |
| Ala | Thr | Gln | Asn | Asp | Val | Asp | Leu | Glu | Gln | Ala | Lys | Lys | Ile | Val | Ala |
| | | | | 325 | | | | | 330 | | | | | 335 | |
| Asn | Asn | Val | Lys | Tyr | Tyr | Ile | Glu | Val | Ala | Asn | Met | Pro | Thr | Thr | Asn |
| | | | 340 | | | | | 345 | | | | | 350 | | |
| Glu | Ala | Leu | Arg | Phe | Leu | Met | Gln | Gln | Pro | Asn | Met | Val | Val | Ala | Pro |
| | | | 355 | | | | | 360 | | | | | 365 | | |
| Ser | Lys | Ala | Val | Asn | Ala | Gly | Gly | Val | Leu | Val | Gly | Phe | Glu | Met |
| | 370 | | | | | 375 | | | | | 380 | | | | |

```
Ser Gln Asn Ser Glu Arg Leu Ser Trp Thr Ala Glu Val Asp Ser
385                 390                 395                 400

Lys Leu His Gln Val Met Thr Asp Ile His Asp Gly Ser Ala Ala Ala
                405                 410                 415

Ala Glu Arg Tyr Gly Leu Gly Tyr Asn Leu Val Ala Gly Ala Asn Ile
            420                 425                 430

Val Gly Phe Gln Lys Ile Ala Asp Ala Met Met Ala Gln Gly Ile Ala
        435                 440                 445

Trp

<210> SEQ ID NO 173
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Ser Lys Tyr Val Asp Arg Val Ile Ala Glu Val Lys Lys Tyr Ala
1               5                   10                  15

Asp Glu Pro Glu Phe Val Gln Thr Val Glu Glu Val Leu Ser Ser Leu
            20                  25                  30

Gly Pro Val Val Asp Ala His Pro Glu Tyr Glu Glu Val Ala Leu Leu
        35                  40                  45

Glu Arg Met Val Ile Pro Glu Arg Val Ile Glu Phe Arg Val Pro Trp
    50                  55                  60

Glu Asp Asp Asn Gly Lys Val His Val Asn Thr Gly Tyr Arg Val Gln
65                  70                  75                  80

Phe Asn Gly Ala Ile Gly Pro Tyr Lys Gly Gly Leu Arg Phe Ala Pro
                85                  90                  95

Ser Val Asn Leu Ser Ile Met Lys Phe Leu Gly Phe Glu Gln Ala Phe
            100                 105                 110

Lys Asp Ser Leu Thr Thr Leu Pro Met Gly Gly Ala Lys Gly Gly Ser
        115                 120                 125

Asp Phe Asp Pro Asn Gly Lys Ser Asp Arg Glu Val Met Arg Phe Cys
130                 135                 140

Gln Ala Phe Met Thr Glu Leu Tyr Arg His Ile Gly Pro Asp Ile Asp
145                 150                 155                 160

Val Pro Ala Gly Asp Leu Gly Val Gly Ala Arg Glu Ile Gly Tyr Met
                165                 170                 175

Tyr Gly Gln Tyr Arg Lys Ile Val Gly Gly Phe Tyr Asn Gly Val Leu
            180                 185                 190

Thr Gly Lys Ala Arg Ser Phe Gly Gly Ser Leu Val Arg Pro Glu Ala
        195                 200                 205

Thr Gly Tyr Gly Ser Val Tyr Tyr Val Glu Ala Val Met Lys His Glu
    210                 215                 220

Asn Asp Thr Leu Val Gly Lys Thr Val Ala Leu Ala Gly Phe Gly Asn
225                 230                 235                 240

Val Ala Trp Gly Ala Ala Lys Lys Leu Ala Glu Leu Gly Ala Lys Ala
                245                 250                 255

Val Thr Leu Ser Gly Pro Asp Gly Tyr Ile Tyr Asp Pro Glu Gly Ile
            260                 265                 270

Thr Thr Glu Glu Lys Ile Asn Tyr Met Leu Glu Met Arg Ala Ser Gly
        275                 280                 285
```

```
Arg Asn Lys Val Gln Asp Tyr Ala Asp Lys Phe Gly Val Gln Phe Phe
    290                 295                 300

Pro Gly Glu Lys Pro Trp Gly Gln Lys Val Asp Ile Ile Met Pro Cys
305                 310                 315                 320

Ala Thr Gln Asn Asp Val Asp Leu Gln Ala Lys Lys Ile Val Ala
                325                 330                 335

Asn Asn Val Lys Tyr Tyr Ile Glu Val Ala Asn Met Pro Thr Thr Asn
                340                 345                 350

Glu Ala Leu Arg Phe Leu Met Gln Gln Pro Asn Met Val Ala Pro
            355                 360                 365

Ser Lys Ala Val Asn Ala Gly Val Leu Val Ser Gly Phe Glu Met
370                 375                 380

Ser Gln Asn Ser Glu Arg Leu Ser Trp Thr Ala Glu Val Asp Ser
385                 390                 395                 400

Lys Leu His Gln Val Met Thr Asp Ile His Asp Gly Ser Ala Ala Ala
                405                 410                 415

Ala Glu Arg Tyr Gly Leu Gly Tyr Asn Leu Val Ala Gly Ala Asn Ile
            420                 425                 430

Val Gly Phe Gln Lys Ile Ala Asp Ala Met Met Ala Gln Gly Ile Ala
            435                 440                 445

Trp

<210> SEQ ID NO 174
<211> LENGTH: 418
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Val Glu Gln Asp Pro Phe Glu Ile Ala Val Lys Gln Leu Glu Arg Ala
1               5                   10                  15

Ala Gln Tyr Met Asp Ile Ser Glu Glu Ala Leu Glu Phe Leu Lys Arg
            20                  25                  30

Pro Gln Arg Ile Val Glu Val Ser Ile Pro Val Glu Met Asp Asp Gly
        35                  40                  45

Ser Val Lys Val Phe Thr Gly Phe Arg Val Gln Tyr Asn Trp Ala Arg
    50                  55                  60

Gly Pro Thr Lys Gly Gly Ile Arg Trp His Pro Glu Glu Thr Leu Ser
65                  70                  75                  80

Thr Val Lys Ala Leu Ala Ala Trp Met Thr Trp Lys Thr Ala Val Met
                85                  90                  95

Asp Leu Pro Tyr Gly Gly Gly Lys Gly Gly Val Ile Cys Asn Pro Lys
            100                 105                 110

Glu Met Ser Asp Arg Glu Lys Glu Arg Leu Ala Arg Gly Tyr Val Arg
        115                 120                 125

Ala Ile Tyr Asp Val Ile Ser Pro Tyr Thr Asp Ile Pro Ala Pro Asp
    130                 135                 140

Val Tyr Thr Asn Pro Gln Ile Met Ala Trp Met Met Asp Glu Tyr Glu
145                 150                 155                 160

Thr Ile Ser Arg Arg Lys Asp Pro Ser Phe Gly Val Ile Thr Gly Lys
                165                 170                 175

Pro Pro Ser Val Gly Gly Ile Val Ala Arg Met Asp Ala Thr Ala Arg
            180                 185                 190
```

Gly Ala Ser Tyr Thr Val Arg Glu Ala Ala Lys Ala Leu Gly Met Asp
            195                 200                 205

Leu Lys Gly Lys Thr Ile Ala Ile Gln Gly Tyr Gly Asn Ala Gly Tyr
    210                 215                 220

Tyr Met Ala Lys Ile Met Ser Glu Glu Tyr Gly Met Lys Val Val Ala
225                 230                 235                 240

Val Ser Asp Thr Lys Gly Gly Ile Tyr Asn Pro Asp Gly Leu Asn Ala
            245                 250                 255

Asp Glu Val Leu Ala Trp Lys Lys Thr Gly Ser Val Lys Asp Phe
            260                 265                 270

Pro Gly Ala Thr Asn Ile Thr Asn Glu Glu Leu Leu Glu Leu Glu Val
            275                 280                 285

Asp Val Leu Ala Pro Ser Ala Ile Glu Glu Val Ile Thr Lys Lys Asn
            290                 295                 300

Ala Asp Asn Ile Lys Ala Lys Ile Val Ala Glu Leu Ala Asn Gly Pro
305                 310                 315                 320

Thr Thr Pro Glu Ala Asp Glu Ile Leu Tyr Glu Lys Gly Ile Leu Ile
            325                 330                 335

Ile Pro Asp Phe Leu Cys Asn Ala Gly Gly Val Thr Val Ser Tyr Phe
            340                 345                 350

Glu Trp Val Gln Asn Ile Thr Gly Asp Tyr Trp Thr Val Glu Glu Thr
            355                 360                 365

Arg Ala Lys Leu Asp Lys Lys Met Thr Lys Ala Phe Trp Asp Val Tyr
            370                 375                 380

Asn Thr His Lys Glu Lys Asn Ile Asn Met Arg Asp Ala Ala Tyr Val
385                 390                 395                 400

Val Ala Val Ser Arg Val Tyr Gln Ala Met Lys Asp Arg Gly Trp Ile
            405                 410                 415

Lys Lys

<210> SEQ ID NO 175
<211> LENGTH: 168
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Leu Arg Gly Phe Ile Ile Gly Arg Phe Gln Pro Phe His Lys Gly His
1               5                   10                  15

Leu Glu Val Ile Lys Lys Ile Ala Glu Val Asp Glu Ile Ile Ile
            20                  25                  30

Gly Ile Gly Ser Ala Gln Lys Ser His Thr Leu Glu Asn Pro Phe Thr
        35                  40                  45

Ala Gly Glu Arg Ile Leu Met Ile Thr Gln Ser Leu Lys Asp Tyr Asp
    50                  55                  60

Leu Thr Tyr Tyr Pro Ile Pro Ile Lys Asp Ile Glu Phe Asn Ser Ile
65                  70                  75                  80

Trp Val Ser Tyr Val Glu Ser Leu Thr Pro Pro Phe Asp Ile Val Tyr
            85                  90                  95

Ser Gly Asn Pro Leu Val Arg Val Leu Phe Glu Glu Arg Gly Tyr Glu
            100                 105                 110

Val Lys Arg Pro Glu Met Phe Asn Arg Lys Glu Tyr Ser Gly Thr Glu
        115                 120                 125

```
Ile Arg Arg Arg Met Leu Asn Gly Glu Lys Trp Glu His Leu Val Pro
        130                 135                 140

Lys Ala Val Val Asp Val Ile Lys Glu Ile Lys Gly Val Glu Arg Leu
145                 150                 155                 160

Arg Lys Leu Ala Gln Thr Asp Lys
                165

<210> SEQ ID NO 176
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Ala Ala Leu Ala Glu Ile Val Ala Gln Leu Asn Ile Tyr Gln Ser Gln
1               5                   10                  15

Val Glu Leu Ile Gln Gln Gln Met Glu Ala Val Arg Ala Thr Ile Ser
            20                  25                  30

Glu Leu Glu Ile Leu Glu Lys Thr Leu Ser Asp Ile Gln Gly Lys Asp
        35                  40                  45

Gly Ser Glu Thr Leu Val Pro Val Gly Ala Gly Ser Phe Ile Lys Ala
    50                  55                  60

Glu Leu Lys Asp Thr Ser Glu Val Ile Met Ser Val Gly Ala Gly Val
65                  70                  75                  80

Ala Ile Lys Lys Asn Phe Glu Asp Ala Met Glu Ser Ile Lys Ser Gln
                85                  90                  95

Lys Asn Glu Leu Glu Ser Thr Leu Gln Lys Met Gly Glu Asn Leu Arg
            100                 105                 110

Ala Ile Thr Asp Ile Met Met Lys Leu Ser Pro Gln Ala Glu Glu Leu
        115                 120                 125

Leu Ala Ala Val Ala
    130

<210> SEQ ID NO 177
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Asn Val Gln His Gln Leu Ala Gln Phe Gln Gln Leu Gln Gln Gln Ala
1               5                   10                  15

Gln Ala Ile Ser Val Gln Lys Ser Thr Val Glu Met Gln Ile Asn Glu
            20                  25                  30

Thr Gln Lys Ala Leu Glu Glu Leu Ser Arg Ala Ala Asp Asp Ala Glu
        35                  40                  45

Val Tyr Lys Ser Ser Gly Asn Ile Leu Ile Arg Val Ala Lys Asp Glu
    50                  55                  60

Leu Thr Glu Glu Leu Gln Glu Lys Leu Glu Thr Leu Gln Leu Arg Glu
65                  70                  75                  80

Lys Thr Ile Glu Arg Gln Glu Glu Arg Val Met Lys Lys Leu Gln Glu
                85                  90                  95

Met Gln Val Asn Ile Gln Glu Ala Met Lys Gly Ala Gly
            100                 105
```

<210> SEQ ID NO 178
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

```
Gln Asn Val Gln His Gln Leu Ala Gln Phe Gln Gln Leu Gln Gln Gln
1               5                   10                  15

Ala Gln Ala Ile Ser Val Gln Lys Gln Thr Val Glu Met Gln Ile Asn
            20                  25                  30

Glu Thr Gln Lys Ala Leu Glu Glu Leu Ser Arg Ala Ala Asp Asp Ala
        35                  40                  45

Glu Val Tyr Lys Ser Ser Gly Asn Ile Leu Ile Arg Val Ala Lys Asp
    50                  55                  60

Glu Leu Thr Glu Glu Leu Gln Glu Lys Leu Glu Thr Leu Gln Leu Arg
65                  70                  75                  80

Glu Lys Thr Ile Glu Arg Gln Glu Glu Arg Val Met Lys Lys Leu Gln
                85                  90                  95

Glu Met Gln Val Asn Ile Gln Glu Ala Met Lys
            100                 105
```

<210> SEQ ID NO 179
<211> LENGTH: 419
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

```
Val Glu Ala Asp Pro Tyr Glu Ile Val Ile Lys Gln Leu Glu Arg Ala
1               5                   10                  15

Ala Gln Tyr Met Glu Ile Ser Glu Glu Ala Leu Glu Phe Leu Lys Arg
            20                  25                  30

Pro Gln Arg Ile Val Glu Val Thr Ile Pro Val Glu Met Asp Asp Gly
        35                  40                  45

Ser Val Lys Val Phe Thr Gly Phe Arg Val Gln His Asn Trp Ala Arg
    50                  55                  60

Gly Pro Thr Lys Gly Gly Ile Arg Trp His Pro Glu Glu Thr Leu Ser
65                  70                  75                  80

Thr Val Lys Ala Leu Ala Ala Trp Met Thr Trp Lys Thr Ala Val Met
                85                  90                  95

Asp Leu Pro Tyr Gly Gly Gly Lys Gly Gly Ile Ile Val Asp Pro Lys
            100                 105                 110

Lys Leu Ser Asp Arg Glu Lys Glu Arg Leu Ala Arg Gly Tyr Ile Arg
        115                 120                 125

Ala Ile Tyr Asp Val Ile Ser Pro Tyr Glu Asp Ile Pro Ala Pro Asp
    130                 135                 140

Val Tyr Thr Asn Pro Gln Ile Met Ala Trp Met Met Asp Glu Tyr Glu
145                 150                 155                 160

Thr Ile Ser Arg Arg Lys Thr Pro Ala Phe Gly Ile Ile Thr Gly Lys
                165                 170                 175

Pro Leu Ser Ile Gly Gly Ser Leu Gly Arg Ile Glu Ala Thr Ala Arg
            180                 185                 190
```

```
Gly Ala Ser Tyr Thr Ile Arg Glu Ala Ala Lys Val Leu Gly Trp Asp
            195                 200                 205

Thr Leu Lys Gly Lys Thr Ile Ala Ile Gln Gly Tyr Gly Asn Ala Gly
        210                 215                 220

Tyr Tyr Leu Ala Lys Ile Met Ser Glu Asp Phe Gly Met Lys Val Val
225                 230                 235                 240

Ala Val Ser Asp Ser Lys Gly Ile Tyr Asn Pro Asp Gly Leu Asn
                245                 250                 255

Ala Asp Glu Val Leu Lys Trp Lys Asn Glu His Gly Ser Val Lys Asp
            260                 265                 270

Phe Pro Gly Ala Thr Asn Ile Thr Asn Glu Glu Leu Leu Glu Leu Glu
        275                 280                 285

Val Asp Val Leu Ala Pro Ala Ala Ile Glu Glu Val Ile Thr Lys Lys
    290                 295                 300

Asn Ala Asp Asn Ile Lys Ala Lys Ile Val Ala Glu Val Ala Asn Gly
305                 310                 315                 320

Pro Val Thr Pro Glu Ala Asp Glu Ile Leu Phe Glu Lys Gly Ile Leu
                325                 330                 335

Gln Ile Pro Asp Phe Leu Cys Asn Ala Gly Gly Val Thr Val Ser Tyr
            340                 345                 350

Phe Glu Trp Val Gln Asn Ile Thr Gly Tyr Tyr Trp Thr Ile Glu Glu
        355                 360                 365

Val Arg Glu Arg Leu Asp Lys Lys Met Thr Lys Ala Phe Tyr Asp Val
    370                 375                 380

Tyr Asn Ile Ala Lys Glu Lys Asn Ile His Met Arg Asp Ala Ala Tyr
385                 390                 395                 400

Val Val Ala Val Gln Arg Val Tyr Gln Ala Met Leu Asp Arg Gly Trp
                405                 410                 415

Val Lys His

<210> SEQ ID NO 180
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Met Asn Pro Val His Ile Leu Ala Lys Lys Gly Glu Val Ala Glu Arg
1               5                   10                  15

Val Leu Val Val Gly Asp Pro Gly Arg Ala Arg Leu Leu Ser Thr Leu
                20                  25                  30

Leu Gln Asn Pro Lys Leu Thr Asn Glu Asn Arg Gly Phe Leu Val Tyr
            35                  40                  45

Thr Gly Lys Tyr Asn Gly Glu Thr Val Ser Ile Ala Thr His Gly Ile
        50                  55                  60

Gly Gly Pro Ser Ile Ala Ile Val Leu Glu Glu Leu Ala Met Leu Gly
65                  70                  75                  80

Ala Asn Val Phe Ile Arg Tyr Gly Thr Thr Gly Ala Leu Val Pro Tyr
                85                  90                  95

Ile Asn Leu Gly Glu Tyr Ile Ile Val Thr Gly Ala Ser Tyr Asn Gln
            100                 105                 110

Gly Gly Leu Phe Tyr Gln Tyr Leu Arg Asp Asn Ala Cys Val Ala Ser
        115                 120                 125
```

```
Thr Pro Asp Phe Glu Leu Thr Asn Lys Leu Val Thr Ser Phe Ser Lys
    130                 135                 140

Arg Asn Leu Lys Tyr Tyr Val Gly Asn Val Phe Ser Ser Asp Ala Phe
145                 150                 155                 160

Tyr Ala Glu Asp Glu Glu Phe Val Lys Lys Trp Ser Ser Arg Gly Asn
                165                 170                 175

Ile Ala Val Glu Met Glu Cys Ala Thr Leu Phe Thr Leu Ser Lys Val
                180                 185                 190

Lys Gly Trp Lys Ser Ala Thr Val Leu Val Ser Asp Asn Leu Ala
                195                 200                 205

Lys Gly Gly Ile Trp Ile Thr Lys Glu Glu Leu Glu Lys Ser Val Met
    210                 215                 220

Asp Gly Ala Lys Ala Val Leu Asp Thr Leu Thr Ser
225                 230                 235

<210> SEQ ID NO 181
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Met Phe Lys His Thr Arg Lys Leu Gln Tyr Asn Ala Lys Pro Asp Arg
1               5                   10                  15

Ser Asp Pro Ile Met Ala Arg Arg Leu Gln Glu Ser Leu Gly Gly Gln
                20                  25                  30

Trp Gly Glu Thr Thr Gly Met Met Ser Tyr Leu Ser Gln Gly Trp Ala
            35                  40                  45

Ser Thr Gly Ala Glu Lys Tyr Lys Asp Leu Leu Leu Asp Thr Gly Thr
    50                  55                  60

Glu Glu Met Ala His Val Glu Met Ile Ser Thr Met Ile Gly Tyr Leu
65                  70                  75                  80

Leu Glu Asp Ala Pro Phe Gly Pro Glu Asp Leu Lys Arg Asp Pro Ser
                85                  90                  95

Leu Ala Thr Thr Met Ala Gly Met Asp Pro Glu His Ser Leu Val His
                100                 105                 110

Gly Leu Asn Ala Ser Leu Asn Asn Pro Asn Gly Ala Ala Trp Asn Ala
            115                 120                 125

Gly Tyr Val Thr Ser Ser Gly Asn Leu Val Ala Asp Met Arg Phe Asn
130                 135                 140

Val Val Arg Glu Ser Glu Ala Arg Leu Gln Val Ser Arg Leu Tyr Ser
145                 150                 155                 160

Met Thr Glu Asp Glu Gly Val Arg Asp Met Leu Lys Phe Leu Leu Ala
                165                 170                 175

Arg Glu Thr Gln His Gln Leu Gln Phe Met Lys Ala Gln Glu Glu Leu
                180                 185                 190

Glu Glu Lys Tyr Gly Ile Ile Val Pro Gly Asp Met Lys Glu Ile Glu
            195                 200                 205

His Ser Glu Phe Ser His Val Leu Met Asn Phe Ser Asp Gly Asp Gly
    210                 215                 220

Ser Lys Ala Phe Glu Gly Gln Val Ala Lys Asp Gly Glu Lys Phe Thr
225                 230                 235                 240

Tyr Gln Glu Asn Pro Glu Ala Met Gly Gly Ile Pro His Ile Lys Pro
                245                 250                 255
```

```
Gly Asp Pro Arg Leu His Asn His Gln Gly
            260                 265

<210> SEQ ID NO 182
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Met Ser Pro Ile His Val Arg Ala His Pro Gly Asp Val Ala Glu Arg
1               5                   10                  15

Val Leu Leu Pro Gly Asp Pro Gly Arg Ala Glu Trp Ile Ala Lys Thr
            20                  25                  30

Phe Leu Gln Asn Pro Arg Arg Tyr Asn Asp His Arg Gly Leu Trp Gly
        35                  40                  45

Tyr Thr Gly Leu Tyr Lys Gly Val Pro Val Ser Val Gln Thr Thr Gly
    50                  55                  60

Met Gly Thr Pro Ser Ala Ala Ile Val Val Glu Glu Leu Val Arg Leu
65                  70                  75                  80

Gly Ala Arg Val Leu Val Arg Val Gly Thr Ala Gly Ala Ala Ser Ser
                85                  90                  95

Asp Leu Ala Pro Gly Glu Leu Ile Val Ala Gln Gly Ala Val Pro Leu
            100                 105                 110

Asp Gly Thr Thr Arg Gln Tyr Leu Glu Gly Arg Pro Tyr Ala Pro Val
        115                 120                 125

Pro Asp Pro Glu Val Phe Arg Ala Leu Trp Arg Arg Ala Glu Ala Leu
    130                 135                 140

Gly Tyr Pro His Arg Val Gly Leu Val Ala Ser Glu Asp Ala Phe Tyr
145                 150                 155                 160

Ala Thr Thr Pro Glu Glu Ala Arg Ala Trp Ala Arg Tyr Gly Val Leu
                165                 170                 175

Ala Phe Glu Met Glu Ala Ser Ala Leu Phe Leu Leu Gly Arg Met Arg
            180                 185                 190

Gly Val Arg Thr Gly Ala Ile Leu Ala Val Ser Asn Arg Ile Gly Asp
        195                 200                 205

Pro Glu Leu Ala Pro Pro Glu Val Leu Gln Glu Gly Val Arg Arg Met
    210                 215                 220

Val Glu Val Ala Leu Glu Ala Val Leu Glu Val
225                 230                 235

<210> SEQ ID NO 183
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Met Ser Pro Ile His Val Arg Ala His Pro Gly Asp Val Ala Glu Arg
1               5                   10                  15

Val Leu Leu Pro Gly Asp Pro Gly Arg Ala Glu Trp Ile Ala Lys Thr
            20                  25                  30

Phe Leu Gln Asn Pro Arg Arg Tyr Asn Asp His Arg Gly Leu Trp Gly
        35                  40                  45
```

Tyr Thr Gly Leu Tyr Lys Gly Val Pro Val Ser Val Gln Thr Thr Gly
            50                  55                  60

Met Gly Thr Pro Ser Ala Ala Ile Val Val Glu Leu Val Arg Leu
 65                  70                  75                  80

Gly Ala Arg Val Leu Val Arg Val Gly Thr Ala Gly Ala Ala Ser Ser
                    85                  90                  95

Asp Leu Ala Pro Gly Glu Leu Ile Val Ala Gln Gly Ala Val Pro Leu
                100                 105                 110

Asp Gly Thr Thr Arg Gln Tyr Leu Glu Gly Arg Pro Tyr Ala Pro Val
                115                 120                 125

Pro Asp Pro Glu Val Phe Arg Ala Leu Trp Arg Arg Ala Glu Ala Leu
        130                 135                 140

Gly Tyr Pro His Arg Val Gly Leu Val Ala Ser Glu Asp Ala Phe Tyr
145                 150                 155                 160

Ala Thr Thr Pro Glu Glu Ala Arg Ala Trp Ala Arg Tyr Gly Val Leu
                165                 170                 175

Ala Phe Glu Met Glu Ala Ser Ala Leu Phe Leu Leu Gly Arg Met Arg
                180                 185                 190

Gly Val Arg Thr Gly Ala Ile Leu Ala Val Ser Asn Arg Ile Gly Asp
                195                 200                 205

Pro Glu Leu Ala Pro Pro Glu Val Leu Gln Glu Gly Val Arg Arg Met
        210                 215                 220

Val Glu Val Ala Leu Glu Ala Val Leu Glu Val
225                 230                 235

<210> SEQ ID NO 184
<211> LENGTH: 299
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Leu Lys His Ile Ile Ser Ala Tyr Asn Phe Ser Arg Asp Glu Leu Glu
 1               5                   10                  15

Asp Ile Phe Ala Leu Thr Asp Lys Tyr Ser Lys Asn Leu Asn Asp Thr
                20                  25                  30

Arg Lys Ile Leu Ser Gly Lys Thr Ile Ser Ile Ala Phe Phe Glu Pro
            35                  40                  45

Ser Thr Arg Thr Tyr Leu Ser Phe Gln Lys Ala Ile Ile Asn Leu Gly
    50                  55                  60

Gly Asp Val Ile Gly Phe Ser Gly Glu Glu Ser Thr Ser Val Ala Lys
 65                  70                  75                  80

Gly Glu Asn Leu Ala Asp Thr Ile Arg Met Leu Asn Asn Tyr Ser Asp
                85                  90                  95

Gly Ile Val Met Arg His Lys Tyr Asp Gly Ala Ser Arg Phe Ala Ser
                100                 105                 110

Glu Ile Ser Asp Ile Pro Val Ile Asn Ala Gly Asp Gly Lys His Glu
            115                 120                 125

His Pro Thr Gln Ala Val Ile Asp Ile Tyr Thr Ile Asn Lys His Phe
        130                 135                 140

Asn Thr Ile Asp Gly Leu Val Phe Ala Leu Leu Gly Asp Leu Lys Tyr
145                 150                 155                 160

Ala Arg Thr Val Asn Ser Leu Leu Arg Ile Leu Thr Arg Phe Arg Pro

```
                165                 170                 175
Lys Leu Val Tyr Leu Ile Ser Pro Gln Leu Arg Ala Arg Lys Glu
            180                 185                 190

Ile Leu Asp Glu Leu Asn Tyr Pro Val Lys Glu Val Glu Asn Pro Phe
            195                 200                 205

Glu Val Ile Asn Glu Val Asp Val Leu Tyr Val Thr Arg Ile Gln Lys
        210                 215                 220

Glu Arg Phe Val Asp Glu Met Glu Tyr Glu Lys Ile Lys Gly Ser Tyr
225                 230                 235                 240

Ile Val Ser Leu Asp Leu Ala Asn Lys Met Lys Lys Asp Ser Ile Ile
                245                 250                 255

Leu His Pro Leu Pro Arg Val Asn Glu Ile Asp Arg Lys Val Asp Lys
            260                 265                 270

Thr Thr Lys Ala Lys Tyr Phe Gly Gln Ala Ser Tyr Gly Val Pro Val
        275                 280                 285

Arg Met Ser Ile Leu Thr Lys Ile Tyr Gly Glu
        290                 295
```

<210> SEQ ID NO 185
<211> LENGTH: 168
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

```
Met Glu Phe Met Met Glu Ile Gln Gly Asn Arg Lys Glu Leu Met Val
1               5                   10                  15

Ser Lys Ile Lys Asn Gly Thr Val Ile Asp His Ile Pro Ala Gly Arg
            20                  25                  30

Ala Phe Ala Val Leu Asn Val Leu Gly Ile Lys Gly His Glu Gly Phe
        35                  40                  45

Arg Ile Ala Leu Val Ile Asn Val Asp Ser Lys Lys Met Gly Lys Lys
    50                  55                  60

Asp Ile Val Lys Ile Glu Asp Lys Glu Ile Ser Asp Thr Glu Ala Asn
65                  70                  75                  80

Leu Ile Thr Leu Ile Ala Pro Thr Ala Thr Ile Asn Ile Val Arg Glu
                85                  90                  95

Tyr Glu Val Val Lys Lys Thr Lys Leu Glu Val Pro Lys Val Val Lys
            100                 105                 110

Gly Ile Leu Lys Cys Pro Asn Pro Tyr Cys Ile Thr Ser Asn Asp Val
        115                 120                 125

Glu Ala Ile Pro Thr Phe Lys Thr Leu Thr Glu Lys Pro Leu Lys Met
    130                 135                 140

Arg Cys Glu Tyr Cys Glu Thr Ile Ile Asp Glu Asn Glu Ile Met Ser
145                 150                 155                 160

Gln Ile Leu Gly Ala Asn Asn Lys
                165
```

<210> SEQ ID NO 186
<211> LENGTH: 299
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 186

Leu Lys His Ile Ile Ser Ala Tyr Asn Phe Ser Arg Asp Glu Leu Glu
1               5                   10                  15

Asp Ile Phe Ala Leu Thr Asp Lys Tyr Ser Lys Asn Leu Asn Asp Thr
            20                  25                  30

Arg Lys Ile Leu Ser Gly Lys Thr Ile Ser Ile Ala Phe Phe Glu Pro
        35                  40                  45

Ser Thr Arg Thr Tyr Leu Ser Phe Gln Lys Ala Ile Ile Asn Leu Gly
    50                  55                  60

Gly Asp Val Ile Gly Phe Ser Gly Glu Glu Ser Thr Ser Val Ala Lys
65                  70                  75                  80

Gly Glu Asn Leu Ala Asp Thr Ile Arg Met Leu Asn Asn Tyr Ser Asp
                85                  90                  95

Gly Ile Val Met Arg His Lys Tyr Asp Gly Ala Ser Arg Phe Ala Ser
            100                 105                 110

Glu Ile Ser Asp Ile Pro Val Ile Asn Ala Gly Asp Gly Lys His Glu
        115                 120                 125

His Pro Thr Gln Ala Val Ile Asp Ile Tyr Thr Ile Asn Lys His Phe
    130                 135                 140

Asn Thr Ile Asp Gly Leu Val Phe Ala Leu Leu Gly Asp Leu Lys Tyr
145                 150                 155                 160

Ala Arg Thr Val Asn Ser Leu Leu Arg Ile Leu Thr Arg Phe Arg Pro
                165                 170                 175

Lys Leu Val Tyr Leu Ile Ser Pro Gln Leu Leu Arg Ala Arg Lys Glu
            180                 185                 190

Ile Leu Asp Glu Leu Asn Tyr Pro Val Lys Glu Val Glu Asn Pro Phe
        195                 200                 205

Glu Val Ile Asn Glu Val Asp Val Leu Tyr Val Thr Arg Ile Gln Lys
    210                 215                 220

Glu Arg Phe Val Asp Glu Met Glu Tyr Glu Lys Ile Lys Gly Ser Tyr
225                 230                 235                 240

Ile Val Ser Leu Asp Leu Ala Asn Lys Met Lys Lys Asp Ser Ile Ile
                245                 250                 255

Leu His Pro Leu Pro Arg Val Asn Glu Ile Asp Arg Lys Val Asp Lys
            260                 265                 270

Thr Thr Lys Ala Lys Tyr Phe Glu Gln Ala Ser Tyr Gly Val Pro Val
        275                 280                 285

Arg Met Ser Ile Leu Thr Lys Ile Tyr Gly Glu
    290                 295

<210> SEQ ID NO 187
<211> LENGTH: 206
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Met Gly Ser Ser His His His His His His Ser Ser Gly Leu Val Pro
1               5                   10                  15

Arg Gly Ser His Met Glu Lys Lys Ile Cys Tyr Phe Glu Glu Pro Gly
            20                  25                  30

Lys Glu Asn Thr Glu Arg Val Leu Glu Leu Val Gly Gly Arg Ala Asp
        35                  40                  45
```

```
Gln Leu Gly Ile Arg Asn Phe Val Val Ala Ser Val Ser Gly Glu Thr
 50                  55                  60

Ala Leu Arg Leu Ser Glu Met Val Glu Gly Asn Ile Val Ser Val Thr
 65                  70                  75                  80

His His Ala Gly Phe Arg Glu Lys Gly Gln Leu Glu Leu Glu Asp Glu
                 85                  90                  95

Ala Arg Asp Ala Leu Leu Glu Arg Gly Val Asn Val Tyr Ala Gly Ser
            100                 105                 110

His Ala Leu Ser Gly Val Gly Arg Gly Ile Ser Asn Arg Phe Gly Gly
        115                 120                 125

Val Thr Pro Val Glu Ile Met Ala Glu Thr Leu Arg Met Val Ser Gln
130                 135                 140

Gly Phe Lys Val Cys Val Glu Ile Ala Ile Met Ala Ala Asp Ala Gly
145                 150                 155                 160

Leu Ile Pro Val Asp Glu Val Ile Ala Ile Gly Gly Thr Ala Trp
                165                 170                 175

Gly Ala Asp Thr Ala Leu Val Leu Thr Pro Ala His Met Asn Ser Val
            180                 185                 190

Phe Asp Leu Arg Ile His Glu Val Ile Ala Met Pro Arg Pro
        195                 200                 205

<210> SEQ ID NO 188
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Met Leu Asp Leu Leu Val Val Ala Pro His Pro Asp Asp Gly Glu Leu
  1               5                  10                  15

Gly Cys Gly Gly Thr Leu Ala Arg Ala Lys Ala Glu Gly Leu Ser Thr
                 20                  25                  30

Gly Ile Leu Asp Leu Thr Arg Gly Glu Met Gly Ser Lys Gly Thr Pro
             35                  40                  45

Glu Glu Arg Glu Lys Glu Val Ala Glu Ala Ser Arg Ile Leu Gly Leu
 50                  55                  60

Asp Phe Arg Gly Asn Leu Gly Phe Pro Asp Gly Gly Leu Ala Asp Val
 65                  70                  75                  80

Pro Glu Gln Arg Leu Lys Leu Ala Gln Ala Leu Arg Arg Leu Arg Pro
                 85                  90                  95

Arg Val Val Phe Ala Pro Leu Glu Ala Asp Arg His Pro Asp His Thr
            100                 105                 110

Ala Ala Ser Arg Leu Ala Val Ala Ala Val His Leu Ala Gly Leu Arg
        115                 120                 125

Lys Ala Pro Leu Glu Gly Glu Pro Phe Arg Val Glu Arg Leu Phe Phe
130                 135                 140

Tyr Pro Gly Asn His Pro Phe Ala Pro Ser Phe Leu Val Lys Ile Ser
145                 150                 155                 160

Ala Phe Ile Asp Gln Trp Glu Ala Val Leu Ala Tyr Arg Ser Gln
                165                 170                 175

Phe Thr Gly Glu Ala Ala Ser Glu Thr Val Gly Pro Lys Gly Val Glu
            180                 185                 190

Ala Arg Lys Ala Met Arg Arg Tyr Trp Gly Asn Tyr Leu Gly Val Asp
        195                 200                 205
```

Tyr Ala Glu Pro Phe Val Ser Pro Leu Pro Val Leu Tyr Val Pro Trp
            210                 215                 220

Ser Arg Ala
225

<210> SEQ ID NO 189
<211> LENGTH: 195
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

His His His His His Ser Ser Gly Leu Val Pro Arg Gly Ser His
1               5                   10                  15

Met Met Asn Pro Phe His Asp Leu Glu Pro Gly Pro Asn Val Pro Glu
            20                  25                  30

Val Val Tyr Ala Leu Ile Glu Ile Pro Lys Gly Ser Arg Asn Lys Tyr
        35                  40                  45

Glu Leu Asp Lys Glu Thr Gly Leu Leu Lys Leu Asp Arg Val Leu Tyr
    50                  55                  60

Thr Pro Phe His Tyr Pro Val Asp Tyr Gly Ile Ile Pro Arg Thr Trp
65                  70                  75                  80

Tyr Glu Asp Gly Asp Pro Phe Asp Ile Met Val Ile Met Arg Glu Pro
                85                  90                  95

Thr Tyr Pro Leu Thr Ile Ile Glu Ala Arg Pro Ile Gly Leu Phe Lys
            100                 105                 110

Met Ile Asp Ser Gly Asp Lys Asp Tyr Lys Val Leu Ala Val Pro Val
        115                 120                 125

Glu Asp Pro Tyr Phe Lys Asp Trp Lys Asp Ile Ser Asp Val Pro Lys
    130                 135                 140

Ala Phe Leu Asp Glu Ile Ala His Phe Phe Lys Arg Tyr Lys Glu Leu
145                 150                 155                 160

Glu Gly Lys Glu Ile Ile Val Glu Gly Trp Glu Gly Ala Glu Ala Ala
                165                 170                 175

Lys Arg Glu Ile Leu Arg Ala Ile Glu Met Tyr Lys Glu Lys Phe Gly
            180                 185                 190

Lys Lys Glu
        195

<210> SEQ ID NO 190
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Met Val Gln Val Glu Lys Gly His Val Ala Val Val Phe Leu Asn Asp
1               5                   10                  15

Pro Glu Arg Arg Asn Pro Leu Ser Pro Glu Met Ala Leu Ser Leu Leu
            20                  25                  30

Gln Ala Leu Asp Asp Leu Glu Ala Asp Pro Gly Val Arg Ala Val Val
        35                  40                  45

Leu Thr Gly Arg Gly Lys Ala Phe Ser Ala Gly Ala Asp Leu Ala Phe
    50                  55                  60

Leu Glu Arg Val Thr Glu Leu Gly Ala Glu Glu Asn Tyr Arg His Ser
65                  70                  75                  80

Leu Ser Leu Met Arg Leu Phe His Arg Val Tyr Thr Tyr Pro Lys Pro
                85                  90                  95

Thr Val Ala Ala Val Asn Gly Pro Ala Val Ala Gly Ala Gly Leu
            100                 105                 110

Ala Leu Ala Cys Asp Leu Val Val Met Asp Glu Glu Ala Arg Leu Gly
            115                 120                 125

Tyr Thr Glu Val Lys Ile Gly Phe Val Ala Ala Leu Val Ser Val Ile
        130                 135                 140

Leu Val Arg Ala Val Gly Glu Lys Ala Ala Lys Asp Leu Leu Leu Thr
145                 150                 155                 160

Gly Arg Leu Val Glu Ala Arg Glu Ala Lys Ala Leu Gly Leu Val Asn
                165                 170                 175

Arg Ile Ala Pro Pro Gly Lys Ala Leu Glu Glu Ala Lys Ala Leu Ala
            180                 185                 190

Glu Glu Val Ala Lys Asn Ala Pro Thr Ser Leu Arg Leu Thr Lys Glu
        195                 200                 205

Leu Leu Leu Ala Leu Pro Gly Met Gly Leu Glu Asp Gly Phe Arg Leu
210                 215                 220

Ala Ala Leu Ala Asn Ala Trp Val Arg Glu Thr Gly Asp Leu Ala Glu
225                 230                 235                 240

Gly Ile Arg Ala Phe Phe Glu Lys Arg Pro Pro Arg Phe
            245                 250

<210> SEQ ID NO 191
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Met Leu Glu Val Val Thr Ala Gly Glu Pro Leu Val Ala Leu Val Pro
1               5                   10                  15

Gln Glu Pro Gly His Leu Arg Gly Lys Arg Leu Leu Glu Val Tyr Val
            20                  25                  30

Gly Gly Ala Glu Val Asn Val Ala Val Ala Leu Ala Arg Leu Gly Val
        35                  40                  45

Lys Val Gly Phe Val Gly Arg Val Gly Glu Asp Glu Leu Gly Ala Met
    50                  55                  60

Val Glu Glu Arg Leu Arg Ala Glu Gly Val Asp Leu Thr His Phe Arg
65                  70                  75                  80

Arg Ala Pro Gly Phe Thr Gly Leu Tyr Leu Arg Glu Tyr Leu Pro Leu
                85                  90                  95

Gly Gln Gly Arg Val Phe Tyr Tyr Arg Lys Gly Ser Ala Gly Ser Ala
            100                 105                 110

Leu Ala Pro Gly Ala Phe Asp Pro Asp Tyr Leu Glu Gly Val Arg Phe
        115                 120                 125

Leu His Leu Ser Gly Ile Thr Pro Ala Leu Ser Pro Glu Ala Arg Ala
    130                 135                 140

Phe Ser Leu Trp Ala Met Glu Glu Ala Lys Arg Arg Gly Val Arg Val
145                 150                 155                 160

Ser Leu Asp Val Asn Tyr Arg Gln Thr Leu Trp Ser Pro Glu Glu Ala

```
                165                 170                 175
Arg Gly Phe Leu Glu Arg Ala Leu Pro Gly Val Asp Leu Leu Phe Leu
            180                 185                 190

Ser Glu Glu Glu Ala Glu Leu Leu Phe Gly Arg Val Glu Glu Ala Leu
        195                 200                 205

Arg Ala Leu Ser Ala Pro Glu Val Val Leu Lys Arg Gly Ala Lys Gly
    210                 215                 220

Ala Trp Ala Phe Val Asp Gly Arg Val Glu Gly Ser Ala Phe Ala
225                 230                 235                 240

Val Glu Ala Val Asp Pro Val Gly Ala Gly Asp Ala Phe Ala Ala Gly
                245                 250                 255

Tyr Leu Ala Gly Ala Val Trp Gly Leu Pro Val Glu Glu Arg Leu Arg
                260                 265                 270

Leu Ala Asn Leu Leu Gly Ala Ser Val Ala Ala Ser Arg Gly Asp His
            275                 280                 285

Glu Gly Ala Pro Tyr Arg Glu Asp Leu Glu Val Leu Leu Lys Ala Thr
        290                 295                 300

Gln Thr Phe Met Arg
305

<210> SEQ ID NO 192
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Met Leu Glu Val Val Thr Ala Gly Glu Pro Leu Val Ala Leu Val Pro
1               5                   10                  15

Gln Glu Pro Gly His Leu Arg Gly Lys Arg Leu Leu Glu Val Tyr Val
            20                  25                  30

Gly Gly Ala Glu Val Asn Val Ala Leu Ala Arg Leu Gly Val
        35                  40                  45

Lys Val Gly Phe Val Gly Arg Val Gly Glu Asp Glu Leu Gly Ala Met
    50                  55                  60

Val Glu Glu Arg Leu Arg Ala Glu Gly Val Asp Leu Thr His Phe Arg
65                  70                  75                  80

Arg Ala Pro Gly Phe Thr Gly Leu Tyr Leu Arg Glu Tyr Leu Pro Leu
                85                  90                  95

Gly Gln Gly Arg Val Phe Tyr Tyr Arg Lys Gly Ser Ala Gly Ser Ala
            100                 105                 110

Leu Ala Pro Gly Ala Phe Asp Pro Asp Tyr Leu Glu Gly Val Arg Phe
        115                 120                 125

Leu His Leu Ser Gly Ile Thr Pro Ala Leu Ser Pro Glu Ala Arg Ala
    130                 135                 140

Phe Ser Leu Trp Ala Met Glu Glu Ala Lys Arg Arg Gly Val Arg Val
145                 150                 155                 160

Ser Leu Asp Val Asn Tyr Arg Gln Thr Leu Trp Ser Pro Glu Glu Ala
                165                 170                 175

Arg Gly Phe Leu Glu Arg Ala Leu Pro Gly Val Asp Leu Leu Phe Leu
            180                 185                 190

Ser Glu Glu Glu Ala Glu Leu Leu Phe Gly Arg Val Glu Glu Ala Leu
        195                 200                 205
```

```
Arg Ala Leu Ser Ala Pro Glu Val Val Leu Lys Arg Gly Ala Lys Gly
    210                 215                 220

Ala Trp Ala Phe Val Asp Gly Arg Val Glu Gly Ser Ala Phe Ala
225                 230                 235                 240

Val Glu Ala Val Asp Pro Val Gly Ala Gly Asp Ala Phe Ala Ala Gly
                245                 250                 255

Tyr Leu Ala Gly Ala Val Trp Gly Leu Pro Val Glu Glu Arg Leu Arg
                260                 265                 270

Leu Ala Asn Leu Leu Gly Ala Ser Val Ala Ala Ser Arg Gly Asp His
            275                 280                 285

Glu Gly Ala Pro Tyr Arg Glu Asp Leu Glu Val Leu Leu Lys Ala Thr
290                 295                 300

Gln Thr Phe Met Arg
305

<210> SEQ ID NO 193
<211> LENGTH: 421
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 193

Met Glu Arg Thr Gly Phe Leu Glu Tyr Val Leu Asn Tyr Val Lys Lys
1               5                   10                  15

Gly Val Glu Leu Gly Gly Phe Pro Glu Asp Phe Tyr Lys Ile Leu Ser
                20                  25                  30

Arg Pro Arg Arg Val Leu Ile Val Asn Ile Pro Val Arg Leu Asp Gly
            35                  40                  45

Gly Gly Phe Glu Val Phe Glu Gly Tyr Arg Val Gln His Cys Asp Val
        50                  55                  60

Leu Gly Pro Tyr Lys Gly Gly Val Arg Phe His Pro Glu Val Thr Leu
65                  70                  75                  80

Ala Asp Asp Val Ala Leu Ala Ile Leu Met Thr Leu Lys Asn Ser Leu
                85                  90                  95

Ala Gly Leu Pro Tyr Gly Gly Ala Lys Gly Ala Val Arg Val Asp Pro
            100                 105                 110

Lys Lys Leu Ser Gln Arg Glu Leu Glu Glu Leu Ser Arg Gly Tyr Ala
        115                 120                 125

Arg Ala Ile Ala Pro Leu Ile Gly Asp Val Val Asp Ile Pro Ala Pro
130                 135                 140

Asp Val Gly Thr Asn Ala Gln Ile Met Ala Trp Met Val Asp Glu Tyr
145                 150                 155                 160

Ser Lys Ile Lys Gly Tyr Asn Val Pro Gly Val Phe Thr Ser Lys Pro
                165                 170                 175

Pro Glu Leu Trp Gly Asn Pro Val Arg Glu Tyr Ala Thr Gly Phe Gly
            180                 185                 190

Val Ala Val Ala Thr Arg Glu Met Ala Lys Lys Leu Trp Gly Gly Ile
        195                 200                 205

Glu Gly Lys Thr Val Ala Ile Gln Gly Met Gly Asn Val Gly Arg Trp
210                 215                 220

Thr Ala Tyr Trp Leu Glu Lys Met Gly Ala Lys Val Ile Ala Val Ser
225                 230                 235                 240

Asp Ile Asn Gly Val Ala Tyr Arg Lys Glu Gly Leu Asn Val Glu Leu
                245                 250                 255
```

```
Ile Gln Lys Asn Lys Gly Leu Thr Gly Pro Ala Leu Val Glu Leu Phe
            260                 265                 270

Thr Thr Lys Asp Asn Ala Glu Phe Val Lys Asn Pro Asp Ala Ile Phe
        275                 280                 285

Lys Leu Asp Val Asp Ile Phe Val Pro Ala Ala Ile Glu Asn Val Ile
    290                 295                 300

Arg Gly Asp Asn Ala Gly Leu Val Lys Ala Arg Leu Val Val Glu Gly
305                 310                 315                 320

Ala Asn Gly Pro Thr Thr Pro Glu Ala Glu Arg Ile Leu Tyr Glu Arg
                325                 330                 335

Gly Val Val Val Pro Asp Ile Leu Ala Asn Ala Gly Gly Val Ile
            340                 345                 350

Met Ser Tyr Leu Glu Trp Val Glu Asn Leu Gln Trp Tyr Ile Trp Asp
            355                 360                 365

Glu Glu Glu Thr Arg Lys Arg Leu Glu Asn Ile Met Val Asn Asn Val
        370                 375                 380

Glu Arg Val Tyr Lys Arg Trp Gln Arg Gly Lys Gly Trp Thr Met Arg
385                 390                 395                 400

Asp Ala Ala Ile Val Thr Ala Leu Glu Arg Ile Tyr Asn Ala Met Lys
                405                 410                 415

Ile Arg Gly Trp Ile
            420

<210> SEQ ID NO 194
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Met Leu Glu Val Val Thr Ala Gly Glu Pro Leu Val Ala Leu Val Pro
1               5                   10                  15

Gln Glu Pro Gly His Leu Arg Gly Lys Arg Leu Leu Glu Val Tyr Val
            20                  25                  30

Gly Gly Ala Glu Val Asn Val Ala Val Ala Leu Ala Arg Leu Gly Val
        35                  40                  45

Lys Val Gly Phe Val Gly Arg Val Gly Glu Asp Glu Leu Gly Ala Met
    50                  55                  60

Val Glu Glu Arg Leu Arg Ala Glu Gly Val Asp Leu Thr His Phe Arg
65                  70                  75                  80

Arg Ala Pro Gly Phe Thr Gly Leu Tyr Leu Arg Glu Tyr Leu Pro Leu
                85                  90                  95

Gly Gln Gly Arg Val Phe Tyr Tyr Arg Lys Gly Ser Ala Gly Ser Ala
            100                 105                 110

Leu Ala Pro Gly Ala Phe Asp Pro Asp Tyr Leu Glu Gly Val Arg Phe
        115                 120                 125

Leu His Leu Ser Gly Ile Thr Pro Ala Leu Ser Pro Glu Ala Arg Ala
    130                 135                 140

Phe Ser Leu Trp Ala Met Glu Glu Ala Lys Arg Arg Gly Val Arg Val
145                 150                 155                 160

Ser Leu Asp Val Asn Tyr Arg Gln Thr Leu Trp Ser Pro Glu Glu Ala
                165                 170                 175

Arg Gly Phe Leu Glu Arg Ala Leu Pro Gly Val Asp Leu Leu Phe Leu
            180                 185                 190
```

-continued

Ser Glu Glu Glu Ala Glu Leu Leu Phe Gly Arg Val Glu Ala Leu
    195                 200                 205

Arg Ala Leu Ser Ala Pro Glu Val Val Leu Lys Arg Gly Ala Lys Gly
    210                 215                 220

Ala Trp Ala Phe Val Asp Gly Arg Val Glu Gly Ser Ala Phe Ala
225                 230                 235                 240

Val Glu Ala Val Asp Pro Val Gly Ala Gly Asp Ala Phe Ala Ala Gly
                245                 250                 255

Tyr Leu Ala Gly Ala Val Trp Gly Leu Pro Val Glu Glu Arg Leu Arg
            260                 265                 270

Leu Ala Asn Leu Leu Gly Ala Ser Val Ala Ala Ser Arg Gly Asp His
        275                 280                 285

Glu Gly Ala Pro Tyr Arg Glu Asp Leu Glu Val Leu Leu Lys Ala Thr
    290                 295                 300

Gln Thr Phe Met Arg
305

<210> SEQ ID NO 195
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Met Glu Arg Thr Phe Val Met Ile Lys Pro Asp Gly Val Arg Arg Gly
1               5                   10                  15

Leu Val Gly Glu Ile Leu Ala Arg Phe Glu Arg Lys Gly Phe Arg Ile
            20                  25                  30

Ala Ala Leu Lys Leu Met Gln Ile Ser Gln Glu Leu Ala Glu Arg His
        35                  40                  45

Tyr Ala Glu His Arg Glu Lys Pro Phe Phe Pro Gly Leu Val Arg Phe
    50                  55                  60

Ile Thr Ser Gly Pro Val Val Ala Met Val Leu Glu Gly Pro Gly Val
65                  70                  75                  80

Val Ala Glu Val Arg Lys Met Met Gly Ala Thr His Pro Lys Asp Ala
                85                  90                  95

Leu Pro Gly Thr Ile Arg Gly Asp Phe Ala Thr Thr Ile Asp Glu Asn
            100                 105                 110

Val Ile His Gly Ser Ala Thr Leu Glu Asp Ala Gln Arg Glu Ile Ala
        115                 120                 125

Leu Phe Phe Arg Pro Glu Glu Leu Leu
    130                 135

<210> SEQ ID NO 196
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Met Leu Ala Ser Leu Glu Ala Arg Tyr Pro Gly Leu Ala Phe Ala Trp
1               5                   10                  15

Pro Arg Pro Gly Val Leu Glu Ile Thr Phe Arg Gly Glu Lys Leu Asn
            20                  25                  30

```
Ala Met Pro Pro Ala Leu His Arg Gly Leu Ala Arg Val Trp Arg Asp
        35                  40                  45

Leu Glu Ala Val Glu Gly Val Arg Ala Val Leu Leu Arg Gly Glu Gly
 50                  55                  60

Gly Val Phe Ser Ala Gly Gly Ser Phe Gly Leu Ile Glu Glu Met Arg
 65                  70                  75                  80

Ala Ser His Glu Ala Leu Leu Arg Val Phe Trp Glu Ala Arg Asp Leu
                 85                  90                  95

Val Leu Gly Pro Leu Asn Phe Pro Arg Pro Val Val Ala Ala Val Glu
            100                 105                 110

Lys Val Ala Val Gly Ala Gly Leu Ala Leu Ala Leu Ala Ala Asp Ile
        115                 120                 125

Ala Val Val Gly Lys Gly Thr Arg Leu Leu Asp Gly His Leu Arg Leu
130                 135                 140

Gly Val Ala Ala Gly Asp His Ala Val Leu Leu Trp Pro Leu Leu Val
145                 150                 155                 160

Gly Met Ala Lys Ala Lys Tyr His Leu Leu Leu Asn Glu Pro Leu Thr
                165                 170                 175

Gly Glu Glu Ala Glu Arg Leu Gly Leu Val Ala Leu Ala Val Glu Asp
            180                 185                 190

Glu Lys Val Tyr Glu Lys Ala Leu Glu Val Ala Glu Arg Leu Ala Gln
        195                 200                 205

Gly Pro Lys Glu Ala Leu His His Thr Lys His Ala Leu Asn His Trp
210                 215                 220

Tyr Arg Ser Phe Leu Pro His Phe Glu Leu Ser Leu Ala Leu Glu Phe
225                 230                 235                 240

Leu Gly Phe Ser Gly Lys Glu Leu Glu Glu Gly Leu Lys Ala Leu Lys
                245                 250                 255

Glu Lys Arg Pro Pro Glu Phe Pro
            260

<210> SEQ ID NO 197
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Met Tyr Glu Leu Tyr Thr Leu Leu Ala Glu Tyr Tyr Asp Thr Ile Tyr
 1               5                  10                  15

Arg Arg Arg Ile Glu Arg Val Lys Ala Glu Ile Asp Phe Val Glu Glu
             20                  25                  30

Ile Phe Lys Glu Asp Ala Lys Arg Glu Val Arg Arg Val Leu Asp Leu
         35                  40                  45

Ala Cys Gly Thr Gly Ile Pro Thr Leu Glu Leu Ala Glu Arg Gly Tyr
     50                  55                  60

Glu Val Val Gly Leu Asp Leu His Glu Met Leu Arg Val Ala Arg
 65                  70                  75                  80

Arg Lys Ala Lys Glu Arg Asn Leu Lys Ile Glu Phe Leu Gln Gly Asp
                 85                  90                  95

Val Leu Glu Ile Ala Phe Lys Asn Glu Phe Asp Ala Val Thr Met Phe
            100                 105                 110

Phe Ser Thr Ile Met Tyr Phe Asp Glu Glu Asp Leu Arg Lys Leu Phe
```

```
            115                 120                 125
Ser Lys Val Ala Glu Ala Leu Lys Pro Gly Gly Val Phe Ile Thr Asp
    130                 135                 140

Phe Pro Cys Trp Phe Tyr Gly Gly Arg Asp Gly Pro Val Val Trp Asn
145                 150                 155                 160

Glu Gln Lys Gly Glu Lys Leu Val Ile Met Asp Trp Arg Glu Val
                165                 170                 175

Glu Pro Ala Val Gln Lys Leu Arg Phe Lys Arg Leu Val Gln Ile Leu
                180                 185                 190

Arg Pro Asn Gly Glu Val Lys Ala Phe Leu Val Asp Asp Glu Leu Asn
            195                 200                 205

Ile Tyr Thr Pro Arg Glu Val Arg Leu Leu Ala Glu Lys Tyr Phe Glu
        210                 215                 220

Lys Val Lys Ile Tyr Gly Asn Leu Lys Arg Glu Leu Ser Pro Asn Asp
225                 230                 235                 240

Met Arg Tyr Trp Ile Val Gly Ile Ala Lys Ser Phe
                245                 250

<210> SEQ ID NO 198
<211> LENGTH: 522
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Ala Met Tyr Glu Lys Pro Pro Val Glu Lys Leu Ile Glu Glu Leu Arg
1               5                   10                  15

Gln Leu Lys Glu Lys Ala Tyr Lys Gly Gly Gly Asp Glu Arg Ile Gln
            20                  25                  30

Phe Gln His Ser Lys Gly Lys Leu Thr Ala Arg Glu Arg Leu Ala Leu
        35                  40                  45

Leu Phe Asp Asp Gly Lys Phe Asn Glu Ile Met Thr Phe Ala Thr Thr
    50                  55                  60

Arg Ala Thr Glu Phe Gly Leu Asp Lys Gln Arg Phe Tyr Gly Asp Gly
65                  70                  75                  80

Val Val Thr Gly Trp Gly Lys Val Asp Gly Arg Thr Val Phe Ala Tyr
                85                  90                  95

Ala Gln Asp Phe Thr Val Leu Gly Gly Ser Leu Gly Glu Thr His Ala
            100                 105                 110

Asn Lys Ile Val Arg Ala Tyr Glu Leu Ala Leu Lys Val Gly Ala Pro
        115                 120                 125

Val Val Gly Ile Asn Asp Ser Gly Gly Ala Arg Ile Gln Glu Gly Ala
    130                 135                 140

Leu Ser Leu Glu Gly Tyr Gly Ala Val Phe Lys Met Asn Val Met Ala
145                 150                 155                 160

Ser Gly Val Ile Pro Gln Ile Thr Ile Met Ala Gly Pro Ala Ala Gly
                165                 170                 175

Gly Ala Val Tyr Ser Pro Ala Leu Thr Asp Phe Ile Ile Met Ile Lys
            180                 185                 190

Gly Asp Ala Tyr Tyr Met Phe Val Thr Gly Pro Glu Ile Thr Lys Val
        195                 200                 205

Val Leu Gly Glu Glu Val Ser Phe Gln Asp Leu Gly Gly Ala Val Val
    210                 215                 220
```

His Ala Thr Lys Ser Gly Val Val His Phe Met Val Asp Ser Glu Gln
225                 230                 235                 240

Glu Ala Ile Asn Leu Thr Lys Arg Leu Leu Ser Tyr Leu Pro Ser Asn
            245                 250                 255

Asn Met Glu Glu Pro Pro Tyr Ile Asp Thr Gly Asp Pro Ala Asp Arg
        260                 265                 270

Asp Ala Thr Gly Val Glu Gln Ile Val Pro Asn Asp Ala Ala Lys Pro
    275                 280                 285

Tyr Asn Met Arg Glu Ile Ile Tyr Lys Ile Val Asp Asn Gly Glu Phe
        290                 295                 300

Leu Glu Val His Lys His Trp Ala Gln Asn Ile Ile Val Gly Phe Ala
305                 310                 315                 320

Arg Ile Ala Gly Asn Val Val Gly Ile Val Ala Asn Asn Pro Glu Glu
                325                 330                 335

Phe Gly Gly Ser Ile Asp Ile Asp Ala Ala Asp Lys Ala Ala Arg Phe
            340                 345                 350

Ile Arg Phe Cys Asp Ala Phe Asn Ile Pro Leu Ile Ser Leu Val Asp
        355                 360                 365

Thr Pro Gly Tyr Val Pro Gly Thr Asp Gln Glu Tyr Lys Gly Ile Ile
    370                 375                 380

Arg His Gly Ala Lys Met Leu Tyr Ala Phe Ala Glu Ala Thr Val Pro
385                 390                 395                 400

Lys Ile Thr Val Ile Val Arg Lys Ser Tyr Gly Gly Ala His Ile Ala
                405                 410                 415

Met Ser Ile Lys Ser Leu Gly Ala Asp Leu Val Tyr Ala Trp Pro Thr
            420                 425                 430

Ala Glu Ile Ala Val Thr Gly Pro Glu Gly Ala Val Arg Ile Leu Tyr
        435                 440                 445

Arg Lys Glu Ile Gln Gln Ala Ser Asn Pro Asp Asp Val Leu Lys Gln
    450                 455                 460

Arg Ile Ala Glu Tyr Arg Lys Leu Phe Ala Asn Pro Tyr Trp Ala Ala
465                 470                 475                 480

Glu Lys Gly Leu Val Asp Asp Val Ile Glu Pro Lys Asp Thr Arg Arg
                485                 490                 495

Val Ile Val Ala Gly Leu Glu Met Leu Lys Thr Lys Arg Glu Tyr Arg
            500                 505                 510

Tyr Pro Lys Lys His Gly Asn Ile Pro Leu
        515                 520

<210> SEQ ID NO 199
<211> LENGTH: 194
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Met Ile Glu Gln Asn Glu Lys Ala Ser Ile Gly Ile Ile Gly Ser
1               5                   10                  15

Gly Leu Tyr Asp Pro Gly Ile Phe Ser Glu Ser Lys Glu Ile Lys Val
            20                  25                  30

Tyr Thr Pro Tyr Gly Gln Pro Ser Asp Phe Ile Thr Ile Gly Lys Ile
        35                  40                  45

Gly Asn Lys Ser Val Ala Phe Leu Pro Arg His Gly Arg Gly His Arg
    50                  55                  60

```
Ile Pro Pro His Lys Ile Asn Tyr Arg Ala Asn Ile Trp Ala Leu Lys
 65                  70                  75                  80

Glu Leu Gly Val Arg Trp Val Ile Ser Val Ser Ala Val Gly Ser Leu
             85                   90                  95

Arg Met Asp Tyr Lys Leu Gly Asp Phe Val Ile Pro Gln Phe Ile
         100                 105                 110

Asp Met Thr Lys Asn Arg Glu Tyr Ser Phe Phe Asp Gly Pro Val Val
             115                 120                 125

Ala His Val Ser Met Ala Asp Pro Phe Cys Asn Ser Leu Arg Lys Leu
130                 135                 140

Ala Ile Glu Thr Ala Lys Glu Leu Asn Ile Lys Thr His Glu Ser Gly
145                 150                 155                 160

Thr Tyr Ile Cys Ile Glu Gly Pro Arg Phe Ser Thr Arg Ala Glu Ser
                165                 170                 175

Arg Thr Trp Arg Glu Val Tyr Lys Ala Asp Ile Ile Gly Met Thr Leu
            180                 185                 190

Val Pro

<210> SEQ ID NO 200
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Met Gly Ser Asp Lys Ile His His His His His Met Lys Val Val
 1               5                  10                  15

Thr Phe Gly Glu Ile Met Leu Arg Leu Ser Pro Pro Asp His Lys Arg
             20                  25                  30

Ile Phe Gln Thr Asp Ser Phe Asp Val Thr Tyr Gly Gly Ala Glu Ala
         35                  40                  45

Asn Val Ala Ala Phe Leu Ala Gln Met Gly Leu Asp Ala Tyr Phe Val
 50                  55                  60

Thr Lys Leu Pro Asn Asn Pro Leu Gly Asp Ala Ala Gly His Leu
 65                  70                  75                  80

Arg Lys Phe Gly Val Lys Thr Asp Tyr Ile Ala Arg Gly Gly Asn Arg
             85                  90                  95

Ile Gly Ile Tyr Phe Leu Glu Ile Gly Ala Ser Gln Arg Pro Ser Lys
         100                 105                 110

Val Val Tyr Asp Arg Ala His Ser Ala Ile Ser Glu Ala Lys Arg Glu
     115                 120                 125

Asp Phe Asp Trp Glu Lys Ile Leu Asp Gly Ala Arg Trp Phe His Phe
130                 135                 140

Ser Gly Ile Thr Pro Pro Leu Gly Lys Glu Leu Pro Leu Ile Leu Glu
145                 150                 155                 160

Asp Ala Leu Lys Val Ala Asn Glu Lys Gly Val Thr Val Ser Cys Asp
                165                 170                 175

Leu Asn Tyr Arg Ala Arg Leu Trp Thr Lys Glu Glu Ala Gln Lys Val
            180                 185                 190

Met Ile Pro Phe Met Glu Tyr Val Asp Val Leu Ile Ala Asn Glu Glu
        195                 200                 205

Asp Ile Glu Lys Val Leu Gly Ile Ser Val Glu Gly Leu Asp Leu Lys
    210                 215                 220
```

```
Thr Gly Lys Leu Asn Arg Glu Ala Tyr Ala Lys Ile Ala Glu Glu Val
225                 230                 235                 240

Thr Arg Lys Tyr Asn Phe Lys Thr Val Gly Ile Thr Leu Arg Glu Ser
                245                 250                 255

Ile Ser Ala Thr Val Asn Tyr Trp Ser Val Met Val Phe Glu Asn Gly
            260                 265                 270

Gln Pro His Phe Ser Asn Arg Tyr Glu Ile His Ile Val Asp Arg Val
        275                 280                 285

Gly Ala Gly Asp Ser Phe Ala Gly Ala Leu Ile Tyr Gly Ser Leu Met
    290                 295                 300

Gly Phe Asp Ser Gln Lys Lys Ala Glu Phe Ala Ala Ala Ser Cys
305                 310                 315                 320

Leu Lys His Thr Ile Pro Gly Asp Phe Val Val Leu Ser Ile Glu Glu
                325                 330                 335

Ile Glu Lys Leu Ala Ser Gly Ala Thr Ser Gly Arg Val Glu Arg
            340                 345                 350

<210> SEQ ID NO 201
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Met Gly Ser Asp Lys Ile His His His His His Met Lys Thr Asp
1               5                   10                  15

Thr Glu Trp Leu Leu Cys Asp Phe His Val His Thr Asn Met Ser Asp
                20                  25                  30

Gly His Leu Pro Leu Gly Glu Val Val Asp Leu Phe Gly Lys His Gly
            35                  40                  45

Val Asp Val Val Ser Ile Thr Asp His Ile Val Asp Arg Arg Thr Leu
50                  55                  60

Glu Gln Arg Lys Arg Asn Gly Glu Pro Leu Gly Ala Ile Thr Glu Asp
65                  70                  75                  80

Lys Phe Gln Asp Tyr Leu Lys Arg Leu Trp Arg Glu Gln Lys Arg Ala
                85                  90                  95

Trp Glu Glu Tyr Gly Met Ile Leu Ile Pro Gly Val Glu Ile Thr Asn
                100                 105                 110

Asn Thr Asp Leu Tyr His Ile Val Ala Val Asp Val Lys Glu Tyr Val
            115                 120                 125

Asp Pro Ser Leu Pro Val Glu Glu Ile Val Glu Lys Leu Lys Glu Gln
        130                 135                 140

Asn Ala Leu Val Ile Ala Ala His Pro Asp Arg Lys Lys Gln Asp Glu
145                 150                 155                 160

Glu His Leu Ser Trp Tyr Leu Trp Ala Asn Met Glu Arg Phe Lys Asp
                165                 170                 175

Thr Phe Asp Ala Trp Glu Ile Ala Asn Arg Asp Asp Leu Phe Asn Ser
            180                 185                 190

Val Gly Val Lys Lys Tyr Arg Tyr Val Ala Asn Ser Asp Phe His Glu
        195                 200                 205

Leu Trp His Val Tyr Ser Trp Lys Thr Leu Val Lys Ser Glu Lys Asn
    210                 215                 220

Ile Glu Ala Ile Lys Glu Ala Ile Arg Lys Asn Thr Asp Val Ala Ile
```

```
225                 230                 235                 240

Tyr Leu Met Arg Lys Asn Arg Leu Ser Ser Leu Ser Asp Val Ile
            245                 250                 255

<210> SEQ ID NO 202
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Met Thr Val Glu Pro Phe Arg Asn Glu Pro Ile Glu Thr Phe Gln Thr
1               5                   10                  15

Glu Glu Ala Arg Arg Ala Met Arg Glu Ala Leu Arg Arg Val Arg Glu
            20                  25                  30

Glu Phe Gly Arg His Tyr Pro Leu Tyr Ile Gly Gly Glu Trp Val Asp
        35                  40                  45

Thr Lys Glu Arg Met Val Ser Leu Asn Pro Ser Ala Pro Ser Glu Val
    50                  55                  60

Val Gly Thr Thr Ala Lys Ala Gly Lys Ala Glu Ala Glu Ala Ala Leu
65                  70                  75                  80

Glu Ala Ala Trp Lys Ala Phe Lys Thr Trp Lys Asp Trp Pro Gln Glu
                85                  90                  95

Asp Arg Ser Arg Leu Leu Lys Ala Ala Leu Met Arg Arg Arg
            100                 105                 110

Lys Arg Glu Leu Glu Ala Thr Leu Val Tyr Glu Val Gly Lys Asn Trp
            115                 120                 125

Val Glu Ala Ser Ala Asp Val Ala Glu Ala Ile Asp Phe Ile Glu Tyr
        130                 135                 140

Tyr Ala Arg Ala Ala Leu Arg Tyr Arg Tyr Pro Ala Val Glu Val Val
145                 150                 155                 160

Pro Tyr Pro Gly Glu Asp Asn Glu Ser Phe Tyr Val Pro Leu Gly Ala
                165                 170                 175

Gly Val Val Ile Ala Pro Trp Asn Phe Pro Val Ala Ile Phe Thr Gly
            180                 185                 190

Met Ile Val Gly Pro Val Ala Val Gly Asn Thr Val Ile Ala Lys Pro
        195                 200                 205

Ala Glu Asp Ala Val Val Val Gly Ala Lys Val Phe Glu Ile Phe His
    210                 215                 220

Glu Ala Gly Phe Pro Pro Gly Val Val Asn Phe Leu Pro Gly Val Gly
225                 230                 235                 240

Glu Glu Val Gly Ala Tyr Leu Val Glu His Pro Arg Ile Arg Phe Ile
                245                 250                 255

Asn Phe Thr Gly Ser Leu Glu Val Gly Leu Lys Ile Tyr Glu Ala Ala
            260                 265                 270

Gly Arg Leu Ala Pro Gly Gln Thr Trp Phe Lys Arg Ala Tyr Val Glu
        275                 280                 285

Thr Gly Gly Lys Asp Ala Ile Ile Val Asp Glu Thr Ala Asp Phe Asp
    290                 295                 300

Leu Ala Ala Glu Gly Val Val Val Ser Ala Tyr Gly Phe Gln Gly Gln
305                 310                 315                 320

Lys Cys Ser Ala Ala Ser Arg Leu Ile Leu Thr Gln Gly Ala Tyr Glu
                325                 330                 335
```

```
Pro Val Leu Glu Arg Val Leu Lys Arg Ala Glu Arg Leu Ser Val Gly
                340                 345                 350

Pro Ala Glu Glu Asn Pro Asp Leu Gly Pro Val Val Ser Ala Glu Gln
            355                 360                 365

Glu Arg Lys Val Leu Ser Tyr Ile Glu Ile Gly Lys Asn Glu Gly Gln
        370                 375                 380

Leu Val Leu Gly Gly Lys Arg Leu Glu Gly Gly Tyr Phe Ile Ala
385                 390                 395                 400

Pro Thr Val Phe Thr Glu Val Pro Pro Lys Ala Arg Ile Ala Gln Glu
                405                 410                 415

Glu Ile Phe Gly Pro Val Leu Ser Val Ile Arg Val Lys Asp Phe Ala
            420                 425                 430

Glu Ala Leu Glu Val Ala Asn Asp Thr Pro Tyr Gly Leu Thr Gly Gly
        435                 440                 445

Val Tyr Ser Arg Lys Arg Glu His Leu Glu Trp Ala Arg Arg Glu Phe
    450                 455                 460

His Val Gly Asn Leu Tyr Phe Asn Arg Lys Ile Thr Gly Ala Leu Val
465                 470                 475                 480

Gly Val Gln Pro Phe Gly Gly Phe Lys Leu Ser Gly Thr Asn Ala Lys
                485                 490                 495

Thr Gly Ala Leu Asp Tyr Leu Arg Leu Phe Leu Glu Met Lys Ala Val
            500                 505                 510

Ala Glu Arg Phe
        515

<210> SEQ ID NO 203
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Met Thr Val Glu Pro Phe Arg Asn Glu Pro Ile Glu Thr Phe Gln Thr
1               5                   10                  15

Glu Glu Ala Arg Arg Ala Met Arg Glu Ala Leu Arg Arg Val Arg Glu
            20                  25                  30

Glu Phe Gly Arg His Tyr Pro Leu Tyr Ile Gly Gly Glu Trp Val Asp
        35                  40                  45

Thr Lys Glu Arg Met Val Ser Leu Asn Pro Ser Ala Pro Ser Glu Val
    50                  55                  60

Val Gly Thr Thr Ala Lys Ala Gly Lys Ala Glu Ala Glu Ala Ala Leu
65                  70                  75                  80

Glu Ala Ala Trp Lys Ala Phe Lys Thr Trp Lys Asp Trp Pro Gln Glu
                85                  90                  95

Asp Arg Ser Arg Leu Leu Leu Lys Ala Ala Leu Met Arg Arg
            100                 105                 110

Lys Arg Glu Leu Glu Ala Thr Leu Val Tyr Glu Val Gly Lys Asn Trp
        115                 120                 125

Val Glu Ala Ser Ala Asp Val Ala Glu Ala Ile Asp Phe Ile Glu Tyr
    130                 135                 140

Tyr Ala Arg Ala Ala Leu Arg Tyr Arg Tyr Pro Ala Val Glu Val Val
145                 150                 155                 160

Pro Tyr Pro Gly Glu Asp Asn Glu Ser Phe Tyr Val Pro Leu Gly Ala
                165                 170                 175
```

```
Gly Val Val Ile Ala Pro Trp Asn Phe Pro Val Ala Ile Phe Thr Gly
            180                 185                 190

Met Ile Val Gly Pro Val Ala Val Gly Asn Thr Val Ile Ala Lys Pro
        195                 200                 205

Ala Glu Asp Ala Val Val Gly Ala Lys Val Phe Glu Ile Phe His
210                 215                 220

Glu Ala Gly Phe Pro Pro Gly Val Val Asn Phe Leu Pro Gly Val Gly
225                 230                 235                 240

Glu Glu Val Gly Ala Tyr Leu Val Glu His Pro Arg Ile Arg Phe Ile
                245                 250                 255

Asn Phe Thr Gly Ser Leu Glu Val Gly Leu Lys Ile Tyr Glu Ala Ala
            260                 265                 270

Gly Arg Leu Ala Pro Gly Gln Thr Trp Phe Lys Arg Ala Tyr Val Glu
        275                 280                 285

Thr Gly Gly Lys Asp Ala Ile Ile Val Asp Glu Thr Ala Asp Phe Asp
    290                 295                 300

Leu Ala Ala Glu Gly Val Val Ser Ala Tyr Gly Phe Gln Gly Gln
305                 310                 315                 320

Lys Cys Ser Ala Ala Ser Arg Leu Ile Leu Thr Gln Gly Ala Tyr Glu
                325                 330                 335

Pro Val Leu Glu Arg Val Leu Lys Arg Ala Glu Arg Leu Ser Val Gly
            340                 345                 350

Pro Ala Glu Glu Asn Pro Asp Leu Gly Pro Val Val Ser Ala Glu Gln
        355                 360                 365

Glu Arg Lys Val Leu Ser Tyr Ile Glu Ile Gly Lys Asn Glu Gly Gln
    370                 375                 380

Leu Val Leu Gly Gly Lys Arg Leu Glu Gly Glu Gly Tyr Phe Ile Ala
385                 390                 395                 400

Pro Thr Val Phe Thr Glu Val Pro Pro Lys Ala Arg Ile Ala Gln Glu
                405                 410                 415

Glu Ile Phe Gly Pro Val Leu Ser Val Ile Arg Val Lys Asp Phe Ala
            420                 425                 430

Glu Ala Leu Glu Val Ala Asn Asp Thr Pro Tyr Gly Leu Thr Gly Gly
        435                 440                 445

Val Tyr Ser Arg Lys Arg Glu His Leu Glu Trp Ala Arg Arg Glu Phe
    450                 455                 460

His Val Gly Asn Leu Tyr Phe Asn Arg Lys Ile Thr Gly Ala Leu Val
465                 470                 475                 480

Gly Val Gln Pro Phe Gly Gly Phe Lys Leu Ser Gly Thr Asn Ala Lys
                485                 490                 495

Thr Gly Ala Leu Asp Tyr Leu Arg Leu Phe Leu Glu Met Lys Ala Val
            500                 505                 510

Ala Glu Arg Phe
        515

<210> SEQ ID NO 204
<211> LENGTH: 177
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Met Lys Val Met Ile Glu Lys Ile Leu Leu Val Gln Thr Leu Lys Arg
```

-continued

```
                1               5                  10                 15
Leu Pro Arg Met Gly Trp Leu Ile Lys Gly Val Gln Glu Pro Glu Ser
                20                 25                 30

Ile Ala Asp His Ser Phe Gly Val Ala Phe Ile Thr Leu Val Leu Ala
                35                 40                 45

Asp Val Leu Glu Lys Arg Gly Lys Arg Ile Asp Val Glu Lys Ala Leu
 50                 55                 60

Lys Met Ala Ile Val His Asp Leu Ala Glu Ala Ile Ile Thr Asp Ile
 65                 70                 75                 80

Pro Leu Ser Ala Gln Glu Phe Val Asp Lys Asp Lys Ala Glu Ala Leu
                85                 90                 95

Val Phe Lys Lys Val Phe Pro Glu Phe Tyr Glu Leu Tyr Arg Glu Tyr
                100                105                110

Gln Glu Cys Ser Ser Pro Glu Ala Gln Leu Val Arg Ile Ala Asp Lys
                115                120                125

Leu Asp Met Ile Leu Gln Ala Tyr Gln Tyr Glu Leu Ser Gly Asn Lys
                130                135                140

Asn Leu Asp Glu Phe Trp Glu Ala Ile Glu Gly Ile Lys Arg Leu Glu
145                150                155                160

Leu Ser Lys Tyr Leu Glu Asp Ile Leu Asn Ser Val Gly Arg Leu Lys
                165                170                175

Ala
```

<210> SEQ ID NO 205
<211> LENGTH: 311
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

```
Met Ala Lys Leu Ile Thr Leu Gly Glu Ile Leu Ile Glu Phe Asn Ala
 1               5                  10                 15

Leu Ser Pro Gly Pro Leu Arg His Val Ser Tyr Phe Glu Lys His Val
                20                 25                 30

Ala Gly Ser Glu Ala Asn Tyr Cys Val Ala Phe Ile Lys Gln Gly Asn
                35                 40                 45

Glu Cys Gly Ile Ile Ala Lys Val Gly Asp Asp Glu Phe Gly Tyr Asn
 50                 55                 60

Ala Ile Glu Trp Leu Arg Gly Gln Gly Val Asp Val Ser His Met Lys
 65                 70                 75                 80

Ile Asp Pro Ser Ala Pro Thr Gly Ile Phe Phe Ile Gln Arg His Tyr
                85                 90                 95

Pro Val Pro Leu Lys Ser Glu Ser Ile Tyr Tyr Arg Lys Gly Ser Ala
                100                105                110

Gly Ser Lys Leu Ser Pro Glu Asp Val Asp Glu Tyr Val Lys Ser
                115                120                125

Ala Asp Leu Val His Ser Ser Gly Ile Thr Leu Ala Ile Ser Ser Thr
                130                135                140

Ala Lys Glu Ala Val Tyr Lys Ala Phe Glu Ile Ala Ser Asn Arg Ser
145                150                155                160

Phe Asp Thr Asn Ile Arg Leu Lys Leu Trp Ser Ala Glu Glu Ala Lys
                165                170                175

Arg Glu Ile Leu Lys Leu Leu Ser Lys Phe His Leu Lys Phe Leu Ile
```

```
                    180                 185                 190
Thr Asp Thr Asp Asp Ser Lys Ile Ile Leu Gly Glu Ser Asp Pro Asp
                195                 200                 205
Lys Ala Ala Lys Ala Phe Ser Asp Tyr Ala Glu Ile Ile Val Met Lys
            210                 215                 220
Leu Gly Pro Lys Gly Ala Ile Val Tyr Tyr Asp Gly Lys Lys Tyr Tyr
225                 230                 235                 240
Ser Ser Gly Tyr Gln Val Pro Val Glu Asp Val Thr Gly Ala Gly Asp
                245                 250                 255
Ala Leu Gly Gly Thr Phe Leu Ser Leu Tyr Tyr Lys Gly Phe Glu Met
            260                 265                 270
Glu Lys Ala Leu Asp Tyr Ala Ile Val Ala Ser Thr Leu Asn Val Met
        275                 280                 285
Ile Arg Gly Asp Gln Glu Asn Leu Pro Thr Thr Lys Asp Ile Glu Thr
    290                 295                 300
Phe Leu Arg Glu Met Lys Lys
305                 310
```

<210> SEQ ID NO 206
<211> LENGTH: 190
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

```
Met Asn Ser Met Glu Leu Leu Ile Ile Lys Glu Arg Arg Ile Asp Tyr
1               5                   10                  15
Asp Gly Ser Ala Ile Arg Ser His Trp Ala Tyr Arg Asn Phe Gly Ile
            20                  25                  30
Leu Gly Asp Ser Leu Val Val Phe Arg Gly Lys Cys Asn Val Lys Val
        35                  40                  45
Glu Glu Met Val Asp Ile Glu Asp Leu Arg Leu Arg Lys Glu Ile Lys
    50                  55                  60
Gly Asp Asp Met Val His Tyr Ile Leu Glu Leu Phe Trp His Pro Asp
65                  70                  75                  80
Ile Leu Leu Ala Ser Ser Leu Gln Lys Leu Leu Ile Ala Arg Leu Val
                85                  90                  95
Glu Leu Leu Trp Asn Tyr Gly Ile Glu Ala Ser Arg Arg Gly Asp Asp
            100                 105                 110
Ile Tyr Val Asn Gly Arg Lys Leu Ser Ile Ser Ile Ala Thr Val Ser
        115                 120                 125
Pro Val Ser Ile Lys Ile His Ile Gly Leu Asn Val Lys Thr Val Gly
    130                 135                 140
Val Pro Pro Gly Val Asp Ala Ile Gly Leu Glu Glu Leu Gly Ile Asp
145                 150                 155                 160
Pro Thr Glu Phe Met Glu Arg Ser Ala Lys Ala Leu Val Glu Glu Ile
                165                 170                 175
Glu Lys Val Arg Lys Asp Ser Leu Lys Val Arg Trp Val Thr
            180                 185                 190
```

<210> SEQ ID NO 207
<211> LENGTH: 69
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 207

Met Gly Lys Val Tyr Lys Lys Val Glu Leu Val Gly Thr Ser Glu Glu
1               5                   10                  15

Gly Leu Glu Ala Ala Ile Gln Ala Ala Leu Ala Arg Ala Arg Lys Thr
            20                  25                  30

Leu Arg His Leu Asp Trp Phe Glu Val Lys Glu Ile Arg Gly Thr Ile
        35                  40                  45

Gly Glu Ala Gly Val Lys Glu Tyr Gln Val Val Leu Glu Val Gly Phe
    50                  55                  60

Arg Leu Glu Glu Thr
65

<210> SEQ ID NO 208
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Met Arg Phe Ser Arg Glu Ala Leu Leu Glu Leu Glu Ala Ser Arg Leu
1               5                   10                  15

Ala Pro Tyr Ala Gln Lys Ala Arg Asp Thr Arg Gly Arg Ala His Pro
            20                  25                  30

Glu Pro Glu Ser Leu Tyr Arg Thr Pro Tyr Gln Lys Asp Arg Asp Arg
        35                  40                  45

Ile Leu His Thr Thr Ala Phe Arg Arg Leu Glu Tyr Lys Thr Gln Val
    50                  55                  60

Leu Pro Gly Trp Ala Gly Asp Tyr Tyr Arg Thr Arg Leu Thr His Thr
65              70                  75                  80

Leu Glu Val Ala Gln Val Ser Arg Ser Ile Ala Arg Ala Leu Gly Leu
                85                  90                  95

Asn Glu Asp Leu Thr Glu Ala Ile Ala Leu Ser His Asp Leu Gly His
            100                 105                 110

Pro Pro Phe Gly His Thr Gly Glu His Val Leu Asn Ala Leu Met Gln
        115                 120                 125

Asp His Gly Gly Phe Glu His Asn Ala Gln Ala Leu Arg Ile Leu Thr
    130                 135                 140

His Leu Glu Val Arg Tyr Pro Gly Phe Arg Gly Leu Asn Leu Thr Tyr
145                 150                 155                 160

Glu Val Leu Glu Gly Ile Ala Thr His Glu Ala Tyr Ser Pro Gly
                165                 170                 175

Phe Lys Pro Leu Tyr Glu Gly Gln Gly Thr Leu Glu Ala Gln Val Val
            180                 185                 190

Asp Leu Ser Asp Ala Ile Ala Tyr Ala Ala His Asp Leu Asp Asp Gly
        195                 200                 205

Phe Arg Ala Gly Leu Leu His Pro Glu Glu Leu Lys Glu Val Glu Leu
    210                 215                 220

Leu Gln Ala Leu Ala Leu Glu Glu Gly Leu Asp Leu Leu Arg Leu Pro
225                 230                 235                 240

Glu Leu Asp Arg Arg Val Leu Val Arg Gln Leu Leu Gly Tyr Phe Ile
                245                 250                 255

```
Thr Ala Ala Ile Glu Ala Thr His Arg Arg Val Glu Glu Ala Gly Val
                260                 265                 270

Gln Ser Ala Glu Ala Val Arg Arg His Pro Ser Arg Leu Ala Ala Leu
            275                 280                 285

Gly Glu Glu Ala Glu Lys Ala Leu Lys Ala Leu Lys Ala Phe Leu Met
        290                 295                 300

Glu Arg Phe Tyr Arg His Pro Glu Val Leu Arg Glu Arg Arg Lys Ala
305                 310                 315                 320

Glu Ala Val Leu Glu Gly Leu Phe Ala Ala Tyr Thr Arg Tyr Pro Glu
                325                 330                 335

Leu Leu Pro Arg Glu Val Gln Ala Lys Ile Pro Glu Glu Gly Leu Glu
            340                 345                 350

Arg Ala Val Cys Asp Tyr Ile Ala Gly Met Thr Asp Arg Phe Ala Leu
        355                 360                 365

Glu Ala Tyr Arg Arg Leu Ser Pro
370                 375

<210> SEQ ID NO 209
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Met Phe Gln Met Ser Glu Thr Glu Arg Thr Leu Val Ile Ile Lys Pro
1               5                   10                  15

Asp Ala Val Val Arg Gly Leu Ile Gly Glu Ile Ile Ser Arg Phe Glu
                20                  25                  30

Lys Lys Gly Leu Lys Ile Val Gly Met Lys Met Ile Trp Ile Asp Arg
            35                  40                  45

Glu Leu Ala Glu Lys His Tyr Glu Glu His Arg Glu Lys Pro Phe Phe
        50                  55                  60

Lys Ala Leu Ile Asp Tyr Ile Thr Lys Thr Pro Val Val Val Met Val
65                  70                  75                  80

Leu Glu Gly Arg Tyr Ala Val Glu Val Val Arg Lys Met Ala Gly Ala
                85                  90                  95

Thr Asp Pro Lys Asp Ala Ala Pro Gly Thr Ile Arg Gly Asp Phe Gly
            100                 105                 110

Leu Glu Val Ser Asp Ala Ile Cys Asn Val Ile His Ala Ser Asp Ser
        115                 120                 125

Lys Glu Ser Ala Glu Arg Glu Ile Ser Leu Phe Phe Lys Pro Glu Glu
    130                 135                 140

Leu Phe Glu Tyr Pro Arg Ala Ala Asp Trp Phe Tyr Lys Lys Gly Ile
145                 150                 155                 160

<210> SEQ ID NO 210
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Met Phe Gln Met Ser Glu Thr Glu Arg Thr Leu Val Ile Ile Lys Pro
1               5                   10                  15
```

Asp Ala Val Val Arg Gly Leu Ile Gly Ile Ile Ser Arg Phe Glu
                20                  25                  30

Lys Lys Gly Leu Lys Ile Val Gly Met Lys Met Ile Trp Ile Asp Arg
            35                  40                  45

Glu Leu Ala Glu Lys His Tyr Glu Glu His Arg Glu Lys Pro Phe Phe
        50                  55                  60

Lys Ala Leu Ile Asp Tyr Ile Thr Lys Thr Pro Val Val Met Val
65                  70                  75                  80

Leu Glu Gly Arg Tyr Ala Val Glu Val Val Arg Lys Met Ala Gly Ala
                85                  90                  95

Thr Asp Pro Lys Asp Ala Ala Pro Gly Thr Ile Arg Gly Asp Phe Gly
            100                 105                 110

Leu Glu Val Ser Asp Ala Ile Cys Asn Val Ile His Ala Ser Asp Ser
        115                 120                 125

Lys Glu Ser Ala Glu Arg Glu Ile Ser Leu Phe Phe Lys Pro Glu Glu
    130                 135                 140

Leu Phe Glu Tyr Pro Arg Ala Ala Asp Trp Phe Tyr Lys Lys Gly Ile
145                 150                 155                 160

<210> SEQ ID NO 211
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Met Val Ile Gly Val Pro Lys Glu Ile Lys Thr Leu Glu Asn Arg Val
1               5                   10                  15

Ala Leu Thr Pro Gly Gly Val Glu Ser Leu Val Arg Arg Gly His Thr
            20                  25                  30

Val Leu Val Glu Arg Gly Ala Gly Glu Gly Ser Gly Leu Ser Asp Ala
        35                  40                  45

Glu Tyr Ala Arg Ala Gly Ala Glu Leu Val Gly Arg Glu Glu Ala Trp
    50                  55                  60

Gly Ala Glu Met Val Val Lys Val Lys Glu Pro Leu Pro Glu Glu Tyr
65                  70                  75                  80

Gly Phe Leu Arg Glu Gly Leu Ile Leu Phe Thr Tyr Leu His Leu Ala
                85                  90                  95

Ala Asp Arg Gly Leu Thr Glu Ala Met Leu Arg Ser Gly Val Thr Gly
            100                 105                 110

Ile Ala Tyr Glu Thr Val Gln Leu Pro Asp Gly Thr Leu Pro Leu Leu
        115                 120                 125

Val Pro Met Ser Glu Val Ala Gly Arg Met Ala Pro Gln Val Gly Ala
    130                 135                 140

Gln Phe Leu Glu Lys Pro Lys Gly Gly Arg Gly Val Leu Leu Gly Gly
145                 150                 155                 160

Val Pro Gly Val Ala Pro Ala Ser Val Val Ile Leu Gly Gly Gly Thr
                165                 170                 175

Val Gly Thr Asn Ala Ala Lys Ile Ala Leu Gly Met Gly Ala Gln Val
            180                 185                 190

Thr Ile Leu Asp Val Asn His Lys Arg Leu Gln Tyr Leu Asp Asp Val
        195                 200                 205

Phe Gly Gly Arg Val Ile Thr Leu Thr Ala Thr Glu Ala Asn Ile Lys
    210                 215                 220

```
Lys Ser Val Gln His Ala Asp Leu Leu Ile Gly Ala Val Leu Val Pro
225                 230                 235                 240

Gly Ala Lys Ala Pro Lys Leu Val Thr Arg Asp Met Leu Ser Leu Met
            245                 250                 255

Lys Glu Gly Ala Val Ile Val Asp Val Ala Val Asp Gln Gly Gly Cys
        260                 265                 270

Val Glu Thr Ile Arg Pro Thr Thr His Ala Glu Pro Thr Tyr Val Val
    275                 280                 285

Asp Gly Val Val His Tyr Gly Val Ala Asn Met Pro Gly Ala Val Pro
        290                 295                 300

Arg Thr Ser Thr Phe Ala Leu Thr Asn Gln Thr Leu Pro Tyr Val Leu
305                 310                 315                 320

Lys Leu Ala Glu Lys Gly Leu Asp Ala Leu Leu Glu Asp Ala Ala Leu
            325                 330                 335

Leu Lys Gly Leu Asn Thr His Lys Gly Arg Leu Thr His Pro Gly Val
        340                 345                 350

Ala Glu Ala Phe Gly Leu Pro Tyr Thr Pro Pro Glu Glu Ala Leu Arg
    355                 360                 365

Gly

<210> SEQ ID NO 212
<211> LENGTH: 693
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Met Arg Ile Leu Lys Ile Tyr Glu Asn Lys Gly Val Tyr Lys Val Val
1               5                   10                  15

Ile Gly Glu Pro Phe Pro Pro Ile Glu Phe Pro Leu Glu Gln Lys Ile
            20                  25                  30

Ser Ser Asn Lys Ser Leu Ser Glu Leu Gly Leu Thr Ile Val Gln Gln
        35                  40                  45

Gly Asn Lys Val Ile Val Glu Lys Ser Leu Asp Leu Lys Glu His Ile
    50                  55                  60

Ile Gly Leu Gly Glu Lys Ala Phe Glu Leu Asp Arg Lys Arg Lys Arg
65                  70                  75                  80

Tyr Val Met Tyr Asn Val Asp Ala Gly Ala Tyr Lys Lys Tyr Gln Asp
                85                  90                  95

Pro Leu Tyr Val Ser Ile Pro Leu Phe Ile Ser Val Lys Asp Gly Val
            100                 105                 110

Ala Thr Gly Tyr Phe Phe Asn Ser Ala Ser Lys Val Ile Phe Asp Val
        115                 120                 125

Gly Leu Glu Glu Tyr Asp Lys Val Ile Val Thr Ile Pro Glu Asp Ser
    130                 135                 140

Val Glu Phe Tyr Val Ile Glu Gly Pro Arg Ile Glu Asp Val Leu Glu
145                 150                 155                 160

Lys Tyr Thr Glu Leu Thr Gly Lys Pro Phe Leu Pro Pro Met Trp Ala
                165                 170                 175

Phe Gly Tyr Met Ile Ser Arg Tyr Ser Tyr Tyr Pro Gln Asp Lys Val
            180                 185                 190

Val Glu Leu Val Asp Ile Met Gln Lys Glu Gly Phe Arg Val Ala Gly
        195                 200                 205
```

-continued

```
Val Phe Leu Asp Ile His Tyr Met Asp Ser Tyr Lys Leu Phe Thr Trp
    210                 215                 220
His Pro Tyr Arg Phe Pro Glu Pro Lys Lys Leu Ile Asp Glu Leu His
225                 230                 235                 240
Lys Arg Asn Val Lys Leu Ile Thr Ile Val Asp His Gly Ile Arg Val
                245                 250                 255
Asp Gln Asn Tyr Ser Pro Phe Leu Ser Gly Met Gly Lys Phe Cys Glu
            260                 265                 270
Ile Glu Ser Gly Glu Leu Phe Val Gly Lys Met Trp Pro Gly Thr Thr
        275                 280                 285
Val Tyr Pro Asp Phe Phe Arg Glu Asp Thr Arg Glu Trp Trp Ala Gly
    290                 295                 300
Leu Ile Ser Glu Trp Leu Ser Gln Gly Val Asp Gly Ile Trp Leu Asp
305                 310                 315                 320
Met Asn Glu Pro Thr Asp Phe Ser Arg Ala Ile Glu Ile Arg Asp Val
                325                 330                 335
Leu Ser Ser Leu Pro Val Gln Phe Arg Asp Asp Arg Leu Val Thr Thr
            340                 345                 350
Phe Pro Asp Asn Val Val His Tyr Leu Arg Gly Lys Arg Val Lys His
        355                 360                 365
Glu Lys Val Arg Asn Ala Tyr Pro Leu Tyr Glu Ala Met Ala Thr Phe
    370                 375                 380
Lys Gly Phe Arg Thr Ser His Arg Asn Glu Ile Phe Ile Leu Ser Arg
385                 390                 395                 400
Ala Gly Tyr Ala Gly Ile Gln Arg Tyr Ala Phe Ile Trp Thr Gly Asp
                405                 410                 415
Asn Thr Pro Ser Trp Asp Asp Leu Lys Leu Gln Leu Gln Leu Val Leu
            420                 425                 430
Gly Leu Ser Ile Ser Gly Val Pro Phe Val Gly Cys Asp Ile Gly Gly
        435                 440                 445
Phe Gln Gly Arg Asn Phe Ala Glu Ile Asp Asn Ser Met Asp Leu Leu
    450                 455                 460
Val Lys Tyr Tyr Ala Leu Ala Leu Phe Phe Pro Phe Tyr Arg Ser His
465                 470                 475                 480
Lys Ala Thr Asp Gly Ile Asp Thr Glu Pro Val Phe Leu Pro Asp Tyr
                485                 490                 495
Tyr Lys Glu Lys Val Lys Glu Ile Val Glu Leu Arg Tyr Lys Phe Leu
            500                 505                 510
Pro Tyr Ile Tyr Ser Leu Ala Leu Glu Ala Ser Glu Lys Gly His Pro
        515                 520                 525
Val Ile Arg Pro Leu Phe Tyr Glu Phe Gln Asp Asp Asp Met Tyr
    530                 535                 540
Arg Ile Glu Asp Glu Tyr Met Val Gly Lys Tyr Leu Leu Tyr Ala Pro
545                 550                 555                 560
Ile Val Ser Lys Glu Glu Ser Arg Leu Val Thr Leu Pro Arg Gly Lys
                565                 570                 575
Trp Tyr Asn Tyr Trp Asn Gly Glu Ile Ile Asn Gly Lys Ser Val Val
            580                 585                 590
Lys Ser Thr His Glu Leu Pro Ile Tyr Leu Arg Glu Gly Ser Ile Ile
        595                 600                 605
Pro Leu Glu Gly Asp Glu Leu Ile Val Tyr Gly Glu Thr Ser Phe Lys
    610                 615                 620
```

Arg Tyr Asp Asn Ala Glu Ile Thr Ser Ser Asn Glu Ile Lys Phe
625                 630                 635                 640

Ser Arg Glu Ile Tyr Val Ser Lys Leu Thr Ile Thr Ser Glu Lys Pro
            645                 650                 655

Val Ser Lys Ile Ile Val Asp Asp Ser Lys Glu Ile Gln Val Glu Lys
            660                 665                 670

Thr Met Gln Asn Thr Tyr Val Ala Lys Ile Asn Gln Lys Ile Arg Gly
            675                 680                 685

Lys Ile Asn Leu Glu
        690

<210> SEQ ID NO 213
<211> LENGTH: 395
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Gly Gly Gly Gly Gly Met Lys Arg Phe Tyr Ile Ala Asn Glu Asp
1               5                   10                  15

Glu Ile Lys Ala Gly Lys Thr Thr Asp Val Tyr Phe Leu Arg Thr Lys
            20                  25                  30

Lys Ile Leu Glu Val Lys Asn Ile Arg Lys Lys Val Leu Ala Asp Val
            35                  40                  45

Thr Thr Thr Ser Leu Pro Asn Asn Trp Arg Trp Gly Val Leu Val Gly
        50                  55                  60

Val Glu Glu Val Ala Lys Leu Leu Glu Gly Ile Pro Val Asn Val Tyr
65              70                  75                  80

Ala Met Pro Glu Gly Thr Ile Phe His Pro Tyr Glu Pro Val Leu Gln
                85                  90                  95

Ile Glu Gly Asp Tyr Ala Asp Phe Gly Ile Tyr Glu Thr Ala Leu Leu
            100                 105                 110

Gly Met Leu Ser Gln Ala Ser Gly Ile Ala Thr Ala Ala Leu Arg Ile
        115                 120                 125

Lys Ile Ala Ala Lys Phe Lys Pro Val Tyr Ser Phe Gly Ile Arg His
    130                 135                 140

Met His Pro Ala Ile Ala Pro Met Ile Asp Arg Ala Ala Phe Ile Gly
145                 150                 155                 160

Gly Cys Asp Gly Val Ser Gly Val Leu Gly Ala Glu Met Met Gly Glu
                165                 170                 175

Lys Ala Val Gly Thr Met Pro His Ala Leu Ile Ile Thr Val Gly Asp
            180                 185                 190

Gln Val Lys Ala Trp Lys Tyr Phe Asp Glu Val Ile Glu Glu Val
        195                 200                 205

Pro Arg Ile Ala Leu Val Asp Thr Phe Tyr Asp Glu Lys Val Glu Ala
    210                 215                 220

Val Met Ala Ala Glu Ala Leu Gly Lys Lys Leu Phe Ala Val Arg Leu
225                 230                 235                 240

Asp Thr Pro Ser Ser Arg Arg Gly Asn Phe Arg Lys Ile Ile Glu Glu
                245                 250                 255

Val Arg Trp Glu Leu Lys Val Arg Gly Tyr Asp Trp Val Lys Ile Phe
            260                 265                 270

Val Ser Gly Gly Leu Asp Glu Glu Lys Ile Lys Glu Ile Val Asp Val
        275                 280                 285

```
Val Asp Ala Phe Gly Val Gly Ala Ile Ala Ser Ala Lys Pro Val
    290                 295                 300

Asp Phe Ala Leu Asp Ile Val Glu Val Glu Gly Lys Pro Ile Ala Lys
305                 310                 315                 320

Arg Gly Lys Leu Ser Gly Arg Lys Gln Val Tyr Arg Cys Glu Asn Gly
                325                 330                 335

His Tyr His Val Val Pro Ala Asn Lys Lys Leu Glu Arg Cys Pro Val
            340                 345                 350

Cys Asn Ala Lys Val Glu Pro Leu Leu Lys Pro Ile Ile Glu Asn Gly
        355                 360                 365

Glu Ile Val Val Glu Phe Pro Lys Ala Arg Glu Ile Arg Glu Tyr Val
    370                 375                 380

Leu Glu Gln Ala Lys Lys Phe Asn Leu Glu Ile
385                 390                 395

<210> SEQ ID NO 214
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Met Asp Leu Thr His Phe Gln Asp Gly Arg Pro Arg Met Val Asp Val
1               5                   10                  15

Thr Glu Lys Pro Glu Thr Phe Arg Thr Ala Thr Ala Glu Ala Phe Val
            20                  25                  30

Glu Leu Thr Glu Glu Ala Leu Ser Ala Leu Glu Lys Gly Gly Val Gly
        35                  40                  45

Lys Gly Asp Pro Leu Val Val Ala Gln Leu Ala Gly Ile Leu Ala Ala
    50                  55                  60

Lys Lys Thr Ala Asp Leu Ile Pro Leu Cys His Pro Leu Pro Leu Thr
65                  70                  75                  80

Gly Val Glu Val Arg Val Glu Leu Leu Lys Ala Glu Lys Arg Val Arg
                85                  90                  95

Ile Glu Ala Thr Val Lys Thr Lys Ala Glu Thr Gly Val Glu Met Glu
            100                 105                 110

Ala Met Thr Ala Cys Ala Val Ala Ala Leu Thr Val Tyr Asp Met Leu
        115                 120                 125

Lys Ala Ala Ser Lys Gly Leu Val Ile Ser Gln Val Arg Leu Leu His
    130                 135                 140

Lys Ala Gly Gly Lys Ser Gly Glu Trp Arg Arg Glu Gln
145                 150                 155

<210> SEQ ID NO 215
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Met Asn Ile Ile Leu Lys Ile Ser Gly Lys Phe Phe Asp Glu Asp Asn
1               5                   10                  15

Val Asp Asn Leu Ile Val Leu Arg Gln Ser Ile Lys Glu Leu Ala Asp
            20                  25                  30
```

```
Asn Gly Phe Arg Val Gly Ile Val Thr Gly Gly Ser Thr Ala Arg
        35                  40                  45

Arg Tyr Ile Lys Leu Ala Arg Glu Ile Gly Ile Glu Ala Tyr Leu
 50                  55                  60

Asp Leu Leu Gly Ile Trp Ala Ser Arg Leu Asn Ala Tyr Leu Val Met
 65                  70                  75                  80

Phe Ser Leu Gln Asp Leu Ala Tyr Met His Val Pro Gln Ser Leu Glu
                 85                  90                  95

Glu Phe Ile Gln Asp Trp Ser His Gly Lys Val Val Thr Gly Gly
                100                 105                 110

Phe Gln Pro Gly Gln Ser Thr Ala Ala Val Ala Ala Leu Val Ala Glu
                115                 120                 125

Ala Ser Ser Ser Lys Thr Leu Val Val Ala Thr Asn Val Asp Gly Val
130                 135                 140

Tyr Glu Lys Asp Pro Arg Ile Tyr Ala Asp Val Lys Leu Ile Pro His
145                 150                 155                 160

Leu Thr Thr Gln Asp Leu Arg Lys Ile Leu Glu Gly Ser Gln Ser Val
                165                 170                 175

Gln Ala Gly Thr Tyr Glu Leu Leu Asp Pro Leu Ala Ile Lys Ile Val
                180                 185                 190

Glu Arg Ser Lys Ile Arg Val Ile Val Met Asn Tyr Arg Lys Leu Asn
                195                 200                 205

Arg Ile Ile Asp Ile Leu Lys Gly Glu Glu Val Ser Ser Ile Ile Glu
    210                 215                 220

Pro Val
225

<210> SEQ ID NO 216
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Gly Ser Met Lys Lys Val Glu Ala Ile Ile Arg Pro Glu Lys Leu Glu
 1               5                  10                  15

Ile Val Lys Lys Ala Leu Ser Asp Ala Gly Tyr Val Gly Met Thr Val
                 20                  25                  30

Ser Glu Val Lys Gly Arg Gly Val Gln Gly Gly Ile Val Glu Arg Tyr
                 35                  40                  45

Arg Gly Arg Glu Tyr Ile Val Asp Leu Ile Pro Lys Val Lys Ile Glu
 50                  55                  60

Leu Val Val Lys Glu Glu Asp Val Asp Asn Val Ile Asp Ile Ile Cys
 65                  70                  75                  80

Glu Asn Ala Arg Thr Gly Asn Pro Gly Asp Gly Lys Ile Phe Val Ile
                 85                  90                  95

Pro Val Glu Arg Val Val Arg Val Arg Thr Lys Glu Glu Gly Lys Glu
                100                 105                 110

Ala Leu Leu Glu His His His
        115

<210> SEQ ID NO 217
<211> LENGTH: 351
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 217

```
Met Gly Ser Asp Lys Ile His His His His His Met Lys Val Val
1               5                   10                  15

Thr Phe Gly Glu Ile Met Leu Arg Leu Ser Pro Pro Asp His Lys Arg
            20                  25                  30

Ile Phe Gln Thr Asp Ser Phe Asp Val Thr Tyr Gly Gly Ala Glu Ala
        35                  40                  45

Asn Val Ala Ala Phe Leu Ala Gln Met Gly Leu Asp Ala Tyr Phe Val
    50                  55                  60

Thr Lys Leu Pro Asn Asn Pro Leu Gly Asp Ala Ala Ala Gly His Leu
65                  70                  75                  80

Arg Lys Phe Gly Val Lys Thr Asp Tyr Ile Ala Arg Gly Gly Asn Arg
                85                  90                  95

Ile Gly Ile Tyr Phe Leu Glu Ile Gly Ala Ser Gln Arg Pro Ser Lys
            100                 105                 110

Val Val Tyr Asp Arg Ala His Ser Ala Ile Ser Glu Ala Lys Arg Glu
        115                 120                 125

Asp Phe Asp Trp Glu Lys Ile Leu Asp Gly Ala Arg Trp Phe His Phe
    130                 135                 140

Ser Gly Ile Thr Pro Pro Leu Gly Lys Glu Leu Pro Leu Ile Leu Glu
145                 150                 155                 160

Asp Ala Leu Lys Val Ala Asn Glu Lys Gly Val Thr Val Ser Cys Asp
                165                 170                 175

Leu Asn Tyr Arg Ala Arg Leu Trp Thr Lys Glu Glu Ala Gln Lys Val
            180                 185                 190

Met Ile Pro Phe Met Glu Tyr Val Asp Val Leu Ile Ala Asn Glu Glu
        195                 200                 205

Asp Ile Glu Lys Val Leu Gly Ile Ser Val Glu Gly Leu Asp Leu Lys
    210                 215                 220

Thr Gly Lys Leu Asn Arg Glu Ala Tyr Ala Lys Ile Ala Glu Glu Val
225                 230                 235                 240

Thr Arg Lys Tyr Asn Phe Lys Thr Val Gly Ile Thr Leu Arg Glu Ser
                245                 250                 255

Ile Ser Ala Thr Val Asn Tyr Trp Ser Val Met Val Phe Glu Asn Gly
            260                 265                 270

Gln Pro His Phe Ser Asn Arg Tyr Glu Ile His Ile Val Asp Arg Val
        275                 280                 285

Gly Ala Gly Asp Ser Phe Ala Gly Ala Leu Ile Tyr Gly Ser Leu Met
    290                 295                 300

Gly Phe Asp Ser Gln Lys Lys Ala Glu Phe Ala Ala Ala Ser Cys
305                 310                 315                 320

Leu Lys His Thr Ile Pro Gly Asp Phe Val Val Leu Ser Ile Glu Glu
                325                 330                 335

Ile Glu Lys Leu Ala Ser Gly Ala Thr Ser Gly Arg Val Glu Arg
            340                 345                 350
```

<210> SEQ ID NO 218
<211> LENGTH: 226
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 218

Met Asn Ile Ile Leu Lys Ile Ser Gly Lys Phe Phe Asp Glu Asp Asn
1               5                   10                  15

Val Asp Asn Leu Ile Val Leu Arg Gln Ser Ile Lys Glu Leu Ala Asp
            20                  25                  30

Asn Gly Phe Arg Val Gly Ile Val Thr Gly Gly Gly Ser Thr Ala Arg
        35                  40                  45

Arg Tyr Ile Lys Leu Ala Arg Glu Ile Gly Ile Gly Glu Ala Tyr Leu
    50                  55                  60

Asp Leu Leu Gly Ile Trp Ala Ser Arg Leu Asn Ala Tyr Leu Val Met
65                  70                  75                  80

Phe Ser Leu Gln Asp Leu Ala Tyr Met His Val Pro Gln Ser Leu Glu
                85                  90                  95

Glu Phe Ile Gln Asp Trp Ser His Gly Lys Val Val Val Thr Gly Gly
            100                 105                 110

Phe Gln Pro Gly Gln Ser Thr Ala Ala Val Ala Ala Leu Val Ala Glu
        115                 120                 125

Ala Ser Ser Lys Thr Leu Val Ala Thr Asn Val Asp Gly Val
    130                 135                 140

Tyr Glu Lys Asp Pro Arg Ile Tyr Ala Asp Val Lys Leu Ile Pro His
145                 150                 155                 160

Leu Thr Thr Gln Asp Leu Arg Lys Ile Leu Glu Gly Ser Gln Ser Val
                165                 170                 175

Gln Ala Gly Thr Tyr Glu Leu Leu Asp Pro Leu Ala Ile Lys Ile Val
            180                 185                 190

Glu Arg Ser Lys Ile Arg Val Ile Val Met Asn Tyr Arg Lys Leu Asn
        195                 200                 205

Arg Ile Ile Asp Ile Leu Lys Gly Glu Glu Val Ser Ser Ile Ile Glu
    210                 215                 220

Pro Val
225

<210> SEQ ID NO 219
<211> LENGTH: 370
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 219

Met Ala Ala Glu Arg Val Phe Ile Ser Pro Ala Lys Tyr Val Gln Gly
1               5                   10                  15

Lys Asn Val Ile Thr Lys Ile Ala Asn Tyr Leu Glu Gly Ile Gly Asn
            20                  25                  30

Lys Thr Val Val Ile Ala Asp Glu Ile Val Trp Lys Ile Ala Gly His
        35                  40                  45

Thr Ile Val Asn Glu Leu Lys Lys Gly Asn Ile Ala Ala Glu Glu Val
    50                  55                  60

Val Phe Ser Gly Glu Ala Ser Arg Asn Glu Val Glu Arg Ile Ala Asn
65                  70                  75                  80

Ile Ala Arg Lys Ala Glu Ala Ala Ile Val Ile Gly Val Gly Gly Gly
                85                  90                  95

Lys Thr Leu Asp Thr Ala Lys Ala Val Ala Asp Glu Leu Asp Ala Tyr
                100                 105                 110

Ile Val Ile Val Pro Thr Ala Ala Ser Thr Asp Ala Pro Thr Ser Ala
            115                 120                 125

Leu Ser Val Ile Tyr Ser Asp Asp Gly Val Phe Glu Ser Tyr Arg Phe
        130                 135                 140

Tyr Lys Lys Asn Pro Asp Leu Val Leu Val Asp Thr Lys Ile Ile Ala
145                 150                 155                 160

Asn Ala Pro Pro Arg Leu Leu Ala Ser Gly Ile Ala Asp Ala Leu Ala
                165                 170                 175

Thr Trp Val Glu Ala Arg Ser Val Ile Lys Ser Gly Lys Thr Met
            180                 185                 190

Ala Gly Gly Ile Pro Thr Ile Ala Ala Glu Ala Ile Ala Glu Lys Cys
        195                 200                 205

Glu Gln Thr Leu Phe Lys Tyr Gly Lys Leu Ala Tyr Glu Ser Val Lys
        210                 215                 220

Ala Lys Val Val Thr Pro Ala Leu Glu Ala Val Val Glu Ala Asn Thr
225                 230                 235                 240

Leu Leu Ser Gly Leu Gly Phe Glu Ser Gly Gly Leu Ala Ala His
                245                 250                 255

Ala Ile His Asn Gly Phe Thr Ala Leu Glu Gly Glu Ile His His Leu
            260                 265                 270

Thr His Gly Glu Lys Val Ala Phe Gly Thr Leu Val Gln Leu Ala Leu
        275                 280                 285

Glu Glu His Ser Gln Gln Glu Ile Glu Arg Tyr Ile Glu Leu Tyr Leu
        290                 295                 300

Cys Leu Asp Leu Pro Val Thr Leu Glu Asp Ile Lys Leu Lys Asp Ala
305                 310                 315                 320

Ser Arg Glu Asp Ile Leu Lys Val Ala Lys Ala Ala Thr Ala Glu Gly
                325                 330                 335

Glu Thr Ile His Asn Ala Phe Asn Val Thr Ala Asp Asp Val Ala Asp
            340                 345                 350

Ala Ile Phe Ala Ala Asp Gln Tyr Ala Lys Ala Tyr Lys Glu Lys His
        355                 360                 365

Arg Lys
    370

<210> SEQ ID NO 220
<211> LENGTH: 370
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Met Ala Ala Glu Arg Val Phe Ile Ser Pro Ala Lys Tyr Val Gln Gly
1               5                   10                  15

Lys Asn Val Ile Thr Lys Ile Ala Asn Tyr Leu Glu Gly Ile Gly Asn
            20                  25                  30

Lys Thr Val Val Ile Ala Asp Glu Ile Val Trp Lys Ile Ala Gly His
        35                  40                  45

Thr Ile Val Asn Glu Leu Lys Lys Gly Asn Ile Ala Ala Glu Glu Val
    50                  55                  60

Val Phe Ser Gly Glu Ala Ser Arg Asn Glu Val Glu Arg Ile Ala Asn
65                  70                  75                  80

```
Ile Ala Arg Lys Ala Glu Ala Ile Val Ile Gly Val Gly Gly Gly
                85                  90                  95

Lys Thr Leu Asp Thr Ala Lys Ala Val Ala Asp Glu Leu Asp Ala Tyr
            100                 105                 110

Ile Val Ile Val Pro Thr Ala Ala Ser Thr Asp Ala Pro Thr Ser Ala
        115                 120                 125

Leu Ser Val Ile Tyr Ser Asp Asp Gly Val Phe Glu Ser Tyr Arg Phe
130                 135                 140

Tyr Lys Lys Asn Pro Asp Leu Val Leu Val Asp Thr Lys Ile Ile Ala
145                 150                 155                 160

Asn Ala Pro Pro Arg Leu Leu Ala Ser Gly Ile Ala Asp Ala Leu Ala
                165                 170                 175

Thr Trp Val Glu Ala Arg Ser Val Ile Lys Ser Gly Gly Lys Thr Met
            180                 185                 190

Ala Gly Gly Ile Pro Thr Ile Ala Ala Glu Ala Ile Ala Glu Lys Cys
        195                 200                 205

Glu Gln Thr Leu Phe Lys Tyr Gly Lys Leu Ala Tyr Glu Ser Val Lys
    210                 215                 220

Ala Lys Val Val Thr Pro Ala Leu Glu Ala Val Val Glu Ala Asn Thr
225                 230                 235                 240

Leu Leu Ser Gly Leu Gly Phe Glu Ser Gly Gly Leu Ala Ala Ala His
                245                 250                 255

Ala Ile His Asn Gly Phe Thr Ala Leu Glu Gly Glu Ile His His Leu
            260                 265                 270

Thr His Gly Glu Lys Val Ala Phe Gly Thr Leu Val Gln Leu Ala Leu
        275                 280                 285

Glu Glu His Ser Gln Gln Glu Ile Glu Arg Tyr Ile Glu Leu Tyr Leu
    290                 295                 300

Cys Leu Asp Leu Pro Val Thr Leu Glu Asp Ile Lys Leu Lys Asp Ala
305                 310                 315                 320

Ser Arg Glu Asp Ile Leu Lys Val Ala Lys Ala Ala Thr Ala Glu Gly
                325                 330                 335

Glu Thr Ile His Asn Ala Phe Asn Val Thr Ala Asp Asp Val Ala Asp
            340                 345                 350

Ala Ile Phe Ala Ala Asp Gln Tyr Ala Lys Ala Tyr Lys Glu Lys His
        355                 360                 365

Arg Lys
    370

<210> SEQ ID NO 221
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Thr Thr Ile Leu Val Val Arg Arg Asn Gly Gln Thr Val Met Gly Gly
1               5                   10                  15

Asp Gly Gln Val Thr Phe Gly Ser Thr Val Leu Lys Gly Asn Ala Arg
            20                  25                  30

Lys Val Arg Lys Leu Gly Glu Gly Lys Val Leu Ala Gly Phe Ala Gly
        35                  40                  45

Ser Val Ala Asp Ala Met Thr Leu Phe Asp Arg Phe Glu Ala Lys Leu
```

```
            50                  55                  60
Arg Glu Trp Gly Gly Asn Leu Thr Lys Ala Ala Val Glu Leu Ala Lys
 65                  70                  75                  80

Asp Trp Arg Thr Asp Arg Val Leu Arg Arg Leu Glu Ala Leu Leu Leu
                 85                  90                  95

Val Ala Asp Lys Glu Asn Ile Phe Ile Ile Ser Gly Asn Gly Glu Val
            100                 105                 110

Ile Gln Pro Asp Asp Ala Ala Ile Gly Ser Gly Gly Pro Tyr
        115                 120                 125

Ala Leu Ala Ala Ala Lys Ala Leu Leu Arg Asn Thr Asp Leu Ser Ala
        130                 135                 140

Arg Glu Ile Val Glu Lys Ala Met Thr Ile Ala Gly Glu Ile Cys Ile
145                 150                 155                 160

Tyr Thr Asn Gln Asn Ile Val Ile Glu Glu Val
                165                 170
```

<210> SEQ ID NO 222
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

```
Met Phe Arg Ile Leu Thr Ile Asn Pro Gly Ser Thr Ser Thr Lys Leu
 1               5                  10                  15

Ser Ile Phe Glu Asp Glu Arg Met Val Lys Met Gln Asn Phe Ser His
                20                  25                  30

Ser Pro Asp Glu Leu Gly Arg Phe Gln Lys Ile Leu Asp Gln Leu Glu
            35                  40                  45

Phe Arg Glu Lys Ile Ala Arg Gln Phe Val Glu Glu Thr Gly Tyr Ser
        50                  55                  60

Leu Ser Ser Phe Ser Ala Phe Val Ser Arg Gly Gly Leu Leu Asp Pro
 65                  70                  75                  80

Ile Pro Gly Gly Val Tyr Leu Val Asp Gly Leu Met Ile Lys Thr Leu
                85                  90                  95

Lys Ser Gly Lys Asn Gly Glu His Ala Ser Asn Leu Gly Ala Ile Ile
            100                 105                 110

Ala His Arg Phe Ser Ser Glu Thr Gly Val Pro Ala Tyr Val Val Asp
        115                 120                 125

Pro Val Val Asp Glu Met Glu Asp Val Ala Arg Val Ser Gly His
        130                 135                 140

Pro Asn Tyr Gln Arg Lys Ser Ile Phe His Ala Leu Asn Gln Lys Thr
145                 150                 155                 160

Val Ala Lys Glu Val Ala Arg Met Met Asn Lys Arg Tyr Glu Met
                165                 170                 175

Asn Leu Val Val Ala His Met Gly Gly Gly Ile Ser Ile Ala Ala His
                180                 185                 190

Arg Lys Gly Arg Val Ile Asp Val Asn Asn Ala Leu Asp Gly Asp Gly
            195                 200                 205

Pro Phe Thr Pro Glu Arg Ser Gly Thr Leu Pro Leu Thr Gln Leu Val
        210                 215                 220

Asp Leu Cys Phe Ser Gly Lys Phe Thr Tyr Glu Glu Met Lys Lys Arg
225                 230                 235                 240
```

Ile Val Gly Asn Gly Gly Leu Val Ala Tyr Leu Gly Thr Ser Asp Ala
            245                 250                 255

Arg Glu Val Val Arg Arg Ile Lys Gln Gly Asp Glu Trp Ala Lys Arg
        260                 265                 270

Val Tyr Arg Ala Met Ala Tyr Gln Ile Ala Lys Trp Ile Gly Lys Met
    275                 280                 285

Ala Ala Val Leu Lys Gly Glu Val Asp Phe Ile Val Leu Thr Gly Gly
290                 295                 300

Leu Ala His Glu Lys Glu Phe Leu Val Pro Trp Ile Thr Lys Arg Val
305                 310                 315                 320

Ser Phe Ile Ala Pro Val Leu Val Phe Pro Gly Ser Asn Glu Glu Lys
            325                 330                 335

Ala Leu Ala Leu Ser Ala Leu Arg Val Leu Arg Gly Glu Glu Lys Pro
        340                 345                 350

Lys Asn Tyr Ser Glu Glu Ser Arg Arg Trp Arg Glu Arg Tyr Asp Ser
    355                 360                 365

Tyr Leu Asp Gly Ile Leu Arg His His His His His
370                 375                 380

<210> SEQ ID NO 223
<211> LENGTH: 362
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Lys Thr Thr Ile Ser Val Ile Lys Ala Asp Ile Gly Ser Leu Ala Gly
1               5                   10                  15

His His Ile Val His Pro Asp Thr Met Ala Ala Ala Asn Lys Val Leu
            20                  25                  30

Ala Ser Ala Lys Glu Gln Gly Ile Ile Leu Asp Tyr Tyr Ile Thr His
        35                  40                  45

Val Gly Asp Asp Leu Gln Leu Ile Met Thr His Thr Arg Gly Glu Leu
    50                  55                  60

Asp Thr Lys Val His Glu Thr Ala Trp Asn Ala Phe Lys Glu Ala Ala
65                  70                  75                  80

Lys Val Ala Lys Asp Leu Gly Leu Tyr Ala Ala Gly Gln Asp Leu Leu
                85                  90                  95

Ser Asp Ser Phe Ser Gly Asn Val Arg Gly Leu Gly Pro Gly Val Ala
            100                 105                 110

Glu Met Glu Ile Glu Glu Arg Ala Ser Glu Pro Ile Ala Ile Phe Met
        115                 120                 125

Ala Asp Lys Thr Glu Pro Gly Ala Tyr Asn Leu Pro Leu Tyr Lys Met
    130                 135                 140

Phe Ala Asp Pro Phe Asn Thr Pro Gly Leu Val Ile Asp Pro Thr Met
145                 150                 155                 160

His Gly Gly Phe Lys Phe Glu Val Leu Asp Val Tyr Gln Gly Glu Ala
                165                 170                 175

Val Met Leu Ser Ala Pro Gln Glu Ile Tyr Asp Leu Leu Ala Leu Ile
            180                 185                 190

Gly Thr Pro Ala Arg Tyr Val Ile Arg Arg Val Tyr Arg Asn Glu Asp
        195                 200                 205

Asn Leu Leu Ala Ala Val Val Ser Ile Glu Arg Leu Asn Leu Ile Ala
    210                 215                 220

```
Gly Lys Tyr Val Gly Lys Asp Asp Pro Val Met Ile Val Arg Leu Gln
225                 230                 235                 240

His Gly Leu Pro Ala Leu Gly Glu Ala Leu Glu Ala Phe Ala Phe Pro
                245                 250                 255

His Leu Val Pro Gly Trp Met Arg Gly Ser His Tyr Gly Pro Leu Met
            260                 265                 270

Pro Val Ser Gln Arg Asp Ala Lys Ala Thr Arg Phe Asp Gly Pro Pro
        275                 280                 285

Arg Leu Leu Gly Leu Gly Phe Asn Val Lys Asn Gly Arg Leu Val Gly
    290                 295                 300

Pro Thr Asp Leu Phe Asp Asp Pro Ala Phe Asp Glu Thr Arg Arg Leu
305                 310                 315                 320

Ala Asn Ile Val Ala Asp Tyr Met Arg Arg His Gly Pro Phe Met Pro
                325                 330                 335

His Arg Leu Glu Pro Thr Glu Met Glu Tyr Thr Thr Leu Pro Leu Ile
            340                 345                 350

Leu Glu Lys Leu Lys Asp Arg Phe Lys Lys
        355                 360

<210> SEQ ID NO 224
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Met Asn Ile Arg Glu Arg Lys Arg Lys His Leu Glu Ala Cys Leu Glu
1               5                   10                  15

Gly Glu Val Ala Tyr Gln Lys Thr Thr Thr Gly Leu Glu Gly Phe Arg
            20                  25                  30

Leu Arg Tyr Gln Ala Leu Ala Gly Leu Ala Leu Ser Glu Val Asp Leu
        35                  40                  45

Thr Thr Pro Phe Leu Gly Lys Thr Leu Lys Ala Pro Phe Leu Ile Gly
50                  55                  60

Ala Met Thr Gly Gly Glu Glu Asn Gly Glu Arg Ile Asn Leu Ala Leu
65                  70                  75                  80

Ala Glu Ala Ala Glu Ala Leu Gly Val Gly Met Met Leu Gly Ser Gly
                85                  90                  95

Arg Ile Leu Leu Glu Arg Pro Glu Ala Leu Arg Ser Phe Arg Val Arg
            100                 105                 110

Lys Val Ala Pro Lys Ala Leu Leu Ile Ala Asn Leu Gly Leu Ala Gln
        115                 120                 125

Leu Arg Arg Tyr Gly Arg Asp Asp Leu Leu Arg Leu Val Glu Met Leu
    130                 135                 140

Glu Ala Asp Ala Leu Ala Phe His Val Asn Pro Leu Gln Glu Ala Val
145                 150                 155                 160

Gln Arg Gly Asp Thr Asp Phe Arg Gly Leu Val Glu Arg Leu Ala Glu
                165                 170                 175

Leu Leu Pro Leu Pro Phe Pro Val Met Val Lys Glu Val Gly His Gly
            180                 185                 190

Leu Ser Arg Glu Ala Ala Leu Ala Leu Arg Asp Leu Pro Leu Ala Ala
        195                 200                 205

Val Asp Val Ala Gly Ala Gly Gly Thr Ser Trp Ala Arg Val Glu Glu
```

Trp Val Arg Phe Gly Glu Val Arg His Pro Glu Leu Cys Glu Ile Gly
225                 230                 235                 240

Ile Pro Thr Ala Arg Ala Ile Leu Glu Val Arg Glu Val Leu Pro His
                245                 250                 255

Leu Pro Leu Val Ala Ser Gly Val Tyr Thr Gly Thr Asp Gly Ala
                260                 265                 270

Lys Ala Leu Ala Leu Gly Ala Asp Leu Leu Ala Val Ala Arg Pro Leu
                275                 280                 285

Leu Arg Pro Ala Leu Glu Gly Ala Glu Arg Val Ala Ala Trp Ile Gly
290                 295                 300

Asp Tyr Leu Glu Glu Leu Arg Thr Ala Leu Phe Ala Ile Gly Ala Arg
305                 310                 315                 320

Asn Pro Lys Glu Ala Arg Gly Arg Val Glu Arg Val
                325                 330

<210> SEQ ID NO 225
<211> LENGTH: 375
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 225

Met Phe Arg Ile Leu Thr Ile Asn Pro Gly Ser Thr Ser Thr Lys Leu
1               5                   10                  15

Ser Ile Phe Glu Asp Glu Arg Met Val Lys Met Gln Asn Phe Ser His
                20                  25                  30

Ser Pro Asp Glu Leu Gly Arg Phe Gln Lys Ile Leu Asp Gln Leu Glu
            35                  40                  45

Phe Arg Glu Lys Ile Ala Arg Gln Phe Val Glu Glu Thr Gly Tyr Ser
    50                  55                  60

Leu Ser Ser Phe Ser Ala Phe Val Ser Arg Gly Gly Leu Leu Asp Pro
65                  70                  75                  80

Ile Pro Gly Gly Val Tyr Leu Val Asp Gly Leu Met Ile Lys Thr Leu
                85                  90                  95

Lys Ser Gly Lys Asn Gly Glu His Ala Ser Asn Leu Gly Ala Ile Ile
            100                 105                 110

Ala His Arg Phe Ser Ser Glu Thr Gly Val Pro Ala Tyr Val Val Asp
        115                 120                 125

Pro Val Val Asp Glu Met Glu Asp Val Ala Arg Val Ser Gly His
    130                 135                 140

Pro Asn Tyr Gln Arg Lys Ser Ile Phe His Ala Leu Asn Gln Lys Thr
145                 150                 155                 160

Val Ala Lys Glu Val Ala Arg Met Met Asn Lys Arg Tyr Glu Glu Met
                165                 170                 175

Asn Leu Val Val Ala His Met Gly Gly Gly Ile Ser Ile Ala Ala His
            180                 185                 190

Arg Lys Gly Arg Val Ile Asp Val Asn Asn Ala Leu Asp Gly Asp Gly
        195                 200                 205

Pro Phe Thr Pro Glu Arg Ser Gly Thr Leu Pro Leu Thr Gln Leu Val
    210                 215                 220

Asp Leu Cys Phe Ser Gly Lys Phe Thr Tyr Glu Glu Met Lys Lys Arg
225                 230                 235                 240

```
Ile Val Gly Asn Gly Gly Leu Val Ala Tyr Leu Gly Thr Ser Asp Ala
            245                 250                 255

Arg Glu Val Val Arg Arg Ile Lys Gln Gly Asp Glu Trp Ala Lys Arg
        260                 265                 270

Val Tyr Arg Ala Met Ala Tyr Gln Ile Ala Lys Trp Ile Gly Lys Met
    275                 280                 285

Ala Ala Val Leu Lys Gly Glu Val Asp Phe Ile Val Leu Thr Gly Gly
290                 295                 300

Leu Ala His Glu Lys Glu Phe Leu Val Pro Trp Ile Thr Lys Arg Val
305                 310                 315                 320

Ser Phe Ile Ala Pro Val Leu Val Phe Pro Gly Ser Asn Glu Glu Lys
            325                 330                 335

Ala Leu Ala Leu Ser Ala Leu Arg Val Leu Arg Gly Glu Glu Lys Pro
        340                 345                 350

Lys Asn Tyr Ser Glu Glu Ser Arg Arg Trp Arg Glu Arg Tyr Asp Ser
    355                 360                 365

Tyr Leu Asp Gly Ile Leu Arg
370                 375

<210> SEQ ID NO 226
<211> LENGTH: 502
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Met Gly Ser Asp Lys Ile His His His His His Met Lys Glu Ile
1               5                   10                  15

Asp Glu Leu Thr Ile Lys Glu Tyr Gly Val Asp Ser Arg Ile Leu Met
            20                  25                  30

Glu Arg Ala Gly Ile Ser Val Val Leu Ala Met Glu Glu Glu Leu Gly
        35                  40                  45

Asn Leu Ser Asp Tyr Arg Phe Leu Val Leu Cys Gly Gly Gly Asn Asn
50                  55                  60

Gly Gly Asp Gly Phe Val Val Ala Arg Asn Leu Leu Gly Val Val Lys
65                  70                  75                  80

Asp Val Leu Val Val Phe Leu Gly Lys Lys Lys Thr Pro Asp Cys Glu
            85                  90                  95

Tyr Asn Tyr Gly Leu Tyr Lys Lys Phe Gly Gly Lys Val Val Glu Gln
        100                 105                 110

Phe Glu Pro Ser Ile Leu Asn Glu Phe Asp Val Val Asp Ala Ile
    115                 120                 125

Phe Gly Thr Gly Leu Arg Gly Glu Ile Thr Gly Glu Tyr Ala Glu Ile
130                 135                 140

Ile Asn Leu Val Asn Lys Ser Gly Lys Val Val Ser Val Asp Val
145                 150                 155                 160

Pro Ser Gly Ile Asp Ser Asn Thr Gly Lys Val Leu Arg Thr Ala Val
            165                 170                 175

Lys Ala Asp Leu Thr Val Thr Phe Gly Val Pro Lys Ile Gly His Ile
        180                 185                 190

Leu Phe Pro Gly Arg Asp Leu Thr Gly Lys Leu Lys Val Ala Asn Ile
    195                 200                 205

Gly His Pro Val His Leu Ile Asn Ser Ile Asn Arg Tyr Val Ile Thr
210                 215                 220
```

```
Arg Glu Met Val Arg Ser Leu Leu Pro Glu Arg Pro Arg Asp Ser His
225                 230                 235                 240

Lys Gly Thr Tyr Gly Lys Val Leu Ile Ile Ala Gly Ser Arg Leu Tyr
            245                 250                 255

Ser Gly Ala Pro Val Leu Ser Gly Met Gly Ser Leu Lys Val Gly Thr
            260                 265                 270

Gly Leu Val Lys Leu Ala Val Pro Phe Pro Gln Asn Leu Ile Ala Thr
            275                 280                 285

Ser Arg Phe Pro Glu Leu Ile Ser Val Pro Ile Asp Thr Glu Lys Gly
            290                 295                 300

Phe Phe Ser Leu Gln Asn Leu Gln Glu Cys Leu Glu Leu Ser Lys Asp
305                 310                 315                 320

Val Asp Val Val Ala Ile Gly Pro Gly Leu Gly Asn Asn Glu His Val
                325                 330                 335

Arg Glu Phe Val Asn Glu Phe Leu Lys Thr Leu Glu Lys Pro Ala Val
                340                 345                 350

Ile Asp Ala Asp Ala Ile Asn Val Leu Asp Thr Ser Val Leu Lys Glu
                355                 360                 365

Arg Lys Ser Pro Ala Val Leu Thr Pro His Pro Gly Glu Met Ala Arg
370                 375                 380

Leu Val Lys Lys Thr Val Gly Asp Val Lys Tyr Asn Tyr Glu Leu Ala
385                 390                 395                 400

Glu Glu Phe Ala Lys Glu Asn Asp Cys Val Leu Val Leu Lys Ser Ala
                405                 410                 415

Thr Thr Ile Val Thr Asp Gly Glu Lys Thr Leu Phe Asn Ile Thr Gly
                420                 425                 430

Asn Thr Gly Leu Ser Lys Gly Gly Ser Gly Asp Val Leu Thr Gly Met
            435                 440                 445

Ile Ala Gly Phe Ile Ala Gln Gly Leu Ser Pro Leu Glu Ala Ser Thr
            450                 455                 460

Val Ser Val Tyr Leu His Gly Phe Ala Ala Glu Leu Phe Glu Gln Asp
465                 470                 475                 480

Glu Arg Gly Leu Thr Ala Ser Glu Leu Leu Arg Leu Ile Pro Glu Ala
                485                 490                 495

Ile Arg Arg Leu Lys Glu
            500

<210> SEQ ID NO 227
<211> LENGTH: 430
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Met Met Val Leu Arg Met Lys Val Glu Trp Tyr Leu Asp Phe Val Asp
1               5                   10                  15

Leu Asn Tyr Glu Pro Gly Arg Asp Glu Leu Ile Val Glu Tyr Tyr Phe
            20                  25                  30

Glu Pro Asn Gly Val Ser Pro Glu Ala Ala Gly Arg Ile Ala Ser
            35                  40                  45

Glu Ser Ser Ile Gly Thr Trp Thr Thr Leu Trp Lys Leu Pro Glu Met
50                  55                  60

Ala Lys Arg Ser Met Ala Lys Val Phe Tyr Leu Glu Lys His Gly Glu
```

65                  70                  75                  80
Gly Tyr Ile Ala Lys Ile Ala Tyr Pro Leu Thr Leu Phe Glu Glu Gly
                85                  90                  95

Ser Leu Val Gln Leu Phe Ser Ala Val Ala Gly Asn Val Phe Gly Met
            100                 105                 110

Lys Ala Leu Lys Asn Leu Arg Leu Leu Asp Phe His Pro Pro Tyr Glu
        115                 120                 125

Tyr Leu Arg His Phe Lys Gly Pro Gln Phe Gly Val Gln Gly Ile Arg
    130                 135                 140

Glu Phe Met Gly Val Lys Asp Arg Pro Leu Thr Ala Thr Val Pro Lys
145                 150                 155                 160

Pro Lys Met Gly Trp Ser Val Glu Glu Tyr Ala Glu Ile Ala Tyr Glu
                165                 170                 175

Leu Trp Ser Gly Gly Ile Asp Leu Leu Lys Asp Asp Glu Asn Phe Thr
            180                 185                 190

Ser Phe Pro Phe Asn Arg Phe Glu Glu Arg Val Arg Lys Leu Tyr Arg
        195                 200                 205

Val Arg Asp Arg Val Glu Ala Glu Thr Gly Glu Thr Lys Glu Tyr Leu
    210                 215                 220

Ile Asn Ile Thr Gly Pro Val Asn Ile Met Glu Lys Arg Ala Glu Met
225                 230                 235                 240

Val Ala Asn Glu Gly Gly Gln Tyr Val Met Ile Asp Ile Val Val Ala
                245                 250                 255

Gly Trp Ser Ala Leu Gln Tyr Met Arg Glu Val Thr Glu Asp Leu Gly
            260                 265                 270

Leu Ala Ile His Ala His Arg Ala Met His Ala Ala Phe Thr Arg Asn
        275                 280                 285

Pro Arg His Gly Ile Thr Met Leu Ala Leu Ala Lys Ala Ala Arg Met
    290                 295                 300

Ile Gly Val Asp Gln Ile His Thr Gly Thr Ala Val Gly Lys Met Ala
305                 310                 315                 320

Gly Asn Tyr Glu Glu Ile Lys Arg Ile Asn Asp Phe Leu Leu Ser Lys
                325                 330                 335

Trp Glu His Ile Arg Pro Val Phe Pro Val Ala Ser Gly Gly Leu His
            340                 345                 350

Pro Gly Leu Met Pro Glu Leu Ile Arg Leu Phe Gly Lys Asp Leu Val
        355                 360                 365

Ile Gln Ala Gly Gly Gly Val Met Gly His Pro Asp Gly Pro Arg Ala
    370                 375                 380

Gly Ala Lys Ala Leu Arg Asp Ala Ile Asp Ala Ala Ile Glu Gly Val
385                 390                 395                 400

Asp Leu Asp Glu Lys Ala Lys Ser Ser Pro Glu Leu Lys Lys Ser Leu
                405                 410                 415

Arg Glu Val Gly Leu Ser Lys Ala Lys Val Gly Val Gln His
            420                 425                 430

<210> SEQ ID NO 228
<211> LENGTH: 430
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

```
Met Met Val Leu Arg Met Lys Val Glu Trp Tyr Leu Asp Phe Val Asp
1               5                   10                  15

Leu Asn Tyr Glu Pro Gly Arg Asp Glu Leu Ile Val Glu Tyr Tyr Phe
            20                  25                  30

Glu Pro Asn Gly Val Ser Pro Glu Ala Ala Gly Arg Ile Ala Ser
        35                  40                  45

Glu Ser Ser Ile Gly Thr Trp Thr Thr Leu Trp Lys Leu Pro Glu Met
50              55                  60

Ala Lys Arg Ser Met Ala Lys Val Phe Tyr Leu Glu Lys His Gly Glu
65              70                  75                  80

Gly Tyr Ile Ala Lys Ile Ala Tyr Pro Leu Thr Leu Phe Glu Glu Gly
                85                  90                  95

Ser Leu Val Gln Leu Phe Ser Ala Val Ala Gly Asn Val Phe Gly Met
            100                 105                 110

Lys Ala Leu Lys Asn Leu Arg Leu Leu Asp Phe His Pro Pro Tyr Glu
            115                 120                 125

Tyr Leu Arg His Phe Lys Gly Pro Gln Phe Gly Val Gln Gly Ile Arg
        130                 135                 140

Glu Phe Met Gly Val Lys Asp Arg Pro Leu Thr Ala Thr Val Pro Lys
145                 150                 155                 160

Pro Lys Met Gly Trp Ser Val Glu Glu Tyr Ala Glu Ile Ala Tyr Glu
                165                 170                 175

Leu Trp Ser Gly Gly Ile Asp Leu Leu Lys Asp Asp Glu Asn Phe Thr
            180                 185                 190

Ser Phe Pro Phe Asn Arg Phe Glu Glu Arg Val Arg Lys Leu Tyr Arg
        195                 200                 205

Val Arg Asp Arg Val Glu Ala Glu Thr Gly Glu Thr Lys Glu Tyr Leu
    210                 215                 220

Ile Asn Ile Thr Gly Pro Val Asn Ile Met Glu Lys Arg Ala Glu Met
225                 230                 235                 240

Val Ala Asn Glu Gly Gly Gln Tyr Val Met Ile Asp Ile Val Val Ala
                245                 250                 255

Gly Trp Ser Ala Leu Gln Tyr Met Arg Glu Val Thr Glu Asp Leu Gly
            260                 265                 270

Leu Ala Ile His Ala His Arg Ala Met His Ala Ala Phe Thr Arg Asn
        275                 280                 285

Pro Arg His Gly Ile Thr Met Leu Ala Leu Ala Lys Ala Ala Arg Met
    290                 295                 300

Ile Gly Val Asp Gln Ile His Thr Gly Thr Ala Val Gly Lys Met Ala
305                 310                 315                 320

Gly Asn Tyr Glu Glu Ile Lys Arg Ile Asn Asp Phe Leu Leu Ser Lys
                325                 330                 335

Trp Glu His Ile Arg Pro Val Phe Pro Val Ala Ser Gly Gly Leu His
            340                 345                 350

Pro Gly Leu Met Pro Glu Leu Ile Arg Leu Phe Gly Lys Asp Leu Val
        355                 360                 365

Ile Gln Ala Gly Gly Gly Val Met Gly His Pro Asp Gly Pro Arg Ala
    370                 375                 380

Gly Ala Lys Ala Leu Arg Asp Ala Ile Asp Ala Ile Glu Gly Val
385                 390                 395                 400

Asp Leu Asp Glu Lys Ala Lys Ser Ser Pro Glu Leu Lys Lys Ser Leu
                405                 410                 415

Arg Glu Val Gly Leu Ser Lys Ala Lys Val Gly Val Gln His
```

<210> SEQ ID NO 229
<211> LENGTH: 444
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 229

```
Met Val Glu Lys Phe Asp Thr Ile Tyr Asp Tyr Tyr Val Asp Lys Gly
1               5                   10                  15

Tyr Glu Pro Ser Lys Lys Arg Asp Ile Ile Ala Val Phe Arg Val Thr
            20                  25                  30

Pro Ala Glu Gly Tyr Thr Ile Glu Gln Ala Ala Gly Ala Val Ala Ala
        35                  40                  45

Glu Ser Ser Thr Gly Thr Trp Thr Thr Leu Tyr Pro Trp Tyr Glu Gln
50                  55                  60

Glu Arg Trp Ala Asp Leu Ser Ala Lys Ala Tyr Asp Phe His Asp Met
65                  70                  75                  80

Gly Asp Gly Ser Trp Ile Val Arg Ile Ala Tyr Pro Phe His Ala Phe
                85                  90                  95

Glu Glu Ala Asn Leu Pro Gly Leu Leu Ala Ser Ile Ala Gly Asn Ile
            100                 105                 110

Phe Gly Met Lys Arg Val Lys Gly Leu Arg Leu Glu Asp Leu Tyr Phe
        115                 120                 125

Pro Glu Lys Leu Ile Arg Glu Phe Asp Gly Pro Ala Phe Gly Ile Glu
    130                 135                 140

Gly Val Arg Lys Met Leu Glu Ile Lys Asp Arg Pro Ile Tyr Gly Val
145                 150                 155                 160

Val Pro Lys Pro Lys Val Gly Tyr Ser Pro Glu Glu Phe Glu Lys Leu
                165                 170                 175

Ala Tyr Asp Leu Leu Ser Asn Gly Ala Asp Tyr Met Lys Asp Asp Glu
            180                 185                 190

Asn Leu Thr Ser Pro Trp Tyr Asn Arg Phe Glu Glu Arg Ala Glu Ile
        195                 200                 205

Met Ala Lys Ile Ile Asp Lys Val Glu Asn Glu Thr Gly Glu Lys Lys
    210                 215                 220

Thr Trp Phe Ala Asn Ile Thr Ala Asp Leu Leu Glu Met Glu Gln Arg
225                 230                 235                 240

Leu Glu Val Leu Ala Asp Leu Gly Leu Lys His Ala Met Val Asp Val
                245                 250                 255

Val Ile Thr Gly Trp Gly Ala Leu Arg Tyr Ile Arg Asp Leu Ala Ala
            260                 265                 270

Asp Tyr Gly Leu Ala Ile His Gly His Arg Ala Met His Ala Ala Phe
        275                 280                 285

Thr Arg Asn Pro Tyr His Gly Ile Ser Met Phe Val Leu Ala Lys Leu
    290                 295                 300

Tyr Arg Leu Ile Gly Ile Asp Gln Leu His Val Gly Thr Ala Gly Ala
305                 310                 315                 320

Gly Lys Leu Glu Gly Gly Lys Trp Asp Val Ile Gln Asn Ala Arg Ile
                325                 330                 335

Leu Arg Glu Ser His Tyr Lys Pro Asp Glu Asn Asp Val Phe His Leu
            340                 345                 350
```

```
Glu Gln Lys Phe Tyr Ser Ile Lys Ala Ala Phe Pro Thr Ser Ser Gly
            355                 360                 365

Gly Leu His Pro Gly Asn Ile Gln Pro Val Ile Glu Ala Leu Gly Thr
        370                 375                 380

Asp Ile Val Leu Gln Leu Gly Gly Thr Leu Gly His Pro Asp Gly
385                 390                 395                 400

Pro Ala Ala Gly Ala Arg Ala Val Arg Gln Ala Ile Asp Ala Ile Met
                405                 410                 415

Gln Gly Ile Pro Leu Asp Glu Tyr Ala Lys Thr His Lys Glu Leu Ala
                420                 425                 430

Arg Ala Leu Glu Lys Trp Gly His Val Thr Pro Val
        435                 440

<210> SEQ ID NO 230
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Met Ala Asn Leu Thr Glu Lys Phe Leu Arg Ile Phe Ala Arg Arg Gly
1               5                   10                  15

Lys Ser Ile Ile Leu Ala Tyr Asp His Gly Ile Glu His Gly Pro Ala
            20                  25                  30

Asp Phe Met Asp Asn Pro Asp Ser Ala Asp Pro Glu Tyr Ile Leu Arg
        35                  40                  45

Leu Ala Arg Asp Ala Gly Phe Asp Gly Val Val Phe Gln Arg Gly Ile
    50                  55                  60

Ala Glu Lys Tyr Tyr Asp Gly Ser Val Pro Leu Ile Leu Lys Leu Asn
65                  70                  75                  80

Gly Lys Thr Thr Leu Tyr Asn Gly Glu Pro Val Ser Val Ala Asn Cys
                85                  90                  95

Ser Val Glu Glu Ala Val Ser Leu Gly Ala Ser Ala Val Gly Tyr Thr
            100                 105                 110

Ile Tyr Pro Gly Ser Gly Phe Glu Trp Lys Met Phe Glu Glu Leu Ala
        115                 120                 125

Arg Ile Lys Arg Asp Ala Val Lys Phe Asp Leu Pro Leu Val Val Glu
    130                 135                 140

Ser Phe Pro Arg Gly Gly Lys Val Val Asn Glu Thr Ala Pro Glu Ile
145                 150                 155                 160

Val Ala Tyr Ala Ala Arg Ile Ala Leu Glu Leu Gly Ala Asp Ala Met
                165                 170                 175

Lys Ile Lys Tyr Thr Gly Asp Pro Lys Thr Phe Ser Trp Ala Val Lys
            180                 185                 190

Val Ala Gly Lys Val Pro Val Leu Met Ser Gly Gly Pro Lys Thr Lys
        195                 200                 205

Thr Glu Glu Asp Phe Leu Lys Gln Val Glu Gly Val Leu Glu Ala Gly
    210                 215                 220

Ala Leu Gly Ile Ala Val Gly Arg Asn Val Trp Gln Arg Arg Asp Ala
225                 230                 235                 240

Leu Lys Phe Ala Arg Ala Leu Ala Glu Leu Val Tyr Gly Gly Lys Lys
                245                 250                 255

Leu Ala Glu Pro Leu Asn Val
            260
```

<210> SEQ ID NO 231
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 231

```
Met Ser Pro Gly Pro Gln Ser Gly Gly Gln Glu Arg Gly Ser Met Glu
1               5                   10                  15

Arg Lys Met Val Glu Leu Glu Asp Thr Gly Leu Thr Phe Ala Thr Glu
            20                  25                  30

Val Asp Leu Glu Arg Leu Gln Ala Leu Ala Ala Glu Trp Leu Gln Val
        35                  40                  45

Ile Gly Glu Asp Pro Gly Arg Glu Gly Leu Leu Lys Thr Pro Glu Arg
    50                  55                  60

Val Ala Lys Ala Trp Ala Phe Leu Thr Arg Gly Tyr Arg Gln Arg Leu
65                  70                  75                  80

Glu Glu Val Val Gly Gly Ala Val Phe Pro Ala Glu Gly Ser Glu Met
                85                  90                  95

Val Val Val Lys Gly Val Glu Phe Tyr Ser Met Cys Glu His His Leu
            100                 105                 110

Leu Pro Phe Phe Gly Lys Val His Ile Gly Tyr Ile Pro Asp Gly Lys
        115                 120                 125

Ile Leu Gly Leu Ser Lys Phe Ala Arg Ile Val Asp Met Phe Ala Arg
    130                 135                 140

Arg Leu Gln Val Gln Glu Arg Leu Ala Val Gln Ile Ala Glu Ala Ile
145                 150                 155                 160

Gln Glu Val Leu Glu Pro Gln Gly Val Gly Val Val Glu Gly Val
                165                 170                 175

His Leu Cys Met Met Met Arg Gly Val Glu Lys Gln His Ser Arg Thr
            180                 185                 190

Val Thr Ser Ala Met Leu Gly Val Phe Arg Glu Asn Gln Lys Thr Arg
        195                 200                 205

Glu Glu Phe Leu Ser His Leu Arg Asp Gly Thr Ala
    210                 215                 220
```

<210> SEQ ID NO 232
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 232

```
Met Ser Pro Gly Pro Gln Ser Gly Gly Gln Glu Arg Gly Ser Met Glu
1               5                   10                  15

Arg Lys Met Val Glu Leu Glu Asp Thr Gly Leu Thr Phe Ala Thr Glu
            20                  25                  30

Val Asp Leu Glu Arg Leu Gln Ala Leu Ala Ala Glu Trp Leu Gln Val
        35                  40                  45

Ile Gly Glu Asp Pro Gly Arg Glu Gly Leu Leu Lys Thr Pro Glu Arg
    50                  55                  60

Val Ala Lys Ala Trp Ala Phe Leu Thr Arg Gly Tyr Arg Gln Arg Leu
65                  70                  75                  80
```

-continued

Glu Glu Val Val Gly Gly Ala Val Phe Pro Ala Glu Gly Ser Glu Met
                85                  90                  95

Val Val Val Lys Gly Val Glu Phe Tyr Ser Met Cys Glu His His Leu
            100                 105                 110

Leu Pro Phe Phe Gly Lys Val His Ile Gly Tyr Ile Pro Asp Gly Lys
            115                 120                 125

Ile Leu Gly Leu Ser Lys Phe Ala Arg Ile Val Asp Met Phe Ala Arg
130                 135                 140

Arg Leu Gln Val Gln Glu Arg Leu Ala Val Gln Ile Ala Glu Ala Ile
145                 150                 155                 160

Gln Glu Val Leu Glu Pro Gln Gly Val Gly Val Val Glu Gly Val
            165                 170                 175

His Leu Cys Met Met Met Arg Gly Val Glu Lys Gln His Ser Arg Thr
            180                 185                 190

Val Thr Ser Ala Met Leu Gly Val Phe Arg Glu Asn Gln Lys Thr Arg
            195                 200                 205

Glu Glu Phe Leu Ser His Leu Arg Asp Gly Thr Ala
            210                 215                 220

<210> SEQ ID NO 233
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Met Ser Pro Gly Pro Gln Ser Gly Gly Gln Glu Arg Gly Ser Met Glu
1               5                   10                  15

Arg Lys Met Val Glu Leu Glu Asp Thr Gly Leu Thr Phe Ala Thr Glu
            20                  25                  30

Val Asp Leu Glu Arg Leu Gln Ala Leu Ala Ala Glu Trp Leu Gln Val
            35                  40                  45

Ile Gly Glu Asp Pro Gly Arg Glu Gly Leu Leu Lys Thr Pro Glu Arg
50                  55                  60

Val Ala Lys Ala Trp Ala Phe Leu Thr Arg Gly Tyr Arg Gln Arg Leu
65                  70                  75                  80

Glu Glu Val Val Gly Gly Ala Val Phe Pro Ala Glu Gly Ser Glu Met
                85                  90                  95

Val Val Val Lys Gly Val Glu Phe Tyr Ser Met Cys Glu His His Leu
            100                 105                 110

Leu Pro Phe Phe Gly Lys Val His Ile Gly Tyr Ile Pro Asp Gly Lys
            115                 120                 125

Ile Leu Gly Leu Ser Lys Phe Ala Arg Ile Val Asp Met Phe Ala Arg
130                 135                 140

Arg Leu Gln Val Gln Glu Arg Leu Ala Val Gln Ile Ala Glu Ala Ile
145                 150                 155                 160

Gln Glu Val Leu Glu Pro Gln Gly Val Gly Val Val Glu Gly Val
            165                 170                 175

His Leu Cys Met Met Met Arg Gly Val Glu Lys Gln His Ser Arg Thr
            180                 185                 190

Val Thr Ser Ala Met Leu Gly Val Phe Arg Glu Asn Gln Lys Thr Arg
            195                 200                 205

Glu Glu Phe Leu Ser His Leu Arg Asp Gly Thr Ala

<210> SEQ ID NO 234
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Met Glu Leu Tyr Leu Asp Thr Ala Ser Leu Glu Ile Arg Glu Ile
1               5                   10                  15

Ala Ala Trp Gly Val Leu Ser Gly Val Thr Thr Asn Pro Thr Leu Val
            20                  25                  30

Ala Lys Ala Phe Ala Ala Lys Gly Glu Ala Leu Thr Glu Glu Ala Phe
        35                  40                  45

Ala Ala His Leu Arg Ala Ile Cys Glu Thr Val Gly Gly Pro Val Ser
    50                  55                  60

Ala Glu Val Thr Ala Leu Glu Ala Glu Ala Met Val Ala Glu Gly Arg
65                  70                  75                  80

Arg Leu Ala Ala Ile His Pro Asn Ile Val Val Lys Leu Pro Thr Thr
                85                  90                  95

Glu Glu Gly Leu Lys Ala Cys Lys Arg Leu Ser Ala Glu Gly Ile Lys
            100                 105                 110

Val Asn Met Thr Leu Ile Phe Ser Ala Asn Gln Ala Leu Leu Ala Ala
        115                 120                 125

Arg Ala Gly Ala Ser Tyr Val Ser Pro Phe Leu Gly Arg Val Asp Asp
    130                 135                 140

Ile Ser Trp Asp Gly Gly Glu Leu Leu Arg Glu Ile Val Glu Met Ile
145                 150                 155                 160

Gln Val Gln Asp Leu Pro Val Lys Val Ile Ala Ala Ser Ile Arg His
                165                 170                 175

Pro Arg His Val Thr Glu Ala Ala Leu Leu Gly Ala Asp Ile Ala Thr
            180                 185                 190

Met Pro His Ala Val Phe Lys Gln Leu Leu Lys His Pro Leu Thr Asp
        195                 200                 205

Ile Gly Leu Lys Arg Phe Leu Glu Asp Trp Glu Lys Val Lys Pro
    210                 215                 220

<210> SEQ ID NO 235
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Met Ile Thr Ala Phe Val Leu Ile Arg Pro Arg Gly Asn Arg Val Gln
1               5                   10                  15

Ala Leu Gly Glu Ala Ile Ala Glu Leu Pro Gln Val Ala Glu Val Tyr
            20                  25                  30

Ser Val Thr Gly Pro Tyr Asp Leu Val Ala Leu Val Arg Leu Lys Asp
        35                  40                  45

Val Glu Glu Leu Asp Asp Val Val Thr Gln Gly Ile Leu Ser Leu Glu
    50                  55                  60

Gly Val Glu Arg Thr Glu Thr Leu Leu Ala Phe Arg Ala Tyr Pro Arg

```
65                  70                  75                  80
Arg Leu Leu Asp Gln Gly Phe Ala Leu Gly Gln Gly
                85                  90

<210> SEQ ID NO 236
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Thr Thr Ile Leu Val Val Arg Arg Asn Gly Gln Thr Val Met Gly Gly
1               5                   10                  15

Asp Gly Gln Val Thr Phe Gly Ser Thr Val Leu Lys Gly Asn Ala Arg
            20                  25                  30

Lys Val Arg Lys Leu Gly Glu Gly Lys Val Leu Ala Gly Phe Ala Gly
        35                  40                  45

Ser Val Ala Asp Ala Met Thr Leu Phe Asp Arg Phe Glu Ala Lys Leu
    50                  55                  60

Arg Glu Trp Gly Gly Asn Leu Thr Lys Ala Ala Val Glu Leu Ala Lys
65                  70                  75                  80

Asp Trp Arg Thr Asp Arg Val Leu Arg Leu Glu Ala Leu Leu
                85                  90                  95

Val Ala Asp Lys Glu Asn Ile Phe Ile Ile Ser Gly Asn Gly Glu Val
            100                 105                 110

Ile Gln Pro Asp Asp Ala Ala Ile Gly Ser Gly Gly Pro Tyr
        115                 120                 125

Ala Leu Ala Ala Ala Lys Ala Leu Leu Arg Asn Thr Asp Leu Ser Ala
    130                 135                 140

Arg Glu Ile Val Glu Lys Ala Met Thr Ile Ala Gly Glu Ile Cys Ile
145                 150                 155                 160

Tyr Thr Asn Gln Asn Ile Val Ile Glu Glu Val
                165                 170

<210> SEQ ID NO 237
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Met Gly Ser Ser His His His His His His Ser Ser Gly Leu Val Pro
1               5                   10                  15

Arg Gly Ser Gly Thr Glu Asn Leu Thr Pro Gln His Met Ala Ser Met
            20                  25                  30

Ala Leu Thr Gly Thr Asp Arg Val Lys Arg Gly Met Ala Glu Met Gln
        35                  40                  45

Lys Gly Gly Val Ile Met Asp Val Val Asn Ala Glu Gln Ala Lys Ile
    50                  55                  60

Ala Glu Ala Ala Gly Ala Val Ala Val Met Ala Leu Glu Arg Val Pro
65                  70                  75                  80

Ala Asp Ile Arg Ala Ala Gly Gly Val Ala Arg Met Ala Asp Pro Thr
                85                  90                  95

Val Ile Glu Glu Val Met Asn Ala Val Ser Ile Pro Val Met Ala Lys
```

```
                    100                 105                 110
Val Arg Ile Gly His Tyr Val Glu Ala Arg Val Leu Glu Ala Leu Gly
            115                 120                 125

Val Asp Tyr Ile Asp Glu Ser Glu Val Leu Thr Pro Ala Asp Glu Glu
        130                 135                 140

Phe His Ile Asp Lys Arg Gln Phe Thr Val Pro Phe Val Cys Gly Cys
145                 150                 155                 160

Arg Asp Leu Gly Glu Ala Ala Arg Ile Ala Glu Gly Ala Ser Met
                165                 170                 175

Leu Arg Thr Lys Gly Glu Pro Gly Thr Gly Asn Ile Val Glu Ala Val
                180                 185                 190

Arg His Met Arg Lys Val Asn Ala Gln Ile Arg Lys Val Val Asn Met
            195                 200                 205

Ser Glu Asp Glu Leu Val Ala Glu Ala Lys Gln Leu Gly Ala Pro Val
        210                 215                 220

Glu Val Leu Arg Glu Ile Lys Arg Leu Gly Arg Leu Pro Val Val Asn
225                 230                 235                 240

Phe Ala Ala Gly Gly Val Thr Thr Pro Ala Asp Ala Ala Leu Met Met
                245                 250                 255

His Leu Gly Ala Asp Gly Val Phe Val Gly Ser Gly Ile Phe Lys Ser
                260                 265                 270

Glu Asn Pro Glu Lys Tyr Ala Arg Ala Ile Val Glu Ala Thr Thr His
            275                 280                 285

Tyr Glu Asp Tyr Glu Leu Ile Ala His Leu Ser Lys Gly Leu Gly Gly
        290                 295                 300

Ala Met Arg Gly Ile Asp Ile Ala Thr Leu Leu Pro Glu His Arg Met
305                 310                 315                 320

Gln Glu Arg Gly Trp
                325

<210> SEQ ID NO 238
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Phe Val Ala Glu Leu Asn Asn Leu Leu Gly Arg Glu Val Gln Val Val
1               5                   10                  15

Leu Ser Asn Gly Glu Val Tyr Lys Gly Val Leu His Ala Val Asp Asn
                20                  25                  30

Gln Leu Asn Ile Val Leu Ala Asn Ala Ser Lys Ala Gly Glu Lys
            35                  40                  45

Phe Asn Arg Val Phe Ile Met Tyr Arg Tyr Ile Val His Ile Asp Ser
        50                  55                  60

Thr Glu Arg Arg Ile Asp Met Arg Glu Phe Ala Lys Gln Ala Glu Lys
65                  70                  75                  80

Ile Phe Pro Gly Met Val Lys Tyr Ile Glu Glu Thr Asn Val Val Leu
                85                  90                  95

Ile Gly Asp Lys Val Arg Val Ser Glu Ile Gly Val Glu Gly Val Gly
            100                 105                 110

Pro Val Ala Glu Arg Ala Lys Arg Leu Phe Glu Glu Phe Leu Lys Arg
        115                 120                 125
```

Tyr Ser
    130

<210> SEQ ID NO 239
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Gly Ala Met Asn Phe Leu Ala Glu Thr Ala His Lys Val Leu Ala Glu
1               5                   10                  15

Ser Leu Asn Asn Leu Val Leu Val Lys Leu Lys Gly Asn Lys Glu Val
            20                  25                  30

Arg Gly Met Leu Arg Ser Tyr Asp Gln His Met Asn Leu Val Leu Ser
        35                  40                  45

Asp Ser Glu Glu Ile Gln Ser Asp Gly Ser Gly Lys Lys Leu Gly Thr
    50                  55                  60

Ile Val Ile Arg Gly Asp Asn Val Ile Leu Ile Ser Pro Leu Gln Thr
65                  70                  75                  80

Ser

<210> SEQ ID NO 240
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Met Gly Ser Asp Lys Ile His His His His His His Met Met Val Ile
1               5                   10                  15

Ser Glu Lys Val Arg Lys Ala Leu Asn Asp Gln Leu Asn Arg Glu Ile
            20                  25                  30

Tyr Ser Ser Tyr Leu Tyr Leu Ser Met Ala Thr Tyr Phe Asp Ala Glu
        35                  40                  45

Gly Phe Lys Gly Phe Ala His Trp Met Lys Lys Gln Ala Gln Glu Glu
    50                  55                  60

Leu Thr His Ala Met Lys Phe Tyr Glu Tyr Ile Tyr Glu Arg Gly Gly
65                  70                  75                  80

Arg Val Glu Leu Glu Ala Ile Glu Lys Pro Pro Ser Asn Trp Asn Gly
                85                  90                  95

Ile Lys Asp Ala Phe Glu Ala Ala Leu Lys His Glu Glu Phe Val Thr
            100                 105                 110

Gln Ser Ile Tyr Asn Ile Leu Glu Leu Ala Ser Glu Glu Lys Asp His
        115                 120                 125

Ala Thr Val Ser Phe Leu Lys Trp Phe Val Asp Glu Gln Val Glu Glu
    130                 135                 140

Glu Asp Gln Val Arg Glu Ile Leu Asp Leu Leu Glu Lys Ala Asn Gly
145                 150                 155                 160

Gln Met Ser Val Ile Phe Gln Leu Asp Arg Tyr Leu Gly Gln Arg Glu
                165                 170                 175

<210> SEQ ID NO 241
<211> LENGTH: 357
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 241

```
Arg Gly Ser His Met Glu Val Arg Asn Met Val Asp Tyr Glu Leu Leu
1               5                   10                  15

Lys Lys Val Val Glu Ala Pro Gly Val Ser Gly Tyr Glu Phe Leu Gly
            20                  25                  30

Ile Arg Asp Val Val Ile Glu Glu Ile Lys Asp Tyr Val Asp Glu Val
        35                  40                  45

Lys Val Asp Lys Leu Gly Asn Val Ile Ala His Lys Lys Gly Glu Gly
    50                  55                  60

Pro Lys Val Met Ile Ala Ala His Met Asp Gln Ile Gly Leu Met Val
65                  70                  75                  80

Thr His Ile Glu Lys Asn Gly Phe Leu Arg Val Ala Pro Ile Gly Gly
                85                  90                  95

Val Asp Pro Lys Thr Leu Ile Ala Gln Arg Phe Lys Val Trp Ile Asp
            100                 105                 110

Lys Gly Lys Phe Ile Tyr Gly Val Gly Ala Ser Val Pro Pro His Ile
        115                 120                 125

Gln Lys Pro Glu Asp Arg Lys Lys Ala Pro Asp Trp Asp Gln Ile Phe
    130                 135                 140

Ile Asp Ile Gly Ala Glu Ser Lys Glu Glu Ala Glu Asp Met Gly Val
145                 150                 155                 160

Lys Ile Gly Thr Val Ile Thr Trp Asp Gly Arg Leu Glu Arg Leu Gly
                165                 170                 175

Lys His Arg Phe Val Ser Ile Ala Phe Asp Asp Arg Ile Ala Val Tyr
            180                 185                 190

Thr Ile Leu Glu Val Ala Lys Gln Leu Lys Asp Ala Lys Ala Asp Val
        195                 200                 205

Tyr Phe Val Ala Thr Val Gln Glu Glu Val Gly Leu Arg Gly Ala Arg
    210                 215                 220

Thr Ser Ala Phe Gly Ile Glu Pro Asp Tyr Gly Phe Ala Ile Asp Val
225                 230                 235                 240

Thr Ile Ala Ala Asp Ile Pro Gly Thr Pro Glu His Lys Gln Val Thr
                245                 250                 255

His Leu Gly Lys Gly Thr Ala Ile Lys Ile Met Asp Arg Ser Val Ile
            260                 265                 270

Cys His Pro Thr Ile Val Arg Trp Leu Glu Glu Leu Ala Lys Lys His
        275                 280                 285

Glu Ile Pro Tyr Gln Leu Glu Ile Leu Leu Gly Gly Gly Thr Asp Ala
    290                 295                 300

Gly Ala Ile His Leu Thr Lys Ala Gly Val Pro Thr Gly Ala Leu Ser
305                 310                 315                 320

Val Pro Ala Arg Tyr Ile His Ser Asn Thr Glu Val Val Asp Glu Arg
                325                 330                 335

Asp Val Asp Ala Thr Val Glu Leu Met Thr Lys Ala Leu Glu Asn Ile
            340                 345                 350

His Glu Leu Lys Ile
        355
```

<210> SEQ ID NO 242
<211> LENGTH: 353

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Met Glu Val Arg Asn Met Val Asp Tyr Glu Leu Leu Lys Lys Val Val
1               5                   10                  15

Glu Ala Pro Gly Val Ser Gly Tyr Glu Phe Leu Gly Ile Arg Asp Val
            20                  25                  30

Val Ile Glu Glu Ile Lys Asp Tyr Val Asp Glu Val Lys Val Asp Lys
        35                  40                  45

Leu Gly Asn Val Ile Ala His Lys Lys Gly Glu Gly Pro Lys Val Met
    50                  55                  60

Ile Ala Ala His Met Asp Gln Ile Gly Leu Met Val Thr His Ile Glu
65                  70                  75                  80

Lys Asn Gly Phe Leu Arg Val Ala Pro Ile Gly Gly Val Asp Pro Lys
                85                  90                  95

Thr Leu Ile Ala Gln Arg Phe Lys Val Trp Ile Asp Lys Gly Lys Phe
            100                 105                 110

Ile Tyr Gly Val Gly Ala Ser Val Pro Pro His Ile Gln Lys Pro Glu
        115                 120                 125

Asp Arg Lys Lys Ala Pro Asp Trp Asp Gln Ile Phe Ile Asp Ile Gly
    130                 135                 140

Ala Glu Ser Lys Glu Glu Ala Glu Asp Met Gly Val Lys Ile Gly Thr
145                 150                 155                 160

Val Ile Thr Trp Asp Gly Arg Leu Glu Arg Leu Gly Lys His Arg Phe
                165                 170                 175

Val Ser Ile Ala Phe Asp Asp Arg Ile Ala Val Tyr Thr Ile Leu Glu
            180                 185                 190

Val Ala Lys Gln Leu Lys Asp Ala Lys Ala Asp Val Tyr Phe Val Ala
        195                 200                 205

Thr Val Gln Glu Glu Val Gly Leu Arg Gly Ala Arg Thr Ser Ala Phe
    210                 215                 220

Gly Ile Glu Pro Asp Tyr Gly Phe Ala Ile Asp Val Thr Ile Ala Ala
225                 230                 235                 240

Asp Ile Pro Gly Thr Pro Glu His Lys Gln Val Thr His Leu Gly Lys
                245                 250                 255

Gly Thr Ala Ile Lys Ile Met Asp Arg Ser Val Ile Cys His Pro Thr
            260                 265                 270

Ile Val Arg Trp Leu Glu Glu Leu Ala Lys Lys His Glu Ile Pro Tyr
        275                 280                 285

Gln Leu Glu Ile Leu Leu Gly Gly Thr Asp Ala Gly Ala Ile His
    290                 295                 300

Leu Thr Lys Ala Gly Val Pro Thr Gly Ala Leu Ser Val Pro Ala Arg
305                 310                 315                 320

Tyr Ile His Ser Asn Thr Glu Val Val Asp Glu Arg Asp Val Asp Ala
                325                 330                 335

Thr Val Glu Leu Met Thr Lys Ala Leu Glu Asn Ile His Glu Leu Lys
            340                 345                 350

Ile

<210> SEQ ID NO 243
<211> LENGTH: 353
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Met Glu Val Arg Asn Met Val Asp Tyr Glu Leu Leu Lys Lys Val Val
1               5                   10                  15

Glu Ala Pro Gly Val Ser Gly Tyr Glu Phe Leu Gly Ile Arg Asp Val
            20                  25                  30

Val Ile Glu Glu Ile Lys Asp Tyr Val Asp Glu Val Lys Val Asp Lys
        35                  40                  45

Leu Gly Asn Val Ile Ala His Lys Lys Gly Glu Gly Pro Lys Val Met
    50                  55                  60

Ile Ala Ala His Met Asp Gln Ile Gly Leu Met Val Thr His Ile Glu
65                  70                  75                  80

Lys Asn Gly Phe Leu Arg Val Ala Pro Ile Gly Gly Val Asp Pro Lys
                85                  90                  95

Thr Leu Ile Ala Gln Arg Phe Lys Val Trp Ile Asp Lys Gly Lys Phe
            100                 105                 110

Ile Tyr Gly Val Gly Ala Ser Val Pro Pro His Ile Gln Lys Pro Glu
        115                 120                 125

Asp Arg Lys Lys Ala Pro Asp Trp Asp Gln Ile Phe Ile Asp Ile Gly
    130                 135                 140

Ala Glu Ser Lys Glu Glu Ala Glu Asp Met Gly Val Lys Ile Gly Thr
145                 150                 155                 160

Val Ile Thr Trp Asp Gly Arg Leu Glu Arg Leu Gly Lys His Arg Phe
                165                 170                 175

Val Ser Ile Ala Phe Asp Asp Arg Ile Ala Val Tyr Thr Ile Leu Glu
            180                 185                 190

Val Ala Lys Gln Leu Lys Asp Ala Lys Ala Asp Val Tyr Phe Val Ala
        195                 200                 205

Thr Val Gln Glu Glu Val Gly Leu Arg Gly Ala Arg Thr Ser Ala Phe
    210                 215                 220

Gly Ile Glu Pro Asp Tyr Gly Phe Ala Ile Asp Val Thr Ile Ala Ala
225                 230                 235                 240

Asp Ile Pro Gly Thr Pro Glu His Lys Gln Val Thr His Leu Gly Lys
                245                 250                 255

Gly Thr Ala Ile Lys Ile Met Asp Arg Ser Val Ile Cys His Pro Thr
            260                 265                 270

Ile Val Arg Trp Leu Glu Glu Leu Ala Lys Lys His Glu Ile Pro Tyr
        275                 280                 285

Gln Leu Glu Ile Leu Gly Gly Gly Thr Asp Ala Gly Ala Ile His
    290                 295                 300

Leu Thr Lys Ala Gly Val Pro Thr Gly Ala Leu Ser Val Pro Ala Arg
305                 310                 315                 320

Tyr Ile His Ser Asn Thr Glu Val Val Asp Glu Arg Asp Val Asp Ala
                325                 330                 335

Thr Val Glu Leu Met Thr Lys Ala Leu Glu Asn Ile His Glu Leu Lys
            340                 345                 350

Ile

<210> SEQ ID NO 244
<211> LENGTH: 175
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Gly His Met Cys Ile Ile Lys Pro Met Asp Asp Val Val Lys Phe Ile
1               5                   10                  15

His Glu Val Gly Ser Leu Lys Leu Thr Pro Arg Ser Gly Trp Leu Lys
            20                  25                  30

Leu Gly Ile Arg Leu Pro Glu Ser Val Ala Glu His Ser Phe Arg Ala
        35                  40                  45

Ala Ile Ile Ala Phe Ile Leu Ala Leu Lys Ser Gly Glu Ser Val Glu
    50                  55                  60

Lys Ala Cys Lys Ala Ala Thr Ala Ala Leu Phe His Asp Leu His Glu
65                  70                  75                  80

Ala Arg Thr Met Asp Leu His Lys Ile Ala Arg Arg Tyr Val Ser Cys
                85                  90                  95

Asp Glu Glu Gly Ala Arg Glu Glu Gln Leu Ser Trp Met Glu Ser Lys
            100                 105                 110

Pro Asp Phe Ser Asp Val Glu Val Tyr Val Ser Asp Ala Asp Lys Leu
        115                 120                 125

Glu Leu Ala Phe Gln Gly Val Glu Tyr Ser Gln Gln Val Ser Tyr Ala
    130                 135                 140

Ile Arg Phe Ala Glu Asn Val Glu Leu Lys Thr Asp Ala Ala Lys Glu
145                 150                 155                 160

Ile Tyr Arg Val Leu Met Glu Arg Lys Asn Pro Val Trp Trp Arg
                165                 170                 175

<210> SEQ ID NO 245
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Met Gln Glu Lys Pro Gln Glu Pro Lys Val Val Gly Val Ile Leu
1               5                   10                  15

Glu Lys Ser Gly Leu Asp Ile Lys Lys Leu Val Asp Lys Leu Val Lys
            20                  25                  30

Ala Thr Ala Ala Glu Phe Thr Thr Tyr Tyr Tyr Thr Ile Leu Arg
        35                  40                  45

Met His Leu Thr Gly Met Glu Gly Glu Gly Leu Lys Glu Ile Ala Glu
    50                  55                  60

Asp Ala Arg Leu Glu Asp Arg Leu His Phe Glu Leu Met Thr Gln Arg
65                  70                  75                  80

Ile Tyr Glu Leu Gly Gly Gly Leu Pro Arg Asp Ile Arg Gln Leu Ala
                85                  90                  95

Asp Ile Ser Ala Cys Ser Asp Ala Tyr Leu Pro Glu Asn Trp Lys Asp
            100                 105                 110

Pro Lys Glu Ile Leu Lys Val Leu Leu Glu Ala Glu Gln Cys Ala Ile
        115                 120                 125

Arg Thr Trp Lys Glu Val Cys Asp Met Thr Tyr Gly Lys Asp Pro Arg
    130                 135                 140
```

Thr Tyr Asp Leu Ala Gln Arg Ile Leu Gln Glu Glu Ile Glu His Glu
145                 150                 155                 160

Ala Trp Phe Leu Glu Leu Leu Tyr Gly Arg Pro Ser Gly His Phe Arg
                165                 170                 175

Arg Ser Ser Pro Gly Asn Ala Pro Tyr Ser Lys Lys
            180                 185

<210> SEQ ID NO 246
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Lys Met Glu Arg Lys Asn Val Trp His His Arg Lys Lys Glu Glu Ile
1               5                   10                  15

Glu Ala Phe Ser Lys Glu Tyr Met Glu Phe Met Ser Lys Ala Lys Thr
                20                  25                  30

Glu Arg Met Thr Val Lys Glu Ile Lys Arg Ile Leu Asp Glu Ser Gly
            35                  40                  45

Phe Val Pro Leu Glu Asp Phe Ala Gly Asp Pro Met Asn Met Thr Val
    50                  55                  60

Tyr Ala Val Asn Arg Gly Lys Ala Ile Ala Phe Arg Val Val Asp
65                  70                  75                  80

Asp Leu Lys Arg Gly Leu Asn Leu Val Val Ala His Ile Asp Ser Pro
                85                  90                  95

Arg Leu Asp Phe Lys Pro Asn Pro Leu Ile Glu Asp Glu Gln Ile Ala
            100                 105                 110

Leu Phe Lys Thr His Tyr Tyr Gly Gly Ile Lys Lys Tyr His Trp Leu
        115                 120                 125

Ser Ile Pro Leu Glu Ile His Gly Val Leu Phe Lys Asn Asp Gly Thr
    130                 135                 140

Glu Ile Glu Ile His Ile Gly Asp Lys Pro Glu Asp Pro Val Phe Thr
145                 150                 155                 160

Ile Pro Asp Leu Leu Pro His Leu Asp Lys Glu Asp Ala Lys Ile Ser
                165                 170                 175

Glu Lys Phe Lys Gly Glu Asn Leu Met Leu Ile Ala Gly Thr Ile Pro
            180                 185                 190

Leu Ser Gly Glu Glu Lys Glu Ala Val Lys Thr Asn Val Leu Lys Ile
        195                 200                 205

Leu Asn Glu Met Tyr Gly Ile Thr Glu Glu Asp Phe Val Ser Gly Glu
    210                 215                 220

Ile Glu Val Val Pro Ala Phe Ser Pro Arg Glu Val Gly Met Asp Arg
225                 230                 235                 240

Ser Leu Ile Gly Ala Tyr Gly Gln Asp Asp Arg Ile Cys Ala Tyr Thr
                245                 250                 255

Ala Leu Arg Ala Leu Leu Ser Ala Asn Pro Glu Lys Ser Ile Gly Val
            260                 265                 270

Ile Phe Phe Asp Lys Glu Glu Ile Gly Ser Asp Gly Asn Thr Gly Ala
        275                 280                 285

Lys Ala Arg Phe Tyr Leu Lys Ala Leu Arg Gln Ile Leu Lys Met Gln
    290                 295                 300

Gly Ala Lys Asp Ser Glu Phe Val Leu Asp Glu Val Leu Glu Asn Thr
305                 310                 315                 320

```
Ser Val Ile Ser Gly Asp Val Cys Ala Ala Val Asn Pro Pro Tyr Lys
                325                 330                 335

Asp Val His Asp Leu His Asn Ala Pro Lys Leu Gly Tyr Gly Val Ala
            340                 345                 350

Leu Val Lys Tyr Thr Gly Ala Arg Gly Lys Tyr Ser Thr Asn Asp Ala
        355                 360                 365

His Ala Glu Phe Val Ala Arg Val Arg Lys Val Leu Asn Glu Gln Gly
    370                 375                 380

Val Ile Trp Gln Val Ala Thr Leu Gly Lys Val Asp Gln Gly Gly Gly
385                 390                 395                 400

Gly Thr Ile Ala Lys Phe Phe Ala Glu Arg Gly Ser Asp Val Ile Asp
                405                 410                 415

Met Gly Pro Ala Leu Leu Gly Met His Ser Pro Phe Glu Ile Ser Ser
            420                 425                 430

Lys Ala Asp Leu Phe Glu Thr Tyr Val Ala Tyr Arg Ser Leu Met Glu
        435                 440                 445

Lys Leu
    450

<210> SEQ ID NO 247
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Gly Lys Val Tyr Lys Lys Val Glu Leu Val Gly Thr Ser Glu Glu Gly
1               5                   10                  15

Leu Glu Ala Ala Ile Gln Ala Ala Leu Ala Arg Ala Arg Lys Thr Leu
            20                  25                  30

Arg His Leu Asp Trp Phe Glu Val Lys Glu Ile Arg Gly Thr Ile Gly
        35                  40                  45

Glu Ala Gly Val Lys Glu Tyr Gln Val Val Leu Glu Val Gly Phe Arg
    50                  55                  60

Leu Glu Glu Thr
65

<210> SEQ ID NO 248
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Met Phe Gly Arg Asp Pro Phe Asp Ser Leu Phe Glu Arg Met Phe Lys
1               5                   10                  15

Glu Phe Phe Ala Thr Pro Met Thr Gly Thr Thr Met Ile Gln Ser Ser
            20                  25                  30

Thr Gly Ile Gln Ile Ser Gly Lys Gly Phe Met Pro Ile Ser Ile Ile
        35                  40                  45

Glu Gly Asp Gln His Ile Lys Val Ile Ala Trp Leu Pro Gly Val Asn
    50                  55                  60

Lys Glu Asp Ile Ile Leu Asn Ala Val Gly Asp Thr Leu Glu Ile Arg
65                  70                  75                  80
```

```
Ala Lys Arg Ser Pro Leu Met Ile Thr Glu Ser Glu Arg Ile Ile Tyr
                85                  90                  95

Ser Glu Ile Pro Glu Glu Glu Ile Tyr Arg Thr Ile Lys Leu Pro
            100                 105                 110

Ala Thr Val Lys Glu Gly Asn Ala Ser Ala Lys Phe Glu Asn Gly Val
            115                 120                 125

Leu Ser Val Ile Leu Pro Lys Ala Glu Ser Ser Ile Lys Lys Gly Ile
            130                 135                 140

Asn Ile Glu
145

<210> SEQ ID NO 249
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Met Gly Ser Asp Lys Ile His His His His His Met Met Val Ile
1               5                   10                  15

Ser Glu Lys Val Arg Lys Ala Leu Asn Asp Gln Leu Asn Arg Glu Ile
                20                  25                  30

Tyr Ser Ser Tyr Leu Tyr Leu Ser Met Ala Thr Tyr Phe Asp Ala Glu
            35                  40                  45

Gly Phe Lys Gly Phe Ala His Trp Met Lys Gln Ala Gln Glu Glu
    50                  55                  60

Leu Thr His Ala Met Lys Phe Tyr Glu Tyr Ile Tyr Glu Arg Gly Gly
65                  70                  75                  80

Arg Val Glu Leu Glu Ala Ile Glu Lys Pro Pro Ser Asn Trp Asn Gly
                85                  90                  95

Ile Lys Asp Ala Phe Glu Ala Ala Leu Lys His Glu Glu Phe Val Thr
            100                 105                 110

Gln Ser Ile Tyr Asn Ile Leu Glu Leu Ala Ser Glu Glu Lys Asp His
            115                 120                 125

Ala Thr Val Ser Phe Leu Lys Trp Phe Val Asp Glu Gln Val Glu Glu
            130                 135                 140

Glu Asp Gln Val Arg Glu Ile Leu Asp Leu Leu Glu Lys Ala Asn Gly
145                 150                 155                 160

Gln Met Ser Val Ile Phe Gln Leu Asp Arg Tyr Leu Gly Gln Arg Glu
                165                 170                 175

<210> SEQ ID NO 250
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Ala Ala Ala Lys Pro Ala Thr Thr Glu Gly Glu Phe Pro Glu Thr Arg
1               5                   10                  15

Glu Lys Met Ser Gly Ile Arg Arg Ala Ile Ala Lys Ala Met Val His
                20                  25                  30

Ser Lys His Thr Ala Pro His Val Thr Leu Met Asp Glu Ala Asp Val
            35                  40                  45
```

```
Thr Lys Leu Val Ala His Arg Lys Lys Phe Lys Ala Ile Ala Ala Glu
 50                  55                  60

Lys Gly Ile Lys Leu Thr Phe Leu Pro Tyr Val Val Lys Ala Leu Val
 65                  70                  75                  80

Ser Ala Leu Arg Glu Tyr Pro Val Leu Asn Thr Ser Ile Asp Asp Glu
                 85                  90                  95

Thr Glu Glu Ile Ile Gln Lys His Tyr Tyr Asn Ile Gly Ile Ala Ala
                100                 105                 110

Asp Thr Asp Arg Gly Leu Leu Val Pro Val Ile Lys His Ala Asp Arg
            115                 120                 125

Lys Pro Ile Phe Ala Leu Ala Gln Glu Ile Asn Glu Leu Ala Glu Lys
130                 135                 140

Ala Arg Asp Gly Lys Leu Thr Pro Gly Glu Met Lys Gly Ala Ser Cys
145                 150                 155                 160

Thr Ile Thr Asn Ile Gly Ser Ala Gly Gly Gln Trp Phe Thr Pro Val
                165                 170                 175

Ile Asn His Pro Glu Val Ala Ile Leu Gly Ile Gly Arg Ile Ala Glu
            180                 185                 190

Lys Pro Ile Val Arg Asp Gly Glu Ile Val Ala Ala Pro Met Leu Ala
            195                 200                 205

Leu Ser Leu Ser Phe Asp His Arg Met Ile Asp Gly Ala Thr Ala Gln
        210                 215                 220

Lys Ala Leu Asn His Ile Lys Arg Leu Leu Ser Asp Pro Glu Leu Leu
225                 230                 235                 240

Leu Met

<210> SEQ ID NO 251
<211> LENGTH: 69
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Met Gly Lys Val Tyr Lys Lys Val Glu Leu Val Gly Thr Ser Glu Glu
 1               5                  10                  15

Gly Leu Glu Ala Ala Ile Gln Ala Ala Leu Ala Arg Ala Arg Lys Thr
                20                  25                  30

Leu Arg His Leu Asp Trp Phe Glu Val Lys Glu Ile Arg Gly Thr Ile
            35                  40                  45

Gly Glu Ala Gly Val Lys Glu Tyr Gln Val Val Leu Glu Val Gly Phe
 50                  55                  60

Arg Leu Glu Glu Thr
65
```

NODE POLYPEPTIDES FOR NANOSTRUCTURE ASSEMBLY

This application is a continuation-in-part of International Application No. PCT/US2009/053628, filed Aug. 13, 2009, which is a continuation-in-part of U.S. application Ser. No. 12/589,529, filed Apr. 27, 2009, which claims the benefit of U.S. Provisional Application No. 61/136,097, filed Aug. 12, 2008, and this application claims the benefit of U.S. Provisional Application No. 61/246,699, filed Sep. 29, 2009, the specifications of which are hereby incorporated by reference in their entirety.

This invention was made with government support under Grant Number 1R43GM077743-01A1 awarded by the National Institutes of Health. The government has certain rights in the invention.

The instant application contains a Sequence Listing which has been submitted in ASCII format via EFS-Web and is hereby incorporated by reference in its entirety. Said ASCII copy, created on Sep. 28, 2010, is named 291459IM.txt and is 603,472 bytes in size.

BACKGROUND OF THE INVENTION

Miniaturization is required for the improvement of existing technologies and the enablement of new ones. For example, increases in the speed and processing power of computing machinery are dependent on further miniaturization. Silicon semiconductor devices, are presently fabricated by a "top down" sequential patterning technology using photolithography, far-ultraviolet lithography, or, more recently, electron beam lithography. Although progress with this technology has been made to produce ever smaller devices, it is generally recognized that the reliable production of structures with consistent sub-10 nanometer features probably lies beyond the capabilities of top-down silicon fabrication technology.

Self-assembling nanosystems might create complex and higher density novel device architectures. Such devices could potentially have applications as biosensors, actuators, biomaterials, or nanoelectronic devices for a wide variety of applications in fields as diverse as medicine and material science.

"Bottom up" techniques of self-assembly are common to biological systems (Padilla et al. 2001; Whitesides et al. 2002; Liu & Amro 2002; Lee et al. 2002; Ringler & Schulz 2003). Several companies are developing nanotechnology based on carbon or silicon-based nanostructures, functionalized carbon nanotubes, or buckyballs. An alternative approach to the development of self-assembled nanostructures makes use of biomolecules like nucleic acids and proteins. Several 2-dimensional and 3-dimensional nanostructures formed of DNA have been generated. (Rothemund 2006; Seeman, 2005ab; Shih 2004).

Whole viruses have been used as substrates for nanostructures, as described in Blum et al. (2004), Blum et al. 2005, Chatterji et al. (2004), Chatterji et al. 2005, and Falkner et al. (2005). Cambrios uses virus structures for material sciences applications (www.cambrios.com).

There have been reports of 1-dimensional (e.g. Medalsy et. al., 2008), 2-dimensional (e.g. Sleytr et. al. 2007), and 3-dimensional protein arrays (e.g. protein crystals) have been reported. Padilla et. al (2001) and Yeates et. al (2004) discuss engineered fusion proteins, produced by using recombinant DNA technology to link the genes coding for subunits of protein multimers of different symmetry, and describe the spontaneous assembly in solution of both tetrahedral complexes and a linear helical filament using the fused protein domain approach.

An alternative approach to the formation of 2-dimensional self-assembling lattices of biomolecules involves diffusional organization on self-assembled monolayers (SAMs) (Liu et. al 1996, Liu & Amro 2002, Lee et al. 2002, Sleytr et al. 2007).

The protein-based assemblies cited above primarily result from the spontaneous association of molecules and so only allow limited control over nanostructure assembly.

In 2003, Ringler & Schulz described the formation of a structure that incorporated a modified form of the tetrameric aldolase RhoA from *E. coli* and streptavidin. They reported the assembly of a 2-dimensional lattice formed of the RhoA tetramers and streptavidin through interaction of the proteins with a self-assembled monolayer.

There are severe limitations in the prior work. For example, the assembly process of Padilla and Ringler & Schulz resulted in the formation of many non-uniform or defective structures with poor quality of the structural assemblies. Because assembly occurred spontaneously, there was no control over the steps of assembly, resulting in partial structures and aggregated complexes. Also, the proteins used in the prior studies were not conformationally stable.

SUMMARY OF THE INVENTION

Several methods according to the invention include the following:

A method of using a template multimeric protein with Cn, Dn, or higher symmetry, that incorporates specific attachment sites for nanostructure struts with predefined stoichiometry and orientation, and is derived from a thermophilic microorganism, as a nanostructure node.

A method of using a list of sequences of multimeric proteins with Cn, Dn or higher symmetries derived from template multimeric proteins (having a template number of polypeptide chains) of thermostable organisms with utility as node templates for the generation of nanostructure nodes including nanostructure node multimeric proteins incorporating specific binding sites for the symmetric attachment of nanostructure struts with defined stoichiometry and orientation.

A method of using a set of sequences with greater than 80 per cent sequence identity with a list of multimeric proteins with Cn, Dn or higher symmetries derived from thermostable organisms with utility as node templates for the generation of nanostructure nodes incorporating specific binding sites for the symmetric attachment of nanostructure struts with defined stoichiometry and orientation.

A method of using a list of sequences of multimeric proteins with Cn symmetry derived from template multimeric proteins (having a template number of polypeptide chains) of thermostable organisms with utility as node templates for the generation of nanostructure nodes including nanostructure node multimeric proteins incorporating specific binding sites for the symmetric attachment of nanostructure struts with defined stoichiometry and orientation.

A method of using a set of sequences with greater than 80 per cent sequence identity with a list of multimeric proteins with Cn symmetry derived from thermostable organisms with utility as node templates for the generation of nanostructure nodes incorporating specific binding sites for the symmetric attachment of nanostructure struts with defined stoichiometry and orientation.

A method of using a protein node incorporating multiple subunit polypeptide chains related by Cn symmetry, with each subunit incorporating two specific amino acid reactive sites (specific amino acid reactive residues) permitting the covalent attachment of biotin groups, subsequently allowing interconnection with streptavidin tetramers (or streptavidin derivative tetramers or avidin tetramers, or avidin derivative tetramers) with defined stoichiometry and orientation.

A method of making a nanostructure node by operating on the 3-dimensional structure of a member of a list of multimeric node template proteins derived from thermostable organisms, to define the amino sequence of nodes that can form nanoassemblies incorporating multimeric nodes and streptavidin or streptavidin-incorporating struts attached with defined stoichiometry and orientation.

A method of making a nanostructure node by operating on the 3-dimensional structure of a member of a list of multimeric node template proteins with Cn symmetry derived from thermostable organisms, to define the amino sequence of nodes that can form planar nanoassemblies incorporating Cn planar nodes and streptavidin or streptavidin-incorporating struts attached with defined stoichiometry and orientation.

A method of making a nanostructure node by operating on the 3-dimensional structure of a member of a list of multimeric node template proteins with Cn symmetry derived from thermostable organisms, using an aligned search procedure with a relative rotational increment of between 0.001 and 5 degrees to define the amino sequence of nodes that can form planar nanoassemblies incorporating Cn planar nodes and streptavidin or streptavidin-incorporating struts attached with defined stoichiometry and orientation.

A method of making an optimal nanostructure node by operating on the 3-dimensional structure of a member of a list of multimeric node template proteins with Cn symmetry derived from thermostable organisms to define the amino sequence of nodes that can form planar nanoassemblies incorporating Cn planar nodes and streptavidin or streptavidin-incorporating struts attached with defined stoichiometry and orientation.

A method of making an optimal nanostructure node that is produced through expression in an *E. coli* bacterium or another heterologous protein expression system.

A method of making an optimal planar nanostructure node by using computer graphics, mathematical, or experimental methods of improving the interface interactions between a Cn polyhedral node and streptavidin resulting in modified node protein amino acid sequences.

A method of making a planar protein node based on a template node sequence from a thermophilic organism that incorporates multiple subunit polypeptide chains related by C3, C4, C5, C6, and C7 symmetry, and that has been modified according to a computer graphical or mathematical method to define and incorporate two reactive amino acid groups permitting the covalent attachment of biotin groups, subsequently allowing Cn-symmetric interconnection between the node and n streptavidin tetramers in a planar orientation.

A method of making a nanostructure node by operating on the 3-dimensional structure of a member of a list of multimeric proteins with Cn symmetry derived from thermostable organisms, to define the amino sequence of nodes that can form polyhedral nanoassemblies incorporating streptavidin or streptavidin-incorporating struts connected to nodes with geometry and stoichiometry corresponding to the apex of a regular polyhedron.

A method of making an optimal nanostructure node by operating on the 3-dimensional structure of a member of a list of multimeric proteins with Cn symmetry derived from thermostable organisms, to define the amino sequence of nodes that can form polyhedral nanoassemblies incorporating streptavidin or streptavidin-incorporating struts connected to nodes with geometry and stoichiometry corresponding to the apex of a regular polyhedron.

A method of making an optimal polyhedral nanostructure node by using computer graphics, mathematical, or experimental methods of improving the interface interactions between a Cn polyhedral node and streptavidin resulting in modified node protein amino acid sequences.

A method of making nanostructure nodes by operating on the 3-dimensional structure of a member of a list of multimeric proteins with Dn or higher symmetry derived from thermostable organisms, to define the amino sequence of nanostructure nodes that can form nanoassemblies incorporating streptavidin or streptavidin-incorporating struts connected to nodes with defined geometry and stoichiometry along node dyad symmetry axes.

A method of making optimal nanostructure nodes by operating on the 3-dimensional structure of a member of a list of multimeric proteins with Dn or higher symmetry derived from thermostable organisms, to define the optimal amino sequence of nodes that can form nanoassemblies incorporating streptavidin or streptavidin-incorporating struts connected to nodes with defined geometry and stoichiometry along node dyad symmetry axes.

A method of making optimal nanostructure nodes using computer graphics, mathematical methods, or experimental methods for defining amino acid sequences of nanostructure nodes with improved interface interactions between a Dn or higher symmetry node and streptavidin.

A method of making a protein node where at least one subunit polypeptide chain has been modified through reaction with a bifunctional reagent to incorporate additional binding or other functionality into the node polypeptide chain.

A method of making a protein node where at least one subunit polypeptide chains have been modified through covalent incorporation of a polypeptide chain sequence coding for protein binding or other functionality.

A method of making a protein node with subunit polypeptide chains related by Cn, Dn or higher symmetry, where some subunits have been covalently interconnected to form a protein multimer with a reduced number of polypeptide chains.

Several embodiments of the invention include the following:

In an embodiment, a nanostructure node generated from a template multimeric protein with Cn, Dn, or higher symmetry, derived from a list of known three-dimensional protein structures with corresponding symmetry as determined from X-ray crystallography, that incorporates specific attachment sites for nanostructure struts with predefined stoichiometry and orientation, and is derived from a thermophilic microorganism, as a nanostructure node.

In an embodiment, a nanostructure node generated from a template multimeric protein with Cn, Dn, or higher symmetry, derived from a protein that is homologous to one derived from a list of known three-dimensional protein structures with corresponding symmetry as determined from X-ray crystallography, that incorporates specific attachment sites for nanostructure struts with predefined stoichiometry and orientation, and is derived from a thermophilic microorganism.

In an embodiment, a protein node where at least one subunit polypeptide chain has been modified through reaction with a bifunctional reagent to incorporate additional binding or other functionality into the node polypeptide chain.

In an embodiment, a protein node where at least one subunit polypeptide chain has been modified through covalent incorporation of a polypeptide chain sequence coding for protein binding or other functionality.

In an embodiment, a protein node with subunit polypeptide chains related by Cn, Dn or higher symmetry, where two of the subunits have been covalently interconnected to form a protein multimer with a reduced number of polypeptide chains, and modified to incorporate specific binding sites for chemical modification leading to the covalent attachment of biotin groups.

In an embodiment, a protein node with subunit polypeptide chains related by Cn, Dn or higher symmetry, where some subunits have been covalently interconnected to form a protein multimer with a reduced number of polypeptide chains, and modified to incorporate specific binding sites for chemical modification leading to the covalent attachment of biotin groups.

In an embodiment, a protein node with subunit polypeptide chains related by Cn, Dn or higher symmetry, where all of subunits have been covalently interconnected to form a protein multimer composed of a single polypeptide chain, and modified to incorporate specific binding sites for chemical modification leading to the covalent attachment of biotin groups.

In an embodiment, a protein node with subunit polypeptide chains related by Cn symmetry, where two of the subunits have been covalently interconnected to form a protein multimer with a reduced number of polypeptide chains, and modified to incorporate specific binding sites for chemical modification leading to the covalent attachment of biotin groups.

In an embodiment, a planar C3 node based on the pdb code:1thj trimer whose subunits have been interconnected using a short polypeptide linker to form a single polypeptide chain or homologues thereof.

In an embodiment, a planar C3 node based on amino acid sequences that are homologous to the pdb code:1thj trimer whose subunits have been interconnected using a short polypeptide linker to form a single polypeptide chain.

In an embodiment, a planar protein node based on the template protein pdb code:1thj, incorporating three subunit polypeptide chains related by C3 symmetry, and incorporating cysteine amino acid residues as reactive sites for the covalent attachment of biotin groups, subsequently allowing C3 symmetric interconnection with 3 streptavidin tetramers (or streptavidin derivative tetramers, or avidin tetramers, or avidin derivative tetramers, or combinations) in a planar orientation.

In an embodiment, a planar protein node based on the template protein pdb code: 1j5s, incorporating three subunit polypeptide chains related by C3 symmetry, and incorporating cysteine amino acid residues as reactive sites for the covalent attachment of biotin groups, subsequently allowing C3 symmetric interconnection with 3 streptavidin tetramers in a planar orientation.

In an embodiment, a planar protein node based on the template protein pdb code:1vcg, incorporating four subunit polypeptide chains related by C4 symmetry, where each subunit incorporates cysteine amino acid residues as reactive sites for the covalent attachment of biotin groups, subsequently allowing C4 symmetric interconnection with 4 streptavidin tetramers in a planar orientation.

In an embodiment, a planar protein node based on the template protein pdb code:2cu0, incorporating four subunit polypeptide chains related by C4 symmetry, where each subunit has been modified according to a computer graphical or mathematical method to define and incorporate two cysteine amino residues as reactive sites for the covalent attachment of biotin groups, subsequently allowing C4 symmetric interconnection with 4 streptavidin tetramers in a planar orientation.

In an embodiment, a planar protein node based on the template node protein pdb code: 1vdh that incorporates five subunit polypeptide chains related by C5 symmetry, and where each subunit incorporates two cysteine amino acid residues, as determined using a computer graphics or mathematical method, as reactive sites for the covalent attachment of biotin groups, subsequently allowing C5 symmetric interconnection with 5 streptavidin tetramers in a planar orientation.

In an embodiment, a planar protein node based on the template node sequence pdb code: 2ekd that incorporates six subunit polypeptide chains related by C6 symmetry, and where each subunit incorporates two cysteine amino acid residues, as determined using a computer graphics or mathematical method, as reactive sites for the covalent attachment of biotin groups, subsequently allowing C6 symmetric interconnection with 6 streptavidin tetramers in a planar orientation.

In an embodiment a planar protein node based on the template node sequence pdb code: 1i81 that incorporates seven subunit polypeptide chains related by C7 symmetry, and where each subunit incorporates two cysteine amino acid residues, as determined using a computer graphics or mathematical method, as reactive sites for the covalent attachment of biotin groups, subsequently allowing C7 symmetric interconnection with 7 streptavidin tetramers in a planar orientation.

In an embodiment, a polyhedral protein node incorporating three subunit polypeptide chains related by C3 symmetry, based on the template protein pdb code: 1v4n, and incorporating specific binding sites for chemical modification leading to the covalent attachment of biotin groups, subsequently allowing interconnection with 3 streptavidin tetramers in an orientation corresponding to the apex of a dodecahedron.

In an embodiment, a polyhedral protein node incorporating three subunit polypeptide chains related by C3 symmetry, based on the template protein pdb code: 1v4n, and incorporating specific binding sites for chemical modification leading to the covalent attachment of biotin groups, subsequently allowing interconnection with 3 streptavidin tetramers in an orientation corresponding to the apex of a truncated icosahedron or "bucky ball" structure.

In an embodiment, a polyhedral protein node incorporating five subunit polypeptide chains related by C5 symmetry, based on the template protein pdb code:1vdh, and incorporating specific binding sites for chemical modification leading to the covalent attachment of biotin groups, subsequently allowing interconnection with 5 streptavidin tetramers in an orientation corresponding to the apex of an icosahedron.

In an embodiment, a protein node based on the tetrameric D2-symmetric node template pdb code:1ma1, where positions on subunits related by D2 symmetry have been modified to incorporate specific cysteine residues allowing covalent attachment of biotin groups and subsequent interconnection with streptavidin tetramers with defined stoichiometry and orientation. According to whether cysteine modifications are introduced along one, two, or all three of the independent dyad axes of the tetramer, streptavidin linked structures with linear, 2-dimensional rectangular, or 3-dimensional orthorhombic lattice geometry may be formed.

In an embodiment, a protein node based on the tetrameric D2-symmetric node template pdb code:1nto. According to whether cysteine modifications are introduced along one, two, or all three of the independent dyad axes of the tetramer, streptavidin linked structures with linear, 2-dimensional rectangular, or 3-dimensional orthorhombic lattice geometry may be formed.

In an embodiment, a protein node based on the tetrameric D2-symmetric node template pdb code:1rtw. According to whether cysteine modifications are introduced along one, two, or all three of the independent dyad axes of the tetramer, streptavidin linked structures with linear, 2-dimensional rectangular, or 3-dimensional orthorhombic lattice geometry may be formed.

In an embodiment, a protein node based on the hexameric D3-symmetric node template pdb code:1b4b. Such nodes have utility in the formation of 2-dimensional and 3-dimensional hexagonal lattices.

In an embodiment, a protein node based on the hexameric D3-symmetric node template pdb code:1hyb. Such nodes have utility in the formation of 2-dimensional and 3-dimensional hexagonal lattices.

In an embodiment, a protein node based on the hexameric D3-symmetric node template pdb code:2prd. Such nodes have utility in the formation of 2-dimensional and 3-dimensional hexagonal lattices.

In an embodiment, a protein node based on the octameric D4-symmetric node template pdb code:1o4v. Such nodes have utility in the formation of 2-dimensional and 3-dimensional lattices with tetragonal node symmetry.

In an embodiment, a protein node based on the octameric D4-symmetric node template pdb code:2h2i. Such nodes have utility in the formation of 2-dimensional and 3-dimensional lattices with tetragonal node symmetry.

In an embodiment, a protein node based on the octameric D4-symmetric node template pdb code:2iel. Such nodes have utility in the formation of 2-dimensional and 3-dimensional lattices with tetragonal node symmetry.

In an embodiment, a protein node based on the dodecameric tetrahedral T23-symmetric node template pdb code:1pvv. Such nodes have utility in the formation of 3-dimensional lattices with cubic symmetry.

In an embodiment, modified forms of the D2-symmetric, tetrameric protein streptavidin (pdb code:1stp), where cysteine residues have been introduced along tetramer dyad axes to protect biotin binding sites or allow subsequent in situ functionalization of nanostructures incorporating streptavidin struts.

In an embodiment, an extended strut composed of a protein node based on a tetrameric D2-symmetric node template pdb code: 1ma1 complexed with two streptavidin tetramers to form an extended nanostructure strut.

Composition of Matter: Assemblies with a Nanostructure Node

In an embodiment, a nanostructure assembly geometry incorporating Cn-symmetric or Dn symmetric nodes and streptavidin or streptavidin-incorporating (or streptavidin derivative, or avidin, or avidin derivative) struts.

In an embodiment, a nanostructure assembly incorporating streptavidin or streptavidin-incorporating struts together with Cn-symmetric or Dn symmetric nodes based on node templates derived from a list of known three-dimensional protein structures with corresponding symmetry as determined from X-ray crystallography, and that incorporate specific attachment sites for nanostructure struts with predefined stoichiometry and orientation, and are derived from thermophilic microorganisms.

In an embodiment, a nanostructure assembly incorporating streptavidin or streptavidin-incorporating struts together with Cn-symmetric or Dn symmetric nodes based on templates that are amino acid sequence homologs of structures derived from a list of known three-dimensional protein structures with corresponding symmetry as determined from X-ray crystallography, and that incorporate specific attachment sites for nanostructure struts with predefined stoichiometry and orientation, and are derived from thermophilic microorganisms.

In an embodiment, a nanostructure assembly incorporating streptavidin or streptavidin-incorporating struts together with D2 symmetric nodes that are based on a modified forms of streptavidin that incorporate specific attachment sites for nanostructure struts with predefined stoichiometry and orientation.

In an embodiment, a nanostructure assembly incorporating Cn-symmetric or Dn symmetric nodes and streptavidin or streptavidin-incorporating struts. The nanostructure may be functionalized through the incorporation of node constructs that have been modified either through reaction with a bifunctional reagent to incorporate additional binding or other functionality into the node polypeptide chain, or where node subunits have been modified through covalent incorporation of a polypeptide chain sequence coding for protein binding or other functionality.

In an embodiment, a nanostructure assembly incorporating Cn-symmetric or Dn symmetric nodes and streptavidin or streptavidin-incorporating struts taking the geometrical form of a radial planar array.

In an embodiment, a nanostructure with 2-dimensional polygonal geometry incorporating Cn-symmetric nodes and streptavidin or streptavidin-incorporating struts.

In an embodiment, a nanostructure with 2-dimensional polygonal geometry incorporating single-chain Cn-symmetric nodes and streptavidin or streptavidin-incorporating struts.

In an embodiment, a nanostructure with 2-dimensional hexagonal polygonal geometry incorporating single-chain C3-symmetric nodes and streptavidin or streptavidin-incorporating struts.

In an embodiment, a nanostructure with 2-dimensional hexagonal polygonal geometry incorporating single-chain C3-symmetric nodes based on node templates derived from a list of known three-dimensional protein structures with corresponding symmetry as determined from X-ray crystallography, and streptavidin or streptavidin-incorporating struts.

In an embodiment, a nanostructure with 2-dimensional hexagonal polygonal geometry incorporating single-chain C3-symmetric nodes based on the node templates pdb code: 1thj.

In an embodiment, a nanostructure with 2-dimensional square polygonal geometry incorporating single-chain C4-symmetric nodes and streptavidin or streptavidin-incorporating struts.

In an embodiment, a nanostructure with 2-dimensional square polygonal geometry incorporating single-chain C4-symmetric nodes based on node templates derived from a list of known three-dimensional protein structures with corresponding symmetry as determined from X-ray crystallography, and streptavidin or streptavidin-incorporating struts.

In an embodiment, a nanostructure with 2-dimensional square polygonal geometry incorporating single-chain C4-symmetric nodes based on the node template pdb code: 1vcg.

In an embodiment, a 2-dimensional lattice incorporating Cn-symmetric nodes and streptavidin or streptavidin-incorporating struts.

In an embodiment, a 2-dimensional lattice incorporating Dn-symmetric nodes and streptavidin or streptavidin-incorporating struts.

In an embodiment, a 2-dimensional hexagonal lattice incorporating C3-symmetric nodes and streptavidin or streptavidin-incorporating struts.

In an embodiment, a 2-dimensional hexagonal lattice incorporating C3-symmetric nodes based on node templates corresponding to the pdb code:1thj protein trimer or the pdb code:1j5s protein trimer and streptavidin or streptavidin-incorporating struts.

In an embodiment, a 2-dimensional square lattice incorporating C4-symmetric nodes and streptavidin or streptavidin-incorporating struts.

In an embodiment, a 2-dimensional square lattice incorporating C4-symmetric nodes homologous to node template sequences corresponding to the pdb code:1vcg protein tetramer and streptavidin or streptavidin-incorporating struts.

In an embodiment, a 2-dimensional square lattice incorporating C4-symmetric nodes based on the node template sequence pdb code:1vcg and streptavidin or streptavidin-incorporating struts.

In an embodiment, a 3-dimensional radial nanostructure incorporating a node derived from thermophilic node templates with Dn, tetrahedral (T23), cubeoctahedral (432), or with icosahedral/dodecahedral (532) symmetry derived from a thermophilic organism, and Dn symmetric nodes and streptavidin or streptavidin-incorporating struts.

In an embodiment, a 3-dimensional radial nanostructure incorporating a node that is homologous to thermophilic node templates with Dn, tetrahedral (T23), cubeoctahedral (432), or with icosahedral/dodecahedral (532) symmetry derived from a thermophilic organism, and Dn symmetric nodes and streptavidin or streptavidin-incorporating struts In an embodiment, a 3-dimensional radial nanostructure incorporating a node with tetrahedral (T23) symmetry based on a dodecameric node and streptavidin or streptavidin-incorporating struts.

In an embodiment, a 3-dimensional radial nanostructure incorporating a node template with tetrahedral (T23) symmetry derived from a list of known three-dimensional protein structures with corresponding symmetry as determined from X-ray crystallography, and streptavidin or streptavidin-incorporating struts.

In an embodiment, a 3-dimensional radial nanostructure incorporating a node with tetrahedral (T23) symmetry based on the dodecameric node template pdb code:1pvv and streptavidin or streptavidin-incorporating struts.

In an embodiment, a 3-dimensional radial nanostructure incorporating a node with cubeoctahedral symmetry based on the 24-subunit node template derived from a thermophilic organism and streptavidin or streptavidin-incorporating struts.

In an embodiment, a 3-dimensional radial nanostructure incorporating a node with cubeoctahedral symmetry based on a 24-subunit node template derived from a list of known three-dimensional protein structures with corresponding symmetry as determined from X-ray crystallography, and streptavidin or streptavidin-incorporating struts.

In an embodiment, a 3-dimensional radial nanostructure incorporating a node with icosahedral/dodecahedral 532 symmetry based on a 60-subunit node template derived from a thermophilic organism and Dn symmetric nodes and streptavidin or streptavidin-incorporating struts.

In an embodiment, a 3-dimensional radial nanostructure incorporating a node with icosahedral/dodecahedral 532 symmetry based on a 60-subunit node template derived from a list of known three-dimensional protein structures with corresponding symmetry as determined from X-ray crystallography, and streptavidin or streptavidin-incorporating struts.

In an embodiment, a 3-dimensional polyhedron formed of streptavidin or streptavidin-incorporating struts, and nodes with Cn symmetry incorporating binding interactions corresponding to the apex geometry of a polyhedron.

In an embodiment, a 3-dimensional polyhedron formed of streptavidin or streptavidin-incorporating struts, and nodes with Cn symmetry template derived from a list of known three-dimensional protein structures with corresponding symmetry as determined from X-ray crystallography, and incorporating binding interactions corresponding to the apex geometry of a polyhedron.

In an embodiment, a 3-dimensional dodecahedron formed of streptavidin or streptavidin-incorporating struts, and nodes with C3 symmetry, incorporating binding interactions corresponding to the apex geometry of a dodecahedron.

In an embodiment, a 3-dimensional dodecahedron formed of streptavidin or streptavidin-incorporating struts, and nodes with C3 symmetry, based on the pdb code:1v4n node protein, incorporating binding interactions corresponding to the apex geometry of a dodecahedron.

In an embodiment, a 3-dimensional "bucky" polyhedron formed of streptavidin or streptavidin-incorporating struts, and nodes with C3 symmetry, incorporating binding interactions corresponding to the apex geometry of a truncated icosahedron.

In an embodiment, a 3-dimensional "bucky" polyhedron formed of streptavidin or streptavidin-incorporating struts, and nodes with C3 symmetry, based on the pdb code:1v4n node protein, incorporating binding interactions corresponding to the apex geometry of a truncated icosahedron.

In an embodiment, a 3-dimensional icosahedron formed of streptavidin or streptavidin-incorporating struts, and nodes with C5 symmetry, incorporating binding interactions corresponding to the apex geometry of an icosahedron.

In an embodiment, a 3-dimensional icosahedron formed of streptavidin or streptavidin-incorporating struts, and nodes with C5 symmetry, based on the pdb code:1vdh node protein, incorporating binding interactions corresponding to the apex geometry of an icosahedron.

In an embodiment, a 3-dimensional, three-connected hexagonal-pattern lattice formed of streptavidin or streptavidin-incorporating struts, and nodes with D3 symmetry, alternatively modified to allow binding to streptavidin in two orientations.

In an embodiment, a 3-dimensional, three-connected hexagonal-pattern lattice formed of streptavidin or streptavidin-incorporating struts, and different nodes with D3 symmetry derived from a list of known three-dimensional protein structures with corresponding symmetry as determined from X-ray crystallography, alternatively modified to allow binding to streptavidin in two orientations.

In an embodiment, a 3-dimensional, three-connected lattice formed of streptavidin or streptavidin-incorporating struts, and nodes with D3 symmetry derived from a list of known three-dimensional protein structures with corresponding symmetry as determined from X-ray crystallography, the same D3 templates being alternatively modified to allow binding to streptavidin in two orientations.

In an embodiment, a 3-dimensional, three-connected lattice formed of streptavidin or streptavidin-incorporating struts, and nodes with D3 symmetry based on the pdb code: 1hyb node protein template, alternatively modified to allow binding to streptavidin in two orientations.

In an embodiment, a nanostructure comprising a 3-dimensional, four-connected, cubic pattern lattice formed of nodes with D4 symmetry and streptavidin or streptavidin-incorporating struts.

In an embodiment, a nanostructure comprising a 3-dimensional, four-connected, cubic pattern lattice formed of streptavidin or streptavidin-incorporating struts, and nodes with D4 symmetry derived from a list of known three-dimensional protein structures with corresponding symmetry as determined from X-ray crystallography, alternatively modified to allow binding to streptavidin in two orientations.

In an embodiment, a 3-dimensional, four-connected lattice formed of streptavidin or streptavidin-incorporating struts, and nodes with D4 symmetry based on the pdb code:2h2i node protein template, alternatively modified to allow binding to streptavidin in two orientations.

In an embodiment, a 3-dimensional, six-connected cubic lattice formed of streptavidin or streptavidin-incorporating struts.

In an embodiment, a 3-dimensional, six-connected cubic lattice formed of streptavidin or streptavidin-incorporating struts, and nodes with tetrahedral symmetry.

In an embodiment, a 3-dimensional, six-connected cubic lattice formed of streptavidin or streptavidin-incorporating struts, and nodes with T23 symmetry derived from a list of known three-dimensional protein structures with corresponding symmetry as determined from X-ray crystallography.

In an embodiment, a 3-dimensional, six-connected cubic lattice formed of streptavidin or streptavidin-incorporating struts, and nodes with tetrahedral symmetry based on the pdb code:1pvv node protein template.

In an embodiment, a nanostructure node protein based on a template sequence derived from a thermostable microorganism and comprising multiple polypeptide chain subunits and specific binding functionality.

In an embodiment, a nanostructure node incorporating 3, 5, or 6 subunits.

In an embodiment, a nanostructure node incorporating 3, 5, or 6 subunits, where the subunits are related by rotational symmetry.

In an embodiment, a nanostructure node multimeric protein incorporating multiple polypeptide subunits related by tetrahedral, octahedral, or icosahedral symmetry.

In an embodiment, a nanostructure node protein based on a template sequence derived from a thermostable microorganism and comprising multiple polypeptide chain subunits, each with a specific binding functionality.

In an embodiment, a nanostructure node protein based on a template sequence derived from a thermostable microorganism and comprising multiple polypeptide chain subunits, where at least one subunit lacks a specific binding functionality.

In an embodiment, a nanostructure node protein based on a template sequence derived from a thermostable microorganism and comprising 4 polypeptide chain subunits, each with a specific binding functionality and related by 4-fold symmetry.

In an embodiment, a nanostructure node protein based on a template sequence derived from a thermostable microorganism and comprising 3, 4, or 6 polypeptide chain subunits incorporating specific binding functionality that lie in a plane.

In an embodiment, a nanostructure node protein based on a template sequence derived from a thermostable microorganism and comprising 3, 4, or 6 polypeptide chain subunits, each with a specific binding functionality and related by rotational symmetry.

In an embodiment, a nanostructure node protein based on a template sequence derived from a thermostable microorganism and comprising 4 polypeptide chain subunits, each with a specific binding functionality, and where at least one specific binding site does not lie within the same plane as the other specific binding sites.

In an embodiment, a nanostructure node protein based on a template sequence derived from a thermostable microorganism and comprising multiple polypeptide chain subunits and wherein a first subunit is covalently bonded to a second subunit.

In an embodiment, a nanostructure node protein based on a template sequence derived from a thermostable microorganism and comprising at least 3 polypeptide chain subunits and wherein at least three subunits are covalently bonded to form a single polypeptide chain.

In an embodiment, a thermostable nanostructure node protein based on a template sequence derived from a thermostable microorganism and comprising multiple polypeptide chain subunits and specific binding functionality.

In an embodiment, a nanostructure node protein based on a template sequence derived from a thermostable microorganism and comprising multiple polypeptide chain subunits and specific binding functionality and where the amino acid sequence of at least one subunit is different from the amino acid sequence of another subunit.

In an embodiment, a nanostructure node protein with at least 80% sequence homology with a template sequence derived from a thermostable microorganism and comprising multiple polypeptide chain subunits and specific binding functionality.

In an embodiment, a trimeric C3-symmetric nanostructure node multimeric protein where the amino acid sequence of each polypeptide subunit has at least 80% sequence identity with an amino acid sequence of the uronate isomerase TM0064 from *Thermotoga maritime* (pdb code:1j5s).

In an embodiment, a tetrameric C4-symmetric nanostructure where the amino acid sequence of each polypeptide subunit has at least 80% amino acid sequence identity with an amino acid sequence of the isopentenyl-diphosphate delta-isomerase (pdb code: 1vcg) from *Thermus thermophilus*.

In an embodiment, a nanostructure node protein based on a template sequence derived from a thermostable microorganism and comprising multiple polypeptide chain subunits and specific binding functionality, wherein each specific binding site incorporates a specific amino acid residue separated from the other specific amino acid residue by a distance of about 20 Angstroms.

In an embodiment, a nanostructure node protein based on a template sequence derived from a thermostable microorganism and comprising multiple polypeptide chain subunits and specific binding functionality, wherein each specific binding site incorporating a specific amino acid residue is separated from the other specific amino acid residue by a distance such that with biotin groups bound to the specific amino acid residues, the biotin groups are positioned to bind with a pair of binding sites on streptavidin.

In an embodiment, a nanostructure node protein based on a template sequence derived from a thermostable microorganism and comprising multiple polypeptide chain subunits and specific binding functionality, where at least one subunit incorporates a polypeptide extension of from 5 to 1000 amino acid residues linked with a peptide bond to the designated amino and/or carboxy terminus.

In an embodiment, a nanostructure node protein based on a template sequence derived from a thermostable microorganism and comprising multiple polypeptide chain subunits and specific binding functionality, where at least one subunit incorporates a polypeptide extension of from 5 to 1000 amino acid residues linked with a peptide bond to the designated amino and/or carboxy terminus that comprises a binding function for a protein or a metallic or other solid surface.

In an embodiment, a nanostructure node protein based on a template sequence derived from a thermostable microorganism and comprising multiple polypeptide chain subunits and specific binding functionality, where at least one subunit incorporates a polypeptide extension of from 5 to 1000 amino acid residues linked with a peptide bond to the designated amino and/or carboxy terminus that comprises an amino acid subsequence that is a substrate for an enzyme.

In an embodiment, a nanostructure node protein based on a template sequence derived from a thermostable microorganism and comprising multiple polypeptide chain subunits and specific binding functionality, where at least one subunit incorporates a polypeptide extension of from 5 to 1000 amino acid residues linked with a peptide bond to the designated amino and/or carboxy terminus that comprises a polypeptide subsequence selected from the group consisting of an immunoglobulin polypeptide, a polyhistidine, a streptavidin binding polypeptide, StrepTag, an antibody binding polypeptide, *staphylococcus* Protein A, *staphylococcus* Protein G, an antigenic polypeptide, and a hapten-binding polypeptide.

In an embodiment, a nanostructure node protein based on a template sequence derived from a thermostable microorganism and comprising multiple polypeptide chain subunits and specific binding functionality, where at least one subunit incorporates a polypeptide extension of from 5 to 1000 amino acid residues linked with a peptide bond to the designated amino and/or carboxy terminus that comprises an antibody binding polypeptide subsequence together with a bound antibody.

In an embodiment, a nanostructure assembly incorporating a multimeric nanostructure node protein together with a specifically bound nanostructure strut.

In an embodiment, a nanostructure node comprising three subunits where two subunits incorporate specific binding sites and one subunit does not. In its C3 symmetric form, the nanostructure node functions as a 120 degree linker between two nanostructure struts.

In an embodiment, a nanostructure node comprising three subunits where one subunit incorporates a specific binding site and two subunits do not. The nanostructure node functions as a cap or terminator for a nanostructure struts.

In an embodiment, a nanostructure node comprising four subunits where three subunits incorporate specific binding sites and one subunit does not. In its C4 symmetric form, the nanostructure node functions as a "T" linker between three nanostructure struts.

In an embodiment, a nanostructure node comprising four subunits where two subunits incorporate specific binding sites and two subunits do not. In its C4 symmetric form, and where two subunits are related by a 180 degree rotation about the C4 axis, the nanostructure node functions as a linear linker between two nanostructure struts.

In an embodiment, a nanostructure node comprising four subunits where two subunits incorporate specific binding sites and two subunits do not. In its C4 symmetric form, and where two subunits are related by a 90 degree rotation about the C4 axis, the nanostructure node functions as a right angle "L" linker between two nanostructure struts.

In an embodiment, a nanostructure node comprising four subunits where one subunit incorporates a specific binding site and three subunits do not. The nanostructure node functions as a cap or terminator for a nanostructure struts.

In an embodiment, a protein superstructure, comprising a multisubunit nanostructure node with specifically bound strut components.

In an embodiment, a protein superstructure, comprising a multisubunit nanostructure node with specifically bound strut components, where the struts are comprised of streptavidin and are bound to the node via biotin groups covalently bound to the specific amino acid residues on the node.

In an embodiment, a protein superstructure, comprising a multisubunit nanostructure node, specifically bound to a surface-immobilized strut component, where the strut is comprised of streptavidin and is bound to the node via biotin groups covalently coupled to the specific amino acid residues on the node.

In an embodiment, a protein superstructure, comprising a multisubunit nanostructure node with specifically bound strut components, where the struts are comprised of streptavidin together with an adaptor protein that is linked to streptavidin through a bifunctional biotin-ATP crosslinking agent.

In an embodiment, a protein superstructure, comprising a multisubunit nanostructure node with specifically bound strut components, where the strut component is an adaptor protein that is linked to the node via ATP derivative groups covalently coupled to specific amino acid residues on the node.

In an embodiment, a protein superstructure, comprising a multisubunit nanostructure node with specifically bound strut components, where the strut component is comprised of a complex of streptavidin and an adaptor protein, all associated through specific linkers.

In an embodiment, a kit, comprising a nanostructure multisubunit node and a monostructure strut.

In an embodiment, a kit, comprising a nanostructure multisubunit node and a monostructure strut comprised of streptavidin.

Several methods according to the invention include the following:

A method of making a thermostable nanostructure node multimeric protein that takes advantage of the thermostability in performing separation from the producing cells, optionally including isolating the thermostable nanostructure node multimeric protein in substantially pure form from the lysate.

A method of making a thermostable nanostructure node multimeric protein that takes advantage of the thermostability in performing separation from the producing cells and uses recombinant DNA technology or site-specific modification techniques to modify a nucleotide sequence of a thermophilic organism for directing the expression of the nanostructure node multimeric protein.

A method of making a thermostable nanostructure node multimeric protein that takes advantage of the thermostability in performing separation from the producing cells and uses a gene fusion technique to modify a nucleotide sequence of a thermophilic organism for directing the expression of the nanostructure node multimeric protein to have at least two subunits covalently interconnected with a polypeptide linker.

A method of making a thermostable nanostructure node multimeric protein that takes advantage of the thermostability in performing separation from the producing cells and involves inserting the nucleotide sequence of a thermophilic organism or a modified nucleotide sequence of a thermophilic organism in the cell host to direct expression of the nanostructure node multimeric protein by the cell host.

A method of making a nanostructure node multimeric protein by combining subunits, some of which have a linker binding site and others of which do not have linker binding sites.

A chromatographic or electrophoretic method of purifying nanostructure node multimeric proteins prepared by mixing combined subunits, some of which have a linker binding site and others of which do not have linker binding sites.

A chromatographic or electrophoretic method of purifying trimeric nanostructure node multimeric proteins prepared by mixing combined subunits, some of which have a linker binding site and others of which do not have linker binding sites.

A chromatographic or electrophoretic method of purifying tetrameric nanostructure node multimeric proteins prepared by mixing combined subunits, some of which have a linker binding site and others of which do not have linker binding sites.

A chromatographic or electrophoretic method of purifying 4-fold symmetric tetrameric nanostructure node multimeric proteins prepared by mixing combined subunits, some of which have a linker binding site and others of which do not have linker binding sites.

A chromatographic or electrophoretic method of purifying 4-fold symmetric tetrameric nanostructure node multimeric proteins prepared by mixing combined subunits, by separation into subfractions incorporating a variable number of subunits with linker binding sites A chromatographic or electrophoretic method of purifying D2 or tetrahedrally symmetric tetrameric nanostructure node multimeric proteins prepared by mixing combined subunits, by separation into subfractions incorporating a variable number of subunits with linker binding sites A method of making a protein nanostructure that includes a nanostructure node multimeric protein binding to a nanostructure strut.

A method of making a protein nanostructure that includes a nanostructure node multimeric protein binding to a nanostructure strut, that allows mixing and reaction of the binding components.

A method of making a protein nanostructure that includes a nanostructure node multimeric protein and nanostructure struts comprising streptavidin.

A method of making a protein nanostructure that includes a nanostructure node multimeric protein incorporating covalently bound iminobiotin groups and nanostructure struts comprising streptavidin.

A method of making a protein nanostructure that includes a nanostructure node multimeric protein incorporating covalently bound photo-ATP groups and nanostructure struts comprising adaptor molecules with ATP binding sites.

A method of using a proteinaceous nanostructure assembly as a pattern or resist masking material for the fabrication of devices with sub-100 nanometer features.

A method of using a 2-dimensional proteinaceous nanostructure assembly as a pattern for the fabrication of devices with sub-100 nanometer features.

A method of using a 2-dimensional proteinaceous nanostructure assembly as a mask for a resist material for the fabrication of devices with sub-100 nanometer features.

A method of using a 3-dimensional proteinaceous nanostructure assembly as a negative patterning material for the fabrication of devices with sub-100 nanometer features.

A method of using a 3-dimensional proteinaceous nanostructure assembly as a patterning material for the fabrication of devices with sub-100 nanometer features.

A method of using a proteinaceous nanostructure assembly as a pattern or resist material for the fabrication of a soft lithography stamp for nanolithography.

A method of using a proteinaceous nanostructure assembly as a pattern or resist material for the fabrication of a semiconductor device.

A method of using a proteinaceous nanostructure assembly as a pattern or resist material for the fabrication of a zero-mode waveguide.

A method of using a proteinaceous nanostructure assembly as a pattern or resist material for the fabrication of a microelectromechanical system (MEMS) device.

A method of using a proteinaceous nanostructure assembly as a pattern or resist material for the fabrication of a nanofluidics device.

A method of making devices with sub-100 nanometer features using a proteinaceous nanostructure assembly as a pattern or resist masking material.

A method of making devices with sub-100 nanometer features using a 2-dimensional proteinaceous nanostructure assembly as a patterning material.

A method of making devices with sub-100 nanometer features using a 2-dimensional proteinaceous nanostructure assembly as a patterning material on substrates composed of metal, glass, a self-assembling monolayer, plastic, ceramic, or a semiconductor material.

A method of making devices with sub-100 nanometer features using a 2-dimensional proteinaceous nanostructure assembly as a pattern that is assembled from engineered nodes derived from a list of thermostable multimers with known structure and optionally, streptavidin or streptavidin-incorporating struts.

A method of making devices with sub-100 nanometer features using a 2-dimensional proteinaceous nanostructure assembly as a method of patterning a resist material.

A method of making devices with sub-100 nanometer features using a 2-dimensional proteinaceous nanostructure assembly as a method of patterning a resist material and binding a node protein or the node protein assembly to the resist layer surface at specific attachment sites through a chemical linkage.

A method of making devices with sub-100 nanometer features using a 2-dimensional proteinaceous nanostructure assembly as a method of patterning a resist material for patterning a substrate composed of metal, glass, a self-assembling monolayer, plastic, ceramic, or a semiconductor material.

A method of making devices with sub-100 nanometer features using a 2-dimensional proteinaceous nanostructure assembly as a pattern for a resist material where the proteinaceous pattern is assembled from engineered nodes derived from a list of thermostable multimers with known structure and optionally, streptavidin or streptavidin-incorporating struts.

A method of making devices with sub-100 nanometer, 3-dimensional channel features, wherein the features form a negative image of a 3-dimensional proteinaceous nanostructure assembly.

A method of making devices with sub-100 nanometer, 3-dimensional channel features, wherein the features form a negative image of a 3-dimensional proteinaceous nanostructure assembly, and binding a node protein or the node protein assembly to the resist layer surface at specific attachment sites through a chemical linkage.

A method of making devices with sub-100 nanometer features with 3-dimensional channel features, wherein the features form a negative image of a 3-dimensional proteinaceous nanostructure assembly, and a substrate is composed of a metal (such as iron, gold, platinum, or silver), a noble metal (such as gold, platinum, or silver), a glass (such as silicon dioxide), a self-assembling monolayer, plastic, a polymer, an organic polymer (such as polytetrafluoroethylene), a ceramic, an organic material, or a semiconductor material (such as silicon or germanium).

A method of making devices with sub-100 nanometer features with 3-dimensional channel features, wherein the features form a negative image of a 3-dimensional proteinaceous nanostructure assembly, and a matrix material comprises a metal (such as iron, gold, platinum, or silver), a noble metal (such as gold, platinum, or silver), a glass (such as silicon dioxide), a self-assembling monolayer, plastic, a polymer, an organic polymer (such as polytetrafluoroethylene) a ceramic, an organic material, or a semiconductor material (such as silicon or germanium).

A method of making devices with sub-100 nanometer, 3-dimensional channel features, wherein the 3-dimensional proteinaceous nanostructure assembly is assembled from engineered nodes derived from a list of thermostable multimers with known structure and optionally, streptavidin or streptavidin-incorporating struts.

A method of making devices with sub-100 nanometer, 3-dimensional features, wherein the features form a replica image of a 3-dimensional proteinaceous nanostructure assembly.

A method of making devices with sub-100 nanometer, 3-dimensional features, wherein the node protein or the node protein assembly is bound to the resist layer surface at specific attachment sites through a chemical linkage.

A method of making devices with sub-100 nanometer, 3-dimensional features, the substrate composed of a metal (such as iron, gold, platinum, or silver), a noble metal (such as gold, platinum, or silver), a glass (such as silicon dioxide), a self-assembling monolayer, plastic, a polymer, an organic polymer (such as polytetrafluoroethylene), an organic material, a ceramic, or a semiconductor material (such as silicon or germanium).

A method of making devices with sub-100 nanometer, 3-dimensional features, wherein the features form a replica image of a 3-dimensional proteinaceous nanostructure assembly, optionally embedded in a matrix material composed of metal, glass, plastic, ceramic, or a semiconductor material.

A method of making devices with sub-100 nanometer, 3-dimensional features, wherein the features form a replica image of a 3-dimensional proteinaceous nanostructure assembly, wherein the replica image is composed of metal, glass, plastic, ceramic, or a semiconductor material.

A method of making devices with sub-100 nanometer, 3-dimensional features, wherein the 3-dimensional proteinaceous nanostructure assembly forming the pattern to be replicated is assembled from engineered nodes derived from a list of thermostable multimers with known structure and optionally, streptavidin or streptavidin-incorporating struts.

A method of making a proteinaceous nanostructure assembly as a pattern or resist material for the fabrication of a soft lithography stamp for nanolithography.

A method of making a proteinaceous nanostructure assembly as a pattern or resist material for the fabrication of a semiconductor device.

A method of making a proteinaceous nanostructure assembly as a pattern or resist material for the fabrication of a zero-mode waveguide.

A method of making a proteinaceous nanostructure assembly as a pattern or resist material for the fabrication of a microelectromechanical system (MEMS) device.

A method of making a proteinaceous nanostructure assembly as a pattern or resist material for the fabrication of a nanofluidics device.

Several embodiments of the invention include the following:

A device that includes a substrate having a surface, a nucleation site on the substrate surface, and a nanostructure node coupled to the nucleation site.

A device that includes a substrate having a surface, a nucleation site on the substrate surface, and a nanostructure node coupled to the nucleation site, with more than one nucleation site on the substrate surface and with the nucleation sites arranged in a periodic, quasiperiodic, or nonperiodic pattern.

A device that includes a substrate having a surface, a nucleation site on the substrate surface, and a nanostructure node coupled to the nucleation site, the substrate comprising, for example, a metal (such as iron, gold, platinum, or silver), a noble metal (such as gold, platinum, or silver), a glass (such as silicon dioxide), a ceramic, a semiconductor (such as silicon or germanium), a carbon allotrope (such as diamond or graphite), a polymer, an organic polymer (such as tetrafluoroethylene), and/or an organic material and the nucleation site comprising, for example, a metal atom (such as iron, gold, platinum, or silver), a noble metal atom (such as a gold, platinum, silver, or copper), a metal and/or noble metal cluster, a chemically reactive molecule, and/or a patch of chemically reactive molecules.

A device that includes a substrate having a surface, a nucleation site on the substrate surface, and a nanostructure node coupled to the nucleation site, the nanostructure node comprising a nanostructure node multimeric protein comprising at least one polypeptide chain. The nanostructure node multimeric protein can have a known 3-dimensional structure, the nanostructure node multimeric protein can essentially have Cn, Dn, or higher symmetry with a number of subunits, the nanostructure node multimeric protein can be stable at a temperature of 70° C. or greater, the nanostructure node multimeric protein can have an amino acid sequence not found in nature, the nanostructure node multimeric protein can include a specific binding site for the attachment of a nanostructure strut with predefined stoichiometry and orientation, the specific binding site can include at least two specific amino acid reactive residues, and each specific amino acid reactive residue can have a covalently attached biotin group. The subunit can include an amino acid sequence having a designated amino and/or carboxy terminus and can include an amino acid (polypeptide) extension of from 5 to 1000 amino acid residues linked with a peptide bond to the designated amino and/or carboxy terminus, and the amino acid extension can include a binding function coupled to the nucleation site. A nanostructure strut can be attached to the specific binding site.

A device includes a substrate having a surface with a node-occupied area and a node-unoccupied area. A nanostructure node can be on the node-occupied area of the surface. A coating can cover the nanostructure node and can cover the surface node-unoccupied area of the surface. The coating can include a metal (such as iron, gold, platinum, or silver), a noble metal (such as gold, platinum, or silver), a glass (such as silicon dioxide), a ceramic, a semiconductor (such as silicon or germanium), a carbon allotrope (such as diamond or graphite), a polymer, an organic polymer (such as tetrafluoroethylene), and/or an organic material.

A device can include a substrate having a surface with a node-occupied area and a node-unoccupied area. The surface can be coated with a resist layer. A nanostructure node can be on the resist layer. The node-occupied area of the surface of the substrate can be coated with the resist layer. The node-unoccupied area of the surface of the substrate can be not coated with the resist layer. The node-unoccupied area of the surface of the substrate can be lower than (recessed with respect to) the node-occupied area of the surface of the substrate.

A device can include a proteinaceous nanostructure assembly comprising a nanostructure node. The device can include a substrate having a surface, and the proteinaceous nanostructure assembly can be coupled to the surface of the substrate. The device can include a first matrix, and the first matrix can interpenetrate the proteinaceous nanostructure assembly. The proteinaceous nanostructure assembly can have the form of a cubic lattice, and the first matrix can have the form of a cubic lattice. The first matrix can include a metal (such as iron, gold, platinum, or silver), a noble metal (such as gold, platinum, or silver), a glass (such as silicon dioxide), a ceramic, a semiconductor (such as silicon or germanium), a polymer, an organic polymer (such as tetrafluoroethylene), and/or an organic material.

A device can include a second matrix material having the same or similar form as a proteinaceous nanostructure assembly. The device can include a second matrix that includes a metal (such as iron, gold, platinum, or silver), a noble metal (such as gold, platinum, or silver), a glass (such as silicon dioxide), a ceramic, a semiconductor (such as silicon or germanium), a polymer, an organic polymer (such as tetrafluoroethylene), and/or an organic material.

BRIEF DESCRIPTION OF THE DRAWINGS

Table 1A lists template protein structures useful for the construction of nanostructure nodes having various symmetries.

Table 1B provides the four character Protein Data Bank code, amino acid sequence (using the standard 1-letter abbreviation for amino acid residues) as contained in the Protein Data Bank database, protein function, and organism from which the amino acid sequence is derived for template protein structures useful for the construction of nanostructure nodes.

Table 2 lists specifications and amino acid sequences for node embodiments with various symmetries.

Figure 1:
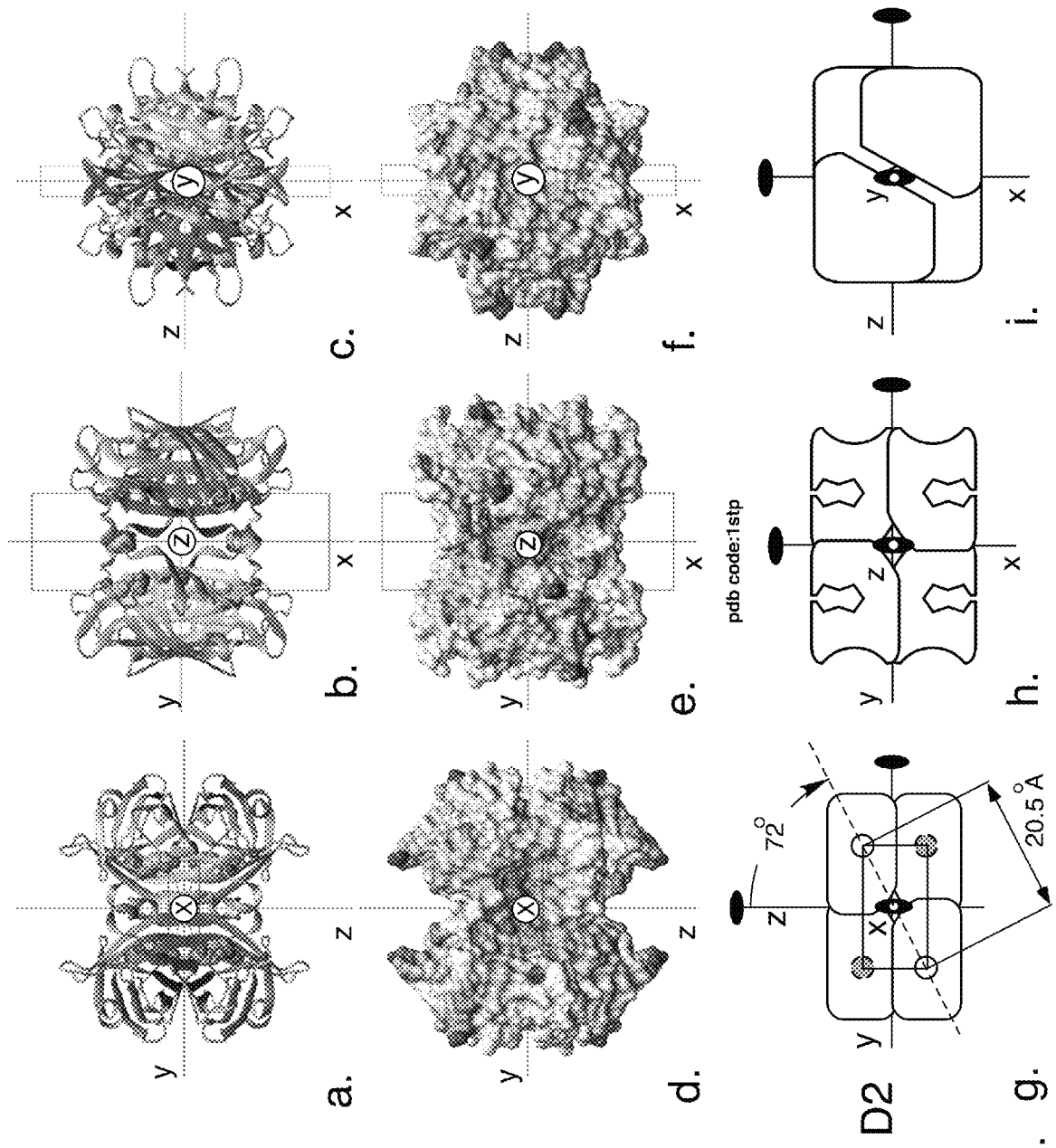

FIG. 1 shows schematic backbone and surface representations of the streptavidin strut molecule, a tetrameric protein with D2 symmetry, indicating geometry of biotin ligand binding sites and interaction geometry of node attachment sites.

Figure 2:
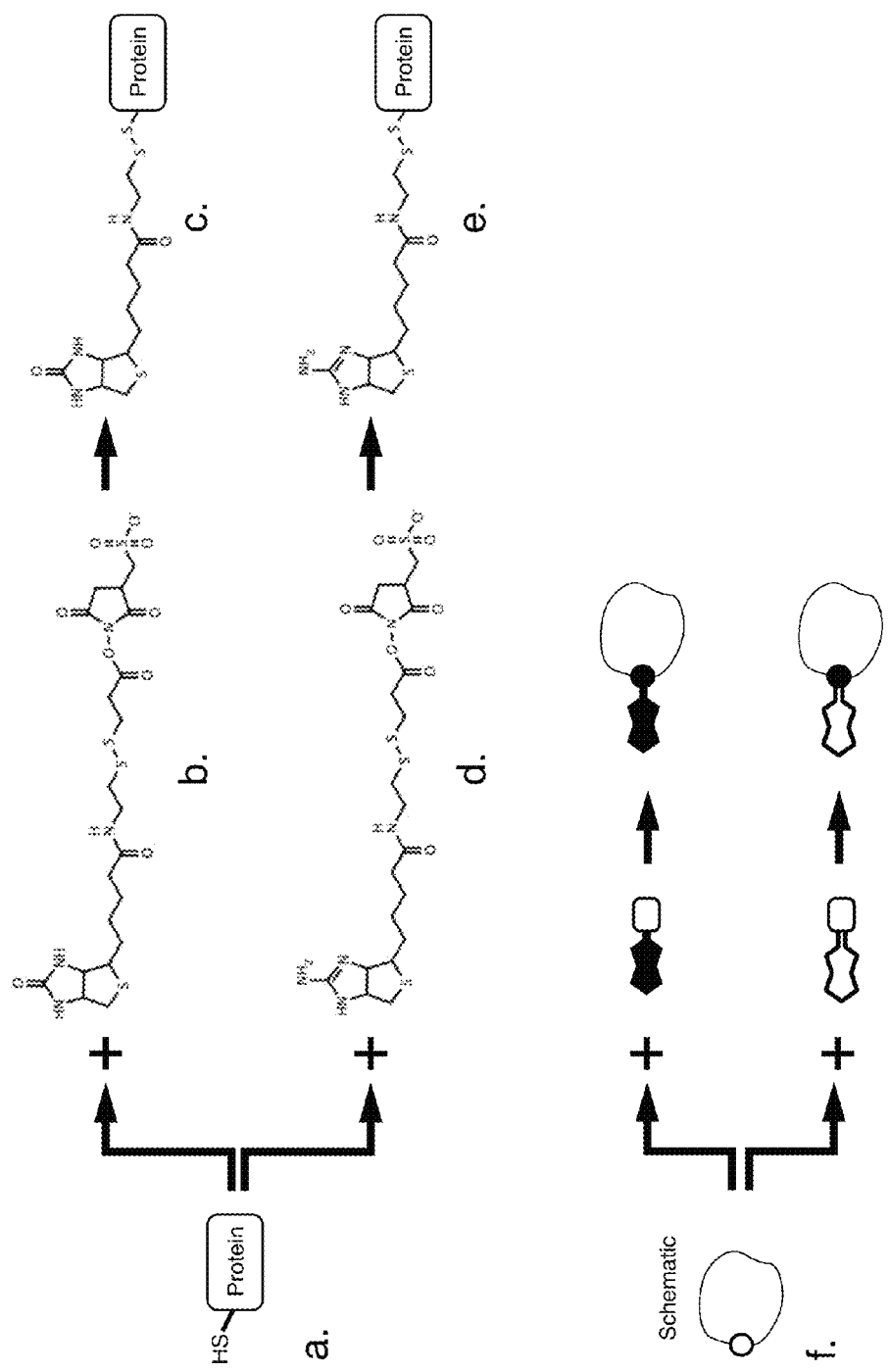

FIG. 2 shows the reaction of protein cysteine sulfhydryl groups with biotinylation reagents.

Figure 3:
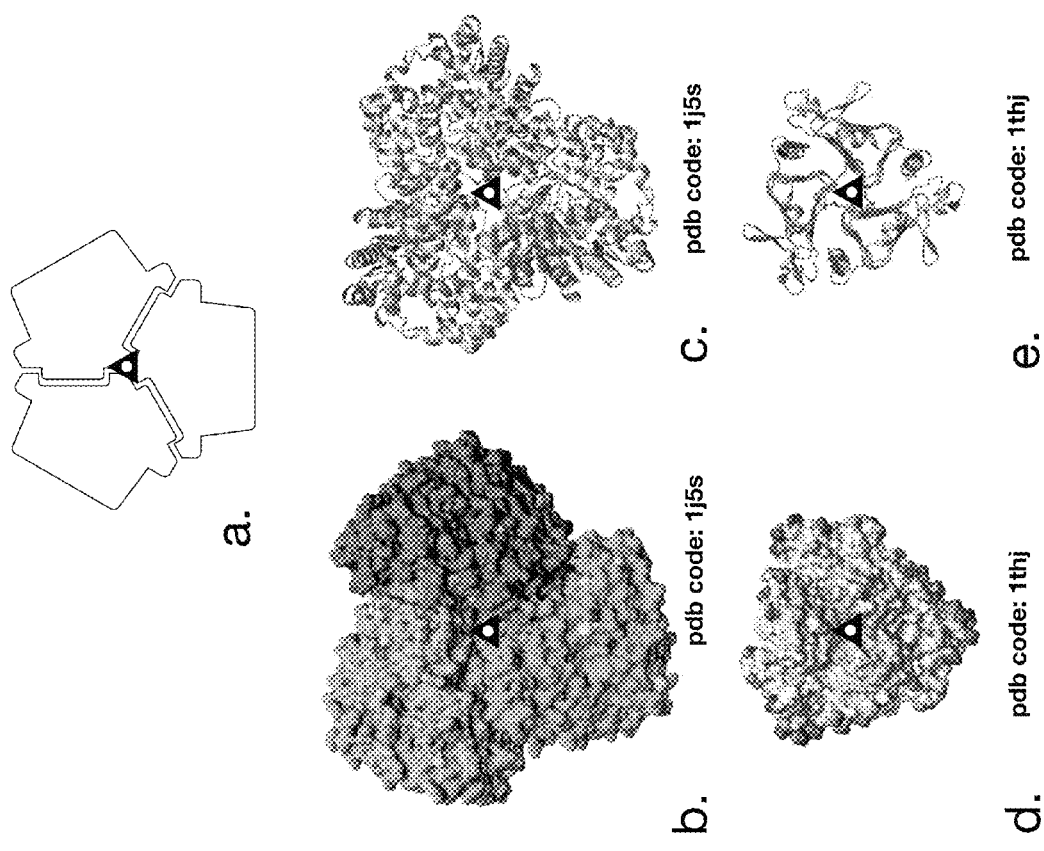

FIG. 3 presents schematic illustrations of nodes with three-fold (C3) rotational symmetry and examples of corresponding protein multimers from thermostable microorganisms useful as node templates.

Figure 4:
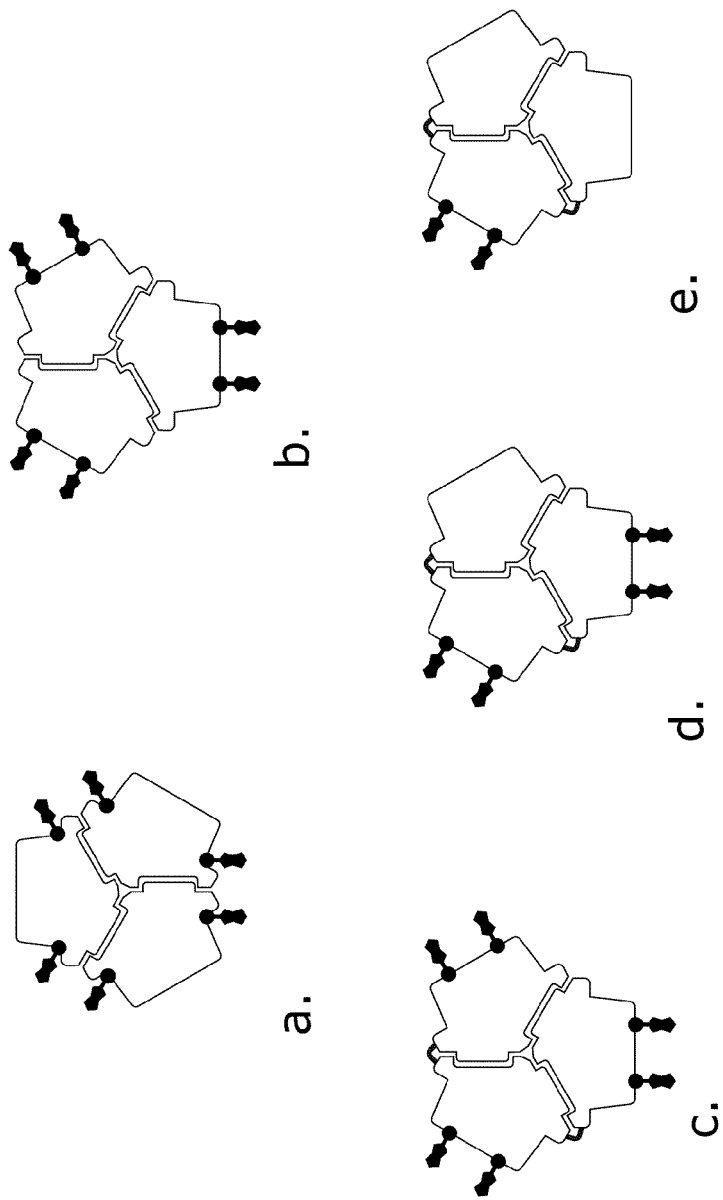

FIG. 4 presents schematic illustrations of single-chain nodes based on protein multimers with three-fold rotational (C3) symmetry.

Figure 5:
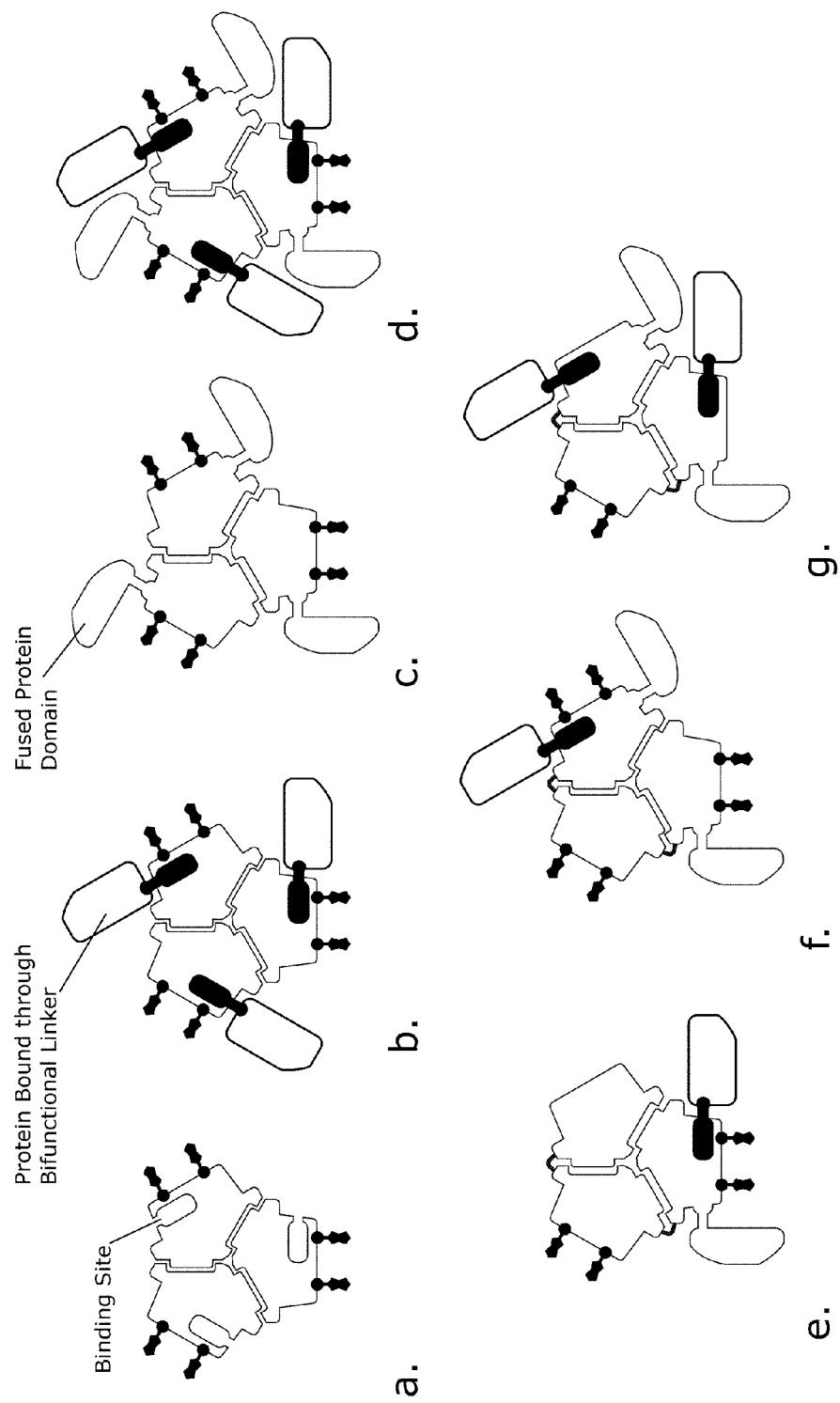

FIG. 5 presents schematic illustrations of multiple and single-chain nodes based protein multimers with three-fold rotational (C3) symmetry, incorporating functional binding sites and fused protein domains.

Figure 6:
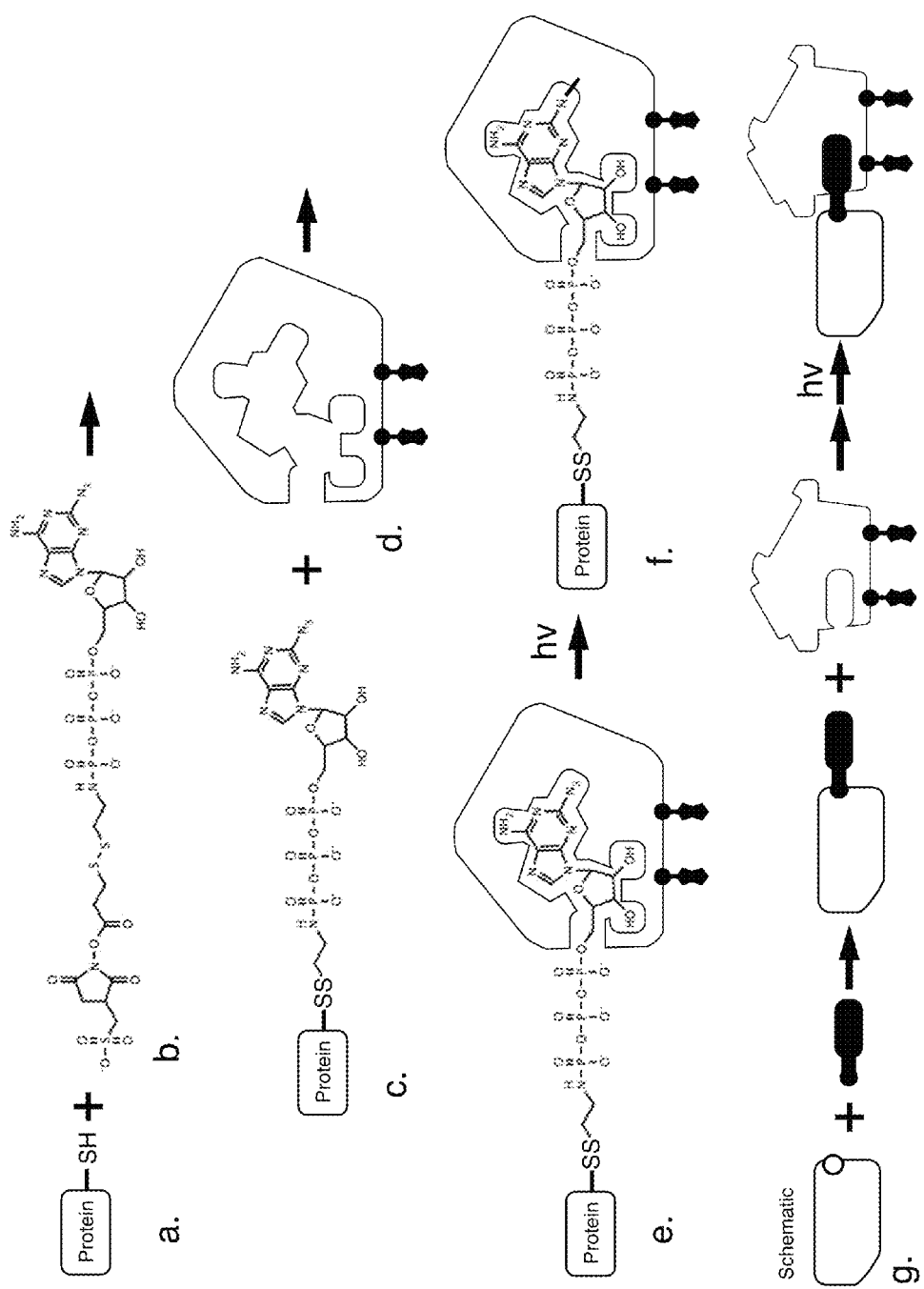

FIG. 6 shows the reaction of protein cysteine sulfhydryl groups with bifunctional crosslinking reagents.

Figure 7:
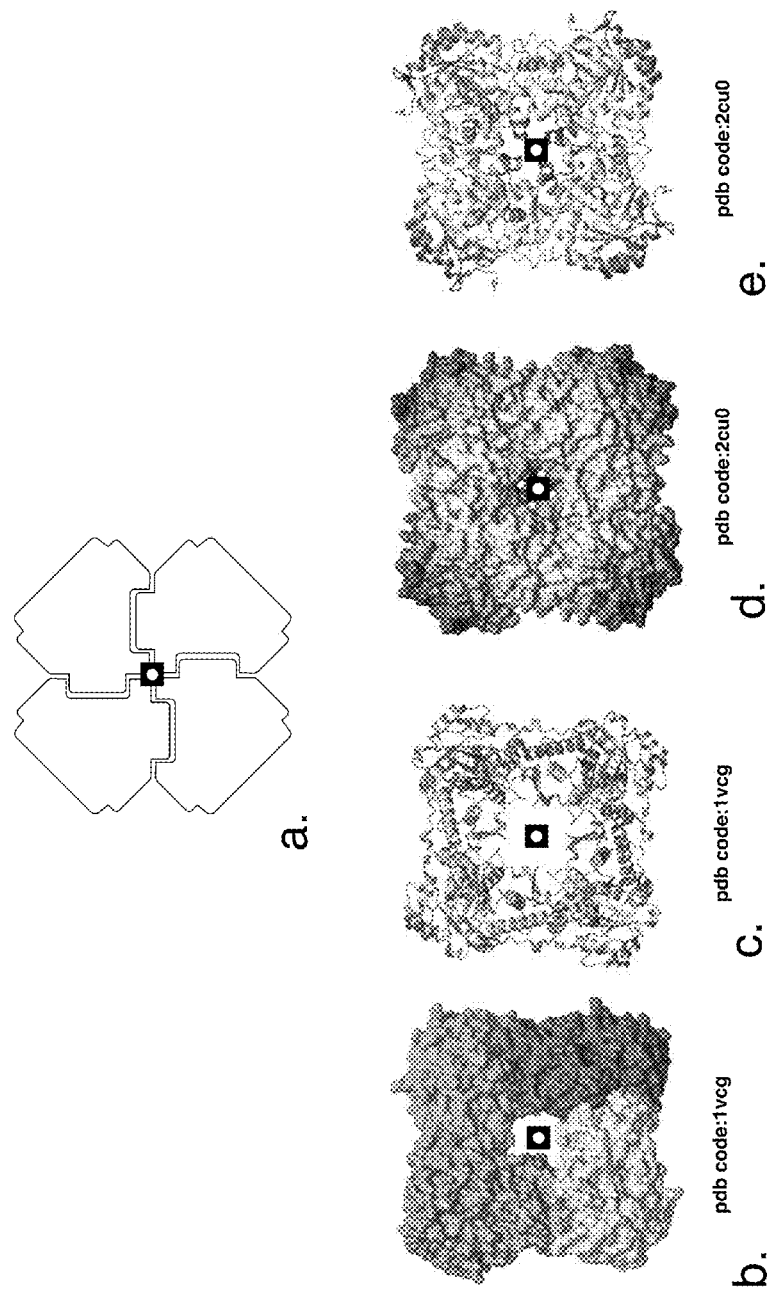

FIG. 7 presents schematic illustrations of nodes with four-fold (C4) rotational symmetry and examples of corresponding protein multimers from thermostable microorganisms useful as node templates.

Figure 8:
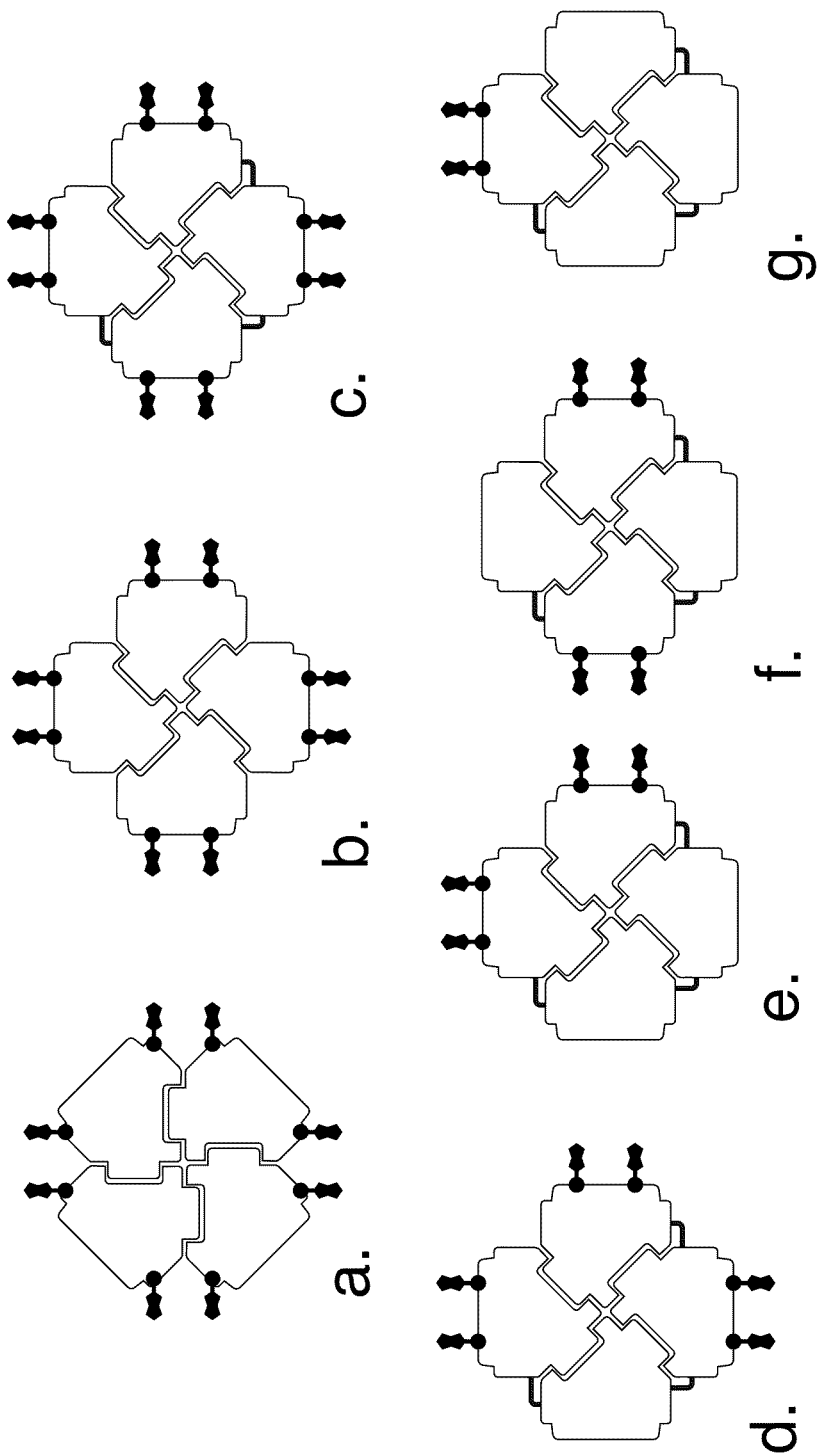

FIG. 8 presents schematic illustrations of single-chain nodes based on a protein multimers with four-fold rotational (C4) symmetry.

Figure 9:
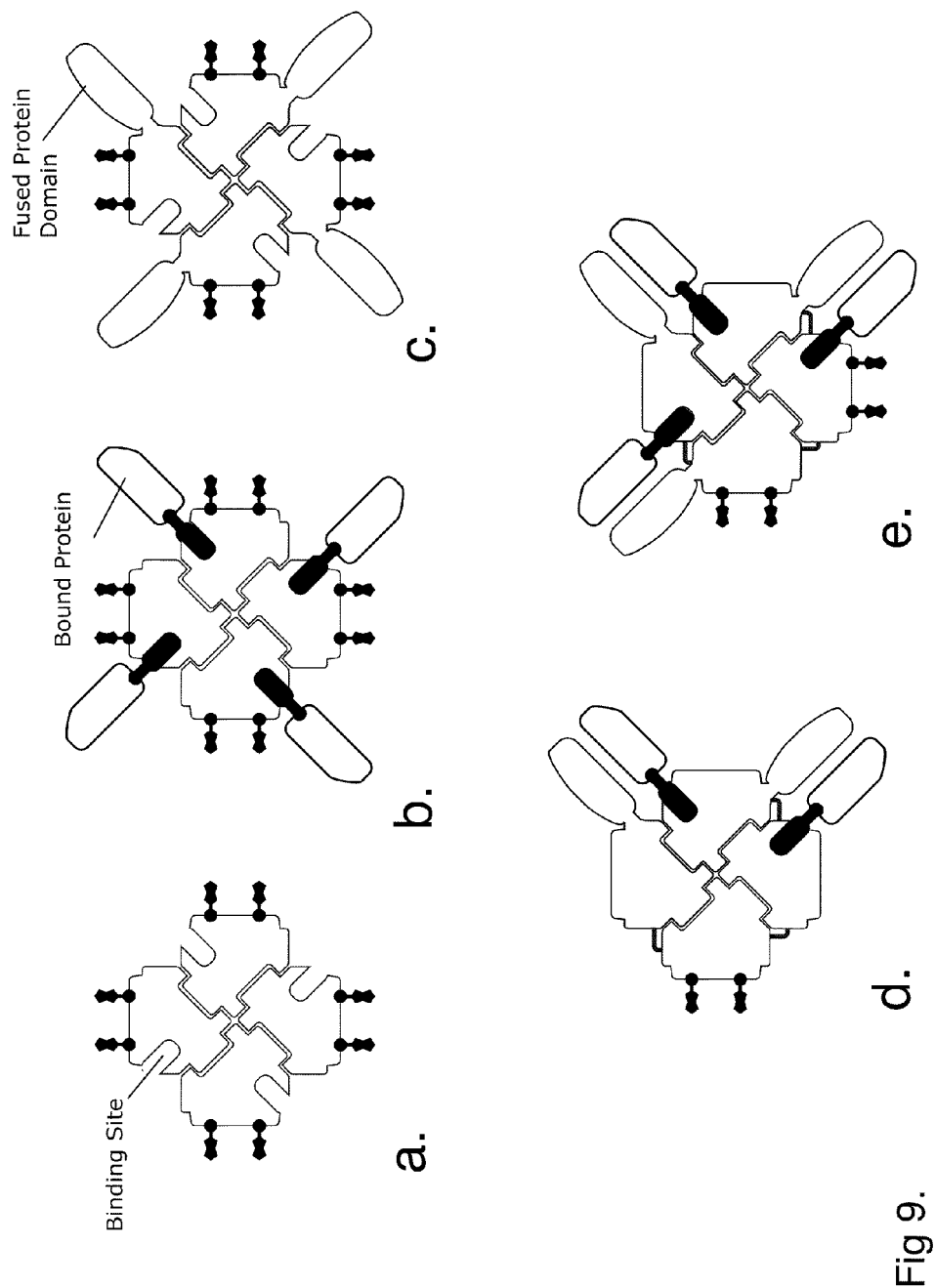

FIG. 9 presents schematic illustrations of multiple and single-chain nodes with four-fold rotational (C4) symmetry, incorporating functional binding sites and fused protein domains.

Figure 10:
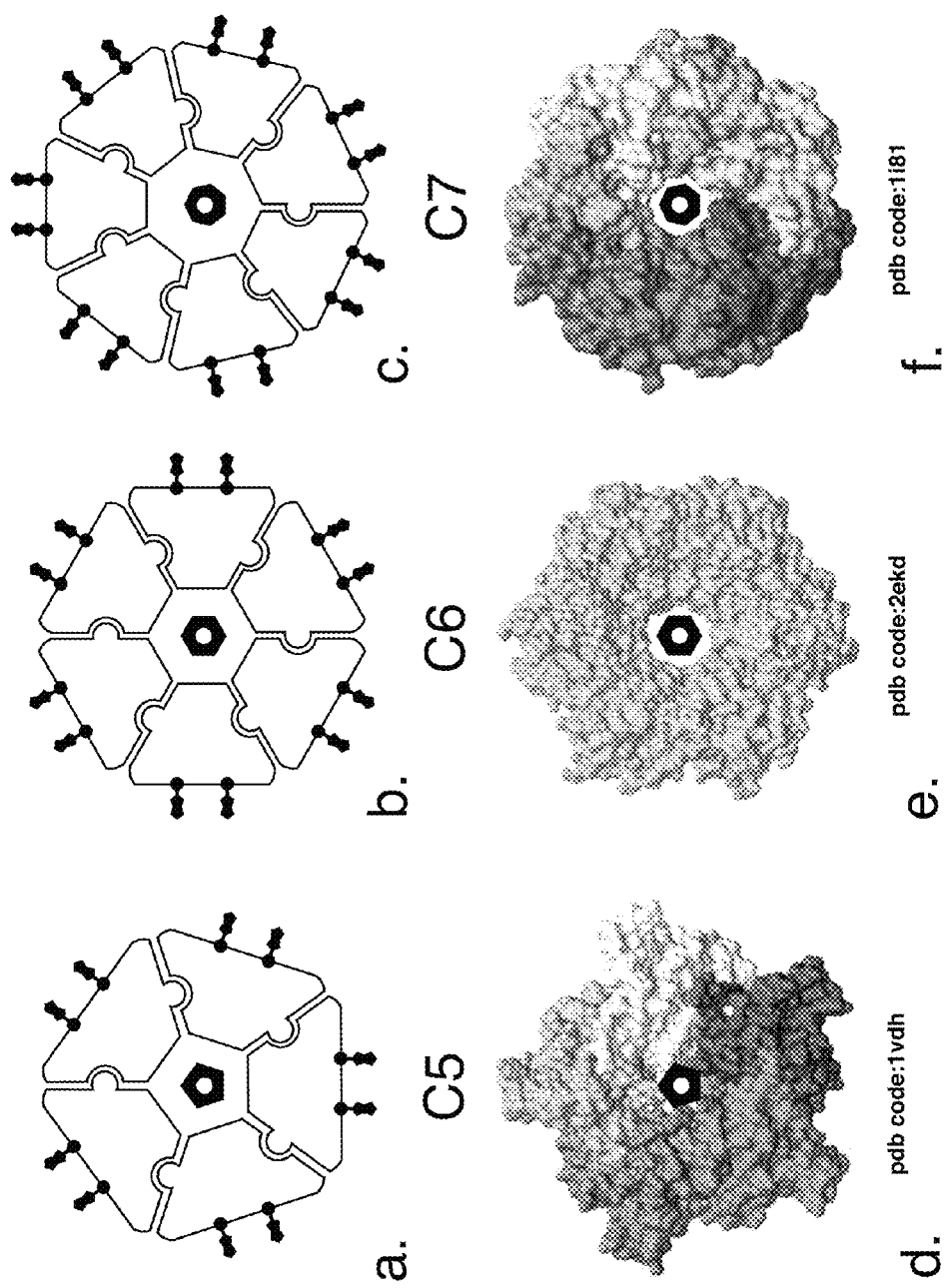

FIG. 10 presents schematic illustrations of nodes with C5, C6, and C7 rotational symmetry and representative examples of corresponding protein multimers from thermostable microorganisms useful as node templates.

Figure 11:
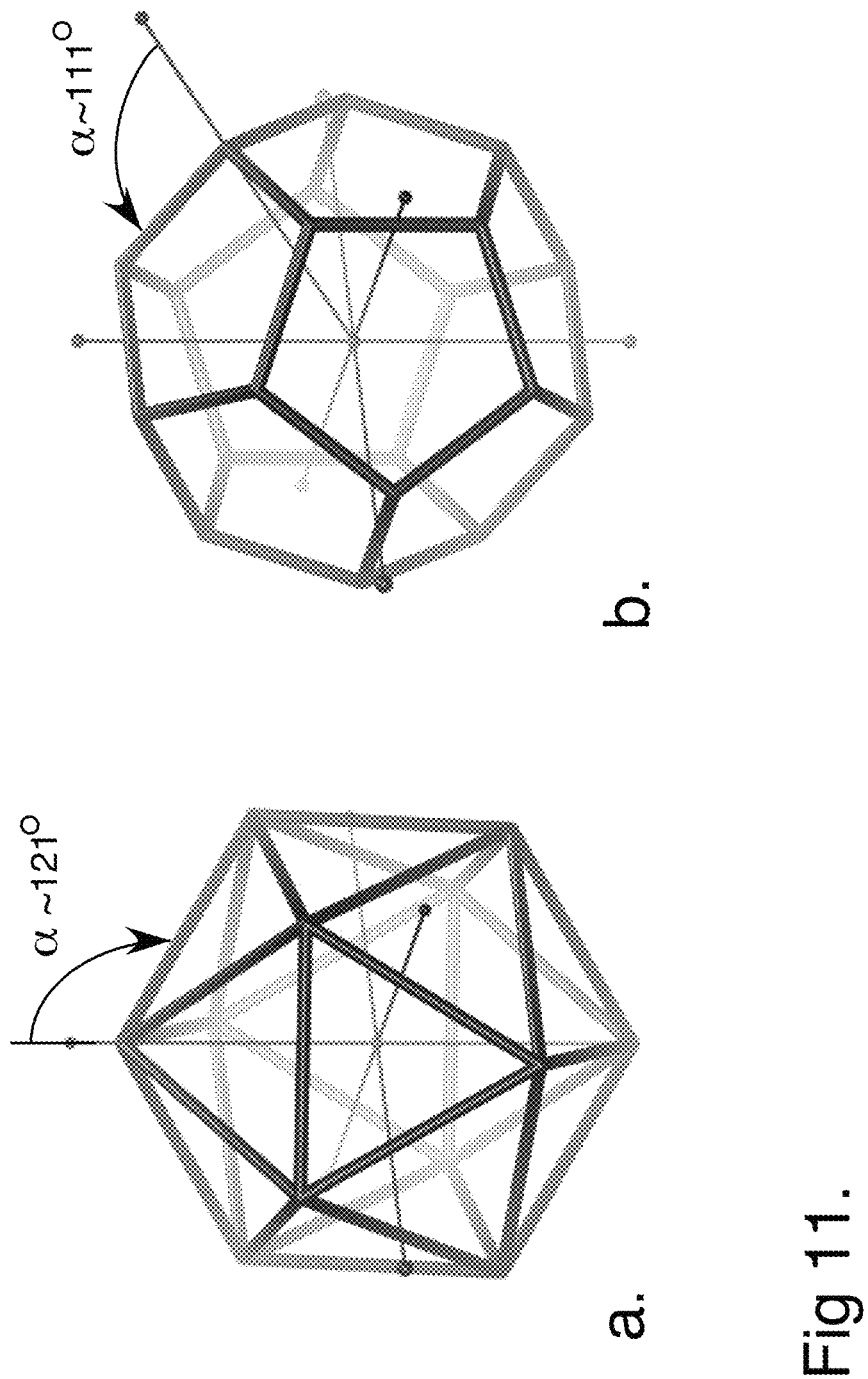

FIG. 11 presents schematic illustrations of 3-dimensional polyhedra incorporating nodes with C3 and C5 symmetry.

Figure 12:
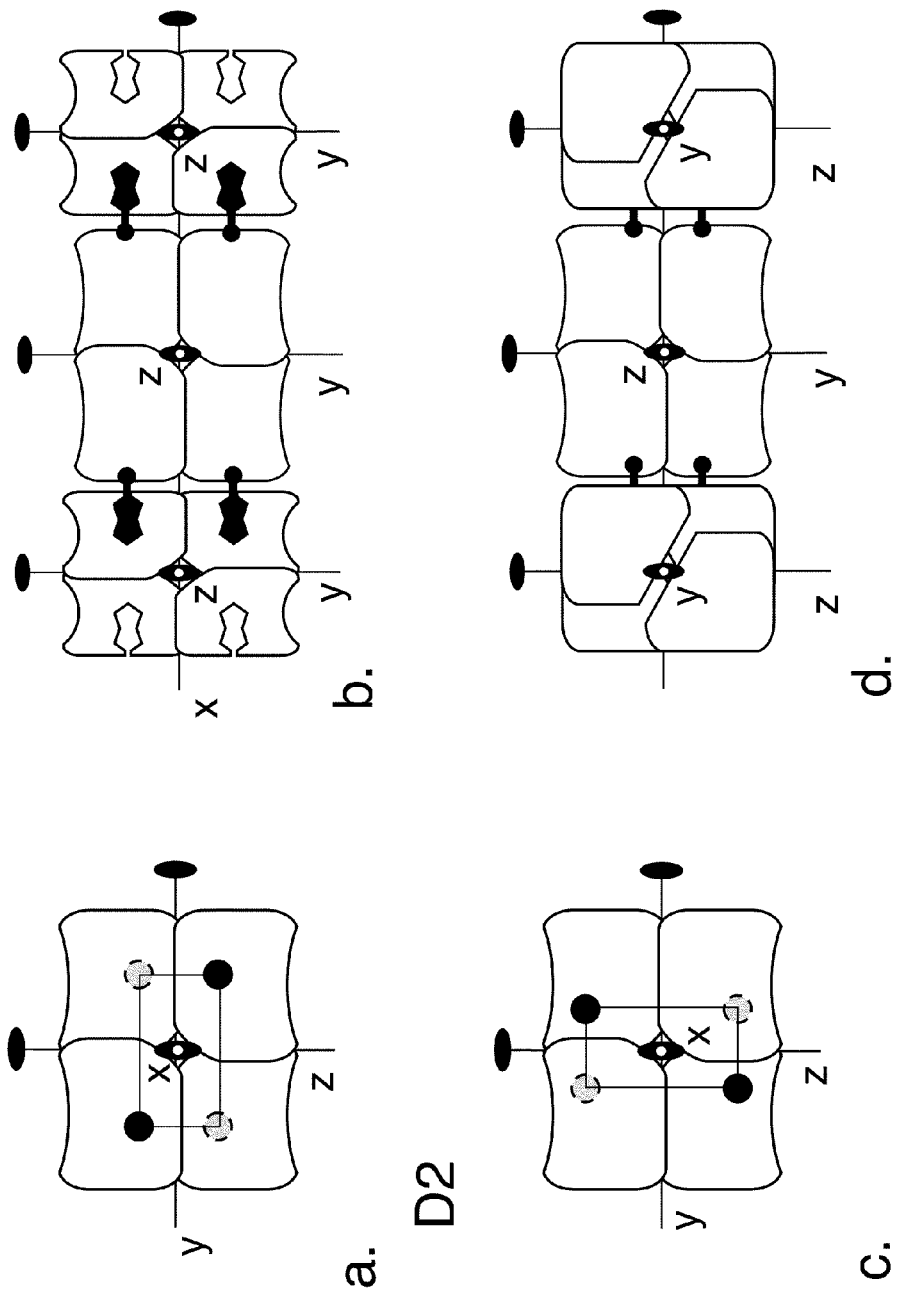

FIG. 12 presents schematic illustrations of D2 symmetric nodes used as strut extenders.

Figure 13:
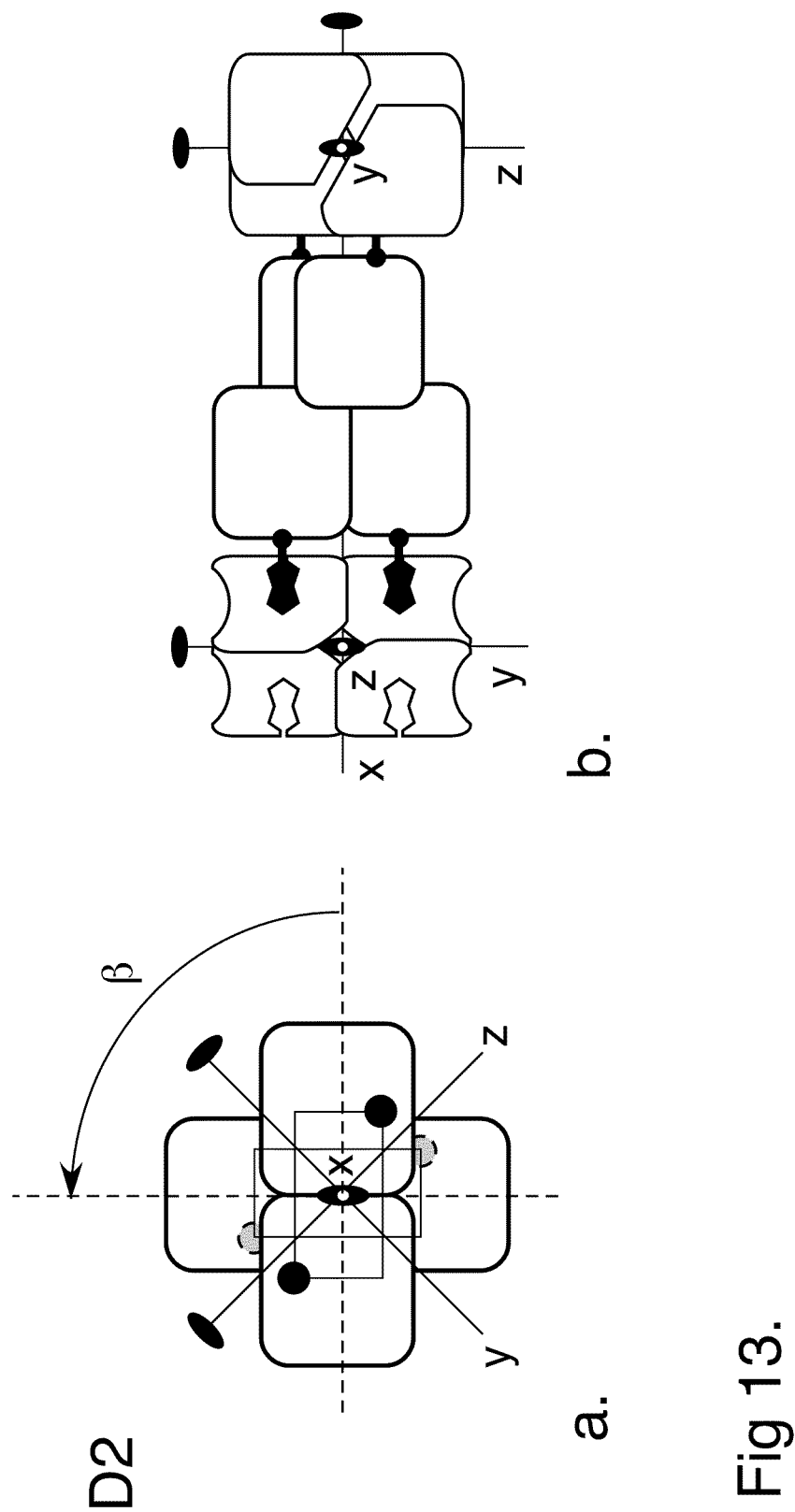

FIG. 13 presents illustrations of a D2 node used as a strut extender that introduces an axial rotation along the strut axis.

Figure 14:
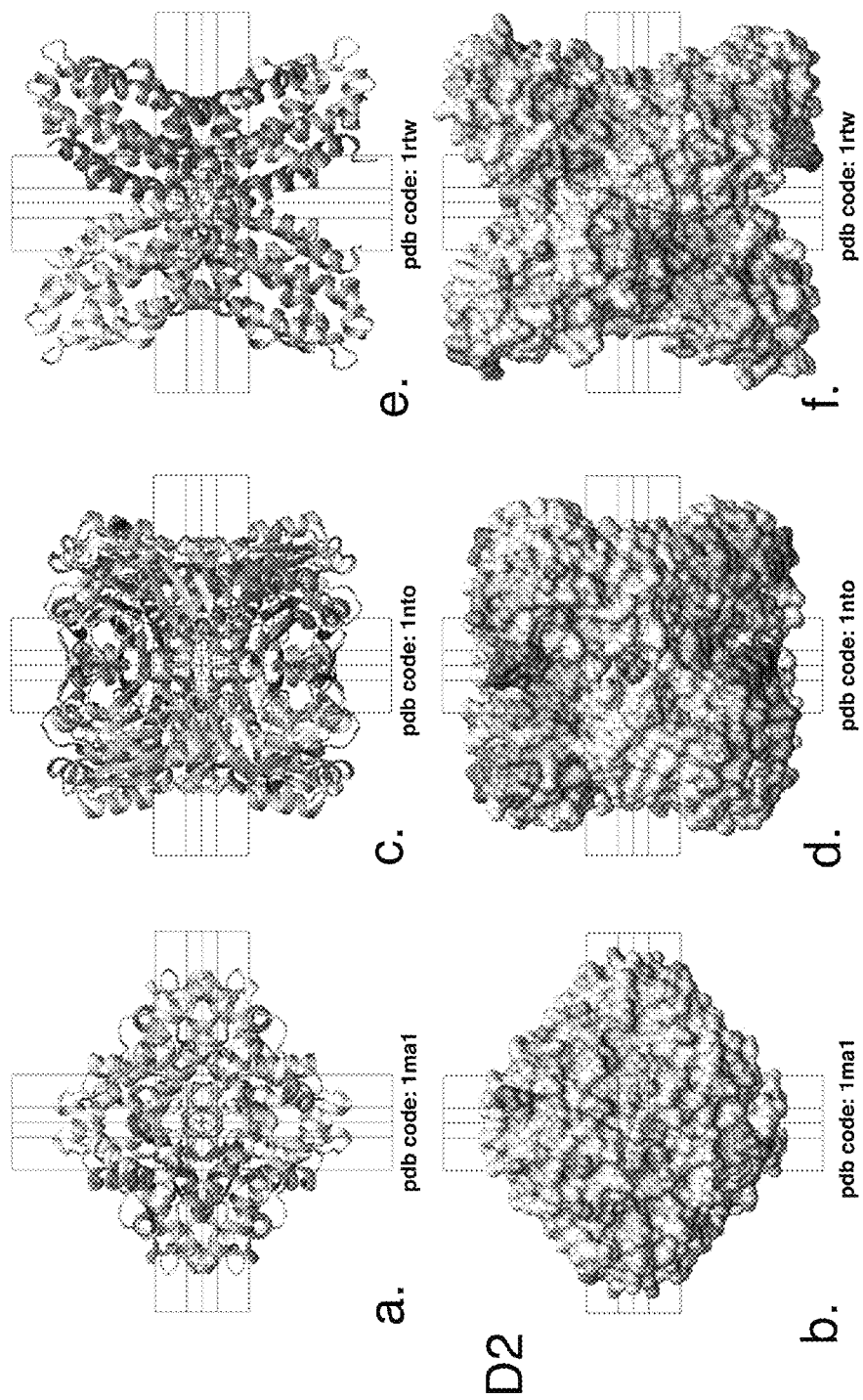

FIG. 14 presents illustrations of D2 symmetric protein multimers from thermostable microorganisms useful as node templates.

FIG. 15 presents schematic illustrations of a hexameric node with D3 symmetry and an octameric node with D4 symmetry.

Figure 16:
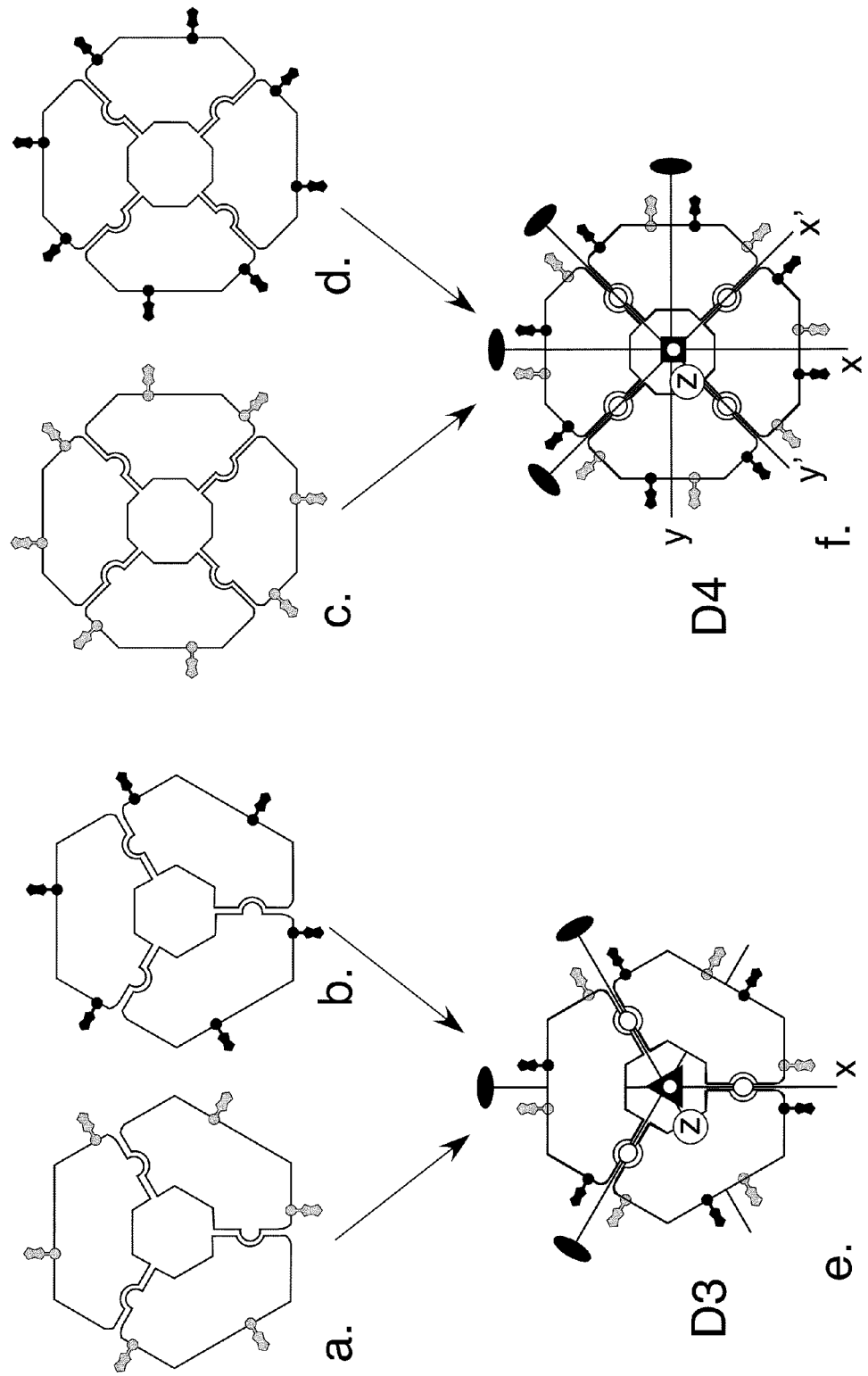

FIG. 16 presents schematic illustrations of a doubly-modified hexameric node with D3 symmetry and an doubly-modified octameric node with D4 symmetry.

Figure 17:
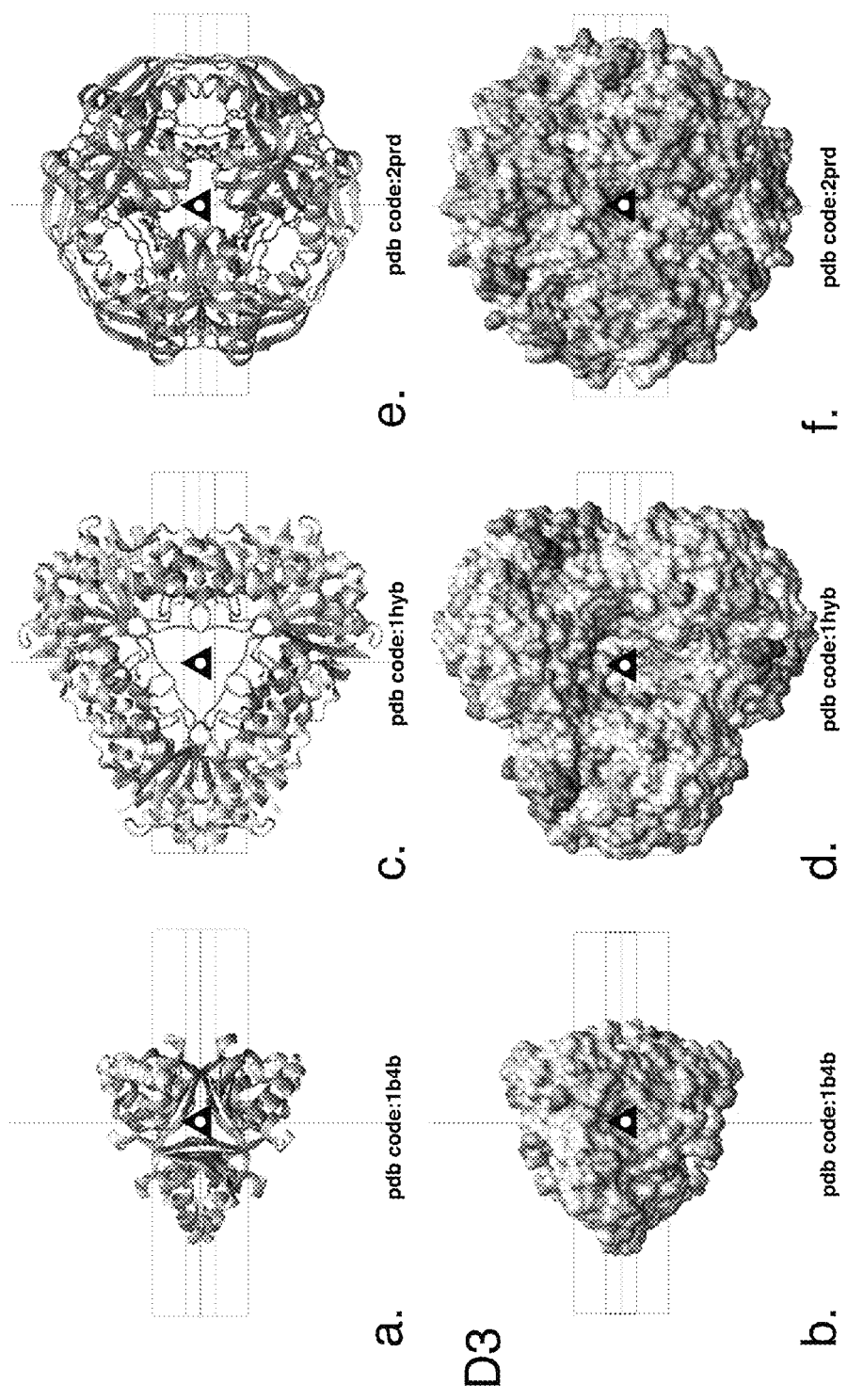

FIG. 17 presents illustrations of hexameric protein multimers with D3 symmetry from thermostable microorganisms useful as node templates.

Figure 18:
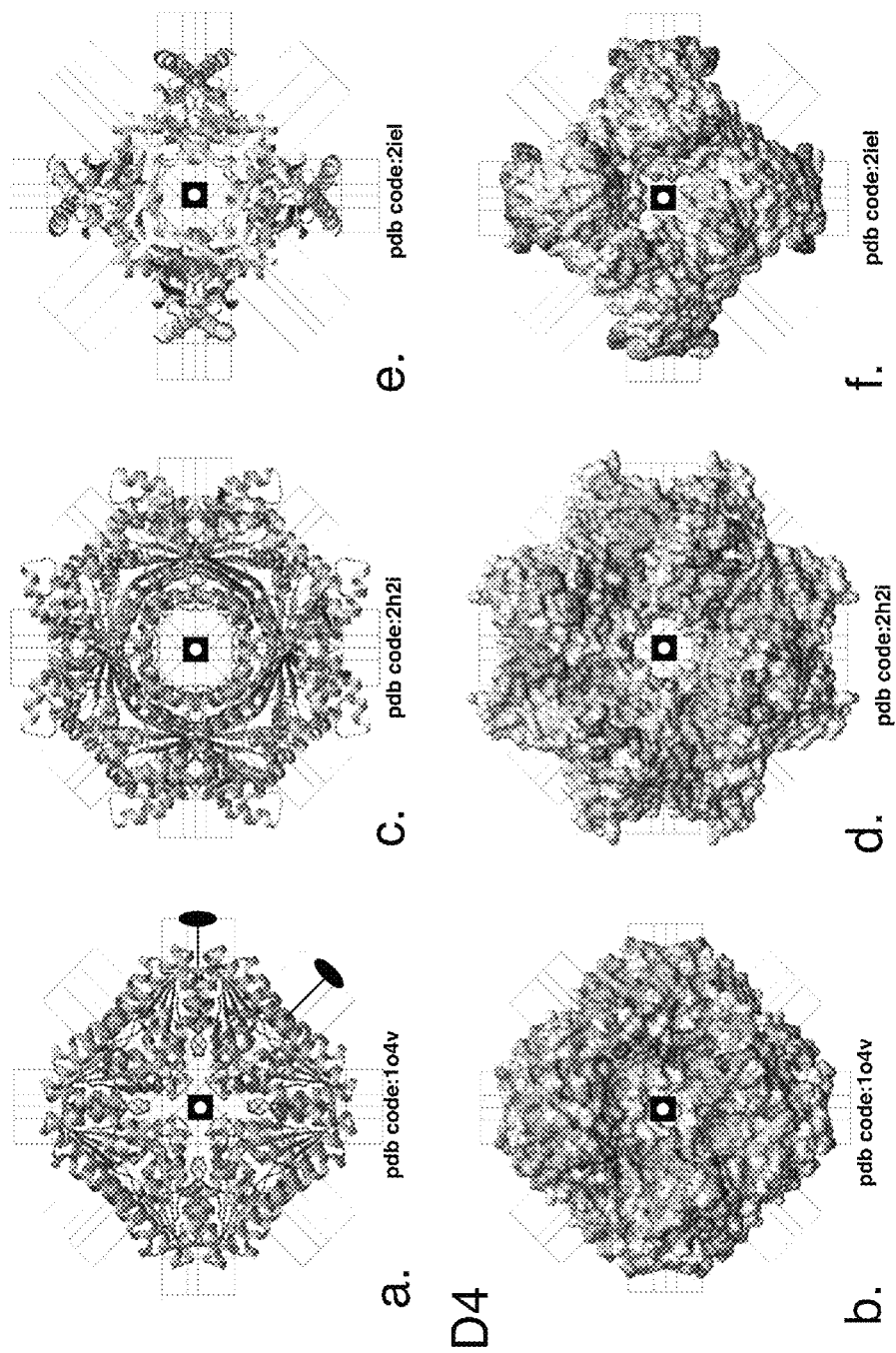

FIG. 18 presents illustrations of octameric protein multimers with D4 symmetry from thermostable microorganisms useful as node templates.

Figure 19:
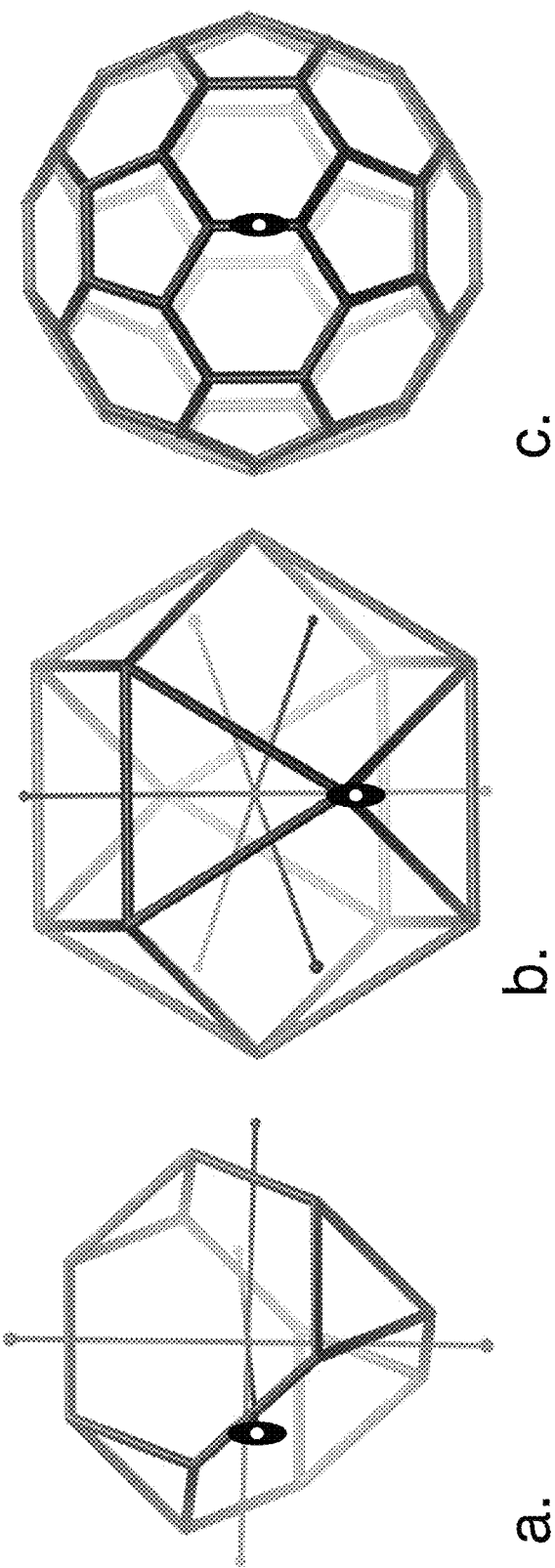

FIG. 19 presents illustrations of regular polyhedra with dyad axes of symmetry.

Figure 20:
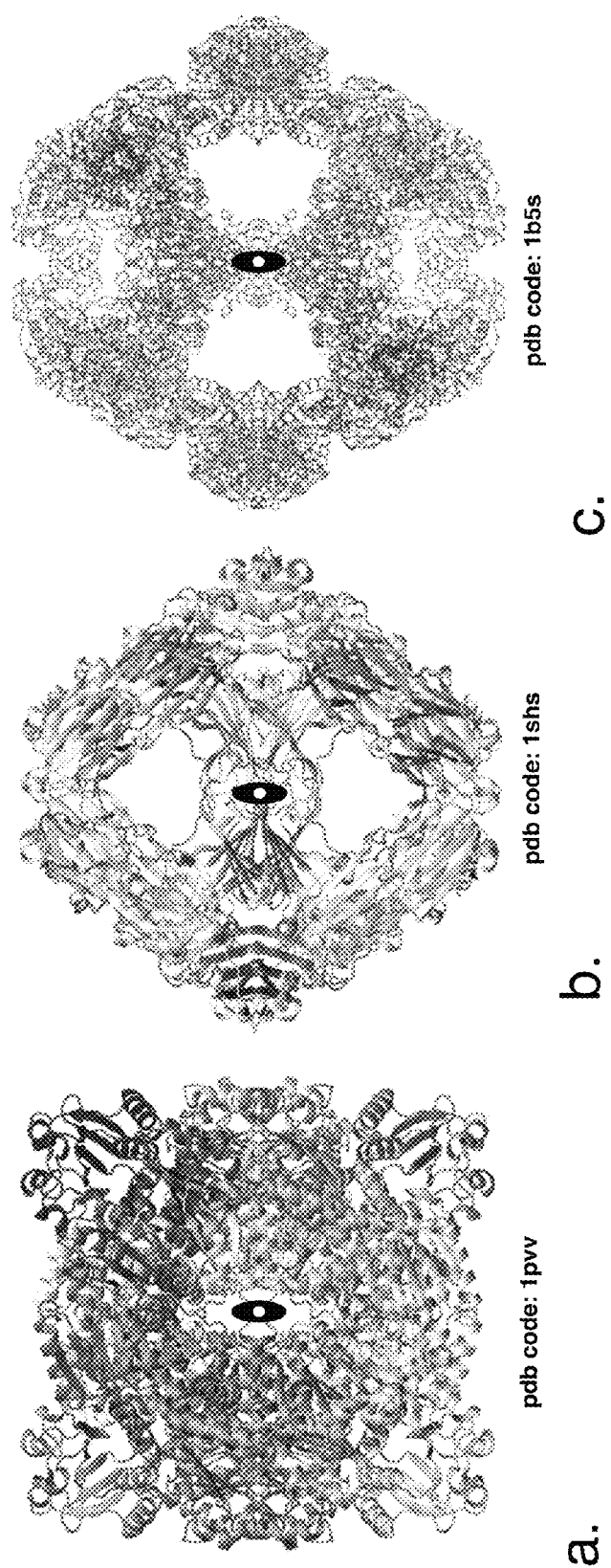

FIG. 20 presents illustrations of protein multimers from thermostable microorganisms having the symmetry properties of regular polyhedra and utility as templates for nanostructure node proteins.

Figure 21:
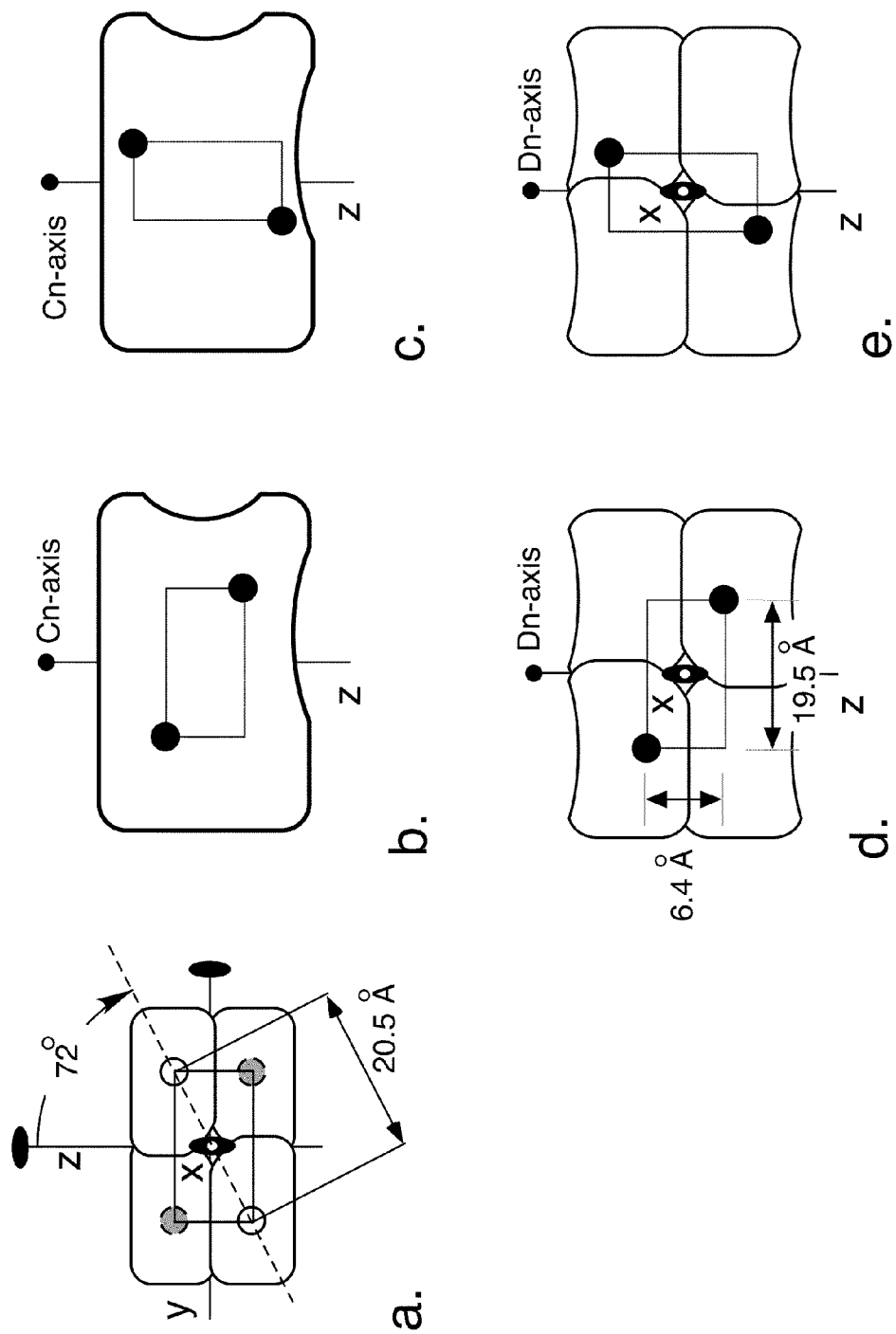

FIG. 21 requirements for complementary binding geometry between streptavidin and node surfaces.

Figure 22:
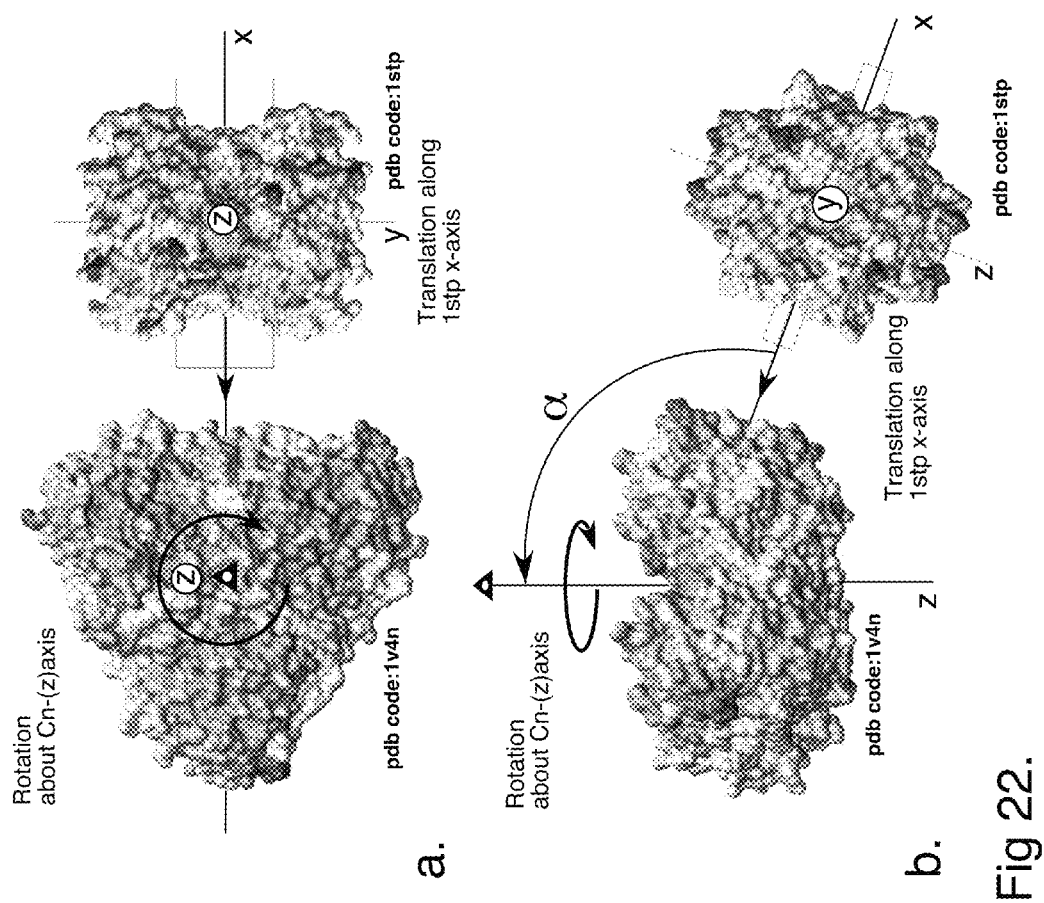

FIG. 22 illustrates methods used to determine the sites of surface amino acid substitution to transform multimeric node templates into nodes able to bind streptavidin with defined relative geometry.

FIG. 23 presents a stereoscopic image of a D2 symmetric protein showing bounding boxes used to determine the sites of surface amino acid substitution to transform multimeric node templates into nodes able to bind streptavidin with defined relative geometry.

Figure 24:
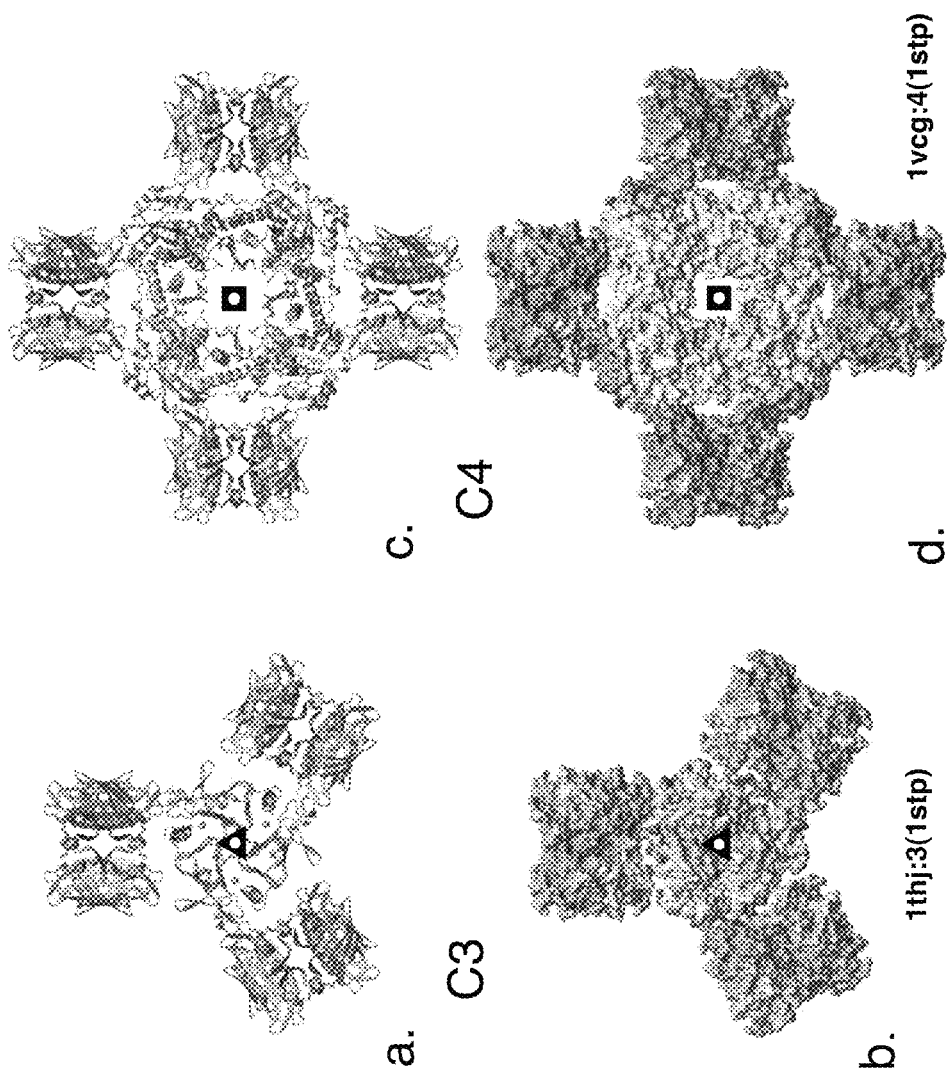

FIG. 24 presents schematic illustrations and computer models of C3 and C4 symmetric nodes together with streptavidin tetramers oriented to allow linkages through biotin linkages.

Figure 25:
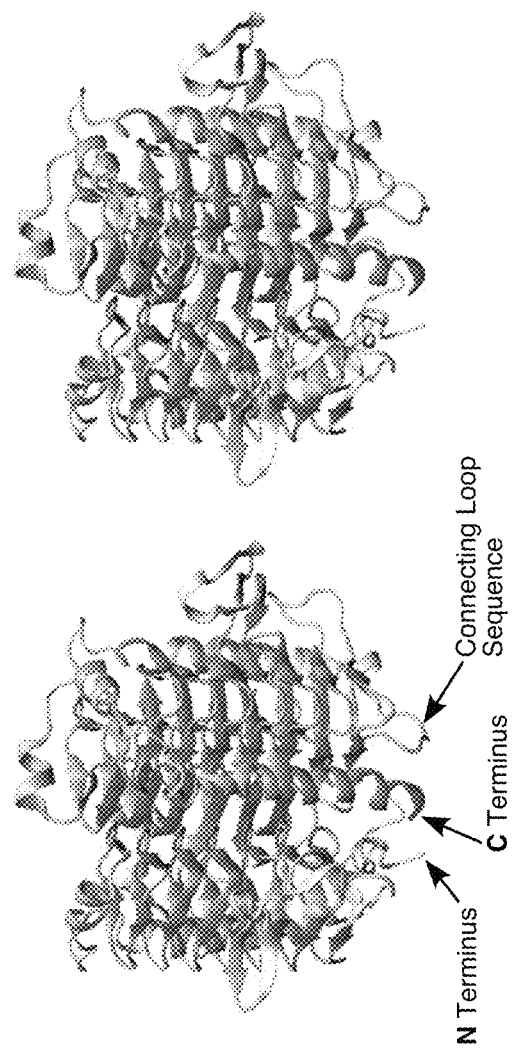

FIG. 25 presents a stereoscopic representation of an engineered single-chain C3 symmetric node.

Figure 26:
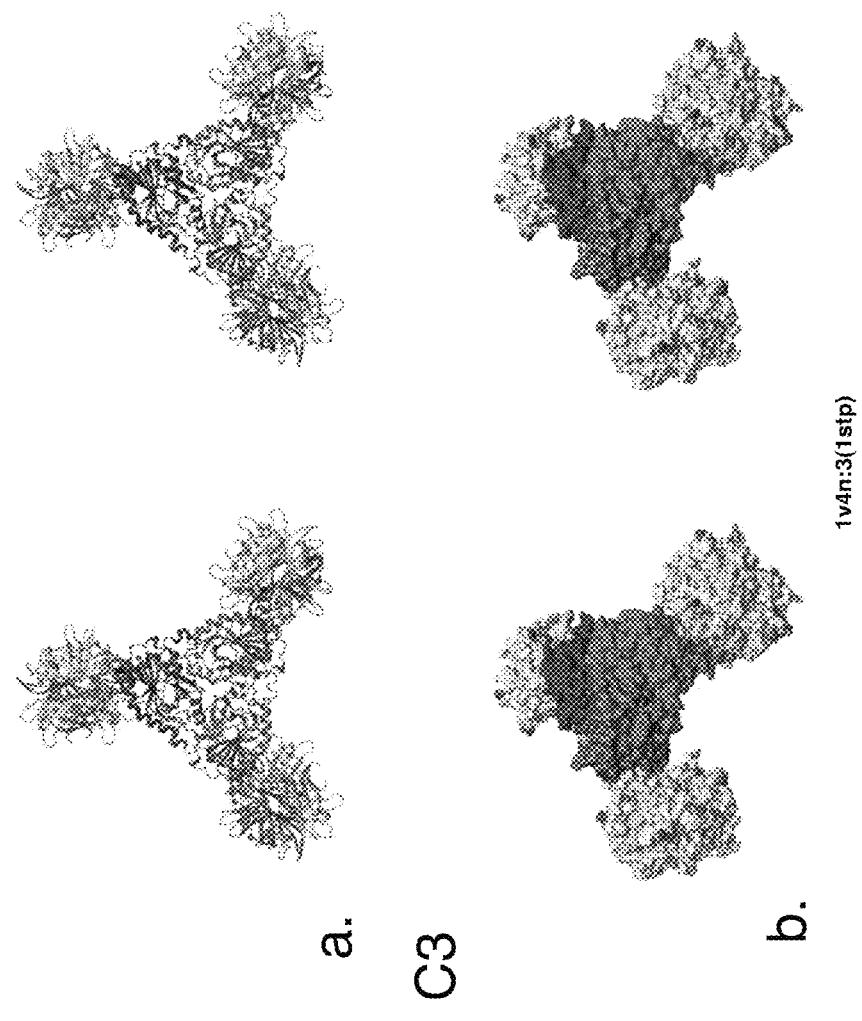

FIG. 26 presents computer models of a C3 symmetric node complexed with three streptavidin tetramers with geometry suitable for the apex formation of a dodecahedron.

Figure 27:
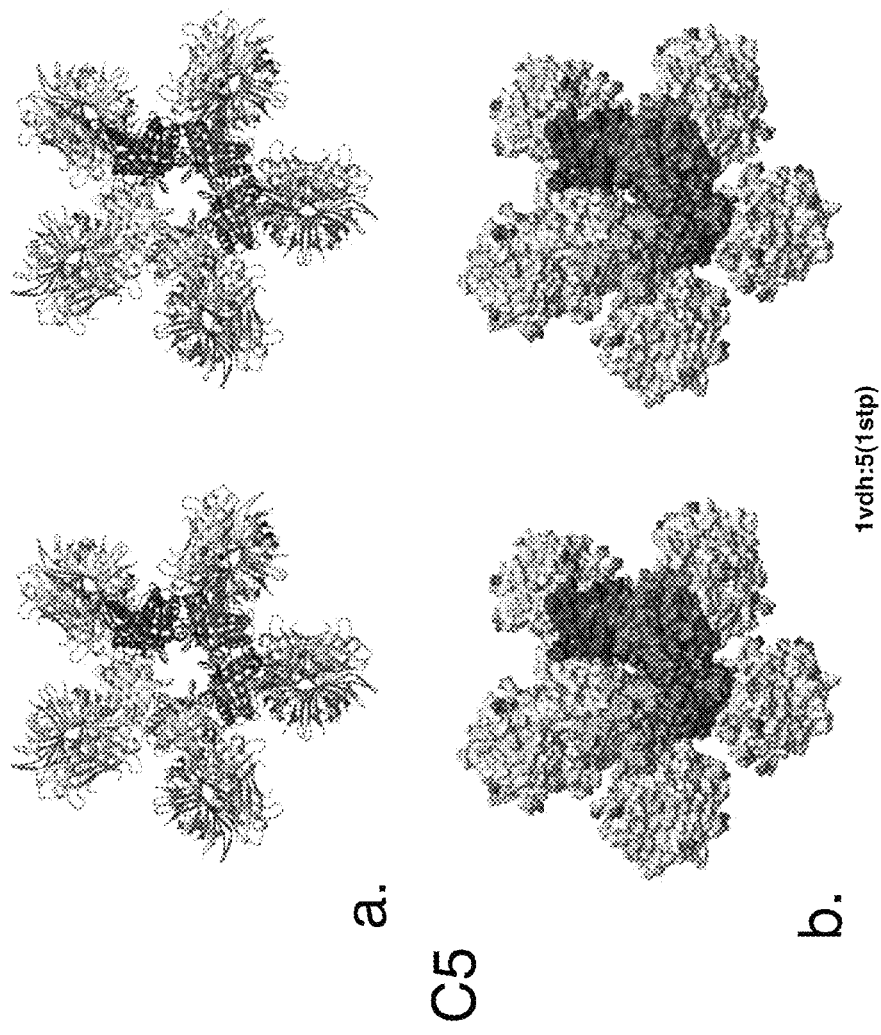

FIG. 27 presents computer models of a C5 symmetric node complexed with five streptavidin tetramers with geometry suitable for the apex formation of an icosahedron.

FIG. 28 presents schematic illustrations of D2 symmetric nodes engineered from streptavidin.

Figure 29:
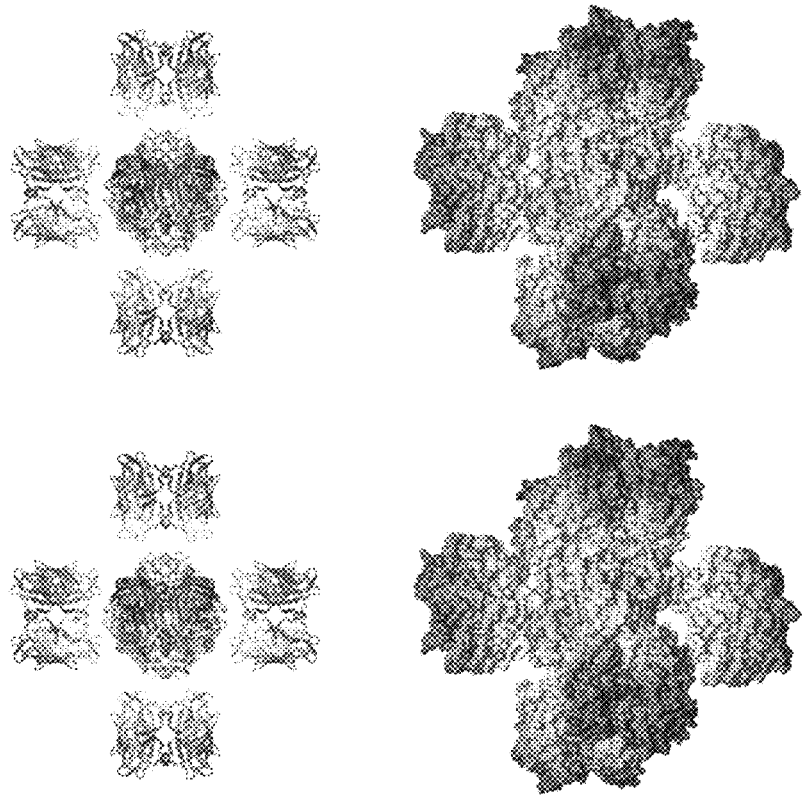

FIG. 29 presents schematic illustrations and computer models of a D2 symmetric node oriented to allow linkages to streptavidin tetramers through biotin linkages along 3 dyad axes.

Figure 30:
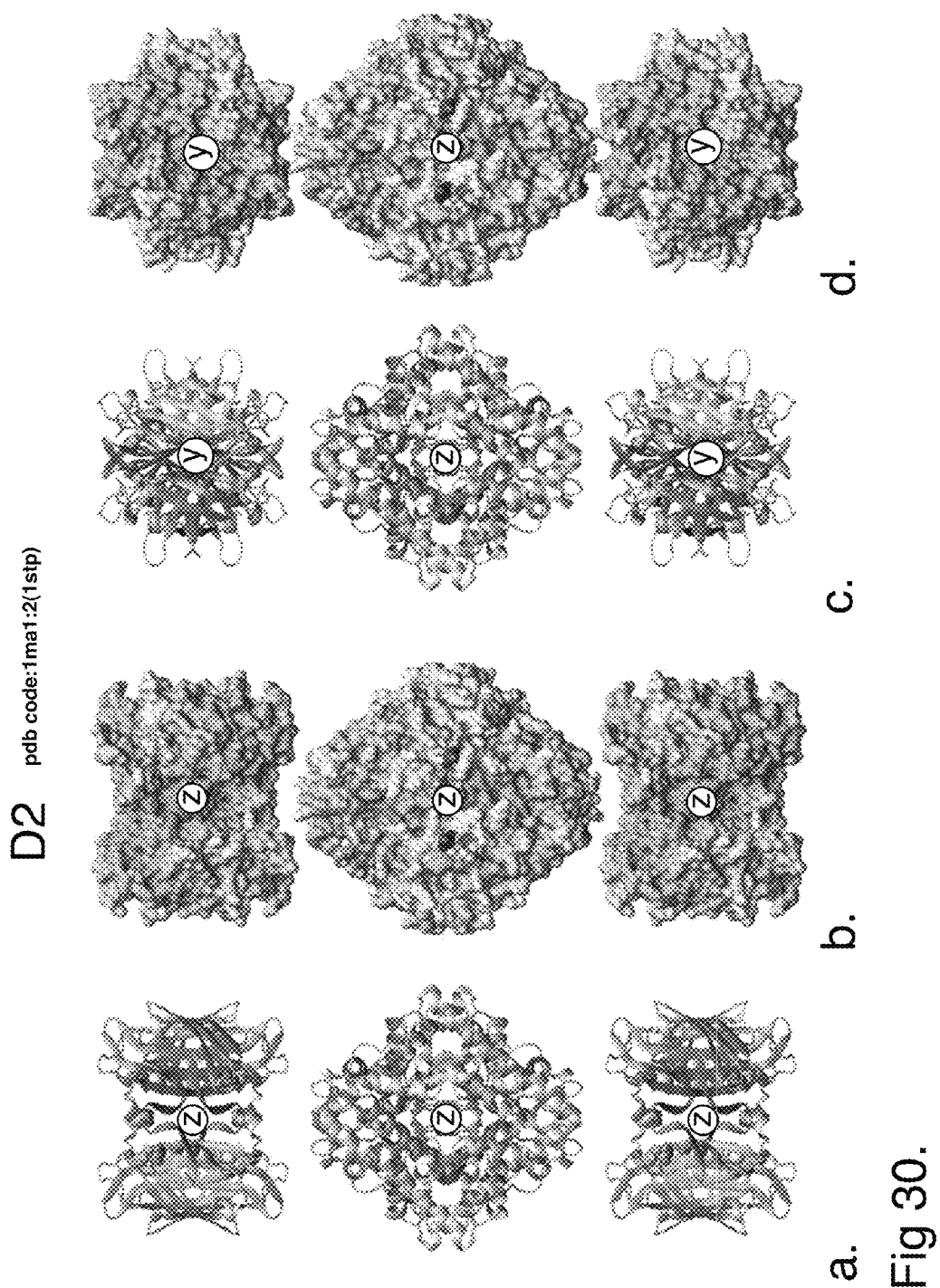

FIG. 30 presents schematic illustrations and computer models of D2 symmetric nodes useful as a strut extender together with streptavidin tetramers oriented to allow biotin linkages along one dyad axis.

Figure 31:
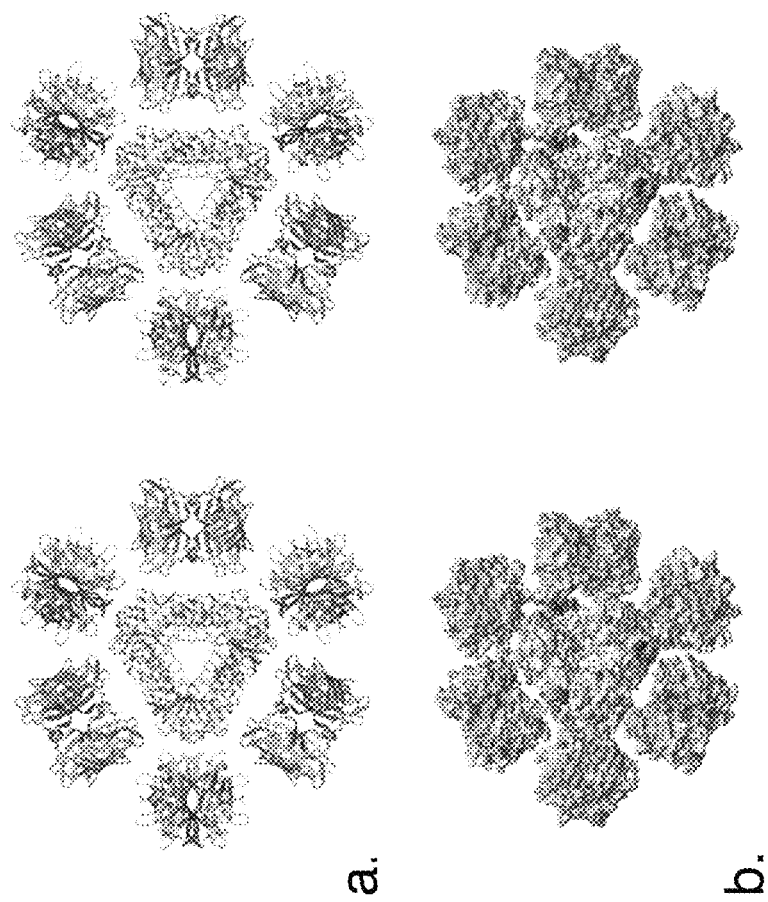

FIG. 31 presents schematic illustrations and computer models of hexameric nodes with D3 symmetry with streptavidin tetramers oriented to allow linkages to streptavidin through biotin linkages along a dyad axis.

Figure 32:
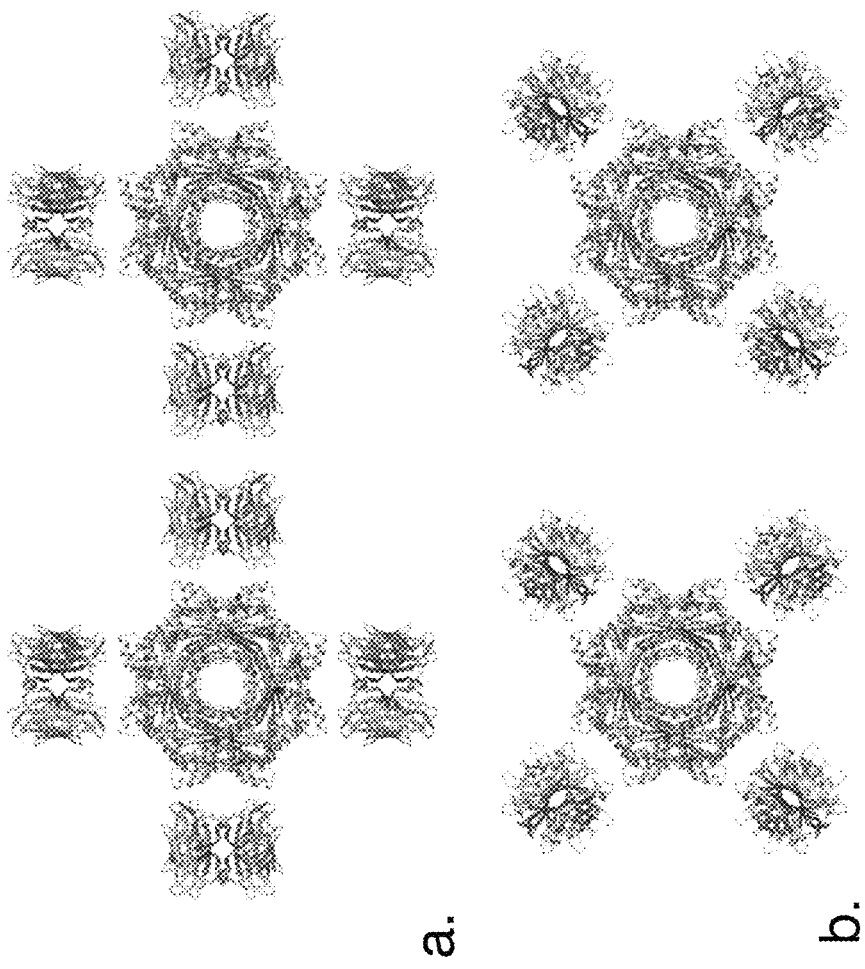

FIG. 32 presents schematic illustrations and computer models of octameric nodes with D4 symmetry with streptavidin tetramers oriented to allow linkages to streptavidin through biotin linkages along dyad axes.

Figure 33:
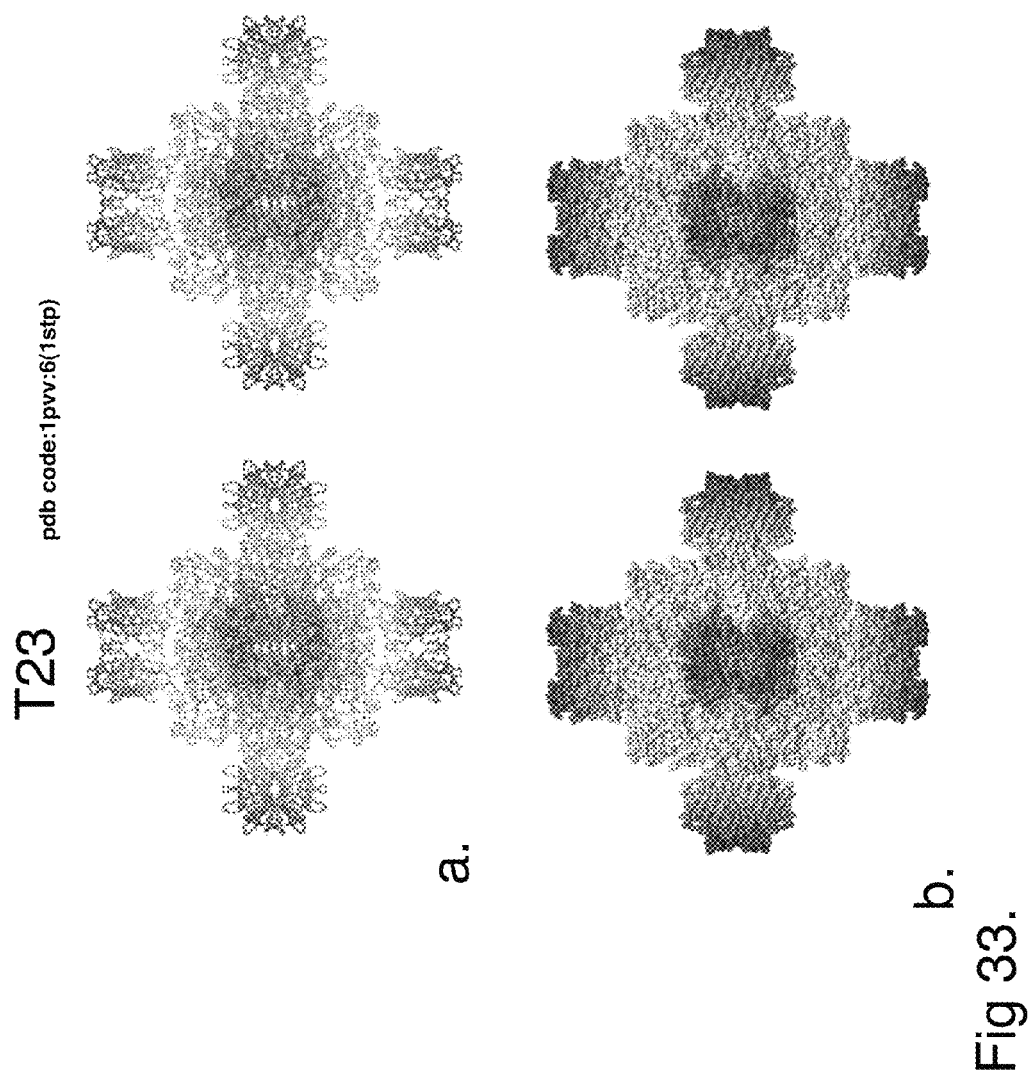

FIG. 33 presents schematic illustrations and computer models of dodacameric nodes with tetrahedral symmetry with streptavidin tetramers oriented to allow linkages through biotin linkages along dyad axes.

Figure 34:
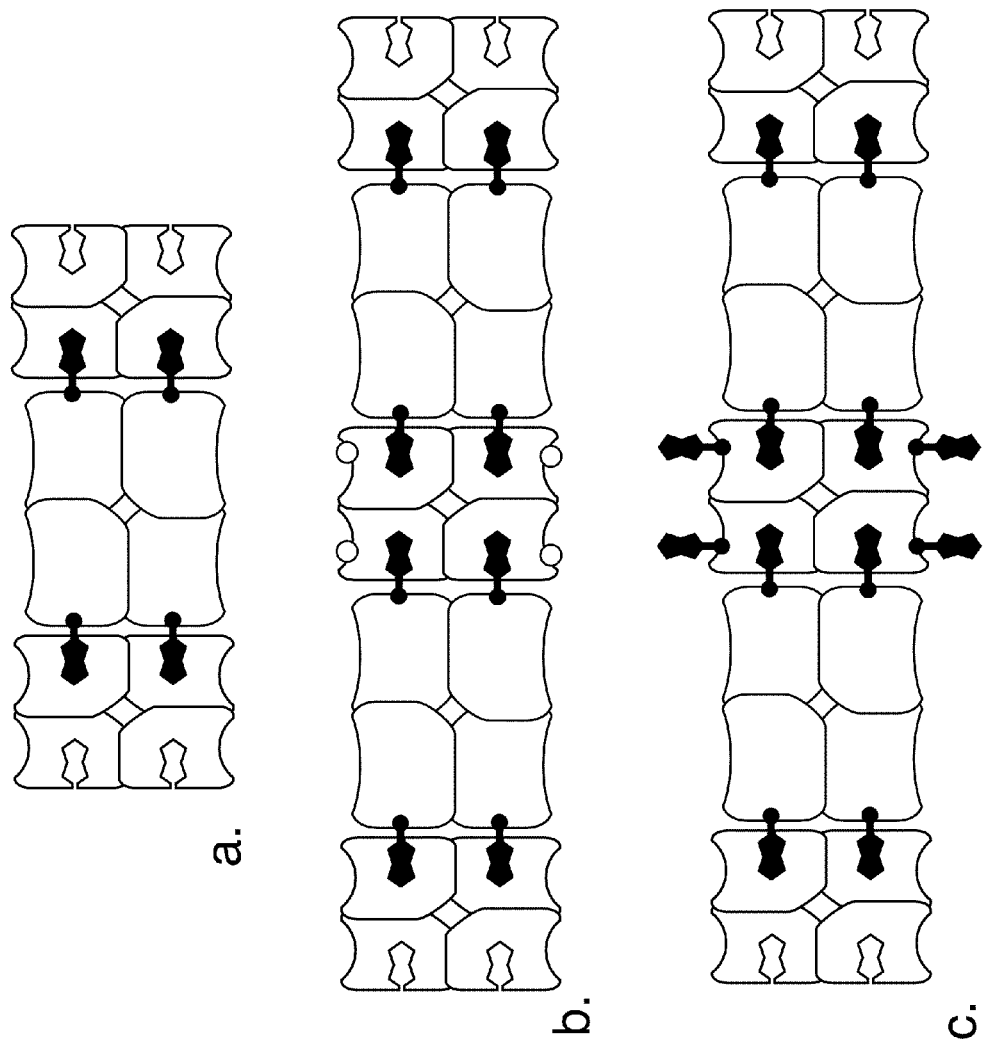

FIG. 34 presents schematic illustrations of complexes of streptavidin with linear strut connectors having D2 symmetry to produce struts of various lengths.

Figure 35:
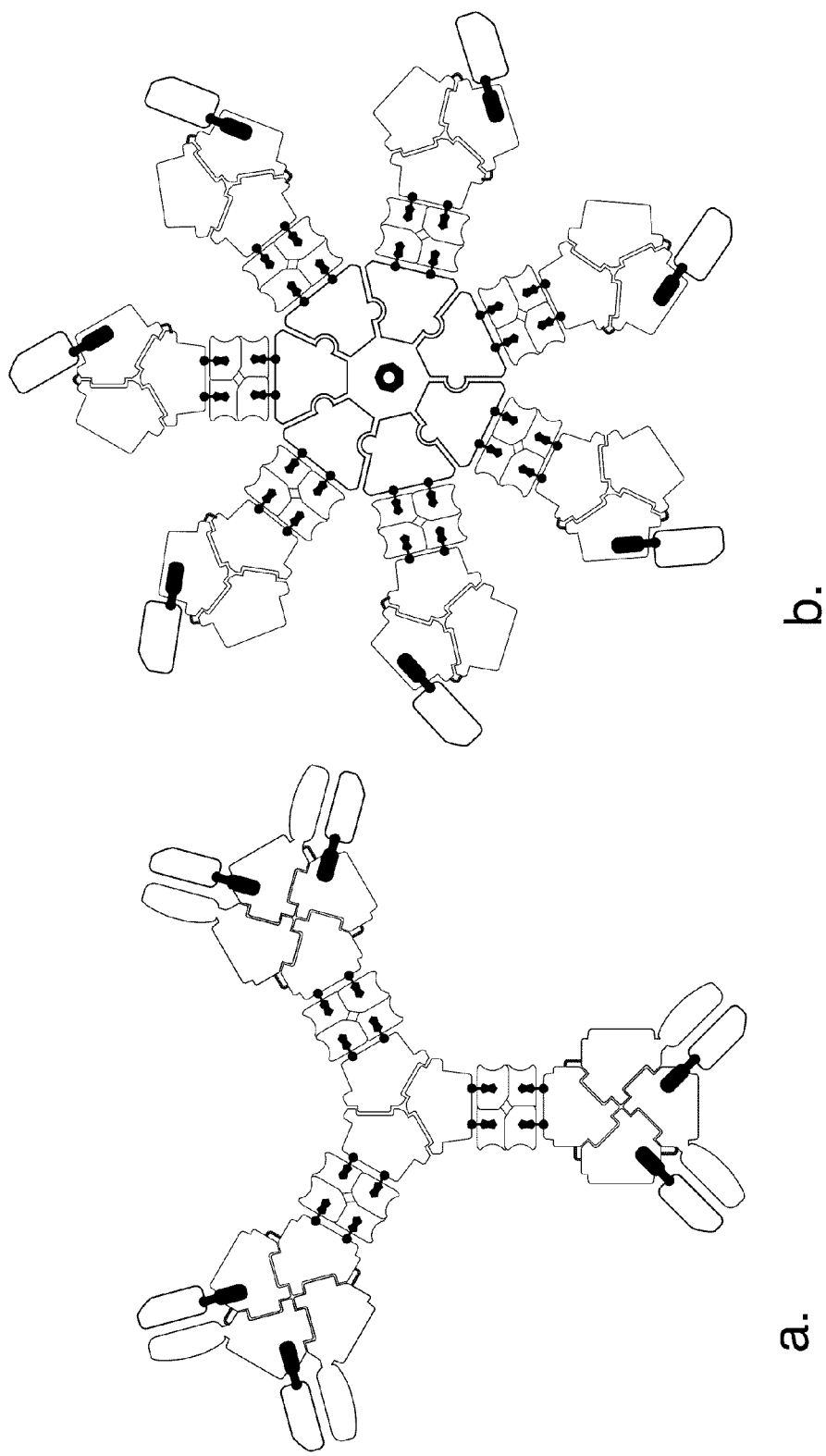

FIG. 35 presents schematic illustrations of streptavidin-linked two-dimensional radial structures formed using variants of nodes with three-fold (C3) and four-fold (C4) and seven-fold (C7) rotational symmetry.

Figure 36:
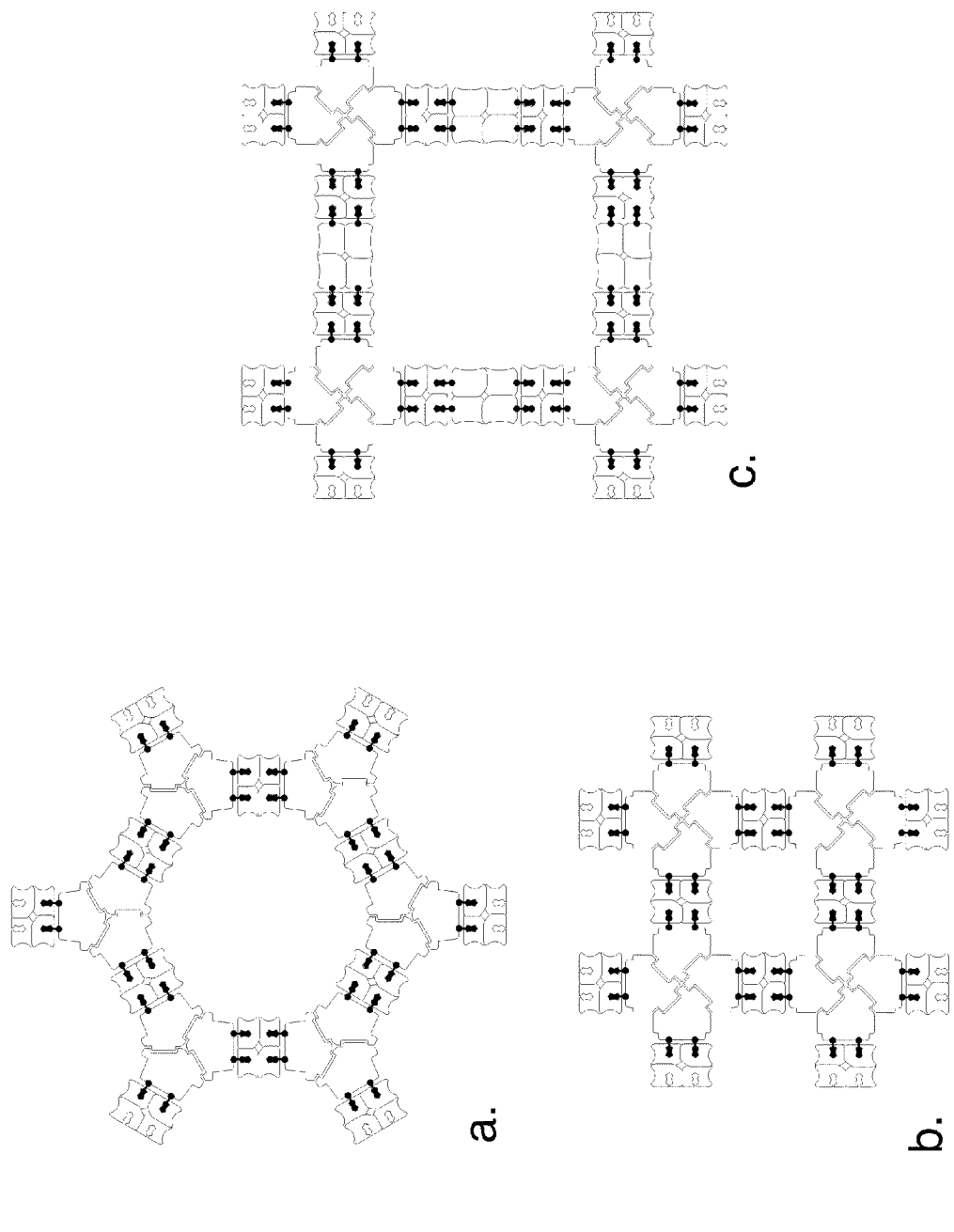

FIG. 36 presents schematic illustrations of streptavidin-linked two-dimensional lattices formed using nodes with three-fold (C3) and four-fold (C4) rotational symmetry.

Figure 37:
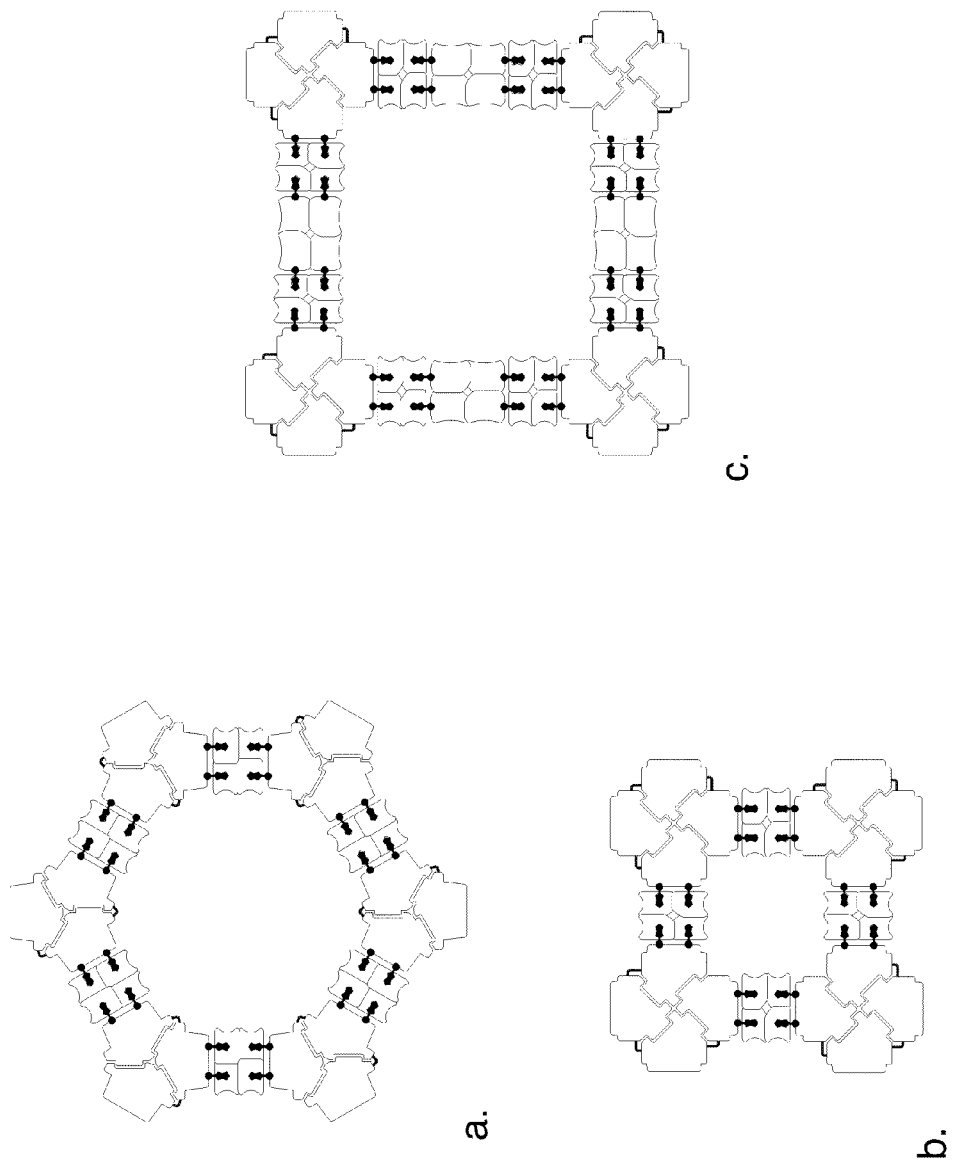

FIG. 37 presents schematic illustrations of streptavidin-linked two-dimensional polygonal structures formed using single-chain variants of nodes with three-fold and four-fold rotational symmetry.

Figure 38:
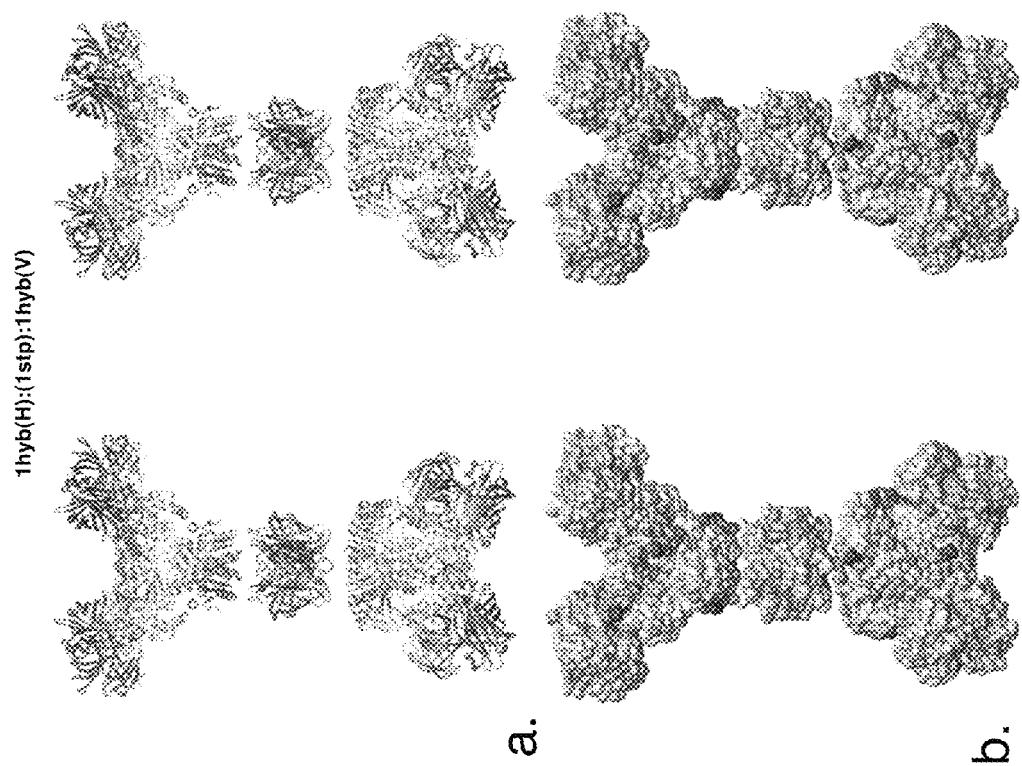

FIG. 38 presents a molecular illustration of two hexameric D3 nodes interconnected by streptavidin enabling formation of a three-connected three-dimensional lattice.

Figure 39:
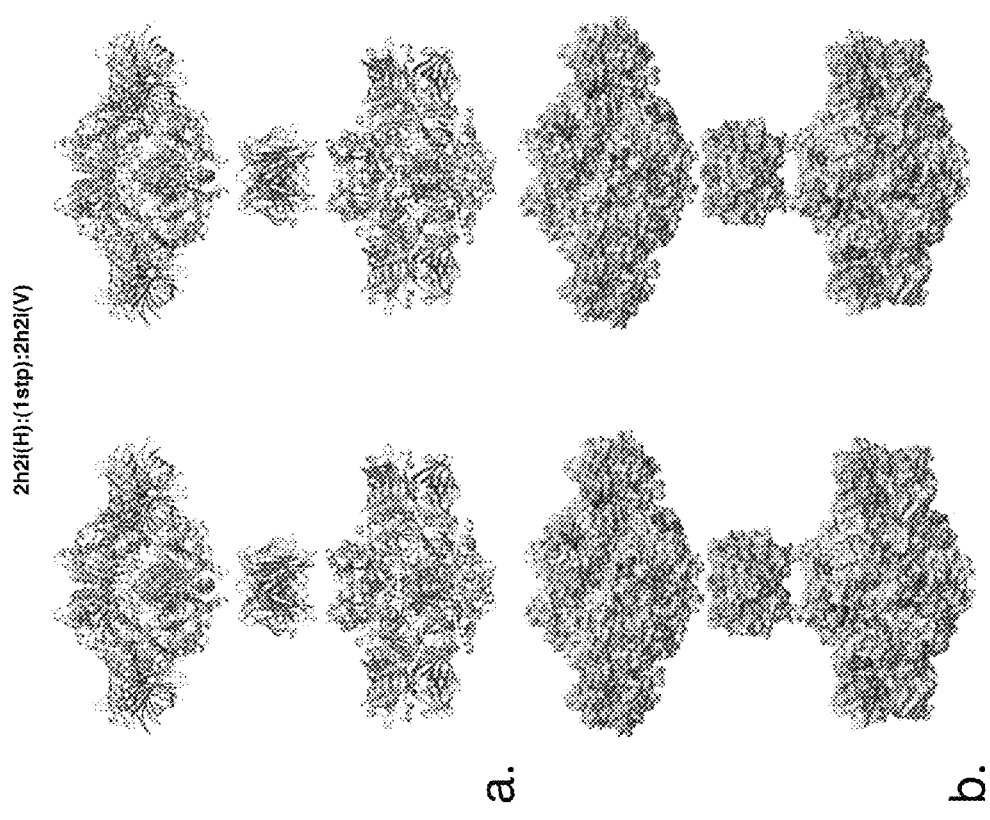

FIG. 39 presents a molecular illustration of two octameric D4 nodes interconnected by streptavidin enabling formation of a four-connected three-dimensional lattice.

Figure 40:
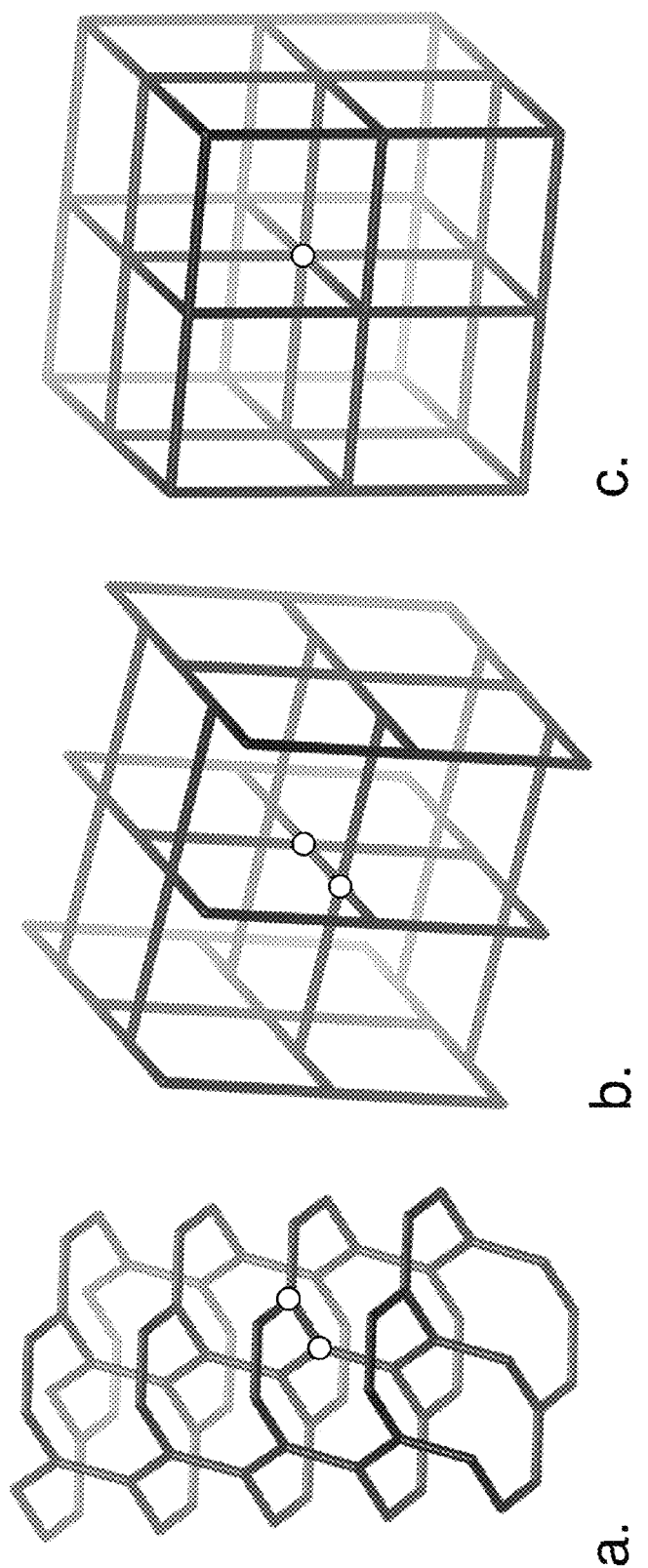

FIG. 40 presents schematic illustrations of various three-dimensional lattices with different node connectivity.

Figure 41:
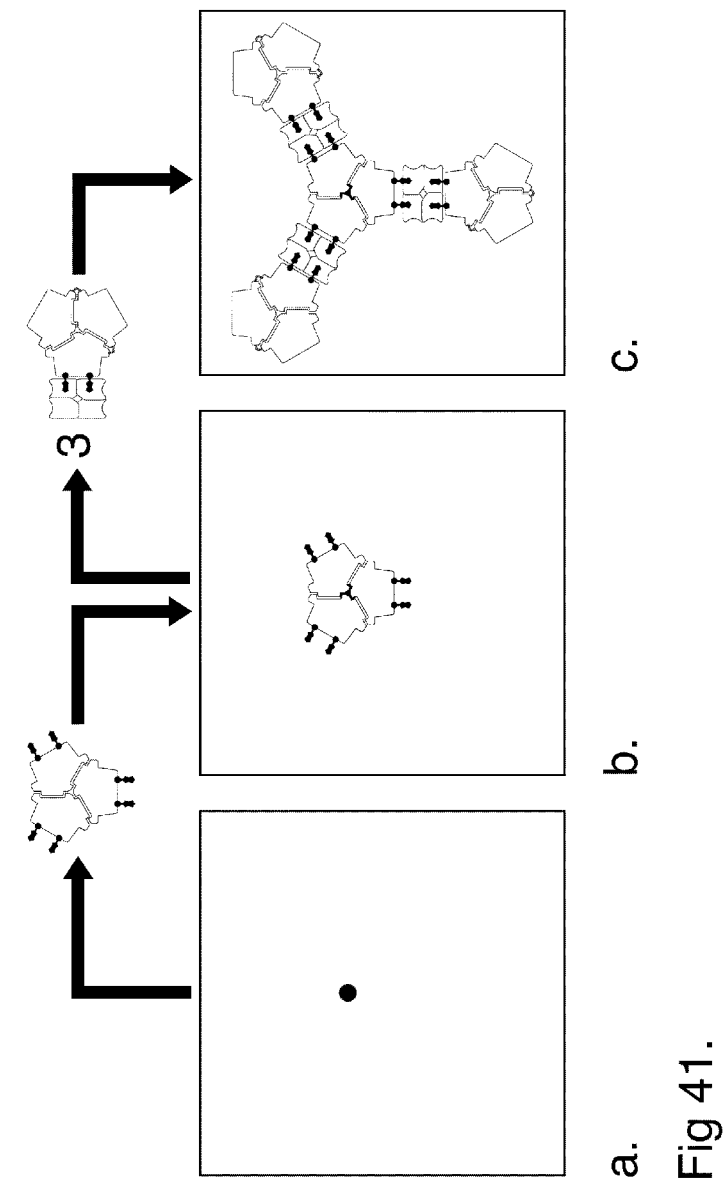

FIG. 41 presents a method of making a proteinaceous nanostructure pattern on a substrate surface.

Figure 42:
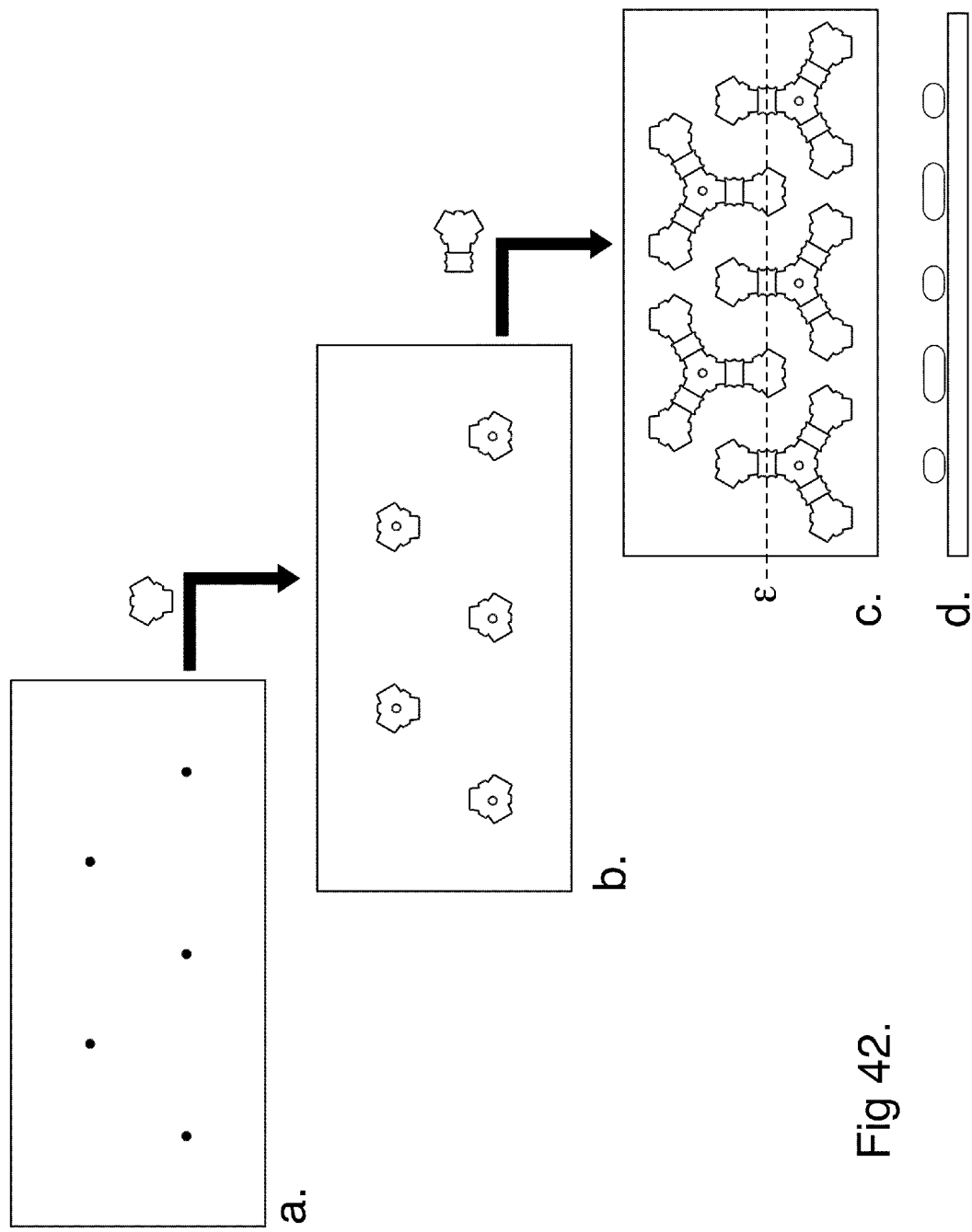

FIG. 42 presents a method of making a repetitively patterned proteinaceous nanostructure on a substrate surface.

Figure 43:
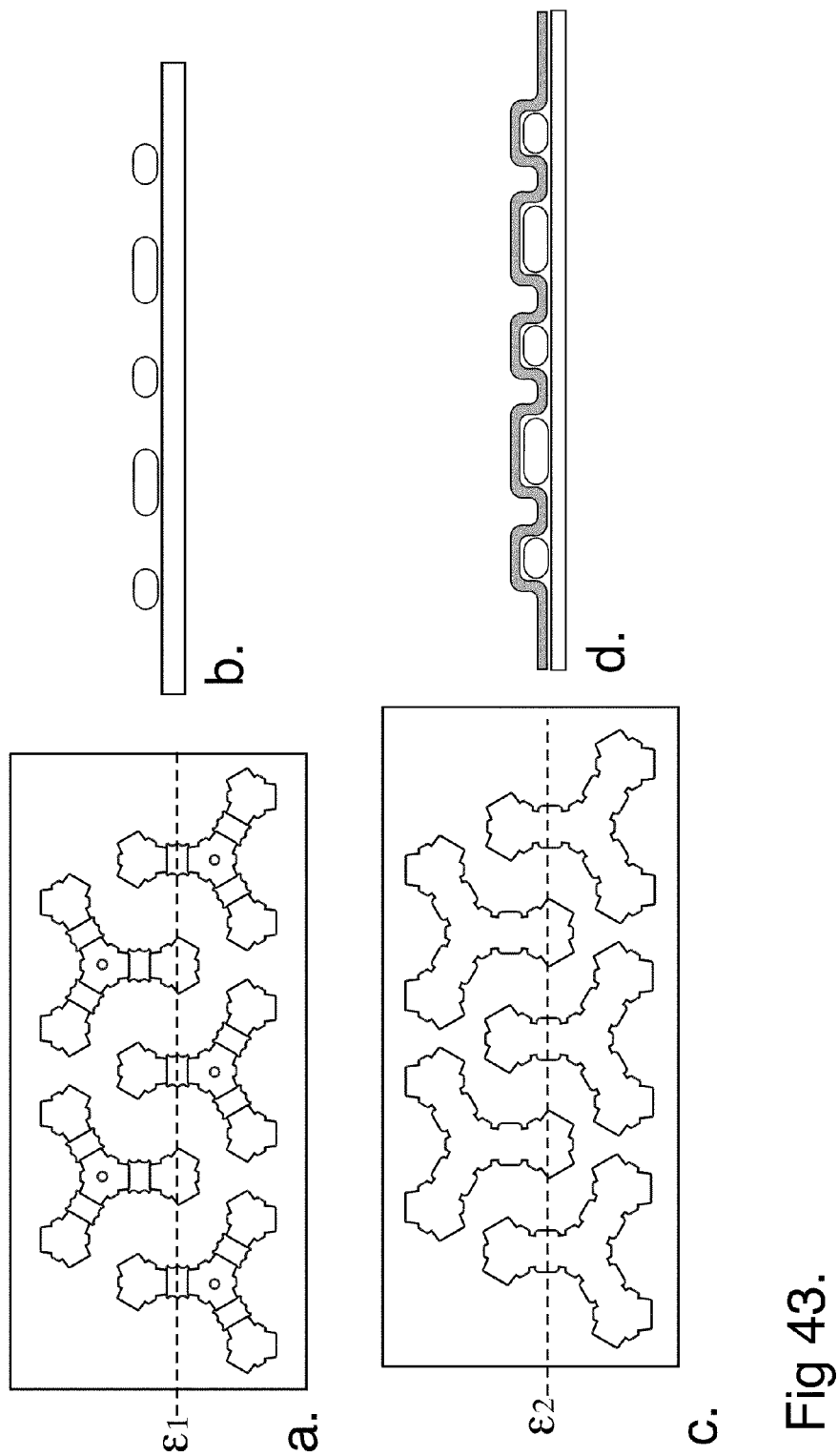

FIG. 43 presents a method of making a coated patterned nanostructure on a substrate surface.

Figure 44:
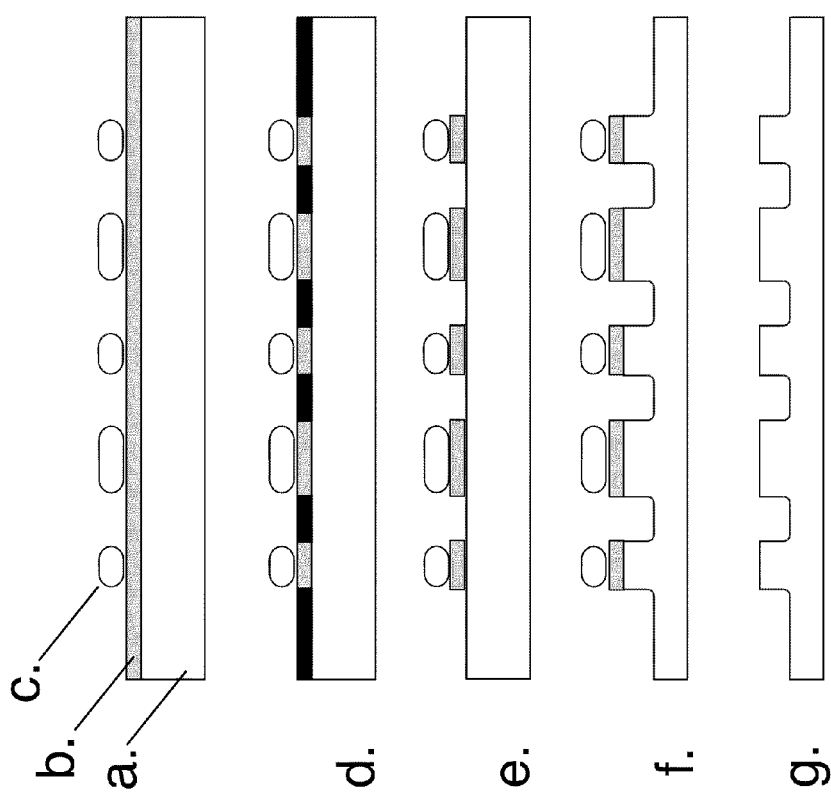

FIG. 44 presents a method of making a patterned structure using a proteinaceous nanostructure as a mask for a photoresist material.

Figure 45:
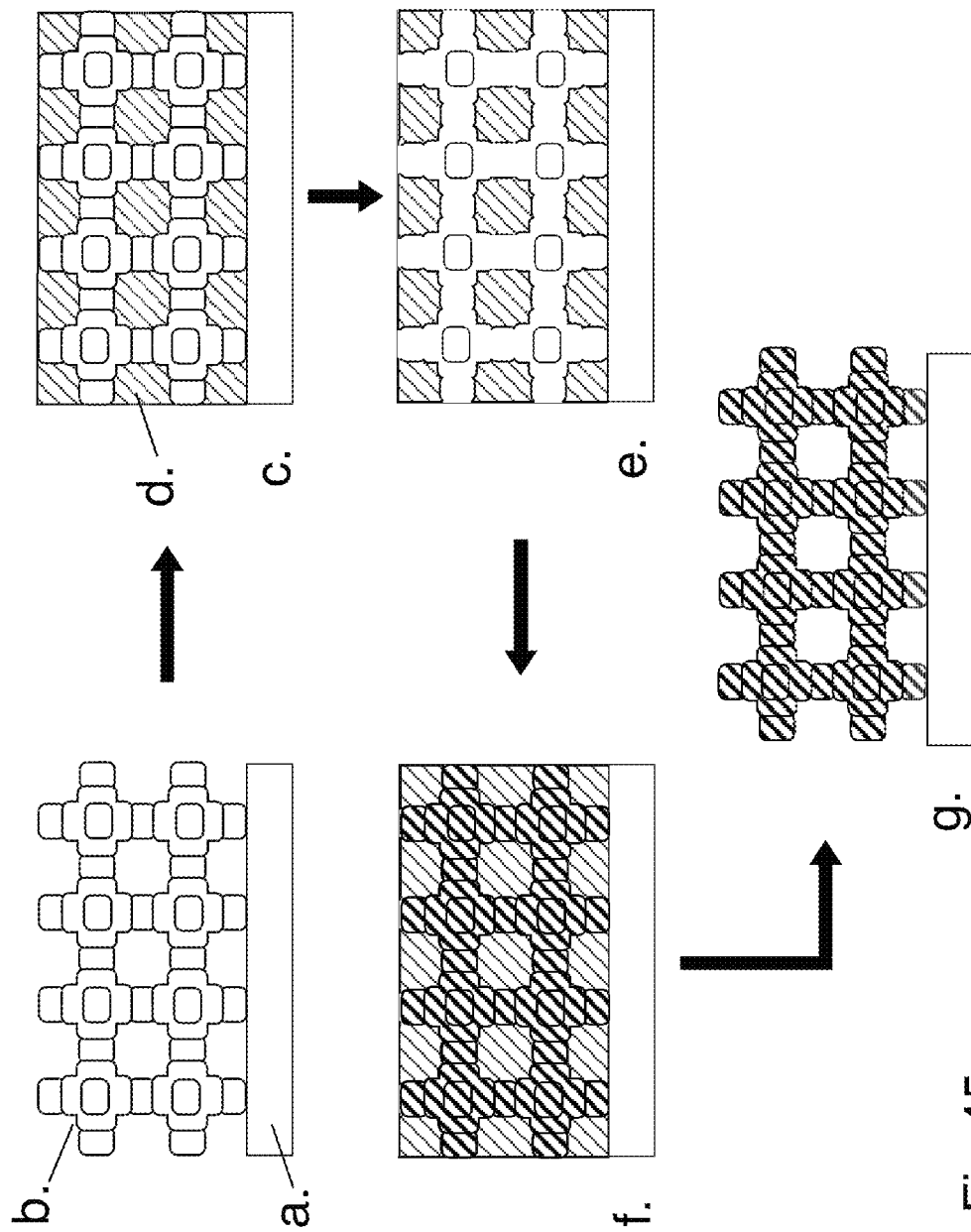

FIG. 45 presents a method of making a 3-dimensionally patterned structure in a solid matrix material or, in additional steps, a replica of a 3-dimensional proteinaceous nanostructure assembly.

Figure 46A:
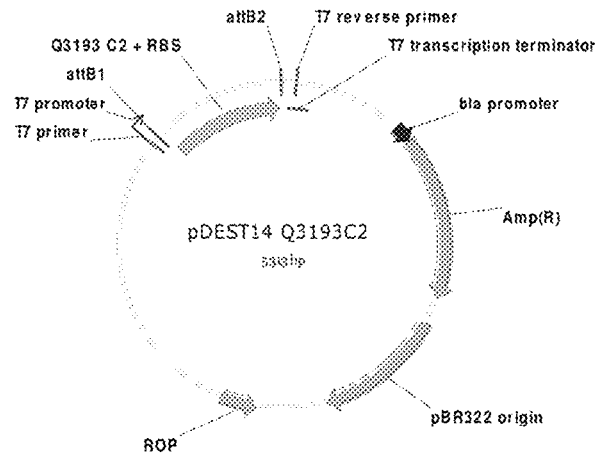
Figure 46B:
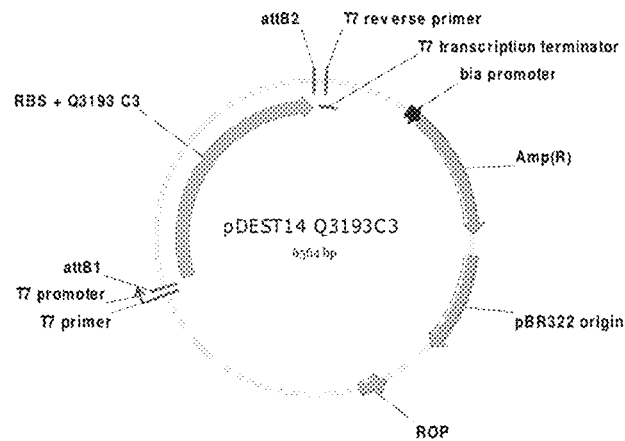
Figure 46C:
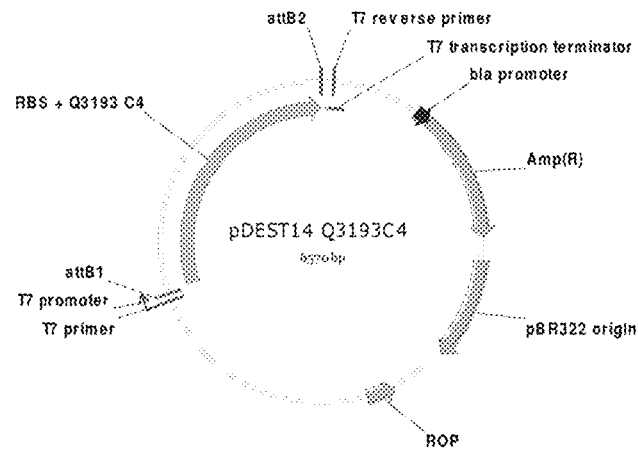

FIGS. 46A-46C present diagrams of the expression vectors EXP14Q3193C2, EXP14Q3193C3, and EXP14Q3193C4.

Figure 47:
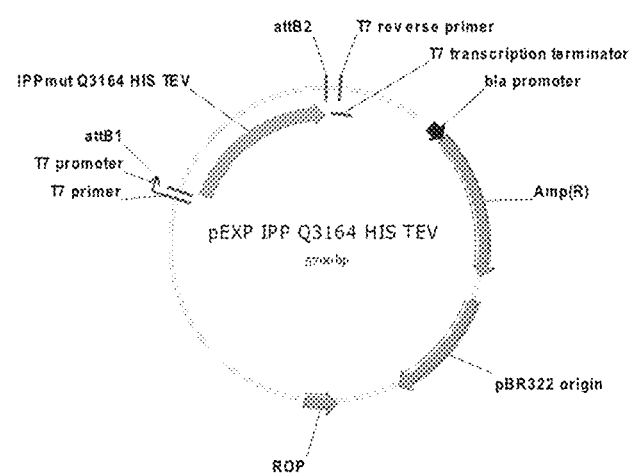

FIG. 47 presents a diagram of the expression vector EXP14Q3164.

Figure 48:
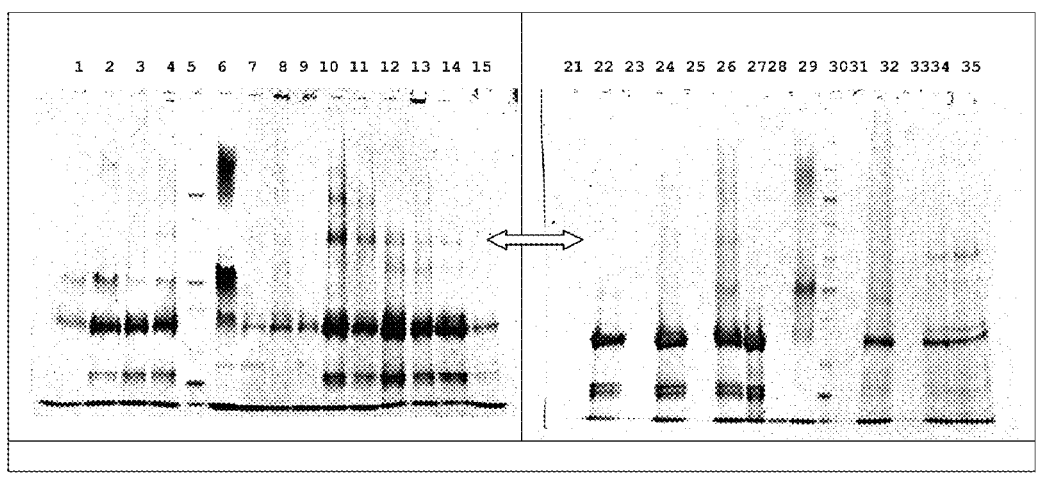

FIG. 48 presents images of electrophoretic analysis of NODE:SAV complexes.

DETAILED DESCRIPTION

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are hereby incorporated by reference in their entirety as if each had been individually incorporated. U.S. provisional patent application Ser. No. 60/996,089 (filed Oct. 26, 2007), 61/136,097 (filed Aug. 12, 2008), 61/173,114 (filed Apr. 27, 2009), 61/173,198 (filed Apr. 27, 2009), 61/177,256 (filed May 11, 2009), and 61/246,699 (filed Sep. 29, 2009), U.S. nonprovisional patent application Ser. No. 12/766,658 (filed Apr. 23, 2010) and Ser. No. 12/589,529 (filed Apr. 27, 2009), and international patent application serial numbers PCT/US2008/012174 (filed Oct. 27, 2008), PCT/US2009/053628 (filed Aug. 13, 2009), PCT/US2010/034248 (filed May 10, 2010) are hereby incorporated by reference in their entirety.

In this document, an amino acid may be indicated by its standard one-letter abbreviation, as understood by one of skill in the art. For example, a polypeptide sequence may be represented by a string of letters.

In this document, indication of a protein having "80 percent or greater sequence identity" with the sequence of another protein is to be understood as including, as alternatives, proteins that are required to have a higher percentage of sequence identity with the other protein. For example, alternatives include proteins that have 90, 95, 98, 99, 99.5, or 99.9 percent or greater sequence identity with the sequence of the other protein. One of skill in the art would understand that given a second amino acid sequence having 80 percent or greater sequence identity to a first amino acid sequence, the three-dimensional protein structure of the second amino acid sequence would be the same or similar to that of the first amino acid sequence. "80 percent or greater sequence identity" can mean that the linear amino acid sequence of a second polypeptide, whether considered as a continuous sequence or as subsections of amino acid sequence of ten or more residues (the order of the subsections with respect to each other being preserved), has identical amino acid residues with a first polypeptide at 80 percent or greater of corresponding sequence positions. For example, a second polypeptide having 20 percent or less of the amino acid residues of a first polypeptide replaced by other amino acid residues would have "80 percent or greater sequence identity". For example, a second polypeptide having every eleventh residue of a first polypeptide deleted would have "80 percent or greater sequence identity" to the first polypeptide, because each string of ten amino acids of the second polypeptide would be identical to a string of ten amino acids of the first polypeptide—such a second polypeptide would have 10/11=91% sequence identity to the first polypeptide. For example, a second polypeptide having an additional residue inserted after every ten amino acids of a first polypeptide would have "80 percent or greater sequence identity" to the first polypeptide—such a second polypeptide would have 10/11=91% sequence identity to the first polypeptide. For example, this document is to be considered to claim those protein sequences meeting the requirements of claim 1 of this document and having 80 percent or greater sequence identity to the amino acid sequences listed in Table 1B. According to the invention, certain residues can be more important to the structural integrity, symmetry, and reactivity of the proteins, and these must be more highly conserved, while other residues can be modified with less of an effect on the node protein. Generally, proteins that are homologous or have sufficient sequence identity are those without changes that would detract from adequate structural integrity, reactivity, and symmetry.

The amino acid sequences listed in Table 1B and Table 2 represent template sequences upon which a nanostructure node multimeric protein, such as that defined by claim 1, can be based. Along with the sequence is listed is the 4 alphanumeric character Protein Data Bank code (pdb code) that contains the crystallographic structure corresponding to the amino acid sequence (in the case of Table 1B, the name of the protein and the organism from which the amino acid sequence is derived is also listed). Note that each amino acid sequence itself listed in Table 1B and Table 2 was derived from the electron density crystallographic structure data in the Protein Data Bank, rather than from, for example, chemical analysis. As such, the amino acid sequences listed in Table 1B and Table 2 can be expected to exhibit some differences from amino acid sequences that would be derived from chemical analysis. For example, certain residues near the terminal N or C residues or present in outlying loops of the 3-dimensional tertiary protein structure may not be represented in the amino acid sequences presented in Tables 1B and 2. However, as is standard in the art, residue numbers indicated in Table 2 (for example, in the context of suggested modifications to the template sequence) correspond to the standard residue numbering assigned in the art to the sequence for the protein, and not necessarily to the number of the residue in the crystallographic-derived sequence presented in Table 2.

Overview of Components and Approach

An objective of the work leading to the present invention, of which several embodiments are presented in this text, is the development of biomolecular components allowing for the systematic and precise fabrication of complex nanodevices with two and 3-dimensional architectures. Proteins, typically having (subunit) dimensions in the range of 3 to 20 nm (or the equivalent, 30 to 200 Angstrom units), and other organic molecules serve as the biomolecular components, and allow for unprecedented miniaturization of devices. By providing proteins with two or more points of controllable attachment, a limited set of a small number of biomolecular components allows for construction of an unlimited number of structures, over the design of which a user has full control. Thus, the biomolecular components will advance research and development into nanodevice applications. The control over assembly and reproducible precision of structures formed by these biomolecular components allows for the fabrication of nanodevices of unprecedented complexity, extent, and diversity.

Described embodiments according to the present invention include molecular components that are extremely stable, easily manufactured and purified, and designed with high precision to enable the controlled assembly of a wide range of one-, two- and 3-dimensional protein-based nanostructure assemblies. Described embodiments according to the present invention include the design and manufacture of such molecular components.

In an embodiment, the protein components of the nanostructure assembly are functional, as appropriate for the development of biological sensors, filters, materials, or bioelectronic devices where charge, spin, or optical properties are intrinsic properties of the protein or prosthetic groups that are bound to the protein structure.

In an embodiment, the protein nanostructure assembly provides a means of high-resolution patterning of a silicon, glass, metal, or other substrate, either by using the protein nanostructure assembly directly as a means of patterning a substrate, or alternatively as a mask for a radiation-sensitive resist. This approach can allow manufacture of microelectronic devices, devices incorporating zero-mode waveguides (Levene et. al, 2003) or microelectromechanical systems (MEMS) using conventional semiconductor fabrication (Widman et. al, 2000) and/or MEMS fabrication technology (Judy, 2001). Additional patterning applications include the generation of soft lithography stamps and molds (Xia & Whitesides 1998, Rogers & Nuzzo 2005) for MEMS and nanofluidic applications.

"Parts Box" Philosophy

The biomolecular components can include molecular-scale "struts" and "nodes". Struts are components that basically function as linear structural elements or linear connectors, and typically have attachment points to nodes oriented in a linear arrangement. Different struts or arrays of strut extenders or adaptors can be used to establish predetermined distances in a structure. Nodes are connectors that can have either two attachment points with defined, for example, non-linear, geometry, or more generally, multiple attachment points with defined geometry. Nodes can be linked together, for example, by struts, to establish the topology of a structure. Thus, with the struts and nodes, structures with 2-dimensional and 3-dimensional geometry can be constructed. Structures organized in two dimensions can be finite to allow the formation of locally structured patterns of molecules arrayed on a surface, or alternatively form infinitely extensible 2-dimensional lattices. The symmetry properties required of nodes suitable to build structures with the regular 2-dimensional geometry are well known from mathematics and crystallography (Williams 1979, Pearce 1979, Vainshtein, 1994). Two-dimensional structures can have utility themselves and/or can be further functionalized through chemical modification or the incorporation of additional specific binding proteins.

Structures organized in three dimensions can also be usefully classified as finite or infinite. Common examples of finite structures potentially constructed using molecular strut and node architecture include dendritic structures as well as the Platonic and Archimedian polyhedra and their many variations (Pugh 1976, Pearce 1979). The strut and node architecture also potentially allows the assembly of infinite 3-dimensional lattices. The symmetry requirements for nodes that can form infinite 3-dimensional lattices have been described comprehensively by Wells and others (Wells 1977, Wells 1979, Williams 1979). Three-dimensional structures can have utility themselves as materials and filters and/or can be further functionalized through chemical modification or the incorporation of additional specific binding proteins.

Assembly of biomolecular components such as struts and nodes can proceed in stages that provide the user with the efficiency and parallel nature characteristic of "bottom-up" self-assembly and the control and ability to form asymmetric and complex structures characteristic of "top-down" manufacturing. Because a limited number of biomolecular components can be combined to produce any one of an unlimited number of structures, attention can be focused on developing a small number of these biomolecular components that serve as a "parts box". Because only a limited number of biomolecular components and associated assembly techniques need be designed, produced, and tested, economies of scale can be achieved, so that inexpensive development and production of nanodevices can be realized. That is, the compositions and methods discussed herein apply the philosophies of interchangeable parts and mass production, which drove unprecedented economic expansion in the last two centuries, to the nanoscale. Providing such a "parts box" of biomolecular components will allow users to experiment with a range of structures and thereby facilitate the development of a new generation of functional nanodevices, biosensors, and biomaterials, potentially finding broad application in areas as diverse as biomedical devices and nanoelectronic applications.

Use of Proteins

Proteins have a number of advantages for use as components and templates for biomolecular components, including, but not limited to the following. Proteins already exist in nature as functional polypeptide units with well-defined 3-dimensional structures, so that effort can focus on tailoring them as building blocks for specific applications, rather than having to develop building blocks from scratch. A very large number of proteins exist, and the detailed atomic structure of many are known, so that there is an excellent chance of finding a protein that, with minimal tailoring, can perform as a desired building block.

Naturally occurring proteins have diverse and sophisticated functionality. They can show high interaction specificity and manifest catalytic properties. They can exhibit interesting and useful optical, magnetic, and redox properties, for example, by incorporating metal centers and a wide variety of prosthetic groups. Such metal centers and prosthetic groups can, as well as the polypeptide sequence itself, be tailored to produce a protein having a desired functionality.

In nature, DNA encodes a polypeptide sequence that spontaneously and reproducibly folds to form a predetermined 3-dimensional protein of thousands of atoms of which each atom is precisely placed. Because proteins as building blocks are reproducible and have precise configuration, they can be relied upon as components in the construction of extensive and complex structures. Naturally occurring proteins frequently form cooperative hierarchical assemblies of great structural and functional complexity. These natural assemblies can be studied to derive assembly techniques and simplify the development of analogous artificial structures having an intended purpose.

Naturally occurring proteins can form highly stable multimeric structures that are symmetric and contain multiple copies of the individual polypeptide chains. Symmetric multimeric structures are geometrically precise. If modification sites are introduced into a component polypeptide chain, then these are symmetrically arrayed in the multimeric structure with great geometrical precision; typically within errors of less than 1-2 Angstrom units (0.1 to 0.2 nM) from structure to structure. Symmetric protein multimers are excellent template structures for the generation of macromolecular protein nodes.

The techniques for modifying proteins by the techniques of molecular biology and synthetic organic chemistry are well established. For example, a selected amino acid unit or subsequence (a plurality) of amino acid units of a natural protein can be substituted with a different natural amino acid, with an artificial amino acid, or with a different subsequence of natural and/or artificial amino acids to modify the natural protein. A natural amino acid, artificial amino acid, or subsequence of natural and/or artificial amino acids can be inserted into the amino acid sequence of a natural protein to modify the natural protein. An amino acid or a subsequence of amino acids can be removed (deleted) from the amino acid sequence of a natural protein to modify the natural protein. Reliable production of large numbers of proteins is a well-established biotechnical procedure. Thus proteins are excellent candidates for a "parts box" with which the philosophies of interchangeable parts and mass production can be applied at the nanoscale.

Applications

The diverse and sophisticated functionality of naturally occurring proteins allows them to perform a wide range of processing and signal transduction functions in nature, including catalysis, chemomechanical, electromechanical, optomechanical, and optoelectronic transduction for sensing and actuation purposes. This anticipates a diverse range of man-made devices that can be produced with a "parts box" of proteins as biomolecular components.

Structures, for example, node:strut nanostructure assemblies, can be assembled from the struts and nodes described herein.

A "parts box" of proteins may initially be applied to make devices that are analogous to or in some way emulate natural systems. For example, two- and 3-dimensional structures formed from struts and nodes, as described herein, may be applied in the fields of biosensors and diagnostics. The specific immobilization and precise geometric control facilitated by strut-node technology presented herein, along with the functionality inherent in proteins, can enable the development of new kinds of sensors incorporating, for example, multiple antibodies specifically immobilized in patterned arrays.

Other applications may not have direct natural analogs, but are intended to interact with natural biological systems. For example, the strut-node technology presented herein can be used in devices that couple directly to living systems, for example, that provide an interface between semiconductor substrates and living organisms and nanostructures. Such devices could, for example, be used as biocompatible materials for prostheses.

Applications of a "parts box" of proteins as biomolecular components are not limited to devices analogous to or for interacting with natural biological systems. For example, structures can be assembled that emulate the architecture and functions of silicon-based microprocessor architecture and computer memory or possess novel material properties. Many materials science and computer applications depend upon the miniaturization of structural features in two or three dimensions to allow the separation and storage of charge, control of electrical conductance or optical properties, or the addressable storage of data in electrical or magnetic form. As such, the technology described is applicable to the development of new electronic devices including improved batteries, capacitors, computer memory, microprocessors, nonlinear optical devices and materials. Additional applications include ultrafilters that provide protection from pathogens like viruses, or have utility in liquid separations or the desalination of salt water.

The protein components of the nanostructure assembly can be functional, as appropriate for the development of biological sensors, filters, materials, or bioelectronic devices where charge, spin, or optical properties are intrinsic properties of the protein or prosthetic groups that are bound to the protein structure.

Alternatively, the protein nanostructure assembly can provide a means of high-resolution patterning of a silicon, glass, metal, or other substrate, so providing high resolution templates or resists that allow production of microelectronic devices, devices incorporating zero-mode waveguides (Levene et al., 2003), or microelectromechanical systems (MEMS) using conventional semiconductor fabrication (Widman et al., 2000) and/or MEMS fabrication technology (Judy, 2001). Thus, the "parts box" strategy can be fundamentally exploited as a way of creating self-assembling or sequentially assembled structures where the nanometer size and designed-in precision of the interaction geometry between the protein molecular components can be used to create complex and highly precise structures in two and three dimensions. These patterns can then be used as optical resists, molds, metallization substrates, or negatives for the fabrication of semiconductor, MEMS, soft lithography molds (Xia & Whitesides 1998, Rogers & Nuzzo 2005), or other devices where miniaturization at the sub-100 nanometer scale is useful.

Biomolecular Components

Protein Stability, Selection, and Engineering

The 3-dimensional atomic structures of over 25,000 proteins are known (see, www.rcsb.org, accessed Oct. 2, 2007), providing an extensive set from which biomolecular components having desired structural and functional characteristics can be selected for a "parts box" (see, scop.mrc-lmb.cam.ac.uk/scop/, accessed Oct. 2, 2007). Moreover, the tools of recombinant DNA technology enable the synthesis of virtually any polypeptide sequence or functional domain fusion, providing the basis for rapidly designing and optimizing novel assemblies from engineered biological macromolecules.

In this document, unless otherwise specified, a reference to a protein or protein amino acid sequence is to be understood to also encompass variations of that protein or protein amino acid sequence including derived proteins or protein amino acid sequences derived from gene fusion techniques and/or circular or cyclic permutation techniques applied to that protein or protein amino acid sequence. For example, in the application of a gene fusion technique, the C-terminal amino acid residue of a normally separate polypeptide chain can be spliced together with the N-terminal amino acid residue of another normally separate polypeptide chain (such a splicing can also encompass a splicing made when one or more amino acid residues normal present at the C-terminus or N-terminus are eliminated, and/or when one or more amino acid residues not normally present at the C-terminus or N-terminus are added, as when a linker sequences is used to splice together two normally separate polypeptide chains). For example, a gene fusion technique can be applied to covalently join polypeptide chains that are normally separate in a multimeric protein, such as a multimeric protein having Cn, Dn, or higher symmetry. A single gene fused polypeptide chain formed from the N separate polypeptide chains of an N-mer can fold into the same or a similar three-dimensional tertiary protein structure as the N separate polypeptide chains. For example, in the application of a circular or cyclic permutation technique, the C-terminal and N-terminal amino acids of a polypeptide chain can be joined and other normally adjacent amino acid residues can be disjoined, so as to create new C-terminal and N-terminal amino acid ends. Gene fusion and circular or cyclic permutation techniques can be combined to create new polypeptide sequences from polypeptide sequences. For example, the N separate polypeptide chains of a native protein N-mer can be cyclically permuted, so that the amino acids at the N-terminus and C-terminus in the native protein are covalently joined, and two amino acid residues normally adjacent to each other and covalently bonded in the native protein are disjoined to become new N-terminal and C-terminal amino acid residues. The new N-terminal amino acid residue of a polypeptide chain can be covalently joined to a new C-terminal amino acid residue of another polypeptide chain (that is normally separate in the native protein) through a gene fusion technique, with or without the addition of an intermediate linker sequence of amino acids and with or without the deletion of one or more amino acids.

Although not widely recognized, numerous studies show that the structural and functional properties of proteins that normally function in aqueous solution are preserved intact when the protein is dehydrated to the level of a few water molecules per protein molecule (Rupley & Careri 1991; Zaks & Klibanov 1988; Fitzpatrick et. al. 1993; Castro & Knubovets 2003; Gupta & Roy 2004). Many examples exist of structural proteins, for example spider silk, that form essentially solid-state structural materials and have thermal stabilities in excess of 100° C. In addition, many proteins that form unusually stable complexes (Weber et al. 1992), or that carry out the biological functions of thermophilic organisms that live in hot environments also have thermal stabilities in excess of 70° C., an environment not very dissimilar from the maximum operating temperatures for conventional semiconductor devices.

Evolutionary forces have allowed living organisms to exploit a wide range of habitats including environments that represent extremes of temperature, salinity, pH, specific mineral content, and/or pressure. The organisms adapted to the most extreme environment like hot springs, thermal vents at the ocean bottom, high salt environments like the Dead Sea, etc. are termed extremeophiles and are generally microorganisms such as bacteria or algae. A subclass of extremeophiles are thermophilic organisms (again, usually microorganisms such as bacteria or algae), which live at substantially higher temperatures (typically above 60 deg C.) than the vast majority of plants and animals populating the terrestrial ecosystem (usually termed mesophilic organisms or mesophiles). Most plants and animals could not survive at such elevated temperatures because the basic molecules responsible for most of the biological functions of the organism, i.e. the polypeptide proteins encoded by the organism's genetic material or DNA, would become denatured. Proteins are poly-amino acid polymers (or polypeptides) of defined sequence that fold to form highly organized 3-dimensional structures. Maintenance of the biological function of a protein as a chemical catalyst, receptor, channel, etc. is completely dependent on the preservation of its properly folded, 3-dimensional structure. The vast majority of proteins of mesophilic organisms become thermally denatured when subjected to temperatures above about 50 deg C. In contrast, and although they are generally composed of exactly the same chemical components (amino-acids) as mesophilic proteins, all of the proteins in thermophilic organisms have evolved their amino acid sequences so that they are especially stable and can maintain their properly folded 3-dimensional structures and biological functions at high temperatures. Although experimental approaches have been developed to improve the thermal stability of mesophilic proteins, these are laborious, costly and often ineffective, so that it is highly advantageous to use proteins from thermophilic organisms in situations where high protein stability is desired. Typically, these applications have included industrial processes that use enzymes to carry out chemical reactions. There have been no reports of using thermostable proteins for nanotechnology applications. The use of engineered thermostable proteins for nanotechnology applications has many advantages.

One advantage is the ease of production of thermostable proteins for nanotechnology applications. Thermostable proteins are much more stable than proteins in found in most bacteria (e.g. *E. coli, B. subtilis*, etc.), insect (e.g. sf9, etc.), or mammalian (e.g. CHO, HELA, etc.) cell lines typically used for recombinant expression of proteins. This greatly facilitates the isolation of these protein since once the thermostable protein has been expressed in the host cell line, it is often possible to gain a significant initial purification simply by treating the cells containing the thermostable protein to denaturing conditions (e.g. by heating or urea treatment) that cause most all of the mesophilic cell components to denature and become insoluble, leaving the thermophilic protein intact and in solution where it can be easily separated from the insoluble cell components by centrifugation, filtration, or a number of other methods. This substantially reduces the time and cost required to produce the materials required for nanotechnology applications.

A second advantage is the ease of production of engineered and chemically modified variants of thermostable proteins for nanotechnology applications. In many cases thermostable proteins that will be used for nanotechnology applications will not be used in their native form as they are found in nature, but in some modified form. However, owing to the very high initial stability of the native forms of thermostable proteins, such modifications are expected to have a relatively small effect on the functional stability of a thermostable protein relative to a protein derived from a mesophilic organism.

Useful modifications of the native thermostable protein can be achieved in two general ways. The first approach involves the modification of the "native" protein amino acid sequence as it occurs in nature through manipulation of the DNA sequence that encodes the protein. The manipulated DNA sequence can then be expressed in an expression system, for example, a bacterium, such as *E. coli*, to produce the desired modified amino acid sequence. This process is generally termed protein engineering and is broadly used in the biotechnology industry. The second general method involves reacting a protein composed of naturally occurring amino acids with chemical reagents or enzymes that post-process the protein to make a chemical derivative of the product encoded by the DNA sequence.

Introduction of modifications in the sequence of proteins using recombinant DNA technology is broadly used in biomedical research and is the basis of many pharmaceutical products. However, with the exception of Salemme & Weber (2007), no reports exist for using protein engineering for structural nanotechnology applications using thermostable proteins. Structural modifications of thermostable proteins intended for nanotechnology applications can be introduced using recombinant DNA technology to modify the DNA sequence that encodes the corresponding protein polypeptide sequence. Useful modifications could include, for example:

a. The introduction of one or more individual substitutions of one amino acid for another at defined positions in the native sequence (commonly termed a site-specific modification). Examples of the utility of such modifications include the substitution of an amino acid like cysteine with a chemically reactive side chain for a non-reactive amino acid like alanine to provide a specific chemical linkage site on the surface of a protein.

b. The addition or deletion of one or more contiguously-bonded amino acids (a polypeptide extension) from either the amino or carboxy terminus of the native protein polypeptide chain. Examples of the utility of such modifications include the addition or removal of sequences or protein domains that may confer additional binding or catalytic functionality to the native protein or that may be structurally disordered.

c. The insertion or deletion of one or more amino acids into the sequence of the native or modified protein sequence. Examples of the utility of such modifications include the insertion of sequences or protein domains that may confer additional binding or catalytic functionality to the native protein.

d. The reconnection of the protein polypeptide chain of the native or native-like sequence, so as to allow the preservation of essentially the same 3-dimensional folded structure of the native protein, but folded from a sequence where the positions of the amino and carboxy termini have been altered or permuted. Examples of the utility of such modifications include the covalent connection of multiple polypeptide chains that normally form an associated complex into a single contiguous polypeptide sequence.

e. The interconnection of multiple copies or types of protein sequences that naturally form multimeric structures in nature composed of multiple polypeptide chains, into a structure made up of a smaller number of continuous polypeptide chains.

In actual application, any or all of the types of the modifications of the native protein sequence described in a. through e. above can be used in combination to produce a modified protein sequence.

The second type of modification, which may often be combined with the gene modification strategies outlined above that alter the native protein sequence, involves the reaction of the modified protein with a chemical reagent or enzyme to produce a "chemically modified" protein. Examples of the utility of such chemical modifications include the formation of a covalent connection between the polypeptide structure and chemical groups with specific protein binding activity. For example, chemical reagents are known that can react covalently with the cysteine groups on the surface of proteins to covalently attach biotin. Biotin is a vitamin that has very high and specific binding affinity for several proteins of the avidin family including streptavidin from *Streptomyces avidinii* and bird avidins. Consequently, proteins that are chemically modified through covalent attachment of biotin groups can form tight and specific interactions with streptavidin and avidin (and derivatives of streptavidin and avidin), and as a result have found wide application in biotechnology and diagnostic applications. Because all chemical reactions, including those that tend to spontaneously modify proteins (e.g. oxidation of sulfur containing amino acids and side chain deamidation of asparagine and glutamine residues) tend to occur more rapidly at high temperatures, proteins that are adapted to be stable at high temperature are also unusually stable to changes in chemical environment. This does not mean that modifications like the biotinylation reaction outlined above will not occur with thermostable proteins, but that there is less likelihood that undesirable side reactions will take place that could give rise to defective molecular structures with reduced assembly fidelity for self-assembling nanostructures.

A third advantage afforded to the use of thermostable proteins is the ease of processing during the production and assembly of nanostructures. The production of components for assembly of nanostructures incorporating thermostable proteins will often involve separation steps using chromatography, electrophoresis or other methods used to isolate biological macromolecules and complexes. The enhanced stability of thermostable proteins relative to mesophilic proteins is an advantage that allows better separations of intermediate reaction products and/or molecular subassemblies using a wider range of separation conditions (e.g. solution pH, ionic strength, range of allowable solvents, presence of detergents, etc.). Similarly, the production of nanodevices that are assembled on self-assembling monolayers or semiconductor substrates like silicon wafers will often involve solution conditions and/or the use of reactive or photo-chemistries where the improved stability of thermostable proteins relative to mesophilic proteins will result in better yields of the desired products and more reliable devices.

A fourth advantage afforded to the use of thermostable proteins in nanodevices relates to the allowable range of practical operating conditions for devices incorporating engineered nanostructures. Many important applications for functional nanodevices will be in temperature environments that are not too much different from those normally tolerated by human beings—nominally 0 deg C. to 50 deg C. In particular, nanodevices designed for medical applications will have to operate at about 37 deg C., the temperature of the human body. Even current semiconductor-based electronics typically do not operate reliably above ~70 deg C. and typically require active cooling in applications like computers. Many proteins from thermophilic organisms, as well as a small number of unusually stable proteins from mesophilic organisms like streptavidin from the microorganism *Streptomyces avidinii*, remain stable above 70 deg C., whereas most proteins from mesophilic organisms denature in the range of 40 to 50 deg C. making them less suitable for nanodevice applications.

Stability of a protein at a given temperature can refer to tertiary stability of the protein, i.e., the protein does not unfold from its three-dimensional folded structure into a disordered or random coiled polypeptide chain or into a structure having only secondary structure such as alpha-helices and beta-pleated sheets. Stability of a protein at a given temperature can refer to quaternary stability of the protein, that is, the subunits of the protein retain their relative spatial arrangement, for example, the subunits of the protein do not disaggregate into individual tertiary structures (or less ordered secondary structures or primary structures (disordered or random coiled polypeptide chains)) and do not undergo a substantial relative spatial rearrangement. Thus, a protein that is stable above 70 deg C. will retain its tertiary structure and/or its quaternary structure above a temperature of 70 deg C.

Most of the biomolecular components describe herein are based on proteins of thermostable microorganisms of known 3-dimensional crystal structure. As outlined above, the use of thermostable proteins provides us with several advantages in economical node production, handling and purification.

The enzymatic binding sites of proteins used as nodes can provide additional sites for functionalization of the nanostructure through covalent binding of inhibitors linked to other chemical moieties or proteins.

Struts

Two fundamental nanoscale biomolecular components of a "parts box" from which a structure, for example, a device, can be assembled are "struts" and "nodes". Struts are molecular components that function as linear connectors. Nodes connect struts and orient them with defined geometries.

Throughout the following descriptions we use standard scientific nomenclature to discuss the symmetry properties of node templates and nodes (Vainstein 1994). For a complete description of point group symmetry and symmetry operation nomenclature see: www.phys.ncl.ac.uk/staff/njpg/symmetry/index.html and <csi.chemie.tu-darmstadt.de/ak/immel/script/redirect.cgi?filename=http://csi.chemie.tu-darmstadt.de/ak/immel/tutorials/symmetry/index.html>

A strut can be formed from streptavidin, a tetrameric protein of 60 kiloDalton molecular weight secreted by the bacterium *Streptomyces avidinii*. FIG. 1 shows molecular models and schematic illustrations of the streptavidin tetramer showing biotin ligand binding sites. The streptavidin tetramer has D2 symmetry with 3 mutually perpendicular two-fold or dyad axes of symmetry relating the 4 subunits of the tetramer. Dyad axes are labeled x,y, and z in FIG. 1. FIGS. 1*a,b*, and *c* show schematic backbone representations of the streptavidin tetramer viewed down the x, z, and y dyad axes of symmetry, respectively. The bound biotin ligands are shown in space filling representation. Also shown in FIGS. 1*a* through *f* is a "bounding box" aligned along the x dyad axis that defines the positions of the biotin ligands along the direction that they make bonded interactions with nodes. FIGS. 1*d,e*, and *f* show surface representations of the streptavidin tetramer viewed down the x, z, and y dyad axes of symmetry respectively. FIGS. 1*g,h*, and *i* show schematic representations used elsewhere in this document for illustrative purposes. In FIG. 1*f*, a schematic view down the x-axis dyad of the streptavidin tetramer, the 2 facing biotin binding sites (shown schematically as open circles) are spaced approximately 20.5 Angstroms apart and aligned along a line that is inclined at a 72 degree angle relative to the z dyad axis of the streptavidin tetramer. The streptavidin tetramer has dimensions of approximately 45 Angstroms (4.5 nanometers) along the x-axis, by 60 Angstroms (6 nanometers) on the y-axis, by 55 Angstroms (5.5 nanometers) on the z-axis.

Weber et al. (1989) determined the X-ray structure of streptavidin and described the origins of its ability to bind the vitamin biotin. Although the biotin:streptavidin interaction is non-covalent, the biotin dissociation constant is about $10^{-14}$M, so that the biotin:streptavidin bond is essentially irreversible. The strength of the biotin:streptavidin bond has led to the broad application of streptavidin in research and diagnostics applications where interaction specificity is required in a complex biological milieu.

In streptavidin, the biotin-binding sites are arranged as pairs where the surface accessible valeric acid side chains of the biotin moieties are oriented along the verticals of an "H" in an orientation that facilitates specific pairwise binding. The biotin binding sites are arranged with D2 symmetry. When bound to the streptavidin biotin-binding sites, the biotin molecules have their terminal valeric acid chains (which are the usual chemical modification sites for generating biotin conjugated reagents) in extended conformation and oriented approximately parallel to the x diad axis of the streptavidin tetramer. The distance between the two closest and approximately parallel pair of bound biotin chain termini is about 20.5 Angstroms, which are aligned along a line that is inclined at a 72 degree angle relative to the z-dyad axis of the streptavidin tetramer (FIG. 1). Thus, when serving as a strut, a streptavidin tetramer can form be linked to other biomolecular components, such as nodes, at two sites through biotin molecules.

Although the present descriptions refer specifically to streptavidin, several related proteins are known (e.g. egg white avidin) that have similar amino acid sequence, structure, and biotin binding properties as streptavidin. These proteins could be substituted for streptavidin in the applications described here.

In addition to streptavidin and its homologues, many other stable protein tetramers with D2 symmetry, such as those derived from thermostable microorganisms, could function as struts either in their native state or through suitable modification of their amino acid sequence, ligand binding functionality, or chemical modification state. Examples of alternative thermostable strut templates with D2 symmetry are given in Table 1.

Nodes

A node can connect two or more struts with predefined orientation of each strut with respect to the other connected struts.

For example, a node can be a symmetric protein multimer. For example, a node can be an enzyme that has catalytic binding sites with high binding specificity for certain substrates and cofactors. A naturally occurring protein can be used in its native state, or can be engineered, for example, using site-specific modification techniques, to render it suitable or optimal for an intended function as a node. Selection of a naturally occurring protein for use as a node can be made from the large number of X-ray crystal structures of stable protein multimers having different symmetries available. Alternatively, selection can be made from protein sequences that have over 70% sequence homology with sequences with known X-ray structures, since it is known that homologous protein sequences also have similar 3-dimensional structures, and the multimeric state of a protein can be determined by physical methods like light scattering, electrophoresis, ultracentrifugation, gel exclusion chromatography, or other methods.

In general, such multimers serving as nodes can be interconnected by biomolecular components serving as struts (such as streptavidin) to create nano-scale structures with defined two- and 3-dimensional geometry.

As outlined in Table 1, suitable multimeric proteins with utility as node templates are known having 3-fold (C3), 4-fold (C4), 5-fold (C5), 6-fold (C6), 7-fold (C7), and other rotational symmetries. In addition, multimeric proteins with utility as node templates are available with higher symmetry, including D2, D3, D4, tetrahedral, cubeoctahedral, icosahedral, and other symmetries. While nodes or node variants having Cn rotational symmetry are primarily suited to the assembly of 2-dimensional planar structures, nodes with higher fold symmetry more naturally lend themselves to the assembly of 3-dimensional structures and lattices. The structures referenced in Table 1 of these and additional proteins that can serve as templates for nodes can be viewed at the Protein Data Bank (PDB) website www.rcsb.org/pdb/home/home.do (accessed Oct. 2, 2007) by entering the appropriate PDB Code as listed in Table 1A. The Protein Data Bank is a Federally supported, archival database that includes complete 3-dimensional structure coordinate data, amino acid sequence data, and links to relevant scientific literature. The structures in the Protein Data Bank are hereby incorporated by reference. Proteins are labeled with their 4-letter protein Protein Data Bank identification code (pdb code) throughout this document. Amino acid sequences as stored in the Protein Data Bank for proteins identified by PDB Code are provided in Table 1B.

For example, site-specific modification techniques can be used to introduce surface cysteine residues at pairs of points on the surface of a multimer to function as a node. Biotinylating reagents, for example, a thiol-reactive biotinylating reagent, can be covalently bonded to such surface cysteine residues to introduce biotin groups at defined, for example, at symmetric points on multimeric node. Thus, a node of defined geometry can be formed. The pairs of biotin groups on the multimer functioning as a node can then be bound to the binding sites on streptavidin tetramers, which can act as struts, to form a two- or 3-dimensional nanostructure.

Reactions of biotinylating reagents that can modify protein cysteine sulfhydryl groups are presented in FIG. 2. FIG. 2*a* shows a free sulfhydryl group on a protein. FIG. 2*b* shows the biotinylation reagent Sulfosuccinimidyl 2-(biotinamido)-ethyl-1,3-dithiopropionate (EZ-Link Sulfo-NHS-SS-Biotin: Pierce). FIG. 2*c* shows the reaction product after biotinylation. FIG. 2*d* shows an analogous reagent for the introduction of 2-imino biotin groups. The binding of imino-biotin to streptavidin is pH dependent. At low pH (~pH4) the imino group becomes charged, causing imino-biotin displacement from the streptavidin biotin binding site Iminobiotin linking is useful for the formation of reversible interactions between streptavidin struts and node proteins. FIG. 2*e* shows the imino-biotin reaction product. FIG. 2*f* shows the above reaction sequences schematically as used in schematic illustrations elsewhere in this application. Although the reagents in FIG. 2 show a specific linker length, biotinylation reagents are readily available with various linker lengths and custom ones are readily synthesized through incorporation of amino-alkyl-thiol coupling groups with variable alkyl or glycol chain lengths.

General Descriptions of Node Geometry

Nodes with Cn Symmetry:

The simplest symmetry that a multimeric note can have is Cn rotational symmetry. Since proteins are polymers composed of L-amino acids they are intrinsically asymmetric, and consequently nodes with Cn symmetry have polarity. As such nodes with Cn symmetry are well-suited to the assembly of 2-dimensional structures on surfaces where, for example, structural features on one polar face of the multimer (which is generally normal to the Cn symmetry axis), can be functionalized to provide the ability to bind to a planar substrate that can be a surface or self-assembling monolayer. FIG. 3*a* shows a schematic view of a three-fold symmetric multimer, while FIGS. 3*b* and 3*c* shows representations of the uronate isomerase protein (TM0064) from *Thermotoga maritima* (Schwarzenbacher et al. 2003, pdb code:1j5s) in space filling and schematic backbone representations respectively. Each chain of the trimer comprises 450 amino acid residues. FIGS. 3*d* and 3*e* shows a representations of a carbonic anhydrase protein from *Methanosarcina thermophila* (Kisker, et al 1996, pdb codes: 1thj & 1qrf) in space filling representation and schematic backbone views respectively. Each chain of the trimer comprises 213 amino acid residues. Additional C3 symmetric node templates are presented in Table 1A.

Single chain constructs of a node protein can be formed. For example, these fused protein multimers can be constructed by incorporating a DNA sequence coding for a polypeptide linker connecting the C-terminus of a first multimer gene to the N-terminus of a second multimer, and so on, to create a single contiguous gene coding for the complete multimer. This approach can allow for the subunits of a multimeric protein to be non-identical. For example, surface cysteine residues for biotinylation can be included in some subunits, but not in other subunits, so that struts can be attached at certain faces of the multimeric protein, but not at others. In addition to the controlling strut-binding geometry, other features of the individual multimer subunits may be individually varied to introduce asymmetry into the node. For example, if the individual multimer subunits have enzyme or cofactor binding sites that can serve as attachment points of additional inorganic, organic or biomolecules that can additionally functionalize the structure, these may be selectively eliminated using recombinant DNA technology to produce nodes where the only some of the binding sites remain intact. Conversely, methods of protein engineering may be used to introduce new binding functionality into the individual multimer subunits to produce single-chain multimeric nodes with asymmetric binding geometry.

Some variations of the structure of C3 multimeric nodes are illustrated in FIG. 4 Each node is composed of a trimeric protein where the subunits have been modified through site-specific mutagenesis to introduce surface amino acid residues that can be chemically modified to introduce pairs of biotin groups with geometry that is complementary to two of the binding sites on the streptavidin tetramer. FIG. 4*a* shows a node that is a trimer formed from three independent, identical chains that are not covalently connected. Two biotins are bound to each chain, so that a streptavidin strut can bind to each subunit. In this construct, the pairs of sites of surface biotinylation that are geometrically complementary to streptavidin are on different subunits. FIG. 4*b* shows a node that is a trimer as formed from three independent, identical chains that are not covalently connected. Two biotins are bound to each chain, so that a streptavidin strut can bind to each subunit. In this construct, the pairs of sites of surface biotinylation that are geometrically complementary to streptavidin are on the same subunits. FIG. 4*c* shows a node based on a protein trimer formed from a single chain construct, that is, with each subunit linked to another by a polypeptide linker. That is, the individual chains of the non-covalently associated trimer have been covalently connected together in a single continuous polypeptide chain. Two biotins are bound to each chain, so that a streptavidin strut can bind to each subunit. FIG. 4*d* shows a node based on a protein trimer formed from a single chain construct. Two of the subunits of the trimer have bound biotin pairs, but the third does not. Thus, only two streptavidin struts can be linked to the trimer. As such, the trimer can serve as a connector between struts, but does not allow branching from one strut to two other struts. FIG. 4e shows a node based on a protein trimer formed from a single chain construct. Only one of the subunits of the trimer has a bound biotin pair; the other two do not. Thus, only one streptavidin strut can be linked to the trimer. As such, the trimer can serve as a terminator of a strut, and cannot serve as a connector or branch point between struts.

Nodes can be functionalized in at least two ways. Nodes may be selected that are enzymes that are characterized by the presence of specific substrate and cofactor binding sites. An approach to functionalizing nodes uses bifunctional crosslinking reagents that specifically bind to binding sites on enzymes for substrates or cofactors (FIG. 5a,b). Bifunctional crosslinking reagents can incorporate an enzyme-specific reactive agent on one end and specific protein-reacting group (for example, a group able to react with cysteine side chain thiol group or a polypeptide chain terminal amine group) on the other end of the linker. For example, many enzymes use ATP as a specific cofactor. FIG. 6 shows reactions of a bifunctional crosslinking reagent incorporating an azido-ATP group on one end (which forms a covalent bond between the reagent and the protein upon ultraviolet light irradiation) and a thiol reactive reagent on the other end that will specifically react with a protein cysteine side chain. Specifically, FIG. 6a shows a protein with a surface cysteine sulfhydryl group that can react with the sulfhydryl reactive reagent (FIG. 6b) incorporating a 2-azidoadenosine 5'-triphosphate group to produce the reaction product in FIG. 6c. The 2-azido ATP modified protein (FIG. 6c) can then bind to an ATP cofactor binding site on a node protein (FIG. 6e). Upon irradiation with UV light, the azido-ATP reacts with amino acid side chains of the node protein in the ATP binding site to form a covalent bond (FIG. 6f). FIG. 6g presents the reaction sequence schematically using symbols used elsewhere in this application. Although the bifunctional reagents in FIG. 6 show a specific linker length, reagents with various linker lengths are readily synthesized through incorporation of amino-alkyl-thiol coupling groups with variable alkyl chain lengths. The preceding and related linkers can be generated using commercially available reagents (Affinity Labeling Technologies, Lexington Ky.; Pierce, Rockford Ill.) or are compounds readily synthesized by one with skill in the art.

The aforementioned azido-ATP analog represents one example, but many additional examples can be envisioned where other biochemical cofactors such as flavins, vitamins, and other biochemical cofactors that bind specifically to proteins can be chemically modified so that they can be photocrosslinked to protein molecules functioning as either struts or nodes in assembled nanostructures.

Many proteins and enzymes naturally incorporate binding sites that are specific for binding substrates and cofactors. In many cases, this binding specificity can be modified, eliminated, or new binding specificity created de novo from site-specific modification of the template protein sequence.

Since di- or multimeric strut or node proteins can potentially be modified forms of enzymes that carry out specific catalytic processes on biochemical substrates, many such nodes built on enzyme templates will incorporate active sites that bind substrates and catalyze reactions with great specificity. For many classes of enzymes, covalent inhibitors or suicide substrates are known that irreversibly inhibit the enzyme activity by forming a highly specific covalent bond with the catalytic amino acid side chain groups in the enzyme's active site. These agents are generally termed suicide substrates or covalent inhibitors of enzyme activity. These agents, when connected to one end of a bifunctional crosslinking reagent as described above, can provide a means of specific immobilization of a protein to an underlying strut-node architecture. For example, immunoglobulins, lectin, or other specific binding molecules could be linked to nanostructures constructed of struts and nodes using this means, as outlined below. FIG. 5b shows a schematic of a C3 symmetric node that is a trimer formed from three independent, identical subunits, where each subunit possesses additional specific binding functionality, and where proteins have been specifically linked to the node using a bifunctional crosslinking reagent. Such functionalization can be used in nanostructures intended to serve in filters, diagnostics or biological sensing applications.

In addition to the use of chemical crosslinking agents as a way to couple proteins to the underlying strut-node structure, it is possible to engineer either nodes or strut components where the nucleotide sequence coding for the node or strut component is modified by a sequence insertion or extended (e.g., in the form of a polypeptide extension) at either the amino or carboxy terminus with nucleotide sequences coding for additional binding function. When these "fused" genes incorporating the binding domain sequences are expressed, the result will be a single continuous polypeptide chain incorporating the encoded linked protein domain. FIG. 5c shows a schematic of a C3 node composed of 3 independent chains, where each chain incorporates a covalently linked or fused protein domain. The fused domains can have utility in both protein isolation and in creating protein assemblies. Examples of such fused domain binding sequences (for example, a polypeptide extension) include immunoglobulin domains, polyhistidine sequences, polypeptide sequences that bind to streptavidin (StrepTag), *Staphylococcus* Protein-A, *Staphylococcus* Protein-G, an antibody binding polypeptide sequence to which an antibody can bind, an antigenic polypeptide sequence, a hapten polypeptide binding sequence, a binding function for a protein or a metallic surface, a polypeptide sequence that is a substrate for an enzyme, and others together with sequences designed to be linkers with greater or lesser conformational flexibility. FIG. 5e shows a single-chain construct of a C3 node where multimer subunits with different functionalities have been interconnected with polypeptide linkers creating an asymmetric multimeric node. Starting from upper right, and going counter-clockwise, the first node subunit has no binding capability (e.g. enzyme active site groups removed through site-specific mutagenesis) or incorporated biotinylation sites, the second node subunit has also had binding capability removed but has incorporated biotinylation sites, and the third subunit incorporates both a fused domain and a protein bound through a bifunctional crosslinking reagent. FIGS. 5f and 5g show additional possibilities that generally illustrate the modularity and combinatorial flexibility of the approach in generating a wide variety of geometries and functionalized structures.

FIG. 7a shows a schematic view of a four-fold (C4) symmetric multimer, while FIGS. 7b and 7c show representations of the isopentenyl-diphosphate delta-isomerase from *Thermus thermophilus* (Wada et al. 2006, pdb code:1vcg) protein in space filling and schematic backbone representation respectively. Each chain of the tetramer incorporates 332 amino acid residues, and a non-covalently bound flavin mononucleotide cofactor. FIGS. 7d and 7e show representations of the inosine-5'-monophosphate dehydrogenase protein from *Pyrococcus horikoshii* (Asada & Kunishima 2006, pdb code:2cu0) in space filling and schematic backbone representation respectively. Each chain of the tetramer incorporates 486 amino acid residues, and a non-covalently bound xanthosine-5'-monophosphate substrate analog. Additional C4 symmetric node templates are presented in Table 1A.

FIGS. 8*a* through 8*g* show schematic views of nodes based on a protein tetramer having four-fold (C4) rotational symmetry. Each node is composed of a tetrameric protein where the subunits have been modified through site-specific mutagenesis to introduce surface amino acid residues that can be chemically modified to introduce pairs of biotin groups with geometry that is complementary to two of the binding sites on the streptavidin tetramer. FIG. 8*a* shows a node that is a tetramer as formed from four independent, identical chains that are not covalently connected. All of the subunits of the tetramer are symmetrically equivalent. Two biotins are bound to each chain, so that a streptavidin strut can bind to each subunit. In this construct, the pairs of sites of surface biotinylation that are geometrically complementary to streptavidin are on different subunits. FIG. 8*b* shows a node that is a tetramer as formed from four independent, identical chains that are not covalently connected. All of the subunits of the tetramer are symmetrically equivalent. Two biotins are bound to each chain, so that a streptavidin strut can bind to each subunit. In this construct, the pairs of sites of surface biotinylation that are geometrically complementary to streptavidin are on the same subunits. FIG. 8*c* shows a node based on a protein tetramer formed from a single chain construct, that is, with each subunit linked to another by a polypeptide linker. That is, in the structure shown in FIG. 8*c* the individual chains of the non-covalently associated tetramer are covalently connected together in a single continuous polypeptide chain. Two biotins are bound to each chain, so that a streptavidin strut can bind to each subunit. FIG. 8*d* shows a node based on a protein tetramer formed from a single chain construct. Three of the subunits of the tetramer have bound biotin pairs, but the fourth does not. Thus, only three streptavidin struts can be linked to the tetramer. As such, the tetramer can serve as a branch point for three struts. FIG. 8*e* shows a node based on a protein tetramer formed from a single chain construct. Two adjacent subunits of the trimer have bound biotin pairs, but the third and fourth subunits do not. Thus, only two streptavidin struts can be linked to the tetramer. As such, the tetramer can serve as a connector between struts, but does not allow branching from one strut to two or more other struts. The tetramer can serve, for example, to form a corner of a rectangular assembly. FIG. 8*f* shows a node based on a protein tetramer formed from a single chain construct. Two opposed subunits of the tetramer have bound biotin pairs; the first and third subunits do not. Because only two streptavidin struts can be linked to the tetramer, the tetramer can serve as a connector between struts, but does not allow branching from one strut to two or more other struts. The tetramer can serve, for example, to form a connector between two struts oriented along the same axis. FIG. 8*g* shows a node based on a protein tetramer formed from a single chain construct. Only one of the subunits of the tetramer has a bound biotin pair; the other three do not. Thus, only one streptavidin strut can be linked to the tetramer. As such, the tetramer can serve as a terminator of a strut, and cannot serve as a connector or branch point between struts. Thus, FIGS. 8*d* through 8*g* show covalently connected tetramers of which the surface binding sites on some subunits have been deleted, creating nodes with various streptavidin binding geometry and valency.

FIG. 9 shows variations of C4 symmetric nodes that have been functionalized and have various geometrical properties. As noted above for C3 nodes, C4 nodes can be functionalized in at least two ways. Nodes may be selected that are enzymes that can be reacted with bifunctional crosslinking reagents that specifically bind to enzyme binding sites for substrates or cofactors. FIG. 9*a* shows a schematic of a C4 symmetric node that is a tetramer formed from four independent, identical subunits, where each subunit possesses additional specific binding functionality corresponding to an enzyme substrate and/or cofactor binding site. FIG. 9*b* shows a schematic of a C4 symmetric node formed from four independent, identical subunits, where proteins have been specifically linked to the node using a bifunctional crosslinking reagent.

As in the case of C3 symmetric nodes, multimer subunits of C4 nodes my also be modified by a sequence insertion or extended at either the amino or carboxy with nucleotide sequences coding for additional binding function. FIG. 9*c* shows a schematic of a C4 node composed of 4 independent chains, where each chain incorporates a covalently linked or "fused" protein domain. FIG. 9*d* shows a single-chain construct of a C4 node where multimer subunits with different functionalities have been interconnected with polypeptide linkers creating an asymmetric multimeric node. Starting from the top, and going counter-clockwise, the first node subunit incorporates a fused binding domain (any substrate or cofactor binding ability of the native template node having been removed through site-specific mutagenesis), the second subunit incorporates streptavidin binding capability, the third subunit incorporates a binding protein linked through a bifunctional linker, and the fourth subunit incorporates both a binding protein linked through a bifunctional linker and a fused binding domain. As outlined above, fused domains could include immunoglobin binding domains such as *Staphylococcus aureus* Protein A, Streptococcal Protein G, nucleotide binding domains, or others while bound proteins could include immunoglobulins or other proteins. The node show in FIG. 9*d* can function as a strut terminator in nanostructures. As outlined below, the ability to precisely position two different kinds of proteins or antibodies in nanostructures with close apposition could have many applications in functional or diagnostic applications. FIG. 9*e* shows an analogous construct that can form a 90 degree corner in a 2-dimensional planar array. Many additional constructs based on C4 symmetric templates are possible through combinations of the features outlined above, retaining all of the properties of modularity and combinatorial flexibility of the approach in generating a wide variety of geometries and functionalized structures.

The following descriptions of nodes with higher symmetry do not generally include explicit descriptions of nodes functionalized through incorporation of fused domains or bound proteins, although it can be recognized that these approaches are equally applicable to node subunits forming complexes of higher symmetry. Similarly, nodes of higher symmetry may be formed using polypeptide chains where two or more of the polypeptide sequences comprising a multimer subunit in the node template structure, have been interconnected to form a single continuous polypeptide chain by interconnection through a polypeptide linker. Thus, design of nodes of higher symmetry can incorporate all of the properties of modularity and combinatorial flexibility of the approach defined above in generating a wide variety of geometries and functionalized structures.

In addition to nodes with C2, C3, and C4 symmetry, natural protein multimers from thermophilic organisms occur with higher Cn rotational symmetry. FIG. 10 presents schematic illustrations of biotinylated nodes with C5 (FIG. 10*a*), C6 (FIG. 10*b*), C7 (FIG. 10*c*) symmetry together will illustrations of thermophile-derived proteins with corresponding symmetry. The C5 symmetric protein shown in surface representation in FIG. 10*c* is a pentameric heme-binding protein from *Thermus thermophilus* HB8 (Ebihara et. al. 2005, pdb code: 1vdh). Each polypeptide chain of the pentamer has 249 amino acid residues. FIG. 10e shows a surface representation of the PH0250 protein from *Pyrococcus horikoshii* OT3 (Asada and Kunishima 2007, pdb code:2ekd) with C6 symmetry. Each polypeptide chain of the hexamer has 207 amino acid residues. FIG. 10f shows a surface representation of an heptameric RNA binding protein from *Methanobacterium thermoautotrophicum* (Collins et. al. 2001, pdb code:1i81) with C7 symmetry. Each polypeptide chain of the heptamer has 83 amino acid residues. Additional Cn symmetric node templates are presented in Table 1A.

Non-Planar Cn Nodes:

In addition to Cn nodes with radial planar symmetry (e.g. with biotinylation sites introduced to orient bound streptavidin tetramers in a plane normal to the Cn axis of the multimeric node), Cn multimers with suitable geometrical features can be site-specifically modified to orient streptavidin tetramers at an angle α to the Cn multimer axis. As shown in FIG. 11, such nodes have utility in the assembly of closed polyhedra for specific values of n and α consistent with polyhedron formation (Pugh 1976, Williams 1979, Pearce, 1979). For example, for the generation of an icosahedron, n=5, and the approximate apex angle α=121.72 degrees (FIG. 11a). For the generation of a dodecahedron, n=3, and the approximate apex angle α=z 110.73 degrees (FIG. 11b). Similar considerations apply to the generation of other regular and irregular polyhedra, such as buckyballs (truncated icosahedron) and buckytubes (Weber 1999) where n=3 and the approximate apex angle α=z 104.15 degrees.

Nodes with Dn Symmetry: Many multimeric structures with Dn symmetry are known from x-ray crystallography studies of proteins from thermophilic organisms (Table 1A). Dn-symmetric structures arise through the combination of dyad symmetry and other rotational symmetry operations (Table 1). Nodes with Dn symmetry are particularly useful in the assembly of extended nanostructures since biotinylation sites can be introduced symmetrically across multimer dyad symmetry axes to precisely complement dyad-related biotin binding sites on streptavidin (FIG. 1).

The simplest Dn symmetry is D2, a symmetric tetramer where the multimer subunits are related by 3 mutually perpendicular dyad axes. As noted in FIG. 1, the streptavidin molecule is itself a tetramer with D2 symmetry. Although tetrameric D2 symmetric nodes can potentially function as 3-dimensional nodes in orthorhombic lattices, they are more practically utilized as strut extenders and/or to provide attachment points for additional functionalization. Many tetrameric multimers with D2-symmetry that exhibit a wide range of geometrical features are known from thermophilic microorganisms (Table 1). Some are relatively flat and rectangular in shape, while others approximate tetrahedral geometry. As outlined in FIG. 12 and the specific embodiments described below, D2 nodes with suitable structural features can be used to control the relative geometrical orientation and rotational geometry of connected streptavidin struts. FIGS. 12a and 12c schematically show projection views of a D2-symmetric node able to connect to two streptavidin tetramers through surface biotinylation sites that are introduced at the D2 node surface through site-specific modification of the template protein sequence, followed by a chemical biotinylation reaction (FIG. 2). In FIGS. 12a and 12c, the biotinylation sites are schematically indicated by black circles (defining the corners of a rectangle) on the front surface of the D2 tetramer and as shaded circles on the rear surface of the tetramer. These biotinylation sites are geometrically complementary to the biotin binding sites on streptavidin (FIG. 1g). As illustrated in FIGS. 12a and c, there are generally two possible orientations for pairs of biotinylation sites that are symmetrically disposed about the D2 (or any other multimer) dyad axis; one where the orientation of the bounding box defining the biotinylation sites is horizontal and which aligns the z-axis dyad of the node with the z-axis dyad of streptavidin (FIG. 12a), and the second where the orientation of the bounding box defining the biotinylation sites is vertical and which aligns the z-axis dyad of the node with the y-axis dyad of streptavidin (FIGS. 1g and 12c). FIGS. 12b and 12d schematically illustrate 2 streptavidin:node:streptavidin complexes, one incorporating a node of the sort shown in FIG. 12a (FIG. 12b), and a second (FIG. 12d) incorporating the node of FIG. 12c. As illustrated, the difference between the complexes is a relative rotation of the streptavidin and node proteins by 90 degrees about the common x-axes of the complexes. In either case, the relative orientations of the terminal free biotin binding sites in the complex are preserved as if the complex were essentially a single streptavidin molecule elongated along the streptavidin x-axis (FIG. 1). Such extended struts are useful for the construction of nanostructures with defined dimensions between nodes as outlined below. The ability to control node orientation in such struts is also a useful property allowing controlled of orientation of additional node functionalizing groups. As noted above for Cn symmetric nodes, many D2 symmetric node structures will incorporate substrate or cofactor binding sites that can be utilized as linkage sites for the introduction of additional protein domains with binding or functional properties. These binding sites provide a means for introducing functional features into the strut components of the nanostructure.

In addition to forming struts that maintain terminal biotin binding site geometry it is possible to construct extended struts where the terminal streptavidin binding sites are oriented at angles other than 180 degrees relative to each other around the common complex x-axis. FIG. 13a schematically shows a projection view of a nearly tetrahedral D2 node where the geometry allows symmetrically equivalent introduction of biotinylation sites in two bounding boxes that are oriented at an angle β to each other along the multimer node x-axis. This feature can introduce a twist in orientation of bound streptavidin tetramers around the common axis of a multimeric complex. FIG. 13b schematically illustrates a streptavidin:node:streptavidin complex where β=90 degrees, so that the relative orientations of the free biotin binding sites on the complex are rotated by 90 degrees along the corresponding streptavidin x-axes (FIG. 1). Extended struts that incorporate some degree of axis rotation of terminal streptavidin binding sites are useful for the geometrical placement of components in nanostructures as well as for construction of 3-dimensional nanostructures with defined dimensions between nodes as outlined below.

FIG. 14 presents illustrations of some D2 symmetric protein multimers useful as node templates. FIG. 14a shows the iron superoxide dismutase protein from *Methanobacterium thermoautotrophicum* (Adams et al. 2002, pdb code:1ma1) in schematic backbone representation and in surface representation (FIG. 14b). FIG. 14c shows the alcohol dehydrogenase protein from *Sulfolobus solfataricus* (Esposito, et. al. 2003, pdb code:1nto) in schematic backbone representation and in surface representation (FIG. 14d). FIG. 14e shows the TenA homolog protein from *Pyrococcus furiosus* (Benach, et. al. 2005, pdb code:1rtw) in schematic backbone representation and in surface representation (FIG. 14f). Also shown in FIG. 14a through f are "bounding boxes" that are aligned along the dyad symmetry axes of the respective D2 symmetric tetramers. The intersections between the molecular surface and the diagonal edges of the box define sites that are symmetric and complementary to the biotin binding in streptavidin, as described in more detail below. Additional structures with D2 symmetry are listed in Table 1.

FIG. 15 presents schematic illustrations of a hexameric node with D3 symmetry and an octameric node with D4 symmetry. As noted above, nodes with Dn symmetry are particularly useful in the assembly of extended nanostructures since biotinylation sites can be introduced symmetrically across multimer dyad symmetry axes to precisely complement dyad-related biotin binding sites on streptavidin (FIG. 1). As schematically illustrated in FIG. 15*a,b,c,d*, this will generally involve introduction of a single site-specific modification in each polypeptide chain of the multimer to introduce a suitable biotinylation site. Note that for multimers with D3 and higher symmetry, there may be several different dyad-related symmetrical sites on the individual multimer subunits that are potentially complementary to the streptavidin dyad-symmetric binding sites. For example, the subunits of the D3 node shown in FIG. 15*e* are shown with biotinylation modification sites on their "faces", but alternative symmetric sites occur that "bridge" between subunits. The situation is similar for the D4 node shown in FIG. 15*f*, except that the 4-fold symmetry creates an additional, symmetrically non-equivalent, set of dyad axes (labeled x' and y' in FIG. 15*f*) in the structure. If the Dn multimer structures are sufficiently large, it may be possible to introduce 2 biotinylation sites into each polypeptide chain of a Dn multimer (FIGS. 16*a,b* and FIGS. 16*c,d*) that are related by multimer dyad symmetry elements and complementary to the dyad symmetry of the biotin binding sites on streptavidin. The resulting structures shown in FIG. 16*e* (D3) and FIG. 16*f* (D4) could bind 6 and 8 streptavidin strut elements, respectively. FIG. 17 presents illustrations of hexameric protein multimers with D3 symmetry and octameric proteins with D4 symmetry useful as node templates.

FIG. 17 presents illustrations of some D3 symmetric protein hexamers useful as node templates. FIG. 17*a* shows the arginine repressor protein from *Bacillus stearothermophilus*. (Ni et. al. 1999, pdb code:1b4b) in schematic backbone representation and in surface representation (FIG. 17*b*). FIG. 17*c* shows the adenylyltransferase protein from *Methanobacterium thermoautotrophicum* (Saridakis et. al 2001, pdb code: 1hyb) in schematic backbone representation and in surface representation (FIG. 17*d*). FIG. 17*e* shows the inorganic pyrophosphatase protein from *Thermus thermophilus* (Teplyakov et. al. 1994, pdb code:2prd) in schematic backbone representation and in surface representation (FIG. 17*f*). Also shown in FIG. 17*a* through *f* are "bounding boxes" that are aligned along the dyad symmetry axes of the respective D3 symmetric hexamers. The intersections between the molecular surface and the diagonal edges of the box define sites that are symmetric and complementary to the biotin binding in streptavidin, as described in more detail below. Additional structures with D3 symmetry are listed in Table 1.

FIG. 18 presents illustrations of some D4 symmetric protein octamers useful as node templates. FIG. 18*a* shows the PurE protein from *Thermotoga maritima* (Schwarzenbacher et. al. 2004, pdb code:1o4v) in schematic backbone representation and in surface representation (FIG. 18*b*). FIG. 18*c* shows the sirtuin protein from *Thermotoga maritima* (Cosgrove et. al. 2006, pdb code:2h2i) in schematic backbone representation and in surface representation (FIG. 18*d*). FIG. 18*e* shows the TT0030 protein from *Thermus Thermophilus* (Zhu et. al. 2006, pdb code:2iel) in schematic backbone representation and in surface representation (FIG. 18*f*). Also shown in FIG. 18*a* through *f* are "bounding boxes" that are aligned along the dyad symmetry axes of the respective D4 symmetric octamers. The intersections between the molecular surface and the diagonal edges of the box define sites that are symmetric and complementary to the biotin binding in streptavidin, as described in more detail below. Additional structures with D4 symmetry are listed in Table 1A.

In addition to multimers with D3 and D4 symmetry, multimers with higher Dn symmetry are also found in thermophilic organisms (Table 1A). These protein multimers have utility as node templates in applications where nanostructures with certain geometrical properties and higher node connectivity is desired than is possible using nodes with D3 and D4 symmetry.

Nodes with Polygonal Symmetry:

In addition to nodes with Dn symmetry, several occurrences exist of symmetric multimeric protein complexes with tetrahedral (usually incorporating 12 protein subunits), cubeoctahedral symmetry (usually incorporating 24 protein subunits), or icosahedral symmetry (usually incorporating 20n subunits). The surfaces of these multimers, which usually form hollow shell structures, range from nearly spherical, to shapes that approximate truncated tetrahedra. As shown schematically in FIG. 19, all of these polyhedra incorporate dyad symmetry elements. For example, FIG. 19*a* shows a truncated tetrahedron, FIG. 19*b* shows a cubeoctahedron, and FIG. 19*c* shows an icosahedron, together with their dyad symmetry axes. Connections made along the dyad axes of these polyhedra can be used to generate structures with features that radiate in three dimensions from a central node. Such dendritic structures may find application in new materials. Some modified polyhedra may serve as nodes in regular 3-dimensional lattices.

FIG. 20 presents illustrations of protein multimers having the symmetry properties of regular polyhedra and utility as templates for nanostructure node proteins. FIG. 20*a* shows the ornithine carbamoyltransferase dodecameric tetrahedral protein complex protein from *Pyrococcus furiosus* (Massant et. al. 2003, pdb code:1pvv) in schematic backbone representation. FIG. 20*b* shows the 24-subunit cubeoctahedral heat shock protein complex from *Methanococcus jannaschii*, (Kim et. al. 1998 pdb code:1shs) in schematic backbone representation. FIG. 20*c* shows the 60-subunit dodecahedral protein complex of the dihydrolipoyl transacetylase catalytic domain (residues 184-425) from *Bacillus stearothermophilus* (Izard, et. al. 1999, pdb code:1b5s) in schematic backbone representation. Additional structures with polyhedral symmetry are listed in Table 1A.

Method of Determining Sites of Site-Specific Modifications on Proteins Suitable for Production of Multimeric Node Proteins with Geometrically Defined Attachment Points for Binding Streptavidin In general, protein multimers suitable for use as node templates can be composed of two or more protein subunits related by symmetry. Node proteins are created by using site-specific mutagenesis to introduce reactive amino acids at specific sites on the template node protein surface that can be subsequently functionalized to allow the geometrically defined attachment of a linear strut through chemical linkages or non-covalent interactions between specific sites on the node and strut. In the current application, the envisioned nanostructures will incorporate streptavidin as a strut, or streptavidin in complex with other proteins that can preserve certain binding and geometrical features of the streptavidin tetramer as outlined above (FIG. 1, FIG. 12) and described elsewhere (Salemme & Weber, 2007). As shown in FIG. 1, streptavidin is a protein tetramer with D2 symmetry that incorporates 4 binding sites for the vitamin biotin. Node proteins suitable for binding streptavidin are template proteins that have been modified through site-specific modification to allow covalent reaction of specific amino acid side chains to covalently attach biotin groups to the node protein.

Many amino acids can potentially be introduced as sites for specific chemical modification on the template node protein surface, including cysteine, methionine, lysine, histidine, tyrosine and arginine. Any other occurrences of an amino acid of a type that is to be introduced through site-specific modification on the node template surface must also be modified through site-specific mutagenesis by substituting a structurally similar amino acid, so that the final node protein subunit sequence incorporates reactive amino acids only at those sites that facilitate the predefined node-strut geometry.

In the present embodiments, the node structures are modified to incorporate cysteine residues, which can be modified with suitable reagents to incorporate covalently bound biotin groups able to bind streptavidin with defined geometry and high affinity (FIG. 2). Cysteine residues occurring on the surface in the naturally occurring sequence of the node template protein are substituted with serine, alanine or another amino acid depending upon the local structural environment.

FIG. 1 illustrates the structure of streptavidin, a D2 tetramer whose subunits are related by three mutually perpendicular two-fold rotational (dyad) axes of symmetry. As illustrated, the biotin binding sites on streptavidin (or more specifically the coordinates of the protein-bound biotin carboxyl oxygen atoms that are the sites of bifunctional chemical reagent attachment) are separated by 20.5 Angstroms and oriented along a line at an angle of 20 degrees relative to the "y" dyad axis of the streptavidin tetramer (as defined in FIG. 1) and at an angle of 72 degrees relative to the "z" dyad axis of the streptavidin tetramer. In general, maximum precision and flexibility in the assembly of streptavidin-linked structures is achieved when the bound streptavidin is positioned with defined geometry relative to the node to which it is bound. For nodes with Cn symmetry, the bound streptavidin should be aligned so that either the y or z-dyad axes of the streptavidin tetramer are aligned parallel with the Cn symmetry axes of Cn symmetric nodes. For nodes with D2 symmetry, the y or z-dyad axes of the streptavidin tetramer are aligned with one of the D2 dyad axes, and the streptavidin x dyad axis is coincident with a second dyad axis of the D2 node (Although there are some exceptions to this rule as shown in FIG. 13). For nodes with Dn symmetry, the y or z-dyad axes of the streptavidin tetramer is aligned with the Dn axis of the node and the streptavidin x dyad axis is coincident with a dyad axis of the Dn node. For polyhedral nodes with dyad axes, the y or z-dyad axes of the streptavidin tetramer are aligned with a major symmetry axis of the node (depending on the polyhedral node symmetry), and the streptavidin x-dyad axis is coincident with a dyad axis of the polyhedral node.

For nanostructures that are assembled through a combination of components linked chemically, it is necessary to ensure precise control of the linking geometry between the structural components. Without intending to be limited by theory, it is likely that imperfections in the interaction geometry of the structures described by Ringler & Schulz (2003) produced cumulative twist that ultimately limited the size of the structures that could self-assemble.

FIG. 21a reiterates the geometry of the biotin binding sites on streptavidin. FIGS. 21b and 21c show schematic views of a node with Cn rotational symmetry, where the Cn symmetry axis defines the z-axis of the structure. In order to assemble extended structures that do not twist when interconnected by streptavidin, the geometry of site-specific modifications on the node template (or more specifically the coordinates of the thiol sulfur atoms of the incorporated cysteine side chains on the node protein) must be complementary to the geometry of the biotin binding sites on streptavidin, and must align the streptavidin z-axis (FIG. 21a) or y-axis (FIG. 21b) with the node Cn or z-axis. This requires that the modification sites on the nodes are oriented at an angle (e.g. −72 degrees) relative to the Cn rotational (z) axis of the node protein complex so that the modification sites are complementary to the biotin binding sites on streptavidin. There can be some variation (for example, 20.5 plus or minus 5 Angstroms) in the separation of the node modification sites, since this variation can be accommodated by adjusting the length of the chemical linking reagent that couples the biotin to the cysteine sulfhydryl groups. However, significant (>5 degrees) variations in the angle from −72 degrees will accumulate to cause extended structures to twist and potentially introduce strain into extended structures.

Stated in other words, two specific amino acid reactive residues (or site-specific modifications) of the nanostructure node multimeric protein (or node template) can be complementary to the geometry of a pair of biotin binding sites on a streptavidin or streptavidin derivative strut. When the two specific amino acid reactive residues are aligned with the pair of biotin binding sites, for example, so that biotin or biotin derivative groups covalently bound to each of the specific amino acid reactive residues can bind to each biotin binding site of a pair on the streptavidin or streptavidin derivative strut, the Cn symmetry axis of the nanostructure node multimeric protein is substantially parallel to a dyad axis of the D2 symmetric streptavidin or streptavidin derivative strut. Substantially parallel can mean, for example, parallel to within less than or equal to, for example, 0.5 degree, 1 degree, 2 degrees, 5 degrees, or 10 degrees.

The above criteria represent general requirements for the assembly of any planar structure incorporating streptavidin struts and nodes with Cn rotational symmetry. It is notable that in the prototype 2-dimensional lattice structure assembled by Ringler and Schulz (2003), the two cysteine residues (Asn 133 to Cys, and Lys 261 to Cys) introduced through site-specific modification on their C4 node protein template, L-rhamnulose-1-phosphate aldolase from *E. coli*, are oriented at 52 degrees relative to the C4 axis of the tetramer, giving each bound streptavidin a slight "propeller" twist relative to the central node. It is consequently evident that extended structures must have been quite strained, and that this was an important contributing factor to their inability to build very extensive 2-dimensional lattices.

Cn Symmetric Node Specification:

Definition of the sites for site-specific modification on Cn symmetric node templates can be determined using computer modeling, computational methods or a combination of these methods. Generally the methods involve a constrained geometrical search for favorable interaction complexes. FIG. 22 schematically illustrates the variable search parameters for Cn and Dn node structures. The Cn search parameters include a rotation of the Cn node about its z-axis, and a translation of streptavidin along its x-axis in the xy plane of the node (FIG. 22a). The method involves initially orienting the Cn template node and streptavidin so that they a) do not spatially overlap, b) are oriented with the Cn (z-axis) of the node parallel to either the y-axis or z-axis of streptavidin, and c) have similar z coordinate values for their respective centers of mass. The node is incrementally rotated about the Cn axis through an angular range somewhat greater than 360/n degrees. For each angular increment about the Cn axis, the streptavidin tetramer is translated along its dyad x-axis until van der Waals contact or near van der Waals contact is made between the atomic coordinates of the node template and atomic coordinates of streptavidin. Each of the resulting streptavidin-node complexes is then examined using computer graphics (Jones et. al. 1990, Humphry et. al. 1996), geometrical, energetic computational methods (Case et. al. 2005), or a combination of these methods to determine the quality of overall fit and feasibility and locations of site-specific modifications on the node template that can provide chemical attachment points for biotin, including the use of coupling reagents with different linker lengths. Parameters describing the complex structure (e.g 3-dimensional model coordinates, computed energy, pictures, etc.) may be then entered into a table. The process outlined above is repeated for relatively small incremental changes in rotation around the template node Cn symmetry axis (for example, about 0.1 to 2.0 degrees in rotation), so that interactions of the Cn node surface and streptavidin are extensively sampled, evaluated and compared. Complexes with the best features are then selected for manufacture using recombinant DNA technology.

Cn Polyhedral Node Specification:

The method outlined above is suitable for nodes that are incorporated into essentially planar, 2-dimensional structures oriented on surfaces. Similar constrained searches can be developed to design nodes for the assembly of 3-dimensional structures. For example, nodes can be designed that can assemble into 3-dimensional polyhedra that such as a regular a regular dodecahedron incorporating C3 symmetric nodes or a regular icosahedron incorporating C5 symmetric nodes (FIG. 11). Additional polyhedral nodes are possible as well. The approach to defining sites for modification is similar to that outlined above for Cn planar nodes, except that the orientation of the approach axis between streptavidin and the Cn axis of the node complex is not 90 degrees, but is the angle $\alpha$ formed between the edge of the polyhedron and a vector from the center of the polyhedron to an apical node (FIG. 22b). As outlined above, the apex angle $\alpha$ for an icosahedron is approximately 121.92 degrees (FIG. 11a) and for a dodecahedron $\alpha$ is approximately 110.93 degrees (FIG. 11b). Similar considerations apply to the generation of other regular and irregular polyhedra, such as buckyballs (truncated icosahedron) and buckytubes (Weber 2199) where n=3 and the approximate apex angle $\alpha$=104.15 degrees.

Dn Node Specification:

Nodes based on node templates with Dn symmetry represent an extensive family with diverse structural geometry (Table 1A). As noted above, structures with dyad symmetry axes such as Dn symmetric structures offer the possibility of symmetric placement of biotin linkage sites on node subunits that are complementary to the binding sites on streptavidin. The process generally produces node subunit proteins that incorporate only a single site-specific modification for the purposes of incorporating a reactive cysteine residue, so that the bound streptavidin tetramer in the complex forms a symmetric link between node subunits oriented by a dyad axis of symmetry.

As outlined in FIGS. 21d and 21e, there are generally two symmetric orientations that are best suited for the formation of extended structures composed of Dn symmetric nodes. These alternative orientations correspond to streptavidin alignments where either the streptavidin z-axis (FIG. 21d, "H" or horizontal) or y-axis (FIG. 21e "V" or vertical) is oriented parallel to the node Dn or z-axis. Definition of the sites for site-specific modification on Dn symmetric node templates can be determined using a constrained computer search (FIG. 21c) where a) the z-axis of the streptavidin tetramer and either the x,y, or z-dyad axes of D2 node are constrained to be parallel, and b) the approach x-axis of streptavidin (which is a dyad axis) is constrained to be coincident with a dyad axis relating subunits of the Dn-symmetric node template. Final complex configurations are those where the atoms of streptavidin and the node make Van der Waals contact or near Van der Waals contact.

Nodes based on node templates with D2 symmetry are appropriate for many applications including formation of 2D and 3D lattices, as well as for strut extenders that connect two streptavidin tetramers in a linear array (FIG. 12b,d). Definition of the sites for site-specific modification on D2 symmetric node templates can be determined using a constrained computer search as outlined above, noting however, that since the D2 node has three mutually perpendicular dyad axes, and that there are 2 alternative streptavidin orientations around each dyad, that there are potentially a total of six possible complex configurations where streptavidin can be symmetrically bonded to a D2 node so that its dyad symmetry axes are coincident and/or perpendicular to the symmetry axes of the node. As examples, FIG. 12a illustrates the case where the streptavidin z-dyad axis is parallel to the z-dyad axis of a D2 node, while FIG. 12c illustrates the example where the streptavidin y-dyad axis is parallel to the z-dyad axis of a D2 node.

Locating the positions on a Dn node surface suitable for the introduction cysteine residues for biotinylation may also be performed through an alternative graphical or mathematical process. Basically this involves the superposition of "bounding boxes" (with dimensions of approximately 6.4 Angstroms by 19.5 Angstroms, FIG. 21d.) that represent the projected positions of the potential biotinylation sites (e.g. sites complementary to the biotin bonding sites in each of the 2 possible streptavidin binding orientations) around each dyad axis in a structure. For example, FIG. 23 shows a stereoscopic view of the D2 symmetric node template pdb code: 1rtw with pairs of bounding boxes embedded along each of the three dyad axes. By examination of the 3-dimensional atomic coordinates of the node template protein using a computer method (Lee and Richards, 1971) it is possible to compile a list of the coordinates of the atoms and/or amino acid residue side chains that lie on the surface of a protein. Specific side chain atoms can be selected for reference in a list; e.g. C$\alpha$ backbone carbon atoms for Gly residues, and C$\beta$ side chain atoms for all other amino acid residues. A computer program can then be used to find the shortest distances between selected amino acid side chain atoms in the exposed atom/residue list and the lines defining the bounding box that project the positions of the biotin binding sites. Alternatively, the C$\beta$ atoms can be identified by inspection using computer graphics modeling programs. The atoms so identified will generally define the amino acid residues in the template sequence that can be mutated to Cys residues, and when functionalized by biotinylation, will form sites that are symmetric to streptavidin and align the Dn axis of the node to either the y-axis or z-axis of streptavidin.

Several of the multimeric nodes shown in this application are shown with embedded bounding boxes (in projection) along node dyad axes.

For D2 nodes with appropriate geometrical features, alternate linear couplers can be engineered that introduce twist between the streptavidin tetramers linked to the D2 node along the complex x-axis (FIG. 13). Identification of modifications sites on the node template involves a process that is slightly different from that described above, where the search (or alternatively, the rotational orientation of the bounding boxes around the complex x-axis) is performed with the z-axes of the streptavidin tetramer and the D2 node oriented at some predetermined angle $\beta$ (FIG. 13a), depending on the total angular twist desired in the final linear coupler. FIG. 13ab shows a special case where a D2 node with nearly tetrahedral symmetry is modified to produce a D2 linear coupler that orients the terminal streptavidin molecules with β=90 degrees.

Additional nodes, appropriate for the formation of extended 3-dimensional lattices, can be based on node templates with D3 or D4 symmetry as detailed below. Definition of the sites for site-specific modification on Dn symmetric node templates can be determined using a constrained computer search process similar to that described above for Cn nodes, where the orientation of the approach axis between streptavidin and the Dn axis of the node complex is 90 degrees, but the search is additionally constrained so that the approach axis along which the streptavidin molecule advanced is coincident with a dyad axis relating subunits of the Dn-symmetric node template. Note that this process generally produces node subunit proteins that incorporate only a single site-specific modification, so that the streptavidin tetramer in the complex forms a symmetric link between node subunits oriented by a dyad axis of symmetry.

Polyhedral Node Specification:

Additional nodes, appropriate for the formation of extended 3-dimensional radial structures or 3-dimensional lattices, can be based on node templates with higher symmetry that incorporate dyad symmetry elements. Observed node symmetries include tetrahedral, cubic, cuboctahedral, and truncated icosahedral (Table 1A). Definition of the sites for site-specific modification on these higher symmetry node templates can be determined using a constrained computer search process similar to that described above for D2 nodes, where the orientation of the x approach axis of streptavidin is constrained to be coincident with a dyad axis relating subunits of the symmetric node template. Note that this process generally produces node subunit proteins that incorporate only a single site-specific modification per subunit, so that the streptavidin tetramers in the complex form symmetric links between node subunits oriented by a dyad axis of symmetry.

For any given modeled complex it may be possible, using computational and modeling methods (Jones 1990, Case et. al. 1995), to further improve the complex through the introduction of site-specific modifications in streptavidin or the template node to improve electrostatic complementarity, van der Waals interactions or other features that will improve the stability or functionality of the complex.

Examples of Specific Node Embodiments

The sequence and symmetry specifications of the several embodiments described below are detailed in Table 2. Table 2 provides the Protein Data Bank code (pdb code) for the node template structure, the node symmetry, the amino acid sequence of the node template (as downloaded from the Protein Data Bank), and the modifications of the sequence that are required to create a node that can be functionalized by biotinylation so that it interacts with streptavidin or other proteins with binding sites disposed with the same geometry as the streptavidin binding sites (Salemme & Weber 2007). Sequence modifications are grouped as "general" and "specific biotinylation sites". General sequence modifications usually represent modifications to replace potentially interfering cysteine residues occurring in a template sequence with structurally similar residues. Depending on the structural environment and role of the cysteine side chain in the template protein, the replacement amino acid may be Ala, Ser, His, Asp, or potentially some other amino acid. Additional sequence modifications that "generally" alter the template protein sequence could include terminal modifications and/or the introduction of subunit linking polypeptide sequences to create single-chain structures. Note that many proteins expressed in E. coli are modified by addition of an N-terminal methionine residue, which is by often counted as residue "zero" of the polypeptide chain for structural purposes and so designated in Protein Data Bank (pdb) coordinate files. In any case, residues designated as sites of modification in Table 2 correspond to the sequence numbering provided in the designated pdb file containing the structural coordinates of the node template.

Specific biotinylation sites are sites for the introduction of Cys residues into the template sequence that will provide optimal geometry and, for Dn and tetrahedral nodes, symmetric placement of the biotinylation sites around the node dyad symmetry axes. The locations of these sites were determined by use of the computer graphical and computational methods defined above. As noted above in FIG. 21 there are generally two orthogonal orientations that streptavidin can take with respect to the major symmetry axes of complexes with Cn, Dn, or higher symmetry. For Cn nodes, these are enumerated as "H" and "V", where the y-axis or z-axis of streptavidin is parallel to the node Cn axis, respectively (FIG. 21b,c). Since streptavidin tetramer makes an asymmetric interaction with Cn node, there are potentially a large number of possible complementary interactions that are feasible for a Cn-node streptavidin-strut interaction. Table 1 generally shows one "H" interaction that analysis suggests provides the best steric and charge complimentarity between streptavidin and the node surface.

As noted above, nodes with Dn or higher symmetry offer the possibility of aligning the dyad symmetry axes of streptavidin with dyad symmetry axes of the node. These are enumerated as "H" and "V" along diad axes (x,y, or z) of a Dn or higher symmetry node (FIG. 21d,e). D2 nodes have three dyad axes, so there are a total of 6 orientations by which streptavidin can be attached to a D2 node. Although it is not physically possible to bind streptavidin in both "H" and "V" orientations simultaneously, there nevertheless arise a large number of combinations for node streptavidin complexes that are possible as outlined in Table 2 G,H,I,J. D3 nodes are special, since interactions made at one end of the dyad axis are different from the other (FIG. 15e, FIG. 17), so that there are a total of 4 possible streptavidin node interaction geometries, producing a total of 8 strut-node interaction patterns (Table 2 KLM). For D4 symmetric nodes (FIG. 15f, FIG. 18) there are two independent dyad axes, giving a total 8 different streptavidin substitution patterns (Table 2 NOP). For tetrahedral nodes, all the dyad axes are symmetrically equivalent, so that there are only 2 possible node:streptavidin orientations possible (Table 2Q).

Three-Fold (C3) Symmetric Planar Node:

FIGS. 24a and 24b respectively show a schematic view and space filling view of a node based on the previously described trimeric C3 symmetric protein 1thj, in covalent complex with 3 bound molecules of streptavidin. (In this an succeeding figures of such complexes, the biotins bound to streptavidin are shown in space filling representation in the schematic diagrams although atomic coordinates for linking atoms or amino acid side chains residues are not shown for simplicity.) Although there are several potential sites of interaction between the surface of 1thj and streptavidin that can be generated using the methods described above, the one shown corresponds to a node construct where a Cys148 to Ala modification and specific biotinylation sites have been introduced at sequence positions 70 (Asp70 to Cys) and 200 (Tyr200 to Cys) in the 1thj polypeptide sequence (Table 2A).

Table 2C also provides a node specification of for C3 trimeric planar node based on the 1j5s protein described above.

Single Chain Variants of Three-Fold (C3) Symmetric Planar Node:

FIG. 25 shows a stereoscopic view of a single chain variant of the 1thj trimer. The sequence of the single-chain trimer incorporates three 207-residue amino acid sequences derived from the original 1thj sequence that are interconnected by two seven residue linkers. Table 2B gives sequence specifications for the trimer variants with both symmetric and asymmetric binding sites for streptavidin as schematically illustrated in FIG. 4c,d,e.

Four-Fold (C4) Symmetric Planar Node:

FIGS. 24c and 24d respectively show a schematic view and space filling view of a node based on the previously described trimeric C4 symmetric protein 1vcg, in covalent complex with 4 bound molecules of streptavidin. Although there are several potential sites of interaction between the surface of 1vcg and streptavidin that can be generated using the methods described above, the illustration shown corresponds to a node construct where Cys14 and Cys236 modifications have been made and specific biotinylation sites have been introduced at sequence positions 44 (Ser44 to Cys) and 49 (Thr49 to Cys) in the 1vcg polypeptide sequence (Table 2E).

Three-Fold (C3) Symmetric Polyhedral Node:

FIG. 26 shows schematic and surface stereoscopic views of a C3 symmetric node, with 3 streptavidin tetramers bound at angles corresponding to an dodecahedron apex (FIG. 11a). The dodecahedral polyhedral node is based upon the structure of a 5'-deoxy-5'-methylthioadenosine phosphorylase homologue from *Sulfolobus tokodaii* (Kitago et al. 2003) protein as the template node, and generated by the methods described above (pdb code: 1v4n). Specific sequence specifications are given in Table 2D. Table 2D also gives a specification for a "bucky" or truncated icosahedral apex node (See FIG. 19.c), based on 1v4n as the node template.

Five-Fold (C5) Symmetric Polyhedral Node:

FIG. 27 shows schematic and surface stereoscopic views of a C5 symmetric node, with 5 streptavidin tetramers bound at angles corresponding to an icosahedron apex (FIG. 11a). The icosahedral polyhedral node is based upon the 1vdh protein (described above FIG. 10d) as the template node, and generated by the methods described above. Specific sequence specifications are given in Table 2F.

Streptavidin D2 Strut Coupler:

As noted above (FIG. 1), streptavidin itself is a tetramer with D2 symmetry and can function as a node in the context of some assemblies. Although not specifically derived from a thermophilic bacterium, streptavidin is unusual for its thermostability both in its unliganded and biotin-bound forms (Weber et. al. 1989, 1992, 1994). FIG. 28 schematically shows streptavidin tetramers that have been modified through site-specific mutagenesis to incorporate four dyad symmetry-related biotinylation sites (e.g. surface cysteine residues), allowing in situ functionalization with biotin to allow the attachment of additional streptavidin tetramers. FIGS. 28a and b respectively show schematic and surface representations where the x-axis of the central "node" streptavidin tetramer is oriented parallel to the z-axes of 2 bound streptavidin tetramers. FIGS. 28c and d respectively show schematic and surface representations where the z-axis of the central "node" streptavidin tetramer is oriented parallel to the z-axes of 2 bound streptavidin tetramers. The specifications for the streptavidin "nodes" modified for binding streptavidin tetramers along streptavidin dyad are given in Table 2G. This method of attaching streptavidin-linked binding or other functional protein domains provides an additional means for creating functionalized struts in nanostructures. Table 2G also provides a specification for a streptavidin "node" with streptavidins bound along the "node" x-axis, so blocking access to the streptavidin "node" biotin binding sites. Such constructs may be useful when it is desirable to protect the "node" biotin binding sites during an intermediate stage of an assembly process.

D2 Nodes:

FIGS. 29a,b show stereoscopic views of a tetrameric D2 node based on the 1ma1 node template in schematic and space filling representation respectively. There are 6 streptavidin tetramers bound to the node, two along each symmetrically independent dyad axis. Table 2H gives the specifications for variations in the 1m1a node based on different orientations of bound streptavidin tetramers (e.g. see FIG. 12,a,c) and combinations of biotinylation sites along each of the three independent node dyad axes. Variations in dyad axis site substitution patterns can produce nodes suitable for the formation of orthorhombic 3D lattices (e.g. the node shown in FIG. 29), 2D rectangular lattices, or linear strut extenders.

FIG. 30 shows illustrations in schematic and space filling representation of two examples of linear struts incorporating a D2 node based on 1ma1 and two streptavidin tetramers. In FIGS. 30a,b streptavidin tetramers are oriented with their z-axes parallel to one of the D2 node dyad axes. In FIGS. 30c,d streptavidin tetramers are oriented with their y-axes parallel to the same D2 node dyad axis. Since there are a total of three independent dyad axes, there are a total of six alternative linear strut complexes that can be formed with a D2 node and two streptavidin tetramers to form linear struts. The specifications for these nodes are included in Table 2H. Table 2I and 2J respectively provide additional specifications for D2 symmetric nodes based on the 1nto and 1rtw node templates.

D3 Nodes:

FIGS. 31a,b show stereoscopic views of a hexameric D3 node based on the 1hyb node template in schematic and space filling representation respectively. There are 6 streptavidin tetramers bound to the node, including 3 tetramers with their y-axes oriented parallel to the D3 node symmetry axis and 3 tetramers with their z-axes oriented parallel to the D3 node symmetry axis. Note that the 2 "poles" of the D3 dyad axes (FIG. 15e) are symmetrically non-equivalent, and that variations can be produced with for example, with 3 bound streptavidin tetramers bound at either pole in either of two orientations (FIG. 12a,c). Table 2L gives the specifications for variations in the 1hyb node based on different orientations of bound streptavidin tetramers (e.g. see FIG. 12,a,c) and combinations of biotinylation sites at poles of the dyad axis. Tables 2K and 2M respectively provide additional specifications for D3 symmetric nodes based on the 1b4b and 2prd node templates.

D4 Nodes:

FIGS. 32a,b show stereoscopic views of two octameric D4 node complexes based on the 2h2i node template in schematic representations. There are 4 streptavidin tetramers bound to each node, along the two symmetrically non-equivalent axes of the D4 node (FIG. 15f). The complex shown in FIG. 31a incorporates streptavidin tetramers with their z-axes oriented parallel to the D4 node symmetry axis, while the complex shown in FIG. 31b incorporates streptavidin tetramers with their y-axes oriented parallel to the D4 node symmetry axis. Table 2O gives the sequence specifications for variations the 2h2i node based on different orientations of bound streptavidin tetramers (e.g. see FIG. 12,a,c) and combinations of biotinylation sites along the symmetrically non-equivalent dyad axes. Tables 2N and 2P respectively provide additional sequence specifications for D4 symmetric nodes based on the 1o4v and 2iel node templates.

Tetrahedral (Cubic Lattice) Node:

FIGS. 33a,b show stereoscopic backbone and space-filling views of a dodecameric (T23) tetrahedral node based on the 1pvv node template in complex with 6 streptavidin complexes bound along the 3 symmetrically equivalent, mutually perpendicular dyad axes of the structure. Table 2Q gives the sequence specifications for the 2 possible binding orientations for streptavidin to the node along the dyad axis.

Examples of One-Dimensional, Two-Dimensional and Three Dimensional Assemblies Constructed with Streptavidin Struts and Nodes of Different Symmetry.

The following describes representative nanoassemblies that can be constructed using the node and strut components described above. Many more possibilities exist than are shown, although the structures outlined fall into several basic classifications.

One Dimensional Structures:

FIG. 34 shows schematic views of struts of different length consisting of combinations of streptavidin and nodes with D2 symmetry. Such constructs are useful in controlling the dimensions of assembled nanostructures. FIG. 34a shows an extended strut incorporating two streptavidin tetramers and a single D2 symmetric node (e.g see FIG. 30ab). FIG. 34b shows an extended strut incorporating three streptavidin tetramers and two D2 symmetric nodes. The central streptavidin has been modified (e.g. see FIG. 28) by the introduction of cysteine residues along one orthogonal dyad axis to allow the biotinylation of the strut after it is incorporated in a nanostructure (FIG. 34c).

2-Dimensional Radial Structures:

FIG. 35 schematically shows examples of radial structures as, for example, could be formed on self-assembling monolayers or anchored to discrete metal particles deposited on a silicon or other non-metallic substrate surface. FIG. 35a shows a C3 node which is linked through streptavidin struts to 3 single-chain C4 tetramers that have all been functionalized as described in FIG. 9. FIG. 35b shows a C7 node which is linked through streptavidin struts to 7 single-chain C3 trimers that are variations of the functionalized trimers described in FIG. 5. The structures can be also be functionalized through modifications introduced into the struts (e.g. see FIGS. 28 and 34). Two-dimensional lattices functionalized with specific binding molecules like immunoglobulin binding domains could find application in diagnostics, biological filters or other applications.

2-Dimensional Lattices:

FIG. 36 schematically shows examples of 2-dimensional lattices, as, for example, could be formed on self-assembling monolayers. FIG. 36a shows a hexagonal lattice incorporating C3 nodes linked through streptavidin struts. FIGS. 36b,c show square lattices incorporating C4 nodes and struts of different lengths to control the lattice dimensions. The struts in FIG. 36c incorporate a D2 strut extender as outlined in FIG. 30. The structures can be functionalized either through modifications introduced into the nodes (e.g FIGS. 5 and 9) or struts (e.g FIGS. 28 and 34). Two-dimensional lattices functionalized with specific binding molecules like immunoglobulin binding domains could find application in diagnostics, biological filters, or other applications.

2-Dimensional Polygon Structures:

FIG. 37 schematically shows examples of 2-dimensional polygonal structures, as, for example, could be formed on self-assembling monolayers. FIG. 37a shows a hexagon array incorporating single-chain C3 nodes linked through streptavidin struts. FIGS. 37b,c show square arrays incorporating single-chain C4 nodes and struts of different lengths to control the lattice dimensions. The struts in FIG. 37c incorporate a D2 strut extender as outlined in FIG. 30. The structures can be functionalized either through modifications introduced into the nodes (e.g see FIGS. 5 and 9) or struts (e.g. see FIGS. 28 and 34). Two-dimensional polygonal structures functionalized with specific binding molecules like immunoglobulin binding domains could find application in diagnostics, biological filters or other applications.

3-Dimensional Radial Structures:

Radial 3-dimensional structures can be produced by the attachment of struts incorporating streptavidin to the dyad axes of polyhedral nodes such as those shown in FIGS. 19 and 20. Struts or terminating nodes of struts can be functionalized either through modifications introduced into the nodes (e.g see FIGS. 5 and 9) or struts (e.g. see FIGS. 28 and 34). Radial structures functionalized with specific binding molecules like immunoglobulin binding domains could find application in diagnostics, biological filters or other applications.

3-Dimensional Polygon Structures:

Three-dimensional polygonal structures with defined geometry and dimensions can be generated through the combination of struts incorporating streptavidin and nodes with the symmetry and geometry corresponding to a polygonal apex node. Representative structures of regular polyhedra are shown in FIGS. 11a,b and FIG. 19c. Examples of apex node structures for regular dodecahedra and icosahedra are given in FIGS. 26 and 27 respectively. Sequence specifications for these nodes are given in Table 2D and 2F respectively. Table 2D also provides a specification for a "bucky" node. Given the great variety of known carbon-based "buckyball" geometries (Weber 1999), it is probable that a corresponding variety of protein-based nanostructures can be generated. Three-dimensional polygonal structures can be functionalized with specific binding molecules like immunoglobulin binding domains and could find application in diagnostics, biological filters or other applications. In addition, 3-dimensional polygonal structures, which are generally hollow inside, can be used to encapsulate or coat organic, inorganic, or biomaterials for imaging, diagnostic, drug delivery or other applications.

3-Dimensional Lattices:

Three-dimensional lattices can be built up from molecular nodes and struts using a number of different strategies, allowing precise control of geometrical and symmetry properties of the resulting lattice. FIG. 38a,b presents stereoscopic views, in schematic and space filling representation, of a 3D lattice node incorporating two variations of a D3 node derived from the node template 1hyb (FIG. 17cd and Table 2L). The two node variations have biotinylation sites that orient bound streptavidin tetramers at 90 degrees to each other (e.g see FIG. 12a,c) along their equivalent dyad axes. Consequently, when a streptavidin tetramer bridges two such nodes, they are rotated 90 degrees relative to each other. FIG. 40a schematically illustrates the 3-connected 3D lattice that can be formed incorporating such linked nodes (shown as two white dots in the schematic lattice illustration).

FIGS. 39a,b present stereoscopic views, in schematic and space filling representation, of a 3D lattice node incorporating two variations of a D4 node derived from the node template 2h2i (FIG. 18cd and Table 2O). The two node variations have biotinylation sites that orient bound streptavidin tetramers at 90 degrees to each other (e.g see FIG. 12a,c) along their equivalent dyad axes. Consequently, when a streptavidin tetramer bridges two such nodes, they are rotated 90 degrees relative to each other. FIG. 40b schematically illustrates the 4-connected 3D lattice that can be formed incorporating such linked nodes (shown as two white dots in the schematic lattice illustration).

FIGS. 40*a,b* present stereoscopic views, in backbone and space filling representation, of a 3D lattice node derived from the dodecahedral node template 1pvv (Table 2Q). FIG. 40*c* schematically illustrates the 6-connected 3D cubic lattice that can be formed by linking such nodes with streptavidin or extended struts. In FIG. 40*c*, the central white dot represents the location of a node.

The nodes and struts of 3-dimensional lattices can be functionalized with specific binding molecules like immunoglobulin binding domains and could find application in diagnostics, biological filters or other applications. In addition, there are many applications where the ability to immobilize magnetic centers, charge, chromophoric groups, or other inorganic, organic, or biological groups at high density and with controlled geometry can lead to useful applications such as batteries, capacitors, non-linear optical materials, data storage, and other devices.

Examples of Nanostructural Assemblies for Nanoscale Patterning and Resist Masks

In addition to applications where the protein components of nanoscale assemblies play a functional role, proteinaceous nanoscale assemblies can provide a means of high-resolution patterning of silicon, glass, metal, or other substrates, to allow production of microelectronic devices, devices incorporating zero-mode waveguides (Levene et. al, 2003) or microelectromechanical systems (MEMS) using conventional semiconductor fabrication (Widman et al., 2000) and/or MEMS fabrication technology (Judy, 2001). The proteinaceous nanoscale assembly can be used directly as a way of introducing a pattern on a substrate material. Alternatively, the proteinaceous nanoscale assembly is used as a way of masking a resist to transfer the pattern of the nanoscale assembly to an underlying substrate material. The approaches outlined below are applicable to both 2-dimensional and 3-dimensional assembly architectures.

FIG. 41 schematically illustrates a method of making a nanostructure pattern on a surface. FIG. 41*a* shows, for example, a substrate that has a semiconductor material surface with a single gold atom or cluster (Haztor-di Picciotto, 2007) or, alternatively, a patch of chemically reactive molecules (e.g., Liu & Amro, 2002) located on the surface to nucleate the formation of the nanostructural assembly. Upon addition (e.g. by contacting the surface with a solution containing the nanostructure node trimer) of a trimeric node construct functionalized with bound biotin groups and modified at one terminus with a reactive moiety (binding function) that enables coupling to the nucleation site on the substrate, the node can be specifically immobilized on the surface (FIG. 41*b*). The immobilized node can be further reacted with nanostructural components incorporating streptavidin or streptavidin-incorporating struts to form immobilized nanostructures such as schematically illustrated in FIG. 41*c*.

FIG. 42 schematically presents a method of making a repetitively patterned protein nanostructure on a metallic or non-metallic substrate following the steps exemplified in FIG. 41 using a simplified representation for the node and strut components. Here a substrate (FIG. 42*a*) is patterned with an array of nucleation sites. The nucleation sites can be arranged in a regular or periodic pattern, a quasiperiodic pattern (such as a Penrose tiling), or a non-periodic predetermined patter. Following the steps of addition of the node proteins to the surface (FIG. 42*b*) and addition of the strepta-vidin-incorporating struts, a patterned array (FIG. 42*c*) is produced. FIG. 42*d* shows a section of the patterned surface at the section line ϵ in FIG. 42*c*.

FIG. 43 presents a method of making a patterned nanostructure assembly with sub-100 nanometer features on a substrate surface. FIG. 43*a* reiterates the patterned surface of FIG. 42*c* and FIG. 43*b* shows the section of FIG. 43*a* at ϵ1. FIG. 43*c* shows the result of using any of several methods of semiconductor fabrication (e.g., using various forms of plasma and/or chemical vapor deposition technology, Widman, et al., 2000) to coat the substrate patterned with the protein nanostructure to produce the patterned surface shown in plan in FIG. 43*c* and in section in FIG. 42*d* (corresponding to the section line ϵ2 in FIG. 43*c*). For example, the patterned substrate can be coated with materials such as a metal (such as iron), a noble metal (such as gold, platinum, or silver), a glass (such as silicon dioxide), a ceramic, a semiconductor (such as silicon or germanium), a carbon allotrope (such as diamond or graphite), a polymer, and/or an organic polymer (such as tetrafluoroethylene). The resulting patterned surface (FIG. 43*c*) can be used as a template for soft lithography (Xia & Whitesides 1998, Rogers & Nuzzo 2005) or as a step in a multistep semiconductor fabrication process (Widman et al., 2000).

FIG. 44 presents a method of making a patterned structure with sub-100 nanometer features on a substrate surface using a proteinaceous nanostructure assembly as a patterned mask superimposed on a photoresist material. FIG. 44*a,b,c* shows a cross section of a protein nanostructure (FIG. 44*c*) superimposed on a layer of a resist material (FIG. 44*b*), that is in turn coated on a substrate to be patterned (FIG. 44*a*). Exposure of the assembly to, for example, irradiation of a suitable nature to modify the resist, produces the structure of FIG. 44*d*, where the superimposed nanostructure has prevented exposure of the resist to the incident radiation. FIG. 44*e* shows the structure where the exposed resist has been dissolved away, for example using chemical means. FIG. 44*f* shows the structure where the exposed substrate surfaces have been etched producing nanoscale features that are complementary to the structural features of the proteinaceous nanoscale assembly used to pattern the resist. FIG. 44*g* shows the structure after the proteinaceous nanoscale assembly and non-reacted resist have been removed, for example by using chemical means. The resulting patterned surface (FIG. 44*g*) can be used as a template for soft lithography (Xia & Whitesides 1998, Rogers & Nuzzo 2005) or as a step in a multistep semiconductor fabrication process (Widman et al., 2000).

Additional example of finite or periodic 2-dimensional proteinaceous nanostructural assemblies that can serve as patterning templates on surfaces are described above and schematically illustrated in FIGS. 35, 36, and 37.

3-dimensional, as well as 2-dimensional, proteinaceous nanostructure assemblies can be used as nanoscale patterning elements. The structures can be coated as outlined in the process of FIG. 43 or, alternatively, serve as a 3-dimensional resist to form a negative of the proteinaceous nanostructural assembly. For example, FIG. 45*ab* schematically shows a cubic lattice structure composed of six-connected cubic nodes (for example, see FIG. 33) and streptavidin struts (FIG. 45*b*) assembled on a solid substrate (FIG. 45*a*). FIG. 45*cd* shows the structure (FIG. 45*c*) embedded in a matrix (FIG. 45*d*) that can polymerize and/or be transformed by chemical reaction, heat, and/or radiation to form a chemically and/or thermally stable matrix material. The matrix (FIG. 45*d*) can interpenetrate the structure (FIG. 45*c*). For example, the matrix (FIG. 45*d*) can itself have the form of a cubic lattice offset from the cubic lattice of the proteinaceous nanostructure assembly. The cubic lattice of the structure (FIG. 45c) and the cubic lattice of the matrix (FIG. 45d) can interpenetrate each other. FIG. 45e shows the structure after chemical, heat, and/or radiation treatment is applied to ablate the proteinaceous nanoscale structure, leaving a "negative" three-dimensional cubic channel structure in the matrix material. That is, the matrix material can occupy the space not occupied by the proteinaceous nanostructure assembly. The matrix material (first matrix material) can include a metal (such as iron), a noble metal (such as gold, platinum, or silver), a glass (such as silicon dioxide), a ceramic, a semiconductor (such as silicon or germanium), a polymer, and/or an organic polymer (such as tetrafluoroethylene). For example, such "negative" structures incorporating nanoscale channels have potential utility as components in nanofluidics systems. FIG. 45f shows the structure of FIG. 45e after further chemical treatment is applied to deposit a metallic or other second matrix material in the negative cavity originally occupied by the proteinaceous nanostructure assembly. The second matrix material can include a metal (such as iron), a noble metal (such as gold, platinum, or silver), a glass (such as silicon dioxide), a ceramic, a semiconductor (such as silicon or germanium), a polymer, and/or an organic polymer (such as tetrafluoroethylene). FIG. 45g shows the structure after chemical, heat, or radiation treatment is applied to remove the first matrix material, leaving a nanoscale structure composed of metal or other second matrix material that is a replica of, that is, has the same or similar form as the original proteinaceous nanostructure assembly. For example, three-dimensional nanoscale assemblies made of metal or semiconductor materials have potential utility as components in semiconductor or MEMS applications.

Additional examples of finite or periodic 3-dimensional proteinaceous nanostructural assemblies are described above and some are schematically illustrated in FIG. 40. Such 3-dimensional structures with nano-dimensional features can have utility as optical or physical waveguides or filters, nanofluidic devices, or in other semiconductor or MEMS applications.

TERMS AND DEFINITIONS

A subunit can be a tertiary polypeptide structure. The amino acid residues in a subunit can be covalently linked through peptide bonds in a polypeptide sequence. A subunit can be formed of one or more polypeptide chains. The polypeptide subunit can, under certain conditions, e.g., certain pH conditions, aggregate with one or more other polypeptide subunits to form a multisubunit node polypeptide that is a quaternary polypeptide structure. For example, in a native streptavidin tetramer, 4 identical subunits, each formed of an identical but separate polypeptide chain, aggregate. A multimeric protein having a symmetry can be formed of several essentially identical subunits that are repeated with an orientation with respect to each other to achieve the symmetry. For example, a Cn symmetric multimeric protein can be formed of n subunits placed about a common axis. For example, a C3 symmetric multimeric protein can be formed of 3 subunits placed about a common axis. For example, a Dn symmetric multimeric protein can be formed of 2n subunits, where each subunit is related to another subunit to form a pair, and each pair of subunits is placed about a common axis. For example, a D4 symmetric multimeric protein can be formed of 8 subunits, where each of 4 pairs of subunits are placed about a common axis. For example, a multimeric protein having the symmetry of a Platonic or Archimedean solid can be formed of a number of subunits equal to the number of edges in each polygonal face of the solid, summed over the polygonal faces. For example, a multimeric protein with tetrahedral symmetry can be formed of a number of subunits equal to the number of edges in a face, 3, times the number of faces, 4, that is, 12 subunits. For example, a multimeric protein with dodecahedral symmetry can be formed of a number of subunits equal to the number of edges in a pentagonal face, 5, times the number of faces, 12, to yield a total of 60 subunits.

Polypeptide subunits (subunits) within the quaternary polypeptide structure can be held to each other by noncovalent bonds (e.g., ionic bonds, van der Waals bonds, and/or hydrophobic bonds) and/or by covalent bonds (e.g., disulfide bridges and/or peptide bonds). Thus, each subunit may be formed of one or more polypeptide chains that are not covalently bound to the polypeptide chains of any other subunit of a quaternary polypeptide structure, each subunit may be formed of a polypeptide chain that is covalently bound to a polypeptide chain of at least one other subunit (e.g., the quaternary polypeptide structure can formed of a number of polypeptide chains less than the number of subunits, for example, the quaternary polypeptide structure can be formed of a single polypeptide chain), or some subunits may be formed of a polypeptide chain not covalently bound to a polypeptide chain of another subunit whereas other subunits are formed of a polypeptide chain that is covalently bound to a polypeptide chain of at least one other subunit.

For example, the amino acid residues of a polypeptide subunit can be in a single polypeptide sequence.

Multimerization can refer to the process in which individual polypeptide subunits aggregate to form a multisubunit node polypeptide. The structure formed by the aggregated subunits can be termed a multimer. Such a multimer can be referred to as having quaternary structure. Three individual polypeptide subunits, each formed of a polypeptide chain that is not covalently linked to another subunit, aggregating under the influence of non-covalent bonds to form a trimer is an example of multimerization. Alternatively, three individual polypeptide subunits can be formed of a polypeptide sequence that is covalently linked to the polypeptide sequence of another subunit, so that the three polypeptide subunits are formed from a single polypeptide chain. Even though the polypeptide subunits are covalently linked through the polypeptide chain, each individual polypeptide subunit can be folded into a separate tertiary structure without the individual polypeptide subunits being assembled into a quaternary trimer. When these polypeptide subunits undergo multimerization, the tertiary structures of the individual polypeptide subunits can come into close proximity, for example, under the influence of non-covalent bonds, to form a quaternary trimer in which a number of amino acid residues of each polypeptide subunit are in close proximity to a number of the amino acid residues of the other polypeptide subunits.

A rotational symmetry axis of an object can be an axis about which a less than full rotation of the object can result in a matching superposition of the object upon itself. An ordering of subunits about the rotational symmetry axis can refer to the subunits corresponding to the N-fold symmetry in a successive clockwise or counter-clockwise sequence when sighting along the rotational symmetry axis.

Features, such as polypeptide subunits of a multisubunit node polypeptide, can be related by a symmetry. Unless otherwise stated, reference to a symmetrical relation herein is to be understood to encompass an essential symmetry relation. That is, features that are essentially related by a symmetry might not be strictly identical. For example, two of the polypeptide subunits may differ from each other in that one, two, or a short oligomeric subsequence of the polypeptide sequences from which they are formed are different. However, this minor difference in the polypeptide sequence does not affect the overall form of the subunit. For example, if one subunit of a trimer has one amino acid in the polypeptide sequence from which it is formed that is different than the corresponding amino acid in the polypeptide sequences of the other two subunits, but the folding of all the subunits is similar, the trimer still can be considered to have three-fold rotational symmetry.

A derivative of an initial molecule includes molecules resulting from the replacement of an atom, group of atoms, bond, or bonds of the initial molecule by a different atom, group of atoms, bond, or bonds and molecules resulting from the addition or deletion of an atom or a group of atoms to the initial molecule, or from the rearrangement of an atom, group of atoms, bond, or bonds of the initial molecule, for example, as in an isomer or stereoisomer. For example, 2-iminobiotin is a derivative of biotin. The structure of 2-iminobiotin is the same as that of biotin, except that the oxygen double bonded to the imidazolidine is replaced with a single bonded primary amine and the single bond between the 2-carbon and the 3-nitrogen of the imidazolidine ring is replaced by a double bond. Examples of nucleobases include cytosine, guanine, adenine, thymine, uracil, 5-methylcytosine, ribothymidine, hypoxanthine, xanthine, 7-methylguanine, and 5,6-dihydrouracil. Examples of nucleobase derivatives include isoguanine, isocytosine, 2-amino-6-(2-thienyl)purine, pyrrole-2-carbaldehyde, and acycloguanosine (Aciclovir). Examples of nucleosides include adenosine, guanosine, 5'-methyluridine, uridine, cytidine, deoxynucleosides, deoxyadenosine, deoxyguanosine, thymidine, deoxyuridine, deoxycytidine, inosine, xanthinosine, 7-methylguanosine, pseudouridine, dihydrouridine, 5-methylcytidine, dideoxynucleosides. Examples of nucleoside derivatives include azidothymidine (Zidovudine), didanosine, vidarabine, cytosine arabinoside (cytarabine), emtricitabine (Emtriva), lamivudine, dideoxycytidine (zalcitabine), abacavir (Ziagen), stavudine (Zerit), idoxuridine, trifluridine (Viroptic). Examples of nucleotides include adenosine monophosphate, adenosine diphosphate, adenosine triphospate, guanosine mono-, di-, and triphosphate, uridine mono-, di-, and triphosphate, cytidine mono-, di-, and triphosphate, thymidine mono-, di-, and triphosphate, cyclic guanosine monophosphate, cyclic adenosine monophospate Examples of nucleotide derivatives include tenofovir disoproxil fumarate (Viread), adefovir dipivoxil (Preveon), and adenosine triphosphate derivatives, such as adenosine 5'-(gamma-thiotriphosphate). Similarly, if a residue of an initial polypeptide is replaced with a different residue, the resultant polypeptide is a derivative of the initial polypeptide. If a group of atoms is added to an initial polypeptide, for example, if a linker molecule having a thiol reactive group and a biotin covalently linked to each other is reacted with a cysteine of the initial polypeptide, so that the biotin becomes bonded through a disulfide to the cysteine, the resultant polypeptide is a derivative of the initial polypeptide. For example, a streptavidin or avidin derivative can have an amino acid residue in the amino acid sequence of streptavidin or avidin replaced with a different amino acid residue. For example, a derivative of avidin is deglycosylated avidin (NeutrAvidin). An analog of a molecule is included within the term derivative.

In the context of a streptavidin strut, the term streptavidin derivative strut, is to be understood as including struts formed of a streptavidin derivative, struts that include streptavidin (wherein the streptavidin may or may not be covalently bonded to other portions of the strut), and struts that include a streptavidin derivative (wherein the streptavidin derivative may or may not be covalently bonded to other portions of the strut).

When a chemical or biochemical group is mentioned, derivatives and analogs of that chemical or biochemical group are also implied. For example, if biotin is recited, 2-iminobiotin is also implied.

A polypeptide extension of a polypeptide subunit can be a polypeptide sequence that is linked to an amino or carboxy terminus of a polypeptide sequence comprising the polypeptide subunit. The polypeptide extension may or may not be folded into the tertiary structure of the polypeptide subunit.

A binding function of a polypeptide sequence (such as a polypeptide extension) can be a subsequence of amino acids to which an atom, group of atoms, or molecule, such as a portion of a protein or a metallic surface, can form a covalent or non-covalent bond.

A polypeptide subsequence can be a continuous set of covalently bonded amino acid residues within a polypeptide sequence. The polypeptide subsequence may comprise all, less than all, or only one of the amino acid residues in the polypeptide sequence.

A nanostructure strut can bind covalently or non-covalently to a specific binding site of a nanostructure node multimeric protein.

A protein, such as a multimeric protein, can include a ligand binding pocket. Such a pocket can be a depression in or inward folding of the surface of the protein. The ligand binding pocket can include a specific binding site. For example, a nanostructure node multimeric protein can include a ligand binding pocket. A nanostructure strut can bind to the ligand binding pocket. For example, the nanostructure strut can include a region of an immunoglobulin that binds to the ligand binding pocket of the nanostructure node multimeric protein. For example, the nanostructure strut can include biotin, iminobiotin, a nucleotide, an enzyme inhibitor, an enzyme activator, an enzyme substrate, an enzyme cofactor, a coenzyme, and/or derivatives that bind to the ligand binding pocket of the nanostructure node multimeric protein.

A bridge molecule can serve to attach two other molecules, such as proteins. For example, a bridge molecule can include a biotin group covalently bound to an adenosine triphosphate (ATP) group. The biotin group can bind to a biotin binding site, such as present on streptavidin, and the adenosine triphosphate (ATP) group can bind to an ATP binding site, such as present on the MJ0577 protein.

A bindable polypeptide subunit, for example, of a multimeric protein, can be capable of binding, directly or through an intermediary molecule, such as a bridge molecule, to another molecule, such as a protein. For example, a bindable subunit can include a specific binding site to which a nanostructure strut, e.g., a streptavidin-containing nanostructure strut, can bind.

A non-bindable polypeptide subunit, for example, of a multimeric protein, can be incapable of binding to another molecule, such as a protein. For example, a non-bindable subunit may lack a specific binding site to which a nanostructure strut, e.g., a streptavidin-containing nanostructure strut, can bind.

Synthesizing a protein can refer to synthesizing a polypeptide sequence with chemical methods, and can refer to synthesizing a polypeptide sequence with molecular biological methods, such as, for example, inserting a gene into a host organism (for example, $E.\ coli$) to induce the host organism to express the protein.

EXAMPLES

Example 1

Expression of 3-Fold Symmetric Node

Synthetic genes and expression vectors for a 3-fold symmetric (C3) protein to be used as a node were constructed. For the synthetic gene and expression vector sequences shown, the vector sequence is in lower case with the promoter underlined and the ribosome binding site in italics, and the open reading frame is in upper case with the initiating Methionine and Stop codons in bold. Amino acid sequences are provided using the standard one letter representation for each amino acid.

Example 1A

EXP14Q3193C2

*E. coli* cells BL21 Star™ (DE3) pLysS with expression vector EXP14Q3193C2 (represented in FIG. 46A) were cultured in 50 mL Terrific Broth supplemented with 0.1 mg/mL ampicillin and 0.034 mg/mL chloramphenicol. The culture was grown overnight at 37° C. to an $OD_{600}$ of 5.53. 0.9 mL was used to inoculate a second culture of 50 mL Terrific Broth supplemented with 0.1 mg/mL ampicillin and 0.034 mg/mL chloramphenicol. The culture was grown overnight at 37° C. to an $OD_{600}$ of 0.807, induced with 0.4 mM IPTG and supplemented with 0.5 mM $ZnSO_4$, then grown for 4 hours at 25° C. to an $OD_{600}$ of 2.69. 0.6 g of cells were collected by low speed centrifugation.

In a second batch, *E. coli* cells BL21 Star™ (DE3) pLysS with expression vector EXP14Q3193C2 were cultured in 50 mL Terrific Broth supplemented with 0.1 mg/mL ampicillin and 0.034 mg/mL chloramphenicol. The culture was grown overnight at 37° C. to an $OD_{600}$ of 5.53. 0.9 mL was used to inoculate a second culture of 50 mL Terrific Broth supplemented with 0.1 mg/mL ampicillin and 0.034 mg/mL chloramphenicol. The culture was grown overnight at 37° C. to an $OD_{600}$ of 0.807, induced with 0.4 mM IPTG and supplemented with 0.5 mM $ZnSO_4$, then grown for 20 hours at 25° C. to an $OD_{600}$ of 20.97. 2.0 g of cells were collected by low speed centrifugation.

In a third batch *E. coli* cells BL21 Star™ (DE3) pLysS with expression vector EXP14Q3193C2 were cultured in 50 mL Luria-Bertani broth supplemented with 0.1 mg/mL ampicillin and 0.034 mg/mL chloramphenicol. The culture was grown overnight at 37° C. to an $OD_{600}$ of 5.53. 0.9 mL was used to inoculate a second culture of 50 mL Luria-Bertani Broth supplemented with 0.1 mg/mL ampicillin and 0.034 mg/mL chloramphenicol. The culture was grown overnight at 37° C. to an $OD_{600}$ of 0.753, induced with 0.4 mM IPTG and supplemented with 0.5 mM $ZnSO_4$, then grown for 4 hours at 25° C. to an $OD_{600}$ of 3.23. 0.8 g of cells were collected by low speed centrifugation.

In a fourth batch *E. coli* cells BL21 Star™ (DE3) pLysS with expression vector EXP14Q3193C2 were cultured in 50 mL Luria-Bertani broth supplemented with 0.1 mg/mL ampicillin and 0.034 mg/mL chloramphenicol. The culture was grown overnight at 37° C. to an $OD_{600}$ of 5.53. 0.9 mL was used to inoculate a second culture of 50 mL Luria-Bertani broth supplemented with 0.1 mg/mL ampicillin and 0.034 mg/mL chloramphenicol. The culture was grown overnight at 37° C. to an $OD_{600}$ of 0.753, induced with 0.4 mM IPTG and supplemented with 0.5 mM $ZnSO_4$, then grown for 20 hours at 25° C. to an $OD_{600}$ of 23.64. 2.4 g of cells were collected by low speed centrifugation.

The nodes formed with the expression vector EXP14Q3193C2 were based on gamma-carbonic anhydrase from *Methanosarcina thermophila*. The C3 symmetric, 3-subunit, synthesized protein was composed of three identical polypeptide chains. The synthesized protein differs from the native protein. Residues Asp70 and Tyr200 were changed to Cys. Cys 148 was changed to Ala (the amino acid residue numbering follows that assigned to the native polypeptide). A His tag that can be cleaved by the Factor Xa protease was added to the C-terminus. Thus, the assembled 3 subunit protein, formed of 3 polypeptide chains, includes a total of 6 surface cysteine residues available for functionalization (for example, with a biotin group) and complexation with 3 streptavidin tetramers.

The gene nucleotide sequence for the synthetic sequence EXP14Q3193C2 incorporated into the EXP14Q3193C2 expression vector was:

[SEQ ID NO 22]
```
gaaggagatatacatATGCAAGAGATTACCGTTGACGAATTTAGCAAT
ATCCGTGAAAACCCGGTTACCCCGTGGAACCCGGAACCGAGCGCCCCC
GGTTATTGACCCGACCGCCTATATTGACCCGGAAGCAAGCGTGATTGG
TGAAGTTACGATTGGCGCAAATGTTATGGTTAGCCCGATGGCGAGCAT
TCGCAGCGATGAAGGTATGCCGATTTTTGTGGGTTGTCGTAGCAATGT
TCAAGATGGTGTTGTCCTGCACGCACTGGAAACGATTAATGAAGAAGG
TGAACCGATTGAAGATAATATTGTTGAAGTTGATGGCAAAGAATACGC
AGTTTATATTGGTAATAATGTTAGCCTGGCCCATCAGAGCCAAGTCCA
CGGTCCGGCCGCAGGCGATGATACGTTTATTGGCATGCAAGCGTTCGT
TTTTAAAAGCAAAGTGGGTAATAATGCAGTTCTGGAACCGCGTAGCGC
AGCGATTGGTGTCACGATCCCGGATGGTCGCTATATCCCGGCCGGTAT
GGTCGTTACCAGCCAAGCAGAAGCAGACAAACTGCCGGAAGTCACCGA
TGATTACGCCTATAGCCATACCAATGAAGCCGTTGTTTGTGTGAATGT
TCATCTGGCGGAAGGTTACAAAGAAACGATTGAAGGCCGTCATCACCA
CCACCCACCACTAAgacccagctttcttgtacaaagtggtcccc.
```

The corresponding amino acid sequence of the one polypeptide chain of the synthetic protein produced by the EXP14Q3193C2 expression vector was:

[SEQ ID NO 25]
```
MQEITVDEFSNIRENPVTPWNPEPSAPVIDPTAYIDPEASVIGEVTIG
ANVMVSPMASIRSDEGMPIFVGCRSNVQDGVVLHALETINEEGEPIED
NIVEVDGKEYAVYIGNNVSLAHQSQVHGPAAVGDDTFIGMQAFVFKSK
VGNNAVLEPRSAAIGVTIPDGRYIPAGMVVTSQAEADKLPEVTDDYAY
SHTNEAVVCVNVHLAEGYKETIEGRHHHHHH
```

Example 1B

EXP14Q3193C3

*E. coli* cells BL21 Star™ (DE3) with expression vector EXP14Q3193C3 (represented in FIG. 46B) were cultured in 50 mL Luria-Bertani broth supplemented with 0.1 mg/mL ampicillin and 0.034 mg/mL chloramphenicol. The culture was grown overnight at 37° C. to an $OD_{600}$ of 6.83. 0.73 mL was used to inoculate a second culture of 50 mL Luria-Bertani broth supplemented with 0.1 mg/mL ampicillin and 0.034 mg/mL chloramphenicol. The culture was grown overnight at 37° C. to an $OD_{600}$ of 0.949, induced with 0.4 mM IPTG and supplemented with 0.5 mM $ZnSO_4$, then grown for 4 hours at 25° C. to an $OD_{600}$ of 2.78. 0.6 g of cells were collected by low speed centrifugation.

In a second batch, E. coli cells BL21 Star™ (DE3) with expression vector EXP14Q3193C3 were cultured in 50 mL Luria-Bertani broth supplemented with 0.1 mg/mL ampicillin and 0.034 mg/mL chloramphenicol. The culture was grown overnight at 37° C. to an $OD_{600}$ of 6.83. 0.73 mL was used to inoculate a second culture of 50 mL Luria-Bertani broth supplemented with 0.1 mg/mL ampicillin and 0.034 mg/mL chloramphenicol. The culture was grown overnight at 37° C. to an $OD_{600}$ of 0.949, induced with 0.4 mM IPTG and supplemented with 0.5 mM $ZnSO_4$, then grown for 20 hours at 25° C. to an $OD_{600}$ of 4.49. 0.8 g of cells were collected by low speed centrifugation.

In a third batch E. coli cells BL21 Star™ (DE3) with expression vector EXP14Q3193C3 were cultured in 50 mL Terrific broth supplemented with 0.1 mg/mL ampicillin and 0.034 mg/mL chloramphenicol. The culture was grown overnight at 37° C. to an $OD_{600}$ of 6.83. 0.73 mL was used to inoculate a second culture of 50 mL Terrific broth supplemented with 0.1 mg/mL ampicillin and 0.034 mg/mL chloramphenicol. The culture was grown overnight at 37° C. to an $OD_{600}$ of 0.796, induced with 0.4 mM IPTG and supplemented with 0.5 mM $ZnSO_4$, then grown for 4 hours at 25° C. to an $OD_{600}$ of 3.94. 0.7 g of cells were collected by low speed centrifugation.

In a fourth batch E. coli cells BL21 Star™ (DE3) with expression vector EXP14Q3193C3 were cultured in 50 mL Terrific broth supplemented with 0.1 mg/mL ampicillin and 0.034 mg/mL chloramphenicol. The culture was grown overnight at 37° C. to an $OD_{600}$ of 6.83. 0.73 mL was used to inoculate a second culture of 50 mL Terrific broth supplemented with 0.1 mg/mL ampicillin and 0.034 mg/mL chloramphenicol. The culture was grown overnight at 37° C. to an $OD_{600}$ of 0.89, induced with 0.4 mM IPTG and supplemented with 0.5 mM $ZnSO_4$, then grown for 20 hours at 25° C. to an $OD_{600}$ of 17.52. 1.9 g of cells were collected by low speed centrifugation.

In a fifth batch E. coli cells BL21 Star™ (DE3) pLysS with expression vector EXP14Q3193C3 were cultured in 50 mL Luria-Bertani broth supplemented with 0.1 mg/mL ampicillin and 0.034 mg/mL chloramphenicol. The culture was grown overnight at 37° C. to an $OD_{600}$ of 5.63. 0.89 mL was used to inoculate a second culture of 50 mL Luria-Bertani broth supplemented with 0.1 mg/mL ampicillin and 0.034 mg/mL chloramphenicol. The culture was grown overnight at 37° C. to an $OD_{600}$ of 0.905, induced with 0.4 mM IPTG and supplemented with 0.5 mM $ZnSO_4$, then grown for 4 hours at 25° C. to an $OD_{600}$ of 2.92. 0.6 g of cells were collected by low speed centrifugation.

In a sixth batch E. coli cells BL21 Star™ (DE3) pLysS with expression vector EXP14Q3193C3 were cultured in 50 mL Luria-Bertani broth supplemented with 0.1 mg/mL ampicillin and 0.034 mg/mL chloramphenicol. The culture was grown overnight at 37° C. to an $OD_{600}$ of 5.63. 0.89 mL was used to inoculate a second culture of 50 mL Luria-Bertani broth supplemented with 0.1 mg/mL ampicillin and 0.034 mg/mL chloramphenicol. The culture was grown overnight at 37° C. to an $OD_{600}$ of 0.905, induced with 0.4 mM IPTG and supplemented with 0.5 mM $ZnSO_4$, then grown for 20 hours at 25° C. to an $OD_{600}$ of 3.62. 0.8 g of cells were collected by low speed centrifugation.

In a seventh batch E. coli cells BL21 Star™ (DE3) pLysS with expression vector EXP14Q3193C3 were cultured in 50 mL Terrific broth supplemented with 0.1 mg/mL ampicillin and 0.034 mg/mL chloramphenicol. The culture was grown overnight at 37° C. to an $OD_{600}$ of 5.63. 0.89 mL was used to inoculate a second culture of 50 mL Terrific broth supplemented with 0.1 mg/mL ampicillin and 0.034 mg/mL chloramphenicol. The culture was grown overnight at 37° C. to an $OD_{600}$ of 0.796, induced with 0.4 mM IPTG and supplemented with 0.5 mM $ZnSO_4$, then grown for 4 hours at 25° C. to an $OD_{600}$ of 3.87. 1.3 g of cells were collected by low speed centrifugation.

In an eighth batch E. coli cells BL21 Star™ (DE3) pLysS with expression vector EXP14Q3193C3 were cultured in 50 mL Terrific broth supplemented with 0.1 mg/mL ampicillin and 0.034 mg/mL chloramphenicol. The culture was grown overnight at 37° C. to an $OD_{600}$ of 5.63. 0.89 mL was used to inoculate a second culture of 50 mL Terrific broth supplemented with 0.1 mg/mL ampicillin and 0.034 mg/mL chloramphenicol. The culture was grown overnight at 37° C. to an $OD_{600}$ of 0.796, induced with 0.4 mM IPTG and supplemented with 0.5 mM $ZnSO_4$, then grown for 20 hours at 25° C. to an $OD_{600}$ of 18.22. 1.9 g of cells were collected by low speed centrifugation.

In a ninth batch E. coli cells BL21 Star™ (DE3) pLysS with expression vector EXP14Q3193C3 were cultured in 375 mL Terrific broth supplemented with 0.1 mg/mL ampicillin and 0.034 mg/mL chloramphenicol. The culture was grown overnight at 37° C. to an $OD_{600}$ of 4.276. The culture was used to inoculate a second culture of 16 L Terrific broth supplemented with 0.1 mg/mL ampicillin and 0.034 mg/mL chloramphenicol. The culture was grown overnight at 37° C. with 30% dissolved oxygen and 400-550 rpm to an $OD_{600}$ of 1.053, induced with 0.4 mM IPTG and supplemented with 0.5 mM $ZnSO_4$, then grown for 19.75 hours at 25° C. to an $OD_{600}$ of 7.34. 182.5 g of cells were collected by low speed centrifugation.

The 3-fold node protein was isolated from the collected E. coli cells with expression vector EXP14Q3193C3 as follows. 10 grams of E. coli cells with EXP14Q3193C3 were suspended in 20 mL 50 mM $KPO_4$ buffer pH 6.8, 30 mg lysozyme, 1 mg DNase I, and one pellet EDTA-free protease inhibitors (Roche). The suspension was held at 4° C. and stirred for 1 hour, then sonicated in 3 sets of 30 1-second pulses. The suspension was centrifuged at 12500×g for 20 min. The soluble portion was subjected to column chromatography on Q-Sepharose equilibrated with 50 mM $KPO_4$ buffer pH 6.8, 0.001 mM $ZnSO_4$. Node protein was eluted by a linear gradient between 50 mM $KPO_4$ buffer pH 6.8, 0.001 mM $ZnSO_4$ and 50 mM $KPO_4$ buffer pH 6.8, 0.001 mM $ZnSO_4$, 1 M NaCl. Node protein fractions were identified by PAGE SDS analyses, then pooled and loaded onto a Phenyl-Sepharose chromatography column equilibrated with 50 mM $KPO_4$ buffer pH 6.8, 0.001 mM $ZnSO_4$, 1 M NaCl. Node protein was eluted from the column by a linear gradient between 50 mM $KPO_4$ buffer pH 6.8, 0.001 mM $ZnSO_4$, 1 M NaCl and 50 mM $KPO_4$ buffer pH 6.8, 0.001 mM $ZnSO_4$. Node protein fractions identified by PAGE SDS analyses were combined and dialyzed against 2 changes of 25 mM $NaPO_4$ buffer pH 8.0 with each change corresponding to at least 10× node protein volume. Dialyzed node protein was mixed with 3 mL Ni agarose resin equilibrated with 25 mM $NaPO_4$ buffer pH 8.0, then reacted for 18 hours with rocking at 4° C. The resin was washed with twice with 15 mL 25 mM NaPO$_4$ buffer pH 8.0, then the node protein was eluted with 25 mM NaPO$_4$ buffer pH 8.0, 250 mM imidazole.

A second, alternative isolation procedure was carried out in a similar manner, except that the Ni agarose resin was used before the Q-sepharose and phenyl-Sepharose chromatographic steps. A third, alternative isolation procedure was carried out in a similar manner, except that the E. coli cells were disrupted by addition of nonionic detergent (B-PER ThermoScientific) instead of by addition of lysozyme followed by stirring and sonication.

The nodes formed with the expression vector EXP14Q3193C3 were based on gamma-carbonic anhydrase from Methanosarcina thermophila. The C3 symmetric, 3-subunit, synthesized protein was composed of a single polypeptide chain. That is, whereas the native protein has a quaternary structure formed from 3 polypeptide chains, in the protein produced from the expression vector EXP14Q3193C3, the 3 polypeptide chains are fused together into a single polypeptide chain that folds into a structure having 3 subunits. The 3 polypeptide chains were fused together with two identical linkers, each having the sequence GGSGGG (Gly-Gly-Ser-Gly-Gly-Gly). The linker extended from the natural C-terminus (residue 212) of a subsequence corresponding to a polypeptide chain in the native protein and forming a subunit to residue 6 of the subsequence in a polypeptide chain forming the adjacent subunit (the amino acid residue numbering follows that assigned to the native polypeptide). Within each polypeptide subsequence corresponding to a polypeptide chain in the native protein, the following substitutions were made: Residues Asp70 and Tyr200 were changed to Cys; and Cys148 was changed to Ala. A His tag that can be cleaved by the Factor Xa protease was added to the C-terminus of the single polypeptide chain. Thus, the assembled 3 subunit protein, formed of a single polypeptide chain, includes a total of 6 surface cysteine residues available for functionalization (for example, with a biotin group) and complexation with 3 streptavidin tetramers.

The gene nucleotide sequence of sequence EXP14Q3193C3 incorporated into the EXP14Q3193C3 expression vector was:

[SEQ ID NO: 23]
ggggacaagtagtacaaaaaagcaggcaccgaaggagatatacatATG
GATGAATTTAGCAATATCCGCGAAAATCCGGTGACCCCGTGGAATCCG
GAACCGAGCGCCCCCGGTTATTGATCCGACGGCATACATCGACCCGGA
AGCCAGCGTGATTGGTGAAGTTACCATCGGCGCCAATGTTATGGTCAG
CCCGATGGCGAGCATCCGCAGCGATGAAGGCATGCCGATCTTTGTGGG
CTGTCGTAGCAATGTGCAGGATGGCGTTGTTCTGCACGCGCTGGAAAC
CATTAATGAAGAAGGCGAACCGATTGAAGACAATATTGTTGAAGTGGA
CGGTAAGGAATATGCAGTGTACATCGGTAACAACGTCAGCCTGGCCCA
TCAGAGCCAAGTCCATGGTCCGGCCGCCGTGGGCGATGATACCATTGG
CATGCAAGCGTTCGTGTTTAAAAGCAAAGTTGGCAATAATGCAGTTCT
GGAACCGCGCAGCGCGGCGATCGGCGTGACCATTCCGGATGGTCGTTA
CATCCCGGCCGGCATGGTGGTCACCAGCCAAGCGGAGGCCGATAAACT
GCCGGAAGTCACCGATGACTATGCCTATAGCCACACCAATGAGGCCGT
CGTGTGCGTGAACGTTCATCTGGCCGAAGGTTATAAAGAAACGGGTGG
TAGCGGCGGCGGCGATGAATTTAGCAATATCCGCGAAAATCCGGTGAC CCCGTGGAATCCGGAGCCGAGCGCACCGGTTARRGATCCGACCGCATA
TATTGATCCGGAGGCCAGCGTTATCGGCGAAGTTACGATCGCGAATGT
TATGGTGAGCCCGATGGCGAGCATTCGCAGCGATGAGGGTATGCCGAT
TTTTGTGGGCTGCCGTAGCAATGTGCAAGATGGTGTGGTCCTGCACGC
ACTGGAGACGATTAACGAGGAAGGTGAACCGATCGAGGACAACATTGT
CGAAGTGGACGGTAAGGAGTATGCGGTGTATATCGGCAACAACGTTAG
CCTGGCCCACCAGAGCCAGGTGCACGGCCCGGCAGCAGTGGGCGATGA
CACGTTTATTGGCATGCAGGCGTTCGTTTTCAAAAGCAAAGTTGGCAA
TAACGCAGTTCTGGAACCGCGTAGCGCAGCGATTGGCGTTACCATCCC
GGATGGCCGTTATATCCCGGCCGGTATGGTCGTTACGCAGGCGGAAGC
AGATAAACTGCCGGAAGTTACCGATGACTATGCCTATAGCCATACCAA
TGAGGCAGTTGTTTGTGTCAATGTCCATCTGGCGGAAGGCTACAAAGA
AACGGGTGGTAGCGGTGGCGGTGATGAATTCAGCAACATCCGTGAAAA
CCCGGTGACCCCGTGGAACCCGGAACCGAGCGCGCCGGTCATTGATCC
GACCGCATATATCGATCCGGAGGCAAGCGTCATTGGCGAAGTTACGAT
TGGCGCCAACGTGATGGTCAGCCCGATGGCCAGCATCCGCAGCGATGA
AGGCATGCCGATTTTTGTTGGTTGCCGTAGCAACGTTCAGGATGGCGT
GGTCCTGCACGCACTGGAAACCATTAACGAAGAAGAGCCGATTGAAGA
TAACATCGTTGAGGTCGACGGTAAAGAATATGCCGTGTATATCGGCAA
CAACGTTAGCCTGGCCCATCAAAGCCAAGTTCATGGTCCGGCCGCGGT
TGGTGATGACACGTTCATTGGCATGCAGGCGTTTGTGTTTAAGAGCAA
AGTGGGTAATAATGCCGTTCTGGAGCCGCGCAGCGCCGCAATCGGCGT
CACCATCCCGGACGGTCGCTACATTCCGGCAGGCATGGTCGTGACCAG
CCAAGCCGAAGCGGACAAACTGCCGGAAGTCACCGATGATTAGCATAC
AGCCACACCAACGAGGCGGTCGTGTGTGTTAATGTGCATCTGGCGGAA
GGTTATAAAGAAACGATTGAAGGCCGTCATCACCACCATCATTGAacc
cagctacttgtacaaagtggtgatgatccggctgctaacaaagcccga
aaggaagctga The corresponding amino acid sequence produced by the EXP14Q3193C3 expression vector was:

[SEQ ID NO: 26]
MDEFSNIRENPVTPWNPEPSAPVIDPTAYIDPEASVIGEVTIGANVM
VSPMASIRSDEGMPIFVGCRSNVQDGVVLHALETINEEGEPIEDNIV
EVDGKEYAVYIGNNVSLAHQSQVHGPAAVGDDFTIGMQAFVFKSKVG
NNAVLEPRSAAIGVTIPDGRYIPAGMVVTSQAEADKLPEVTDDYAYS
HTNEAVVCVNVHLAEGYKETGGSGGGDEFSNIRENPVTPWNPEPSAP
VIDPTAYIDPEASVIGEVTIGANVMVSPMASIRSDEGMPIFVGCRSN
VQDGVVLHALETINEEGEPIEDNIVEVDGKEYAVYIGNNVSLAHQSQ
VHGPAAVGDDFTIGMQAFVFKSKVGNNAVLEPRSAAIGVTIPDGRYI
PAGMVVTSQAEADKLPEVTDDYAYSHTNEAVVCVNVHLAEGYKETGG

-continued

SGGGDEFSNIRENPVTPWNPEPSAPVIDPTAYIDPEASVIGEVTIGA

NVMVSPMASIRSDEGMPIFVGCRSNVQDGVVLHALETINEEGEPIED

NIVEVDGKEYAVYIGNNVSLAHQSQVHGPAAVGDDTFIGMQAFVFKS

KVGNNAVLEPRSAAIGVTIPDGRYIPAGMVVTSQAEADKLPEVTDDY

AYSHTNEAVVCVNVHLAEGYKETIEGRHHHHHH

Example 1C

EXP14Q3193C4

E. coli cells BL21 Star™ (DE3) with expression vector EXP14Q3193C4 (represented in FIG. 46C) were cultured in 50 mL Terrific broth supplemented with 0.1 mg/mL ampicillin and 0.034 mg/mL chloramphenicol. The culture was grown overnight at 37° C. to an $OD_{600}$ of 6.04. 0.83 mL was used to inoculate a second culture of 50 mL Terrific broth supplemented with 0.1 mg/mL ampicillin and 0.034 mg/mL chloramphenicol. The culture was grown overnight at 37° C. to an $OD_{600}$ of 0.963, induced with 0.4 mM IPTG and supplemented with 0.5 mM $ZnSO_4$, then grown for 4 hours at 25° C. to an $OD_{600}$ of 7.57. 0.7 g of cells were collected by low speed centrifugation.

In a second batch E. coli cells BL21 Star™ (DE3) with expression vector EXP14Q3193C4 were cultured in 50 mL Terrific broth supplemented with 0.1 mg/mL ampicillin and 0.034 mg/mL chloramphenicol. The culture was grown overnight at 37° C. to an $OD_{600}$ of 6.04. 0.83 mL was used to inoculate a second culture of 50 mL Terrific broth supplemented with 0.1 mg/mL ampicillin and 0.034 mg/mL chloramphenicol. The culture was grown overnight at 37° C. to an $OD_{600}$ of 0.963, induced with 0.4 mM IPTG and supplemented with 0.5 mM $ZnSO_4$, then grown for 20 hours at 25° C. to an $OD_{600}$ of 22.8. 2.1 g of cells were collected by low speed centrifugation.

The nodes formed with the expression vector EXP14Q3193C4 were based on gamma-carbonic anhydrase from Methanosarcina thermophila. The C3 symmetric, 3-subunit, synthesized protein was composed of a single polypeptide chain. That is, whereas the native protein has a quaternary structure formed from 3 polypeptide chains, in the protein produced from the expression vector EXP14Q3193C4, the 3 polypeptide chains are fused together into a single polypeptide chain that folds into a structure having 3 subunits. The 3 polypeptide chains were fused together with two identical linkers, each having the sequence GGSGGG (Gly-Gly-Ser-Gly-Gly-Gly). The linker extended from the natural C-terminus (residue 212) of a subsequence corresponding to a polypeptide chain in the native protein and forming a subunit to residue 6 of the subsequence in a polypeptide chain forming the adjacent subunit (the amino acid residue numbering follows that assigned to the native polypeptide). Following the N-terminus, within the first two polypeptide subsequences corresponding to a polypeptide chain in the native protein, the following substitutions were made: Residues Asp70 and Tyr200 were changed to Cys; and Cys148 was changed to Ala. In the third polypeptide subsequence, that is, the subsequence before the C-terminus, Cys148 was changed to Ala, but residues Asp70 and Tyr200 were left unchanged. A His tag that can be cleaved by the Factor Xa protease was added to the C-terminus of the single polypeptide chain. Thus, two of the subunits of the assembled 3 subunit protein, formed of a single polypeptide chain, included a total of 4 surface cysteine residues available for functionalization (for example, with a biotin group) and complexation with 2 streptavidin tetramers. That is, two of the subunits can complex with a streptavidin each, but the third subunit cannot complex with a streptavidin.

The gene nucleotide sequence of sequence EXP14Q3193C4 incorporated into the EXP14Q3193C4 expression vector was:

[SEQ ID NO 24]
cgatgcgtccggcgtagaggatcgagatctcgatcccgcgaaatt<u>aat</u>

<u>acgactcactata</u>gggagaccacaacggtaccctctagatcacaagta gtacaaaaaagcaggcaccgaa<u>ggagatatacat</u>ATGGATGAATTTAG

CAATATTCGCGAAAACCCGGTTACCCCGTGGAACCCGGAACCGAGCGC

GCCGGTTATCGACCCGACGGCCTACATTGATCCGGAGGCAAGCGTGAT

TGGTGAAGTGACGATTGGTGCAAATGTCATGGTGAGCCCGATGGCGAG

CATTCGTAGCGATGAAGGTATGCCGATTTTCGTTGGTTGTCGTAGCAA

TGTTCAAGATGGTGTTGTTCTGCACGCCCTGGAAACCATTAATGAAGA

AGGTGAGCCGATTGAAGACAACATCGTTGAAGTTGATGGTAAAGAATA

CGCGGTTTATATCGGCAACAACGTCAGCCTGGCACATCAGAGCCAAGT

TCATGGTCCGGCAGCAGTGGGCGATGATACGATTGGTATGCAAGCATT

CGTTTTTAAAAGCAAAGTTGGTAATAATGCAGTTCTGGAACCGCGCAG

CGCAGCAATTGGTGTTACCATTCCGGATGGTCGTTATATCCCGGCCGG

TATGGTGGTGACGAGCCAGGCGGAAGCAGATAAACTGCCGGAAGTGAC

GGATGATTATGCCTATAGCCATACCAATGAAGCAGTCGTGTGTGTTAA

CGTGCACCTGGCCGAAGGTTACAAAGAAACGGGCGGTGGTAGCGGTGG

CGGCGATGAATTTAGCAATACCGTGAAAACCCGGTTACCCGTGGAATC

CGGAACCGAGCGCACCGGTTATTGATCCGACGGCATATATCGACCCGG

AGGCAAGCGTGATTGGCGAAGTTACGGGCGCAAATGTGATGGTTAGCC

CGATGGCCAGCATTCGTAGCGATGAAGGCATGCCGATTTTTGTGGCTG

CCGCAGCAATGTTCAAGATGGTGTTGTCCTGCACGCACTGGAGACCAT

CAATGAAGAAGGTGAACCGATTGAAGATAACATCGTCGAAGTTGACGG

CAAAGAATATGCGGTGTATATTGGCAATAATGTCAGCCTGGCACATCA

AAGCCAAGTTCACGGTCCGGCAGCAGTGGGCGATGATACCTTTATTGG

CATGCAAGCGTTTGTTTTCAAAAGCAAAGTCGGCAATAATGCAGTTCT

GGAACCGCGCGCAGCGCAGCGATTGGCGTCACGATCCCGGATGGTCGT

TATATTCCGGCCGGCATGGTGGTGAGCCAGGCAGAAGCAGATAAACTG

CCGGAAGTGACCGATGACTATGCCTATAGCCATACGAACGAAGCCGTT

GTTTGCGTGAACGTGCACCTGGCAGAAGGCTACAAAGAAACCGGTGGT

GGCAGCGGCGGCGGTGATGAATTCAGCAATATTCGCGAAAATCCGGTC

ACCCCGTGGAATCCGGAACCGAGCGCCCCGGTCATTGACCCGACGGCA

TATATTGATCCGGAAGCAAGCGTTATTGGTGAAGTTACGATTGGTGCA

AACGTGATGGTGAGCCCGATGGCGAGCATTCGCAGCGATGAGGGCATG

CCGATTTTTGTGGGCGATCGCAGCAATGTTCAAGATGGTGTTGTCCTG

CACGCCCTGGAAACCATCAATGAAGGCGAACCGATTGAAGACAATATT

-continued

```
GTGGAAGTCGATGGTAAAGAATACGCAGTCTATATTGGTAATAATGTT

AGCCTGGCACATCAGAGCCAAGTCCACGGTCCGGCCGCAGTGGGTGAT

GACAGTTTATTGGTATGCAAGCATTTGTGTTTAAAAGCAAAGTCGGTA

ACAATGCAGTTCTGGAACCGCGCAGCGCAGCAATCGGCGTTACGATCC

CGGATGGCCGTTATATCCCGGCGGGTATGGTGGTTACGAGCCAAGCAG

AAGCGGATAAACTGCCGGAAGTTACGGATGATTATGCCTATAGCCATA

CGAACGAAGCGGTTGTCTACGTTAACGTGCATCTGGCGGAGGGTTACA

AAGAAACGATTGAGGGTCATCATCACCATCATCATTGAaacccagctt tc
```

The corresponding amino acid sequence produced by the EXP14Q3193C4 expression vector was:

[SEQ ID NO 27]
```
MDEFSNIRENPVTPWNPEPSAPVIDPTAYIDPEASVIGEVTIGANVMV

SPMASIRSDEGMPIFVGCRSNVQDGVVLHALETINEEGEPIEDNIVEV

DGKEYAVYIGNNVSLAHQSQVHGPAAVGDDTFIGMQAFVFKSKVGNNA

VLEPRSAAIGVTIPDGRYIPAGMVVTSQAEADKLPEVTDDYAYSHTNE

AVVCVNVHLAEGYKETGGSGGGDEFSNIRENPVTPWNPEPSAPVIDPT

AYIDPEASVIGEVTIGANVMVSPMASIRSDEGMPIFVGCRSNVQDGVV

LHALETINEEGEPIEDNIVEVDGKEYAVYIGNNVSLAHQSQVHGPAAV

GDDTFIGMQAFVFKSKVGNNAVLEPRSAAIGVTIPDGRYIPAGMVVTS

QAEADKLPEVTDDYAYSHTNEAVVCVNVHLAEGYKETGGSGGGDEFSN

IRENPVTPWNPEPSAPVIDPTAYIDPEASVIGEVTIGANVMVSPMASI

RSDEGMPIFVGDRSNVQDGVVLHALETINEEGEPIEDNIVEVDGKEYA

VYIGNNVSLAHQSQVHGPAAVGDDTFIGMQAFVFKSKVGNNAVLEPRS

AAIGVTIPDGRYIPAGMVVTSQAEADKLPEVTDDYAYSHTNEAVVYVN

VHLAEGYKETIEGRHHHHHH
```

Thus, all of the proteins expressed by the vectors EXP14Q3193C2 (Example 1A), EXP14Q3193C3 (Example 1B), and EXP14Q3193C4 (Example 1C), could be (and were) expressed in *E. coli*. The proteins were stable to proteolysis by *E. coli* proteases as evidenced by the presence of bands of the appropriate molecular weight that appeared in Western blots using anti-His tag antibodies. This strongly suggested that the proteins were properly folded. It was found that the protein expression by vector EXP14Q3193C3 (Example 1B) was higher than that for EXP14Q3193C4 (Example 1C). The isolated band resulting from the EXP14Q3193C3 variant was sequenced by mass spectrometry and confirmed the identity of the protein.

Example 2

Expression of 4-Fold Symmetric Node

Synthetic genes and expression vectors for a 4-fold symmetric protein to be used as a node were constructed. The 4-fold node protein produced was IPP (isopentenyl pyrophosphate) isomerase with the following amino acid changes: the cysteine (C) at the 14 position was replaced by alanine; the serine (S) at the 44 position was replaced by cysteine (C); the threonine (T) at the 49 position was replaced by cysteine (C); and the cysteine (C) at the 237 position was replaced by serine (S). Furthermore, a histidine tag was added at the N-terminus

*E. coli* cells BL21 Star™ (DE3) pLysS with expression vector EXP14Q3164 (represented in FIG. 47) were cultured in 50 mL Terrific Broth supplemented with 0.1 mg/mL ampicillin. The culture was grown overnight at 37° C. with rotation at 225 rpm. The culture was induced with 0.4 mM IPTG, then grown for 18.25 hours at 25.3° C. to an $OD_{600}$ of 21.28. 2.1 g of cells were collected by low speed centrifugation.

In a second batch, *E. coli* cells BL21 Star™ (DE3) pLysS with expression vector EXP14Q3164 were cultured in 9 mL Terrific Broth supplemented with 0.1 mg/mL ampicillin and 0.2 mg/mL riboflavin. The culture was grown overnight at 37° C. with rotation at 225 rpm. The culture was used to inoculate a second culture of 1.0 L Terrific Broth supplemented with 0.1 mg/mL ampicillin and 0.2 mg/mL riboflavin. The culture was grown to an $OD_{600}$ of 1.39 when 0.4 mM IPTG was added. The culture continued to grow for 20.25 additional hours at 25.0° C. to an $OD_{600}$ of 0.70. 4.6 g of cells were collected by low speed centrifugation.

In a third batch, *E. coli* cells BL21 Star™ (DE3) pLysS with expression vector EXP14Q3164 were cultured in 8.6 mL Terrific Broth supplemented with 0.1 mg/mL ampicillin, 0.034 mg/mL chloramphenicol and 0.2 mg/mL riboflavin. The culture was grown overnight at 37° C. with rotation at 225 rpm. The culture was used to inoculate a second culture of 1 L Terrific Broth supplemented with 0.1 mg/mL ampicillin, 0.034 mg/mL chloramphenicol and 0.2 mg/mL riboflavin. The culture was grown to an $OD_{600}$ of 0.868 when 0.4 mM IPTG was added. The culture continued to grow for 3.0 additional hours at 25.8° C. to an $OD_{600}$ of 4.23. 8.6 g of cells were collected by low speed centrifugation.

In a fourth batch, *E. coli* cells BL21 Star™ (DE3) pLysS with expression vector EXP14Q3164 were cultured in 50 mL Luria-Bertani broth supplemented with 0.1 mg/mL ampicillin and 0.034 mg/mL chloramphenicol. The culture was grown overnight at 37° C. with rotation at 225 rpm. The culture with an $OD_{600}$ of 0.761 was induced with 0.4 mM IPTG and supplemented with 0.2 mg/mL riboflavin, then grown for 4 hours at 37.0° C. to an $OD_{600}$ of 4.46. 0.5 g of cells were collected by low speed centrifugation.

In a fifth batch, *E. coli* cells BL21 Star™ (DE3) with expression vector EXP14Q3164 were cultured in 50 mL Terrific broth supplemented with 0.1 mg/mL ampicillin and 0.034 mg/mL chloramphenicol. The culture was grown overnight at 37° C. with rotation at 225 rpm. The culture with an $OD_{600}$ of 0.797 was induced with 0.4 mM IPTG and supplemented with 0.2 mg/mL riboflavin, then grown for 4 hours at 37.0° C. to an $OD_{600}$ of 14.06. 1.1 g of cells were collected by low speed centrifugation.

In a sixth batch, *E. coli* cells BL21 Star™ (DE3) with expression vector EXP14Q3164 were cultured in 50 mL Luria-Bertani broth supplemented with 0.1 mg/mL ampicillin and 0.034 mg/mL chloramphenicol. The culture was grown overnight at 37° C. with rotation at 225 rpm. The culture with an $OD_{600}$ of 0.774 was induced with 0.4 mM IPTG and supplemented with 0.2 mg/mL riboflavin, then grown for 4 hours at 37.0° C. to an $OD_{600}$ of 8.46. 0.7 g of cells were collected by low speed centrifugation.

In a seventh batch, *E. coli* cells BL21 Star™ (DE3) with expression vector EXP14Q3164 were cultured in 50 mL Terrific broth supplemented with 0.1 mg/mL ampicillin and 0.034 mg/mL chloramphenicol. The culture was grown overnight at 37° C. with rotation at 225 rpm. The culture with an $OD_{600}$ of 0.797 was induced with 0.4 mM IPTG and supplemented with 0.2 mg/mL riboflavin, then grown for 4 hours at 37.0° C. to an $OD_{600}$ of 14.06. 1.1 g of cells were collected by low speed centrifugation.

In an eighth batch, E. coli cells BL21 Star™ (DE3) with expression vector EXP14Q3164 were cultured in 50 mL Luria-Bertani broth supplemented with 0.1 mg/mL ampicillin and 0.034 mg/mL chloramphenicol. The culture was grown overnight at 37° C. with rotation at 225 rpm. The culture with an $OD_{600}$ of 0.825 was induced with 0.4 mM IPTG and supplemented with 0.2 mg/mL riboflavin, then grown for 4 hours at 25.0° C. to an $OD_{600}$ of 4.17. 0.6 g of cells were collected by low speed centrifugation.

In a ninth batch, E. coli cells BL21 Star™ (DE3) with expression vector EXP14Q3164 were cultured in 50 mL Terrific broth supplemented with 0.1 mg/mL ampicillin and 0.034 mg/mL chloramphenicol. The culture was grown overnight at 37° C. with rotation at 225 rpm. The culture with an $OD_{600}$ of 0.75 was induced with 0.4 mM IPTG and supplemented with 0.2 mg/mL riboflavin, then grown for 4 hours at 25.0° C. to an $OD_{600}$ of 5.36. 0.9 g of cells were collected by low speed centrifugation.

In a tenth batch, E. coli cells BL21 Star™ (DE3) pLysS with expression vector EXP14Q3164 were cultured in 50 mL Luria-Bertani broth supplemented with 0.1 mg/mL ampicillin and 0.034 mg/mL chloramphenicol. The culture was grown overnight at 37° C. with rotation at 225 rpm. The culture with an $OD_{600}$ of 0.694 was induced with 0.4 mM IPTG and supplemented with 0.2 mg/mL riboflavin, then grown for 4 hours at 25.0° C. to an $OD_{600}$ of 2.66. 0.6 g of cells were collected by low speed centrifugation.

In an eleventh batch, E. coli cells BL21 Star™ (DE3) pLysS with expression vector EXP14Q3164 were cultured in 50 mL Terrific broth supplemented with 0.1 mg/mL ampicillin and 0.034 mg/mL chloramphenicol. The culture was grown overnight at 37° C. with rotation at 225 rpm. The culture with an $OD_{600}$ of 0.795 was induced with 0.4 mM IPTG and supplemented with 0.2 mg/mL riboflavin, then grown for 4 hours at 25.0° C. to an $OD_{600}$ of 4.81. 0.8 g of cells were collected by low speed centrifugation.

In a twelfth batch, E. coli cells BL21 Star™ (DE3) pLysS with expression vector EXP14Q3164 were cultured in 345 mL Terrific broth supplemented with 0.1 mg/mL ampicillin and 0.034 mg/mL chloramphenicol. The culture was grown overnight at 37° C. with rotation at 400-800 rpm. The culture was used to inoculate a second culture of 16 L Terrific Broth supplemented with 0.1 mg/mL ampicillin and 0.034 mg/mL chloramphenicol. The culture was grown to an $OD_{600}$ of 0.885 when 0.4 mM IPTG and 200 microg/mL riboflavin were added. The culture continued to grow for 4.0 additional hours at 37° C. to an $OD_{600}$ of 12.154. 323.3 g of cells were collected by low speed centrifugation.

The 4-fold node protein was isolated from the collected E. coli cells with expression vector EXP14Q3164 through a first isolation procedure as follows. 4.5 grams of E. coli cells BL21 Star™ (DE3) pLysS with expression vector EXP14Q3164 were suspended in 40 mL nonionic detergent (B-PER ThermoScientific) and allowed to react for 15 min. The cell suspension was clarified by centrifugation at 12500×g for 15 min. The supernatant was heated to 60° C. and held at that temperature for 15 min. Insoluble proteins were removed by centrifugation at 12500×g for 15 min and the clear yellow supernatant was dialyzed against two changes of a solution of 50 mM $NaPO_4$ buffer at pH 8.0 and 0.5 M NaCl, where each change was at least 10× the supernatant volume. After dialysis, the supernatant was incubated with 1 mL Ni agarose resin equilibrated with a solution of 50 mM $NaPO_4$ buffer at pH 8.0 and 0.5 M NaCl while held at 4° C. and gently rocked for 18 hr. Following two 15 mL washes each of a solution of 50 mM sodium phosphate buffer at pH 8.0 and 0.5 M NaCl with 20 and 40 mM imidazole, 4-fold node protein was eluted from the Ni agarose using a solution of 250 mM imidazole, 0.5 M NaCl, and 50 mM sodium phosphate buffer at pH 8.0. Centrifugal concentrators were used to exchange the buffer to a solution of 25 mM sodium phosphate and 0.1 M NaCl at pH 7.4, and then concentrate the 4-fold node protein to ~5 mg/mL, as determined spectrophotometrically.

A second, alternative isolation procedure was carried out in a similar manner as the first isolation procedure, except that E. coli cells BL21 Star™ (DE3) pLysS with expression vector EXP14Q3164 were suspended in 40 mL of solution with 50 mM $NaPO_4$ buffer at pH 8.0, 0.5 M NaCl, 40 mg lysozyme, 1 mg DNase I, and protease inhibitors (one pellet EDTA-free protease inhibitors (Roche) or 0.1 mL HALT™ protease cocktail (Pierce)), incubated for 1 hr with stirring at 4° C., and then sonicated for three increments of 30 pulses of 1-second duration.

A third, alternative isolation procedure was carried out in a similar manner as the first isolation procedure, except that the 4-fold node protein was further purified by dialysis against PBS pH 7.4, and then chromatographed on a size exclusion column of Superose-12 equilibrated with PBS pH 7.4 operated at a flow rate of either 0.1 mL/min or 0.4 mL/min.

A fourth, alternative isolation procedure was carried out in a similar manner as the second, alternative isolation procedure, except that the 4-fold node protein was further purified by dialysis against PBS pH 7.4, and then chromatographed on a size exclusion column of Superose-12 equilibrated with PBS pH 7.4 operated at a flow rate of either 0.1 mL/min or 0.4 mL/min.

The gene nucleotide sequence for the sequence EXP14Q3164 incorporated into the EXP14Q3164 expression vector was as follows. For the synthetic gene sequence shown, the open reading frame is in upper case with the initiating Methionine and Stop codons in bold.

[SEQ ID NO 28]

ATGAGCTATTATCACCATCATCATCATCATGACTATGATATCCCGACC

ACCGAAAATCTGTATTTCCAAGGTATGAACATCCGTGAACGCAAACGT

AAACATCTGGAAGCGGCCCTGGAAGGTGAAGTTGCATATCAAAAAACG

ACCACCGGTCTGGAAGGTTTCCGTCTGCGCTATCAAGCCCTGGCCGGT

CTGGCACTGTGTGAAGTCGATCTGTGTACCCCGTTTCTGGGTAAAACG

CTGAAAGCCCCGTTCCTGATTGGTGCAATGACGGGTGGTGAAGAAAAC

GGTGAACGTATCAATCTGGCACTGGCCGAAGCCGCCGAAGCCCTGGGT

GTGGGTATGATGCTGGGTAGCGGCCGTATTCTGCTGGAGCGTCCGGAA

GCCCTGCGTAGCTTTCGTGTCCGTAAAGTTGCACCGAAAGCACTGCTG

ATTGCGAATCTGGGTCTGGCACAACTGCGTCGTTATGGTCGCGATGAT

CTGCTGCGCCTGGTCGAAATGCTGGAAGCCGATGCCCTGGCCTTTCAT

GTTAATCCGCTGCAAGAAGCAGTCCAACGTGGTGATACCGATTTCCGT

GGTCTGGTTGAACGTCTGGCCGAACTGCTGCCGCTGCCGTTCCCGGTT

ATGGTCAAAGAAGTTGGCCACGGTCTGAGCCGTGAAGCAGCCCTGGCA

CTGCGTGATCTGCCGCTGGCCGCAGTTGATGTTGCAGGTGCGGGTGGT

ACGAGCTGGGCACGTGTTGAAGAATGGGTTCGTTTTGGTGAAGTCCGC

-continued

```
CACCCGGAACTGAGCGAAATTGGCATTCCGACGGCCCGCGCGATTCTG

GAAGTTCGTGAAGTTCTGCCGCATCTGCCGCTGGTTGCAAGCGGCGGT

GTTTATACCGGCACCGATGGCGCAAAAGCACTGGCACTGGGCGCCGAT

CTGCTGGCGGTTGCGCGTCCGCTGCTGCGCCCGGCCCTGGAAGGTGCA

GAACGTGTTGCGGCGTGGATTGGTGATTACCTGGAAGAACTGCGTACC

GCACTGTTTGCGATTGGTGCACGTAATCCGAAAGAAGCCCGCGGTCGT

GTCGAACGCGTCTAA
```

The corresponding amino acid sequence of the protein produced by the EXP14Q3164 expression vector was as follows. The amino acid sequence is provided using the standard one letter representation for each amino acid.

[SEQ ID NO 29]
```
MSYYHHHHHHDYDIPTTENLYFQGMNIRERKRKHLEAALEGEVAYQKT

TTGLEGFRLRYQALAGLALCEVDLCTPFLGKTLKAPFLIGAMTGGEEN

GERINLALAEAAEALGVGMMLGSGRILLERPEALRSFRVRKVAPKALL

IANLGLAQLRRYGRDDLLRLVEMLEADALAFHVNPLQEAVQRGDTDFR

GLVERLAELLPLPFPVMVKEVGHGLSREAALALRDLPLAAVDVAGAGG

TSWARVEEWVRFGEVRHPELSEIGIPTARAILEVREVLPHLPLVASGG

VYTGTDGAKALALGADLLAVARPLLRPALEGAERVAAWIGDYLEELRT

ALFAIGARNPKEARGRVERV
```

This amino acid sequence of the 4-fold node protein produced by the EXP14Q3164 expression vector was confirmed by mass spectrometry.

Example 3

Biotinylation of a 4-Fold Symmetric Node

Biotin-containing reagents were covalently linked to cysteine residues on the 4-fold node using the following procedure. The node was equilibrated in neutral or acidic buffers such as phosphate buffer saline (PBS) pH 7.4 or 20 mM sodium phosphate buffer pH 6.8 for reaction with biotinylation reagents N-d-biotinamido-N'-(3-maleimidopropionamido)-4,7,10-trioxatridecane-1,13-diamine (MAL-dPEG™3-biotin, Quanta BioDesign, Powell Ohio) and N-d-biotinamido-N'-(3-maleimidopropionamido)-3,6,9,12,15,18,21,24,27,30,33-undecaoxapentatriacontane-1,35-diamine (MAL-dPEG™11-biotin, Quanta BioDesign, Powell Ohio) or N-[6-(biotinamido)hexyl]-3'-(2'-pyridyldithio)propionamide (biotin-HPDP, PierceNet) by dialysis (Spectra/Por, 10 000 MW cutoff dialysis tubing, Cole-Palmer). Node was then concentrated to a volume of about 0.5 mL and a concentration of at least 1 mg/mL using centrifugal protein concentrator (PierceNet) and protein concentration determined by using an $A_{460}$ extinction coefficient of 11,300 $M^{-1}$ $cm^{-1}$. For example, 0.2 mL of node solution at a concentration of 21 mg/mL and 0.13 mL of a node solution at 28 mg/mL were used. Solutions of biotin-containing reagents were prepared by adding solid reagent to buffer or solvent. For maleimide-reactive reagents (MAL-dPEG™11-biotin and MAL-dPEG™3-biotin) the buffer was 20 mM sodium phosphate buffer pH 6.8 or PBS pH 7.4 and for the sulfur-reactive biotinylation reagent biotin-HPDP, the dissolving solution was dimethyl sulfoxide (DMSO). For example, 2.7 mg MAL-dPEG™3-biotin was dissolved in 0.05 mL PBS pH 7.4, 3.3 mg MAL-dPEG™11-biotin was dissolved in 0.05 mL PBS pH 7.4, and 2.8 mg biotin-HPDP was dissolved in 0.5 mL DMSO. Biotinylation reagents were added to the node solutions very soon after dissolution of the solid reagent. The final molar concentration of biotinylation reagent in the reaction was in excess of the node concentration. In separate reactions, the molar ratios of MAL-dPEG™3-biotin:node were 2.5:1 and 3.6:1, and the molar ratios of MAL-dPEG™11-biotin:node were 2.0:1 and 2.8:1. The reaction was allowed to progress for at least 2 hours. Unreacted reagent was then removed by centrifugation through a size exclusion resin (Zeba Desalting Column, PierceNet).

Example 4

Formation of Node:Streptavidin (NODE:SAV) Complexes

NODE:SAV complexes were formed in solution by mixing the streptavidin and derivatized (biotinylated) 4-fold node (NODE) solutions, generally by the addition of more concentrated streptavidin to the biotinylated NODE. Streptavidin solutions were prepared by dissolving lyophilized *Streptomyces avidinii* streptavidin (ProZyme, San Leandro, Calif.) in 50 mM sodium phosphate buffer pH 6.8, 0.25 M NaCl to achieve a final concentration of 1 or 10 mg/mL. Streptavidin solutions were also prepared by dissolving lyophilized *Streptomyces avidinii* streptavidin (ProZyme, San Leandro, Calif.) in PBS pH 7.4 at a concentration of 15 mg/mL. 0.50 mL of streptavidin solution was chromatographed on a Superose12 column equilibrated with PBS pH 7.4 and operated at flow rates from 0.2 to 0.4 mL/min. Eluted streptavidin fractions were combined and concentrated using centrifugal concentrators (iCON concentrators, Pierce). Streptavidin concentration was determined using an $A_{280}$ extinction coefficient of 41326 $M^{-1}$ $cm^{-1}$. Using this procedure, 0.2 mL of a 9.4 mg/mL SAV solution and 0.12 mL of a 28.5 mg/mL SAV solution were prepared. NODE:SAV complexes were formed in solution by adding 0.002 mL aliquots of streptavidin solution at a concentration of 10 mg/mL in 50 mM sodium phosphate buffer pH 6.8, 0.25 M NaCl to a reaction volume of 100 µL derivatized node at a concentration of 30 mg/mL in 20 mM sodium phosphate buffer pH 6.8 until an equimolar stoichiometry of NODE to SAV was achieved. The reaction equilibrated at room temperature for three days. NODE:SAV complexes were analyzed using 4-12% TRIS-Glycine PAGE gels under denaturing conditions where solutions to be analyzed were heated in the presence of dithiothreitol (DTT) and sodium dodecyl sulfate (SDS).

NODE:SAV complexes were also formed by immobilizing the derivatized node on a surface, then reacting SAV with the immobilized NODE. Following the manufacturer's instructions, 0.30 mL of Ni-NTA agarose resin (Invitrogen) was equilibrated with PBS pH 7.4. After 0.9 mg node derivatized with MAL-dPEG™3-biotin was added to the resin and allowed to equilibrate for 2 hrs, 0.7 mg SAV in PBS pH 7.4 was added. The resin with derivatized node and SAV was equilibrated by mixing for 12 hours on an orbital rotator. The NODE:SAV complex was eluted from the resin by washing with 50 mM phosphate buffer pH 8, 0.5 M NaCl, 0.25 M imidazole. NODE:SAV complexes were analyzed using 4-12% TRIS-Glycine PAGE gels under denaturing conditions where solutions to be analyzed were heated in the presence of DTT and SDS.

NODE:SAV complexes were also formed by immobilizing the derivatized node on a resin, adding streptavidin, eluting the NODE:SAV complex, then adding additional streptavidin to the eluted NODE:SAV complex. For example, 0.30 mL of Ni-NTA agarose resin (Invitrogen) was equilibrated with PBS pH 7.4. After 0.9 mg MAL-dPEG™11-biotin derivatized node was added to the resin and allowed to equilibrate for 2 hrs, 0.25 mg SAV in PBS pH 7.4 was added to the mixture. The resin with derivatized node and SAV was equilibrated by mixing for 12 hours on an orbital rotator. The NODE:SAV complex was eluted from the resin by washing with 50 mM phosphate buffer pH 8, 0.5 M NaCl, 0.25 M imidazole. To the NODE:SAV complex in solution, 0.3 mg SAV was added and the mixture allowed to equilibrate for 12 hrs. NODE:SAV complexes were analyzed using 4-12% TRIS-Glycine PAGE gels under denaturing conditions where solutions to be analyzed were heated in the presence of DTT and SDS. In a separate reaction, 0.30 mL of Ni-NTA agarose resin (Invitrogen) was equilibrated with PBS pH 7.4. After 0.9 mg biotin-HPDP derivatized node was added to the resin and allowed to equilibrate for 2 hrs, 0.06 mg SAV in PBS pH 7.4 was added, and the resin with derivatized node and SAV equilibrated by mixing for 12 hours on an orbital rotator. The NODE:SAV complex was eluted from the resin by washing with 50 mM phosphate buffer pH 8, 0.5 M NaCl, 0.25 M imidazole. To the NODE:SAV complex in solution, 0.37 mg SAV was added and the mixture allowed to equilibrate for 12 hrs. NODE: SAV complexes were analyzed using 4-12% TRIS-Glycine PAGE gels under denaturing conditions where solutions to be analyzed were heated in the presence of DTT and SDS.

Example 5

Electrophoretic analysis of NODE:SAV complexes was carried out. The panels presented in FIG. 48 show PAGE analyses using 8-16% Precise™ gels (Pierce) and BupH™ Tris-HEPES-SDS running buffer (Pierce). Lanes are numbered on the top. Novex Sharp (Invitrogen) molecular weight standards are in lanes 5 and 30, and correspond to standardized proteins of 260, 160, 110, 80, 60, 50, 40, 30 and 20 kDa.

In this study, the streptavidin tetramer subunits, which were obtained by fermentation from *Streptomyces avidinii*, had a range of molecular weights. For the purpose of this study, the average molecular weight of the streptavidin tetramer was understood to be approximately 52 kDa.

The 4-fold node is IPP isomerase from *Thermus thermophilus*. The native molecular weight is 35.9 kDa per chain, that is, 143.6 kDa per tetramer. With the added tags, the molecular weight of the construct used is higher.

The samples were prepared under conditions where the streptavidin:biotin complex is stable (Gonzalez M, Bagatolli L A, Echabe I, Arrondo J L R, Argarana C E, Cantor C R, Fidelio G D "Interaction of Biotin with Streptavidin" J Biol Chem (1997) 272:112288-11294). Other proteins under these conditions are not stable.

Samples were heated to at least 85° C. for 10 min with SDS. In lanes 22, 24, 26, 32, 34, and 35 and lanes 10, 12, and 14, complexes eluted from a solid support were analyzed. In lanes 1, 2, 3, and 4 and lanes 7, 9, 11, 13, and 15 complexes formed by first immobilizing the node, reacting it with streptavidin, eluting the complex from a solid support, and then reacting that complex with excess streptavidin in solution were analyzed. In lanes 1, 2, 3, 4, 6, 22, 24, 26, 29, 32, 34 and 35, samples were reacted with excess biotin for 15 min prior to the heating step. In lanes 2, 7, 14, 15, 22 and 35 complexes formed from the 4-fold node biotinylated with biotin-HPDP were analyzed. In lanes 1, 4, 9, 10, 11, 26 and 32 complexes formed from the 4-fold node biotinylated with MAL-dPEG™3-biotin were analyzed. In lanes 3, 8, 12, 13, 24 and 34 complexes formed from the 4-fold node biotinylated with MAL-dPEG™11-biotin were analyzed.

The bands shown in lane 10 were understood to correspond to protein entities as follows. The lower molecular weight band of 15 kDa or less was understood to correspond to streptavidin monomer arising from the unliganded tetramer that denatures under the conditions (compare lane 28, which analyzed the unliganded SAV tetramer) and to smaller fragments from IPP isomerase (compare lane 27, which analyzed IPP isomerase prior to biotinylation). The two bands about 20 kDa were understood to correspond to degraded IPP isomerase. These 20 kDa MW bands were present in Lane 27, which analyzed IPP isomerase prior to biotinylation. The bands were not present in complexes prepared with newly prepared IPP isomerase. The degradation appears to occur at a specific site. In the initial stages, IPP isomerase appears as a doublet of molecular weight just less than 40 kDa. Both subbands of the doublet were sequenced by mass spectrometry (MS). Both subbands gave the same sequence; the coverage of both samples was about 68%, and both sequences confirmed that the bands were IPP isomerase. Because IPP isomerase was isolated by affinity chromatography using the N-terminal His tag, it was understood that the cleavage site was near the C-terminus The lane 10 band at about 40 kDa was understood to correspond to the IPP isomerase monomer. Lane 27 represented the control analysis, which showed IPP isomerase prior to biotinylation.

The lane 10 band at about 50 kDa was understood to correspond to the streptavidin:biotin tetramer. Lanes 6 and 29 represent the control analyses. The liganded tetramer was stable under these conditions (the unliganded streptavidin was unstable, compare lanes 28 and 29 which differed only in that biotin was added for 15 minutes to the sample analyzed in lane 29).

The lane 10 band at about 70 kDa (indicated by the double-ended arrow) was understood to correspond to the streptavidin tetramer (52 kDa) in complex with one chain (36 kDa) of the IPP isomerase 4-fold node. This band was entirely absent from the control analyses of streptavidin (lane 28), streptavidin:biotin complex (lanes 6 and 29), and IPP isomerase (lane 27). The conclusion that the 70 kDa band corresponded to the NODE:SAV complex was reached upon consideration of the control analyses of lanes 6, 27, 28, and 29 and of analyses of a number of NODE: SAV complexes prepared by different methods and with different biotinylation reagents. These analyses make use of the denaturation of all proteins at temperatures above 85 deg C., except the liganded streptavidin (which is stable to about 115 deg C.). Activity assays of IPP isomerase show thermal denaturation within 15 minutes at 75 deg C.

The lane 10 band at about 110 kDa may correspond to the streptavidin tetramer bound to two node chains. The streptavidin would be bound to two node chains by acting as a link between the two node chains. The band at 110 kDa in lane 26, which analyzed the sample about 1 hour after elution from the resin, was smaller than the band at 110 kDa in lane 10, which analyzed the sample about 4 days after elution from the resin. These observations are consistent with the understanding that streptavidin linking two node chains is more likely to occur in solution than when the node is immobilized, and supports the conclusion that the 110 kDa band corresponds to the streptavidin tetramer bound to two node chains. By contrast, the 110 kDa band probably did not correspond to an aggregate of streptavidin:biotin tetramers, because the band for such aggregates was higher in molecular weight (compare lane 6).

One node chain bound to the streptavidin tetramer would be about 88 kDa (52+36). Two node chains bound to the streptavidin tetramer would be about 124 kDa (52+36+36). The appearance of the one node chain:streptavidin complex at the position corresponding to about 70 kDa for the standard, and the appearance of the two node chain:streptavidin complex at the position corresponding to about 110 kDa suggests that both complexes migrated faster in the gel than the molecular weight standards of 70 and 110 kDa. It is well appreciated in the art that complex protein structures can exhibit different migration rates than standards. The mobility in an SDS PAGE gel represents that of an extended unfolded polypeptide. In the case of such an extended unfolded polypeptide, mobility scales with molecular weight, so that higher molecular weight (longer) polypeptide chains move more slowly in the gel matrix. However, in the complexes considered in the present case, it is understood that the mass of the migrating species is not contained in a single chain and one of the molecules (streptavidin) is folded.

When a large quantity of the streptavidin:biotin complex was added to the lanes, higher aggregates that appeared as wide bands between the 110 kDa and 160 kDa markers were observed. For example, lane 6 was overloaded with streptavidin:biotin complex.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

REFERENCES

Adams J J, Anderson B F, Renault J P, Verchere-Beaur C, Morgenstern-Badarau I, Jameson G B (2002) "Structure and properties of the atypical iron superoxide dismutase from *Methanobacterium thermoautotrophicum*" To be published (2002) (pdb code:1mai)

Benach J, Edstrom W C, Lee I, Das K, Cooper B, Xiao R, Liu J, Rost B, Acton T B, Montelione G T, Hunt J F. "The 2.35 A structure of the TenA homolog from *Pyrococcus furiosus* supports an enzymatic function in thiamine metabolism" (2005) *Acta Crystallogr., Sect. D* 61: 589-598 (pdb code:1rtw)

Blum A S, Soto C M, Wilson C D, Cole J D, Kim M, Gnade B, Chatterji A, Ochoa W F, Lin T, Johnson J, Ratna B R "Cowpea mosaic virus as a scaffold for 3-D patterning of gold nanoparticles" *Nano Lett* (2004) 4:867.

Blum A S, Soto C M, Wilson C D, Brower T L, Pollack S K, Schull T L, Chatterji A, Lin T, Johnson J E, Amsinck C, Franzon P, Shashidhar R, Ratna B R "An engineered virus as a scaffold for three-dimensional self-assembly on the nanoscale" *Small* (2005) 1:702.

Case, D A Cheatham T E, Darden T, Gohlke H, Luo R, Merz, K M, Onufriev A, Simmerling C, Wang B, Woods R. "The Amber biomolecular simulation programs" (2005) *J. Computat. Chem.* 26, 1668-1688 (amber.scripps.edu/)

Castro G R, Knubovets T "Homogeneous biocatalysis in organic solvents and water-organic mixtures" *Crit Rev Biotechnol* (2003) 23:195-231.

Chatterji A, Ochoa W F, Paine M, Ratna B R, Johnson J E, Lin T "New addresses on an addressable virus nanoblock; uniquely reactive Lys residues on cowpea mosaic virus" *Chem Biol* (2004) 11:855.

Chatterji A, Ochoa W F, Ueno T, Lin T, Johnson J E "A virus-based nanoblock with tunable electrostatic properties" *Nano Lett* (2005) 5:597.

Cosgrove M S, Bever K, Avalos J L, Muhammad S, Zhang X., Wolberger C. "The structural basis of sirtuin substrate affinity" (2006) *Biochemistry* 45: 7511-7521 (pdb code: 2h2i)

Eigler D M, Schweizer E K "Positioning single atoms with a scanning tunnelling microscope" *Nature* (1990) 344:524-526.

Esposito L, Bruno I, Sica F, Raia, C A, Giordano A, Rossi M, Mazzarella L, Zagari A. "Structural study of a single-point mutant of *Sulfolobus solfataricus* alcohol dehydrogenase with enhanced activity" (2003) *Febs Lett.* 539: 14-18 (pdb code: 1nto)

Falkner J C, Turner M E, Bosworth J K, Trentler T J, Johnson J E, Lin T, Colvin V L "Virus crystals as nanocomposite scaffolds" *J Am Chem Soc* (2005) 127:5274.

Fitzpatrick P A, Steinmetz A C U, Ringe D, Klibanov A M "Enzyme Crystal Structure in a Neat Organic Solvent" *Proc Nat Acad Sci USA* (1993) 90:8653.

Gupta M N, Roy I "Enzymes in organic media: Forms, functions and applications" *Eur J Biochem* (2004) 271:2575-2583.

Hatzor-de Picciotto A, Wissner-Gross A D, Lavallee G, and Weiss P S "Arrays of $Cu^{2+}$-Complexed Organic Clusters Grown on Gold Nano Dots" (2007) Journal of Experimental Nanoscience, 2: 3-11

Hofmann K, Wood S W, Brinton C C, Montibeller J A, Finn F M "Iminobiotin affinity columns and their application to retrieval of streptavidin" *Proc Natl Acad Sci USA* (1980) 77:4666-4668.

Humphrey W, Dalke A, Schulten K "VMD: visual molecular dynamics" *J Mol Graph.* (1996) February; 14(1):33-8-27-8. www.ks.uiuc.edu/Research/vmd/

Izard T, Aevarsson A, Allen M D, Westphal A H, Perham R N, de Kok A, Hol W G "Principles of quasi-equivalence and Euclidean geometry govern the assembly of cubic and dodecahedral cores of pyruvate dehydrogenase complexes" (1999) *Proc. Natl. Acad. Sci. USA* 96: 1240-1245 (pdb code: 1b5s)

Jones T A, Bergdoll M, Kjeldgaard M "O: A macromolecular modeling environment" In: Crystallographic and Modeling Methods in Molecular Design. Eds.: C. Bugg & S. Ealick. Springer-Verlag Press (1990) 189-195. (xray.bmc.uu.se/~alwyn/)

Kim K K, Kim R, Kim S H "Crystal structure of a small heat-shock protein" (1998) *Nature* 394: 595-599 (pdb code: 1shs)

Judy J W, "Microelectromechanical systems (MEMS): fabrication, design and applications" (2001) *Smart Mater. Struct.* 10 1115-1134

Kisker C, Schindelin, H, Alber B E, Ferry J G, Rees, D C "A left-hand beta-helix revealed by the crystal structure of a carbonic anhydrase from the archaeon *Methanosarcina thermophila*" (1996) EMBO J. v15 pp. 2323-30 (pdb code: 1thj)

Kitago Y, Yasutake Y, Sakai N, Tsujimura, M, Yao M., Watanabe N., Kawarabayasi, Y., Tanaka, I. (2003) "Crystal structure of 5'-deoxy-5'-methylthioadenosine phosphorylase homologue from *Sulfolobus tokodaii*" To be Published (pdb code: 1v4n)

Lee B K, Richards F M "The interpretation of protein structures: Estimation of static accessibility" (1971)" *J. Mol. Biol.* 55, 379-400.

Lee K B, Park S, Mirkin C A, Smith J C, Mrksich M "Protein Nanoarrays Generated By Dip-Pen Nanolithography" *Science* (2002) 295:1702-1705.

Levene M J, Korlach J, Turner S W, Foquet M, Craighead H G, Webb W W "Zero-Mode Waveguides for Single-Molecule Analysis at High Concentrations" (2003) Science 299: 682-686

Liu G Y, Xu S, Qian Y "Nanofabrication of Self-Assembled Monolayers Using Scanning Probe Lithography" *Nanotechnology* (1996) 7:376-380.

Liu G Y, Amro N A "Positioning protein molecules on surfaces: A nanoengineering approach to supramolecular chemistry" *Proc Nat Acad Sci* (2002) 99:5165-5170.

Massant J, Wouters J, Glansdorff N "Refined structure of *Pyrococcus furiosus* ornithine carbamoyltransferase at 1.87 A" (2003) *Acta Crystallogr.*, Sect. D 59: 2140-2149 (pdb code: 1pvv)

Medalsy I, Dgany O, Sowwan M, Cohen H, Yukashevska A, Wolf S G, Wolf A Koster A, Almog O, Marton I, Pouny Y, Altman A, Shoseyov O, Porath D "SP1 Protein-Based Nanostructures and Arrays" (2008) *Nano Lett.*, 8 (2), 473-477

Ni J, Sakanyan V, Charlier D, Glansdorff N, Van Duyne G D, "Structure of the arginine repressor from *Bacillus stearothermophilus*." (1999) *Nat. Struct. Biol.* 6: 427-432 (pdb code: 1b4b)

Padilla J E, Colovos C, Yeates T O "Nanohedra: Using symmetry to design self-assembling protein cages, layers, crystals, and filaments" *Proc Nat Acad Sci USA* (2001) 98:2217-2221.

Pearce, P, "Structure in Nature is a Strategy for Design" (1979) MIT Press, Cambridge Protein Data Bank. www.rcsb.org/pdb/

Pugh, A, "Polyhedra a Visual Approach" (1976) University of California Press, Berkeley Ringler P, Schulz G "Self-Assembly of Proteins into Designed Networks" *Science* (2003) 302:106-109.

Rogers J A. & Nuzzo R G "Recent progress in Soft Lithography" (2005) *Materials Today* 8:50-56.

Rothemund P W K "Folding DNA to create nanoscale shapes and patterns" *Nature* (2006) 440:297-302.

Rupley J A, Careri G "Protein hydration and function" *Adv Protein Chem* (1991) 41:37-172.

Salemme, F R, Weber, P C "Streptavidin Macromolecular Adaptor And Complexes (2007) US Provisional Patent Saridakis V, Christendat D, Kimber M S, Dharamsi A, Edwards A M, Pai E F "Insights into ligand binding and catalysis of a central step in NAD+ synthesis: structures of *Methanobacterium thermoautotrophicum* NMN adenylyltransferase complexes." (2001) *J. Biol. Chem.* 276: 7225-7232 (pdb code: 1hyb)

Schwarzenbacher R et al. and Wilson I A, "Crystals Structure of Uronate Isomerase (TM0064) From *Thermotoga maritima* at 2.85 A Resolution" *Proteins: Struct, Funct & Bioinform* (2003) 53:142-145.

Schwarzenbacher R et al. and Wilson I A, "Crystal structure of a phosphoribosylaminoimidazole mutase PurE (TM0446) from *Thermotoga maritima* at 1.77 A resolution" (2004) *Proteins* 55: 474-478 (pdb code: 104v)

Seeman N C "From Genes to Machines: DNA Nanomechanical Devices" *Trends in Biochemical Sciences* (2005a) 30:119-235.

Seeman N C "Structural DNA Nanotechnology: An Overview" Methods in Molecular Biology 303: Bionanotechnology Protocols, Editors, Sandra J. Rosenthal and David W. Wright, Humana Press, Totowa, N.J. (2005b) pp. 143-166.

Shih W M, Quispe J D, Joyce G F A "1.7-kilobase single-stranded DNA that folds into a nanoscale octahedron" *Nature* (2004) 427:618-621.

Sleytr U B, Egelseer E M, Ilk N, Pum D, Schuster B. "S Layers as Basic Building Block for a Molecular Construction Kit" (2008) *FEBS J.* 274:323-334.

Sligar S G, Salemme F R "Protein engineering for molecular electronics" *Curr Opin Biotechnol* (1992) 3:388-393.

Teplyakov, A., Obmolova, G., Wilson, K. S., Ishii, K., Kaji, H., Samejima, T., Kuranova, I. "Crystal structure of inorganic pyrophosphatase from *Thermus thermophilus*" (1994) *Protein Sci.* 3: 1098-1107 (pdb code: 2prd)

Weber P C, Ohlendorf D H, Wendoloski J J, Salemme F R "Structural Origins of High Affinity Biotin Binding to Streptavidin" *Science* (1989) 243:85-88. (pdb code:1stp)

Weber P C, Wendoloski J J, Pantoliano M W, Salemme F R "Crystallographic and Thermodynamic Comparison of Natural and Synthetic Ligands Bound to Streptavidin" *J Amer Chem Soc* (1992) 114:3197-3200.

Weber P C, Wendoloski J J, Pantoliano M W, Salemme F R "Structure-Based Design of Synthetic Azobenzene Ligands for Streptavidin" *J Amer Chem Soc* (1994) 116: 2717-2724.

Weber S (1999) jcrystal.com/steffenweber/gallery/Fullerenes/Fullerenes.html

Wells A F, "Three Dimensional Nets and Polyhedra" (1977) Wiley, New York

Wells A F, "Further Studies of Three Dimensional Nets" (19779) American Crystallographic Association Monograph No. 8

Widman D, Freidrich H, Mader H, "Technology of Integrated Circuits" (2000) Springer-Verlag New York, LLC (340pp) ISBN-13: 9783540661993

Williams R, "The Geometrical Foundation of Natural Structure" (1979) Dover, N.Y.

Vainshtein B K, "Modern Crystallography, 1: Fundamentals of Crystals" (1994) Springer, New York, Whitesides G M, Mathias J P, Seto C T. "Molecular Self Assembly and Nanochemistry: A chemical strategy for the synthesis for the synthesis of nanostructures" (1991) *Science* 254, 1312-1319

Whitesides G M, Boncheva M "Beyond molecules: Self-assembly of mesoscopic and macroscopic components" *Proc Nat Acad Sci USA* (2002) 99:4769-4774.

Xia Y & Whitesides G "Soft Lithography" (1998) *Annu. Rev. Mater. Sci.* 28, 153-184.

Yeates T O, Padilla J E, Colovos C, "Self Assembling Proteins" U.S. Pat. No. 6,756,039 (2004)

Zaks A, Klibanov A M "Enzymatic catalysis in nonaqueous solvents" *J Biol Chem* (1988) 263:3194-3201.

Zhu J, Huang J, Stepanyuk G, Chen L, Chang J, Zhao M, Xu H, Liu Z L, Rose J P, Wang B C. "Crystal Structure of Tt0030 from *Thermus thermophilus* at 1.6 Angstroms Resolution" To be Published 2006 (pdb code: 2iel)

TABLE 1A

Symmetry and Applications of Thermostable Protein Nodes

| Symmetry | Symmetry Operations | Subunit Number | Application | Protein Data Bank (PDB) Code http://www.rcsb.org/pdb/home/home.do |
|---|---|---|---|---|
| C3 | E, C3 | 3 | Planar Node, 2D lattice, Dodecahedral & Polyhedral Node | 1fsz 1ge8 1isq 1j2v 1j5s 1kht 1ki9 1kwg 1l1s 1ml4 1n2m 1n13 1o5j 1qrf 1thj 1ufy 1uku 1v4n 1v8d 1vke 1wvq 1wzn 1x25 2b33 2cz4 2dcl 2dhr 2dt4 2hik 2nwl |
| C4 | E, C4, C2 | 4 | Planar Node, 2D lattice, Polyhedral Node | 1bkb 1nc7 1vcg 1vrd 2cu0 2fk5 2flf |
| C5 | E, C5 | 5 | Planar Node, 2D lattice, Icosahedral PolyNode | 1t0t 1vdh 1w8s 2b99 2bbh 2bbj 2hn1 2hn2 2iub |
| C6 | E, C6, C3, C2 | 6 | Planar, 2D lattice Node | 1i8f 1ljo 2a1b 2a18 2di4 2dr3 2ekd 2ewh |
| C7 | E, C7 | 7 | Planar Node | 1h64 1i4k 1i81 1jbm 1jri 1m5q 1mgq |
| D2 | E, 3C2 | 4 | Strut Extenders & Adaptors, 2D and 3D Lattice Nodes | 1a0e 1bxb 1do6 1dof 1gtd 1hyg 1i1g 1ik6 1ixr 1j1y 1j2w 1jg8 1jvb 1knv 1lk5 1lvw 1m8k 1ma1 1nto 1nvg 1o2a 1o54 1r37 1ris 1rtw 1stp 1u9y 1udd 1uir 1usy 1uxt 1v6t 1v8o 1v8p 1vc2 1vco 1vdk 1vjp 1vk8 1vl2 1vlv 1vr6 1w3i 1wb7 1wb8 1wlu 1ws9 1wyt 1x0l 1x1e 1x10 1xtt 1y56 1z54 2b5d 2bri 2cb1 2cd9 2cdc 2cx9 2czc 2d1y 2d8a 2d29 2df5 2dfa 2drh 2dsl 2e1a 2e9f 2eba 2ebj 2eo5 2ep5 2gl0 2gm7 2h6e 2hae 2hmf 2iss 2ldb 2p3n 2ph3 2yym 3pfk |
| D3 | E, C3, 3C2 | 6 | 2D & 3D Nodes & Lattices | 1aup 1b4b 1bgv 1bvu 1f9a 1fxk 1gtm 1hyb 1je0 1jku 1odi 1odk 1pg5 1qw9 1t57 1uan 1ude 1uiy 1v1a 1v1s 1v9l 1v19 1wkl 1wz8 1wzn 1x0u 2a8y 2afb 2anu 2bja 2bjk 2cqz 2cz8 2dcn 2ddz 2dev 2dqb 2dxf 2dya 2eez 2g3m 2i14 2ide 2j4j 2j9d 2prd 2afb 2j4k |
| D4 | E, C4, 5C2 | 8 | 2D & 3D Nodes & Lattices | 1jpu 1jq5 1m4y 1o4v 1saz 1umg 1vcf 1x9j 2ax3 2cwx 2d69 2h2i 2iel |
| D5 | E, C5, 5C2 | 10 | 3D Nodes | 1geh 1w8s 1wm9 1wuq 1wur 1wx0 2djw |
| D6 | E, C6, C3, 7C2 | 12 | 3D Nodes & Lattices | 1m4y 1znn |
| D7 | E, D7, 7C2 | 14 | 3D Nodes | 1m5q 1th7 |
| T23 Tetrahedral | E, 4C3, 3C2 | 12 | 1) 3D-Radial Nodes 2) Cubic Lattice (Diad Strut Connections) 2) Tetrahedral Structures & Lattices (C3 Strut Connections) | 1pvv 1vlg 1xfo 1y0r 1y0y 1yoy 2clb 2glf 2v18 |
| O (432) Cuboctahedral | E, 3C4, 4C3, 9C2 | 24 | 3D-Radial Nodes, Lattices | 1shs 1vlg |
| Dodecahedral (532) | E, 6C5, 10C3, 15C2 | 60 | 3D-Radial Nodes, Lattices | 1b5s |
| Other | E, 4C3, 3 C2 | 12 | 3D-Radial Nodes, Lattices | 2cz8 |

Structures are designated by their Protein Data Bank Codes < http://www.rcsb.org/pdb/home/home.do >. Structures in bold text are illustrated in the application. For a complete description of point group symmetry and symmetry operation nomenclature see Vainstein (1994) or: http://www.phys.ncl.ac.uk/staff/njpg/symmetry/index.html and <http://csi.chemie.tu-darmstadt.de/ak/immel/script/redirect.cgi?filename=http://csi.chemie.tu-darmstadt.de/ak/immel/tutorials/symmetry/index.html>

TABLE 1B

Subunit Amino Acid Sequences of Symmetric Protein Nodes Structures are designated by Symmetry Type and Protein Data Bank Codes <http://www.rcsb.org/pdb/home/home.do>.

C3 Symmetry (3 Polypeptide Chains)

1fsz *Methanocaldococcus jannaschii* Cell Division Protein
MKFLKNVLEEGSKLEEFNELELSPEDKELLEYLQQTKAKITVVGCGGA
GNNTITRLKMEGIEGAKTVAINTDAQQLIRTKADKKILIGKKLTRGLG
AGGNPKIGEEAAKESAEEIKAAIQDSDMVFITCGLGGGTGTGSAPVVA
EISKKIGALTVAVVTLPFVMEGKVRMKNAMEGLERLKQHTDTLVVIPN
EKLFEIVPNMPLKLAFKVADEVLINAVKGLVELITKDGLINVDFADVK
AVMNNGGLAMIGIGESDSEKRAKEAVSMALNSPLLDVDIDGATGALIH
VMGPEDLTLEEAREVVATVSSRLDPNATIIWGATIDENLENTVRVLLV
ITGVQSRIEFTDTGLKRKKLELTGIPKIGSHHHHHH
[SEQ ID NO: 30]

1ge8 *Pyrococcus furiosus* DNA Binding Protein
MPFEIVFEGAKEFAQLIDTASKLIDEAAFKVTEDGISMRAMDPSRVVL
IDLNLPSSIFSKYEVVEPETIGVNLDHLKKILKRGKAKDTLILKKGEE
NFLEITIQGTATRTFRVPLIDVEEMEVDLPELPFTAKVVVLGEVLKDA
VKDASLVSDSIKFIARENEFIMKAEGETQEVEIKLTLEDEGLLDIEVQ TABLE 1B-continued Subunit Amino Acid Sequences of Symmetric
Protein Nodes Structures are designated by
Symmetry Type and Protein Data Bank Codes
<http://www.rcsb.org/pdb/home/home.do>.

EETKSAYGVSYLSDMVKGLGKADEVTIKFGNEMPMQMEYYIRDEGRLT
FLLAPRVEE
[SEQ ID NO: 31]

1isq *Pyrococcus furiosus* DNA Binding Protein
MPFEIVFEGAKEFAQLIDTASKLIDEAAFKVTEDGISMRAMDPSRVVL
IDLNLPSSIFSKYEVVEPETIGVNLDHLKKILKRGKAKDTLILKKGEE
NFLEITIQGTATRTFRVPLIDVEEMEVDLPELPFTAKVVVLGEVLKDA
VKDASLVSDSIKFIARENEFIMKAEGETQEVEIKLTLEDEGLLDIEVQ
EETKSAYGVSYLSDMVKGLGKADEVTIKFGNEMPMQMEYYIRDEGRLT
FLLAPRVEE
[SEQ ID NO: 32]

1j2v *Pyrococcus horikoshii* ot3 hypothetical
periplasmic divalent cation tolerance protein
MIIVYTTFPDWESAEKVVKTLLKERMIACANLREHRAFYWWEGKIEED
KEVGAILKTREDLWEELKERIKELHPYDVPAIIRIDVDDVNEDYLKWL
IEETKK
[SEQ ID NO: 33]

1j5s *Thermotoga maritima* URONATE ISOMERASE
MGSDKIHHHHHMFLGEDYLLTNRAAVRLFNEVKDLPIVDPHNHLDAK
DIVENKPWNDIWEVEGATDHYVWELMRRCGVSEEYITGSRSNKEKWLA
LAKVFPRFVGNPTYEWIHLDLWRRFNIKKVISEETAEEIWEETKKKLP
EMTPQKLLRDMKVEILCTTDDPVSTLEHHRKAKEAVEGVTILPTWRPD
RAMNVDKEGWREYVEKMGERYGEDTSTLDGFLNALWKSHEHFKEHGCV
ASDHALLEPSVYYVDENRARAVHEKAFSGEKLTQDEINDYKAFMMVQF
GKMNQETNWVTQLHIGALRDYRDSLFKTLGPDSGGDISTNFLRIAEGL
RYFLNEFDGKLKIVLYVLDPTHLPTISTIARAFPNVYVGAPWWFNDSP
FGMEMHLKYLASVDLLYNLAGMVTDSRKLLSFGSRTEMFRRVLSNVVG
EMVEKGQIPIKEARELVKHVSYDGPKALFFG
[SEQ ID NO: 7]

1kht *Methanococcus voltae* adenylate kinase
MKNKVVVVTGVPGVGSTTSSQLAMDNLRKEGVNYKMVSFGSVMFEVAK
EENLVSDRDQMRKMDPETQKRIQKMAGRKIAEMAKESPVAVDTHSTVS
TPKGYLPGLPSWVLNELNPDLIIVVETTGDEILMRRMSDETRVRDLDT
ASTIEQHQFMNRCAAMSYGVLTGATVKIVQNRNGLLDQAVEELTNVLR
[SEQ ID NO: 34]

1ki9 *Methanothermococcus thermolithotrophicus*
adenylate kinase
MKNKLVVVTGVPGVGGTTITQKAMEKLSEEGINYKMVNFGTVMFEVAQ
EENLVEDRDQMRKLDPDTQKRIQKLAGRKIAEMVKESPVVVDTHSTIK
TPKGYLPGLPVWVLNELNPDIIIVVETSGDEILIRRLNDETRNRDLET
TAGIEEHQIMNRAAAMTYGVLTGATVKIIQNKNNLLDYAVEELISVLR
[SEQ ID NO: 35]

1kwg *Thermus thermophilus* BETA-GALACTOSIDASE
MLGVCYYPEHWPKERWKEDARRMREAGLSHVRIGEFAWALLEPEPGRL
EWGWLDEAIATLAAEGLKVVLGTPTATPPKWLVDRYPEILPVDREGRR
RRFGGRRHYCFSSPVYREEARRIVTLLAERYGGLEAVAGFQTDNEYGC
HDTVRCYCPRCQEAFRGWLEARYGTIEALNEAWGTAFWSQRYRSFAEV
ELPHLTVAEPNPSHLLDYYRFASDQVRAFNRLQVEILRAHAPGKFVTH
NFMGFFTDLDAFALAQDLDFASWDSYPLGFTDLMPLPPEEKLRYARTG
HPDVAAFHHDLYRGVGRGRFWVMEQQPGPVNWAPHNPSPAPGMVRLWT
WEALAHGAEVVSYFRWRQAPFAQEQMHAGLHRPDSAPDQGFFEAKRVA
EELAALALPPVAQAPVALVFDYEAAWIYEVQPQGAEEWSYLGLVYLFYS
ALRRLGLDVDVVPPGASLRGYAFAVVPSLPIVREEALEAFREAEGPVL
FGPRSGSKTETFQIPKELPPGPLQALLPLKVVRVESLPPGLLEVAEGA
LGRFPLGLWREWVEAPLKPLLTFQDGKGALYREGRYLYLAAWPSPELA
GRLLSALAAEAGLKVLSLPEGLRLRRRGTWVFAFNYGPEAVEAPASEG
ARFLLGSRRVGPYDLAVWEEA
[SEQ ID NO: 36]

1lls *Methanothermobacter thermautotrophicus*
hypothetical protein MTH1491
MVDYRVVFHIDEDDESRVLLLISNVRNLMADLESVRIEVVAYSMGVNV
LRRDSEYSGDVSELTGQGVRFCACSNTLRASGMDGDDLLEGVDVVSSG
VGHIVRRQTEGWAYIRP
[SEQ ID NO: 37]

1m14 *Pyrococcus abyssi* Aspartate
Transcarbamoylase
MDWKGRDVISIRDFSKEDIETVLATAERLERELKEKGQLEYAKGKILA TLFFEPSTRTRLSFESAMHRLGGAVIGFAEASTSSVKKGESLRDTIKT
VEQYCDVIVIRHPKEGAARLAAEVAEVPVINAGDGSNQHPTQTLLDLY
TIKKEFGRIDGLKIGLLGDLKYGRTVHSLAEALTFYDVELYLISPELL
RMPRHIVEELREKGMKVVETTTLEDVIGKLDVLYVTRIQKERFPDEQE
YLKVKGSYQVNLKVLEKAKDELRIMHPLPRVDEIHPEVDNTKHAIYFR
QVFNGVPVRMALLALVLGVI
[SEQ ID NO: 38]

1n2m *Methanocaldococcus jannaschii* Pyruvoyl-
dependent arginine decarboxylase
MNAEINPLHAYFKLPNTVSLVAGSSEGETPLNAFDGALLNAGIGNVNL
IRISAIMPPEAEIVPLPKLPMGALVPTAYGYIISDVPGETISAAISVA
IPKDKSLCGLIMEYEGKCSKKEAEKTVREMAKIGFEMRGWELDRIESI
AVEHTVEKLGCAFAAAALWYK
[SEQ ID NO: 39]

1n13 *Methanocaldococcus jannaschii* Pyruvoyl-
dependent arginine decarboxylase alpha chain
XIMPPEAEIVPLPKLPMGALVPTAYGYIISDVPGETISAAISVAIPKD
KSLCGLIMEYEGKCSKKEAEKTVREMAKIGFEMRGWELDRIESIAVEH
TVEKLGCAFAAAALWYK
[SEQ ID NO: 40]

*Methanocaldococcus jannaschii* Pyruvoyl-
dependent arginine decarboxylase beta chain
MNAEINPLHAYFKLPNTVSLVAGSSEGETPLNAFDGALLNAGIGNVNL
IRIS
[SEQ ID NO: 41]

1o5j *Thermotoga maritima* periplasmic divalent
cation tolerance protein
MGSDKIHHHHHMILVYSTFPNEEKALEIGRKLLEKRLIACFNAFEIR
SGYWWKGEIVQDKEWAAIFKTTEEKEKELYEELRKLHPYETPAIFTLK
VENVLTEYMNWLRESVL
[SEQ ID NO: 42]

1qrf *Methanosarcina thermophila* gamma-CARBONIC
ANHYDRASE
QEITVDEFSNIRENPVTPWNPEPSAPVIDPTAYIDPQASVIGEVTIGA
NVMVSPMASIRSDEGMPIFVGDRSNVQDGVVLHALETINEEGEPIEDN
IVEVDGKEYAVYIGNNVSLAHQSQVHGPAAVGDDTFIGMQAFVFKSKV
GNNCVLEPRSAAIGVTIPDGRYIPAGMVVTSQAEADKLPEVTDDYAYS
HTNEAVVYVNVHLAEGYKETS
[SEQ ID NO: 43]

1thj *Methanosarcina thermophila* gamma-CARBONIC
ANHYDRASE
MQEITVDEFSNIRENPVTPWNPEPSAPVIDPTAYIDPEASVIGEVTIG
ANVMVSPMASIRSDEGMPIFVGDRSNVQDGVVLHALETINEEGEPIED
NIVEVDGKEYAVYIGNNVSLAHQSQVHGPAAVGDDTFIGMQAFVFKSK
VGNNCVLEPRSAAIGVTIPDGRYIPAGMVVTSQAEADKLPEVTDDYAY
SHTNEAVVYVNVHLAEGYKETS
[SEQ ID NO: 1]

1ufy *Thermus thermophilus* hb8 Chorismate mutase
MVRGIRGAITVEEDTPEAIHQATRELLLKMLEANGIQSYEELAAVIFT
VTEDLTSAFPAEAARQIGMHRVPLLSAREVPVPGSLPRVIRVLALWNT
DTPQDRVRHVYLREAVRLRPDLESAQ
[SEQ ID NO: 44]

1uku *Pyrococcus horikoshii* ot3 periplasmic
divalent cation tolerance protein CutA
MIIVYTTFPDWESAEKVVKTLLKERLIACANLREHRAFYWWEGKIEED
KEVGAILKTREDLWEELKERIKELHPYDVPAIIRIDVDDVNEDYLKWL
IEETKK
[SEQ ID NO: 45]

1v4n *Sulfolobus tokodaii* hypothetical
5'-methylthioadenosine phosphorylase
MMIEPKEKASIGIIGGSGLYDPQILTNVKEIKVYTPYGEPSDNIILGE
LEGRKVAFLPRHGRGHRIPPHKINYRANIWALKSLGVKWVIAVSAVGS
LRLDYKPGDFVVPNQFIDMTKGRTYTFFDGPTVAHVSMADPFCEHLRS
IILDSAKDLGITTHDKGTYICIEGPRFSTRAESIVWKEVFKADIIGMT
LVPEVNLACEAEMCYSVIGMVTDYDVFADIPVTAEEVTKVMAENTAKV
KKLLYEVIRRLPEKPDERKCSCCQALKTALVLEHHHHHHHH TABLE 1B-continued Subunit Amino Acid Sequences of Symmetric
Protein Nodes Structures are designated by
Symmetry Type and Protein Data Bank Codes
<http://www.rcsb.org/pdb/home/home.do>.

[SEQ ID NO: 8]

1v8d *Thermus thermophilus* hypothetical protein
(TT1679)
MRRGSGNPERPSLSRDGLRVPPPCPGKRGPGHFSGYHGGMEGIRRAAQ
RAAEEFLQAPPMAPGSLFVLGGSTSEVLGERVGTRPSLEAAHAVLEGL
LPPLLERGVHVAVQACEHLNRALVVERETARAFGKEEVAVFPHPKAGG
AKATAAFLRFRDPVMVESLKAQAHGGMDIGGVLIGMHLRPVAVPLRLS
VRKIGEAVLLAAKTRPKLVGGARAVYTREEMLKKLEEFLPKPP
[SEQ ID NO: 46]

1vke *Thermotoga maritima* msb8 carboxy-
muconolactone decarboxylase family protein
MGSDKIHHHHHHMEYKKFVEARRELNEKVLSRGTLNTKRFFNLDSAVY
RPGKLDVKTKELMGLVASTVLRCDDCIRYHLVRCVQEGASDEEIFEAL
DIALVVGGSIVIPHLRRAVGFLEELREMEKNGETISL
[SEQ ID NO: 47]

1wvq *Pyrobaculum aerophilum* hypothetical protein
PAE2307
MTDMSIKFELIDVPIPQGTNVIIGQAHFIKTVEDLYEALVTSVPGVKF
GIAFCEASGKRLVRHEANDEELRNLAIDLCKKIAAGHVFVIYIRNAWP
INVLNAIKNVPEVVRIFAATANPLKVIVAEVEPERRGVVGVVDGHSPL
GVETEKDREERKKFLREVVKYKL
[SEQ ID NO: 48]

1wzn *Pyrococcus horikoshii* ot3 SAM-dependent
methyltransferase
MYELYTLLAEYYDTIYRRRIERVKAEIDFVEEIFKEDAKREVRRVLDL
ACGTGIPTLELAERGYEVVGLDLHEEMLRVARRKAKERNLKIEFLQGD
VLEIAFKNEFDAVTMFFSTIMYFDEEDLRKLFSKVAEEALKPGGVFITD
FPCWFYGGRDGPVVWNEQKGEEKLVIMDWREVEPAVQKLRFKRLVQIL
RPNGEVKAFLVDDELNIYTPREVRLLAEKYFEKVKIYGNLKRELSPND
MRYWIVGIAKSF
[SEQ ID NO: 49]

1x25 *Sulfolobus tokodaii* str. 7 Hypothetical
UPF0076 protein ST0811
GSHMETVFTEKAPKPVGPYSQAIKVGNTLYVSGQIPIDPRTNEIVKGD
IKVQTRQVLDNIKEIVKAAGFSLSDVAMAFVFLKDMNMFNDFNSVYAE
YFKDKPPARVTVEVSRLPKDALIEIAVICSKG
[SEQ ID NO: 50]

2b33 *Thermotoga maritima* msb8 protein synthesis
inhibitor, putative
MGSDKIHHHHHHMKRFVETDKAPKAIGPYSQAVVVGNMMFVSGQIPID
PETGELVQGTIEEKTERVLENLKAILEAGGFSLKDVVKVTVPTTSMDY
FQRVNEVYSRYFGDHRPARSFVAVAQLPRNVEIEIEAIAVKEGE
[SEQ ID NO: 51]

2cz4 *Thermus thermophilus* hb8 hypothetical
protein TTHA0516 (bound acetate)
GSSHHHHHHSSGLVPRGSHMDLVPLKLVTIVAESLLEKRLVEEVKRLG
AKGYTITPARGEGSRGIRSVDWEGQNIRLETIVSEEVALRILQRLQEE
YFPHYAVIAYVENVWVVRGEKYV
[SEQ ID NO: 52]

2dcl *Pyrococcus horikoshii* Hypothetical UPF0166
protein PH1503
MVEVEHWNTLRLRIYIGENDKWEGRPLYKVIVEKLREMGIAGATVYRG
IYGFGKKSRVHSSDVIRLSTDLPIIVEVVDRGHNIEKVVNVIKPMIKD
GMITVEPTIVLWVGTQEEIKKFEEDAIAERQ
[SEQ ID NO: 53]

2dhr *Thermus thermophilus* Whole Cytosolic Region
of ATP-Dependent Protease FtsH
RNGRAGPSDSAFSFTKSRARVLTEAPKVTFKDVAGAEEAKEELKEIVE
FLKNPSRFHEMGARIPKGVLLVGPPGVGKTHLARAVAGEARVPFITAS
GSDFVEMFVGVGAARVRDLFETAKRHAPCIVFIDEIDAVGRKRGSGVG
GGNDEREQTLNQLLVEMDGFEKDTAIVVMAATNRPDILDPALLRPGRF
DRQIAIDAPDVKGREQILRIHARGKPLAEDVDLALLAKRTPGFVGADL
ENLLNEAALLAAREGRRKITMKDLEEAADRVMMLPAKKSLVLSPRDRR
ITAYHEAGHALAAHFLEHADGVHKVTIVPRGRALGFMMPRREDMLHWS
RKRLLDQIAVALAGRAAEEIVFDDVTTGAENDFRQATELARRMITEWG
MHPEFGPVAYAVREDYLGGYDVRQYSEETAKRIDEAVRRLIEEQYQRV TABLE 1B-continued Subunit Amino Acid Sequences of Symmetric
Protein Nodes Structures are designated by
Symmetry Type and Protein Data Bank Codes
<http://www.rcsb.org/pdb/home/home.do>.

KALLLEKREVLERVAETLLERETLTAEEFQRVVEGLPLEAPEEARERE
PPRVVPKVKPGGALGGA
[SEQ ID NO: 54]

2dt4 *Pyrococcus horikoshii* Hypothetical protein
PH0802
MVTGMFSLGRTYLFRVPEGEELLTYIKNFCKKEGIETAIINGIGTLKN
PKIGYFLEEKKEYKVIPLKGSYELISLIGNVSLKDGEPFVHAHVSLGN
EEGIVFGGHLVEGEVFVAEIFLQELKGEKIERKPTKYGLALWEELKL
[SEQ ID NO: 55]

2hik *Sulfolobus solfataricus* PCNA1 (SS00397) DNA
binding
MFKIVYPNAKDFFSFINSITNVTDSIILNFTEDGIFSRHLTEDKVLMA
IMRIPKDVLSEYSIDSPTSVKLDVSSVKKILSKASSKKATIELTETDS
GLKIIIRDEKSGAKSTIYIKAEKGQVEQLTEPKVNLAVNFTTDESVLN
VIAADVTLVGEEMRISTEEDKIKIEAGEEGKRYVAFLMKDKPLKELSI
DTSASSSYSAEMFKDAVKGLRGFSAPTMVSFGENLPMKIDVEAVSGGH
MIFWIAPRLLEHHHHHH
[SEQ ID NO: 56]

2nwl *Pyrococcus horikoshii* glutamate symport
protein
MGLYRKYIEYPVLIKILIGLILGAIVGLILGHYGYAHAVHTYVKPFGD
LFVRLLKMLVMPIVFASLVVGAASISPARLGRVGVKIVVYYLLTSAFA
VTLGIIMARLFNPGAGIHLAVGGQQFQPHQAPPLVHILLDIVPTNPFG
ALANGQVLPTIFFAIILGIAITYLMNSENEKVRKSAETLLDAINGLAE
AMYKIVVDPVGPVFALIAYVMAEQGVHVVGELAKVTAAVYVGLT
LQILLVYFVLLKIYGIDPISFIKHAKDAMLTAFVTRSSSGTLPVTMRV
AKEMGISEGIYSFTLPLGATINMDGTALYQGVCTFFIANALGSHLTVG
QQLTIVLTAVLASIGTAGVPGAGAIMLAMVLHSVGLPLTDPNVAAAYA
MILGIDAILDMGRTMVNVTGDLTGTAIVAKTEGTLVPR
[SEQ ID NO: 57]

C4 Symmetry (4 Polypeptide chains)

1bkb *Pyrobaculum aerophilum* TRANSLATION
INITIATION FACTOR 5A
KWVMSTKYVEAGELKEGSYVVIDGEPCRVVEIEKSKTGKHGSAKARIV
AVGVFDGGKRTLSLPVDAQVEVPIIEKFTAQILSVSGDVIQLMDMRDY
KTIEVPMKYVEEEAKGRLAPGAEVEVWQILDRYKIIRVKG
[SEQ ID NO: 58]

1nc7 *Thermotoga maritima* hypothetical protein
TM1070
MGSSHHHHHHSSGRENLYFQGHMNGARKWFFPDGYIPNGKRGYLVSHE
SLCIMNTGDETAKIRITFLFEDSKPVVHEVEISPMKSLHLRLDKLGIP
KCKPYSIMAESNVPVVMQLSRLDVGKNHYTLMTTIGYWEEGS
[SEQ ID NO: 59]

1vcg *Thermus thermophilus* isopentenyl-
diphosphate delta-isomerase
MNIRERKRKHLEACLEGEVAYQKTTTGLEGFRLRYQALAGLALSEVDL
TTPFLGKTLKAPFLIGAMTGGEENGERINLALAEAAEALGVGMMLGSG
RILLERPEALRSFRVRKVAPKALLIANLGLAQLRRYGRDDLLRLVEML
EADALAFHVNPLQEAVQRGDTDFRGLVERLAELLPLPFPVMVKEVGHG
LSREAALALRDLPLAAVDVAGAGGTSWARVEEWVRFGEVRHPELCEIG
IPTARAILEVREVLPHLPLVASGGVYTGTDGAKALALGADLLAVARPL
LRPALEGAERVAAWIGDYLEELRTALFAIGARNPKEARGRVERV
[SEQ ID NO: 9]

1vrd *Thermotoga maritima* msb8 inosine-5'-
monophosphate dehydrogenase
MGSDKIHHHHHHMKEALTFDDVLLVPQYSEVLPKDVKIDTRLTRQIRI
NIPLVSAAMDTVTEAALAKALAREGGIGIIHKNLTPDEQARQVSIVKK
TENGIIYDPITVTPDMTVKEAIDLMAEYKIGGLPVVDEEGRLVGLLTN
RDVRFEKNLSKKIKDLMTPREKLIVAPPDISLEKAKEILHQHRIEKLP
LVSKDNKLVGLITIKDIMSVIEHPNAARDEKGRLLVGAAVGTSPETME
RVEKLVKAGVDVIVIDTAHGHSRRVIETLEMIKADYPDLPVVAGNVAT
PEGTEALIKAGADAVKVGVGPGSICTTRVVAGVGVPQLTAVMECSEVA
RKYDVPIIADGGIRYSGDIVKALAAGAESVMVGSIFAGTEEAPGETIL
YQGRKYAYRGMGSLGAMRSGSADRYGQEGENKFVPEGIEGMVPYKGT
VKDVVHQLVGGLRSGMGYIGARTIKELQEKAVFVKITPAGVKESHPHD
IIITKESPNYWVQA TABLE 1B-continued Subunit Amino Acid Sequences of Symmetric
Protein Nodes Structures are designated by
Symmetry Type and Protein Data Bank Codes
<http://www.rcsb.org/pdb/home/home.do>.

[SEQ ID NO: 60]
2cu0 *Pyrococcus horikoshii* Inosine-5'-
monophosphate dehydrogenase
MGKFVEKLEKAIKGYTFDDVLLIPQATEVEPKDVDVSTRITPNVKLNI
PILSAAMDTVTEWEMAVAMAREGGLGVIHRNMGIEEQVEQVKRVKRAE
RLIVEDVITIAPDETVDFALFLMEKHGIDGLPVVEDEKVVGIITKKDI
AAREGKLVKELMTKEVITVPESIEVEEAALKIMIENRIDRLPVVDERGK
LVGLITMSDLVARKKYKNAVRDENGELLVAAAVSPFDIKRAIELDKAG
VDVIVVDTAHAHNLKAIKSMKEMRQKVDADFIVGNIANPKAVDDLTFA
DAVKVGIGPGSICTTRIVAGVGVPQITAVAMVADRAQEYGLYVIADGG
IRYSGDIVKAIAAGADAVMLGNLLAGTKEAPGKEVIINGRKYKQYRGM
GSLGAMMKGGAERYYQGGYMKTRKFVPEGVEGVVPYRGTVSEVLYQLV
GGLKAGMGYVGARNIRELKEKGEFVIITHAGIKESHPHDIIITNEAPN
YPLEKF

[SEQ ID NO: 61]
2fk5 *Thermus thermophilus* hb8 fuculose-1-
phosphate aldolase
MRARLYAAFRQVGEDLFAQGLISATAGNFSVRTKGGFLITKSGVQKAR
LTPEDLLEVPLEGPIPEGASVESVVHREVYRRTGARALVHAHPRVAVA
LSFHLSRLRPLDLEGQHYLKEVPVLAPKTVSATEEAALSVAEALREHR
ACLLRGHGAFAVGLKEAPEEALLEAYGLMTTLEESAQILLYHRLWQGA
GPALGGGE

[SEQ ID NO: 62]
2flf *Thermus thermophilus* hb8 fuculose-1-
phosphate aldolase
MRARLYAAFRQVGEDLFAQGLISATAGNFSVRTKGGFLITKSGVQKAR
LTPEDLLEVPLEGPIPEGASVESVVHREVYRRTGARALVHAHPRVAVA
LSFHLSRLRPLDLEGQHYLKEVPVLAPKTVSATEEAALSVAEALREHR
ACLLRGHGAFAVGLKEAPEEALLEAYGLMTTLEESAQILLYHRLWQGA
GPALGGGE

[SEQ ID NO: 63]

C5 Symmetry (5 Polypeptide chains)

1t0t *Geobacillus stearothermophilus* APC35880
Unknown Function
MSEAAQTLDGWYCLHDFRTIDWSAWKTLPNEEREAAISEFLALVDQWE
TTESEKQGSHAVYTIVGQKADILFMILRPTLDELHEIETALNKTKLAD
YLLPAYSYVSVVELSNYLASGSEDPYQIPEVRRRLYPILPKTNYICFY
PMDKRRQGNDNWYMLSMEQRRELMRAHG

[SEQ ID NO: 64]
1vdh *Thermus thermophilus* muconolactone
isomerase-like protein
MERHVPEPTHTLEGWHVLHDFRLLDFARWFSAPLEAREDAWEELKGLV
REWRELEEAGQGSYGIYQVVGHKADLLFLNLRPGLDPLLEAEARLSRS
AFARYLGRSYSFYSVVELGSQEKPLDPESPYVKPRLTPRVPKSGYVCF
YPMNKRRQGQDNWYMLPAKERASLMKAHGETGRKYQGEVMQVISGAQG
LDDWEWGVDLFSEDPVQFKKIVYEMRFDEVSARYGEFGPFFVGKYLDE
EALRAFLGL

[SEQ ID NO: 10]
1w8s *Thermoproteus tenax* FRUCTOSE-BISPHOSPHATE
ALDOLASE CLASS I
MANLTEKFLRIFARRGKSIILAYDHGIEHGPADFMDNPDSADPEYILR
LARDAGFDGVVFQRGIAEKYYDGSVPLILKLNGKTTLYNGEPVSVANC
SVEEAVSLGASAVGYTIYPGSGFEWKMFEELARIKRDAVKFDLPLVVE
SFPRGGKVVNETAPEIVAYAARIALELGADAMKIKYTGDPKTFSWAVK
VAGKVPVLMSGGPKTKTEEDFLKQVEGVLEAGALGIAVGRNVWQRRDA
LKFARALAELVYGGKKLAEPLNV

[SEQ ID NO: 65]
2b99 *Methanocaldococcus jannaschii* Riboflavin
synthase
MTKKVGIVDTTFARVDMASIAIKKLKELSPNIKIIRKTVPGIKDLPVA
CKKLLEEEGCDIVMALGMPGKAEKDKVCAHEASLGLMLAQLMTNKHII
EVFVHEDEAKDDKELDWLAKRRAEEHAENVYYLLFKPEYLTRMAGKGL
RQGFEDAGPARE TABLE 1B-continued Subunit Amino Acid Sequences of Symmetric
Protein Nodes Structures are designated by
Symmetry Type and Protein Data Bank Codes
<http://www.rcsb.org/pdb/home/home.do>.

[SEQ ID NO: 66]
2bbh *Thermotoga maritima* divalent cation
transport-related protein
GSHMEEKRLSAKKGLPPGTLVYTGKYREDFEIEVMNYSIEEFREFKTT
DVESVLPFRDSSTPTWINITGIHRTDVVQRVGEFFGTHPLVLEDILNV
HQRPKVEFFENYVFIVLKMFTYDKNLHELESEQVSLILTKNCVLMFQE
KIGDVFDPVRERIRYNRGIIRKKRADYLLYSLIDALVDDYFVLLEKID
DEIDVLEEEVLERPEKETVQRTHQLKRNLVELRKTIWPLREVLSSLYR
DVPPLIEKETVPYFRDVYDHTIQIADTVE

[SEQ ID NO: 67]
2bbj *Thermotoga maritima* divalent cation
transport-related protein
GSHMEEKRLSAKKGLPPGTLVYTGKYREDFEIEVMNYSIEEFREFKTT
DVESVLPFRDSSTPTWINITGIHRTDVVQRVGEFFGIHPLVLEDILNV
HQRPKVEFFENYVFIVLKMFTYDKNLHELESEQVSLILTKNCVLMFQE
KIGDVFDPVRERIRYNRGIIRKKRADYLLYSLIDALVDDYFVLLEKID
DEIDVLEEEVLERPEKETVQRTHQLKRNLVELRKTIWPLREVLSSLYR
DVPPLIEKETVPYFRDVYDHTIQIADTVETFRDIVSGLLDVYLSSVSN
KTNEVMKVLTIIATIFMPLTFIAGIYGMNFEYMPELRWKWGYPVVLAV
MGVIAVIMVVYFKKKKWL

[SEQ ID NO: 68]
2hn1 *Archaeoglobus fulgidus* Magnesium and cobalt
transporter
GSHMRIPATIKKKMALPPATPVFTGEKKVEETKITAAIYDEKSVEFKE
LEVGELESVVRSALALNKKLWIDVVGVHDESLIAKICEFLGIHPLAAE
DILNTAQRVKIEDYDDHLFLVLKILLYNETLEIDQLSLVLKKNLVATF
EEREYWILDSIRSRLKSGGRMRKLAGDYLAYTILDAVVDSYFEALLKI
SDEIEVLEDEVVSGDSTLIGKIHSLKREILAFRNAVWPLRDVLSFFTR
VEHELIGEEVKVYYRDVYDHAVRLME

[SEQ ID NO: 69]
2hn2 *Thermotoga maritima* Magnesium transport
protein corA
GSHMEEKRLSAKKGLPPGTLVYTGKYREDFEIEVMNYSIEEFREFKTT
DVESVLPFRDSSTPTWINITGIHRTDVVQRVGEFFGIHPLVLEDILNV
HQRPKVEFFENYVFIVLKMFTYDKNLHELESEQVSLILTKNCVLMFQE
KIGDVFDPVRERIRYNRGIIRKKRADYLLYSLIDALVDDYFVLLEKID
DEIDVLEEEVLERPEKETVQRTHQLKRNLVELRKTIWPLREVLSSLYR
DVPPLIEKETVPYFRDVYDHTIQIADTVETFRDIVSGLLDVYLSSVSN
KTNEVMKVLTIIATIFMPLTFIAGIYGMNFEYMPELRWKWGYPVVLAV
MGVIAVIMVVYFKKKKWL

[SEQ ID NO: 70]
2iub *Thermotoga maritima* DIVALENT CATION
TRANSPORT-RELATED PROTEIN
MGSDKIHHHHHHMEEKRLSAKKGLPPGTLVYTGKYREDFEIEVMNYSI
EEFREFKTTDVESVLPFRDSSTPTWINITGIHRTDVVQRVGEFFGIHP
LVLEDILNVHQRPKVEFFENYVFIVLKMFTYDKNLHELESEQVSLILT
KNCVLMFQEKIGDVFDPVRERIRYNRGIIRKKRADYLLYSLIDALVDD
YFVLLEKIDDEIDVLEEEVLERPEKETVQRTHQLKRNLVELRKTIWPL
REVLSSLYRDVPPLIEKETVPYFRDVYDHTIQIADTVETFRDIVSGLL
DVYLSSVSNKTNEVMKVLTIIATIFMPLTFIAGIYGMNFEYMPELRWK
WGYPVVLAVMGVIAVIMVVYFKKKKWL

[SEQ ID NO: 71]

C6 Symmetry (6 Polypeptide chains)

1i8f *Pyrobaculum aerophilum* PUTATIVE SNRNP
SM-LIKE PROTEIN
MASDISKCFATLGATLQDSIGKQVLVKLRDSHEIRGILRSFDQHVNLL
LEDAEEIIDGNVYKRGTMVVRGENVLFISPVPG

[SEQ ID NO: 72]
1ljo *Archaeoglobus fulgidus* Archaeal Sm-like
protein AF-Sm2
GAMVLPNQMVKSMVGKIIRVEMKGEENQLVGKLEGVDDYMNLYLTNAM
ECKGEEKVRSLGEIVLRGNNVVLIQPQEE

[SEQ ID NO: 73]
2a1b *Synechocystis sp.* pcc 6803 Carbon dioxide
concentrating mechanism protein
MSIAVGMIETRGFPAVVEAADSMVKAARVTLVGYEKIGSGRVTVIVRG TABLE 1B-continued Subunit Amino Acid Sequences of Symmetric
Protein Nodes Structures are designated by
Symmetry Type and Protein Data Bank Codes
<http://www.rcsb.org/pdb/home/home.do>.

DVSGVQASVSAGIEAANRVNGGEVLSTHIIARPHENLEYVLPIRYTEE
VEQFRTYGVPRGLEHHHHHH
[SEQ ID NO: 74]

2a18 *Synechocystis sp.* pcc 6803 Carbon dioxide
concentrating mechanism protein
MSAQSAVGSIETIGFPGILAAADAMVKAGRITIVGYIRAGSARFTLNI
RGDVQEVKTAMAAGIDAINRTEGADVKTWVIIPRPHENVVAVLPIDFS
PEVEPFREAAEGLNRRGVPRGLEHHHHHH
[SEQ ID NO: 75]

2di4 *Aquifex aeolicus* Cell division protein ftsH
homolog
FQGPLGSHMTISPKEKEKIAIHEAGHALMGLVSDDDDKVHKISIIPRG
MALGVTQQLPIEDKHIYDKKDLYNKILVLLGGRAAEEVFFGKDGITTG
AENDLQRATDLAYRMVSMWGMSDKVGPIAIRRVANPFLGGMTTAVDTS
PDLLREIDEEVKRIITEQYEKAKAIVEEYKEPLKAVVKKLLEKETITC
EEFVEVPKLYGIELKDKCKKEELFDKDRKSEENKELKSEEVKEEVV
[SEQ ID NO: 76]

2dr3 *Pyrococcus horikoshii* ot3 UPF0273 protein
PH0284 Unknown Function
MTRRVKTGIPGVDEILHGGIPERNVVLLSGGPGTGKTIFSQQFLWNGL
KMGEPGIYVALEEHPVQVRQNMAQFGKPVYEEKGMFAMVDAFTAGI
GKSKEYEKYIVHDLTDIREFIEVLRQAIRDINAKRVVVDSVTTLYINK
PAMARSIILQLKRVLAGTGCTSIFVSQVSVGERGFGGPGVEHGVDGII
RLDLDEIDGELKRSLIVWKMRGTSHSMRRHPFDITDKGIIVYPDKVLK
RGKVLEL
[SEQ ID NO: 77]

2ekd *Pyrococcus horikoshii* ot3 Hypothetical
protein PH0250
MQMNSEKFFKLFRVGETVLVEYSGTSRAELLLYYIVNNSKLPIVVDDI
LDTYYEFYTRLKVAGFDVAPLENVQVIKMGGTKDIGRVIGRLNISKYV
ISEQEYMEIVSQLKDYPVINPVLGLHKLILLGNTFENINVVKMVSNYV
GREERIAFYFVNRNVIEKHSSPILDLLEEVVTSILEITDSGIIIKKSI
KDEIAGKIVSPLLNF
[SEQ ID NO: 78]

2ewh *Halothiobacillus neapolitanus* Major
carboxysome shell protein 1A
MADVTGIALGMIETRGLVPAIEAADAMTKAAEVRLVGRQFVGGGYVTV
LVRGETGAVNAAVRAGADACERVGDGLVAAHIIARVHSEVENILPKAP
QA
[SEQ ID NO: 79]

C7 Symmetry (7 Polypeptide chains)

1h64 *Pyrococcus abyssi* SNRNP SM-LIKE PROTEIN
MAERPLDVIHRSLDKDVLVILKKGFEFRGRLIGYDIHLNVVLADAEMI
QDGEVVKRYGKIVIRGDNVLAISPTEE
[SEQ ID NO: 80]

1i4k *Archaeoglobus fulgidus* PUTATIVE SNRNP
SM-LIKE PROTEIN
MPPRPLDVLNRSLKSPVIVRLKGGREFRGTLDGYDIHMNLVLLDAEEI
QNGEVVRKVGSVVIRGDTVVFVSPAPGGE
[SEQ ID NO: 81]

1i81 *Methanothermobacter thermautotrophicus*
PUTATIVE SNRNP SM-LIKE PROTEIN
GSVIDVSSQRVNVQRPLDALGNSLNSPVIIKLKGDREFRGVLKSFDLH
MNLVLNDAEELEDGEVTRRLGTVLIRGDNIVYISP
[SEQ ID NO: 82]

1jbm *Methanothermobacter thermautotrophicus*
PUTATIVE SNRNP SM-LIKE PROTEIN
MIDVSSQRVNVQRPLDALGNSLNSPVIIKLKGDREFRGVLKSFDLHMN
LVLNDAEELEDGEVTRRLGTVLIRGDNIVYISRGKLAA
[SEQ ID NO: 83]

1jri *Methanothermobacter thermautotrophicus*
Sm-like Archaeal Protein 1 (SmAP1)
MIDVSSQRVNVQRPLDALGNSLNSPVIIKLKGDREFRGVLKSFDLHMN
LVLNDAEELEDGEVTRRLGTVLIRGDNIVYISRGKLA
[SEQ ID NO: 84]

1m5q *Pyrobaculum aerophilum* small nuclear
ribonucleoprotein homolog
FVAELNNLLGREVQVVLSNGEVYKGVLHAVDNQLNIVLANASNKAGEK
FNRVFIMYRYIVHIDSTERRIDMREFAKQAEKIFPGMVKYIEETNVVL
IGDKVRVSEIGVEGVGPVAERAKRLFEEFLKRYS
[SEQ ID NO: 85]

1mgq *Methanothermobacter thermautotrophicus*
SM -LIKE PROTEIN
GSVIDVSSQRVNVQRPLDALGNSLNSPVIIKLKGDREFRGVLKSFDLH
MNLVLNDAEELEDGEVTRRLGTVLIRGDNIVYISP
[SEQ ID NO: 86]

D2 Symmetry (4 Polypetide chains)

1a0e *Thermotoga neapolitana* XYLOSE ISOMERASE
AEFFPEIPKVQFEGKESTNPLAFKFYDPEEIIDGKPLKDHLKFSVAFW
HTFVNEGRDPFGDPTADRPWNRYTDPMDKAFARVDALFEFCEKLNIEY
FCFHDRDIAPEGKTLRETNKILDKVVERIKERMKDSNVKLLWGTANLF
SHPRYMHGAATTCSADVFAYAAAQVKKALEITKELGGEGYVFWGGREG
YETLLNTDLGFELENLARFLRMAVDYAKRIGFTGQFLIEPKPKEPTKH
QYDFDVATAYAFLKSHGLDEYFKFNIEANHATLAGHTFQHELRMARIL
GKLGSIDANQGDLLLGWDTDQFPTNVYDTTLAMYEVIKAGGFTKGGLN
FDAKVRRASYKVEDLFIGHIAGMDTFALGFKVAYKLVKDGVLDKFIEE
KYRSFREGIGRDIVEGKVDFEKLEEYIIDKETIELPSGKQEYLESLIN
SYIVKTILELR
[SEQ ID NO: 87]

1bxb *Thermus thermophilus* hb8 XYLOSE ISOMERASE
MYEPKPEHRFTFGLWTVGNVGRDPFGDAVRERLDPVYVVHKLAELGAY
GVNLHDEDLIPRGTPPQERDQIVRRFKKALDETGLKVPMVTANLFSDP
AFKDGAFTSPDPWVRAYALRKSLETMDLGAELGAEIYVVWPGREGAEV
EATGKARKVWDWVREALNFMAAYAEDQGYGYRFALEPKPNEPRGDIYF
ATVGSMLAFIHTLDRPERFGLNPEFAHETMAGLNFVHAVAQALDAGKL
FHIDLNDQRMSRFDQDLRFGSENLKAAFFLVDLLESSGYQGPRHFDAH
ALRTEDEEGVWAFARGCMRTYLILKERAEAFREDPEVKELLAAYYQED
PAALALLGPYSREKAEALKRAELPLEAKRRRGYALERLDQLAVEYLLG
VRG
[SEQ ID NO: 88]

1do6 *Pyrococcus furiosus* SUPEROXIDE REDUCTASE
MISETIRSGDWKGEKHVPVIEYEREGELVKVKVQVGKEIPHPNTTEHH
IRYIELYFLPEGENFVYQVGRVEFTAHGESVNGPNTSDVYTEPIAYFV
LKTKKKGKLYALSYCNIHGLWENEVTLE
[SEQ ID NO: 89]

1dof *Pyrobaculum aerophilum* ADENYLOSUCCINATE
LYASE
MHVSPFDWRYGSEEIRRLFTNEAIINAYLEVERALVCALEELGVAERG
CCEKVNKASVSADEVYRLERETGHDILSLVLLLEQKSGCRYVHYGATS
NDIIDTAWALLIRRALAAVKEKARAVGDQLASMARKYKTLEMVGRTHG
QWAEPITLGFKFANYYYELYIACRQLALAEEFIRAKIGGAVGTMASWG
ELGLEVRRRVAERLGLPHHVITTQVAPRESFAVLASALALMAAVFERL
AVEIRELSRPEIGEVVEGGGGSSAMPHKANPTASERIVSLARYVRALT
HVAFENVALWHERDLTNSANERVWIPEALLALDEILTSALRVLKNVYI
DEERITENLQKALPYILTEFHMNRMIKEGASRAEAYKKAKEVKALTFE
YQKWPVERLIEDALSLKLC
[SEQ ID NO: 90]

1gtd *Methanobacterium thermoautotrophicum*
Mth169, a Crucial Component of
Phosphoribosylformylglycinamidine Synthetase
MKFMVEVRIRLKKGMLNPEAATIERALALLGYEVEDTDTTDVITFTMD
EDSLEAVEREVEDMCQRLLCNPVIHDYDVSINEMSSH
[SEQ ID NO: 91]

1hyg *Methanocaldococcus jannaschii*
L-LACTATE/MALATE DEHYDROGENASE
MKVTIIGASGRVGSATALLLAKEPFMKDLVLIGREHSINKLEGLREDI
YDALAGTRSDANIYVESDENLRIIDESDVVIITSGVPRKEGMSRMDLA
KTNAKIVGKYAKKIAEICDTKIFVITNPVDVMTYKALVDSKFERNQVF
GLGTHLDSLRFKVAIAKFFGVHIDEVRTRIIGEHGDSMVPLLSATSIG
GIPIQKFERFKELPIDEIIEDVKTKGEQIIRLKGGSEFGPAAAILNVV TABLE 1B-continued Subunit Amino Acid Sequences of Symmetric
Protein Nodes Structures are designated by
Symmetry Type and Protein Data Bank Codes
<http://www.rcsb.org/pdb/home/home.do>.

RCIVNNEKRLLTLSAYVDGEFDGIRDVCIGVPVKIGRDGIEEVVSIEL
DKDEIIAFRKSAEIIKKYCEEVKNL
[SEQ ID NO: 92]

1ilg Pyrococcus furiosus TRANSCRIPTIONAL
REGULATOR LRPA
MKVTIIGASGRVGSATALLLAKEPFMKDLVLIGREHSINKLEGLREDI
YDALAGTRSDANIYVESDENLRIIDESDVVIITSGVPRKEGMSRMDLA
KTNAKIVGKYAKKIAEICDTKIFVITNPVDVMTYKALVDSKFERNQVF
GLGTHLDSLRFKVAIAKFFGVHIDEVRTRIIGEHGDSMVPLLSATSIG
GIPIQKFERFKELPIDEIIEDVKTKGEQIIRLKGGSEFGPAAAILNVV
RCIVNNEKRLLTLSAYVDGEFDGIRDVCIGVPVKIGRDGIEEVVSIEL
DKDEIIAFRKSAEIIKKYCEEVKNL
[SEQ ID NO: 93]

1ik6 Pyrobaculum aerophilum pyruvate
dehydrogenase
MKVTIIGASGRVGSATALLLAKEPFMKDLVLIGREHSINKLEGLREDI
YDALAGTRSDANIYVESDENLRIIDESDVVIITSGVPRKEGMSRMDLA
KTNAKIVGKYAKKIAEICDTKIFVITNPVDVMTYKALVDSKFERNQVF
GLGTHLDSLRFKVAIAKFFGVHIDEVRTRIIGEHGDSMVPLLSATSIG
GIPIQKFERFKELPIDEIIEDVKTKGEQIIRLKGGSEFGPAAAILNVV
RCIVNNEKRLLTLSAYVDGEFDGIRDVCIGVPVKIGRDGIEEVVSIEL
DKDEIIAFRKSAEIIKKYCEEVKNL
[SEQ ID NO: 94]

1ixr Thermus thermophilus Holliday junction DNA
helicase ruvA
MIRYLRGLVLKKEAGGFVLLAGGVGFFLQAPTPFLQALEEGKEVGHT
HLLLKEEGLSLYGFPDEENLALFELLLSVSGVGPKVALALLSALPPRL
LARALLEGDARLLTSASGVGRRLAERIALELKGKVPPHLLAGEKVESE
AAEEAVMALAALGFKEAQARAVVLDLLAQNPKARAQDLIKEALKRLRM
EDLALRPKTLDEYIGQERLKQKLRVYLEAAKARKEPLEHLLLFGPPGL
GKTTLAHVIAHELGVNLRVTSGPAIEKPGDLAAILANSLEEGDILFID
EIHRLSRQAEEHLYPAMEDFVMDIVIGQGPAARTIRLELPRFTLIGAT
TRPGLITAPLLSRFGIVEHLEYYTPEELAQGVMRDARLLGVRITEEAA
LEIGRRSRGTMRVARLFRRVRDFAQVAGEEVITRERALEALAALGLD
ELGLEKRDREILEVLILRFGGGPVGLATLATALSEDPGTLEEVHEPYL
IRQGLLKRTPRGRVATELARRHL
[SEQ ID NO: 95]

1jly Thermus thermophilus hb8 Thioesterase PaaI
MRDPFMEALGLKVLHLAPGEAVVAGEVRADHLNLHGTAHGGFLYALAD
SAFALASNTRGPAVALSCRMDYFRPLGAGARVEARAVEVNLSRRTATY
RVEVVSEGKLVALFTGTVFRLGGDGDDVPAGTGNLAPREA
[SEQ ID NO: 96]

1j2w Thermus thermophilus Aldolase protein
MDLAAHIDHTLLKPTATLEEVAKAAEEALEYGFYGLCIPPSYVAWVRA
RYPHAPFRLVTVVGFPLGYQEKEVKALEAALACARGADEVDMVLHLGR
AKAGDLDYLEAEVRAVREAVPQAVLKVILETGYFSPEEIARLAEEAIR
GGADFLKTSTGFGPRGASLEDVALLVRVAQGRAQVKAAGGIRDRETAL
RMLKAGASRLGTSSGVALVAGEGGTLGY
[SEQ ID NO: 97]

1jg8 Thermotoga maritima L-allo-threonine
aldolase
GPHMMIDLRSDTVTKPTEEMRKAMAQAEVGDDVYGEDPTINELERLAA
ETFGKEAALFVPSGTMGNQVSIMAHTQRGDEVILEADSHIFWYEVGAM
AVLSGVMPHPVPGKNGAMDPDDVRKAIRPRNIHFPRTSLIAIENTHNR
SGGRVVPLENIKEICTIAKEHGINVHIDGARIFNASIASGVPVKEYAG
YADSVMFCLSKGLCAPVGSVVVGDRDFIERARKARKMLGGGMRQAGVL
AAAGIIALTKMVDRLKEDHENARFLALKLKEIGYSVNPEDVKTNMVIL
RTDNLKVNAHGFIEALRNSGVLANAVSDTEIRLVTHKDVSRNDIEEAL
NIFEKLFRKFS
[SEQ ID NO: 98]

1jvb Sulfolobus solfataricus NAD(H)-DEPENDENT
ALCOHOL DEHYDROGENASE
MRAVRLVEIGKPLSLQEIGVPKPKGPQVLIKVEAAGVCHSDVHMRQGR
FGNLRIVEDLGVKLPVTLGHEIAGKIEEVGDEVVGYSKGDLVAVNPWQ
GEGNCYYCRIGEEHLCDSPRWLGINFDGAYAEYVIVPHYKYMYKLRRL
NAVEAAPLTCSGITTYRAVRKASLDPTKTLLVVGAGGGLGTMAVQIAK
AVSGATIIGVDVREEAVEAAKRAGADYVINASMQDPLAEIRRITESKG
VDAVIDLNNSEKTLSVYPKALAKQGKYVMVGLFGADLHYAPLITLSE TABLE 1B-continued Subunit Amino Acid Sequences of Symmetric
Protein Nodes Structures are designated by
Symmetry Type and Protein Data Bank Codes
<http://www.rcsb.org/pdb/home/home.do>.

IQFVGSLVGNQSDFLGIMRLAEAGKVKPMITKTMKLEEANEAIDNLEN
FKAIGRQVLIP
[SEQ ID NO: 99]

1knv Geobacillus stearothermophilus Bse634I
restriction endonuclease
MTTNLTNSNCVEEYKENGKTKIRIKPFNALIELYHHQTPTGSIKENLD
KLENYVKDVVKAKGLAIPTSGAFSNTRGTWFEVMIAIQSWNYRVKREL
NDYLIIKMPNVKTFDFRKIFDNETREKLHQLEKSLLTHKQQVRLITSN
PDLLIIRQKDLIKSEYNLPINKLTHENIDVALTLFKDIEGKCKWDSLV
AGVGLKTSLRPDRRLQLVHEGNILKSLFAHLKMRYWNPKAEFKYYGAS
SEPVSKADDDALQTAATHTIVNVNSTPERAVDDIFSLTSFEDIDKMLD
QIIKK
[SEQ ID NO: 100]

1lk5 Pyrococcus horikoshii D-Ribose-5-Phosphate
Isomerase
MNVEEMKKIAAKEALKFIEDDMVIGLGTGSTTAYFIKLLGEKLKRGEI
SDIVGVPTSYQAKLLAIEHDIPIASLDQVDAIDVAVDGADEVDPNLNL
IKGRGAALTMEKIIEYRAGTFIVLVDERKLVDYLCQKMPVPIEVIPQA
WKAIIEELSIFNAKAELRMGVNKDGPVITDNGNFIIDAKFPRIDDPLD
MEIELNTIPGVIENGIFADIADIVIVGTREGVKKLER
[SEQ ID NO: 101]

1lvw Methanothermobacter thermautotrophicus
glucose-1-phosphate thymidylyltransferase
GAHMKGIVLAGGSGTRLYPITRAVSKQLLPIYDKPMIYYPLSVLMLAG
IRDILIISTPRDLPLYRDLLGDGSQFGVRFSYRVQEEPRGIADAFIVG
KDFIGDSKVALVLGDNVFYGHRFSEILRRAASLEDGAVIFGYYVRDPR
PFGVVEFDSEGRVISIEEKPSRPKSNYVVPGLYFYDNQVVEIARRIEP
SDRGELEITSVNEEYLRMGKLRVELMRGMAWLDTGTHDGLLEASSFI
ETIQKRQGFYIACLEEIAYNNGWITREDVLEMAEKLEKTDYGKYLRDL
AEGNFHG
[SEQ ID NO: 102]

1m8k Methanothermobacter thermautotrophicus
Nicotinamide-nucleotide Adenylyltransferase
VMTMRGLLVGRMQPFHRGALQVIKSILEEVDELIICIGSAQLSHSIRD
PFTAGERVMMLTKALSENGIPASRYYIIPVQDIECNALWVGHIKMLTP
PFDRVYSGNPLVQRLFSEDGYEVTAPPLFYRDRYSGTEVRRRMLDDGD
WRSLLPESVVEVIDEINGVERIKHLAKKEVSELGGIS
[SEQ ID NO: 103]

1mal Methanothermobacter thermautotrophicus
superoxide dismutase
MNDLEKKFYELPELPYPYDALEPHISREQLTIHHQKHHQAYVDGANAL
LRKLDEARESDTDVDIKAALKELSPHVGGYVLHLFFWGNMGPADECGG
EPSGKLAEYIEKDFGSFERFRKEFSQAAISAEGSGWAVLTYCQRTDRL
FIMQVEKHNVNVIPHFRILLVLDVWEHAYYIDYRNVRPDYVEAFWNIV
NWKEVEKRFEDIL
[SEQ ID NO: 12]

1nto Sulfolobus solfataricus NAD-dependent
alcohol dehydrogenase
MRAVRLVEIGKPLSLQEIGVPKPKGPQVLIKVEAAGVCHSDVHMRQGR
FGNLRIVEDLGVKLPVTLGHEIAGKIEEVGDEVVGYSKGDLVAVNPWQ
GEGNCYYCRIGEEHLCDSPRWLGINFDGAYAEYVIVPHYKYMYKLRRL
NAVEAAPLTCSGITTYRAVRKASLDPTKTLLVVGAGGGLGTMAVQIAK
AVSGATIIGVDVREEAVEAAKRAGADYVINASMQDPLAEIRRITESKG
VDAVIDLNYSEKTLSVYPKALAKQGKYVMVGLFGADLHYAPLITLSE
IQFVGSLVGNQSDFLGIMRLAEAGKVKPMITKTMKLEEANEAIDNLEN
FKAIGRQVLIP
[SEQ ID NO: 13]

1nvg Sulfolobus solfataricus NAD-dependent
alcohol dehydrogenase
MRAVRLVEIGKPLSLQEIGVPKPKGPQVLIKVEAAGVCHSDVHMRQGR
FGNLRIVEDLGVKLPVTLGHEIAGKIEEVGDEVVGYSKGDLVAVNPWQ
GEGNCYYCRIGEEHLCDSPRWLGINFDGAYAEYVIVPHYKYMYKLRRL
NAVEAAPLTCSGITTYRAVRKASLDPTKTLLVVGAGGGLGTMAVQIAK
AVSGATIIGVDVREEAVEAAKRAGADYVINASMQDPLAEIRRITESKG
VDAVIDLNYSEKTLSVYPKALAKQGKYVMVGLFGADLHYAPLITLSE
IQFVGSLVGNQSDFLGIMRLAEAGKVKPMITKTMKLEEANEAIDNLEN
FKAIGRQVLIP TABLE 1B-continued Subunit Amino Acid Sequences of Symmetric
Protein Nodes Structures are designated by
Symmetry Type and Protein Data Bank Codes
<http://www.rcsb.org/pdb/home/home.do>.

[SEQ ID NO: 104]

1o2a *Thermotoga maritima* Thymidylate synthase
thyX
MGSDKIHHHHHHMKIDILDKGFVELVDVMGNDLSAVRAARVSFDMGLK
DEERDRHLIEYLMKHGHETPFEHIVFTFHVKAPIFVARQWFRHRIASY
NELSGRYSKLSYEFYIPSPERLEGYKTTIPPERVTEKISEIVDKAYRT
YLELIESGVPREVARIVLPLNLYTRFFWTVNARSLMNFLNLRADSHAQ
WEIQQYALAIARIFKEKCPWTFEAFLKYAYKGDILKEVQV
[SEQ ID NO: 105]

1o54 *Thermotoga maritima* SAM-dependent
O-methyltransferase
MGSDKIHHHHHHVGKVADTLKPGDRVLLSFEDESEFLVDLEKDKKLHT
HLGIIDLNEVFEKGPGEIIRTSAGKKGYILIPSLIDEIMNMKRRTQIV
YPKDSSFIAMMLDVKEGDRIIDTGVGSGAMCAVLARAVGSSGKVFAYE
KREEFAKLAESNLTKWGLIERVTIKVRDISEGFDEKDVDALFLDVPDP
WNYIDKCWEALKGGGRFATVCPTTNQVQETLKKLQELPFIRIEVWESL
FRPYKPVPERLRPVDRMVAHTAYMIFATKVCRREETE
[SEQ ID NO: 106]

1r37 *Sulfolobus solfataricus* NAD-dependent
alcohol dehydrogenase
MRAVRLVEIGKPLSLQEIGVPKPKGPQVLIKVEAAGVCHSDVHMRQGR
FGNLRIVEDLGVKLPVTLGHEIAGKIEEVGDEVVGYSKGDLVAVNPWQ
GEGNCYYCRIGEEHLCDSPRWLGINFDGAYAEYVIVPHYKYMYKLRRL
NAVEAAPLTCSGITTYRAVRKASLDPTKTLLVVGAGGGLGTMAVQIAK
AVSGATIIGVDVREEAVEAAKRAGADYVINASMQDPLAEIRRITESKG
VDAVIDLNNSEKTLSVYPKALAKQGKYVMVGLFGADLHYHAPLITLSE
IQFVGSLVGNQSDFLGIMRLAEAGKVKPMITKTMKLEEANEAIDNLEN
FKAIGRQVLIP
[SEQ ID NO: 107]

1ris *Thermus thermophilus* RIBOSOMAL PROTEIN S6
MRRYEVNIVLNPNLDQSQLALEKEIIQRALENYGARVEKVEELGLRRL
AYPIAKDPQGYFLWYQVEMPEDRVNDLARELRIRDNVRRVMVVKSQEP
FLANA
[SEQ ID NO: 108]

1rtw *Pyrococcus furiosus* dsm 3638
transcriptional activator, putative
MFSEELIKENENIWRRFLPHKFLIEMAENTIKKENFEKWLVNDYYFVK
NALRFMALLMAKAPDDLLPFFAESIYYISKELEMFEKKAQELGISLNG
EIDWRAKSYVNYLLSVASLGSFLEGFTALYCEEKAYYEAWKWVRENLK
ERSPYQEFINHWSSQEFGEYVKRIEKILNSLAEKHGEFEKERAREVFK
EVSKFELIFWDIAYGGEGNVLEHHHHHH
[SEQ ID NO: 14]

1stp *Streptomyces avidinii* STREPTAVIDIN
DPSKDSKAQVSAAEAGITGTWYNQLGSTFIVTAGADGALTGTYESAVG
NAESRYVLTGRYDSAPATDGSGTALGWTVAWKNNYRNAHSATTWSGQY
VGGAEARINTQWLLTSGTTEANAWKSTLVGHDTFTKVKPSAASIDAAK
KAGVNNGNPLDAVQQ
[SEQ ID NO: 11]

1u9y *Methanocaldococcus jannaschii* Ribose-
phosphate pyrophosphokinase
MIVVSGSQSQNLAFKVAKLLNTKLTRVEYKRFPDNEIYVRIVDEINDD
EAVIINTQKNQNDAIVETILLCDALRDEGVKKITLVAPYLAYARQDKK
FNPGEAISIRALAKIYSNIVDKLITINPHETHIKDFFTIPFIYGDAVP
KLAEYVKDKLNDPIVLAPDKGALEFAKTASKILNAEYDYLEKTRLSPT
EIQIAPKTLDAKDRDVFIVDDIISTGGTMATAVKLLKEQGAKKIIAAC
VHPVLIGDALNKLYSAGVEEVVGTDTYLSEVSKVSVAEVIVDLL
[SEQ ID NO: 109]

1udd *Pyrococcus horikoshii* ot3 transcriptional
regulator lipid binding protein
MRVMITDKLRRDSEQIWKKIFEHPFVVQLYSGTLPLEKFKFYVLQDFN
YLVGLTRALAVISSKAEYPLMAELIELARDEVTVEVENYVKLLKELDL
TLEDAIKTEPTLVNSAYMDFMLATAYKGNIIEGLTALLPCFWSYAEIA
EYHKDKLRDNPIKIYREWGKVYLSNEYLNLVGRLRKIIDSSGHSGYDR
LRRIFITGSKFELAFWEMAWRGGDVFLEHHHHHH TABLE 1B-continued Subunit Amino Acid Sequences of Symmetric
Protein Nodes Structures are designated by
Symmetry Type and Protein Data Bank Codes
<http://www.rcsb.org/pdb/home/home.do>.

[SEQ ID NO: 110]

1uir *Thermus thermophilus* Polyamine
Aminopropyltransferase
MDYGMYFFEHVTPYETLVRRMERVIASGKTPFQDYFLFESKGFGKVLI
LDKDVQSTERDEYIYHETLVHPAMLTHPEPKRVLIVGGGEGATLREVL
KHPTVEKAVMVDIDGELVEVAKRHMPEWHQGAFDDPRAVLVIDDARAY
LERTEERYDVVIIDLTDPVGEDNPARLLYTVEFYRLVKAHLNPGGVMG
MQTGMILLTHHRVHPVVHRTVREAFRYVRSYKNHIPGFFLNFGFLLAS
DAFDPAAFSEGVIEARIRERNLALRHLTAPYLEAMFVLPKDLLEALEK
ETMVSTDQNPFYVTPEGEARQAPYKG
[SEQ ID NO: 111]

1usy *Thermotoga maritima* ATP PHOSPHO-
RIBOSYLTRANSFERASE REGULATORY SUBUNIT
MDFLDFEKVFSFYSKATKKGFSPFFVPALEKAEEPAGNFFLDRKGNLF
SIREDFTKTVLNHRKRYSPDSQIKVWYADFVYRYSGSDLVAEYQLGLE
KVPRNSLDDSLEVLEIIVESASEFFEGPVIVEIGHTGVYEDLLKEIPK
DLHEKVLNLIDTKNLAEIEFLSHMKKIDLSRVEKIIEDSIYRRSPEHL
KTMDLPLSVREDLLSASSFLQEKFPTVSVEIDLTLARTIEEYCGLIFT
IYDTSSSRLVAAGGEYTVNGEKGVGGSIFLEGKTC
[SEQ ID NO: 112]

*Thermotoga maritima* ATP
PHOSPHORIBOSYLTRANSFERASE
MLKLAIPKGRLEEKVMTYLKKTGVIFERESSILREGKDIVCFMVRPFD
VPTYLVHGVADIGFCGTDVLLEKETSLIQPFFIPTNISRMVLAGPKGR
GIPEGEKRIATKFPNVTQRYCESKGWHCRIIPLKGSVELAPIAGLSDL
IVDITETGRTLKENNLEILDEIFVIRTHVVVNPSYRTKREKVVSFLE
KLQEVIEHDSNEQSRG
[SEQ ID NO: 113]

1uxt *Thermoproteus tenax* GLYCERALDEHYDE-3-
PHOSPHATE DEHYDROGENASE (NADP+)
MRAGLLEGVIKEKGGVPVYPSYLAGEWGGSGQEIEVKSPIDLATIAKV
ISPSREEVERTLDVLFKRGRWSARDMPGTERLAVLRKAADIIERNLDV
FAEVLVMNAGKPKSAAVGEVKAAVDRLRLAELDLKKIGGDYIPGDWTY
DTLETEGLVRREPLGVVAAITPFNYPLFDAVNKITYSFIYGNAVVVKP
SISDPLPAAMAVKALLDAGFPPDAIALLNLPGKEAEKIVADDRVAAVS
FTGSTEVGERVVKVGGVKQYVMELGGGDPAIVLEDADLDLAADKIARG
IYSYAGQRCDAIKLVLAERPVYGKLVEEVAKRLSSLRVGDPRDPTVDV
GPLISPSAVDEMMAAIEDAVEKGGRVLAGGRRLGPTYVQPTFVEAPAD
RVKDMVLYKREVFAPVALAVEVKDLDQAIELANGRPYGLDAAVFGRDV
VKIRRAVRLLEVGAIYINDMPRHGIGYYPFGGRKKSGVFREGIGYAVE
AVTAYKTIVFPNYKGKGVWKYE
[SEQ ID NO: 114]

1v6t *Pyrococcus horikoshii* ot3 Hypothetical
UPF0271 Lactam Utilization Protein PH0986
MRVDLNSDLGESFGRYKLGLDEEVMKYITSANVACGWHAGDPLVMRKT
VRLAKENDVQVGAHPGYPDLMGFGRRYMKLTPEEARNYILYQVGALYA
FAKAEGLELQHVKPHGALYNAMVKEEDLARAVIEGILDFDKDLILVTL
SNSRVADIAEEMGLKVAHEVFADRAYNPDGTLVPRGRPGAVIEDKEEI
AERVISMVKDGGIRAINGEWVDLKVDTICVHGDNPKAVEITSYIRKVL
EEEGVKIVPMKEFIR
[SEQ ID NO: 115]

1v8o *Pyrobaculum aerophilum* hypothetical
exonuclease protein PAE2754
MSYYHHHHHHDYDIPTTENLYFQGAMAVEYLVDASALYALAAHYDKWI
KHREKLAILHLTIYEAGNALWKEARLGRVDWAAASRHLKKVMSSFKVL
EDPPLDEVMRVAVERGLTFYDASYAYVAESSGLVLVTQDRELLAKTKG
AIDVETLLVRLAAQ
[SEQ ID NO: 116]

1v8p *Pyrobaculum aerophilum* hypothetical
exonuclease protein PAE2754
MSYYHHHHHHDYDIPTTENLYFQGAMAVEYLVDASALYALAAHYDKWI
KHREKLAILHLTIYEAGNALWKEARLGRVDWAAASRHLKKVLSSFKVL
EDPPLDEVLRVAVERGLTFYDASYAYVAESSGLVLVTQDRELLAKTKG
AIDVETLLVRLAAQ
[SEQ ID NO: 117]

1vc2 *Thermus thermophilus* Glyceraldehyde
3-Phosphate Dehydrogenase

TABLE 1B-continued

Subunit Amino Acid Sequences of Symmetric
Protein Nodes Structures are designated by
Symmetry Type and Protein Data Bank Codes
<http://www.rcsb.org/pdb/home/home.do>.

MKVGINGFGRIGRQVFRILHERGVEVALINDLTDNKTLAHLLKYDSTY
GRFPGAVGYDEENLYVDGKAIRATAIKDPREIPWKQAGVGVVVESTGV
FTDGEKARAHLEAGAKKVIITAPAKNEDITVVLGVNHEQYDPAKHHIL
SNASCTTNSLAPVMKVLEKAFGVEKALMTTVHSYTNDQRLLDLPHKDL
RRARAAALNIIPTTTGAAKATALVLPSLKGRFDGMALRVPTPTGSISD
ITALLKREVTAEEVNAALKAAAEGPLKGILAYTEDEIVLRDIVMDPHS
SIVDGKLTKAIGNLVKVFAWYDNEWGYANRVADLVELVLKKGV
[SEQ ID NO: 118]

1vco Thermus thermophilus CTP synthetase
MNGSADAGPRPRKYVFITGGVVSSLGKGILTSSLGALLRARGYRVTAI
KIDPYVNVDAGTMRPYEHGEVKIRGHFKTADGAETDLDIGHYERFLDMDLSRG
NNLTTGQVYLSVIQKERRGEYLSQTVQVIPHITDEIKERIRKVAEEQK
AEIVVVEVGGTVGDIESLPFLEAIRQFRFDEGEGNTLYLHLTLVPYLE
TSEEFKTKPTQHSVATLRGVGIQPDILVLRSARPVPEEVRRKVALFTN
VRPGHVFSSPTVEHLYEVPLLLEEQGLGRAVERALGLEAVIPNLSFWQ
EAVRVLKHPERTVKIAIAGKYVKMPDAYLSLLEALRHAGIKNRARVEV
KWVDAESLEAADLEEAPRDVSGILVPGGFGVRGIEGKVRAAQYARERK
IPYLGICLGLQIAVIEFARNVAGLKGANSTEFDPHTPHPVIDLMPEQL
EVEGLGGTMRLGDWPMRIKPGTLLHRLYGKEEVLERHRHRYEVNPLYV
DGLERAGLVVSATTPGMRGRGAGLVEAIELKDHPFFLGLQSHPEFKSR
PMRPSPPFVGFVEAALAYQERA
[SEQ ID NO: 119]

1vdk Thermus thermophilus hb8 Fumarate hydratase
class II
MEYRIERDTMGEVRVPADKYWGAQTQRSLENFRIGTDRFRMPLEIIRA
YGMLKKAAARANLELGELPEEIAKAIIQAAEEVVQGKWDDHFPLVVFQ
TGSGTQTNMNVNEVIANRASEILGKPLGSKYAHPNDHVNRGQSSNDTF
PTAMYVAVALALHQRLYPAVEGLIRTFTAKAQAFDQIVKVGRTHLMDA
VPITLGQEIGSWAAQLKTTLAAVKEMEKGLYNLAIGGTAVGTGLNAHP
RFGELVAKYLAEETGLPFRVAENRFAALAAHDELVNVMGAIRTLAGAL
MKIGNDVRWLASGPYAGIGEITIPANEPGSSIMPGKVNPTQVEALTMV
VVRVYGNDHTVAFAGSQGNFQLNVYKPVMAYSTLESINLLADAVASFD
AHLAQGIEPNLERIEEYLQKNPMLATALNKAIGYDKAAEIVKKALKEK
KTLKQAALELGYLTEEEFDRIVVPMRLAKPHEGA
[SEQ ID NO: 120]

1vjp Thermotoga maritima msb8 Myo-inositol-1-
phosphate synthase-related protein
MGSDKIHHHHHHMVKVLILGQGYVASTFVAGLEKLRKGEIEPYGVPLA
RELPIGFEDIKIVGSYDVDRAKIGKKLSEVVKQYWNDVDSLTSDPEIR
KGVHLGSVRNLPIEAEGLEDSMTLKEAVDTLVKEWTELDPDVIVNTCT
TEAFVPFGNKEDLLKAIENNDKERLTATQVYAYAAALYANKRGGAAFV
NVIPTFIANDPAFVELAKENNLVVFGDDGATGATPFTADVLSHLAQRN
RYVKDVAQFNIGGNMDFLALTDDGKNKSKEFTKSSIVKDILGYDAPHY
IKPTGYLEPLGDKKFIAIHIEYVSFNGATDELMINGRINDSPALGGLL
VDLVRLGKIALDRKEFGTVYPVNAFYMKNPGPAEEKNIPRIIAYEKMR
IWAGLKPKWL
[SEQ ID NO: 121]

1vk8 Thermotoga maritima hypothetical protein
TM0486
MGSDKIHHHHHHMPKVTVSIKVVPAVEDGRLHEVIDRAIEKISSWGMK
YEVGPSNTTVEGEFEEIMDRVKELARYLEQFAKRFVLQLDIDYKAGGI
TIEEKVSKYR
[SEQ ID NO: 122]

1vl2 Thermotoga maritima Argininosuccinate
synthase
MGSDKIHHHHHHMKEKVVLAYSGGLDTSVILKWLCEKGFDVIAYVANV
GQKDDFVAIKEKALKTGASKVYVEDLRREFVTDYIFTALLGNAMYEGR
YLLGTAIARPLIAKRQVEIAEKEGAQYVAHGATGKGNDQVRFELTYAA
LNPNLKVISPWKDPEFLAKFKGRTDLINYAMEKGIPIKVSKKRPYSED
ENLMHISHEAGKLEDPAHIPDEDVFTWTVSPKDAPDEETLLEIHFENG
IPVEVVNLKDGTEKTDPLELFEYLNEVGAKNGVGRLDMVENRFIGIKS
RGVYETPGATILWIAHRDLEGITMDKEVMHLRDMLAPKFAELIYNGFW
FSPEMEFLLAAFRKAQENVTGKVTVSIYKGNVMPVARYSPYSLYNPEL
SSMDVEGGFDATDSKGFININIHALRLKVHQLVKKGYQR
[SEQ ID NO: 123]

1vlv Thermotoga maritima Ornithine
carbamoyltransferase
MGSDKIHHHHHHMSVNLKGRSLLTLLDFSPEEIRYLLDISKQVKMENR
SKLRTERFKGMTLAMIFEKRSTRTRLAFETAFAEEGGHPIFLSPNDIH TABLE 1B-continued Subunit Amino Acid Sequences of Symmetric
Protein Nodes Structures are designated by
Symmetry Type and Protein Data Bank Codes
<http://www.rcsb.org/pdb/home/home.do>.

LGAKESLEDTARVLGRMVDAIMFRGYKQETVEKLAEYSGVPVYNGLTD
EFHPTQALADLMTIEENFGRLKGVKVVFMGDTRNNVATSLMIACAKMG
MNFVACGPEELKPRSDVFKRCQEIVKETDGSVSFTSNLEEALAGADVV
YTDVWASMGEEDKEKERMALLKPYQVNERVMEMTGKSETIFMHCLPAV
KGQEVTYEVIEGKQSRVWDEAENRKHTIKAVMIATLL
[SEQ ID NO: 124]

1vr6 Thermotoga maritima Phospho-2-dehydro-3-
deoxyheptonate aldolase
MGSDKIHHHHHHMIVVLKPGSTEEDIRKVVKLAESYNLKCHISKGQER
TVIGIIGDDRYVVADKFESLDCVESVVRVLKPYKLVSREFHPEDTVID
LGDVKIGNGYFTIIAGPCSVEGREMLMETAHFLSELGVKVLRGGAYKP
RTSPYSFQGLGEKGLEYLREAADKYGMYVVTEALGEDDLPKVAEYADI
IQIGARNAQNFRLLSKAGSYNKPVLLKRGFMNTIEEFLLSAEYIANSG
NTKIILCERGIRTFEKATRNTLDISAVPIIRKESHLPILVDPSHSGGR
RDLVIPLSRAAIAVGAHGIIVEVHPEPEKALSDGKQSLDFELFKELVQ
EMKKLADALGVKVN
[SEQ ID NO: 125]

1w3i Sulfolobus solfataricus 2-KETO-3-DEOXY
GLUCONATE ALDOLASE
PEIITPIITPFTKDNRIDKEKLKIHAENLIRKGIDKLFVNGTTGLGPS
LSPEEKLENLKAVYDVTNKIIFQVGGLNLDDAIRLAKLSKDFDIVGIA
SYAPYYYPRMSEKHLVKYFKTLCEVSPHPVYLYNYPTATGKDIDAKVA
KEIGCFTGVKDTIENIIHTLDYKRLNPNMLVYSGSDMLIATVASTGLD
GNVAAGSNYLPEVTVTIKKLAMERKIDEALKLQFLHDEVIEASRIFGS
LSSNYVLTKYFQGYDLGYPRPPIFPLDDEEERQLIKKVEGIRAKLVEL
KILKE
[SEQ ID NO: 126]

1wb7 Sulfolobus solfataricus SUPEROXIDE
DISMUTASE [FE]
TLQIQFKKYELPPLPYKIDALEPYISKDIIDVHYNGHHKGFVNGANSL
LERLEKVVKGDLQTGQYDIQGIIRGLTFNINGHKLHALYWENMAPSGK
GGGKPGGALADLINKQYGSFDRFKQVFTETANSLPGTGWAVLYYDTES
GNLQIMTFENHFQNHIAEIPIILILDEFEHAYYLQYKNKRADYVNAWW
NVVNWDAAEKKLQKYLTK
[SEQ ID NO: 127]

1wb8 Sulfolobus solfataricus SUPEROXIDE
DISMUTASE [FE]
TLQIQFKKYELPPLPYKIDALEPYISKDIIDVHYNGHHKGYVNGANSL
LERLEKVVKGDLQTGQYDIQGIIRGLTFNINGHKLHALYWENMAPSGK
GGGKPGGALADLINKQYGSFDRFKQVFTETANSLPGTGWAVLYYDTES
GNLQIMTFENHFQNHIAEIPIILILDEFEHAYYLQYKNKRADYVNAWW
NVVNWDAAEKKLQKYLTK
[SEQ ID NO: 128]

1wlu Thermus thermophilus hb8 phenylacetic acid
degradation protein PaaI
MRDPFMEALGLKVLHLAPGEAVVAGEVRADHLNLHGTAHGGFLYALAD
SAFALASNTRGPAVALSCRMDYFRPLGAGARVEARAVEVNLSRRTATY
RVEVVSEGKLVALFTGTVFRLGGDGDDVPAGTGNLAPREA
[SEQ ID NO: 129]

1ws9 Thermus thermophilus hb8 acyl-CoA
dehydrogenase
MGLWFEEGAEERQVLGPFREFLKAEVAPGAAERDRTGAFPWDLVRKLA
EFGVFGALVPEAYGGAGLSTRLFARMVEAIAYYDGALATVASHNSLA
TGHILLAGSEAQKEAFLPKLASGEALGAWGLTEPGSGSDAAALKTKAE
KVEGGWRLNGTKQFITQGSVAGVYVVMARTDPPPSPERKHQGISAFAF
FRPERGLKVGRKEEKLGLTASDTAQLILEDLFVPEEALLGERGKGFYD
VLRVLDGGRIGIAAMAVGLGQAALDYALAYAKGREAFGRPIAEFEGVS
FKLAEAATELEAARLLYLKAAELKDAGRPPTLEAAQAKLFASEAAVKA
CDEAIQILGGYGYVKDYPVERYWRDARLTRIGEGTSEILKLVIARRLL
EAV
[SEQ ID NO:130]

1wyt Thermus thermophilus hb8 glycine
dehydrogenase (decarboxylating) subunit 1
MDYTPHTEEEIREMLRRVGAASLEDLFAHLPKEILSPPIDLPEPLPEW
KVLEELRRLAAQNLPAHKAFLGGGVRSHVPPVVQALAARGEFLTAYT
PYQPEVSQGVLQATFEYQTMIAELAGLEIANASMYDGATALAEGVLLA
LRETGRMGVLVSQGVHPEYRAVLRAYLEAVGAKLLTPLEGGRTPLPE
VGEEVGAVVVQNPNFLGALEDLGPFAEAAHGAGALFVAVADPLSLGVL TABLE 1B-continued Subunit Amino Acid Sequences of Symmetric
Protein Nodes Structures are designated by
Symmetry Type and Protein Data Bank Codes
<http://www.rcsb.org/pdb/home/home.do>.

KPPGAYGADIAVGDGQSLGLPMGFGGPHFGFLATKKAFVRQLPGRLVS
ETVDVEGRRGFILTLQAREQYIRRAKAKSNITTNAQLTALMGAMYLAA
LGPEGLREVALKSVEMAHKLHALLLEVPGVRPFTPKPFFNEFALALPK
DPEAVRRALAERGFHGATPVPREYGENLALFAATELHEEEDLLALREA
LKEVLA
[SEQ ID NO: 131]

*Thermus thermophilus* hb8 glycine dehydrogenase
subunit 2 (P-protein)
MSFPLIFERSRKGRRGLKLVKAVPKAEDLIPKEHLREVPPRLPEVDEL
TLVRHYTGLSRRQVGVDTTFYPLGSCTMKYNPKLHEEAARLFADLHPY
QDPRTAQGALRLMWELGEYLKALTGMDAITLEPAAGAHGELTGILIIR
AYHEDRGEGRTRRVVLVPDSAHGSNPATASMAGYQVREIPSGPEGEVD
LEALKRELGPHVAALMLTNPNTLGLFERRILEISRLCKEAGVQLYYDG
ANLNAIMGWARPGDMGFDVVHLNLHKTFTVPHGGGGPGSGPVGVKAHL
APYLPVPLVERGEEGFYLDFDRPKSIGRVRSFYGNFLALVRAWAYIRT
LGLEGLKKAAALAVLNARYLKELLKEKGYRVPYDGPSMHEFVAQPPEG
FRALDLAKGLLELGFHPPTVYFPLIVKEALMVEPTETEAKETLEAFAE
AMGALLKKPKEWLENAPYSTPVRRLDELRANKHPKLTYFDEG
[SEQ ID NO: 132]

1x01 *Thermus thermophilus* Homoisocitrate
dehydrogenase
AYRICLIEGDGIGHEVIPAARRVLEATGLPLEFVEAEAGWETFERRGT
SVPEETVEKILSCHATLFGAATSPTRKVPGFFGAIRYLRRRLDLYANV
RPAKSRPVPGSRPGVDLVIVRENTEGLYVEQERRYLDVAIADAVISKK
ASERIGRAALRIAEGRPRKTLHIAHKANVLPLTQGLFLDTVKEVAKDF
PLVNVQDIIVDNCAMQLVMRPERFDVIVTTNLLGDILSDLAAGLVGGL
GLAPSGNIGDTTAVFEPVHGSAPDIAGKGIANPTAAILSAAMMLDYLG
EKEAAKRVEKAVDLVLERGPRTPDLGGDATTEAFTEAVVEALKSL
[SEQ ID NO: 133]

1x1e *Thermus thermophilus* hb8 2-deoxy-
D-gluconate 3-dehydrogenase
MERKALVTGGSRGIGRAIAEALVARGYRVAIASRNPEEAAQSLGAVPL
PTDLEKDDPKGLVKRALEALGGLHVLVHAAAVNVRKPALELSYEEWRR
VLYLHLDVAFLLAQAAAPHMAEAGWGRVLFIGSVTTFTAGGPVPIPAY
TTAKTALLGLTRALAKEWARLGIRVNLLCPGYVETEFTLPLRQNPELY
EPITARIPMGRWARPEEIARVAAVLCGDEAEYLTGQAVAVDGGFLAY
[SEQ ID NO: 134]

1x10 *Pyrococcus furiosus* Pyrrolidone-carboxylate
peptidase
MKVLVTGFEPFGGEKINPTERIAKDLDGIKIGDAQVFGRVLPVVFGKA
KEVLEKTLEEIKPDIAIHVGLAPGRSAISIERIAVNAIDARIPDNEGK
KIEDEPIVPGAPTAYFSTLPIKKIMKKLHERGIPAYISNSAGLYLSNY
VMYLSLHHSATKGYPKMSGFIHVPYIPEQIIDKIGKGQVPPSMSYEMA
LEAVKVAIEVALEELL
[SEQ ID NO: 135]

1xtt *Sulfolobus solfataricus* Probable uracil
phosphoribosyltransferase
MPLYVIDKPITLHILTQLRDKYTDQINFRKNLVRLGRILGYEISNTLD
YEIVEVETPLGVKTKGVDITDLNNIVIINILRAAVPLVEGLLKAFPKA
RQGVIGASRVEVDGKEVPKDMDVYIYYKKIPDIRAKVDNVIIADPMIA
TASTMLKVLEEVVKANPKRIYIVSIISSEYGVNKILSKYPFIYLFTVA
IDPELNNKGYILPGLGDAGDRAFG
[SEQ ID NO: 136]

1y56 *Pyrococcus horikoshii* ot3 hypothetical
protein PH1363
MLMRPLDLTEKRGKKVTIYFEGKELEAYEGEKLPVALLANEIYWLTTS
NEGRKRGAFTFGPVPMTVNGVKGLEARRIKVKDGMKIERQGYYDFHEE
PVVEPGEIERVVVDVAIIGGGPAGIGAALELQQYLTVALIEERGWLGG
DMWLKGIKQEGFNKDSRKVVEELVGKLNENTKIYLETSALGVFDKGEY
FLVPVVRGDKLIEILAKRVVLATGAIDSTMLFENNDMPGVFRRDFALE
VMNVWEVAPGRKVAVTGSKADEVIQELERWGIDYVHIPNVKRVEGNEK
VERVIDMNNHEYKVDALIFADGRRPDINPITQAGGKLRFRRGYYSPVL
DEYHRIKDGIYVAGSAVSIKPHYANYLEGKLVGAYILKEFGYDAQPCI
YEEKLREYEPESLSIPRIPLDKFNLEDVQICGCDVSLKKVDEVIRKGI
TDLQIIKRLTHLAMGFCQGRYCLFNGAVVVSQRTGKKLSEIDLPVARS
PIKNVKMGILARR
[SEQ ID NO: 137]

*Pyrococcus horikoshii* ot3 sarcosine oxidase
MLPEKSEIVVIGGGIVGVTIAHELAKRGEEVTVIEKRFIGSGSTFRCG
TGIRQQFNDEANVRVMKRSVELWKKYSEEYGFSFKQTGYLFLLYDDEE
VKTFKRNIEIQNKFGVPTKLITPEEAKEIVPLLDISEVIAASWNPTDG
KADPFEATTAFAVKAKEYGAKLLEYTEVKGFLIENNEIKGVKTNKGII
KTGIVVNATNAWANLINAMAGIKTKIPIEPYKHQAVITQPIKRGTINP
MVISFKYGHAYLTQTFHGGIIGGSIGYEIGPTYDLTPTYEFLREVSYYF
TKIIPALKNLLILRTWAGYYAKTPDSNPAIGRIEELNDYYIAAGFSGH
GFMMAPAVGEMVAELITKGKTKLPVEWYDPYRFERGELRTAALQMG
[SEQ ID NO: 138]

1z54 *Thermus thermophilus* hb8 probable
thioesterase
MESVTRIKVRYAETDQMGVVHHSVYAVYLEAARVDFLERAGLPYHRVE
ARGVFFPVVELGLTFRAPARFGEVVEVRTRLAELSSRALLFRYRVERE
GVLLAEGFTRHLCQVGERAARIPEDIYRALSVLHLK
[SEQ ID NO: 139]

2b5d *Thermotoga maritima* msb8 alpha-Amylase
MRGKILIFLHAHLPYVHHPEYDHFLEERWLFEAITETYIPLLMMFDEI
EDFRLTMSITPPLMEMLSSRDLQEKYERHMEKLIELANKEVERTKKEH
PLKHKMAKFYREHFEKILNVFRSYDGNILEGFKKYQETGKLEIVTCNA
THAFLPLYQMYPEVVNAQITVGVKNYEKHMKKHPRGIWLAECGYYQGL
DLYLAQNNVEYFFVDSHAFWFADEQPRYGVYRPIMTPSGVFAFARDPE
SSEQVWSAAVGYPGDPRYREFYRDIGFDREMEYIKDYIDPSGVRINTG
IKYHRITSKSLDASQKEYYDIDLAMEAVEEHARDFLHHKKESQARRLMD
IMGVEPVIVAPFDAELFGHWWFEGVFFLKRFFELVNESKDLKLVTASE
VIDTLEEVQIATPADSSWGAGGYYETWLNGTNDWIYRHLHEMIERMID
LSKKYYNSSDPLVERVLNQMLRELFLAQSSDWAFIMTTRTSVQYAENR
TKLHIKRFLNLYDQLVSGRIDEEMLRYYEWTDAIFPEINFRVMARDVI
[SEQ ID NO: 140]

2bri *Pyrococcus furiosus* URIDYLATE KINASE
MRIVFDIGGSVLVPENPDIDFIKEIAYQLTKVSEDHEVAVVVGGGKLA
RKYIEVAEKFNSSETFKDFIGIQITRANAMLLIAALREKAYPVVVEDF
WEAWKAVQLKKIPVMGGTHPGHTTDAVAALLAEFLKADLLVVITNVDG
VYTADPKKDPTAKKIKKMKPEELLEIVGKGIEKAGSSSVIDPLAAKII
ARSGIKTIVIGKEDAKDLFRVIKGDHNGTTIEP
[SEQ ID NO: 141]

2cbl *Thermus thermophilus* O-ACETYL HOMOSERINE
SULFHYDRYLASE
MEYTTLAVLAGLPEDPHGAVGLPIYAVAAYGFKTLEEGQERFATGEGY
VYARQKDPTAKALEERLKALEGALEAVVLASGQAATFAALLALLRPGD
EVVAAKGLFGQTIGLFGQVLSLMGVTVRYVDPEPEAVREALSAKTRAV
FVETVANPALLVPDLEALATLAEEAGVALVVDNTFGAAGALCRPLAWG
AHVVVESLTKWASGHGSVLGGAVLSRETELWRNYPQFLQPDLKGQIPW
EALRARCFPERVRTLGLSLCGMALSPFNAYLLFQGLETVALRVARMSE
TARFLAERLQGHPKVKALRYPGLPEDPAHRNARKYLASGGPILTLDLG
DLERASRFLGAIRLLKAANLGDARTLLVHPWTTTHSRLKEEARLQAGV
TPGLVRVSVGLEDPLDLLALFEEALEAV
[SEQ ID NO: 142]

2cd9 *Sulfolobus solfataricus* GLUCOSE
DEHYDROGENASE
MKAIIVKPPNAGVQVKDVDEKKLDSYGKIKIRTIYNGICGTDREIVNG
KLTLSTLPKGKDFLVLGHEAIGVVEESYHGFSQGDLVMPVNRRGCGIC
RNCLVGRPDFCETGEFGEAGIHKMDGFMREWWYDDPKYLVKIPKSIED
IGILAQPLADIEKSIEEILEVQKRVPVWTCDDGTLNCRKVLVVGTGPI
GVLFTLLFRTYGLEVWMANRREPTEVEQTVIEETKTNYYNSSNGYDKL
KDSVGKFDVIIDATGADVNILGNVIPLLGRNGVLGLFGFSTSGSVPLD
YKTLQEIVHTNKTIIGLVNGQKPHFQQAVVHLASWKTLYPKAAKMLIT
KTVSINDEKELLKVLREKEHGEIKIRILWE
[SEQ ID NO: 143]

2cdc *Sulfolobus solfataricus* GLUCOSE
DEHYDROGENASE GLUCOSE 1-DEHYDROGENASE, DHG-1
MKAIIVKPPNAGVQVKDVDEKKLDSYGKIKIRTIYNGICGTDREIVNG
KLTLSTLPKGKDFLVLGHEAIGVVEESYHGFSQGDLVMPVNRRGCGIC
RNCLVGRPDFCETGEFGEAGIHKMDGFMREWWYDDPKYLVKIPKSIED
IGILAQPLADIEKSIEEILEVQKRVPVWTCDDGTLNCRKVLVVGTGPI
GVLFTLLFRTYGLEVWMANRREPTEVEQTVIEETKTNYYNSSNGYDKL
KDSVGKFDVIIDATGADVNILGNVIPLLGRNGVLGLFGFSTSGSVPLD TABLE 1B-continued Subunit Amino Acid Sequences of Symmetric
Protein Nodes Structures are designated by
Symmetry Type and Protein Data Bank Codes
<http://www.rcsb.org/pdb/home/home.do>.

YKTLQEIVHTNKTIIGLVNGQKPHFQQAVVHLASWKTLYPKAAKMLIT
KTVSINDEKELLKVLREKEHGEIKIRILWE
[SEQ ID NO: 144]

2cx9 *Thermus thermophilus* acyl-CoA dehydrogenase
MGLWFEEGAEERQVLGPFREFLKAEVAPGAAERDRTGAFPWDLVRKLA
EFGVFGALVPEAYGGAGLSTRLFARMVEAIAYYDGALALTVASHNSLA
TGHILLAGSEAQKEAFLPKLASGEALGAWGLTEPGSGSDAAALKTKAE
KVEGGWRLNGTKQFITQGSVAGVYVVMARTDPPPSPERKHQGISAFAF
FRPERGLKVGRKEEKLGLTASDTAQLILEDLFVPEEALLGERGKGFYD
VLRVLDGGRIGIAAMAVGLGQAALDYALAYAKGREAFGRPIAEFEGVS
FKLAEAATELEAARLLYLKAAELKDAGRPFTLEAAQAKLFASEAAVKA
CDEAIQILGGYGYVKDYPVERYWRDARLTRIGEGTSEILKLVIARRLL
EAV
[SEQ ID NO: 145]

2czc *Pyrococcus horikoshii* ot3 Glyceraldehyde-3-
phosphate dehydrogenase
MKVKVGVNGYGTIGKRVAYAVTKQDDMELIGITKTKPDFEAYRAKELG
IPVYAASEEFIPRFEKEGFEVAGTLNDLLEKVDIIVDATPGGIEKHIM
PLYEKAGVKAIFQGGEKADVAEVSFVAQANYEAALGKNYVRVVSCNTT
GLVRTLSAIREYADYVYAVMIRRAADPNDTKRGPINAIKPTVEVPSHH
GPDVQTVIPINIETMAFVVPTTLMHVHSVMVELKKPLTKDDVIDIFEN
TTRVLLFEKEKGFDSTAQIIEFARDLHREWNNLYEIAVWKESINIKGN
RLFYIQAVHQESDVIPENIDAIRAMFELADKWDSIKKTNKSLGILK
[SEQ ID NO: 146]

2dly *Thermus thermophilus* hypothetical protein
TT0321 oxidoreductase
MGLFAGKGVLVTGGARGIGRAIAQAFAREGALVALCDLRPEGKEVAEA
IGGAFFQVDLEDERERVRFVEEAAYALGRVDVLVNNAAIAAPGSALTV
RLPEWRRVLEVNLTAPMHLSALAAREMRKVGGGAIVNVASVQGLFAEQ
ENAAYNASKGGLVNLTRSLALDLAPLRIRVNAVAPGAIATEAVLEAIA
LSPDPERTRRDWEDLHALRRLGKPEEVAEAVLFLASEKASFITGAILP
VDGGMTASFMMAGRPV
[SEQ ID NO: 147]

2d8a *Pyrococcus horikoshii* ot3 Probable
L-threonine 3-dehydrogenase
MSEKMVAIMKTKPGYGAELVEVDVPKPGPGEVLIKVLATSICGTDLHI
YEWNEWAQSRIKPPQIMGHEVAGEVVEIGPGVEGIEVGDYVSVETHIV
CGKCYACRRGQYHVCQNTKIFGVDTDGVFAEYAVVPAQNIWKNPKSIP
PEYATLQEPLGNAVDTVLAGPISGKSVLITGAGPLGLLGIAVAKASGA
YPVIVSEPSDFRRELAKKVGADYVINPFEEDVVKEVMDITDGNGVDVF
LEFSGAPKALEQGLQAVTPAGRVSLLGLYPGKVTIDFNNLIIFKALTI
YGITGRHLWETWYTVSRLLQSGKLNLDPIITHKYKGFDKYEEAFELMR
AGKTGKVVFMLK
[SEQ ID NO: 148]

2d29 *Thermus thermophilus* hb8 acyl-CoA
dehydrogenase
MGLWFEEGAEERQVLGPFREFLKAEVAPGAAERDRTGAFPWDLVRKLA
EFGVFGALVPEAYGGAGLSTRLFARMVEAIAYYDGALALTVASHNSLA
TGHILLAGSEAQKEAFLPKLASGEALGAWGLTEPGSGSDAAALKTKAE
KVEGGWRLNGTKQFITQGSVAGVYVVMARTDPPPSPERKHQGISAFAF
FRPERGLKVGRKEEKLGLTASDTAQLILEDLFVPEEALLGERGKGFYD
VLRVLDGGRIGIAAMAVGLGQAALDYALAYAKGREAFGRPIAEFEGVS
FKLAEAATELEAARLLYLKAAELKDAGRPFTLEAAQAKLFASEAAVKA
CDEAIQILGGYGYVKDYPVERYWRDARLTRIGEGTSEILKLVIARRLL
EAV
[SEQ ID NO: 149]

2df5 *Pyrococcus furiosus* Pyrrolidone-carboxylate
peptidase
MKVLVTGFEPFGGEKINPTERIAKDLDGIKIGDAQVFGRVLPVVFGKA
KEVLEKTLEEIKPDIAIHVGLAPGRSAISIERIAVNAIDARIPDNEGK
KIEDEPIVPGAPTAYFSTLPIKKIMKKLHERGIPAYISNSAGLYLCNY
VMYLSLHHSATKGYPKMSGFIHVPYIPEQIIDKIGKGQVPPSMCYEME
LEAVKVAIEVALTQDMINKST
[SEQ ID NO: 150]

2dfa *Thermus thermophilus* hb8 Hypothetical
UPF0271 protein TTHB195 lactam utilization
MKVDLNADAGESYGAFAYGHDREIFPLVSSANLACGFHGGSPGRILEA
VRLAKAHGVAVGAHPGFPDLVGFGRREMALSPEEVYADVLYQIGALSA FLKAEGLPLHHVKPHGALYLKACRDRETARAIALAVKAFDPGLPLVVL
PGTVYEEEARKAGLRVVLEAFPERAYLRSGQLAPRSMPGSWITDPEEA
ARRALRMVLEGKVEALDGGEVAVRADTLCIHGDNPNAPEVARAVREAL
EQAGVEVRAF
[SEQ ID NO: 151]

2drh *Pyrococcus horikoshii* ot3 361aa long
hypothetical D-aminopeptidase
MKAQELGIKIGVFKPGKRNKITDVKGVKVGHVTLIKGKGKLIPGKGPV
RTGVTAILPHEGNIYKEKVLAGAFVMNGYSKPVGLIQLWELGTIETPI
ILTNTLSIGTAVEGLLDYILEENEDIGVTTGSVNPLVLECNDSYLNDI
RGRHVKREHVVEAIKRADEDFEEGAVGAGTGMSAFEFKGGIGSASRIV
EIEGKKYTVGALVLSNFGRREDLTIAGVPVGLELKNWPGRGGEGKGSI
IMIIATDAPLTGRQLNRVAKRAIVGLARTGGYAYNGSGDIAVAFSTAN
RIKHYEKEVIEIKALPDSVISPLFKATAEAVEEAIINSLLEARTMDGR
DNHVRYALPKEELLRIMRRYGRLEE
[SEQ ID NO: 152]

2ds1 *Thermus thermophilus* hb8 Phenylacetic acid
degradation protein PaaI
MRDPFMEALGLKVLHLAPGEAVVAGEVRADHLDLHGTAHGGFLYALAD
SAFALASNTRGPAVALSCRMDYFRPLGAGARVEARAVEVNLSRRTATY
RVEVVSEGKLVALFTGTVFRLGGDGDDVPAGTGNLAPREA
[SEQ ID NO: 153]

2ela *Pyrococcus horikoshii* ot3 75aa long
hypothetical regulatory protein AsnC
MVTAFILMVTAAGKEREVMEKLLAMPEVKEAYVVYGEYDLIVKVETDT
LKDLDQFITEKIRKMPEIQMTSTMIAI
[SEQ ID NO: 154]

2e9f *Thermus thermophilus* hb8 Argininosuccinate
lyase
MAHRTWGGRFGEGPDALAARFNASLAFDRALWREDLWQNRVHARMLHA
VGLLSAEELEAILKGLDRIEEEIEAGTFPWREELEDVHMNLEARLTEL
VGPPGGKLHTARSRNDQVATDLRLYLRGAIDELLALLLALRRVLVREA
EKHLDPLYVLPGYTHLQRAQPVLLAHWFLAYYEMLKRDAGRLEDAKER
LNESPLGAAALAGTGFPIDRHFTARELGFKAPMRNSLDAVASRDFALE
VLSALNIGMLHLSRMAEELILYSTEEFGFVEVPDAFATGSSIMPQKKN
PDILELIRAKAGRVLGAFVGLSAVVKGLPLAYNKDLQEDKEPLLDALA
TYRDSLRLLAALLPGLKWRRERMWRAAEGGYTLATELADYLAEKGLPF
REAHHVVGRLVRRLVEEGRALKDLTLEELQAHHPLFAEDALPLLRLET
AIHRRRSYGGTAPEAVRERLEEAKKEVGLD
[SEQ ID NO: 155]

2eba *Thermus thermophilus* hb8 Putative
glutaryl-CoA dehydrogenase
MLDFYALEDLLTPEEKEVQKAARRFLEKEALPHIRDWWEEGVFPTHLI
PRFAELGFLGPTLPPEYGGAGVSSAAYGLICYELERVDSGLRSFVSVQ
SSLVMYPIYAYGSEEQKREFLPKLARGEMVGCFGLTEPDGGSDPYGNM
KTRARREGDTWVLNGTKMWITNGNLAHLAVIWAKDEGGEVLGFLVPTD
TPGFQAREVKRKMSLRASVTSELVLEEVRVPESLRLPKALGLKAPLSC
LTQARFGIAWGAMGALEAVYEEAVAFAKSRSTFGEPLAKKQLVQAKLA
EMLAWHTEGLLLAWRLARLKDEGKLTPAQVSLAKRQNVWKALQAARMA
RDILGGSGITLEYHAIRHMLNLETVYTYEGTHDVHTLVLGREITGLNA
F
[SEQ ID NO: 156]

2ebj *Thermus thermophilus* hb8 Pyrrolidone
carboxyl peptidase
MILVTGFEPFGSLEHNPSQALLDLLPSEVDGKPLRKAVLPVDAEALGE
ALEDLHREGPKAVLHLGLAEDRPVLTLERLAVNLLDFPRPDNRGRVLE
DLPIVPGGPLALPARFPVKPVLARWREAGIPGRPSLSAGSYLCNQAFY
LSLYRLPEEVPVGFLHLPPDETLALKRPRPYVPLEVQARAVRLALEHL
[SEQ ID NO: 157]

2eo5 *Sulfolobus tokodaii* str. 7 419aa long
hypothetical aminotransferase
MLSRKIIEESDIYLATSTRDPELFPLVIDHGEGVWIYDVDGNKYLDFT
SGIGVNNLGWNPSHPEVIKIGIEQMQKLAHAAANDFYNIPQLELAKKLV
TYSPGNFQKKVFFSNSGTEAIEASIKVVKNTGRKYIIAFLGGFHGRTF
GSISLTASKAVQRSIVGPFMPGVIHVPYPNPYRNPWHINGYENPSELV
NRVIEFIEDYIFVNLVPPEEVAGIFFEPIQGEGGYVIPPKNFFAELQK
LAKKYGILLVDDEVQMGLGRTGKLFAIENFNTVPDVITLAKALGGGIM
PIGATIFRKDLDFKPGMHSNTFGGNALACAIGSKVIDIVKDLLPHVNE TABLE 1B-continued Subunit Amino Acid Sequences of Symmetric
Protein Nodes Structures are designated by
Symmetry Type and Protein Data Bank Codes
<http://www.rcsb.org/pdb/home/home.do>.

IGKIFAEELQGLADDVRGIGLAWGLEYNEKKVRDRIIGESFKRGLLLL
PAGRSAIRVIPPLVISEEEAKQGLDILKKVIKVVK
[SEQ ID NO: 158]

2ep5 Sulfolobus tokodaii 350aa long hypothetical
aspartate-semialdehyde dehydrogenase
MADKIKVSLLGSTGMVGQKMVKMLAKHPYLELVKVSASPSKIGKKYKD
AVKWIEQGDIPEEVQDLPIVSTNYEDHKDVDVVLSALPNELAESIELE
LVKNGKIVVSNASPFRMDPDVPLINPEINWEHLELLKFQKERKGWKGI
LVKNPNCTAAIMSMPIKPLIEIATKSKIIITTLQAVSGAGYNGISFMA
IEGNIIPYIKGEEDKIAKELTKLNGKLENNQIIPANLDSTVTSIRVPT
RVGHMGVINIVTNERINIEEIKKTLKNFKSLPQQKNLPTAPKQPIIVR
DEEDRPQPIIDVNAESGMAVTVGRIRHENNVLRLVVLGDNLVRGAAGI
TILTVEVMKELGYI
[SEQ ID NO: 159]

2g10 Pyrobaculum aerophilum str. im2 conserved
hypothetical protein
MTDMSIKFELIDVPIPQGTNVIIGQAHFIKTVEDLYEALVTSVPGVKF
GIAFCEASGKRLVRHEANDEELRNLAIDLCKKIAAGHVFVIYIRNAWP
INVLNAIKNVPEVVRIFAATANPLKVIVAEVEPERRGVVGVVDGHSPL
GVETEKDREERKKFLREVVKYKL
[SEQ ID NO: 160]

2gm7 Pyrobaculum aerophilum str. im2 tenA
homolog/Thi-4 Thiaminase
MALHHHHHHGVTGELRRRADGIWQRILAHPFVAELYAGTLPMEKFKYY
LLQDYNYLVNFAKALSLAASRAPSVDLMKTALELAYGTVTGEMANYEA
LLKEVGLSLRDAAEAEPNRVNVSYMAYLKSTCALEGFYQCMAALLPCF
WSYAEIAERHGGKLRENPVHVYKKWASVYLSPEYRGLVERLRAVLDSS
GLSAEELWPYFKEASLYELEFWQAAYEGH
[SEQ ID NO: 161]

2h6e Sulfolobus solfataricus p2 D-arabinose
1-dehydrogenase
MVKSKAALLKKFSEPLSIEDVNIPEPQGEEVLIRIGGAGVCRTDLRVW
KGVEAKQGFRLPIILGHENAGTIVEVGELAKVKKGDNVVVYATWGDLT
CRYCREGKFNICKNQIIPGQTTNGGFSEYMLVKSSRWLVKLNSLSPVE
AAPLADAGTTSMGAIRQALPFISKFAEPVVIVNGIGGLAVYTIQILKA
LMKNITIVGISRSKKHRDFALELGADYVSEMKDAESLINKLTDGLGAS
IAIDLVGTEETTYNLGKLLAQEGAIILVGMEGKRVSLEAFDTAVWNKK
LLGSNYGSLNDLEDVVRLSESGKIKPYIIKVPLDDINKAFTNLDEGRV
DGRQVITP
[SEQ ID NO: 162]

2hae Thermotoga maritima Malate oxidoreductase
MSLDALELHRFLKGKIRTALPVEKVDRETLSLLYTPGVADVARACAED
PEKTYVYTSRWNTVAVVSDGSAVLGLGNIGPYGALPVMEGKAFLFKAF
ADIDAFPICLSESEEEKIISIVKSLEPSFGGINLEDIGAPKCFRILQR
LSEEMNIPVFHDDQQGTAVVVSAAFLNALKLTEKKIEEVKVVVNGIGA
AGYNIVKFLLDLGVKNVVAVDRKGILNENDPETCLNEYHLEIARITNP
ERLSGDLETALEGADFFIGVSRGNILKPEWIKKMSRKPVIFALANPVP
EIDPELAREAGAFIVATGRSDHPNQVNNLLAFPGIMKGAVEKRSKITK
NMLLSAVEAIARSCEPEPERIIPEAFDMKVHLNVYTAVKGSAEGHHHH
HH
[SEQ ID NO: 163]

2hmf Methanocaldococcus jannaschii Probable
aspartokinase
TTVMKFGGTSVGSGERIRHVAKIVTKRKKEDDDVVVVSAMSEVTNAL
VEISQQALDVRDIAKVGDFIKFIREKHYKAIEEAIKSEEIKEEVKKII
DSRIEELEKVLIGVAYLGELTPKSRDYILSFGERLSSPILSGAIRDLG
EKSIALEGGEAGIITDNNFGSARVKRLEVKERLLPLLKEGIIPVVTGF
IGTTEEGYITTLGRGGSDYSAALIGYGLDADIIEIWTDVSGVYTTDPR
LVPTARRIPKLSYIEAMELAYFGAKVLHPRTIEPAMEKGIPILVKNTF
EPESEGTLITNDMEMSDSIVKAISTIKNVALINIFGAGMVGVSGTAAR
IFKALGEEEVNVILISQGSSETNISLVVSEEDVDKALKALKREFGDFG
KKSFLNNLIRDVSVDKDVCVISVVGAGMRGAKGIAGKIFTAVSESGA
NIKMIAQGSSEVNISFVIDEKDLLNCVRKLHEKFIEK
[SEQ ID NO: 164]

2iss (D2 Dodecamer) Thermotoga maritima
Pyridoxal biosynthesis lyase pdxS
MGSSHHHHHHSSGLVPRGSHMEIKKGTWIIKKGFAEMFKGGVIMDVTS
AEQAKIAEEEAGAVAVMALERVPADIRKEGGVARMSASIAKIREIMEAVS IPVMAKVRIGHIAEAKILEELGVDFIDESEVLTPADDRFHINKHEFKV
PFVCGARDLGEALRRIAEGAAMIRTKGEAGTGNVVEAVKHMRRVMEQI
KQVTKMEDEELVAYGKEIGAPVELLREVKRLGRLPVVNFAAGGVATPA
DAALMMMLGADGVFVGSGIFKSKDPRKMAKAMVLAVTYWDNPRILLKI
SEDIGEPMRGLDVEELEVRMQERGW
[SEQ ID NO: 165]

Thermotoga maritima Glutamine amidotransferase
subunit pdxT
MGSSHHHHHHSSGLVPRGSHMKIGVLGVQGDVREHVEALHKLGVETLI
VKLPEQLDMVDGLILPGGESTTMIRILKEMDMDEKLVERINNGLPVFA
TCAGVILLAKRIKNYSQEKLGVLDITVERNAYGRQVESFETFVEIPAV
GKDPFRAIFIRAPRIVETGKNVEILATYDYDPVLVKEGNILACTFHPE
LTDDLHRYFLEMVK
[SEQ ID NO: 166]

21db Geobacillus stearothermophilus L-LACTATE
DEHYDROGENASE
MKNNGGARVVVIGAGFVGASYVFALMNQGIADEIVLIDANESKAIGDA
MDFNHGKVFAPKPVDIWHGDYDDCRDADLVVICAGANQKPGETRLDLV
DKNIAIFRSIVESVMASGFQGLFLVATNPVDILTYATWKFSGLPHERV
IGSGTILDTARFRFLLGEYFSVAPQNVHAYIIGEHGDTELPVWSQAYI
GVMPIRKLVESKGEEAQKDLERIFVNVRDAAYQIIEKKGATYYGIAMG
LARVTRAILHNENAILTVSAYLDGLYGERDVYIGVPAVINRNGIREVI
EIELNDDEKNRFHHSAATLKSVLARAFTR
[SEQ ID NO: 167]

2p3n Thermotoga maritima msb8 Inositol-1-
monophosphatase
MDRLDFSIKLLRKVGHLLMIHWGRVDNVEKKTGFKDIVTEIDREAQRM
IVDEIRKFFPDENIMAEEGIFEKGDRLWIIDPIDGTINFVHGLPNFSI
SLAYVENGEVKLGVVHAPALNETLYAEEGSGAFFNGERIRVSENASLE
ECVGSTGSYVDFTGKFIERMEKRTRRIRILGSAALNAAYVGAGRVDFF
VTWRINPWDIAAGLIIVKEAGGMVTDFSGKEANAFSKNFIFSNGLIHD
EVVKVVNEVVEEIGGK
[SEQ ID NO: 168]

2ph3 Thermus thermophilus hb8 3-oxoacyl-]acyl
carrier protein] reductase
MRKALITGASRGIGRAIALRLAEDGFALAIHYGQNREKAEEVAEEARR
RGSPLVAVLGANLLEAEAATALVHQAAEVLGGLDTLVNNAGITRDTLL
VRMKDEDWEAVLEANLSAVFRTTREAVKLMMKARFGRIVNITSVVGIL
GNPGQANYVASKAGLIGFTRAVAKEYAQRGITVNAVAPGFIETEMTER
LPQEVKEAYLKQIPAGRFGRPEEVAEAVAFLVSEKAGYITGQTLCVDG
GLTPH
[SEQ ID NO: 169]

2yym Thermus thermophilus hb8
4-hydroxyphenylacetate-3-hydroxylase
MARTGAEYIEALKTRPPNLWYKGEKVEDPTTHPVFRGIVRTMAALYDL
QHDPRYREVLTYEEEGKRHGMSFLIPKTKEDLKRRGQAYKLWADQNLG
MMGRSPDYLNAVVMAYAASADYFGEFAENVRNYYRYLRDQDLATTHAL
TNPQVNRARPPSGQPDPYIPVGVVKQTEKGIVVRGARMTATFPLADEV
LIFPSILLQAGSEKYALAFALPTSTPGLHFVCREALVGGDSPFDHPLS
SRVEEMDCLVIFDDVLVPWERVFILGNVELCNNAYGATGALNHMAHQV
VALKTAKTEAFLGVAALMAEGIGADVYGHVQEKIAEIIVYLEAMRAFW
TRAEEEAKENAYGLLVPDRGALDGARNLYPRLYPRIREILEQIGASGL
ITLPSEKDFKGPLGPFLEKFLQGAALEAKERVALFRLAWDMTLSGFGA
RQELYERFFFGDPVRMYQTLYNVYNKEPYKERIHAFLKESLKVFEEVQ
A
[SEQ ID NO: 170]

3pfk Geobacillus stearothermophilus
PHOSPHOFRUCTOKINASE
MKRIGVLTSGGDSPGMNAAIRSVVRKAIYHGVEVYGVYHGYAGLIAGN
IKKLEVGDVGDIIHRGGTILYTARCPEFKTEEGQKKGIEQLKKHGIQG
LVVIGGDGSYQGAKKLTEHGFPCVGVPGTIDNDIPGTDFTIGFDTALN
TVIDAIDKIRDTATSHERTYVIEVMGRHAGDIALWSGLAGGAETILIP
EADYDMNDVIARLKRGHERGKKHSIIIVAEGVGSGVDFGRQIQEATGF
ETRVTVLGHVQRGGSPTAFDRVLASRLGARAVELLLEGKGGRCVGIQN
NQLVDHDIAEALANKHTIDQRMYALSKELSI TABLE 1B-continued Subunit Amino Acid Sequences of Symmetric
Protein Nodes Structures are designated by
Symmetry Type and Protein Data Bank Codes
<http://www.rcsb.org/pdb/home/home.do>.

[SEQ ID NO: 171]

D3 Symmetry (6 Polypeptide chains)

1aup *Clostridium symbiosum* NAD-SPECIFIC
GLUTAMATE DEHYDROGENASE
SKYVDRVIAEVEKKYADEPEFVQTVEEVLSSLGPVVDAHPEYEEVALL
ERMVIPERVIEFRVPWEDDNGKVHVNTGYRVQFNGAIGPYLGGLRFAP
SVNLSIMKFLGFEQAFKDSLTTLPMGGAKGGSDFDPNGKSDREVMRFC
QAFMTELYRHIGPDIDVPAGDLGVGAREIGYMYGQYRKIVGGFYNGVL
TGKARSFGGSLVRPEATGYGSVYYVEAVMKHENDTLVGKTVALAGFGN
VAWGAAKKLAELGAKAVTLSGPDGYIYDPEGITTEEKINYMLEMRASG
RNKVQDYADKFGVQFFPGEKPWGQKVDIIMPCATQNDVDLEQAKKIVA
NNVKYYIEVANMPTTNEALRFLMQQPNMVVAPSKAVNAGGVLVVGFEM
SQNSERLSWTAEEVDSKLHQVMTDIHDGSAAAAERYGLGYNLVAGANI
VGFQKIADAMMAQGIAW
[SEQ ID NO: 172]

1b4b *Geobacillus stearothermophilus* ARGININE
REPRESSOR
ALVDVFIKLDGTGNLLVLRTLPGNAHAIGVLLDNLDWDEIVGTICGDD
TCLIICRTPKDAKKVSNQLLSML
[SEQ ID NO: 15]

1bgv *Clostridium symbiosum* GLUTAMATE
DEHYDROGENASE
SKYVDRVIAEVEKKYADEPEFVQTVEEVLSSLGPVVDAHPEYEEVALL
ERMVIPERVIEFRVPWEDDNGKVHVNTGYRVQFNGAIGPYKGGLRFAP
SVNLSIMKFLGFEQAFKDSLTTLPMGGAKGGSDFDPNGKSDREVMRFC
QAFMTELYRHIGPDIDVPAGDLGVGAREIGYMYGQYRKIVGGFYNGVL
TGKARSFGGSLVRPEATGYGSVYYVEAVMKHENDTLVGKTVALAGFGN
VAWGAAKKLAELGAKAVTLSGPDGYIYDPEGITTEEKINYMLEMRASG
RNKVQDYADKFGVQFFPGEKPWGQKVDIIMPCATQNDVDLEQAKKIVA
NNVKYYIEVANMPTTNEALRFLMQQPNMVVAPSKAVNAGGVLVSGFEM
SQNSERLSWTAEEVDSKLHQVMTDIHDGSAAAAERYGLGYNLVAGANI
VGFQKIADAMMAQGIAW
[SEQ ID NO: 173]

1bvu *Thermococcus litoralis* PROTEIN (GLUTAMATE
DEHYDROGENASE)
VEQDPFEIAVKQLERAAQYMDISEEALEFLKRPQRIVEVSIPVEMDDG
SVKVFTGFRVQYNWARGPTKGGIRWHPEETLSTVKALAAWMTWKTAVM
DLPYGGGKGGVICNPKEMSDREKERLARGYVRAIYDVISPYTDIPAPD
VYTNPQIMAWMMDEYETISRRKDPSFGVITGKPPSVGGIVARMDATAR
GASYTVREAAKALGMDLKGKTIAIQGYGNAGYYMAKIMSEEYGMKVVA
VSDTKGGIYNPDGLNADEVLAWKKKTGSVKDFPGATNITNEELLELEV
DVLAPSAIEEVITKKNADNIKAKIVAELANGPTTPEADEILYEKGILI
IPDFLCNAGGVTVSYFEWVQNITGDYWTVEETRAKLDKKMTKAFWDVY
NTHKEKNINMRDAAYVVAVSRVYQAMKDRGWIKK
[SEQ ID NO: 174]

1f9a *Methanocaldococcus jannaschii* HYPOTHETICAL
PROTEIN MJ0541 a nicotinamide
mononucleotide adenylyltransferase
LRGFIIGRFQPPHKGHLEVIKKIAEEVDEIIIGIGSAQKSHTLENPFT
AGERILMITQSLKDYDLTYYPIPIKDIEFNSIWVSYVESLTPPFDIVY
SGNPLVRVLFEERGYEVKRPEMFNRKEYSGTEIRRRMLNGEKWEHLVP
KAVVDVIKEIKGVERLRKLAQTDK
[SEQ ID NO: 175]

1fxk *Methanothermobacter thermautotrophicus*
PREFOLDIN
AALAEIVAQLNIYQSQVELIQQQMEAVRATISELEILEKTLSDIQGKD
GSETLVPVGAGSFIKAELKDTSEVIMSVGAGVAIKKNFEDAMESIKSQ
KNELESTLQKMGENLRAITDIMMKLSPQAEELLAAVA
[SEQ ID NO: 176]

*Methanothermobacter thermautotrophicus* PREFOLDIN
NVQHQLAQFQQLQQQAQAISVQKQTVEMQINETQKALEELSRAADDAE
VYKSSGNILIRVAKDELTEELQEKLETLQLREKTIERQEERVMKKLQE
MQVNIQEAMKGAG TABLE 1B-continued Subunit Amino Acid Sequences of Symmetric
Protein Nodes Structures are designated by
Symmetry Type and Protein Data Bank Codes
<http://www.rcsb.org/pdb/home/home.do>.

[SEQ ID NO: 177]

*Methanothermobacter thermautotrophicus*
(PREFOLDIN)
QNVQHQLAQFQQLQQQAQAISVQKQTVEMQINETQKALEELSRAADDA
EVYKSSGNILIRVAKDELTEELQEKLETLQLREKTIERQEERVMKKLQ
EMQVNIQEAMK
[SEQ ID NO: 178]

1gtm *Pyrococcus furiosus* dsm 3638 GLUTAMATE
DEHYDROGENASE
VEADPYEIVIKQLERAAQYMEISEEALEFLKRPQRIVEVTIPVEMDDG
SVKVFTGFRVQHNWARGPTKGGIRWHPEETLSTVKALAAWMTWKTAVM
DLPYGGGKGGIIVDPKKLSDREKERLARGYIRAIYDVISPYEDIPAPD
VYTNPQIMAWMMDEYETISRRKTPAFGIITGKPLSIGGSLGRIEATAR
GASYTIREAAKVLGWDTLKGKTIAIQGYGNAGYYLAKIMSEDFGMKVV
AVSDSKGGIYNPDGLNADEVLKWKNEHGSVKDFPGATNITNEELLELE
VDVLAPAAIEEVITKKNADNIKAKIVAEVANGPVTPEADEILFEKGIL
QIPDFLCNAGGVTVSYFEWVQNITGYYWTIEEVRERLDKKMTKAFYDV
YNIAKEKNIHMRDAAYVVAVQRVYQAMLDRGWVKH
[SEQ ID NO: 179]

1hyb *Methanothermobacter thermautotrophicus*
NICOTINAMIDE MONONUCLEOTIDE ADENYLYLTRANSFERASE
MMTRGLLVGRMQPFHRGALQVIKSILEEVDELIICIGSAQLSHSIRD
PFTAGERVMMLTKALSENGIPASRYYIIPVQDIECNALWVGHIKMLTP
PFDRVYSGNPLVQRLFSEDGYEVTAPPLFYRDRYSGTEVRRRMLDDGD
WRSLLPESVVEVIDEINGVERIKHLAKKEVSELGGIS
[SEQ ID NO: 16]

1je0 *Sulfolobus solfataricus*
5'-METHYLTHIOADENOSINE PHOSPHORYLASE
MNPVHILAKKGEVAERVLVVGDPGRARLLSTLLQNPKLTNENRGFLVY
TGKYNGETVSIATHGIGGPSIAIVLEELAMLGANVFIRYGTTGALVPY
INLGEYIIVTGASYNQGGLFYQYLRDNACVASTPDFELTNKLVTSFSK
RNLKYYVGNVFSSDAFYAEDEEFVKKWSSRGNIAVEMECATLFTLSKV
KGWKSATVLVVSDNLAKGGIWITKEELEKSVMDGAKAVLDTLTS
[SEQ ID NO: 180]

1jku *Lactobacillus plantarum pseudocatalase*
MFKHTRKLQYNAKPDRSDPIMARRLQESLGGQWGETTGMMSYLSQGWA
STGAEKYKDLLLDTGTEEMAHVEMISTMIGYLLEDAPFGPEDLKRDPS
LATTMAGMDPEHSLVHGLNASLNNPNGAAWNAGYVTSSGNLVADMRFN
VVRESEARLQVSRLYSMTEDEGVRDMLKFLLARETQHQLQFMKAQEEL
EEKYGIIVPGDMKEIEHSEFSHVLMNFSDGDGSKAFEGQVAKDGEKFT
YQENPEAMGGIPHIKPGDPRLHNHQG
[SEQ ID NO: 181]

1odi *Thermus thermophilus* PURINE NUCLEOSIDE
PHOSPHORYLASE
MSPIHVRAHPGDVAERVLLPGDPGRAEWIAKTFLQNPRRYNDHRGLWG
YTGLYKGVPVSVQTTGMGTPSAAIVVEELVRLGARVLVRVGTAGAASS
DLAPGELIVAQGAVPLDGTTRQYLEGRPYAPVPDPEVFRALWRRAEAL
GYPHRVGLVASEDAFYATTPEEARAWARYGVLAFEMEASALFLLGRMR
GVRTGAILAVSNRIGDPELAPPEVLQEGVRRMVEVALEAVLEV
[SEQ ID NO: 182]

1odk *Thermus thermophilus* PURINE NUCLEOSIDE
PHOSPHORYLASE
MSPIHVRAHPGDVAERVLLPGDPGRAEWIAKTFLQNPRRYNDHRGLWG
YTGLYKGVPVSVQTTGMGTPSAAIVVEELVRLGARVLVRVGTAGAASS
DLAPGELIVAQGAVPLDGTTRQYLEGRPYAPVPDPEVFRALWRRAEAL
GYPHRVGLVASEDAFYATTPEEARAWARYGVLAFEMEASALFLLGRMR
GVRTGAILAVSNRIGDPELAPPEVLQEGVRRMVEVALEAVLEV
[SEQ ID NO: 183]

1pg5 *Sulfolobus acidocaldarius* Aspartate
carbamoyltransferase
LKHIISAYNFSRDELEDIFALTDKYSKNLNDTRKILSGKTISIAFFEP
STRTYLSFQKAIINLGGDVIGFSGEESTSVAKGENLADTIRMLNNYSD
GIVMRHKYDGASRFASEISDIPVINAGDGKHEHPTQAVIDIYTINKHF
NTIDGLVFALLGDLKYARTVNSLLRILTRFRPKLVYLISPQLLRARKE
ILDELNYPVKEVENPFEVINEVDVLYVTRIQKERFVDEMEYEKIKGSY
IVSLDLANKMKKDSIILHPLPRVNEIDRKVDKTTKAKYFEQASYGVPV
RMSILTKIYGE TABLE 1B-continued Subunit Amino Acid Sequences of Symmetric
Protein Nodes Structures are designated by
Symmetry Type and Protein Data Bank Codes
<http://www.rcsb.org/pdb/home/home.do>.

[SEQ ID NO: 184]

*Sulfolobus acidocaldarius* Aspartate
carbamoyltransferase regulatory chain
MEFMMEIQGNRKELMVSKIKNGTVIDHIPAGRAFAVLNVLGIKGHEGF
RIALVINVDSKKMGKKDIVKIEDKEISDTEANLITLIAPTATINIVRE
YEVVKKTKLEVPKVVKGILKCPNPYCITSNDVEAIPTFKTLTEKPLKM
RCEYCETIIDENEIMSQILGANNK
[SEQ ID NO: 185]

1gw9 *Geobacillus stearothermophilus* Alpha-L-
arabinofuranosidase
LKHIISAYNFSRDELEDIFALTDKYSKNLNDTRKILSGKTISIAFFEP
STRTYLSFQKAIINLGGDVIGFSGEESTSVAKGENLADTIRMLNNYSD
GIVMRHKYDGASRFASEISDIPVINAGDGKHEHPTQAVIDIYTINKHF
NTIDGLVFALLGDLKYARTVNSLLRILTRFRPKLVYLISPQLLRARKE
ILDELNYPVKEVENPFEVINEVDVLYVTRIQKERFVDEMEYEKIKGSY
IVSLDLANKMKKDSIILHPLPRVNEIDRKVDKTTKAKYFEQASYGVPV
RMSILTKIYGE
[SEQ ID NO: 186]

1t57 *Methanothermobacter thermautotrophicus*
Conserved Protein MTH1675
MGSSHHHHHHSSGLVPRGSHMEKKICYFEEPGKENTERVLELVGERAD
QLGIRNFVVASVSGETALRLSEMVEGNIVSVTHHAGFREKGQLELEDE
ARDALLERGVNVYAGSHALSGVGRGISNRFGGVTPVEIMAETLRMVSQ
GFKVCVEIAIMAADAGLIPVDEEVIAIGGTAWGADTALVLTPAHMNSV
FDLRIHEVIAMPRP
[SEQ ID NO: 187]

1uan *Thermus thermophilus* hypothetical protein
TT1542
MLDLLVVAPHPDDGELGCGGTLARAKAEGLSTGILDLTRGEMGSKGTP
EEREKEVAEASRILGLDFRGNLGFPDGGLADVPEQRLKLAQALRRLRP
RVVFAPLEADRHPDHTAASRLAVAAVHLAGLRKAPLEGEPFRVERLFF
YPGNHPFAPSFLVKISAFIDQWEAAVLAYRSQFTGEAASETVGPKGVE
ARKAMRRYWGNYLGVDYAEPFVSPLPVLYVPWSRA
[SEQ ID NO: 188]

1ude *Pyrococcus horikoshii* Inorganic
pyrophosphatase
HHHHHHSSGLVPRGSHMMNPFHDLEPGPNVPEVVYALIEIPKGSRNKY
ELDKETGLLKLDRVLYTPFHYPVDYGIIPRTWYEDGDPFDIMVIMREP
TYPLTIIEARPIGLFKMIDSGDKDYKVLAVPVEDPYFKDWKDISDVPK
AFLDEIAHFFKRYKELEGKEIIVEGWEGAEAAKREILRAIEMYKEKFG
KKE
[SEQ ID NO: 189]

1uiy *Thermus thermophilus* Enoyl-CoA Hydratase
MVQVEKGHVAVVFLNDPERRNPLSPEMALSLLQALDDLEADPGVRAVV
LTGRGKAFSAGADLAFLERVTELGAEENYRHSLSLMRLFHRVYTYPKP
TVAAVNGPAVAGGAGLALACDLVVMDEEARLGYTEVKIGFVAALVSVI
LVRAVGEKAADLLLTGRLVEAREAKALGLVNRIAPPGKALEEAKALA
EEVAKNAPTSLRLTKELLLALPGMGLEDGFRLAALANAWVRETGDLAE
GIRAFFEKRPPRF
[SEQ ID NO: 190]

1vla *Thermus thermophilus* Enoyl-CoA Hydratase
MLEVVTAGEPLVALVPQEPGHLRGKRLLEVYVGGAEVNVAVALARLGV
KVGFVGRVGEDELGAMVEERLRAEGVDLTHFRRAPGFTGLYLREYLPL
GQGRVFYYRKGSAGSALAPGAFDPDYLEGVRFLHLSGITPALSPEARA
FSLWAMEEAKRRGVRVSLDVNYRQTLWSPEEARGFLERALPGVDLLFL
SEEEAELLFGRVEEALRALSAPEVVLKRGAKGAWAFVDGRRVEGSAFA
VEAVDPVGAGDAFAAGYLAGAVWGLPVEERLRLANLLGASVAASRGDH
EGAPYREDLEVLLKATQTFMR
[SEQ ID NO: 191]

1vls *Thermus thermophilus* 2-KETO-3-
DEOXYGLUCONATE KINASE
MLEVVTAGEPLVALVPQEPGHLRGKRLLEVYVGGAEVNVAVALARLGV
KVGFVGRVGEDELGAMVEERLRAEGVDLTHFRRAPGFTGLYLREYLPL
GQGRVFYYRKGSAGSALAPGAFDPDYLEGVRFLHLSGITPALSPEARA
FSLWAMEEAKRRGVRVSLDVNYRQTLWSPEEARGFLERALPGVDLLFL
SEEEAELLFGRVEEALRALSAPEVVLKRGAKGAWAFVDGRRVEGSAFA
VEAVDPVGAGDAFAAGYLAGAVWGLPVEERLRLANLLGASVAASRGDH
EGAPYREDLEVLLKATQTFMR
[SEQ ID NO: 192]

1v91 *Pyrobaculum islandicum* glutamate
dehydrogenase
MERTGFLEYVLNYVKKGVELGGFPEDFYKILSRPRRVLIVNIPVRLDG
GGFEVFEGYRVQHCDVLGPYKGGVRFHPEVTLADDVALAILMTLKNSL
AGLPYGGAKGAVRVDPKKLSQRELEELSRGYARAIAPLIGDVVDIPAP
DVGTNAQIMAWMVDEYSKIGYNVPGVFTSKPPELWGNPVREYATGFG
VAVATREMAKKLWGGIEGKTVAIQGMGNVGRWTAYWLEKMGAKVIAVS
DINGVAYRKEGLNVELIQKNKGLTGPALVELFTTKDNAEFVKNPDAIF
KLDVDIFVPAAIENVIRGDNAGLVKARLVVEGANGPTTPEAERILYER
GVVVVPDILANAGGVIMSYLEWVENLQWYIWDEEETRKRLENIMVNNV
ERVYKRWQREKGWTMRDAAIVTALERIYNAMKIRGWI
[SEQ ID NO: 193]

1v19 *Thermus thermophilus* 2-KETO-3-
DEOXYGLUCONATE KINASE
MLEVVTAGEPLVALVPQEPGHLRGKRLLEVYVGGAEVNVAVALARLGV
KVGFVGRVGEDELGAMVEERLRAEGVDLTHFRRAPGFTGLYLREYLPL
GQGRVFYYRKGSAGSALAPGAFDPDYLEGVRFLHLSGITPALSPEARA
FSLWAMEEAKRRGVRVSLDVNYRQTLWSPEEARGFLERALPGVDLLFL
SEEEAELLFGRVEEALRALSAPEVVLKRGAKGAWAFVDGRRVEGSAFA
VEAVDPVGAGDAFAAGYLAGAVWGLPVEERLRLANLLGASVAASRGDH
EGAPYREDLEVLLKATQTFMR
[SEQ ID NO: 194]

1wkl *Thermus thermophilus* nucleotide diphosphate
kinase
MERTFVMIKPDGVRRGLVGEILARFERKGFRIAALKLMQISQELAERH
YAEHREKPFFPGLVRFITSGPVVAMVLEGPGVVAEVRKMMGATHPKDA
LPGTIRGDFATTIDENVIHGSATLEDAQREIALFFRPEELL
[SEQ ID NO: 195]

1wz8 *Thermus thermophilus* hb8 enoyl-CoA
hydratase
MLASLEARYPGLAFAWPRPGVLEITFRGEKLNAMPPALHRGLARVWRD
LEAVEGVRAVLLRGEGGVFSAGGSFGLIEEMRASHEALLRVFWEARDL
VLGPLNFPRPVVAAVEKVAVGAGLALALAADIAVVGKGTRLLDGHLRL
GVAAGDHAVLLWPLLVGMAKAYHLLLNEPLTGEEAERLGLVALAVED
EKVYEKALEVAERLAQGPKEALHHTKHALNHWYRSFLPHFELSLALEF
LGFSGKELEEGLKALKEKRPPEFP
[SEQ ID NO: 196]

1wzn *Pyrococcus horikoshii* ot3 SAM-dependent
methyltransferase
MYELYTLLAEYYDTIYRRRIERVKAEIDFVEEIFKEDAKREVRRVLDL
ACGTGIPTLELAERGYEVVGLDLHEEMLRVARRKAKERNLKIEFLQGD
VLEIAFKNEFDAVTMFFSTIMYFDEEDLRKLFSKVAEALKPGGVFITD
FPCWFYGGRDGPVVWNEQKGEEKLVIMDWREVEPAVQKLRFKRLVQIL
RPNGEVKAFLVDDELNIYTPREVRLLAEKYFEKVKIYGNLKRELSPND
MRYWIVGIAKSF
[SEQ ID NO: 197]

1x0u *Sulfolobus tokodaii* str. 7 hypothetical
methylmalonyl-CoA decarboxylase a subunit
AMYEKPPVEKLIEELRQLKEKAYKGGGDERIQFQHSKGKLTARERLAL
LFDDGKFNEIMTFATTRATEFGLDKQRFYGDGVVTGWGKVDGRTVFAY
AQDFTVLGGSLGETHANKIVRAYELALKVGAPVVGINDSGGARIQEGA
LSLEGYGAVFKMNVMASGVIPQITIMAGPAAGGAVYSPALTDFIIMIK
GDAYYMFVTGPEITKVVLGEEVSFQDLGGAVVHATKSGVVHFMVDSEQ
EAINLTKRLLSYLPSNNMEEPPYIDTGDPADRDATGVEQIVPNDAAKP
YNMREIIYKIVDNGEFLEVHKHWAQNIIVGFARIAGNVVGIVANNPEE
FGGSIDIDAADKAARFIRFCDAFNIPLISLVDTPGYVPGTDQEYKGII
RHGAKMLYAFAEATVPKITVIVRKSYGGAHIAMSIKSLGADLVYAWPT
AEIAVTGPEGAVRILYRKEIQQASNPDDVLKQRIAEYRKLFANPYWAA
EKGLVDDVIEPKDTRRVIVAGLEMLKTKREYRYPKKHGNIPL
[SEQ ID NO: 198]

2a8y *Sulfolobus solfataricus*
5'-methylthioadenosine phosphorylase (mtaP)
MIEQNEKASIGIIGGSGLYDPGIFSESKEIKVYTPYGQPSDFITIGKI
GNKSVAFLPRHGRGHRIPPHKINYRANIWALKELGVRWVISVSAVGSL
RMDYKLGDFVIPDQFIDMTKNREYSFFDGPVVAHVSMADPFCNSLRKL TABLE 1B-continued Subunit Amino Acid Sequences of Symmetric
Protein Nodes Structures are designated by
Symmetry Type and Protein Data Bank Codes
<http://www.rcsb.org/pdb/home/home.do>.

AIETAKELNIKTHESGTYICIEGPRFSTRAESRTWREVYKADIIGMTL
VP
[SEQ ID NO: 199]

2afb *Thermotoga maritima* msb8 2-keto-3-
deoxygluconate kinase
MGSDKIHHHHHHMKVVTFGEIMLRLSPPDHKRIFQTDSFDVTYGGAEA
NVAAFLAQMGLDAYFVTKLPNNPLGDAAAGHLRKFGVKTDYIARGGNR
IGIYFLEIGASQRPSKVVYDRAHSAISEAKREDFDWEKILDGARWFHF
SGITPPLGKELPLILEDALKVANEKGVTVSCDLNYRARLWTKEEAQKV
MIPFMEYVDVLIANEEDIEKVLGISVEGLDLKTGKLNREAYAKIAEEV
TRKYNFKTVGITLRESISATVNYWSVMVFENGQPHFSNRYEIHIVDRV
GAGDSFAGALIYGSLMGFDSQKKAEFAAAASCLKHTIPGDFWLSIEEI
EKLASGATSGRVER
[SEQ ID NO: 200]

2anu *Thermotoga maritima* msb8 hypothetical
protein TM0559 metal-dependent phosphoesterase
MGSDKIHHHHHHMKTDTEWLLCDFHVHTNMSDGHLPLGEVVDLFGKHG
VDVVSITDHIVDRRTLEQRKRNGEPLGALETDKFQDYLKRLWREQKRA
WEEYGMILIPGVEITNNTDLYHIVAVDVKEYVDPSLPVEEIVEKLKEQ
NALVIAAHPDRKKQDEEHLSWYLWANMERFKDTFDAWEIANRDDLFNS
VGVKKYRYVANSDFHELWHVYSWKTLVKSEKNIEAIKEAIRKNTDVAI
YLMRKNRLSSLSDVI
[SEQ ID NO: 201]

2bja *Thermus thermophilus* 1-PYRROLINE-
5-CARBOXYLATE DEHYDROGENASE
MTVEPFRNEPIETFQTEEARRAMREALRRVREEFGRHYPLYIGGEWVD
TKERMVSLNPSAPSEVVGTTAKAGKAEAEAALEAAWKAFKTWKDWPQE
DRSRLLLKAAALMRRRKRELEATLVYEVGKNWVEASADVAEAIDFIEY
YARAALRYRYPAVEVVPYPGEDNESFYVPLGAGVVIAPWNFPVAIFTG
MIVGPVAVGNTVIAKPAEDAVVVGAKVFEIFHEAGFPPGVVNFLPGVG
EEVGAYLVEHPRIRFINFTGSLEVGLKIYEAAGRLAPGQTWFKRAYVE
TGGKDAIIVDETADFDLAAEGVVVSAYGFQGQKCSAASRLILTQGAYE
PVLERVLKRAERLSVGPAEENPDLGPVVSAEQERKVLSYIEIGKNEGQ
LVLGGKRLEGEGYFIAPTVFTEVPPKARIAQEEIFGPVLSVIRVKDFA
EALEVANDTPYGLTGGVYSRKREHLEWARREFHVGNLYFNRKITGALV
GVQPFGGFKLSGTNAKTGALDYLRLFLEMKAVAERF
[SEQ ID NO: 202]

2bjk *Thermus thermophilus*
1-PYRROLINE-5-CARBOXYLATE DEHYDROGENASE
MTVEPFRNEPIETFQTEEARRAMREALRRVREEFGRHYPLYIGGEWVD
TKERMVSLNPSAPSEVVGTTAKAGKAEAEAALEAAWKAFKTWKDWPQE
DRSRLLLKAAALMRRRKRELEATLVYEVGKNWVEASADVAEAIDFIEY
YARAALRYRYPAVEVVPYPGEDNESFYVPLGAGVVIAPWNFPVAIFTG
MIVGPVAVGNTVIAKPAEDAVVVGAKVFEIFHEAGFPPGVVNFLPGVG
EEVGAYLVEHPRIRFINFTGSLEVGLKIYEAAGRLAPGQTWFKRAYVE
TGGKDAIIVDETADFDLAAEGVVVSAYGFQGQKCSAASRLILTQGAYE
PVLERVLKRAERLSVGPAEENPDLGPVVSAEQERKVLSYIEIGKNEGQ
LVLGGKRLEGEGYFIAPTVFTEVPPKARIAQEEIFGPVLSVIRVKDFA
EALEVANDTPYGLTGGVYSRKREHLEWARREFHVGNLYFNRKITGALV
GVQPFGGFKLSGTNAKTGALDYLRLFLEMKAVAERF
[SEQ ID NO: 203]

2cqz *Pyrococcus horikoshii* ot3 177aa long
hypothetical protein
MKVMIEKILLVQTLKRLPRMGWLIKGVQEPESIADHSFGVAFITLVLA
DVLEKRGKRIDVEKALKMAIVHDLAEAIITDIPLSAQEFVDKDKAEAL
VFKKVFPEFYELYREYQECSSPEAQLVRIADKLDMILQAYQYELSGNK
NLDEFWEAIEEIKRLELSKYLEDILNSVGRLKA
[SEQ ID NO: 204]

2dcn *Sulfolobus tokodaii* str. 7 hypothetical
fructokinase
MAKLITLGEILIEFNALSPGPLRHVSYFEKHVAGSEANYCVAFIKQGN
ECGIIAKVGDDEFGYNAIEWLRGQGVDVSHMKIDPSAPTGIFFIQRHY
PVPLKSESIYYRKGSAGSKLSPEDVDEEYVKSADLVHSSGITLAISST
AKEAVYKAFEIASNRSPDTNIRLKLWSAEEAKREILKLLSKFHLKFLI
TDTDDSKIILGESDPDKAAKAFSDYAEIIVMKLGPKGAIVYYDGKKYY
SSGYQVPVEDVTGAGDALGGTFLSLYYKGFEMEKALDYAIVASTLNVM
IRGDQENLPTTKDIETFLREMKK

[SEQ ID NO: 205]

2ddz *Pyrococcus horikoshii* ot3 190aa long
hypothetical protein
MNSMELLIIKERRIDYDGSAIRSHWAYRNFGILGDSLVVFRGKCNVKV
EEMVDIEDLRLRKEIKGDDMVHYILELFWHPDILLASSLQKLLIARLV
ELLWNYGIEASRRGDDIYVNGRKLSISIATVSPVSIKIHIGLNVKTVG
VPPGVDAIGLEELGIDPTEFMERSAKALVEEIEKVRKDSLKVRWVT
[SEQ ID NO: 206]

2dev *Thermus thermophilus* tt0972 protein
MGKVYKKVELVGTSEEGLEAAIQAALARARKTLRHLDWFEVKEIRGTI
GEAGVKEYQVVLEVGFRLEET
[SEQ ID NO: 207]

2dqb *Thermus thermophilus* hb8
*Deoxyguanosinetriphosphate triphosphohydrolase*,
putative
MRFSREALLELEASRLAPYAQKARDTRGRAHPEPESLYRTPYQKDRDR
ILHTTAFRRLEYKTQVLPGWAGDYYRTRLTHTLEVAQVSRSIARALGL
NEDLTEAIALSHDLGHPPFGHTGEHVLNALMQDHGGFEHNAQALRILT
HLEVRYPGFRGLNLTYEVLEGIATHEAAYSPGFKPLYEGQGTLEAQVV
DLSDAIAYAAHDLDDGFRAGLLHPEELKEVELLQALALEEGLDLLRLP
ELDRRVLVRQLLGYFITAAIEATHRRVEEAGVQSAEAVRRHPSRLAAL
GEEAEKALKALKAFLMERFYRHPEVLRERRKAEAVLEGLFAAYTRYPE
LLPREVQAKIPEEGLERAVCDYIAGMTDRFALEAYRRLSP
[SEQ ID NO: 208]

2dxf *Pyrococcus horikoshii* ot3 Nucleoside
diphosphate kinase
MFQMSETERTLVIIKPDAVVRGLIGEIISRFEKKGLKIVGMKMIWIDR
ELAEKHYEEHREKPFFKALIDYITKTPVVVMVLEGRYAVEVVRKMAGA
TDPKDAAPGTIRGDFGLEVSDAICNVIHASDSKESAEREISLFFKPEE
LFEYPRAADWFYKKGI
[SEQ ID NO: 209]

2dya *Pyrococcus horikoshii* ot3 Nucleoside
diphosphate kinase
MFQMSETERTLVIIKPDAVVRGLIGEIISRFEKKGLKIVGMKMIWIDR
ELAEKHYEEHREKPFFKALIDYITKTPVVVMVLEGRYAVEVVRKMAGA
TDPKDAAPGTIRGDFGLEVSDAICNVIHASDSKESAEREISLFFKPEE
LFEYPRAADWFYKKGI
[SEQ ID NO: 210]

2eez *Thermus thermophilus* hb8 Alanine
dehydrogenase
MVIGVPKEIKTLENRVALTPGGVESLVRRGHTVLVERGAGEGSGLSDA
EYARAGAELVGREEAWGAEMVVKVKEPLPEEYGFLREGLILFTYLHLA
ADRGLTEAMLRSGVTGIAYETVQLPDGTLPLLVPMSEVAGRMAPQVGA
QFLEKPKGGRGVLLGGVPGVARASVVILGGGTVGTNAAKIALGMGAQV
TILDVNHKRLQYLDDVFGGRVITLTATEANIKKSVQHADLLIGAVLVP
GAKAPKLVTRDMLSLMKEGAVIVDVAVDQGGCVETIRPTTHAEPTYVV
DGVVHYGVANMPGAVPRTSTFALTNQTLPYVLKLAEKGLDALLEDAAL
LKGLNTHKGRLTHPGVAEAFGLPYTPPEEALRG
[SEQ ID NO: 211]

2g3m *Sulfolobus solfataricus* Alpha-glucosidase
MRILKIYENKGVYKVVIGEPFPPIEFPLEQKISSNKSLSELGLTIVQQ
GNKVIVEKSLDLKEHIIGLGEKAFELDRKRKRYVMYNVDAGAYKKYQD
PLYVSIPLFISVKDGVATGYFFNSASKVIFDVGLEEYDKVIVTIPEDS
VEFVIEGPRIEDVLEKYTELTGKPFLPPMWAFGYMISRYSYYPQDKV
VELVDIMQKEGFRVAGVFLDIHYMDSYKLFTWHPYRFPEPKKLIDELH
KRNVKLITIVDHGIRVDQNYSPFLSGMGKFCEIESGELFVGKMWPGTT
VYPDFFREDTREWWAGLISEWLSQGVDGIWLDMNEPTDFSRAIEIRDV
LSSLPVQFRDDRLVTTFPDNVVHYLRGKRVKHEKVRNAYPLYEAMATF
KGFRTSHRNEIFILSRAGYAGIQRYAFIWTGDNTPSWDDLKLQLQLVL
GLSISGVPFVGCDIGGFGQGRNFAEIDNSMDLLVKYYALALFPPFYRSH
KATDGIDTEPVFLPDYYKEKVKEIVELRYKFLPYIYSLALEASEKGHP
VIRPLFYEFQDDDDMYRIEDEYMVGKYLLYAPIVSKEESRLVTLPRGK
WYNYWNGEIINGKSVVKSTHELPIYLREGSIIPLEGDELIVYGETSFK
RYDNAEITSSSNEIKFSREIYVSKLTITSEKPVSKIIVDDSKEIQVEK
TMQNTYVAKINQKIRGKINLE

TABLE 1B-continued

Subunit Amino Acid Sequences of Symmetric Protein Nodes Structures are designated by Symmetry Type and Protein Data Bank Codes <http://www.rcsb.org/pdb/home/home.do>.

[SEQ ID NO: 212]

2il4 *Pyrococcus furiosus* Nicotinate-nucleotide pyrophosphorylase
GGGGGGMKRFYIANEDEIKAGKTTDVYFLRTKKILEVKNIRKKVLADV
TTTSLPNNWRWGVLVGVEEVAKLLEGIPVNVYAMPEGTIFHPYEPVLQ
IEGDYADFGIYETALLGMLSQASGIATAALRIKIAAKFKPVYSFGIRH
MHPAIAPMIDRAAFIGGCDGVSGVLGAEMMGEKAVGTMPHALIITVGD
QVKAWKYFDEVIEEEVPRIALVDTFYDEKVEAVMAAEALGKKLFAVRL
DTPSSRRGNFRKIIEEVRWELKVRGYDWVKIFVSGGLDEEKIKEIVDV
VDAFGVGGAIASAKPVDFALDIVEVEGKPIAKRGKLSGRKQVYRCENG
HYHVVPANKKLERCPVCNAKVEPLLKPIIENGEIVVEFPKAREIREYV
LEQAKKFNLEI

[SEQ ID NO: 213]

2ide *Thermus thermophilus* hb8 Molybdenum cofactor biosynthesis protein C
MDLTHFQDGRPRMVDVTEKPETFRTATAEAFVELTEEALSALEKGGVG
KGDPLVVAQLAGILAAKKTADLIPLCHPLPLTGVEVRVELLKAEKRVR
IEATVKTKAETGVEMEAMTACAVAALTVYDMLKAASKGLVISQVRLLH
KAGGKSGEWRREQ

[SEQ ID NO: 214]

2j4j *Sulfolobus solfataricus* URIDYLATE KINASE
MNIILKISGKFFDEDNVDNLIVLRQSIKELADNGFRVGIVTGGGSTAR
RYIKLAREIGIGEAYLDLLGIWASRLNAYLVMFSLQDLAYMHVPQSLE
EFIQDWSHGKVVVTGGFQPGQSTAAVAALVAEASSSKTLVVATNVDGV
YEKDPRIYADVKLIPHLTTQDLRKILEGSQSVQAGTYELLDPLAIKIV
ERSKIRVIVMNYRKLNRIIDILKGEEVSSIIEPV

[SEQ ID NO: 215]

2j9d *Methanococcus jannaschii* HYPOTHETICAL NITROGEN REGULATORY PII-LIKE PROTEIN MJ0059
GSMKKVEAIIRPEKLEIVKKALSDAGYVGMTVSEVKGRGVQGGIVERY
RGREYIVDLIPKVKIELVVKEEDVDNVIDIICENARTGNPGDGKIFVI
PVERVVRVRTKEEGKEALLEHHH

[SEQ ID NO: 216]

2prd *Thermus thermophilus* hb8 PYROPHOSPHATE PHOSPHOHYDROLASE
ANLKSLPVGDKAPEVVHMVIEVPRGSGNKYEYDPDLGAIKLDRVLPGA
QFYPGDYGFIPSTLAEDGDPLDGLVLSTYPLLPGVVVEVRVVGLLLME
DEKGGDAKVIGVVAEDQRLDHIQDIGDVPEGVKQEIQHFFETYKALEA
KKGKWVKVTGWRDRKAALEEVRACIARYKG

[SEQ ID NO: 17]

2afb *Thermotoga maritima* msb8 2-keto-3-deoxygluconate kinase
MGSDKIHHHHHHMKVVTFGEIMLRLSPPDHKRIFQTDSFDVTYGGAEA
NVAAFLAQMGLDAYFVTKLPNNPLGDAAAGHLRKFGVKTDYIARGGNR
IGIYFLEIGASQRPSKVVYDRAHSAISEAKREDFDWEKILDGARWFHF
SGITPPLGKELPLILEDALKVANEKGVTVSCDLNYRARLWTKEEAQKV
MIPFMEYVDVLIANEEDIEKVLGISVEGLDLKTGKLNREAYAKIAEEV
TRKYNFKTVGITLRESISATVNYWSVMVFENGQPHFSNRYEIHIVDRV
GAGDSFAGALIYGSLMGFDSQKKAEFAAAASCLKHTIPGDFVVLSIEE
IEKLASGATSGRVER

[SEQ ID NO: 217]

2j4k *Sulfolobus solfataricus* URIDYLATE KINASE
MNIILKISGKFFDEDNVDNLIVLRQSIKELADNGFRVGIVTGGGSTAR
RYIKLAREIGIGEAYLDLLGIWASRLNAYLVMFSLQDLAYMHVPQSLE
EFIQDWSHGKVVVTGGFQPGQSTAAVAALVAEASSSKTLVVATNVDGV
YEKDPRIYADVKLIPHLTTQDLRKILEGSQSVQAGTYELLDPLAIKIV
ERSKIRVIVMNYRKLNRIIDILKGEEVSSIIEPV

[SEQ ID NO: 218]

D4 Symmetry (8 Polypeptide chains)

1jpu *Geobacillus stearothermophilus* glycerol dehydrogenase
MAAERVFISPAKYVQGKNVITKIANYLEGIGNKTVVIADEIVWKIAGH
TIVNELKKGNIAAEEVVFSGEASRNEVERIANIARKAEAAIVIGVGGG
KTLDTAKAVADELDAYIVIVPTAASTDAPTSALSVIYSDDGVFESYRF
YKKNPDLVLVDTKIIANAPPRLLASGIADALATWVEARSVIKSGGKTM
AGGIPTIAAEAIAEKCEQTLFKYGKLAYESVKAKVVTPALEAVVEANT
LLSGLGFESGGLAAAHAIHNGFTALEGEIHHLTHGEKVAFGTLVQLAL
EEHSQQEIERYIELYLCLDLPVTLEDIKLKDASREDILKVAKAATAEG
ETIHNAFNVTADDVADAIFAADQYAKAYKEKHRK

[SEQ ID NO: 219]

1jq5 *Geobacillus stearothermophilus* Glycerol dehydrogenase
MAAERVFISPAKYVQGKNVITKIANYLEGIGNKTVVIADEIVWKIAGH
TIVNELKKGNIAAEEVVFSGEASRNEVERIANIARKAEAAIVIGVGGG
KTLDTAKAVADELDAYIVIVPTAASTDAPTSALSVIYSDDGVFESYRF
YKKNPDLVLVDTKIIANAPPRLLASGIADALATWVEARSVIKSGGKTM
AGGIPTIAAEAIAEKCEQTLFKYGKLAYESVKAKVVTPALEAVVEANT
LLSGLGFESGGLAAAHAIHNGFTALEGEIHHLTHGEKVAFGTLVQLAL
EEHSQQEIERYIELYLCLDLPVTLEDIKLKDASREDILKVAKAATAEG
ETIHNAFNVTADDVADAIFAADQYAKAYKEKHRK

[SEQ ID NO: 220]

1m4y *Thermotoga maritima* ATP-dependent protease hs1V
TTILVVRRNGQTVMGGDGQVTFGSTVLKGNARKVRKLGEGKVLAGFAG
SVADAMTLFDRFEAKLREWGGNLTKAAVELAKDWRTDRVLRRLEALLL
VADKENIFIISGNGEVIQPDDDAAAIGSGGPYALAAAKALLRNTDLSA
REIVEKAMTIAGEICIYTNQNIVIEEV

[SEQ ID NO: 221]

1o4v *Thermotoga maritima* phosphoribosyl-aminoimidazole mutase PurE
MGSDKIHHHHHHPRVGIIMGSDSDLPVMKQAAEILEEFGIDYEITIV
SAHRTPDRMFEYAKNAEERGIEVVIAGAGGAAHLPGMVASITHLPVIG
VPVKTSTLNGLDSLFSIVQMPGGVPVATVAINNAKNAGILAASILGIK
YPEIARKVKEYKERMKREVLEKAQRLEQIGYKEYLNQKE

[SEQ ID NO: 18]

1saz *Thermotoga maritima* Probable butyrate kinase 2
MFRILTINPGSTSTKLSIFEDERMVKMQNFSHSPDELGRFQKILDQLE
FREKIARQFVEETGYSLSSFSAFVSRGGLLDPIPGGVYLVDGLMIKTL
KSGKNGEHASNLGAIIAHRFSSETGVPAYVVDPVVVDEMEDVARVSGH
PNYQRKSIFHALNQKTVAKEVARMMNKRYEEMNLVVAHMGGGISIAAH
RKGRVIDVNNALDGDGPFTPERSGTLPLTQLVDLCFSGKFTYEEMKKR
IVGNGGLVAYLGTSDAREVVRRIKQGDEWAKRVYRAMAYQIAKWIGKM
AAVLKGEVDFIVLTGGLAHEKEFLVPWITKRVSFIAPVLVFPGSNEEK
ALALSALRVLRGEEKPKNYSEESRRWRERYDSYLDGILRHHHHHH

[SEQ ID NO: 222]

1umg *Sulfolobus tokodaii* str. 7 385aa long conserved hypothetical protein
KTTISVIKADIGSLAGHHIVHPDTMAAANKVLASAKEQGIILDYYITH
VGDDLQLIMTHTRGELDTKVHETAWNAFKEAAKVAKDLGLYAAGQDLL
SDSFSGNVRGLGPGVAEMEIEERASEPIAIFMADKTEPGAYNLPLYKM
FADPFNTPGLVIDPTMHGGFKFEVLDVYQGEAVMLSAPQEIYDLLALI
GTPARYVIRRVYRNEDNLLAAVVSIERLNLIAGKYVGKDDPVMIVRLQ
HGLPALGEALEAFAFPHLVPGWMRGSHYGPLMPVSQRDAKATRFDGPP
RLLGLGFNVKNGRLVGPTDLFDDPAFDETRRLANIVADYMRRHGPFMP
HRLEPTEMEYTTLPLILEKLKDRFKK

[SEQ ID NO: 223]

1vcf *Thermus thermophilus* isopentenyl-diphosphate delta-isomerase
MNIRERKRKHLEACLEGEVAYQKTTTGLEGFRLRYQALAGLALSEVDL
TTPFLGKTLKAPFLIGAMTGGEENGERINLALAEAAEALGVGMMLSG
RILLERPEALRSFRVRKVAPKALLIANLGLAQLRRYGRDDLLRVEML
EADALAFHVNPLQEAVQRGDTDFRGLVERLAELLPLPFPVMVKEVGHG
LSREAALALRDLPLAAVDVAGAGGTSWARVEEWVRFGEVRHPELCEIG
IPTARAILEVREVLPHLPLVASGGVYTGTDGAKALALGADLLAVARPL
LRPALEGAERVAAWIGDYLEELRTALFAIGARNPKEARGRVERV

[SEQ ID NO: 224]

1x9j *Thermotoga maritima* Probable butyrate kinase 2
MFRILTINPGSTSTKLSIFEDERMVKMQNFSHSPDELGRFQKILDQLE
FREKIARQFVEETGYSLSSFSAFVSRGGLLDPIPGGVYLVDGLMIKTL
KSGKNGEHASNLGAIIAHRFSSETGVPAYVVDPVVVDEMEDVARVSGH
PNYQRKSIFHALNQKTVAKEVARMMNKRYEEMNLVVAHMGGGISIAAH
RKGRVIDVNNALDGDGPFTPERSGTLPLTQLVDLCFSGKFTYEEMKKR TABLE 1B-continued Subunit Amino Acid Sequences of Symmetric
Protein Nodes Structures are designated by
Symmetry Type and Protein Data Bank Codes
<http://www.rcsb.org/pdb/home/home.do>.

IVGNGGLVAYLGTSDAREVVRRIKQGDEWAKRVYRAMAYQIAKWIGKM
AAVLKGEVDFIVLTGGLAHEKEFLVPWITKRVSFIAPVLVFPGSNEEK
ALALSALRVLRGEEKPKNYSEESRRWRERYDSYLDGILR
[SEQ ID NO: 225]

2ax3 *Thermotoga maritima* msb8 hypothetical
protein TM0922
MGSDKIHHHHHMKEIDELTIKEYGVDSRILMERAGISVVLAMEEELG
NLSDYRFLVLCGGGNNGGDGFVVARNLLGVVKDVLVVFLGKKKTPDCE
YNYGLYKKFGGKVVEQFEPSILNEFDVVVDAIFGTGLRGEITGEYAEI
INLVNKSGKVVVSVDVPSGIDSNTGKVLRTAVKADLTVTFGVPKIGHI
LFPGRDLTGKLKVANIGHPVHLINSINRYVITREMVRSLLPERPRDSH
KGTYGKVLIIAGSRLYSGAPVLSGMGSLKVGTGLVKLAVPFPQNLIAT
SRFPELISVPIDTEKGFFSLQNLQECLELSKDVDVVAIGPGLGNNEHV
REFVNEFLKTLEKPAVIDADAINVLDTSVLKERKSPAVLTPHPGEMAR
LVKKTVGDVKYNYELAEEFAKENDCVLVLKSATTIVTDGEKTLFNITG
NTGLSKGGSGDVLTGMIAGFIAQGLSPLEASTVSVYLHGFAAELFEQD
ERGLTASELLRLIPEAIRRLKE
[SEQ ID NO: 226]

2cwx *Pyrococcus horikoshii* ot3 Ribulose
bisphosphate carboxylase
MMVLRMKVEWYLDFVDLNYEPGRDELIVEYYFEPNGVSPEEAAGRIAS
ESSIGTWTTLWKLPEMAKRSMAKVFYLEKHGEGYIAKIAYPLTLFEEG
SLVQLFSAVAGNVFGMKALKNLRLLDFHPPYEYLRHFKGPQFGVQGIR
EFMGVKDRPLTATVPKPKMGWSVEEYAEIAYELWSGGIDLLKDDENFT
SPPFNRFEERVRKLYRVRDRVEAETGETKEYLINITGPVNIMEKRAEM
VANEGGQYVMIDIVVAGWSALQYMREVTEDLGLAIHAHRAMHAAFTRN
PRHGITMLALAKAARMIGVDQIHTGTAVGKMAGNYEEIKRINDFLLSK
WEHIRPVFPVASGGLHPGLMPELIRLFGKDLVIQAGGGVMGHPDGPRA
GAKALRDAIDAAIEGVDLDEKAKSSPELKKSLREVGLSKAKVGVQH
[SEQ ID NO: 227]

2d69 *Pyrococcus horikoshii* ot3 Ribulose
bisphosphate carboxylase
MMVLRMKVEWYLDFVDLNYEPGRDELIVEYYFEPNGVSPEEAAGRIAS
ESSIGTWTTLWKLPEMAKRSMAKVFYLEKHGEGYIAKIAYPLTLFEEG
SLVQLFSAVAGNVFGMKALKNLRLLDFHPPYEYLRHFKGPQFGVQGIR
EFMGVKDRPLTATVPKPKMGWSVEEYAEIAYELWSGGIDLLKDDENFT
SPPFNRFEERVRKLYRVRDRVEAETGETKEYLINITGPVNIMEKRAEM
VANEGGQYVMIDIVVAGWSALQYMREVTEDLGLAIHAHRAMHAAFTRN
PRHGITMLALAKAARMIGVDQIHTGTAVGKMAGNYEEIKRINDFLLSK
WEHIRPVFPVASGGLHPGLMPELIRLFGKDLVIQAGGGVMGHPDGPRA
GAKALRDAIDAAIEGVDLDEKAKSSPELKKSLREVGLSKAKVGVQH
[SEQ ID NO: 228]

2h2i *Thermotoga maritima* NAD-dependent
deacetylase
MKMKEFLDLLNESRLTVTLTGAGISTPSGIPDFRGPNGIYKKYSQNVF
DIDFFYSHPEEFYRFAKEGIFPMLQAKPNLAHVLLAKLEEKGLIEAVI
TQNIDRLHQRAGSKKVIELHGNVEEYYCVRCEKKYTVEDVIKKLESSD
VPLCDDCNSLIRPNIVFFGENLPQDALREAIGLSSRASLMIVLGSSLV
VYPAAELPLITVRSGGKLVIVNLGETPFDDIATLKYNMDVVEFARRVM
EEGGIS
[SEQ ID NO: 19]

2ie1 *Thermus thermophilus* Hypothetical Protein
TT0030
MARYLVVAHRTAKSPELAAKLKELLAQDPEARFVLLVPAVPPPGWVYE
ENEVRRAEEEAAAAKRALEAQGIPVEEAKAGDISPLLAIEEELLAHP
GAYQGIVLSTLPPGLSRWLRLDVHTQAERFGLPVIHVIAQAA
[SEQ ID NO: 20]

D5 Symmetry (10 Polypeptide chains)

1geh *Thermococcus kodakarensis* kod1 RIBULOSE-1,
5-BISPHOSPHATE CARBOXYLASE/OXYGENASE
MVEKFDTIYDYYVDKGYEPSKKRDIIAAVFRVTPAEGYTIEQAAGAVAA
ESSTGTWTTLYPWYEQERWADLSAKAYDFHDMGDGSWIVRIAYPFHAF
EEANLPGLLASIAGNIFGMKRVKGLRLEDLYFPEKLIREFDGPAFGIE
GVRKMLEIKDRPIYGVVPKPKVGYSPEEFEKLAYDLLSNGADYMKDDE
NLTSPWYNRFEERAEIMAKIIDKVENETGEKKTWFANITADLLEMEQR
LEVLADLGLKHAMVDVVITGWGALRYIRDLAADYGLAIHGHRAMHAAF
TRNPYHGISMFVLAKLYRLIGIDQLHVGTAGAGKLEGGKWDVIQNARI
LRESHYKPDENDVFHLEQKFYSIKAAFPTSSGGLHPGNIQPVIEALGT TABLE 1B-continued Subunit Amino Acid Sequences of Symmetric
Protein Nodes Structures are designated by
Symmetry Type and Protein Data Bank Codes
<http://www.rcsb.org/pdb/home/home.do>.

DIVLQLGGGTLGHPDGPAAGARAVRQAIDAIMQGIPLDEYAKTHKELA
RALEKWGHVTPV
[SEQ ID NO: 229]

1w8s *Thermoproteus tenax* FRUCTOSE-BISPHOSPHATE
ALDOLASE CLASS I
MANLTEKFLRIFARRGKSIILAYDHGIEHGPADFMDNPDSADPEYILR
LARDAGFDGVVFQRGIAEKYYDGSVPLIKLNGKTTLYNGEPVSVANC
SVEEAVSLGASAVGYTIYPGSGFEWKMFEELARIKRDAVKFDLPLVVE
SFPRGGKVVNETAPEIVAYAARIALELGADAMKIKYTGDPKTFSWAVK
VAGKVPVLMSGGPKTKTEEDFLKQVEGVLEAGALGIAVGRNVWQRRDA
LKFARALAELVYGGKKLAEPLNV
[SEQ ID NO: 230]

1wm9 *Thermus thermophilus* hb8 GTP cyclohydrolase
I
MSPGPQSGGQERGSMERKMVELEDTGLTFATEVDLERLQALAAEWLQV
IGEDPGREGLLKTPERVAKAWAFLTRGYRQRLEEVVGGAVFPAEGSEM
VVVKGVEFYSMCEHHLLPFFGKVHIGYIPDGKILGLSKFARIVDMFAR
RLQVQERLAVQIAEAIQEVLEPQGVGVVVEGVHLCMMMRGVEKQHSRT
VTSAMLGVFRENQKTREEFLSHLRDGTA
[SEQ ID NO: 231]

1wuq *Thermus thermophilus* GTP cyclohydrolase I
MSPGPQSGGQERGSMERKMVELEDTGLTFATEVDLERLQALAAEWLQV
IGEDPGREGLLKTPERVAKAWAFLTRGYRQRLEEVVGGAVFPAEGSEM
VVVKGVEFYSMCEHHLLPFFGKVHIGYIPDGKILGLSKFARIVDMFAR
RLQVQERLAVQIAEAIQEVLEPQGVGVVVEGVHLCMMMRGVEKQHSRT
VTSAMLGVFRENQKTREEFLSHLRDGTA
[SEQ ID NO: 232]

1wur *Thermus thermophilus* GTP cyclohydrolase I
MSPGPQSGGQERGSMERKMVELEDTGLTFATEVDLERLQALAAEWLQV
IGEDPGREGLLKTPERVAKAWAFLTRGYRQRLEEVVGGAVFPAEGSEM
VVVKGVEFYSMCEHHLLPFFGKVHIGYIPDGKILGLSKFARIVDMFAR
RLQVQERLAVQIAEAIQEVLEPQGVGVVVEGVHLCMMMRGVEKQHSRT
VTSAMLGVFRENQKTREEFLSHLRDGTA
[SEQ ID NO: 233]

1wx0 *Thermus thermophilus* hb8 transaldolase
MELYLDTASLEEIREIAAWGVLSGVTTNPTLVAKAFAAKGEALTEEAF
AAHLRAICETVGGVPVSAEVTALEAEAMVAEGRRLAAIHPNIVVKLPTT
EEGLKACKRLSAEGIKVNMTLIFSANQALLAARAGASYVSPFLGRVDD
ISWDGGELLREIVEMIQVQDLPVKVIAASIRHPRHVTEAALLGADIAT
MPHAVFKQLLKHPLTDIGLKRFLEDWEKVKP
[SEQ ID NO: 234]

2djw *Thermus thermophilus* hb8 probable
transcriptional regulator, AsnC family
MITAFVLIRPRGNRVQALGEAIAELPQVAEVYSVTGPYDLVALVRLKD
VEELDDVVTQGILSLEGVERTETLLAFRAYPRRLLDQGFALGQG
[SEQ ID NO: 235]

D6 Symmetry (12 Polypeptide chains)

1m4y *Thermotoga maritima* ATP-dependent protease
hs1V
TTILVVRRNGQTVMGGDGQVTFGSTVLKGNARKVRKLGEGKVLAGFAG
SVADAMTLFDRFEAKLREWGGNLTKAAVELAKDWRTDRVLRRLEALLL
VADKENIFIISGNGEVIQPDDDAAAIGSGGPYALAAAKALLRNTDLSA
REIVEKAMTIAGEICIYTNQNIVIEEV
[SEQ ID NO: 236]

1znn *Geobacillus stearothermophilus* PLP SYNTHASE
MGSSHHHHHHSSGLVPRGSGTENLTPQHMASMALTGTDRVKRGMAEMQ
KGGVIMDVVNAEQAKIAEAAGAVAVMALERVPADIRAAGGVARMADPT
VIEEVMNAVSIPVMAKVRIGHYVEARVLEALGVDYIDESEVLTPADEE
FHIDKRQFTVPPFVCGCRDLGEAARRIAEGASMLRTKGEPGTGNIVEAV
RHMRKVNAQIRKVVNMSEDELVAEAKQLGAPVEVLREIKRLGRLPVVN

TABLE 1B-continued

Subunit Amino Acid Sequences of Symmetric
Protein Nodes Structures are designated by
Symmetry Type and Protein Data Bank Codes
<http://www.rcsb.org/pdb/home/home.do>.

FAAGGVTTPADAALMMHLGADGVFVGSGIFKSENPEKYARAIVEATTH
YEDYELIAHLSKGLGGAMRGIDIATLLPEHRMQERGW
[SEQ ID NO: 237]

D7 Symmetry (14 Polypeptide chains)

1m5q *Pyrobaculum aerophilum* small nuclear
ribonucleoprotein homolog
FVAELNNLLGREVQVVLSNGEVYKGVLHAVDNQLNIVLANASNKAGEK
FNRVFIMYRYIVHIDSTERRIDMREFAKQAEKIFPGMVKYIEETNVVL
IGDKVRVSEIGVEGVGPVAERAKRLFEEFLKRYS
[SEQ ID NO: 238]

1th7 *Sulfolobus solfataricus* Small nuclear
riboprotein protein
GAMNFLAETAHKVLAESLNNLVLVKLGNKEVRGMLRSYDQHMNLVLS
DSEEIQSDGSGKKLGTIVIRGDNVILISPLQTS
[SEQ ID NO: 239]

T23 Symmetry (12 Polypeptide chains)

1pvv *Pyrococcus furiosus* Ornithine
carbamoyltransferase
MVVSLAGRDLLCLQDYTAEEIWTILETAKMFKIWQKIGKPHRLLEGKT
LAMIFQKPSTRTRVSFEVAMAHLGGHALYLNAQDLQLRRGETIADTAR
VLSRYVDAIMARVYDHKDVEDLAKYATVPVINGLSDFSHPCQALADYM
TIWEKKGTIKGVKVVYVGDGNNVAHSLMIAGTKLGADVVVATPEGYEP
DEKVIKWAEQNAAESGGSFELLHDPVKAVKDADVIYTDVWASMGQEAE
AEERRKIFRPFQVNKDLVKHAKPDYMFMHCLPAHRGEEVTDDVIDSPN
SVVWDQAENRLHAQKAVLALVMGGIKF
[SEQ ID NO: 21]

1vlg *Thermotoga maritima* msb8 ferritin
MGSDKIHHHHHHMMVISEKVRKALNDQLNREIYSSYLYLSMATYFDAE
GFKGFAHWMKKQAQEELTHAMKFYEYIYERGGRVELEAIEKPPSNWNG
IKDAFEAALKHEEFVTQSIYNILELASEEKDHATVSFLKWFVDEQVEE
EDQVREILDLLEKANGQMSVIFQLDRYLGQRE
[SEQ ID NO: 240]

1xfo *Pyrococcus horikoshii* Fry operon protein
FrvX
RGSHMEVRNMVDYELLKKVVEAPGVSGYEFLGIRDVVIEEIKDYVDEV
KVDKLGNVIAHKKGEGPKVMIAAHMDQIGLMVTHIEKNGFLRVAPIGG
VDPKTLIAQRFKVWIDKGKFIYGVGASVPPHIQKPEDRKKAPDWDQIF
IDIGAESKEEAEDMGVKIGTVITWDGRLERLGKHRFVSIAFDDRIAVY
TILEVAKQLKDAKADVYFVATVQEEVGLRGARTSAFGIEPDYGFAIDV
TIAADIPGTPEHKQVTHLGKGTAIKIMDRSVICHPTIVRWLEELAKKH
EIPYQLEILLGGGTDAGAIHLTKAGVPTGALSVPARYIHSNTEVVDER
DVDATVELMTKALENIHELKI
[SEQ ID NO: 241]

1y0r *Pyrococcus horikoshii* Fry operon protein
FrvX
MEVRNMVDYELLKKVVEAPGVSGYEFLGIRDVVIEEIKDYVDEVKVDK
LGNVIAHKKGEGPKVMIAAHMDQIGLMVTHIEKNGFLRVAPIGGVDPK
TLIAQRFKVWIDKGKFIYGVGASVPPHIQKPEDRKKAPDWDQIFIDIG
AESKEEAEDMGVKIGTVITWDGRLERLGKHRFVSIAFDDRIAVYTILE
VAKQLKDAKADVYFVATVQEEVGLRGARTSAFGIEPDYGFAIDVTIAA
DIPGTPEHKQVTHLGKGTAIKIMDRSVICHPTIVRWLEELAKKHEIPY
QLEILLGGGTDAGAIHLTKAGVPTGALSVPARYIHSNTEVVDERDVDA
TVELMTKALENIHELKI
[SEQ ID NO: 242]

1y0y *Pyrococcus horikoshii* Fry operon protein
FrvX
MEVRNMVDYELLKKVVEAPGVSGYEFLGIRDVVIEEIKDYVDEVKVDK
LGNVIAHKKGEGPKVMIAAHMDQIGLMVTHIEKNGFLRVAPIGGVDPK
TLIAQRFKVWIDKGKFIYGVGASVPPHIQKPEDRKKAPDWDQIFIDIG
AESKEEAEDMGVKIGTVITWDGRLERLGKHRFVSIAFDDRIAVYTILE
VAKQLKDAKADVYFVATVQEEVGLRGARTSAFGIEPDYGFAIDVTIAA
DIPGTPEHKQVTHLGKGTAIKIMDRSVICHPTIVRWLEELAKKHEIPY
QLEILLGGGTDAGAIHLTKAGVPTGALSVPARYIHSNTEVVDERDVDA
TVELMTKALENIHELKI
[SEQ ID NO: 243]

1yoy *Archaeoglobus fulgidus* dsm 4304
hypothetical protein AF1432
GHMCIIKPMDDVVKFIHEVGSLKLTPRSGWLKLGIRLPESVAEHSFRA
AIIAFILALKSGESVEKACKAATAALFHDLHEARTMDLHKIARRYVSC
DEEGAREEQLSWMESKPDFSDVEVYVSDADKLELAFQGVEYSQQVSYA
IRFAENVELKTDAAKEIYRVLMERKNPVWWR
[SEQ ID NO: 244]

2c1b *Sulfolobus solfataricus* DPS-LIKE PROTEIN
MQEKPQEPKVVGVEILEKSGLDIKKLVDKLVKATAAEFTTYYYYTILR
MHLTGMEGEGLKEIAEDARLEDRLHFELMTQRIYELGGGLPRDIRQLA
DISACSDAYLPENWKDPKEILKVLLEAEQCAIRTWKEVCDMTYGKDPR
TYDLAQRILQEEIEHEAWFLELLYGRPSGHFRRSSPGNAPYSKK
[SEQ ID NO: 245]

2glf *Thermotoga maritima* Probable M18-family
aminopeptidase 1
KMERKNVWHHRKKEEIEAFSKEYMEFMSKAKTERMTVKEIKRILDESG
FVPLEDFAGDPMNMTVYAVNRGKAIAAFRVVDDLKRGLNLVVAHIDSP
RLDFKPNPLIEDEQIALFKTHYYGGIKKYHWLSIPLEIHGVLFKNDGT
EIEIHIGDKPEDPVFTIPDLLPHLDKEDAKISEKFKGENLMLIAGTIP
LSGEEKEAVKTNVLKILNEMYGITEEDFVSGEIEVVPAFSPREVGMDR
SLIGAYGQDDRICAYTALRALLSANPEKSIGVIFFDKEEIGSDGNTGA
KARFYLKALRQILKMQGAKDSEFVLDEVLENTSVISGDVCAAVNPPYK
DVHDLHNAPKLGYGVALVKYTGARGKYSTNDAHAEFVARVRKVLNEQG
VIWQVATLGKVDQGGGGTIAKFFAERGSDVIDMGPALLGMHSPFEISS
KADLFETYVAYRSLMEKL
[SEQ ID NO: 246]

2vl8 *Thermus thermophilus* DODECIN
GKVYKKVELVGTSEEGLEAAIQAALARARKTLRHLDWFEVKEIRGTIG
EAGVKEYQVVLEVGFRLEET
[SEQ ID NO:247]

O432 CubOctahedral Symmetry (24 Polypeptide
chains)

1shs *Methanocaldococcus jannaschii* SMALL HEAT
SHOCK PROTEIN
MFGRDPFDSLFERMFKEFFATPMTGTTMIQSSTGIQISGKGFMPISII
EGDQHIKVIAWLPGVNKEDIILNAVGDTLEIRAKRSPLMITESERIIY
SEIPEEEEIYRTIKLPATVKEENASAKFENGVLSVILPKAESSIKKGI
NIE
[SEQ ID NO: 248]

1vlg *Thermotoga maritima* msb8 ferritin
MGSDKIHHHHHHMMVISEKVRKALNDQLNREIYSSYLYLSMATYFDAE
GFKGFAHWMKKQAQEELTHAMKFYEYIYERGGRVELEAIEKPPSNWNG
IKDAFEAALKHEEFVTQSIYNILELASEEKDHATVSFLKWFVDEQVEE
EDQVREILDLLEKANGQMSVIFQLDRYLGQRE
[SEQ ID NO: 249]

Dodecahedral (532) Symmetry (60 Polypeptide
chains)

1b5s *Geobacillus stearothermophilus*
DIHYDROLIPOAMIDE ACETYLTRANSFERASE
AAAKPATTEGEFPETREKMSGIRRAIAKAMVHSKHTAPHVTLMDEADV

TABLE 1B-continued

Subunit Amino Acid Sequences of Symmetric Protein Nodes Structures are designated by Symmetry Type and Protein Data Bank Codes <http://www.rcsb.org/pdb/home/home.do>.

TKLVAHRKKFKAIAAEKGIKLTFLPYVVKALVSALREYPVLNTSIDDE
TEEIIQKHYYNIGIAADTDRGLLVPVIKHADRKPIFALAQEINELAEK
ARDGKLTPGEMKGASCTITNIGSAGGQWFTPVINHPEVAILGIGRIAE
KPIVRDGEIVAAPMLALSLSFDHRMIDGATAQKALNHIKRLLSDPELL
LM

[SEQ ID NO: 250]

Other E, C3, C2 (12 Subunits)

2cz8 Thermus thermophilus hb8 tt0972 protein
MGKVYKKVELVGTSEEGLEAAIQAALARARKTLRHLDWFEVKEIRGTI
GEAGVKEYQVVLEVGFRLEET
[SEQ ID NO:251]

TABLE 2

Specifications of Thermostable Node Proteins

| No, PDB ID, Symmetry | Description, Template Sequence, Site-Directed Modifications |
|---|---|

Part 1.

2.A (1thj) (C3) Description: Three-fold (C3) Planar Symmetric Node
Template Sequence:
MQEITVDEFSNIRENPVTPWNPEPSAPVIDPTAYIDPEASVIGEVTIGANVMVSPMASIRSDEGMPIFVGDRSNVQDGVV
LHALETINEEGEPIEDNIVEVDGKEYAVYIGNNVSLAHQSQVHGPAAVGDDTFIGMQAFVFKSKVGNNCVLEPRSAAIGV
TIPDGRYIPAGMVVTSQAEADKLPEVTDDYAYSHTNEAVVYVNVHLAEGYKETS [SEQ ID NO: 1]
Sequence Modifications:
General: Cys148 to Ala
Specific Biotinylation Sites:
1. Asp70 to Cys, Tyr200 to Cys

Part 2.

2.B (1thj) (C3) Description: Single-Chain Three-fold (C3) Planar Symmetric Node
Native template sequence (1thj):
MQEITVDEFSNIRENPVTPWNPEPSAPVIDPTAYIDPEASVIGEVTIGANVMVSPMASIRSDEGMPIFVGDRSNVQDGVV
LHALETINEEGEPIEDNIVEVDGKEYAVYIGNNVSLAHQSQVHGPAAVGDDTFIGMQAFVFKSKVGNNCVLEPRSAAIGV
TIPDGRYIPAGMVVTSQAEADKLPEVTDDYAYSHTNEAVVYVNVHLAEGYKETS [SEQ ID NO: 2]
Single Chain Template Sequences:
Template A: (DEFSNIRENP VTPWNPEPSA PVIDPTAYID PEASVIGEVT IGANVMVSPM ASIRSDEGMP
IFVGDRSNVQ DGVVLHALET INEEGEPIED NIVEVDGKEY AVYIGNNVSL AHQSQVHGPA AVGDDTFIGM
QAFVFKSKVG NNCVLEPRSA AIGVTIPDGR YIPAGMVVTS QAEADKLPEV TDDYAYSHTN EAVVYVNVHL
AEGYKQT) [SEQ ID NO: 3]
Template B: (DEFSNIRENP VTPWNPEPSA PVIDPTAYID PEASVIGEVT IGANVMVSPM ASIRSDEGMP
IFVGDRSNVQ DGVVLHALET INEEGEPIED NIVEVDGKEY AVYIGNNVSL AHQSQVHGPA AVGDDTFIGM
QAFVFKSKVG NNCVLEPRSA AIGVTIPDGR YIPAGMVVTS QAEADKLPEV TDDYAYSHTN EAVVYVNVHL
AEGYKQT) [SEQ ID NO: 3]
Linker A: (GGGSGGG) [SEQ ID NO: 4]
Linker B: (GGGSGGGG) [SEQ ID NO: 5]
Sequence Modifications:
General:
Template A: Cys143 to Ala, Delete N-term 6 residues (MQEITV) [SEQ ID NO: 6]
Template B: Cys143 to Ala, Delete N-term 6 residues (MQEITV) [SEQ ID NO: 6]
Specific Biotinylation Sites:
1. (Template A) Asp65 to Cys, Tyr195 to Cys
2. (Template B) None
Single Chain Linked Sequences:
1. Template A - Linker A - Template A - Linker A - Template A
2. Template A - Linker B - Template A - Linker B - Template A
3. Template A - Linker A - Template A - Linker A - Template B
4. Template A - Linker A - Template B - Linker A - Template B
5. Template B - Linker A - Template A - Linker A - Template A
6. Template A - Linker B - Template B - Linker B - Template B
7. & etc.

Part 3.

2.C 1j5s (C3) Description: Three-fold (C3) Planar Symmetric Node
Template Sequence:
MGSDKIHHHHHHMFLGEDYLLTNRAAVRLFNEVKDLPIVDPHNHLDAKDIVENKPWNDIWEVEGATDHYVWELMRRCGVS
EEYITGSRSNKEKWLALAKVFPRFVGNPTYEWIHLDLWRRFNIKKVISEETAEEIWEETKKKLPEMTPQKLLRDMEVEIL
CTTDDPVSTLEHHRKAKEAVEGVTILPTWRPDRAMNVDKEGWREYVEKMGERYGEDTSTLDGFLNALWKSHEHFKEHGCV
ASDHALLEPSVYYVDENRARAVHEKAFSGEKLTQDEINDYKAFMMVQFGKMNQETNWVTQLHIGALRDYRDSLFKTLGPD
SGGDISTNFLRIAEGLRYFLNEFDGKLKIVLYVLDPTHLPTISTIARAFPNVYVGAPWWFNDSPFGMEMHLKYLASVDLL
YNLAGMVTDSRKLLSFGSRTEMFRRVLSNVVGEMVEKGQIPIKEARELVKHVSYDGPKALFFG [SEQ ID NO: 7]

TABLE 2-continued

Specifications of Thermostable Node Proteins

| No, PDB ID, Symmetry | Description, Template Sequence, Site-Directed Modifications |
|---|---|
| | Sequence Modifications:<br>General: Cys65 to Ala, Cys149 to Ser, Cys227 to Ala<br>Specific Biotinylation Sites: Lys42 to Cys, Ser77 to Cys |
| 2.D 1v4n (C3) | Description: Three-Fold (C3) Polyhedral Node<br>Template Sequence:<br>MMIEPKEKASIGIIGGSGLYDPQILTNVKEIKVYTPYGEPSDNIILGELEGRKVAFLPRHGRGHRIPPHKINYRANIWAL<br>KSLGVKWVIAVSAVGSLRLDYKPGDFVVPNQFIDMTKGRTYTFFDGPTVAHVSMADPFCEHLRSIILDSAKDLGITTHDK<br>GTYICIEGPRFSTRAESIVWKEVFKADIIGMTLVPEVNLACEAEMCYSVIGMVTDYDVFADIPVTAEEVTKVMAENTAKV<br>KKLLYEVIRRLPEKPDERKCSCCQALKTALVLEHHHHHHHH [SEQ ID NO: 8]<br>Sequence Modifications:<br>General: Cys165 to Ala or Ser<br>Cys139-Cys206(SS) or Cys139 to Ala, Cys 206 to Ala<br>Cys201-Cys262(SS) or Cys201 to Ala, Cys 262 to Ala<br>Cys260-Cys263(SS) or Cys260 to Ala, Cys 263 to Ala<br>Specific Biotinylation Sites:<br>1. Dodecahedral Node: Ile24 to Cys, Ile31 to Cys,<br>2. Truncated Icosahedral "Bucky" Node: Thr230 to Cys, Lys 267 to Cys |

Part 4.

| | |
|---|---|
| 2.E 1vcg (C4) | Description: Four Fold (C4) Planar Symmetric Node<br>Template Sequence:<br>MNIRERKRKHLEACLEGEVAYQKTTTGLEGFRLRYQALAGLALSEVDLTTPFLGKTLKAPFLIGAMTGGEENGERINLAL<br>AEAAEALGVGMMLGSGRILLERPEALRSFRVRKVAPKALLIANLGLAQLRRYGRDDLLRLVEMLEADALAFHVNPLQEAV<br>QRGDTDFRGLVERLAELLPLPFPVMVKEVGHGLSREAALALRDLPLAAVDVAGAGGTSWARVEEWVRFGEVRHPELCEIG<br>IPTARAILEVREVLPHLPLVASGGVYTGTDGAKALALGADLLAVARPLLRPALEGAERVAAWIGDYLEELRTALFAIGAR<br>NPKEARGRVERV [SEQ ID NO 9]<br>Sequence Modifications:<br>General: Cys14 to Ala, Cys237 to Ser or Ala<br>Specific Biotinylation Sites:<br>1. Ser44 to Cys, Thr49 to Cys, |
| 2.F 1vdh (C5) | Description: Five-fold (C5) Icosahedral Node<br>Template Sequence:<br>MERHVPEPTHTLEGWHVLHDFRLLDFARWFSAPLEAREDAWEELKGLVREWRELEEAGQGSYGIYQVVGHKADLLFLNLR<br>PGLDPLLEAEARLSRSAFARYLGRSYSFYSVVELGSQEKPLDPESPYVKPRLTPRVPKSGYVCFYPMNKRRQGQDNWYML<br>PAKERASLMKAHGETGRKYQGEVMQVISGAQGLDDWEWGVDLFSEDPVQFKKIVYEMRFDEVSARYGEFGPFFVGKYLDE<br>EALRAFLGL [SEQ ID NO: 10]<br>Sequence Modifications:<br>General: Cys 152 to Ala<br>Specific Biotinylation Sites:<br>1. LYS 45 to Cys, Ala 57 to Cys |

Part 5.

| | |
|---|---|
| 2.G (1stp) (D2) | Description: Biotin Functionalized Streptavidin Derivatives<br>Template Sequence:<br>DPSKDSKAQVSAAEAGITGTWYNQLGSTFIVTAGADGALTGTYESAVGNAESRYVLTGRYDSAPATDGSGTALGWTVAWK<br>NNYRNAHSATTWSGQYVGGAEARINTQWLLTSGTTEANAWKSTLVGHDTFTKVKPSAASIDAAKKAGVNNGNPLDAVQQ<br>[SEQ ID NO: 11]<br>Sequence Modifications:<br>General: None<br>Specific Biotinylation Sites:<br>1. (A)(X-Axis Biotin Binding Blocking Site) Asn49 to Cys<br>2. (B)(Y-Dyad Axis) Asn81 to Cys<br>3. (C)(Z-Dyad Axis) Asn119 to Cys<br>4. A + B + C,<br>5. A + C,<br>6. B + C,<br>7. B + A |

Part 6.

| | |
|---|---|
| 2.H 1ma1 (D2) | Description: D2 Symmetric Node<br>Template Sequence:<br>MNDLEKKFYELPELPYPYDALEPHISREQLTIHHQKHHQAYVDGANALLRKLDEARESDTDVDIKAALKELSFHVGGYVL<br>HLFFWGNMGPADECGGEPSGKLAEYIEKDFGSFERFRKEFSQAAISAEGSGWAVLTYCQRTDRLFIMQVEKHNVNVIPHF<br>RILLVLDVWEHAYYIDYRNVRPDYVEAFWNIVNWKEVEKRFEDIL [SEQ ID NO: 12]<br>Sequence Modifications:<br>General: Cys93 to Ser or Thr, Cys137 to Ala<br>Specific Biotinylation Sites:<br>1. HX: Ser57 to Cys<br>2. VX: Glu127 to Cys<br>3. HY: Glu27 to Cys |

TABLE 2-continued

Specifications of Thermostable Node Proteins

| No, PDB ID, Symmetry | Description, Template Sequence, Site-Directed Modifications |
|---|---|
| | 4. VY: Tyr176 to Cys<br>5. HZ: Gln138 to Cys<br>6. VX: Arg 199 to Cys<br>7. HX + HY + HZ<br>8. VX + VY + VZ<br>9. HX + VY + VZ etc.<br>10. HX + HY,<br>11. HY + HZ<br>12. VX + HY etc. |

Part 7.

| 2.I 1nto (D2) | Description: D2 Symmetric Node<br>Template Sequence:<br>MRAVRLVEIGKPLSLQEIGVPKPKGPQVLIKVEAAGVCHSDVEMRQGRFGNLRIVEDLGVKLPVTLGHEIAGKIEEVGDE<br>VVGYSKGDLVAVNPWQGEGNCYYCRIGEEHLCDSPRWLGINFDGAYAEYVIVPHYKYMYKLRRLNAVEAAPLTCSGITTY<br>RAVRKASLDPTKTLLVVGAGGGLGTMAVQIAKAVSGATIIGVDVREEAVEAAKRAGADYVINASMQDPLAEIRRITESKG<br>VDAVIDLNYSEKTLSVYPKALAKQGKYVMVGLFGADLHYHAPLITLSEIQFVGSLVGNQSDFLGIMRLAEAGKVKPMITK<br>TMKLEEANEAIDNLENFKAIGRQVLIP [SEQ ID NO: 13]<br>Sequence Modifications:<br>General: Cys38 to Ala, Cys101 to His, Cys112 to His, Cys104 to His, Cys154 to<br>Ser (Zn Ion binding sites)<br>Specific Biotinylation Sites:<br>1. HX: Glu251 to Cys<br>2. VX: Leu283 to Cys<br>3. HY: Val81 to Cys<br>4. VY: Arg116 to Cys<br>5. HZ: Leu99 to Cys<br>6. VX: Leu308 to Cys<br>7. HX + HY + HZ<br>8. VX + VY + VZ<br>9. HX + VY + VZ etc.<br>10. HX + HY,<br>11. HY + HZ<br>12. VX + HY etc. |
|---|---|

Part 8.

| 2.J 1rtw (D2) | Description: D2 Symmetric Node<br>Template Sequence:<br>MFSEELIKENENIWRRFLPHKFLIEMAENTIKKENFEKWLVNDYYFVKNALRFMALLMAKAPDDLLPFFAESIYYISKEL<br>EMFEKKAQELGISLNGEIDWRAKSYVNYLLSVASLGSFLEGFTALYCEEKAYYEAWKWVRENLKERSPYQEFINHWSSQE<br>FGEYVKRIEKILNSLAEKHGEFEKERAREVFKEVSKFELIFWDIAYGGEGNVLEHHHHHH [SEQ ID NO: 14]<br>Sequence Modifications:<br>General: Cys 127 to Ala or Ser<br>Specific Biotinylation Sites:<br>1. HX: Lys196 to Cys<br>2. VX: Asn42 to Cys<br>3. HY: Pro67 to Cys<br>4. VY: Ile76 to Cys<br>5. HZ: Glu185 to Cys<br>6. VZ: Glu177 to Cys<br>7. HX + HY + HZ<br>8. VX + VY + VZ<br>9. HX + VY + VZ etc.<br>10. HX + HY,<br>11. HY + HZ<br>12. VX + HY etc. |
|---|---|
| 2.K 1b4b (D3) | Description: D3 Symmetric Node<br>Template Sequence:<br>ALVDVFIKLDGTGNLLVLRTLPGNAHAIGVLLDNLDWDEIVGTICGDDTCLIICRTPKDAKKVSNQLLSML<br>[SEQ ID NO: 15]<br>Sequence Modifications:<br>General: Cys123 to Ala, Cys128 to Ala (SS Bridge in Native), Cys132 to Ala<br>Specific Biotinylation Sites:<br>1. HX(+): Leu99 to Cys<br>2. HV(+): Asp111 to Cys<br>3. HX(−): Val108 to Cys<br>4. HV(−): Val81 to Cys<br>5. HX(+) + HX(−),<br>6. VX(+) + VX(−),<br>7. HX(+) + VX(−),<br>8. VX(+) + HX(−), |

TABLE 2-continued

Specifications of Thermostable Node Proteins

| No, PDB ID, Symmetry | Description, Template Sequence, Site-Directed Modifications |
|---|---|

Part 9.

2.L 1hyb (D3)  Description: D3 Symmetric Node
Template Sequence:
MMTMRGLLVGRMQPFHRGALQVIKSILEEVDELIICIGSAQLSHSIRDPFTAGERVMMLTKALSENGIPASRYYIIPVQD
IECNALWVGHIKMLTPPFDRVYSGNPLVQRLFSEDGYEVTAPPLFYRDRYSGTEVRRRMLDDGDWRSLLPESVVEVIDEI
NGVERIKHLAKKEVSELGGIS [SEQ ID NO: 16]
Sequence Modifications:
General: Cys36 to Ala, Cys83 to Ser or Thr
Specific Biotinylation Sites:
1. HX(+): Met93 to Cys
2. VX(+): Ser113 to Cys
3. HX(−): Glu32 to Cys
4. VX(−): SER64 to Cys
5. HX(+) + HX(−),
6. VX(+) + VX(−),
7. HX(+) + VX(−),
8. VX(+) + HX(−), 2.M 2prd (D3)  Description: D3 Symmetric Node
Template Sequence:
ANLKSLPVGDKAPEVVHMVIEVPRGSGNKYEYDPDLGAIKLDRVLPGAQFYPGDYGFIPSTLAEDGDPLDGLVLSTYPLL
PGVVVEVRVVGLLLMEDEKGGDAKVIGVVAEDQRLDHIQDIGDVPEGVKQEIQHFFETYKALEAKKGKWVKVTGWRDRKA
ALEEVRACIARYKG [SEQ ID NO: 17]
Sequence Modifications:
General: Cys 168 to Ser or Thr
Specific Biotinylation Sites:
1. HX(+): Glu126 to Cys
2. VX(+): Asp120 to Cys
3. HX(−): Gln133 to Cys
4. VX(−): Trp149 to Cys
5. HX(+) + HX(−),
6. VX(+) + VX(−),
7. HX(+) + VX(−),
8. VX(+) + HX(−), Part 10.

2.N 1o4v (D4)  Description: D4 Symmetric Node
Template Sequence:
MGSDKIHHHHHHVPRVGIIMGSDSDLPVMKQAAEILEEFGIDYEITIVSAHRTPDRMFEYAKNAEERGIEVIIAGAGGAA
HLPGMVASITHLPVIGVPVKTSTLNGLDSLFSIVQMPGGVPVATVAINNAKNAGILAASILGIKYPEIARKVKEYKERMK
REVLEKAQRLEQIGYKEYLNQKE [SEQ ID NO: 18]
Sequence Modifications:
General: None
Specific Biotinylation Sites:
1. HX: His79 to Cys
2. VX: Pro2 to Cys
3. HX': Asn51 to Cys
4. VX': Thr41 to Cys
5. HX + HX',
6. HX + VX',
7. VX + VX',
8. VX + HX'

2.O 2h2i (D4)  Description: D4 Symmetric Node
Template Sequence:
MKMKEFLDLLNESRLTVTLTGAGISTPSGIPDFRGPNGIYKKYSQNVFDIDFFYSHPEEFYRFAKEGIFPMLQAKPNLAH
VLLAKLEEKGLIEAVITQNIDRLHQRAGSKKVIELHGNVEEYYCVRCEKKYTVEDVIKKLESSDVPLCDDCNSLIRPNIV
FFGENLPQDALREAIGLSSRASLMIVLGSSLVVYPAAELPLITVRSGGKLVIVNLGETPFDDIATLKYNMDVVEFARRVM
EEGGIS [SEQ ID NO: 19]
Sequence Modifications:
General: None (Cys ligate to Zn) or Cys133 to Ala, Cys136 to Ala, Cys156 to
Ala, Cys159 to Ala
Specific Biotinylation Sites:
1. HX: Cys 124 to Cys
2. VX: Glu120 to Cys
3. HX': Val145 to Cys
4. VX': Asn46 to Cys Part 11.

2.P 2iel (D4)  Description: D4 Symmetric Node
Template Sequence:

TABLE 2-continued

Specifications of Thermostable Node Proteins

| No, PDB ID, Symmetry | Description, Template Sequence, Site-Directed Modifications |
|---|---|
| | MARYLVVAHRTAKSPELAAKLKELLAQDPEARFVLLVPAVPPPGWVYEENEVRRRAEEEAAAAKRALEAQGIPVEEAKAG<br>DISPLLAIEEELLAHPGAYQGIVLSTLPPGLSRWLRLDVHTQAERFGLPVIHVIAQAA [SEQ ID NO: 20]<br>Sequence Modifications:<br>General: None<br>Specific Biotinylation Sites:<br>1. HX: Ala94 to Cys<br>2. VX: Arg113 to Cys<br>3. HX': Arg53 to Cys<br>4. VX': Val46 to Cys |
| 2.Q 1pvv (T23) | Description: Tetrahedral Node with Diad axes Directed to form Cubic Lattice<br>Template Sequence:<br>MVVSLAGRDLLCLQDYTAEEIWTILETAKMFKIWQKIGKPHRLLEGKTLAMIFQKPSTRTRVSFEVAMAHLGGHALYLNA<br>QDLQLRRGETIADTARVLSRYVDAIMARVYDHKDVEDLAKYATVPVINGLSDFSHPCQALADYMTIWEKKGTIKGVKVVY<br>VGDGNNVAHSLMIAGTKLGADVVVATPEGYEPDEKVIKWAEQNAAESGGSFELLHDPVKAVKDADVIYTDVWASMGQEAE<br>AEERRKIFRPFQVNKDLVKHAKPDYMFMHCLPAHRGEEVTDDVIDSPNSVVWDQAENRLHAQKAVLALVMGGIKF<br>[SEQ ID NO: 21]<br>Sequence Modifications:<br>General: Cys 11 to Thr or Ser, Cys136 to Thr or Ser, Cys269 to Thr or Ser<br>Specific Biotinylation Sites:<br>1. H: Arg7 to Cys<br>2. V: Thr122 to Cys |

---

We claim:

1. A nanostructure node, comprising
a multimeric protein having at least one polypeptide chain and a known three-dimensional structure with Cn symmetry with a Cn symmetry axis or with Dn symmetry with a Dn symmetry axis,
wherein the multimeric protein has stable tertiary structure at a temperature of 70° C. or greater and a modified amino acid sequence comprising a specific binding site positioned with predefined stoichiometry and orientation for attachment of a nanostructure strut,
wherein the specific binding site comprises a pair of reactive amino acid residues, each reactive amino acid residue covalently attached to a moiety independently selected from the group consisting of a biotin group, a biotin derivative group, iminobiotin, an adenosine triphosphate (ATP) group, an adenosine triphosphate (ATP) derivative group, a nucleobase group, a nucleobase derivative group, a nucleoside group, a nucleoside derivative group, a nucleotide group, and a nucleotide derivative group, so that a pair of moieties are attached to the specific binding site, wherein the nanostructure strut has three dyad axes and two pairs of moiety binding sites, the first pair of moiety binding sites related to the second pair of moiety binding sites by a dyad axis, the first moiety binding site of the first pair related to the second moiety binding site of the first pair by a dyad axis, and the first moiety binding site of the second pair related to the second moiety binding site of the second pair by a dyad axis, wherein the pair of moieties attached to the specific binding site of the multimeric protein can bind with the first or second pair of moiety binding sites on the nanostructure strut, so that the Cn or Dn symmetry axis of the multimeric protein is parallel to within 5 degrees to one of the three dyad axes of the nanostructure strut.

2. The nanostructure node of claim 1,
wherein the first moiety binding site is separated from the second moiety binding site of the first pair of the nanostructure strut by a first distance and
wherein the pair of reactive amino acid residues of the multimeric protein are separated from each other by a second distance approximately equal to the first distance.

3. The nanostructure node of claim 1,
wherein the moiety covalently attached to the reactive amino acid residue is selected from the group consisting of a biotin group and a biotin derivative group and binds to streptavidin or a streptavidin derivative strut.

4. The nanostructure node of claim 3, wherein each moiety of the pair of moieties is separated from the other by a distance of from about 15 Angstroms to about 25 Angstroms.

5. The nanostructure node of claim 3, wherein the multimeric protein is selected from the group consisting of proteins having an amino acid sequence with 80 percent or greater sequence identity to that of a pdb code protein 1fsz [SEQ ID NO: 30], 1ge8 [SEQ ID NO: 31], 1isq [SEQ ID NO: 32], 1j2v [SEQ ID NO: 33], 1kht [SEQ ID NO: 34], 1ki9 [SEQ ID NO: 35], 1kwg [SEQ ID NO: 36], 1l1s [SEQ ID NO: 37], 1ml4 [SEQ ID NO: 38], 1n2m [SEQ ID NO: 39], 1n13 [SEQ ID NO: 40], 1o5j [SEQ ID NO: 42], 1qrf [SEQ ID NO: 43], 1thj [SEQ ID NO: 1], 1ufy [SEQ ID NO: 44], 1uku [SEQ ID NO: 45], 1v4n [SEQ ID NO: 8], 1v8d [SEQ ID NO: 46], 1vke [SEQ ID NO: 47], 1wvq [SEQ ID NO: 48], 1wzn [SEQ ID NO: 49], 1x25 [SEQ ID NO: 50], 2b33 [SEQ ID NO: 51], 2cz4 [SEQ ID NO: 52], 2dcl [SEQ ID NO: 53], 2dhr [SEQ ID NO: 54], 2dt4 [SEQ ID NO: 55], 2hik [SEQ ID NO: 56], 2nwl [SEQ ID NO: 57], 1bkb [SEQ ID NO: 58], 1nc7 [SEQ ID NO: 59], 1vrd [SEQ ID NO: 60], 2cu0 [SEQ ID NO: 61], 2fk5 [SEQ ID NO: 62], 2flf [SEQ ID NO: 63], 1t0t [SEQ ID NO: 64], 1vdh [SEQ ID NO: 10], 1w8s [SEQ ID NO: 65], 2b99 [SEQ ID NO: 66], 2bbh [SEQ ID NO: 67], 2bbj [SEQ ID NO: 68], 2hn1 [SEQ ID NO: 69], 2hn2 [SEQ ID NO: 70], 2iub [SEQ ID NO: 71], 1i8f [SEQ ID NO: 72], 1ljo [SEQ ID NO: 73], 2alb [SEQ ID NO: 74], 2a18 [SEQ ID NO: 75], 2di4 [SEQ ID NO: 76], 2dr3 [SEQ ID NO: 77], 2ekd [SEQ ID NO: 78], 2ewh [SEQ ID NO: 79], 1h64 [SEQ ID NO: 80], 1i4k [SEQ ID NO: 81], 1i81 [SEQ ID NO: 82], 1jbm [SEQ ID NO: 83], 1jri [SEQ ID NO: 84], 1m5q [SEQ ID NO: 85], 1mgq [SEQ ID NO: 86], 1a0e [SEQ ID NO: 87], 1bxb [SEQ ID NO: 88], 1do6 [SEQ ID NO: 89], 1dof [SEQ ID NO: 90], 1gtd [SEQ ID NO: 91], 1hyg [SEQ ID NO: 92], 1ilg [SEQ ID NO: 93], 1ik6 [SEQ ID NO: 94], 1ixr [SEQ ID NO: 95], 1jly [SEQ ID NO: 96], 1j2w [SEQ ID NO: 97], 1jg8 [SEQ ID NO: 98], 1jvb [SEQ ID NO: 99], 1knv [SEQ ID NO: 100], 1lk5 [SEQ ID NO: 101], 1lvw [SEQ ID NO: 102], 1m8k [SEQ ID NO: 103], 1mal [SEQ ID NO: 12], 1nto [SEQ ID NO: 13], 1nvg [SEQ ID NO: 104], 1o2a [SEQ ID NO: 105], 1o54 [SEQ ID NO: 106], 1r37 [SEQ ID NO: 107], 1ris [SEQ ID NO: 108], 1rtw [SEQ ID NO: 14], 1u9y [SEQ ID NO: 109], 1udd [SEQ ID NO: 110], 1uir [SEQ ID NO: 111], 1usy [SEQ ID NO: 112], 1uxt [SEQ ID NO: 114], 1v6t [SEQ ID NO: 115], 1v8o [SEQ ID NO: 116], 1v8p [SEQ ID NO: 117], 1vc2 [SEQ ID NO: 118], 1vco [SEQ ID NO: 119], 1vdk [SEQ ID NO: 120], 1vjp [SEQ ID NO: 121], 1vk8 [SEQ ID NO: 122], 1v12 [SEQ ID NO: 123], 1vlv [SEQ ID NO: 124], 1vr6 [SEQ ID NO: 125], 1w3i [SEQ ID NO: 126], 1wb7 [SEQ ID NO: 127], 1wb8 [SEQ ID NO: 128], 1wlu [SEQ ID NO: 129], 1ws9 [SEQ ID NO: 130], 1wyt [SEQ ID NO: 131], 1x01 [SEQ ID NO: 133], 1xle [SEQ ID NO: 134], 1x10 [SEQ ID NO: 135], 1xtt [SEQ ID NO: 136], 1y56 [SEQ ID NO: 137], 1z54 [SEQ ID NO: 139], 2b5d [SEQ ID NO: 140], 2bri [SEQ ID NO: 141], 2cb1 [SEQ ID NO: 142], 2cd9 [SEQ ID NO: 143], 2cdc [SEQ ID NO: 144], 2cx9 [SEQ ID NO: 145], 2czc [SEQ ID NO: 146], 2dly [SEQ ID NO: 147], 2d8a [SEQ ID NO: 148], 2d29 [SEQ ID NO: 149], 2df5 [SEQ ID NO: 150], 2dfa [SEQ ID NO: 151], 2drh [SEQ ID NO: 152], 2dsl [SEQ ID NO: 153], 2e1a [SEQ ID NO: 154], 2e9f [SEQ ID NO: 155], 2eba [SEQ ID NO: 156], 2ebj [SEQ ID NO: 157], 2eo5 [SEQ ID NO: 158], 2ep5 [SEQ ID NO: 159], 2g10 [SEQ ID NO: 160], 2 gm7 [SEQ ID NO: 161], 2h6e [SEQ ID NO: 162], 2hae [SEQ ID NO: 163], 2hmf [SEQ ID NO: 164], 2iss [SEQ ID NO: 165], 2ldb [SEQ ID NO: 167], 2p3n [SEQ ID NO: 168], 2ph3 [SEQ ID NO: 169], 2yym [SEQ ID NO: 170], 3pfk [SEQ ID NO: 171], 1aup [SEQ ID NO: 172], 1bgv [SEQ ID NO: 173], 1bvu [SEQ ID NO: 174], 1f9a [SEQ ID NO: 175], 1fxk [SEQ ID NO: 176], 1gtm [SEQ ID NO: 179], 1hyb [SEQ ID NO: 16], 1je0 [SEQ ID NO: 180], 1jku [SEQ ID NO: 181], 1odi [SEQ ID NO: 182], 1odk [SEQ ID NO: 183], 1pg5 [SEQ ID NO: 184], 1qw9 [SEQ ID NO: 186], 1t57 [SEQ ID NO: 187], 1uan [SEQ ID NO: 188], 1ude [SEQ ID NO: 189], 1uiy [SEQ ID NO: 190], 1vla [SEQ ID NO: 191], 1vls [SEQ ID NO: 192], 1v9l [SEQ ID NO: 193], 1v19 [SEQ ID NO: 194], 1wkl [SEQ ID NO: 195], 1wz8 [SEQ ID NO: 196], 1wzn [SEQ ID NO: 197], 1x0u [SEQ ID NO: 198], 2a8y [SEQ ID NO: 199], 2afb [SEQ ID NO: 200], 2anu [SEQ ID NO: 201], 2bja [SEQ ID NO: 202], 2bjk [SEQ ID NO: 203], 2cqz [SEQ ID NO: 204], 2dcn [SEQ ID NO: 205], 2ddz [SEQ ID NO: 206], 2dev [SEQ ID NO: 207], 2dqb [SEQ ID NO: 20], 2dxf [SEQ ID NO: 209], 2dya [SEQ ID NO: 210], 2eez [SEQ ID NO: 211], 2g3m [SEQ ID NO: 212], 2i14 [SEQ ID NO: 213], 2ide [SEQ ID NO: 214], 2j4j [SEQ ID NO: 215], 2j9d [SEQ ID NO: 216], 2prd [SEQ ID NO: 17], 2j4k [SEQ ID NO: 218], 1jpu [SEQ ID NO: 219], 1jq5 [SEQ ID NO: 220], 1m4y [SEQ ID NO: 221], 1o4v [SEQ ID NO: 18], 1saz [SEQ ID NO: 222], 1umg [SEQ ID NO: 223], 1vcf [SEQ ID NO: 224], 1x9j [SEQ ID NO: 225], 2ax3 [SEQ ID NO: 226], 2cwx [SEQ ID NO: 227], 2d69 [SEQ ID NO: 228], 2h2i [SEQ ID NO: 19], 2iel [SEQ ID NO: 20], 1geh [SEQ ID NO: 229], 1w8s [SEQ ID NO: 230], 1wm9 [SEQ ID NO: 231], 1wuq [SEQ ID NO: 232], 1wur [SEQ ID NO: 233], 1wx0 [SEQ ID NO: 234], 2djw [SEQ ID NO: 235], 1m4y [SEQ ID NO: 236], 1znn [SEQ ID NO: 237], 1m5q [SEQ ID NO: 238], or 1th7 [SEQ ID NO: 239].

6. The nanostructure node of claim 1, wherein at least one polypeptide chain of the multimeric protein is bonded to a bifunctional reagent with additional binding or a functionality selected from the group consisting of catalytic, chemomechanical, electromechanical, optomechanical, and optoelectronic functionality.

7. The nanostructure node of claim 1, wherein at least one polypeptide chain of the multimeric protein comprises an amino acid sequence that exhibits protein binding or a functionality selected from the group consisting of catalytic, chemomechanical, electromechanical, optomechanical, and optoelectronic functionality.

8. The nanostructure node of claim 3, wherein the multimeric protein comprises a single polypeptide chain.

9. The nanostructure node of claim 3,
   wherein the multimeric protein has Cn symmetry and a Cn symmetry axis,
   wherein the specific binding site comprises two specific amino acid reactive residues,
   wherein the streptavidin or streptavidin derivative strut has three dyad axes and two pairs of biotin binding sites, the first pair related to the second pair by a dyad axis, and the first binding site of a pair related to the second binding site of the pair by a dyad axis,
   wherein the two specific amino acid reactive residues are complementary to the geometry of a pair of biotin binding sites on the streptavidin or streptavidin derivative strut, so that when the two specific amino acid reactive residues are aligned with a pair of biotin binding sites, the Cn symmetry axis of the nanostructure node multimeric protein is substantially parallel to a dyad axis of the streptavidin or streptavidin derivative strut.

10. The nanostructure node of claim 9, wherein the multimeric protein has an amino acid sequence given in Table 2B or has an amino acid sequence with greater than 80 percent sequence identity with a sequence provided in Table 2B.

11. The nanostructure node of claim 9,
    having a C3-symmetric planar structure,
    wherein the multimeric protein has an amino acid sequence with greater that 80 percent identity to the amino acid sequence of the pdb code:1thj [SEQ ID NO: 1] or of the pdb code:1j5s [SEQ ID NO: 7] protein trimer.

12. The nanostructure node of claim 9,
    having a C4-symmetric planar structure,
    wherein the multimeric protein has an amino acid sequence with greater than 80 percent identity to the amino acid sequence of the pdb code:1vcg [SEQ ID NO: 9] or of the pdb code:2cu0 [SEQ ID NO: 61] protein tetramer.

13. The nanostructure node of claim 9,
    selected from the group consisting of a C5-symmetric planar node wherein the protein has an amino acid sequence with greater than 80 percent identity to that of the pdb code:1vdh [SEQ ID NO: 10] protein pentamer, a C6-symmetric planar node wherein the protein has an amino acid sequence with greater than 80 percent identity to that of the pdb code:2ekd [SEQ ID NO: 78] protein hexamer, and a C7-symmetric planar node wherein the protein has greater than 80 percent identity to that of the pdb code:1i81 [SEQ ID NO: 82] protein heptamer.

14. The nanostructure node of claim 3,
    selected from the group consisting of a C3-symmetric apex node, wherein the protein has an amino acid sequence with at least 80 percent identity to the amino acid sequence of the pdb code:1v4n [SEQ ID NO: 8] protein trimer, and a C5-symmetric apex node, wherein the protein has an amino acid sequence with at least 80 percent identity to the amino acid sequence of the pdb code:1vdh [SEQ ID NO: 10] protein pentamer and
    wherein the streptavidin or streptavidin derivative strut binds to the multimeric protein with a geometry selected from the group consisting of dodecahedral apex geometry, "buckyball" geometry, truncated icosahedral apex geometry, and icosahedral apex geometry.

15. The nanostructure node of claim 3,
    having D2 symmetry,
    wherein the multimeric protein has an amino acid sequence with at least 80 percent identity to an amino acid sequence selected from the group consisting of the pdb code:1ma1 [SEQ ID NO: 12] protein tetramer, the pdb code:1nto [SEQ ID NO: 13] protein tetramer, the pdb code:1rtw [SEQ ID NO: 14] protein tetramer, and the pdb code:1stp [SEQ ID NO: 11] protein tetramer and
    wherein the streptavidin or streptavidin derivative strut binds to the multimeric protein with a geometry selected from the group consisting of linear, 2-dimensional rectangular, and 3-dimensional orthorhombic lattice geometry.

16. The nanostructure node of claim 3,
    having D3 symmetry,
    wherein the multimeric protein has an amino acid sequence with at least 80 percent identity to the amino acid sequence selected from the group consisting of the pdb code:1b4b [SEQ ID NO: 15] protein hexamer, the pdb code:1hyb [SEQ ID NO: 16] protein hexamer, and the pdb code:2prd [SEQ ID NO: 17] protein hexamer and
    wherein the streptavidin or streptavidin derivative strut binds to the multimeric protein with hexagonal geometry.

17. The nanostructure node of claim 3,
    having D4 symmetry,
    wherein the multimeric protein has an amino acid sequence with at least 80 percent identity to an amino acid sequence selected from the group consisting of the pdb code:1o4v [SEQ ID NO: 18] protein octamer, the pdb code:2h2i [SEQ ID NO: 19] protein octamer, and the pdb code:2iel [SEQ ID NO: 20] protein octamer and
    wherein streptavidin or streptavidin derivative strut binds to the multimeric protein with rectangular geometry.

18. A nanostructure node chain:streptavidin complex, comprising:
    a polypeptide chain of a nanostructure node; and
    a streptavidin or streptavidin derivative tetramer having biotin binding sites,
    wherein the nanostructure node comprises a multimeric protein having a known three-dimensional structure, with Cn, Dn, or higher symmetry,
    wherein the multimeric protein has stable tertiary structure at a temperature of 70° C. or greater and a modified amino acid sequence,
    wherein the polypeptide chain comprises two cysteine residues, each functionalized with a biotin or biotin derivative group, and
    wherein the biotin or biotin derivative groups of the two cysteine residues are bound to two biotin binding sites of the streptavidin or streptavidin derivative tetramer.

19. The nanostructure node chain:streptavidin complex of claim 18, wherein the multimeric protein comprises an IPP isomerase or an IPP isomerase derivative.

20. The nanostructure node chain: streptavidin complex of claim 18,
    further comprising a second polypeptide chain of the nanostructure node,
    wherein the second polypeptide chain comprises two cysteine residues, each functionalized with a biotin or biotin derivative group, and
    wherein the biotin or biotin derivative groups of the two cysteine residues of the second polypeptide chain are bound to two biotin binding sites of the streptavidin or streptavidin derivative tetramer.

21. An extended nano structure strut, comprising:
    the nanostructure node of claim 3, and further comprising a first streptavidin strut and a second streptavidin strut,
    wherein the nanostructure node has at least two specific binding sites and wherein the first streptavidin strut is bound to a first specific binding site and the second streptavidin strut is bound to the second specific binding site.

22. A nanostructural assembly, comprising:
a nanostructure node according to claim 1; and
a nanostructure strut bound to the specific binding site.

23. The nanostructural assembly of claim 22, wherein the nanostructure strut comprises streptavidin and/or a streptavidin derivative.

24. The nanostructural assembly of claim 22, wherein the nanostructural assembly has the form of a radial planar array.

25. The nanostructural assembly of claim 22,
wherein the nanostructural assembly has the form of a planar polygon and the nanostructure node has a symmetry selected from the group consisting of Cn symmetry and Dn symmetry.

26. The nanostructural assembly of claim 22,
wherein the nanostructural assembly comprises a lattice having the form of a regular plane tiling selected from the group consisting of a triangular tiling (with the nanostructure node having C6 symmetry or D6 symmetry), a square tiling (with the nanostructure node having C4 symmetry or D4 symmetry), and a hexagonal tiling (with the nanostructure node having C3 symmetry or D3 symmetry).

27. The nanostructural assembly of claim 22, wherein the nanostructural assembly comprises a lattice having the form of a square tiling (with the nanostructure node having D2 symmetry).

28. The nanostructural assembly of claim 22,
wherein the nanostructural assembly has the form of a 3-dimensional radial array, and
wherein the nanostructure node has a symmetry selected from the group consisting of Dn, tetrahedral, cuboctahedral, icosahedral, and dodecahedral symmetry.

29. The nanostructural assembly with the form of a 3-dimensional radial array of claim 28,
wherein the nanostructural assembly has the form of a 3-dimensional radial array with six arms directed along three mutually perpendicular axes and
wherein the nanostructure node has tetrahedral (T23) symmetry.

30. A nanostructural assembly with the form of a 3-dimensional radial array of claim 28,
wherein the nanostructural assembly has the form of a 3-dimensional radial array with 18 arms directed toward the apices of a cuboctahedron and
wherein the nanostructure node has cuboctahedral symmetry.

31. A nanostructural assembly with the form of a 3-dimensional radial array of claim 28,
wherein the nanostructural assembly has the form of a 3-dimensional radial array with 30 arms directed along the dyad axes of a dodecahedron and
wherein the nanostructure node has dodecahedral symmetry.

32. The nanostructural assembly of claim 22, having a form selected from the group consisting of a regular 3-dimensional polyhedron, an Archimedean solid, and a Catalan solid.

33. The nanostructural assembly of claim 22, having the form of a three-connected, hexagonal-pattern, three-dimensional lattice.

34. The nanostructural assembly of claim 22, having the form of a four-connected, cubic-pattern, three-dimensional lattice.

35. The nanostructural assembly of claim 22, having the form of a six-connected, cubic, three-dimensional lattice.

36. The nanostructure node of claim 1,
wherein a polypeptide chain comprises an amino acid sequence having a designated amino and/or carboxy terminus and
further comprising a polypeptide extension of from 5 to 1000 amino acid residues linked with a peptide bond to the designated amino and/or carboxy terminus.

37. The nanostructure node of claim 36, wherein the polypeptide extension comprises a binding function for a protein, metallic, or other surface.

38. The nanostructure node of claim 36, wherein the polypeptide extension comprises an amino acid sequence that is a substrate for an enzyme.

39. The nanostructure node of claim 36, wherein the polypeptide extension comprises a subsequence selected from the group consisting of an immunoglobulin polypeptide, a polyhistidine, a streptavidin binding polypeptide, StrepTag, an antibody binding polypeptide, *staphylococcus* Protein A, *staphylococcus* Protein G, an antigenic polypeptide, and a hapten-binding polypeptide.

40. The nanostructure node of claim 36,
wherein the polypeptide extension comprises an antibody binding polypeptide subsequence and
further comprising an antibody bound to the antibody binding polypeptide subsequence.

41. The nanostructure node multimeric protein of claim 1,
wherein the multimeric protein comprises three subunits,
wherein at least one and at most two subunits comprise a specific binding site.

42. The nanostructure node of claim 1,
wherein the multimeric protein comprises four subunits,
wherein at least one and at most three subunits comprise a specific binding site.

43. The nanostructural assembly of claim 22,
wherein the streptavidin is immobilized on a surface.

44. The nanostructural assembly of claim 22, further comprising:
a protein comprising an adenosine triphosphate (ATP) binding site;
and a bridge molecule having a biotin group covalently bound to an adenosine triphosphate (ATP) group;
wherein the bridge molecule is bound to the biotin binding sites on the streptavidin and the ATP binding site.

45. A nanostructural assembly comprising:
a nanostructure node according to claim 3; and
a protein comprising an adenosine triphosphate (ATP) binding site,
wherein the moiety covalently attached to each specific amino acid reactive residue is selected from the group consisting of an adenosine triphosphate (ATP) group or an adenosine triphosphate (ATP) derivative group;
wherein the ATP or ATP derivative group is bound to the ATP binding site.

46. A device, comprising:
a substrate having a surface;
a nucleation site on the substrate surface; and
the nanostructure node of claim 1 coupled to the nucleation site.

47. The device of claim 46,
wherein the substrate is selected from the group consisting of a metal, a noble metal, a glass, a ceramic, a semiconductor, a polymer, an organic polymer, an organic material, and combinations and
wherein the nucleation site is selected from the group consisting of a metal atom, a noble metal atom, a metal cluster, a noble metal cluster, a chemically reactive molecule, a patch of chemically reactive molecules, and combinations.

48. The device of claim 46,
wherein the substrate is selected from the group consisting of iron, gold, platinum, silver, silicon dioxide, silicon, germanium, a carbon allotrope, diamond, graphite, polytetrafluoroethylene, and combinations and
wherein the nucleation site is selected from the group consisting of an iron atom, a gold atom, a platinum atom, a silver atom, a copper atom, and combinations.

49. The device of claim 46,
wherein a polypeptide chain of the nanostructure node comprises an amino acid sequence having a designated amino and/or carboxy terminus and
further comprising a polypeptide extension of from 5 to 1000 amino acid residues linked with a peptide bond to the designated amino and/or carboxy terminus,
wherein the polypeptide extension comprises a binding function coupled to the nucleation site.

50. A device, comprising:
a substrate having a surface with a node-occupied area and a node-unoccupied area;
the nanostructure node of claim 1 on the node-occupied area of the surface; and
a coating that covers the nanostructure node and covers the surface node-unoccupied area of the surface.

51. The device of claim 50, wherein the coating is selected from the group consisting of a metal, a noble metal, d glass, a ceramic, a semiconductor, a carbon allotrope, a polymer, an organic polymer, an organic material, and combinations.

52. A device, comprising:
a substrate having a surface with a node-occupied area and a node-unoccupied area;
the surface coated with a resist layer; and
the nanostructure node of claim 1 on the resist layer.

53. A device, comprising
the nanostructural assembly of claim 22; and
a first matrix,
wherein the first matrix interpenetrates the nanostructural assembly.

54. The device of claim 53,
wherein the nanostructural assembly has the form of a cubic lattice and
wherein the first matrix has the form of a cubic lattice.

55. The device of claim 53, wherein the first matrix comprises a metal, a noble metal, a glass, a ceramic, a semiconductor, a polymer, an organic polymer, and an organic material.

56. A method of using a multimeric protein as a nanostructure node, comprising
dissolving a nanostructure strut in an aqueous solution,
dissolving the nanostructure node of claim 1 in the aqueous solution or immobilizing the nanostructure node on a surface and exposing the immobilized nanostructure node to the aqueous solution, and
allowing the nanostructure strut to bind to the nanostructure node at the specific binding site.

57. The method of claim 56,
wherein the nanostructure strut comprises streptavidin,
wherein the specific binding site comprises at least two reactive amino acid residues,
wherein each reactive amino acid residue has a covalently attached iminobiotin group,
wherein allowing the nanostructure strut to bind to the nanostructure node comprises increasing the pH of the aqueous solution to at least about 7 to induce the iminobiotin group to bind to the streptavidin of the nanostructure strut.

58. The method of claim 56,
wherein the specific binding site comprises at least two reactive amino acid residues,
wherein each reactive amino acid residue has a covalently attached photo-activated nucleotide,
wherein the nanostructure strut comprises an adenosine triphosphate binding (ATP) binding site, and
wherein allowing the nanostructure strut to bind to the nanostructure node comprises irradiating the aqueous solution with light to induce the photo-activated nucleotide to bind to the ATP binding site.

59. A method of using a nanostructural assembly to mask a resist material for the fabrication of devices with sub-100 nanometer features, comprising
providing the nanostructural assembly of claim 22 and a resist material and
placing the nanostructural assembly on the surface of the resist material.

60. The method of claim 59, where the device is selected from the group consisting of a nanolithography stamp, a semiconductor device, a waveguide, a zero-mode waveguide, a microelectromechanical system (MEMS), a nanofluidics system, a filter, a two-dimensional planar filter, and combinations.

61. A method of using a nanostructural assembly as a patterning material for the fabrication of devices with sub-100 nanometer features comprising
providing the nanostructural assembly of claim 22,
preparing a substrate surface to introduce at least one specific protein attachment site,
binding the nanostructure node to the surface at the at least one specific protein attachment site through chemical linkages, and
coating the nanostructural assembly with a material.

62. A method of using a nanostructural for patterning a resist material for the fabrication of devices with sub-100 nanometer features comprising
providing the nanostructural assembly of claim 22,
coating a substrate surface with a continuous resist layer whose chemical properties are altered by irradiation with a suitable type of radiation;
preparing the resist layer surface to introduce at least one specific protein attachment site;
placing the nanostructure node on the resist layer surface at a predetermined location;
exposing the surface with the nanostructure node to radiation, wherein the surface of the resist lying underneath the nanostructure node is protected from the radiation;
removing the irradiated resist material through a chemical action;
etching the surface with the nanostructure node and underlying resist to form a pattern that is complementary to the structure of the nanostructure node;
removing, using chemical or other means, the nanostructure node and underlying resist to leave a pattern on the substrate surface that is complementary to the structure of the nanostructure node.

63. A method of using a nanostructural assembly as a patterning material for the fabrication of devices with sub-100 nanometer channels comprising
providing the nanostructural assembly of claim 22,
embedding the nanostructural assembly with a matrix material;

treating the nanostructural assembly with radiation, light, heat, and/or chemicals to remove or ablate the nanostructural assembly, leaving the matrix material with internal channels presenting a negative impression of the original nanostructural assembly.

64. The method of claim 63, further comprising:

coating or chemically treating the negative impression created in the matrix material to deposit a second matrix material in the negative space originally occupied by the nanostructural assembly;

treating the assembly with radiation, light, heat, and/or chemicals to remove or ablate the matrix material, leaving a three-dimensional nanostructure assembly comprising the second matrix material with features of the original nanostructural assembly.

* * * * *